US012655174B2

(12) United States Patent
Hu et al.

(10) Patent No.: US 12,655,174 B2
(45) Date of Patent: Jun. 16, 2026

(54) ADENOSINE A3 RECEPTOR AGONISTS, PREPARATION METHODS AND USES THEREOF

(71) Applicant: ZHEJIANG VIMGREEN PHARMACEUTICALS, LTD., Hangzhou (CN)

(72) Inventors: Chongbo Hu, Hangzhou (CN); Jinqi Ye, Hangzhou (CN); Shuhua Pan, Hangzhou (CN); Ning Hu, Hangzhou (CN); Tingting Pan, Hangzhou (CN); Long Zhao, Hangzhou (CN); Zhengshu Chen, Hangzhou (CN); Sanxing Sun, Hangzhou (CN)

(73) Assignee: ZHEJIANG VIMGREEN PHARMACEUTICALS, LTD., Hangzhou (CN)

( * ) Notice: Subject to any disclaimer, the term of this patent is extended or adjusted under 35 U.S.C. 154(b) by 433 days.

(21) Appl. No.: 18/270,117

(22) PCT Filed: Dec. 29, 2021

(86) PCT No.: PCT/CN2021/142384

§ 371 (c)(1),
(2) Date: Jun. 28, 2023

(87) PCT Pub. No.: WO2022/143740

PCT Pub. Date: Jul. 7, 2022

(65) Prior Publication Data

US 2024/0116975 A1 Apr. 11, 2024

(30) Foreign Application Priority Data

Dec. 29, 2020 (CN) ........................ 202011601817.6

(51) Int. Cl.
*C07H 19/167* (2006.01)

(52) U.S. Cl.
CPC ................................. *C07H 19/167* (2013.01)

(58) Field of Classification Search
CPC .................................................. C07H 19/167
USPC .......................................... 536/27.62, 27.22
See application file for complete search history.

(56) References Cited

U.S. PATENT DOCUMENTS

| | | | |
|---|---|---|---|
| 2004/0116376 A1 | 6/2004 | Elzein et al. |
| 2009/0156544 A1 | 6/2009 | Elzein et al. |
| 2020/0115404 A1 | 4/2020 | Wang et al. |

FOREIGN PATENT DOCUMENTS

| | | | |
|---|---|---|---|
| CN | 1538972 A | 10/2004 |
| CN | 101472925 A | 7/2009 |
| CN | 108697719 A | 10/2018 |
| WO | 9502604 A1 | 1/1995 |
| WO | 03029264 A2 | 4/2003 |
| WO | 03061670 A1 | 7/2003 |
| WO | 2008156513 A2 | 12/2008 |
| WO | 2020247546 A1 | 12/2020 |

OTHER PUBLICATIONS

Wolff, Manfred E. "Burger's Medicinal Chemistry, 5ed, Part I", John Wiley & Sons, 1995, pp. 975-977. (Year: 1995).*
Banker, G.S. et al., "Modern Pharmaceutics, 3ed.", Marcel Dekker, New York, 1996, p. 596 (Year: 1996).*
Cosyn et al., Journal of Medicinal Chemistry, vol. 49(25), 2006, pp. 7373-7383. (Year: 2006).*
PCT/CN2021/142384 International Search Report dated Mar. 29, 2022.
Bar-Yehuda, S., et al., Induction of an Antiinflammatory Effect and Prevention of Cartilage Damage in Rat Knee Osteoarthritis by CF101 Treatment, Arthritis & Rheumatism, vol. 60, No. 10, pp. 3061-3071, American College of Rheumatology, Oct. 2009.
Berge, S.M., et al., Pharmaceutical Salts, J of Pharmaceutical Sciences, vol. 66, No. 1, Jan. 1977.
Cosyn, L., et al., 2-Triazole-Substituted Adenosines: a new Class of Selective A3 Adenosine Receptor Agonists, Partial Agonists, and Antagonists, J of Medicinal Chemistry, vol. 49, pp. 7373-7383, Am Chemical Society, Nov. 15, 2006.
Gessi, S., et al., Elevated Expression of A3 Adenosine Receptors in Human Colorectal Cancer is Reflected in Peripheral Blood Cells, Clinical Cancer Research, vol. 10, pp. 5895-5901, Am Assoc for Cancer Research, Sep. 1, 2004.
Jacobson, K.A., et al., Treatment of chronic neuropathic pain: purine receptor modulation, Pain, 161(7), pp. 1425-1441, Jul. 2020.
Madi, L., et al., The A3 Adenosine Receptor is Highly Expressed in Tumor versus Normal Cells: Potential Target for Tumor Growth Inhibition, Clinical Cancer Research, vol. 10, pp. 4472-4479, Am Assoc for Cancer Research, Jul. 1, 2004.
Mulloy, D.P., et al., Adenosine A3 Receptor Activation Attenuates Lung Ischemia-Reperfusion Injury, Ann Thorac Sug, 95(5), pp. 1762-1767, The Society of Thoracic Surgeons, Elsevier Inc., May 2013.
Ochaion, A., et al., The anti-inflammatory target A3 adenosine receptor is over-expressed in rheumatoid arthritis, psoriasis and Crohn's disease, Cellular Immunologygy, vol. 258, pp. 115-122, Elsevier Inc., Mar./May 2009.
Ren, T., et al., Abnormal expression and its role of adenosine A3 receptor in colonic mucosa epithelium of patients with ulcerative colitis, Int J Dig Dis, vol. 38, No. 6, China Academic Journal, Dec. 25, 2018.
Wang, J-L., et al., Progress in Biological Effects of Adenosine A3 Receptor, Medical Recapitulate, vol. 14, No. 23, China Academic Journal, Dec. 2008.
Xiong, H-Y., et al., The effects and mechanisms of an A3 adenosine receptors agonist against myo-cardial ischemic reperfusion injury, Chin J ECC, vol. 14, No., 3, China Academic Journal, Sep. 15, 2016.
European 21914472.2 Extended European Search Report dated Apr. 10, 2024.

(Continued)

*Primary Examiner* — Traviss C McIntosh, III
(74) *Attorney, Agent, or Firm* — Sughrue Mion, PLLC

(57) ABSTRACT

The present application relates to novel compounds that have modulating or activating effect on the activity of adenosine A3 receptor, preparation methods for the series of compounds, pharmaceutical compositions of the series of compounds, and pharmaceutical uses of the series of compounds.

5 Claims, No Drawings

(56) References Cited

OTHER PUBLICATIONS

Li, A-H., et al., Structure-Activity Relationships and Molecular Modeling of 3,5-Diacyl-2,4dialykpyridine Derivatives as Selective A3 Adenosine Receptor Antagonists, Journal of Medicinal Chemistry, American Chemical Society, US, vol. 41, No. 17, pp. 3186-3201, Jan. 1, 1998.

Vittori, S., et al., Synthesis and Receptor Affinity of Polysubstituted Adenosines, Nucleosides and Nucleotides, Taylor & Francis, US, vol. 18, No. 4&5, pp. 739-740, Jan. 1, 1999.

Zhu, R., et al., N6-Ethyl-2-alkynyl NECAs, selective human A3 adenosine receptor agonists, Bioorganic & Medicinal Chemistry Letters, Science Direct, Elsevier Ltd., Amsterdam, NL, vol. 16, No. 9, pp. 2416-2418, May 1, 2006.

* cited by examiner

ADENOSINE A3 RECEPTOR AGONISTS, PREPARATION METHODS AND USES THEREOF

CROSS REFERENCE TO RELATED APPLICATIONS

This application is a National Stage Application and claims priority under 35 U.S.C. § 371 to Patent Cooperation Treaty application PCT/CN2021/142384, filed Dec. 29, 2021, which claims the benefit of China Patent Application 202011601817.6 filed Dec. 29, 2020. Priority is claimed to these applications and the disclosure of these prior applications is considered part of the disclosure of this application and to the extent allowed the entire contents of the aforementioned applications are incorporated herein.

TECHNICAL FIELD

The present application relates to the field of pharmaceuticals, and in particular to adenosine A3 receptor agonists, and their preparation methods and uses thereof.

BACKGROUND OF THE INVENTION

Adenosine is an endogenous substance and an important functional regulator of local tissues. Adenosine is ubiquitous throughout the body and released by almost all types of cells. In addition, adenosine may also be directly produced in extracellular spaces by ATP breakdown through a series of extracellular enzymes, mainly including ectonucleotide triphosphate diphosphohydrolase-1 (CD39) and extracellular-5'-nucleotidase (CD73). Generally speaking, under unfavorable metabolic conditions, the adenosine concentration increases. For example, hypoxia may lead to increased ATP breakdown and increased adenosine production. The local concentration of adenosine also increases during inflammation due to massive ATP degradation and it exerts an anti-inflammatory effect by binding to adenosine receptors (AR). Since adenosine is unstable, it usually acts only in the local area of its production by binding with an adenosine receptor.

The adenosine A3 receptor (A3AR or A3R) is also known as ADORA3 and is a subtype of the AR family. The adenosine receptor family also comprises 3 other subtypes, namely, the adenosine A1 receptor (A1R), adenosine A2A receptor (A2AR), and adenosine A2B receptor (A2BR). Each adenosine receptor is encoded by a separate gene and has different physiological properties [Wangjunli et al, Medical Recapitulate, 2008, 14 (12), 3585-3587]. The A3AR is primarily coupled to Gi. It is generally considered that A3AR is mainly involved in cellular regulation with two second messengers, cyclic adenosine monophosphate (cAMP) and calcium ion ($Ca^{2+}$). Through the adenylate cyclase (AC) pathway, after activated, the A3AR can decrease intracellular cAMP level by inhibiting the activity of adenylate cyclase and regulate cell growth and differentiation accordingly. Through the phospholipase C (PLC) pathway, after activated, the A3AR can further release calcium ions by activating phospholipase C. Then the calcium ion act as a second messenger to initiate various cell reactions and generate the corresponding biological effects.

At present, a number of studies have shown that A3AR can mediate various important biological mechanisms of action and is a potential target for the treatment of various pathological diseases. In particular, by activating the A3AR, an A3AR agonist may play a great therapeutic role in preventing or treating inflammation, cancer, ischemic injury, and pains, protecting nerves and myocardium, and treating eye diseases, etc.

In the aspect of myocardial protection, there is plenty of evidence indicating that A3AR may mediate beneficial anti-inflammatory effect during reperfusion and reduce the injury to myocardial tissues. The A3AR is activated at the initial stage of the reperfusion and may significantly reduce the myocardial infarction area by preventing apoptosis and necrosis, thereby obtaining the myocardial protective effect. According to the study of Xiong Hongyan et al [Xiong Hongyan et al, J. Chinese Journal of Extracorporeal Circulation, 2016, 14 (3), 172-176], the activated A3AR during the reperfusion injury process could upregulate the phosphorylation of proapoptotic protein (BAD), reduce the activity of caspase-3 and inhibit cell apoptosis, and thus exert the myocardial protective effect. The myocardial protective function of A3AR agonists may be used as adjuvant therapy in patients with myocardial infarction, or used to reduce reperfusion injury during cardiac surgery.

In the aspect of treating inflammation and autoimmune disease: the A3AR plays a crucial role in the immune regulation process of adenosine. The A3AR is widely expressed in immune cells and can effectively inhibit chemotaxis and oxidative burst of neutrophils. The A3AR is expressed at high density on eosinophils and mediates two important anti-inflammatory functions of the eosinophils, namely, inhibition of degranulation and inhibition of reactive oxygen production. The activation of A3AR further inhibits the release of tumor necrosis factor □ (TNF-α□) by human monocytes, inhibits TNF-α□-induced neutrophil degranulation, and regulates T cell function. Similarly, the A3AR may also have an anti-inflammatory effect by reducing fever and energy consumption. In many patients with autoimmune inflammations, such as patients with rheumatoid arthritis, Crohn's disease, psoriasis, etc., since A3AR is significantly upregulated in peripheral blood mononuclear cells (PBMCs) of the patients, the A3AR may also be a useful biomarker. After lymphocytes are obtained from patients with rheumatoid arthritis, the activation of the A3AR may reduce the NF-κB signal and decrease production of inflammatory cytokines and matrix metalloproteinases. After the colonic mucosal tissues are obtained with colonoscopy from patients with ulcerative colitis, the application of A3AR agonist can also inhibit the NF-κB signaling pathway and the expression of its downstream inflammatory factors in human colonic epithelial cells, and thus exert an anti-inflammatory effect [Ren Tianhua et al, International Journal of Digestive Diseases, 2018, 38 (6), 407-412]. In human lung tissue, the A3AR is mainly expressed in mast cells and eosinophils, and its activation by A3AR agonists can attenuate the inflammatory response. Therefore, A3AR agonists are potential novel drugs for the treatment of asthma. A3AR agonists may also have immuno-suppressive effects on inflammatory cells. Thus it is possible to use the mechanism to develop new drugs for treating rheumatoid arthritis. In line with this, in a rat arthritis model, A3AR agonists were indeed able to prevent cartilage injury, osteoclast/osteophyte generation, bone injury, and the formation of pannus and lymphocytic infiltration [Bar-Yehuda et al, Arthritis Rheum. 2009, 60: 3061-3071].

In the aspect of preventing cancer: studies have found that A3AR is over-expressed in cancer cells, but lowly expressed in normal cells [Gessi et al., Clin. Cancer Res. 2004, 210, 5895-5901; Madi et al., Clin. Cancer Res., 2004, 10, 4472-4479; Ochaion et al., Cell. Immunol. 2009, 258, 115-122]. Through agonistic interaction with A3AR on tumor cells, adenosine can directly play the anti-tumor function. The thyroid cancer, lung cancer, breast cancer, colon cancer, liver cancer, pancreatic cancer, prostate cancer, and kidney cancer are all treatable conditions. In addition, an up-regulation of the A3AR on colorectal and liver cancer cells is also directly reflected on PBMCs. Therefore, the expression level of A3AR on PBMCs can also be a useful tumor marker. The anti-cancer mechanism of A3AR agonists may include: 1) inhibiting the telomerase activity and arresting cells in G0/G1 phase; 2) causing a PI3K-dependent phosphorylation of Akt, and in turn reducing basal phosphorylation levels of extracellular signal-regulated kinase 1/2; 3) downregulating Wnt and NF-κB signaling pathways; and 4) activating natural killer cells and inhibiting tumor development.

In the aspect of treating neuropathic pain: neuropathic pain is a considerable problem and causes great suffering to patients. Few drugs are currently available for treating neuropathic pain. A few limited therapeutic options (e.g., drugs involving opioids, epinephrine, and calcium channel modulators) have significant side effects, yet may not adequately relieve the pain. A study has found that A3AR agonists could block the signaling pathway of neuropathic pain (including the pain caused by chemotherapeutic drugs, bone cancer pain, and other types of pain). Experiment in an animal model suggest that this may be a promising new method for pain relief that not only prevents or reverses the pain caused by nerve injury, but does not cause tolerance or addiction like opioid drugs [Jacobson et al., Pain, 2020, 161: 1425-1441].

In the aspect of protecting nerve cells: a study has found that the activation of A3AR may protect the central nervous system, and can protect the brain and the retina from injury caused by ischemia, hypoxia or ischemia reperfusion, and A3AR is a very potential target for treating various central nervous system diseases. For example, both in-vivo and in-vitro experiments have shown that the activation of A3AR can dilate cerebral blood vessels, inhibit adhesion and infiltration of inflammatory cells, and inhibit platelet aggregation, thereby reducing vascular endothelial injury caused by inflammatory cells. The activation of A3AR can also inhibit the generation of oxygen free radicals and nitric oxide, reduce brain damage, improve cerebral blood flow, and prevent neurons from anoxic depolarization, while reduce energy consumption in nerve cells and exert neuroprotective effects at the same time. The activation of A3AR can further prevent retinal neurodegeneration and stimulate neurite growth of retinal ganglion cells. Like many retinal neurodegenerative diseases, since the death of retinal nerve cells, particularly retinal ganglion cells, is a significant disease feature, A3AR agonists are potential drugs for treating glaucoma, diabetic retinopathy, and other retinal neurodegenerative diseases.

In the aspect of treating respiratory diseases: a study has found that in a series of respiratory diseases, A3AR has a very high expression level in lung tissues. A3AR agonists can decrease pulmonary arterial pressure and increase pulmonary oxygenation at the same time. In a study of ischemia-reperfusion injury of lungs by Mulloy et al. [Mulloy et al., Ann. Thorac. Surg., 2013, 95(5), 1762-7], A3AR agonists can significantly reduce inflammation and improve lung function in mice by reducing the activation, chemotaxis, and infiltration of neutrophils. A3AR agonists are expected to have great therapeutic use in treating respiratory diseases such as pneumonia and respiratory dysfunction.

In the aspect of treating non-alcoholic fatty liver disease and non-alcoholic steatohepatitis: a study has found that A3AR agonists can exert therapeutic effect on nonalcoholic fatty liver disease (NAFLD) and nonalcoholic steatohepatitis (NASH) by three mechanisms. The three mechanisms are the anti-fat effect, anti-inflammation effect, and anti-fibrosis effect respectively. At the molecular level, the upstream of Wnt/β-catenin and NF-κB pathways is controlled by PI3K. The activation of A3AR can inhibit the activity of PI3K, which is reflected in that the activation of A3AR can reduce the protein expression level of α-SMA (α-SMA is controlled by the PI3K, and its expression level can be used as a biomarker of hepatic fibrosis). In hepatic stellate cells, the Wnt/β-catenin pathway is involved in the pathogenesis of hepatic fibrosis and steatosis, and plays a prominent role in the process of hepatic steatosis, inflammation, and fibrosis. Therefore, A3AR agonists are potential effective drugs for treating NAFLD/NASH.

In view of the great potential of A3AR agonists for therapeutic treatment, there is an urgent need for compounds with improved selectivity, pharmacokinetics, and pharmacologic effect than existing A3AR agonists. This will maximize the value of this type of drugs for disease treatment.

Content of the Invention

The present application provides a series of novel compounds that have modulating or activating effect on the activity of A3AR, preparation methods for the series of compounds, pharmaceutical compositions of the series of compounds, and pharmaceutical uses of the series of compounds. The series of compounds may be used as highly effective A3AR agonists, and have various pharmacological effects on preventing tumor and inflammation, pain alleviation, neuroprotection, myocardium protection, eye disease treatment, and anti-infection, etc. The methods for synthesizing the compounds of the present application are mild, easy to run, and suitable for industrial large-scale production.

In one aspect, the present application provides a compound of formula I,

Formula I

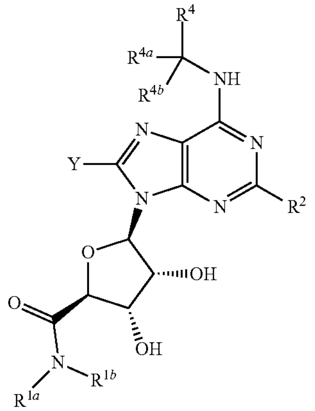

or a pharmaceutically acceptable salt thereof, wherein $R^{1a}$ and $R^{1b}$ may each be independently selected from hydrogen and the following groups that are optionally substituted: $C_1$-$C_{10}$ alkyl, $C_1$-$C_{10}$ alkoxy, $C_1$-$C_{10}$ aminoalkyl, $C_2$-$C_{10}$ alkenyl, $C_2$-$C_{10}$ alkynyl, $C_3$-$C_{10}$ cycloalkyl, $C_3$-$C_{10}$ heterocycloalkyl, bridged-ring, heterobridged-ring, spiro or heterospiro; or $R^{1a}$ and $R^{1b}$ may join to form $C_3$-$C_{10}$ heterocyclyl, heterobridged-ring, and heterospiro;

$R^2$ may be selected from hydrogen, halogen, and the following groups that are optionally substituted: $C_1$-$C_{10}$ alkyl, $C_1$-$C_{10}$ alkoxy, $C_1$-$C_{10}$ aminoalkyl, $C_2$-$C_{10}$ alkenyl, $C_2$-$C_{10}$ alkynyl, 5-8 membered aryl, 5-8 membered heteroaryl, fused-ring, $C_3$-$C_{10}$ cycloalkyl, $C_3$-$C_{10}$ heterocycloalkyl, bridged-ring, heterobridged-ring, spiro, and heterospiro;

$R^4$ may be selected from hydrogen, deuterium, halogen, hydroxyl, and the following groups that are optionally substituted: $C_1$-$C_{10}$ alkyl, $C_1$-$C_{10}$ alkoxy, $C_1$-$C_{10}$ aminoalkyl, $C_3$-$C_{10}$ cycloalkyl, $C_3$-$C_{10}$ heterocycloalkyl, aryl, heteroaryl, fused-ring, $C_1$-$C_{10}$ alkyl-aryl, $C_1$-$C_{10}$ alkyl-heteroaryl, and $C_1$-$C_{10}$ alkyl-fused-ring;

$R^{4a}$ and $R^{4b}$ may each be independently selected from hydrogen, deuterium, halogen, hydroxyl, amino, and the following groups that are optionally substituted: $C_1$-$C_{10}$ alkyl, $C_1$-$C_{10}$ aminoalkyl, $C_3$-$C_{10}$ cycloalkyl, and $C_3$-$C_{10}$ heterocycloalkyl; or $R^{4a}$ and $R^{4b}$ may join to form $C_3$-$C_{10}$ cycloalkyl, $C_3$-$C_{10}$ heterocyclyl, heterobridged-ring, and heterospiro; and Y may be selected from hydrogen, deuterium, halogen, amino, hydroxyl, cyano, and the following groups that are optionally substituted: $C_1$-$C_{10}$ alkyl, $C_1$-$C_{10}$ alkoxy, and $C_1$-$C_{10}$ aminoalkyl.

In some embodiments, the compound of formula I is a compound of formula II:

Formula II

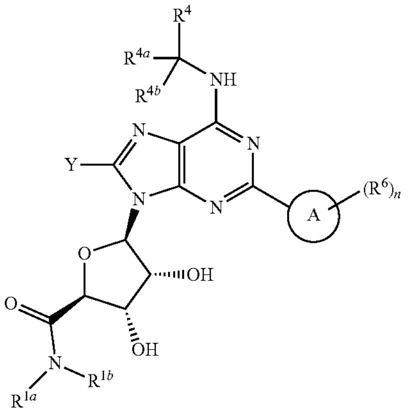

or a pharmaceutically acceptable salt thereof, wherein ring A may be 5-8 membered aryl, 5-8 membered heteroaryl, and fused-ring;

$R^{1a}$ and $R^{1b}$ may each be independently selected from hydrogen and the following groups that are optionally substituted: $C_1$-$C_{10}$ alkyl, $C_1$-$C_{10}$ alkoxy, $C_1$-$C_{10}$ aminoalkyl, $C_2$-$C_{10}$ alkenyl, $C_2$-$C_{10}$ alkynyl, $C_3$-$C_{10}$ cycloalkyl, $C_3$-$C_{10}$ heterocycloalkyl, bridged-ring, heterobridged-ring, spiro or heterospiro; or $R^{1a}$ and $R^{1b}$ may join to form $C_3$-$C_{10}$ heterocyclyl, heterobridged-ring, and heterospiro;

$R^4$ may be selected from hydrogen, deuterium, halogen, hydroxyl, and the following groups that are optionally substituted: $C_1$-$C_{10}$ alkyl, $C_1$-$C_{10}$ alkoxy, $C_1$-$C_{10}$ aminoalkyl, $C_3$-$C_{10}$ cycloalkyl, $C_3$-$C_{10}$ heterocycloalkyl, aryl, heteroaryl, fused-ring, $C_1$-$C_{10}$ alkyl-aryl, $C_1$-$C_{10}$ alkyl-heteroaryl, and $C_1$-$C_{10}$ alkyl-fused-ring;

$R^{4a}$ and $R^{4b}$ may each be independently selected from hydrogen, deuterium, halogen, hydroxyl, amino, and the following groups that are optionally substituted: $C_1$-$C_{10}$ alkyl, $C_1$-$C_{10}$ aminoalkyl, $C_3$-$C_{10}$ cycloalkyl, and $C_3$-$C_{10}$ heterocycloalkyl; or $R^{4a}$ and $R^{4b}$ may join to form $C_3$-$C_{10}$ cycloalkyl, $C_3$-$C_{10}$ heterocyclyl, heterobridged-ring, and heterospiro; and $R^6$ may be selected from amino, halogen, nitro, hydroxyl, —S(O)R, $S(O)_2NHR$, —C(O)R, —C(O)OR, —OC(O)R, —OC(O)OR, acetyl, cyano, acylamino, sulfonyl, aminocarbonyl, aminosulfonyl, phosphoryl, and the following groups that are optionally substituted: $C_1$-$C_{10}$ alkyl, $C_1$-$C_{10}$ alkoxy, $C_1$-$C_{10}$ aminoalkyl, $C_3$-$C_{10}$ cycloalkyl, $C_3$-$C_{10}$ heterocyclylalkyl, 5-10 membered aryl, 5-10 membered heteroaryl, $C_2$-$C_{10}$ alkenyl, and $C_2$-$C_{10}$ alkynyl, and n is any integer from 0 to 9, for example, n may be 0, 1, 2, 3, 4, 5, 6, 7, 8 or 9; and Y may be selected from hydrogen, deuterium, halogen, amino, hydroxyl, cyano, and the following groups that are optionally substituted: $C_1$-$C_{10}$ alkyl, $C_1$-$C_{10}$ alkoxy, and $C_1$-$C_{10}$ aminoalkyl.

For example, $R^{1a}$ and Y are hydrogen. The compound of formula I may have a structure shown in Formula II-A:

Formula II-A

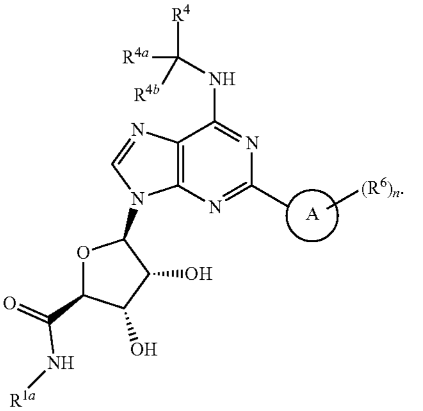

In some embodiments, ring A may be selected from the following structures:

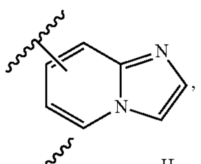,
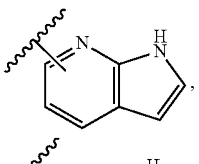,
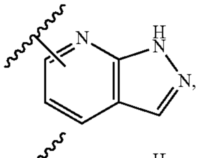,
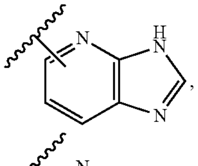,
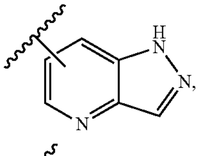,
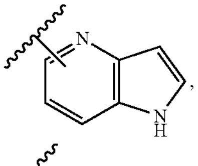,
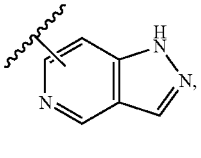,
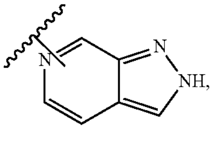, -continued
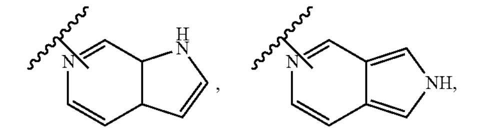,
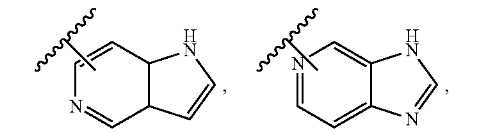,
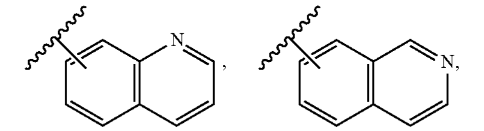,
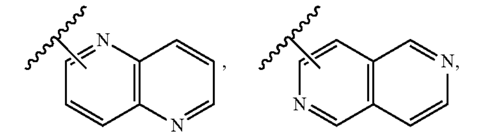,
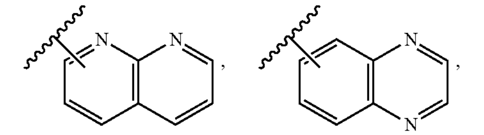,
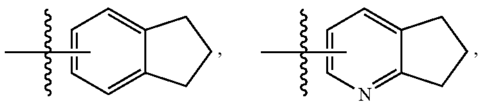,
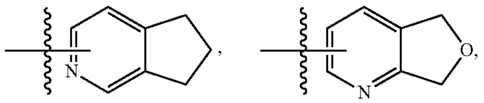,
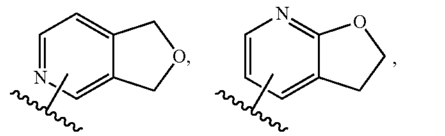,
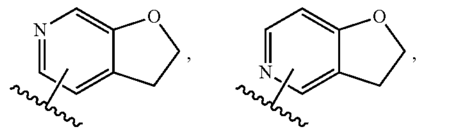,
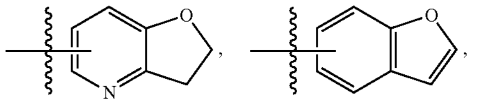,
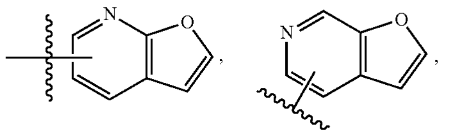,
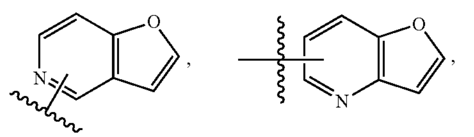,
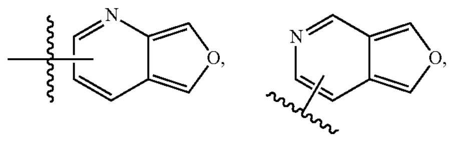,
-continued
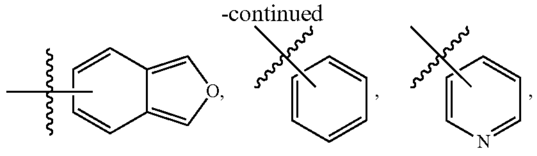,
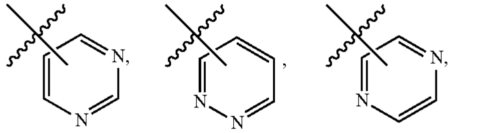,
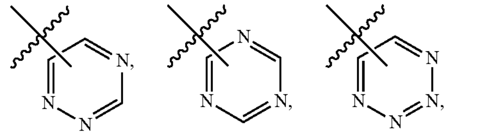,
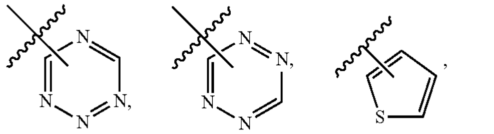,
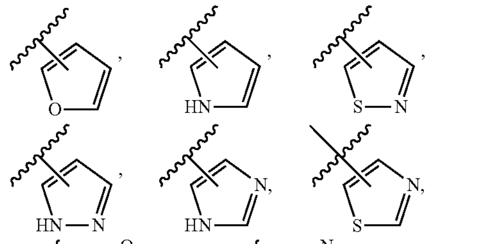,
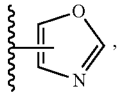
and
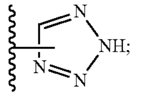;
and the structures may each be substituted by one or more $R^6$ at any position.
In some embodiments, $R^4$ may be selected from:
H, deuterium, halogen, $CD_3$, $CH_3$, $CF_3$, $CH_3O$, $CF_3O$, $CH_3CH_2$, $CH_3CH_2O$, $CH_3CH_2CH_2$, $CF_3CH_2$, $CF_3CH_2O$ or the following structures:
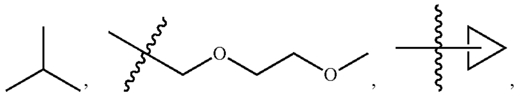,
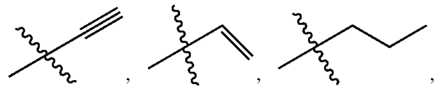,
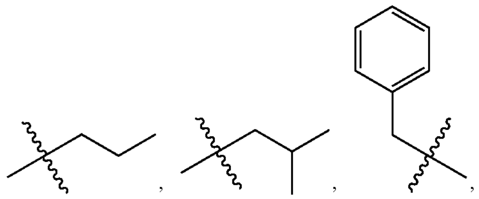,
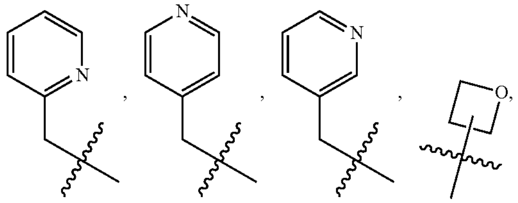, -continued

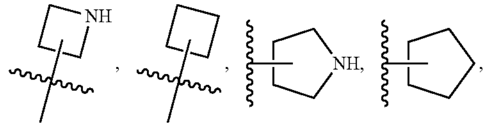

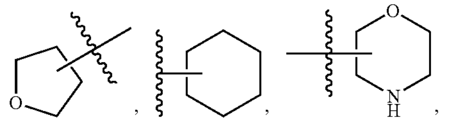

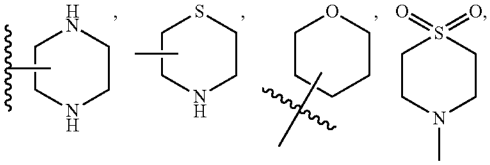

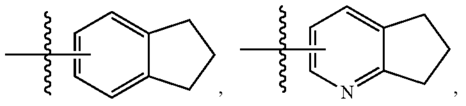

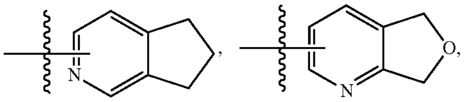

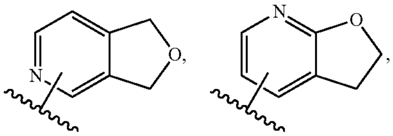

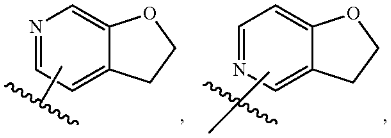

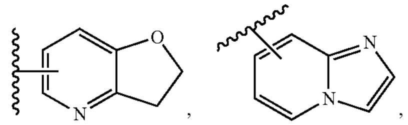

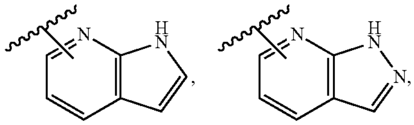

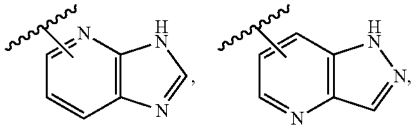

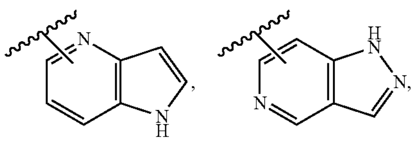

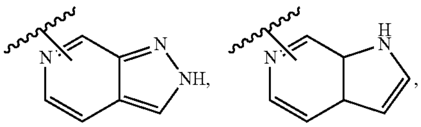

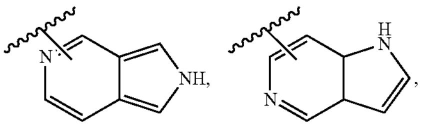

-continued

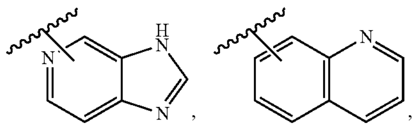

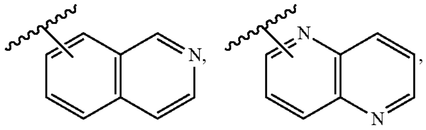

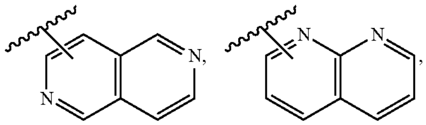

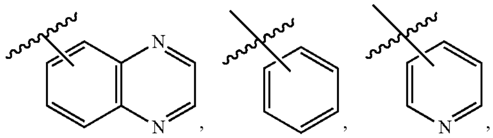

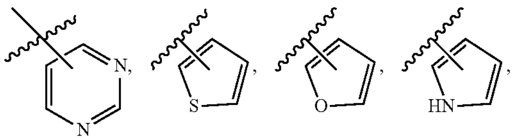

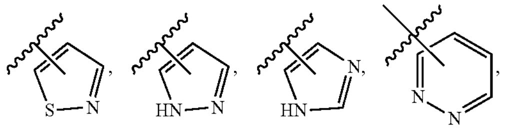

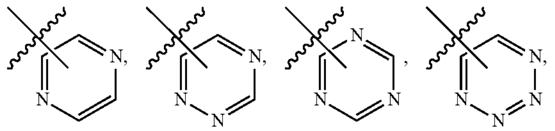

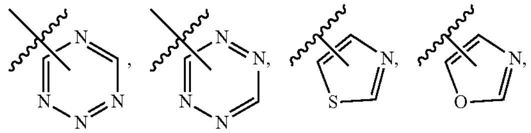

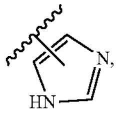 and 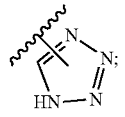

and the structures may be optionally substituted.

In some embodiments, $R^{4a}$ and $R^{4b}$ may be independently selected from, but not limited to the following groups or structures:

hydrogen, deuterium, halogen, vinyl, isopropyl, —$CD_3$, —$CH_3$, —$CF_3$, $CH_3O$—, $CF_3O$—, $CH_3CH_2$—, $CH_3CH_2O$—, $CH_3CH_2CH_2$—, $CF_3CH_2$—, $CF_3CH_2O$—, or $R^{4a}$ and $R^{4b}$ are joint to form the following structures:

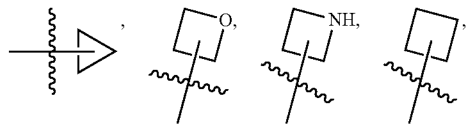

-continued

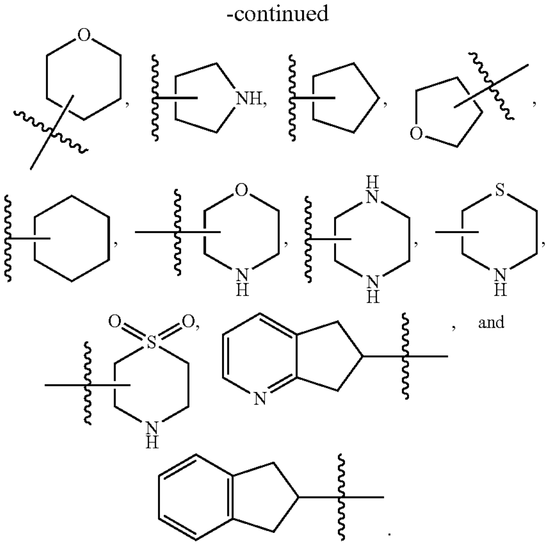

, and

In some embodiments, the compound of formula II may be a compound of formula VIII or a compound of formula IX:

Formula VIII

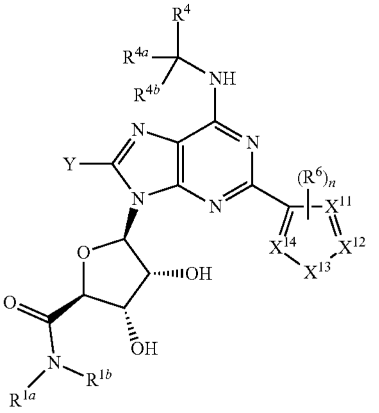

or

Formula IX

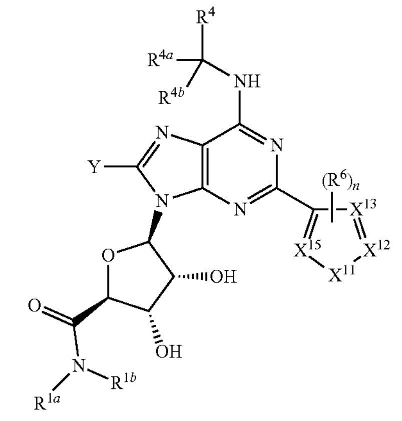

or a pharmaceutically acceptable salt thereof, wherein $X^{11}$, $X^{12}$, $X^{14}$, and $X^{15}$ may each be independently CH or N, and $X^{13}$ is independently N, O, or S;

$R^{1a}$ and $R^{1b}$ may each be independently selected from hydrogen and the following groups that are optionally substituted: $C_1$-$C_{10}$ alkyl, $C_1$-$C_{10}$ alkoxy, $C_1$-$C_{10}$ aminoalkyl, $C_2$-$C_{10}$ alkenyl, $C_2$-$C_{10}$ alkynyl, $C_3$-$C_{10}$ cycloalkyl, $C_3$-$C_{10}$ heterocycloalkyl, bridged-ring, heterobridged-ring, spiro or heterospiro; or $R^{1a}$ and $R^{1b}$ are joint to form $C_3$-$C_{10}$ heterocyclyl, heterobridged-ring, and heterospiro;

$R^{4a}$ and $R^{4b}$ may each be independently selected from hydrogen, deuterium, halogen, hydroxyl, amino, and the following groups that are optionally substituted: $C_1$-$C_{10}$ alkyl, $C_1$-$C_{10}$ aminoalkyl, $C_3$-$C_{10}$ cycloalkyl, and $C_3$-$C_{10}$ heterocycloalkyl; or $R^{4a}$ and $R^{4b}$ are joint to form $C_3$-$C_{10}$ cycloalkyl, $C_3$-$C_{10}$ heterocyclyl, heterobridged-ring, and heterospiro;

$R^6$ may be selected from amino, halogen, nitro, hydroxyl, —S(O)R, $S(O)_2NHR$, —C(O)R, —C(O)OR, —OC(O)R, —OC(O)OR, acetyl, cyano, acylamino, sulfonyl, aminocarbonyl, aminosulfonyl, phosphoryl, and the following groups that are optionally substituted: $C_1$-$C_{10}$ alkyl, $C_1$-$C_{10}$ alkoxy, $C_1$-$C_{10}$ aminoalkyl, $C_3$-$C_{10}$ cycloalkyl, $C_3$-$C_{10}$ heterocyclylalkyl, 5-10 membered aryl, 5-10 membered heteroaryl, $C_2$-$C_{10}$ alkenyl, and $C_2$-$C_{10}$ alkynyl, and n is any integer from 0 to 4; and Y may be selected from hydrogen, deuterium, halogen, amino, hydroxyl, cyano, and the following groups that are optionally substituted: $C_1$-$C_{10}$ alkyl, $C_1$-$C_{10}$ alkoxy, and $C_1$-$C_{10}$ aminoalkyl.

In some embodiments, the compound of formula II is a compound of formula III:

Formula III

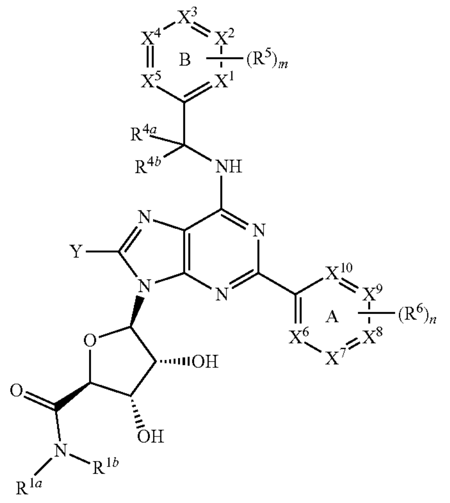

or a pharmaceutically acceptable salt thereof, wherein $X^1$, $X^2$, $X^3$, $X^4$, $X^5$, $X^6$, $X^7$, $X^8$, $X^9$, and $X^{10}$ may each be independently CH or N;

$R^{1a}$ and $R^{1b}$ may each be independently selected from hydrogen and the following groups that are optionally substituted: $C_1$-$C_{10}$ alkyl, $C_1$-$C_{10}$ alkoxy, $C_1$-$C_{10}$ aminoalkyl, $C_2$-$C_{10}$ alkenyl, $C_2$-$C_{10}$ alkynyl, $C_3$-$C_{10}$ cycloalkyl, $C_3$-$C_{10}$ heterocycloalkyl, bridged-ring, heterobridged-ring, spiro or heterospiro; or $R^{1a}$ and $R^{1b}$ may join to form $C_3$-$C_{10}$ heterocyclyl, heterobridged-ring, and heterospiro;

$R^{4a}$ and $R^{4b}$ may each be independently selected from hydrogen, deuterium, halogen, hydroxyl, amino, and the following groups that are optionally substituted: $C_1$-$C_{10}$ alkyl, $C_1$-$C_{10}$ aminoalkyl, $C_3$-$C_{10}$ cycloalkyl, and $C_3$-$C_{10}$ heterocycloalkyl; or $R^{4a}$ and $R^{4b}$ may join to form $C_3$-$C_{10}$ cycloalkyl, $C_3$-$C_{10}$ heterocyclyl, heterobridged-ring, and heterospiro; and $R^5$ and $R^6$ may each be independently selected from amino, halogen, nitro, hydroxyl, —S(O)R, $S(O)_2NHR$, —C(O)R, —C(O)OR, —OC(O)R, —OC(O)OR, acetyl, cyano, acylamino, sulfonyl, aminocarbonyl, aminosulfonyl, phosphoryl, and the following groups that are optionally substituted: $C_1$-$C_{10}$ alkyl, $C_1$-$C_{10}$ alkoxy, $C_1$-$C_{10}$ aminoalkyl, $C_3$-$C_{10}$ cycloalkyl, $C_3$-$C_{10}$ heterocyclylalkyl, 5-10 membered aryl, 5-10 membered heteroaryl, $C_2$-$C_{10}$ alkenyl, and $C_2$-$C_{10}$ alkynyl, and m and n are each independently any integer from 0 to 5; and Y may be selected from hydrogen, deuterium, halogen, amino, hydroxyl, cyano, and the following groups that are optionally substituted: $C_1$-$C_{10}$ alkyl, $C_1$-$C_{10}$ alkoxy, and $C_1$-$C_{10}$ aminoalkyl.

In some embodiments, ring A in the compound of formula III is selected from the following structures:

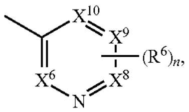 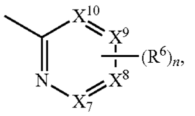

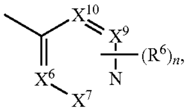 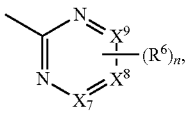

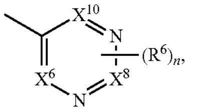 and 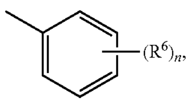

wherein $X^6$, $X^7$, $X^8$, $X^9$, and $X^{10}$ are each independently CH or N, n is any integer from 0 to 5.

In some embodiments, ring B in the compound of formula III is selected from the following structures:

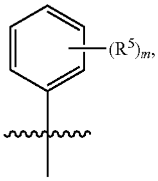 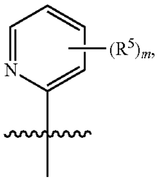 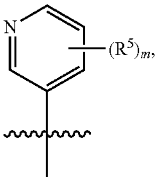

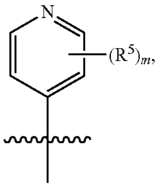 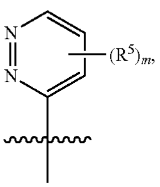 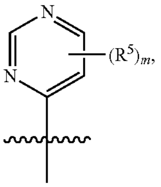

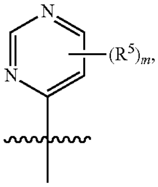 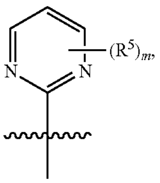 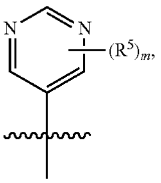

-continued

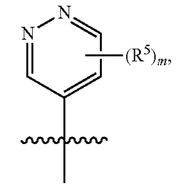 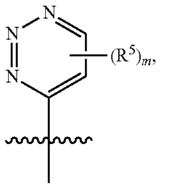 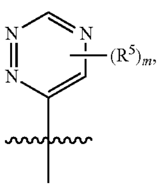

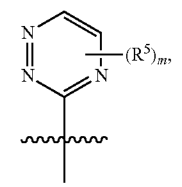 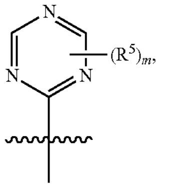 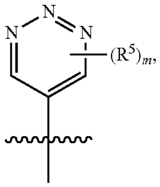

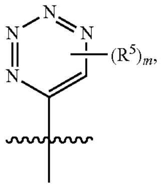 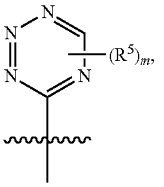 and 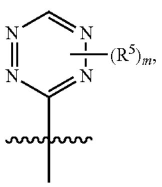

wherein m is any integer from 0 to 5.

For example, the compound of formula III may be selected from the following structures:

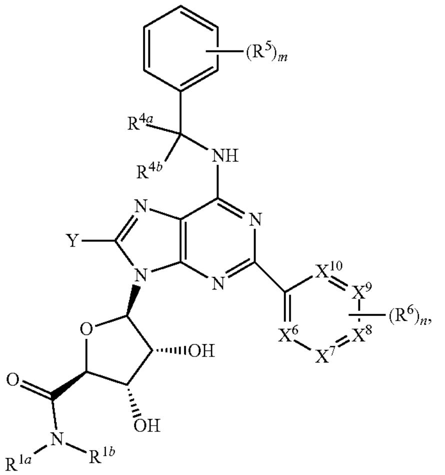

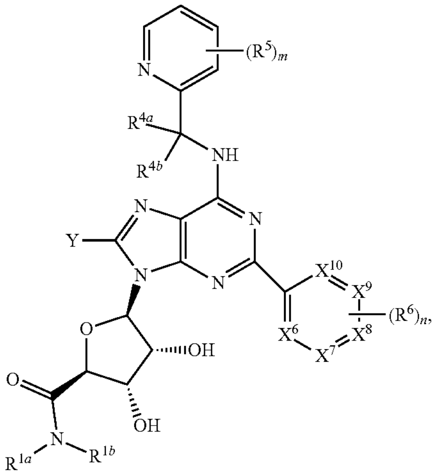

-continued
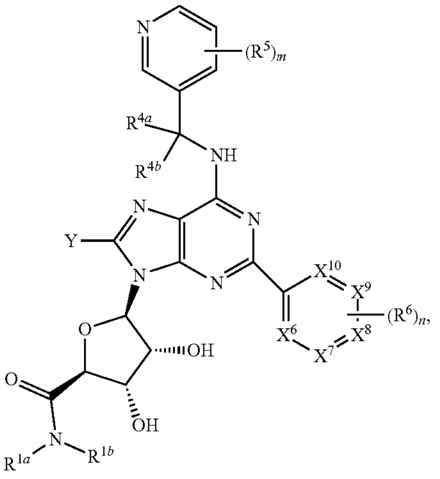
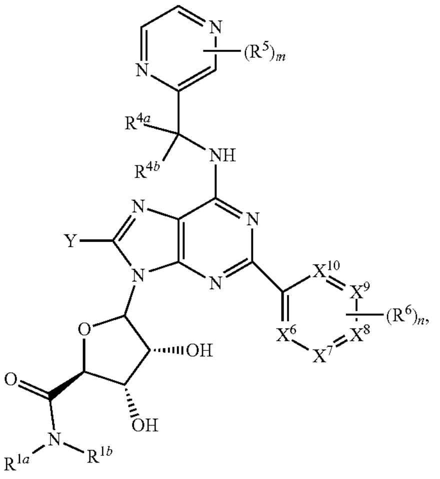
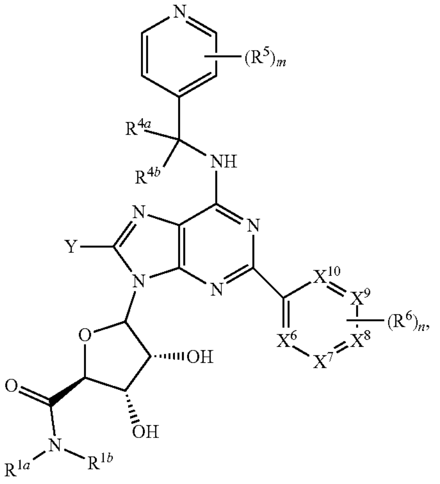
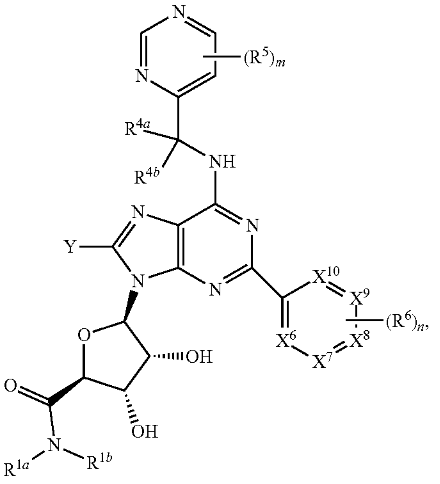
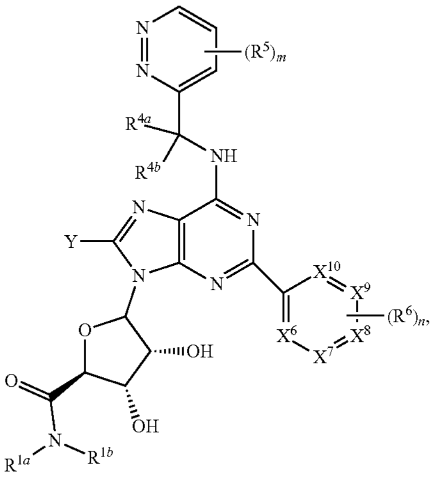
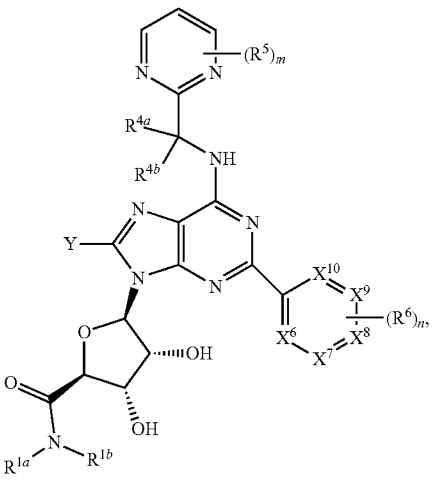

-continued
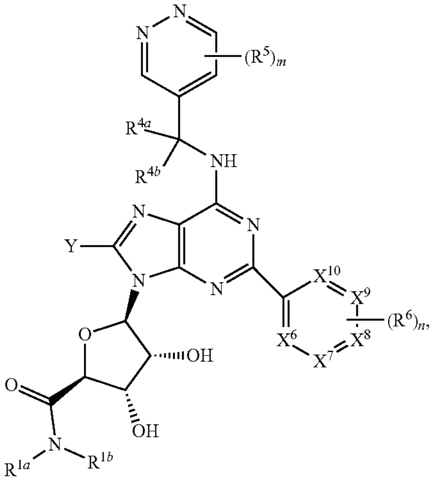
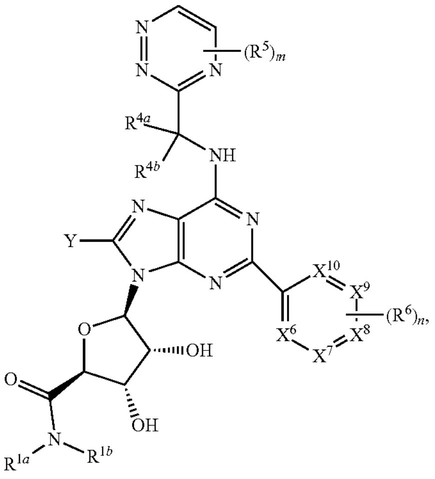
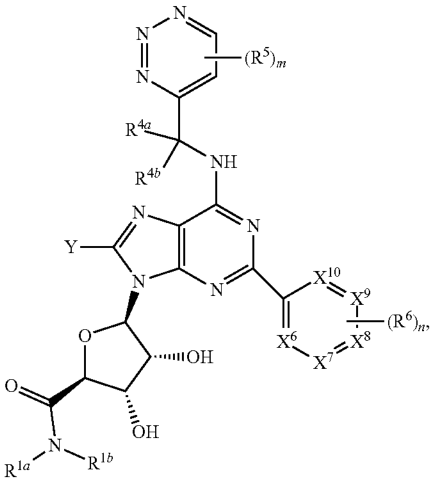
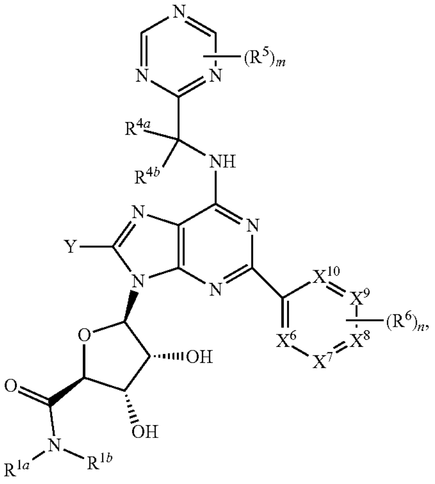
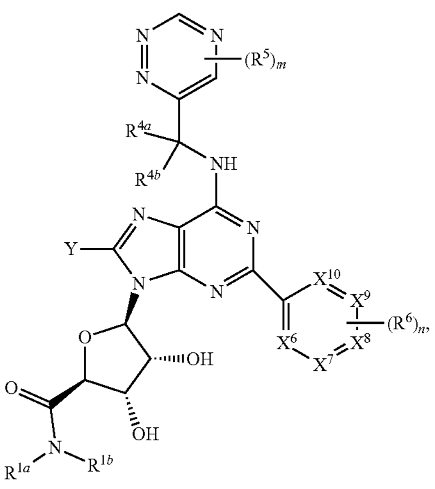
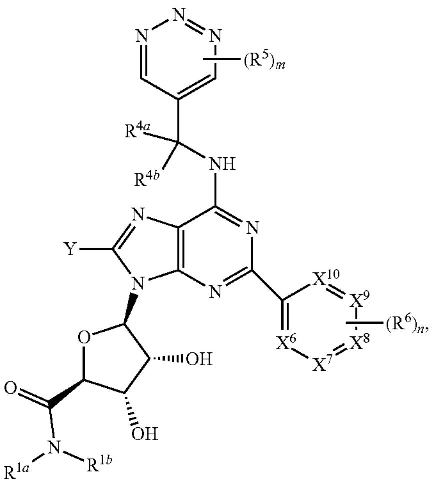
-continued -continued
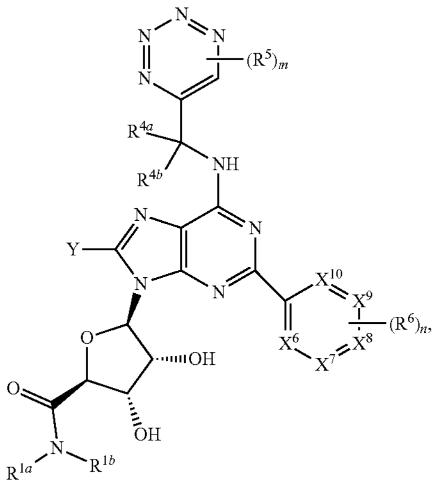
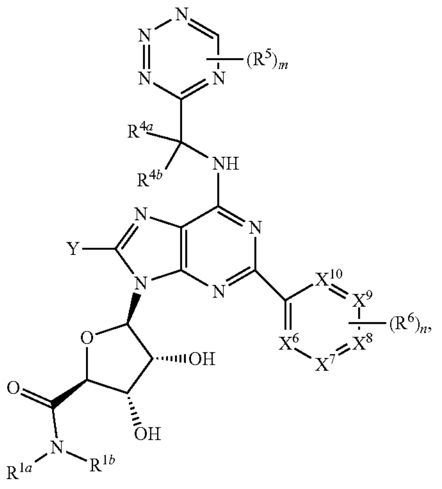
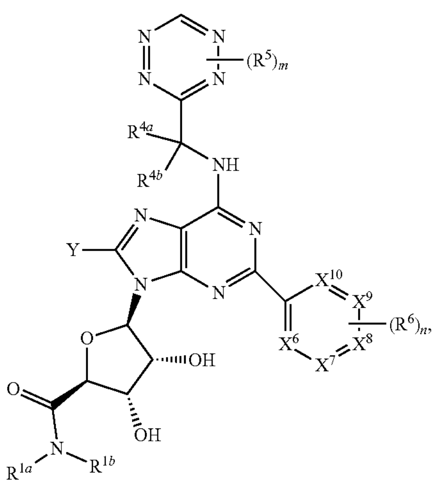
-continued
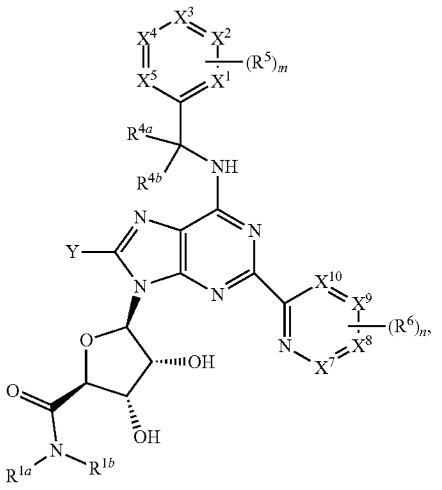
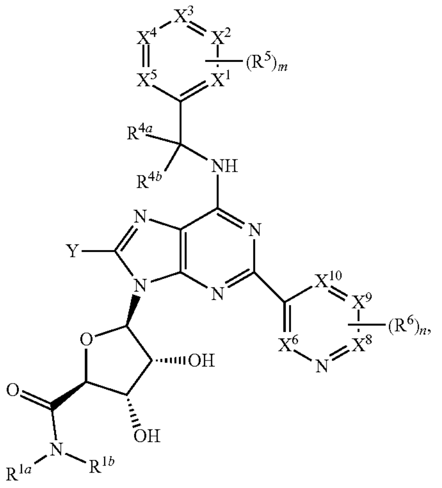
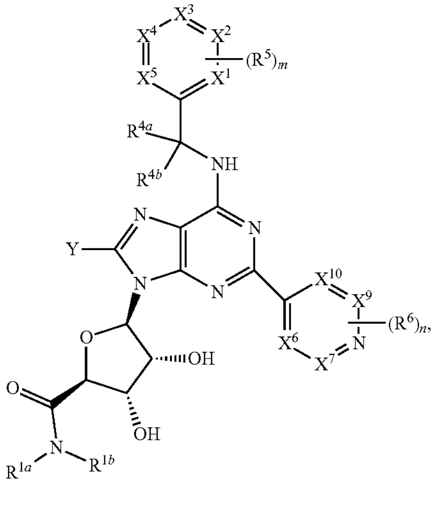

-continued

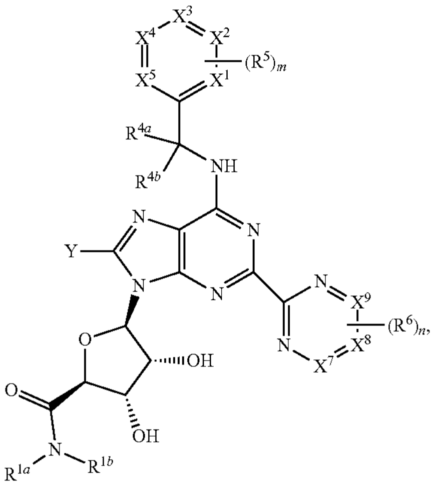

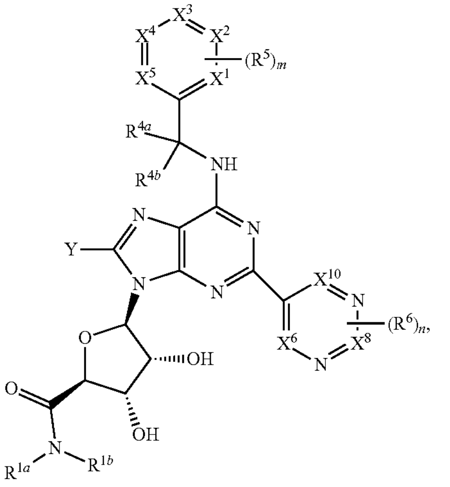

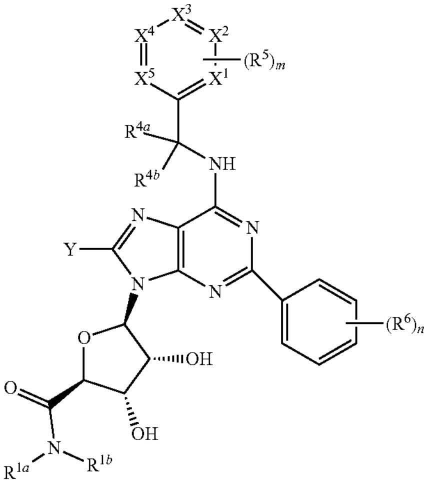

and

-continued

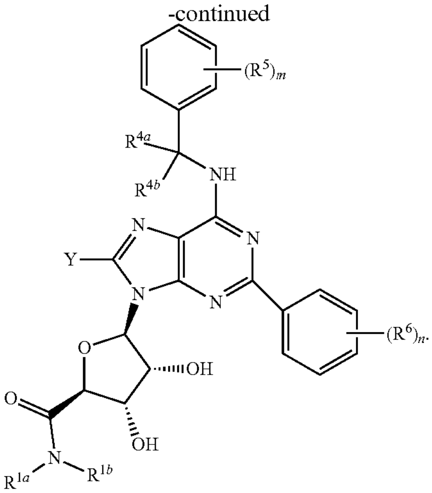

In some embodiments, $R^{4a}$ and $R^{4b}$ may each be independently further selected from the following groups: H, deuterium, F, $—CD_3$, $—CH_3$, $—CF_3$, $CH_3O—$, $CF_3O—$, $CH_3CH_2—$, $CH_3CH_2O—$, $CH_3CH_2CH_2—$, $CF_3CH_2—$, and $CF_3CH_2O—$. For example, $R^{4a}$ and $R^{4b}$ may be H.

In some embodiments, the compound of formula III is a compound of formula IV:

Formula IV

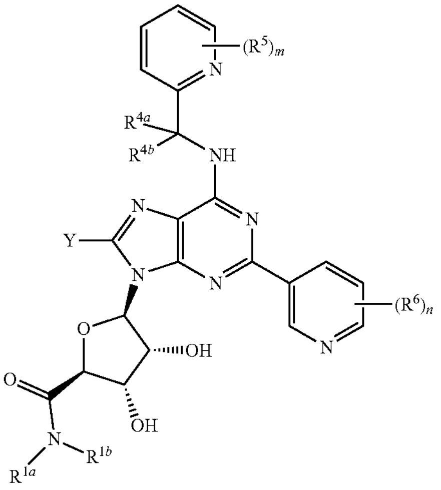

or a pharmaceutically acceptable salt thereof, wherein $R^{1a}$ and $R^{1b}$ may each be independently selected from hydrogen and the following groups that are optionally substituted: $C_1$-$C_{10}$ alkyl, $C_1$-$C_{10}$ alkoxy, $C_1$-$C_{10}$ aminoalkyl, $C_2$-$C_{10}$ alkenyl, $C_2$-$C_{10}$ alkynyl, $C_3$-$C_{10}$ cycloalkyl, $C_3$-$C_{10}$ heterocycloalkyl, bridged-ring, heterobridged-ring, spiro or heterospiro; or $R^{1a}$ and $R^{1b}$ may join to form $C_3$-$C_{10}$ heterocyclyl, heterobridged-ring, and heterospiro;

$R^{4a}$ and $R^{4b}$ may each be independently selected from hydrogen, deuterium, halogen, hydroxyl, amino, and the following groups that are optionally substituted: $C_1$-$C_{10}$ alkyl, $C_1$-$C_{10}$ aminoalkyl, $C_3$-$C_{10}$ cycloalkyl, and $C_3$-$C_{10}$ heterocycloalkyl; or $R^{4a}$ and $R^{4b}$ may join to form $C_3$-$C_{10}$ cycloalkyl, $C_3$-$C_{10}$ heterocyclyl, heterobridged-ring, and heterospiro; and $R^5$ and $R^6$ may each be independently selected from amino, halogen, nitro, hydroxyl, —S(O)R, $S(O)_2NHR$, —C(O)R, —C(O)OR, —OC(O)R, —OC(O)OR, acetyl, cyano, acylamino, sulfonyl, aminocarbonyl, aminosulfonyl, phosphoryl, and the following groups that are optionally substituted: $C_1$-$C_{10}$ alkyl, $C_1$-$C_{10}$ alkoxy, $C_1$-$C_{10}$ aminoalkyl, $C_3$-$C_{10}$ cycloalkyl, $C_3$-$C_{10}$ heterocyclylalkyl, 5-10 membered aryl, 5-10 membered heteroaryl, $C_2$-$C_{10}$ alkenyl, and $C_2$-$C_{10}$ alkynyl, and m and n are each independently any integer from 0 to 4; and Y may be selected from hydrogen, deuterium, halogen, amino, hydroxyl, cyano, and the following groups that are optionally substituted: $C_1$-$C_{10}$ alkyl, $C_1$-$C_{10}$ alkoxy, and $C_1$-$C_{10}$ aminoalkyl.

For example, $R^{1b}$, $R^{4a}$, $R^{4b}$, and Y may all be H. The compound of formula IV may be a structure of formula IV-A:

Formula IV-A

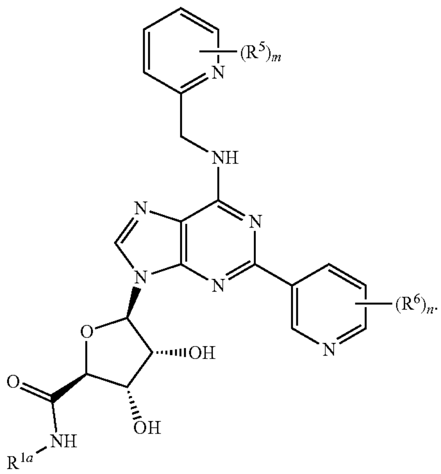

In some embodiments, the compound of formula IV is a compound of formula VI:

Formula VI

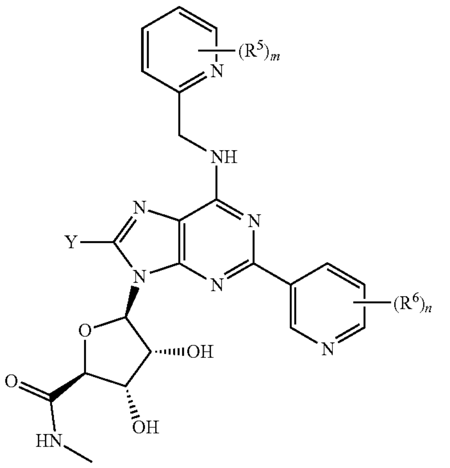

or a pharmaceutically acceptable salt thereof, wherein $R^5$ and $R^6$ may each be independently selected from amino, halogen, nitro, hydroxyl, —S(O)R, $S(O)_2NHR$, —C(O)R, —C(O)OR, —OC(O)R, —OC(O)OR, acetyl, cyano, acylamino, sulfonyl, aminocarbonyl, aminosulfonyl, phosphoryl, and the following groups that are optionally substituted: $C_1$-$C_{10}$ alkyl, $C_1$-$C_{10}$ alkoxy, $C_1$-$C_{10}$ aminoalkyl, $C_3$-$C_{10}$ cycloalkyl, $C_3$-$C_{10}$ heterocyclylalkyl, 5-10 membered aryl, 5-10 membered heteroaryl, $C_2$-$C_{10}$ alkenyl, and $C_2$-$C_{10}$ alkynyl, and m and n are each independently any integer from 0 to 4; and Y may be selected from hydrogen, deuterium, halogen, amino, hydroxyl, cyano, and the following groups that are optionally substituted: $C_1$-$C_{10}$ alkyl, $C_1$-$C_{10}$ alkoxy, and $C_1$-$C_{10}$ aminoalkyl.

In some embodiments, the compound of formula III is a compound of formula V:

Formula V

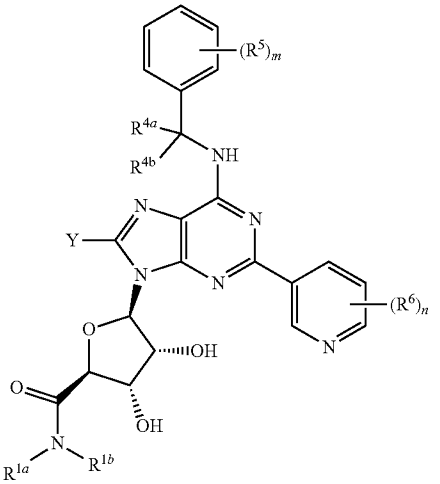

or a pharmaceutically acceptable salt thereof, wherein $R^{1a}$ and $R^{1b}$ may each be independently selected from hydrogen and the following groups that are optionally substituted: $C_1$-$C_{10}$ alkyl, $C_1$-$C_{10}$ alkoxy, $C_1$-$C_{10}$ aminoalkyl, $C_2$-$C_{10}$ alkenyl, $C_2$-$C_{10}$ alkynyl, $C_3$-$C_{10}$ cycloalkyl, $C_3$-$C_{10}$ heterocycloalkyl, bridged-ring, heterobridged-ring, spiro or heterospiro; or $R^{1a}$ and $R^{1b}$ may join to form $C_3$-$C_{10}$ heterocyclyl, heterobridged-ring, and heterospiro;

$R^{4a}$ and $R^{4b}$ may each be independently selected from hydrogen, deuterium, halogen, hydroxyl, amino, and the following groups that are optionally substituted: $C_1$-$C_{10}$ alkyl, $C_1$-$C_{10}$ aminoalkyl, $C_3$-$C_{10}$ cycloalkyl, and $C_3$-$C_{10}$ heterocycloalkyl; or $R^{4a}$ and $R^{4b}$ may join to form $C_3$-$C_{10}$ cycloalkyl, $C_3$-$C_{10}$ heterocyclyl, heterobridged-ring, and heterospiro; and $R^5$ and $R^6$ may each be independently selected from amino, halogen, nitro, hydroxyl, —S(O)R, $S(O)_2NHR$, —C(O)R, —C(O)OR, —OC(O)R, —OC(O)OR, acetyl, cyano, acylamino, sulfonyl, aminocarbonyl, aminosulfonyl, phosphoryl, and the following groups that are optionally substituted: $C_1$-$C_{10}$ alkyl, $C_1$-$C_{10}$ alkoxy, $C_1$-$C_{10}$ aminoalkyl, $C_3$-$C_{10}$ cycloalkyl, $C_3$-$C_{10}$ heterocyclylalkyl, 5-10 membered aryl, 5-10 membered heteroaryl, $C_2$-$C_{10}$ alkenyl, and $C_2$-$C_{10}$ alkynyl, and m and n may each independently be any integer from 0 to 4; and Y may be selected from hydrogen, deuterium, halogen, amino, hydroxyl, cyano, and the following groups that are optionally substituted: $C_1$-$C_{10}$ alkyl, $C_1$-$C_{10}$ alkoxy, and $C_1$-$C_{10}$ aminoalkyl.

In some embodiments, $R^{4a}$ and $R^{4b}$ may each independently be hydrogen, deuterium, halogen, hydroxyl, amino, or the following groups that are optionally substituted: $C_1$-$C_{10}$ alkyl, $C_1$-$C_{10}$ halogenated alkyl, and $C_1$-$C_{10}$ aminoalkyl. For example, $R^{4a}$ and $R^{4b}$ may both be H.

In some embodiments, Y may be hydrogen or halogen.

For example, $R^{11}$, $R^{4a}$, $R^{4b}$, and Y may all be H. The compound of formula V may be a structure of formula V-A:

Formula V-A

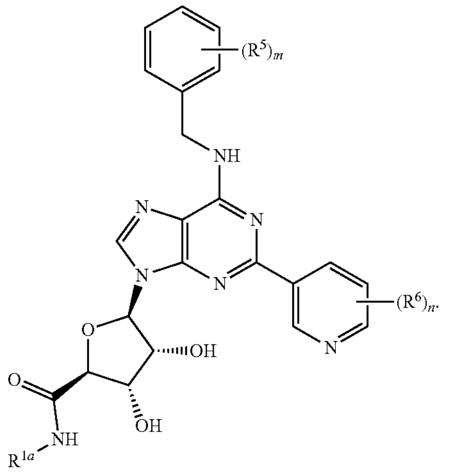

In some embodiments, the compound of formula V is a compound of formula VII:

Formula VII

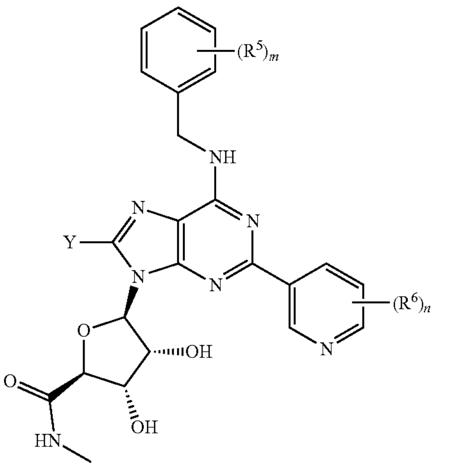

or a pharmaceutically acceptable salt thereof, wherein $R^5$ and $R^6$ may each be independently selected from amino, halogen, nitro, hydroxyl, —S(O)R, $S(O)_2NHR$, —C(O)R, —C(O)OR, —OC(O)R, —OC(O)OR, acetyl, cyano, acylamino, sulfonyl, aminocarbonyl, aminosulfonyl, phosphoryl, and the following groups that are optionally substituted: $C_1$-$C_{10}$ alkyl, $C_1$-$C_{10}$ alkoxy, $C_1$-$C_{10}$ aminoalkyl, $C_3$-$C_{10}$ cycloalkyl, $C_3$-$C_{10}$ heterocyclylalkyl, 5-10 membered aryl, 5-10 membered heteroaryl, $C_2$-$C_{10}$ alkenyl, and $C_2$-$C_{10}$ alkynyl, and n is any integer from 0 to 4; and Y may be selected from hydrogen, deuterium, halogen, amino, hydroxyl, cyano, and the following groups that are optionally substituted: $C_1$-$C_{10}$ alkyl, $C_1$-$C_{10}$ alkoxy, and $C_1$-$C_{10}$ aminoalkyl.

In some embodiments, in the compound of formula I, the optionally substituted groups comprise substituted or unsubstituted groups, and substituents of the optionally substituted groups comprise deuterium, halogen, —CN, =O, =N—OH, =N—OR, =N—R, OR, —C(O)R, —C(O)OR, —OC(O)R, —OC(O)OR, —C(O)NHR, —C(O)$NR_2$, —OC(O)NHR, —OC(O)$NR_2$, —SR—, —S(O)R, —$S(O)_2R$, —NHR, —$N(R)_2$, —NHC(O)R, —NRC(O)R, —NHC(O)OR, —NRC(O)OR, $S(O)_2NHR$, —$S(O)_2N(R)_2$, —$NHS(O)_2NR_2$, —$NRS(O)_2NR_2$, —$NHS(O)_2R_2$, —$NRS(O)_2R$, $C_1$-$C_8$ alkyl, $C_1$-$C_8$ alkoxy, aryl, heteroaryl, cycloalkyl, heterocycloalkyl, $C_1$-$C_8$ alkyl substituted by halogen, and $C_1$-$C_8$ alkoxy substituted by halogen, wherein each R is independently selected from hydrogen, deuterium, halogen, $C_1$-$C_8$ alkyl, $C_1$-$C_8$ alkoxy, aryl, heteroaryl, cycloalkyl, heterocycloalkyl, $C_1$-$C_8$ alkyl substituted by halogen, and $C_1$-$C_8$ alkoxy substituted by halogen.

In some embodiments, the compound of formula I comprises the following compounds or pharmaceutically acceptable salts thereof:

| Compd. No. | Structural formula of compound | Compound name |
|---|---|---|
| 1 | 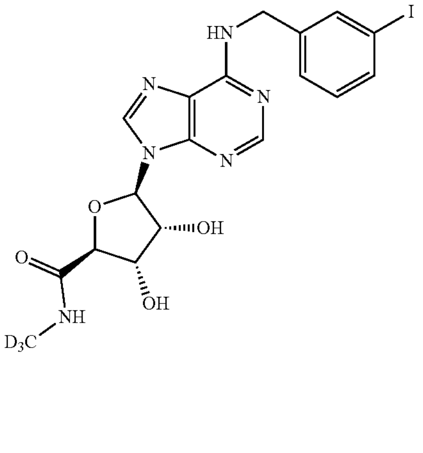 | (2S,3S,4R,5R)-5-(6-(3-iodobenzylamino)-9H-purin-9-yl)-3,4-dihydroxyl-N-(methyl-d3)-tetrahydrofuran-2-formamide |

-continued

| Compd. No. | Structural formula of compound | Compound name |
| --- | --- | --- |
| 2 | 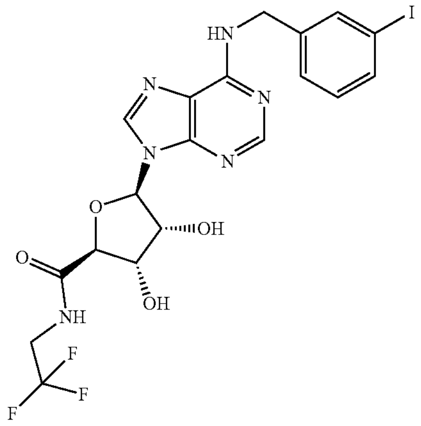 [SMILES: O=C(NCC(F)(F)F)[C@H]1O[C@@H](n2cnc3c(NCc4cccc(I)c4)ncnc32)[C@H](O)[C@@H]1O] | (2S,3S,4R,5R)-5-(6-(3-iodophenylamino)-9H-purin-9-yl)-3,4-dihydroxyl-N-(2,2,2-trifluoroethyl)-tetrahydrofuran-2-formamide |
| 3 | 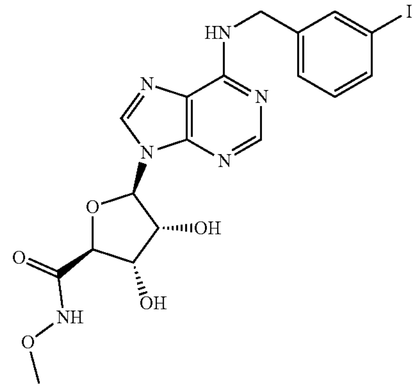 [SMILES: CONC(=O)[C@H]1O[C@@H](n2cnc3c(NCc4cccc(I)c4)ncnc32)[C@H](O)[C@@H]1O] | (2S,3S,4R,5R)-5-(6-(3-iodobenzylamino)-9H-purin-9-yl)-3,4-dihydroxyl-N-methoxy-tetrahydrofuran-2-formamide |
| 4 | 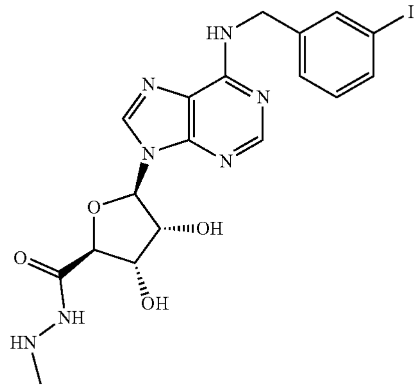 [SMILES: CNNC(=O)[C@H]1O[C@@H](n2cnc3c(NCc4cccc(I)c4)ncnc32)[C@H](O)[C@@H]1O] | (2S,3S,4R,5R)-5-(6-(3-iodobenzylamino)-9H-purin-9-yl)-3,4-dihydroxyl-N'-methyl-tetrahydrofuran-2-carbohydrazide |
| 5 | 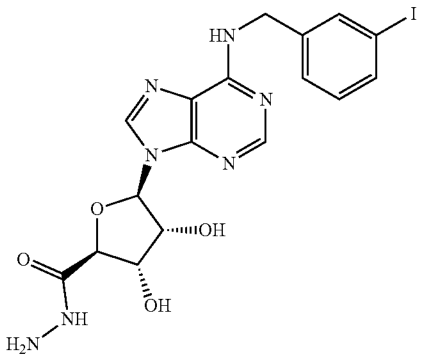 [SMILES: NNC(=O)[C@H]1O[C@@H](n2cnc3c(NCc4cccc(I)c4)ncnc32)[C@H](O)[C@@H]1O] | (2S,3S,4R,5R)-5-(6-(3-iodobenzylamino)-9H-purin-9-yl)-3,4-dihydroxyltetrahydrofuran-2-carbohydrazide |

-continued

| Compd. No. | Structural formula of compound | Compound name |
|---|---|---|
| 6 | 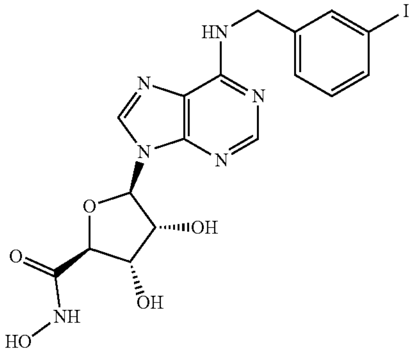 [SMILES: O=C(NO)[C@H]1O[C@@H](n2cnc3c(NCc4cccc(I)c4)ncnc32)[C@H](O)[C@@H]1O] | (2S,3S,4R,5R)-5-(6-(3-iodobenzylamino)-9H-purin-9-yl)-N,3,4-trihydroxyltetrahydrofuran-2-formamide |
| 7 | 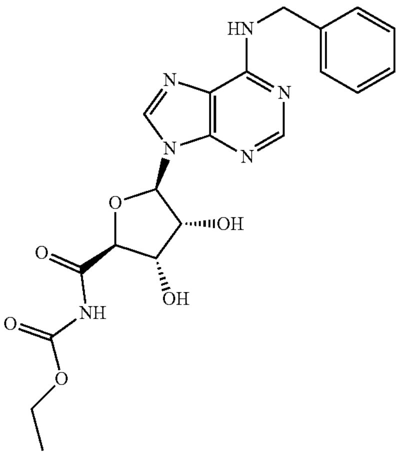 [SMILES: CCOC(=O)NC(=O)[C@H]1O[C@@H](n2cnc3c(NCc4ccccc4)ncnc32)[C@H](O)[C@@H]1O] | (2S,3S,4R,5R)-2-(6-(benzylamino)-9H-purin-9-yl)-3,4-dihydroxyltetrahydrofuran-5-carbonylaminoethyl formate |
| 8 | 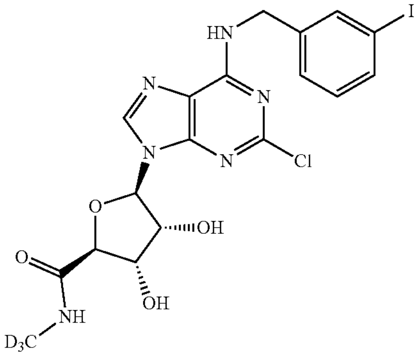 [SMILES: [2H]C([2H])([2H])NC(=O)[C@H]1O[C@@H](n2cnc3c(NCc4cccc(I)c4)nc(Cl)nc32)[C@H](O)[C@@H]1O] | (2S,3S,4R,5R)-5-(6-(3-iodobenzylamino)-2-chloro-9H-purin-9-yl)-3,4-dihydroxyl-N-(methyl-d3)-tetrahydrofuran-2-formamide |
| 9 | 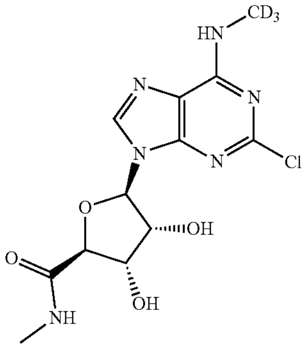 [SMILES: [2H]C([2H])([2H])Nc1nc(Cl)nc2c1ncn2[C@@H]1O[C@H](C(=O)NC)[C@@H](O)[C@H]1O] | (2S,3S,4R,5R)-5-(2-chloro-6-((methyl-d3)-amino)-9H-purin-9-yl)-3,4-dihydroxyl-N-methyl-tetrahydrofuran-2-formamide |

-continued

| Compd. No. | Structural formula of compound | Compound name |
| --- | --- | --- |
| 10 | 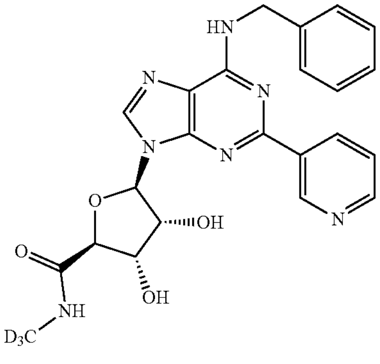 [SMILES: [2H]C([2H])([2H])NC(=O)[C@H]1O[C@@H](n2cnc3c(NCc4ccccc4)nc(-c4cccnc4)nc32)[C@H](O)[C@@H]1O] | (2S,3S,4R,5R)-5-(6-(benzylamino)-2-(pyridin-3-yl)-9H-purin-9-yl)-3,4-dihydroxyl-N-(methyl-d3)-tetrahydrofuran-2-formamide |
| 11 | 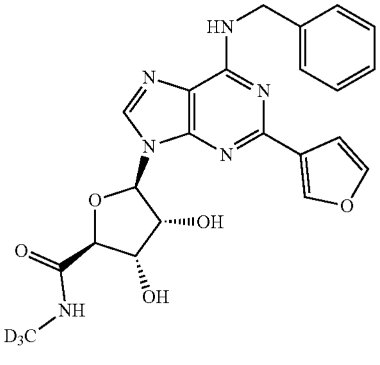 | (2S,3S,4R,5R)-5-(6-(benzylamino)-2-(furan-3-yl)-9H-purin-9-yl)-3,4-dihydroxyl-N-(methyl-d3)-tetrahydrofuran-2-formamide |
| 12 | 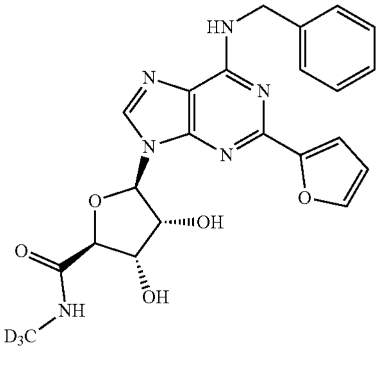 [SMILES: [2H]C([2H])([2H])NC(=O)[C@H]1O[C@@H](n2cnc3c(NCc4ccccc4)nc(-c4ccco4)nc32)[C@H](O)[C@@H]1O] | (2S,3S,4R,5R)-5-(6-(benzylamino)-2-(furan-2-yl)-9H-purin-9-yl)-3,4-dihydroxyl-N-(methyl-d3)-tetrahydrofuran-2-formamide |
| 13 | 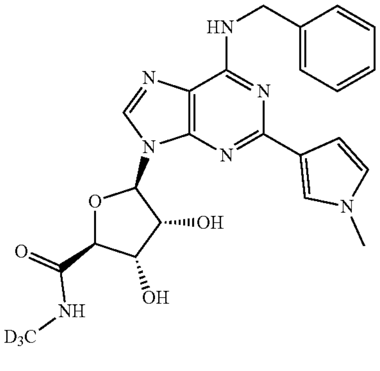 | (2S,3S,4R,5R)-5-(6-(benzylamino)-2-(1-methyl-1H-pyrrol-3-yl)-9H-purin-9-yl)-3,4-dihydroxyl-N-(methyl-d3)-tetrahydrofuran-2-formamide |

-continued

| Compd. No. | Structural formula of compound | Compound name |
|---|---|---|
| 14 | 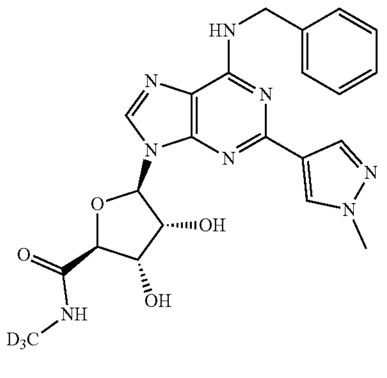 [SMILES: [2H]C([2H])([2H])NC(=O)[C@H]1O[C@@H](n2cnc3c(NCc4ccccc4)nc(-c4cnn(C)c4)nc32)[C@H](O)[C@@H]1O] | (2S,3S,4R,5R)-5-(6-(benzylamino)-2-(1-methyl-1H-pyrazolyl-4-yl)-9H-purin-9-yl)-3,4-dihydroxyl-N-(methyl-d3)-tetrahydrofuran-2-formamide |
| 15 | 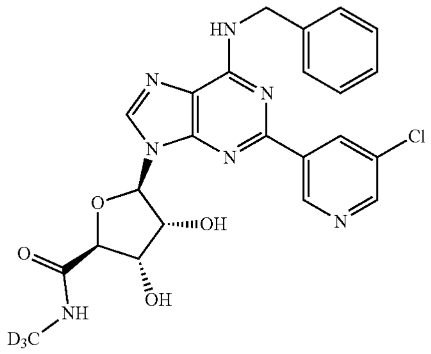 [SMILES: [2H]C([2H])([2H])NC(=O)[C@H]1O[C@@H](n2cnc3c(NCc4ccccc4)nc(-c4cncc(Cl)c4)nc32)[C@H](O)[C@@H]1O] | (2S,3S,4R,5R)-5-(6-(benzylamino)-2-(5-chloropyridin-3-yl)-9H-purin-9-yl)-3,4-dihydroxyl-N-(methyl-d3)-tetrahydrofuran-2-formamide |
| 16 | 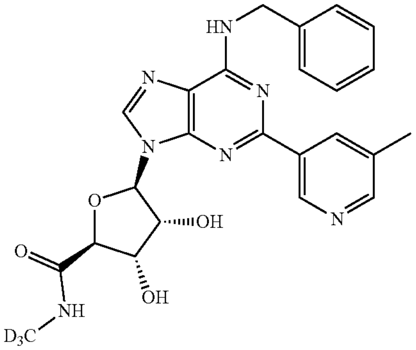 [SMILES: [2H]C([2H])([2H])NC(=O)[C@H]1O[C@@H](n2cnc3c(NCc4ccccc4)nc(-c4cncc(C)c4)nc32)[C@H](O)[C@@H]1O] | (2S,3S,4R,5R)-5-(6-(benzylamino)-2-(5-methylpyridin-3-yl)-9H-purin-9-yl)-3,4-dihydroxyl-N-(methyl-d3)-tetrahydrofuran-2-formamide |
| 17 | 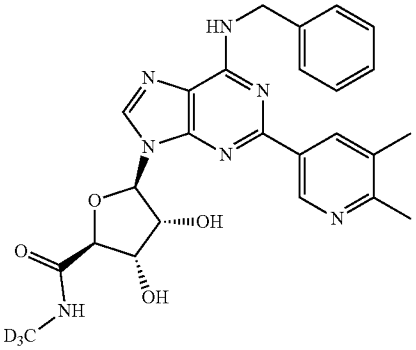 | (2S,3S,4R,5R)-5-(6-(benzylamino)-2-(5,6-dimethylpyridin-3-yl)-9H-purin-9-yl)-3,4-dihydroxyl-N-(methyl-d3)-tetrahydrofuran-2-formamide |

-continued

| Compd. No. | Structural formula of compound | Compound name |
|---|---|---|
| 18 | 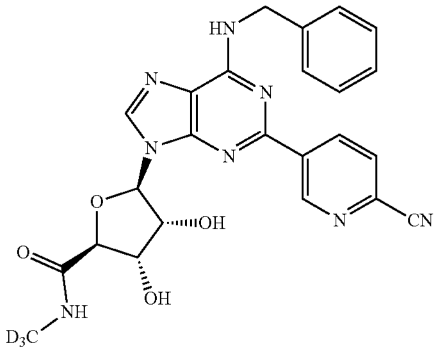 | (2S,3S,4R,5R)-5-(6-(benzylamino)-2-(6-cyanopyridin-3-yl)-9H-purin-9-yl)-3,4-dihydroxyl-N-(methyl-d3)-tetrahydrofuran-2-formamide |
| 19 | 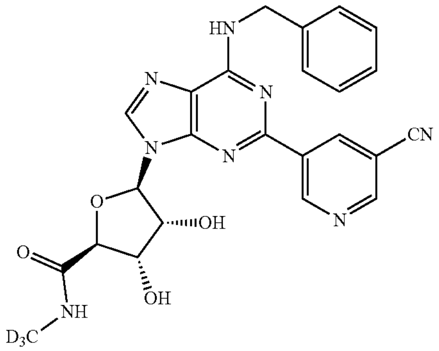 [SMILES: [2H]C([2H])([2H])NC(=O)[C@H]1O[C@@H](n2cnc3c(NCc4ccccc4)nc(-c4cncc(C#N)c4)nc32)[C@H](O)[C@@H]1O] | (2S,3S,4R,5R)-5-(6-(benzylamino)-2-(5-cyanopyridin-3-yl)-9H-purin-9-yl)-3,4-dihydroxyl-N-(methyl-d3)-tetrahydrofuran-2-formamide |
| 20 | 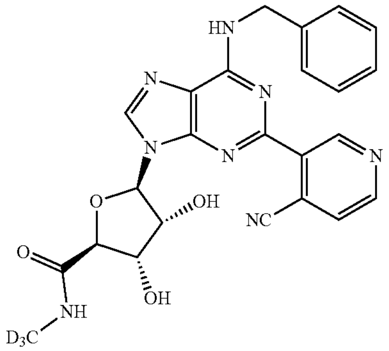 [SMILES: [2H]C([2H])([2H])NC(=O)[C@H]1O[C@@H](n2cnc3c(NCc4ccccc4)nc(-c4cnccc4C#N)nc32)[C@H](O)[C@@H]1O] | (2S,3S,4R,5R)-5-(6-(benzylamino)-2-(4-cyanopyridin-3-yl)-9H-purin-9-yl)-3,4-dihydroxyl-N-(methyl-d3)-tetrahydrofuran-2-formamide |
| 21 | 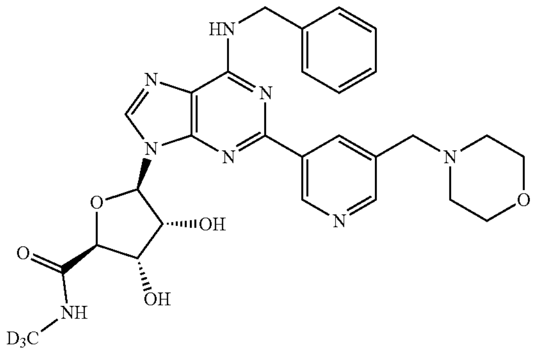 [SMILES: [2H]C([2H])([2H])NC(=O)[C@H]1O[C@@H](n2cnc3c(NCc4ccccc4)nc(-c4cncc(CN5CCOCC5)c4)nc32)[C@H](O)[C@@H]1O] | (2S,3S,4R,5R)-5-(6-(benzylamino)-2-(5-morpholinomethyl)pyridin-3-yl)-9H-purin-9-yl)-3,4-dihydroxyl-N-(methyl-d3)-tetrahydrofuran-2-formamide |

-continued

| Compd. No. | Structural formula of compound | Compound name |
|---|---|---|
| 22 | 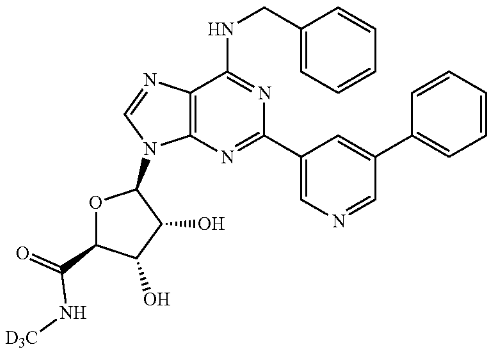 [SMILES: [2H]C([2H])([2H])NC(=O)[C@H]1O[C@@H](n2cnc3c(NCc4ccccc4)nc(-c4cncc(-c5ccccc5)c4)nc32)[C@H](O)[C@@H]1O] | (2S,3S,4R,5R)-5-(6-(benzylamino)-2-(5-phenylpyridin-3-yl)-9H-purin-9-yl)-3,4-dihydroxyl-N-(methyl-d3)-tetrahydrofuran-2-formamide |
| 23 | 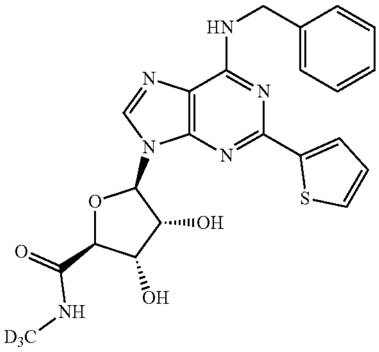 | (2S,3S,4R,5R)-5-(6-(benzylamino)-2-(thiophen-2-yl)-9H-purin-9-yl)-3,4-dihydroxyl-N-(methyl-d3)-tetrahydrofuran-2-formamide |
| 24 | 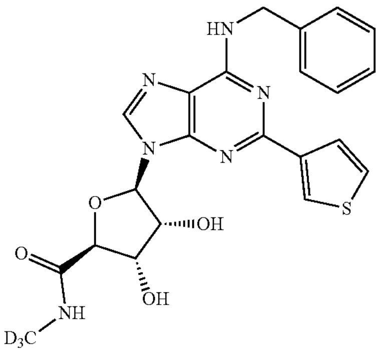 [SMILES: [2H]C([2H])([2H])NC(=O)[C@H]1O[C@@H](n2cnc3c(NCc4ccccc4)nc(-c4ccsc4)nc32)[C@H](O)[C@@H]1O] | (2S,3S,4R,5R)-5-(6-(benzylamino)-2-(thiophen-3-yl)-9H-purin-9-yl)-3,4-dihydroxyl-N-(methyl-d3)-tetrahydrofuran-2-formamide |
| 25 | 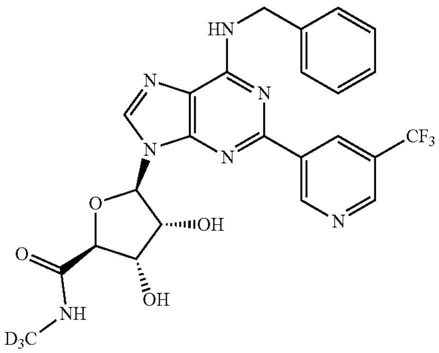 | (2S,3S,4R,5R)-5-(6-(benzylamino)-2-(5-trifluoromethyl)pyridin-3-yl)-9H-purin-9-yl)-3,4-dihydroxyl-N-(methyl-d3)-tetrahydrofuran-2-formamide |

-continued

| Compd. No. | Structural formula of compound | Compound name |
|---|---|---|
| 26 | 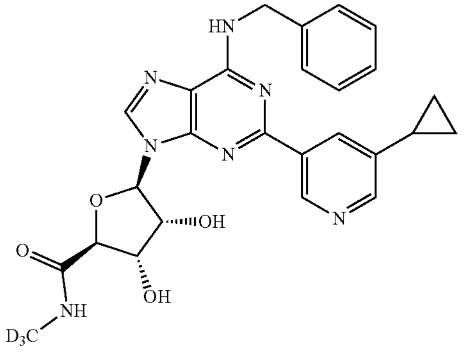 [SMILES: [2H]C([2H])([2H])NC(=O)[C@H]1O[C@@H](n2cnc3c(NCc4ccccc4)nc(-c4cncc(C5CC5)c4)nc32)[C@H](O)[C@@H]1O] | (2S,3S,4R,5R)-5-(6-(benzylamino)-2-(5-cyclopropylpyridin-3-yl)-9H-purin-9-yl)-3,4-dihydroxyl-N-methyl-3-tetrahydrofuran-2-formamide |
| 27 | 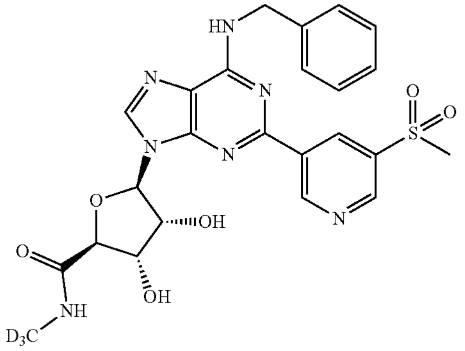 [SMILES: [2H]C([2H])([2H])NC(=O)[C@H]1O[C@@H](n2cnc3c(NCc4ccccc4)nc(-c4cncc(S(C)(=O)=O)c4)nc32)[C@H](O)[C@@H]1O] | (2S,3S,4R,5R)-5-(6-(benzylamino)-2-(5-(methylsulfo)pyridin-3-yl)-9H-purin-9-yl)-3,4-dihydroxyl-N-(methyl-d3)-tetrahydrofuran-2-formamide |
| 28 | 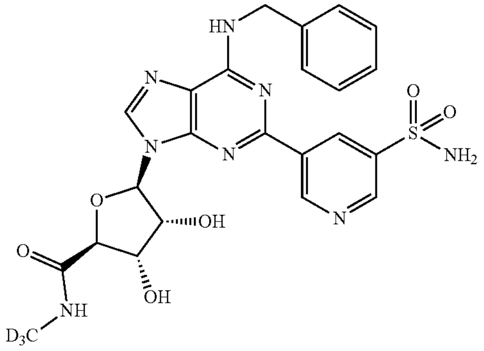 [SMILES: [2H]C([2H])([2H])NC(=O)[C@H]1O[C@@H](n2cnc3c(NCc4ccccc4)nc(-c4cncc(S(N)(=O)=O)c4)nc32)[C@H](O)[C@@H]1O] | (2S,3S,4R,5R)-5-(6-(benzylamino)-2-(5-(sulfamide)pyridin-3-yl)-9H-purin-9-yl)-3,4-dihydroxyl-N-(methyl-d3)-tetrahydrofuran-2-formamide |
| 29 | 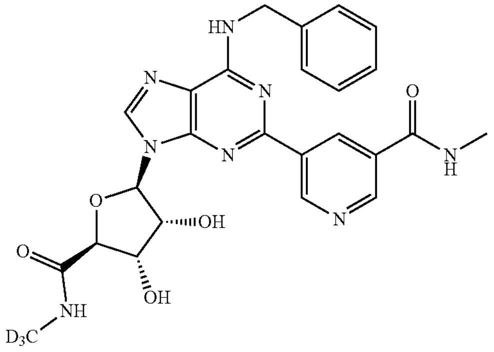 [SMILES: [2H]C([2H])([2H])NC(=O)[C@H]1O[C@@H](n2cnc3c(NCc4ccccc4)nc(-c4cncc(C(=O)NC)c4)nc32)[C@H](O)[C@@H]1O] | 5-(6-(benzylamino)-9-((2S,3S,4R,5R)-3,4-dihydroxyl-5-((methyl-d3)-aminobenzyl)-tetrahydrofuran-2-yl)-9H-purin-2-yl)-N-methylnicotinamide |

-continued

| Compd. No. | Structural formula of compound | Compound name |
|---|---|---|
| 30 | 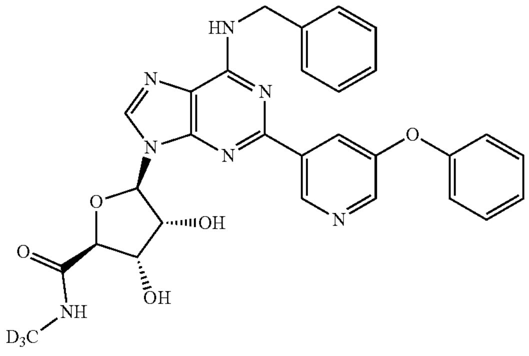 [SMILES: [2H]C([2H])([2H])NC(=O)[C@H]1O[C@@H](n2cnc3c(NCc4ccccc4)nc(-c4cncc(Oc5ccccc5)c4)nc32)[C@H](O)[C@@H]1O] | (2S,3S,4R,5R)-5-(6-(benzylamino)-2-(5-phenoxypyridin-3-yl)-9H-purin-9-yl)-3,4-dihydroxyl-N-(methyl-d3)-tetrahydrofuran-2-formamide |
| 31 | 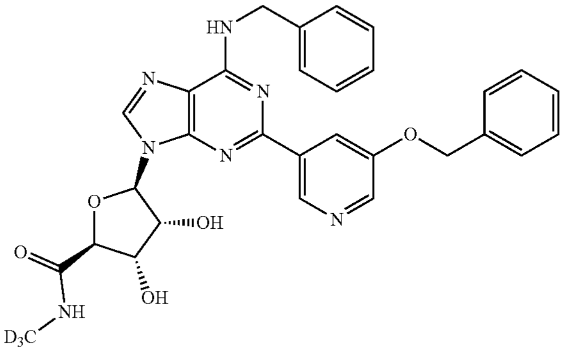 [SMILES: [2H]C([2H])([2H])NC(=O)[C@H]1O[C@@H](n2cnc3c(NCc4ccccc4)nc(-c4cncc(OCc5ccccc5)c4)nc32)[C@H](O)[C@@H]1O] | (2S,3S,4R,5R)-5-(6-(benzylamino)-2-(5-(benzyloxy)pyridin-3-yl)-9H-purin-9-yl)-3,4-dihydroxyl-N-(methyl-d3)-tetrahydrofuran-2-formamide |
| 32 | 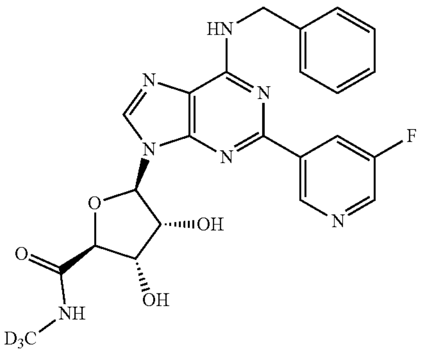 [SMILES: [2H]C([2H])([2H])NC(=O)[C@H]1O[C@@H](n2cnc3c(NCc4ccccc4)nc(-c4cncc(F)c4)nc32)[C@H](O)[C@@H]1O] | (2S,3S,4R,5R)-5-(6-(benzylamino)-2-(5-fluoropyridin-3-yl)-9/-purin-9-yl)-3,4-dihydroxyl-N-(methyl-d3)-tetrahydrofuran-2-formamide |
| 33 | 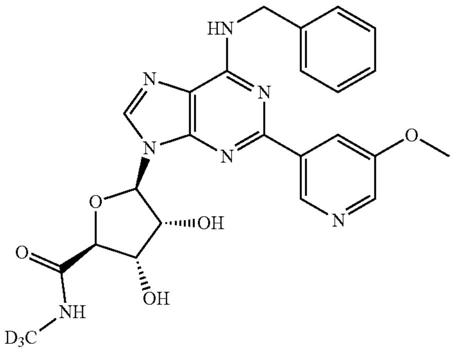 | (2S,3S,4R,5R)-5-(6-(benzylamino)-2-(5-methoxypyridin-3-yl)-9H-purin-9-yl)-3,4-dihydroxyl-N-(methyl-d3)-tetrahydrofuran-2-formamide |

-continued

| Compd. No. | Structural formula of compound | Compound name |
|---|---|---|
| 34 | 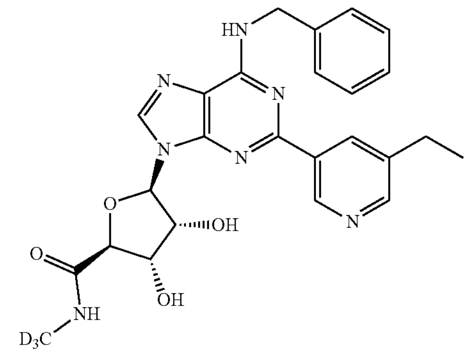 [SMILES: [2H]C([2H])([2H])NC(=O)[C@H]1O[C@@H](n2cnc3c(NCc4ccccc4)nc(-c4cncc(CC)c4)nc32)[C@H](O)[C@@H]1O] | (2S,3S,4R,5R)-5-(6-(benzylamino)-2-(5-ethylpyridin-3-yl)-9H-purin-9-yl)-3,4-dihydroxyl-N-(methyl-d3)-tetrahydrofuran-2-formamide; |
| 35 | 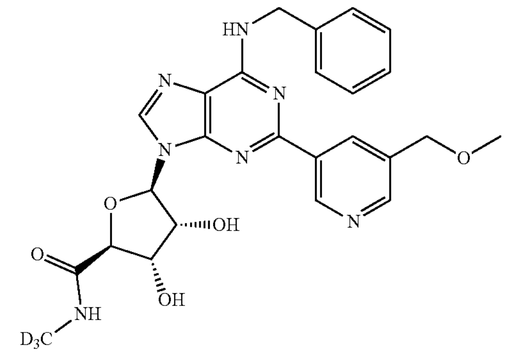 [SMILES: [2H]C([2H])([2H])NC(=O)[C@H]1O[C@@H](n2cnc3c(NCc4ccccc4)nc(-c4cncc(COC)c4)nc32)[C@H](O)[C@@H]1O] | (2S,3S,4R,5R)-5-(6-(benzylamino)-2-(5-(methoxymethyl)pyridin-3-yl)-9H-purin-9-yl)-3,4-dihydroxyl-N-(methyl-d3)-tetrahydrofuran-2-formamide |
| 36 | 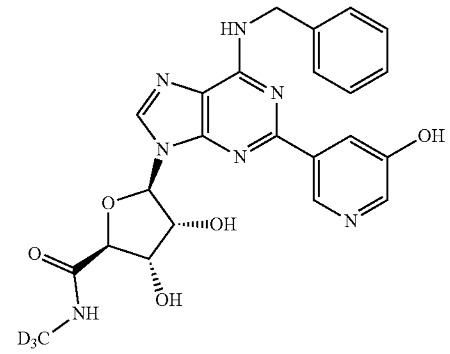 | (2S,3S,4R,5R)-5-(6-(benzylamino)-2-(5-hydroxylpyridin-3-yl)-9H-purin-9-yl)-3,4-dihydroxyl-N-(methyl-d3)-tetrahydrofuran-2-formamide |
| 37 | 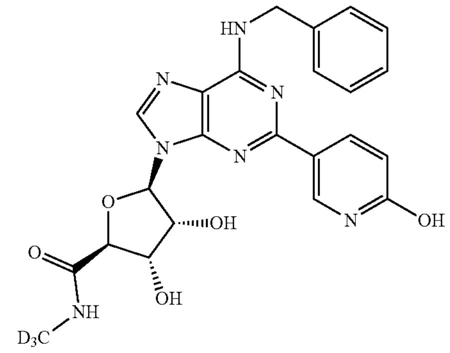 | (2S,3S,4R,5R)-5-(6-(benzylamino)-2-(6-hydroxylpyridin-3-yl)-9H-purin-9-yl)-3,4-dihydroxyl-N-(methyl-d3)-tetrahydrofuran-2-formamide |

-continued

| Compd. No. | Structural formula of compound | Compound name |
|---|---|---|
| 38 | 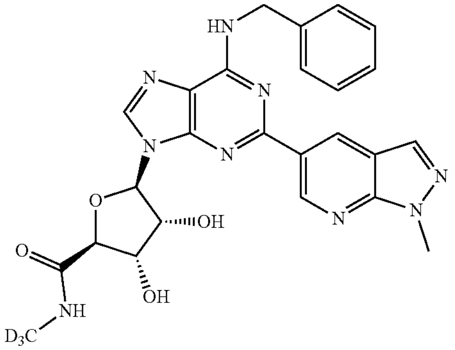 [SMILES: [2H]C([2H])([2H])NC(=O)[C@H]1O[C@@H](n2cnc3c(NCc4ccccc4)nc(-c4cnc5c(cnn5C)c4)nc32)[C@H](O)[C@@H]1O] | (2S,3S,4R,5R)-5-(6-(benzylamino)-2-(1-methyl-1H-pyrazolin[3,4-b]pyridin-5-yl)-9H-purin-9-yl)-3,4-dihydroxyl-N-(methyl-d3)-tetrahydrofuran-2-formamide |
| 39 | 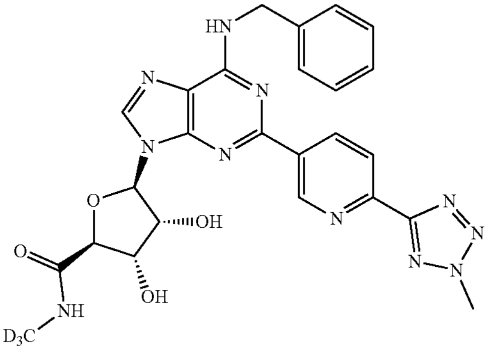 [SMILES: [2H]C([2H])([2H])NC(=O)[C@H]1O[C@@H](n2cnc3c(NCc4ccccc4)nc(-c4ccc(-c5nnn(C)n5)nc4)nc32)[C@H](O)[C@@H]1O] | (2S,3S,4R,5R)-5-(6-(benzylamino)-2-(6-(2-methyl-2H-tetrazol-5-yl)pyridin-3-yl)-9H-purin-9-yl)-3,4-dihydroxyl-N-(methyl-d3)-tetrahydrofuran-2-formamide |
| 40 | 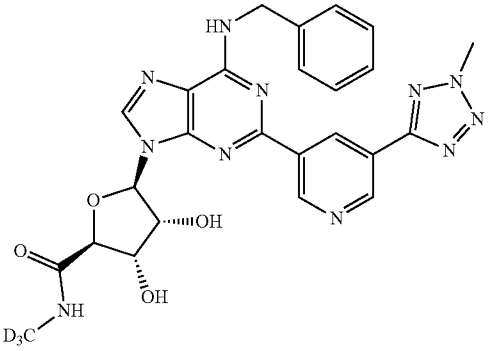 [SMILES: [2H]C([2H])([2H])NC(=O)[C@H]1O[C@@H](n2cnc3c(NCc4ccccc4)nc(-c4cncc(-c5nnn(C)n5)c4)nc32)[C@H](O)[C@@H]1O] | (2S,3S,4R,5R)-5-(6-(benzylamino)-2-(5-(2-methyl-2H-tetrazol-5-yl)pyridin-3-yl)-9H-purin-9-yl)-3,4-dihydroxyl-N-(methyl-d3)-tetrahydrofuran-2-formamide |
| 41 | 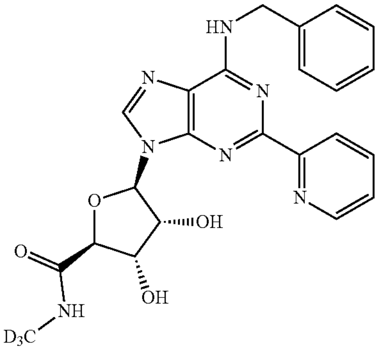 [SMILES: [2H]C([2H])([2H])NC(=O)[C@H]1O[C@@H](n2cnc3c(NCc4ccccc4)nc(-c4ccccn4)nc32)[C@H](O)[C@@H]1O] | (2S,3S,4R,5R)-5-(6-(benzylamino)-2-(pyridin-2-yl)-9H-purin-9-yl)-3,4-dihydroxyl-N-(methyl-d3)-tetrahydrofuran-2-formamide |

-continued

| Compd. No. | Structural formula of compound | Compound name |
|---|---|---|
| 42 | 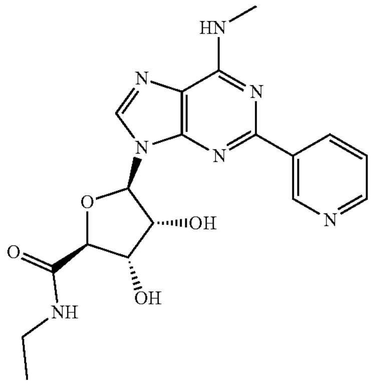 [SMILES: CCNC(=O)[C@H]1O[C@@H](n2cnc3c(NC)nc(-c4cccnc4)nc32)[C@H](O)[C@@H]1O] | (2S,3S,4R,5R)-N-ethyl-3,4-dihydroxyl-5-(6-(methylamino)-2-(pyridin-3-yl)-9H-purin-9-yl)-tetrahydrofuran-2-formamide |
| 43 | 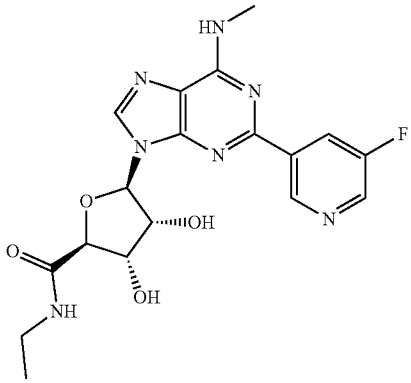 [SMILES: CCNC(=O)[C@H]1O[C@@H](n2cnc3c(NC)nc(-c4cncc(F)c4)nc32)[C@H](O)[C@@H]1O] | (2S,3S,4R,5R)-N-ethyl-5-(2-(5-fluoropyridin-3-yl)-6-(methylamino)-9H-purin-9-yl)-3,4-dihydroxyl-tetrahydrofuran-2-formamide |
| 44 | 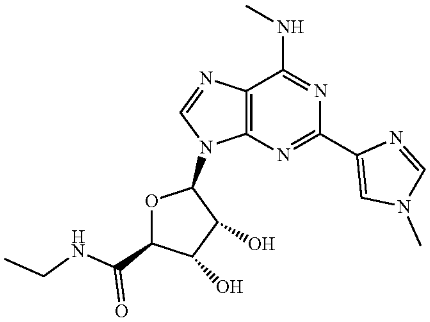 [SMILES: CCNC(=O)[C@H]1O[C@@H](n2cnc3c(NC)nc(-c4cn(C)cn4)nc32)[C@H](O)[C@@H]1O] | (2S,3S,4R,5R)-N-ethyl-3,4-dihydroxyl-5-(2-(1-methyl-1H-imidazol-4-yl)-6-(methylamino)-9H-purin-9-yl)tetrahydrofuran-2-carboxamide |
| 45 | 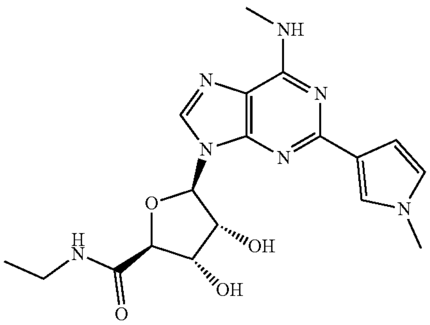 [SMILES: CCNC(=O)[C@H]1O[C@@H](n2cnc3c(NC)nc(-c4ccn(C)c4)nc32)[C@H](O)[C@@H]1O] | (2S,3S,4R,5R)-N-ethyl-3,4-dihydroxyl-5-(2-(1-methyl-1H-pyrrol-3-yl)-6-(methylamino)-9H-purin-9-yl)tetrahydrofuran-2-carboxamide |

-continued

| Compd. No. | Structural formula of compound | Compound name |
|---|---|---|
| 46 | 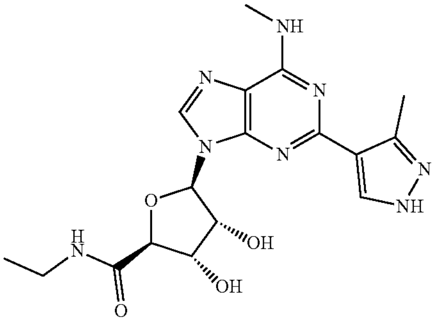 [SMILES: CCNC(=O)[C@H]1O[C@@H](n2cnc3c(NC)nc(-c4c[nH]nc4C)nc32)[C@H](O)[C@@H]1O] | (2S,3S,4R,5R)-N-ethyl-3,4-dihydroxyl-5-(2-(3-methyl-1H-pyrazol-4-yl)-6-(methylamino)-9H-purin-9-yl)tetrahydrofuran-2-formamide |
| 47 | 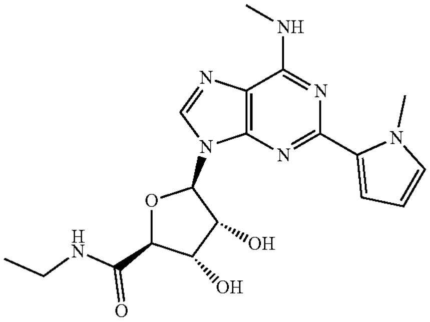 [SMILES: CCNC(=O)[C@H]1O[C@@H](n2cnc3c(NC)nc(-c4cccn4C)nc32)[C@H](O)[C@@H]1O] | (2S,3S,4R,5R)-N-ethyl-3,4-dihydroxyl-5-(2-(1-methyl-1H-pyrrol-2-yl)-6-(methylamino)-9H-purin-9-yl)tetrahydrofuran-2-carboxamide |
| 48 | 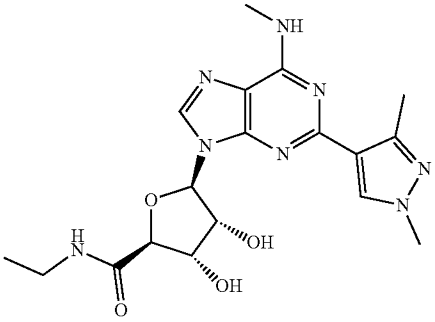 [SMILES: CCNC(=O)[C@H]1O[C@@H](n2cnc3c(NC)nc(-c4cn(C)nc4C)nc32)[C@H](O)[C@@H]1O] | (2S,3S,4R,5R)-5-(2-(1,3-dimethyl-1H-pyrazol-4-yl)-6-(methylamino)-9H-purin-9-yl)-N-ethyl-3,4-dihydroxyltetrahydrofuran-2-carboxamide |
| 49 | 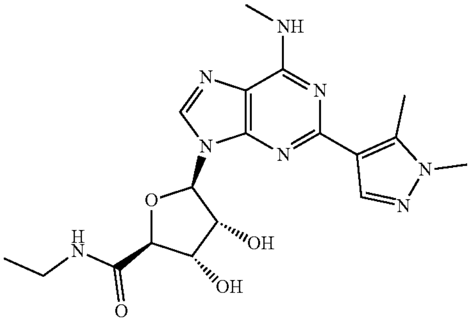 [SMILES: CCNC(=O)[C@H]1O[C@@H](n2cnc3c(NC)nc(-c4cnn(C)c4C)nc32)[C@H](O)[C@@H]1O] | (2S,3S,4R,5R)-5-(2-(1,5-dimethyl-1H-pyrazol-4-yl)-6-(methylamino)-9H-purin-9-yl)-N-ethyl-3,4-dihydroxyltetrahydrofuran-2-carboxamide |

-continued

| Compd. No. | Structural formula of compound | Compound name |
|---|---|---|
| 50 | 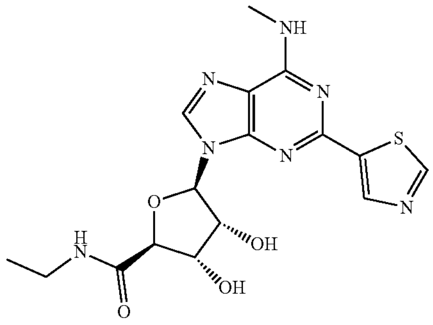 [SMILES: CCNC(=O)[C@H]1O[C@@H](n2cnc3c(NC)nc(-c4cncs4)nc32)[C@H](O)[C@@H]1O] | (2S,3S,4R,5R)-N-ethyl-3,4-dihydroxyl-5-(6-(methylamino)-2-(thiazol-5-yl)-9H-purin-9-yl)tetrahydrofuran-2-carboxamide |
| 51 | 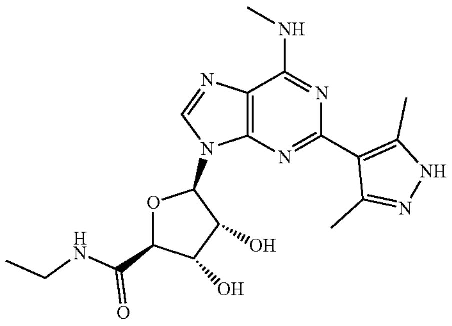 [SMILES: CCNC(=O)[C@H]1O[C@@H](n2cnc3c(NC)nc(-c4c(C)n[nH]c4C)nc32)[C@H](O)[C@@H]1O] | (2S,3S,4R,5R)-5-(2-(3,5-dimethyl-1H-pyrazol-4-yl)-6-(methylamino)-9H-purin-9-yl)-N-ethyl-3,4-dihydroxyltetrahydrofuran-2-carboxamide |
| 52 | 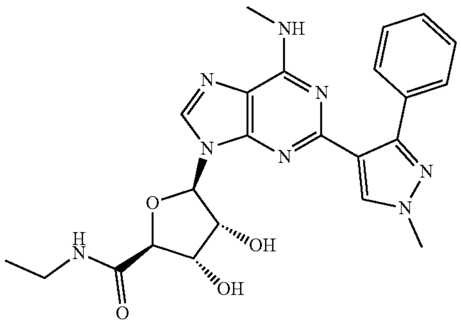 [SMILES: CCNC(=O)[C@H]1O[C@@H](n2cnc3c(NC)nc(-c4cn(C)nc4-c4ccccc4)nc32)[C@H](O)[C@@H]1O] | (2S,3S,4R,5R)-N-ethyl-3,4-dihydroxyl-5-(2-(1-methyl-3-phenyl-1H-pyrazol-4-yl)-6-(methylamino)-9H-purin-9-yl)tetrahydrofuran-2-carboxamide |
| 53 | 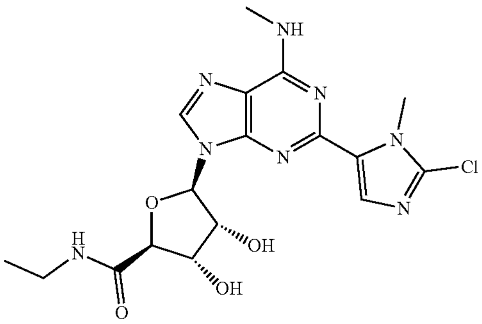 [SMILES: CCNC(=O)[C@H]1O[C@@H](n2cnc3c(NC)nc(-c4cnc(Cl)n4C)nc32)[C@H](O)[C@@H]1O] | (2S,3S,4R,5R)-5-(2-(2-chloro-1-methyl-1H-imidazol-5-yl)-6-(methylamino)-9H-purin-9-yl)-N-ethyl-3,4-dihydroxyltetrahydrofuran-2-carboxamide |

-continued

| Compd. No. | Structural formula of compound | Compound name |
|---|---|---|
| 54 | 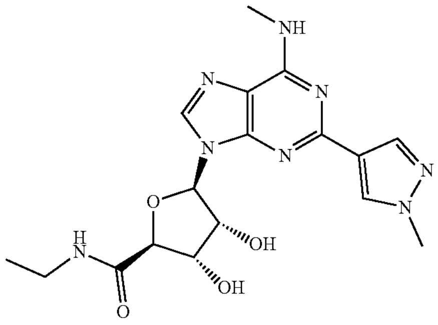 [SMILES: CCNC(=O)[C@H]1O[C@@H](n2cnc3c(NC)nc(-c4cnn(C)c4)nc32)[C@H](O)[C@@H]1O] | (2S,3S,4R,5R)-N-ethyl-3,4-dihydroxyl-5-(2-(1-methyl-1H-pyrazol-4-yl)-6-(methylamino)-9H-purin-9-yl)tetrahydrofuran-2-carboxamide |
| 55 | 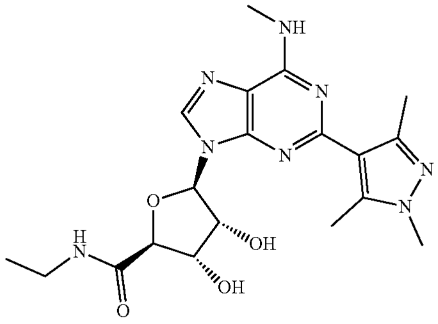 [SMILES: CCNC(=O)[C@H]1O[C@@H](n2cnc3c(NC)nc(-c4c(C)nn(C)c4C)nc32)[C@H](O)[C@@H]1O] | (2S,3S,4R,5R)-N-ethyl-3,4-dihydroxyl-5-(6-(methylamino)-2-(1,3,5-trimethyl-1H-pyrazol-4-yl)-9H-purin-9-yl)tetrahydrofuran-2-carboxamide |
| 56 | 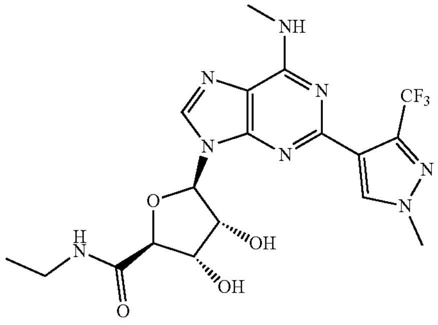 [SMILES: CCNC(=O)[C@H]1O[C@@H](n2cnc3c(NC)nc(-c4cn(C)nc4C(F)(F)F)nc32)[C@H](O)[C@@H]1O] | (2S,3S,4R,5R)-N-ethyl-3,4-dihydroxyl-5-(2-(1-methyl-3-(trifluoromethyl)-1H-pyrazol-4-yl)-6-(methylamino)-9H-purin-9-yl)tetrahydrofuran-2-carboxamide |
| 57 | 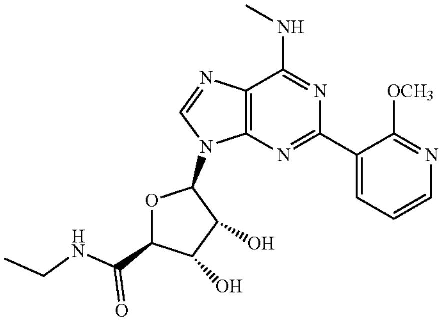 [SMILES: CCNC(=O)[C@H]1O[C@@H](n2cnc3c(NC)nc(-c4cccnc4OC)nc32)[C@H](O)[C@@H]1O] | (2S,3S,4R,5R)-N-ethyl-3,4-dihydroxyl-5-(2-(2-methoxypyridin-3-yl)-6-(methylamino)-9H-purin-9-yl)tetrahydrofuran-2-carboxamide |

-continued

| Compd. No. | Structural formula of compound | Compound name |
| --- | --- | --- |
| 58 | 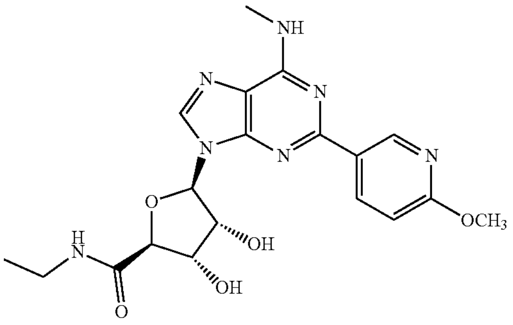 [SMILES: CCNC(=O)[C@H]1O[C@@H](n2cnc3c(NC)nc(-c4ccc(OC)nc4)nc32)[C@H](O)[C@@H]1O] | (2S,3S,4R,5R)-N-ethyl-3,4-dihydroxyl-5-(2-(6-methoxypyridin-3-yl)-6-(methylamino)-9H-purin-9-yl)tetrahydrofuran-2-carboxamide |
| 59 | 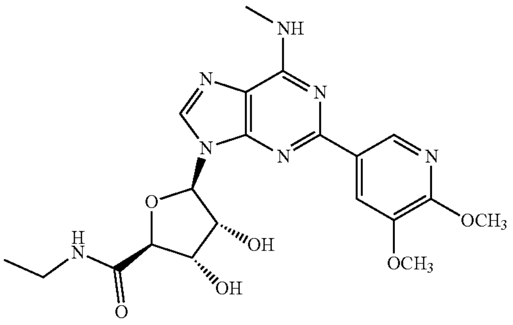 [SMILES: CCNC(=O)[C@H]1O[C@@H](n2cnc3c(NC)nc(-c4cnc(OC)c(OC)c4)nc32)[C@H](O)[C@@H]1O] | (2S,3S,4R,5R)-5-(2-(5,6-dimethoxypyridin-3-yl)-6-(methylamino)-9H-purin-9-yl)-N-ethyl-3,4-dihydroxyltetrahydrofuran-2-carboxamide |
| 60 | 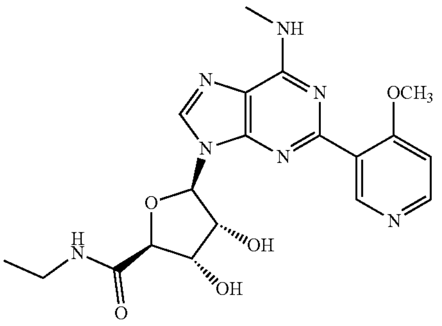 [SMILES: CCNC(=O)[C@H]1O[C@@H](n2cnc3c(NC)nc(-c4cnccc4OC)nc32)[C@H](O)[C@@H]1O] | (2S,3S,4R,5R)-N-ethyl-3,4-dihydroxyl-5-(2-(4-methoxypyridin-3-yl)-6-(methylamino)-9H-purin-9-yl)tetrahydrofuran-2-carboxamide |
| 61 | 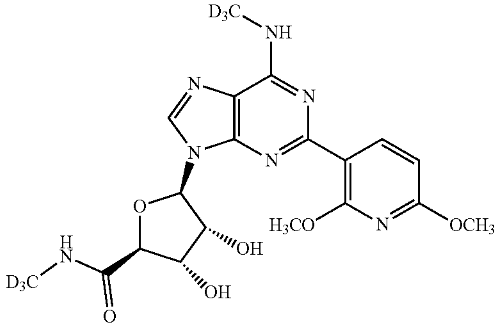 [SMILES: [2H]C([2H])([2H])NC(=O)[C@H]1O[C@@H](n2cnc3c(NC([2H])([2H])[2H])nc(-c4ccc(OC)nc4OC)nc32)[C@H](O)[C@@H]1O] | (2S,3S,4R,5R)-5-(2-(2,6-dimethoxypyridin-3-yl)-6-((methyl-d3)-amino)-9H-purin-9-yl)-3,4-dihydroxyl-N-methyl-D3-tetrahydrofuran-2-carboxamide |

-continued

| Compd. No. | Structural formula of compound | Compound name |
| --- | --- | --- |
| 62 | 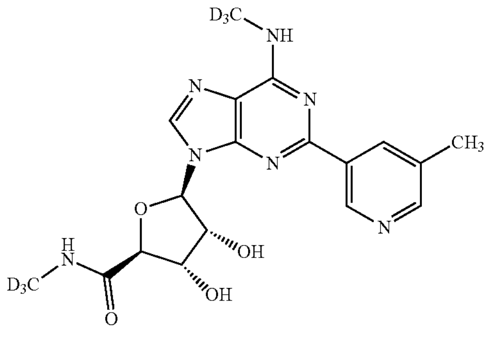 [SMILES: [2H]C([2H])([2H])NC(=O)[C@H]1O[C@@H](n2cnc3c(NC([2H])([2H])[2H])nc(-c4cncc(C)c4)nc32)[C@H](O)[C@@H]1O] | (2S,3S,4R,5R)-3,4-dihydroxyl-N-(methyl-d3)-5-(6-((methyl-d3)-amino)-2-(5-methylpyridin-3-yl)-9H-purin-9-yl)tetrahydrofuran-2-carboxamide |
| 63 | 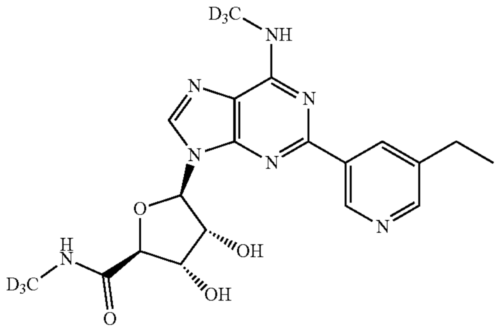 [SMILES: [2H]C([2H])([2H])NC(=O)[C@H]1O[C@@H](n2cnc3c(NC([2H])([2H])[2H])nc(-c4cncc(CC)c4)nc32)[C@H](O)[C@@H]1O] | (2S,3S,4R,5R)-5-(2-(5-ethylpyridin-3-yl)-6-((methyl-d3)-amino)-9H-purin-9-yl)-3,4-dihydroxyl-N-(methyl-d3)-tetrahydrofuran-2-carboxamide |
| 64 | 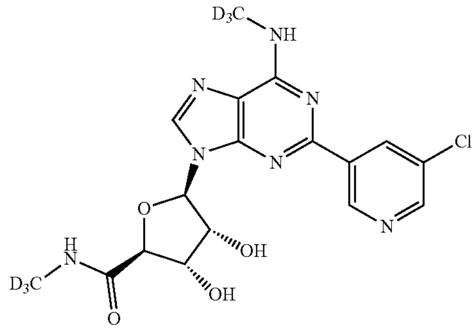 [SMILES: [2H]C([2H])([2H])NC(=O)[C@H]1O[C@@H](n2cnc3c(NC([2H])([2H])[2H])nc(-c4cncc(Cl)c4)nc32)[C@H](O)[C@@H]1O] | (2S,3S,4R,5R)-5-(2-(5-chloropyridin-3-yl)-6-((methyl-d3)-amino)-9H-purin-9-yl)-3,4-dihydroxyl-N-(methyl-d3)-tetrahydrofuran-2-carboxamide |
| 65 | 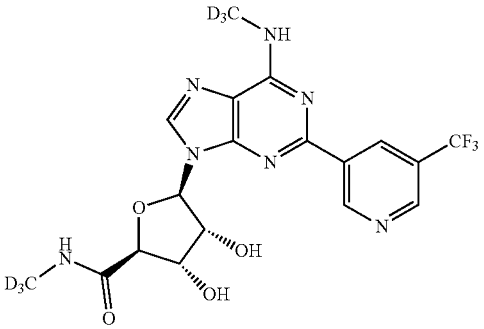 | (2S,3S,4R,5R)-3,4-dihydroxyl-N-(methyl-d3)-5-(6-((methyl-d3)-amino)-2-(5-(trifluoromethyl)pyridin-3-yl)-9H-purin-9-yl)tetrahydrofuran-2-carboxamide |

-continued

| Compd. No. | Structural formula of compound | Compound name |
|---|---|---|
| 66 | 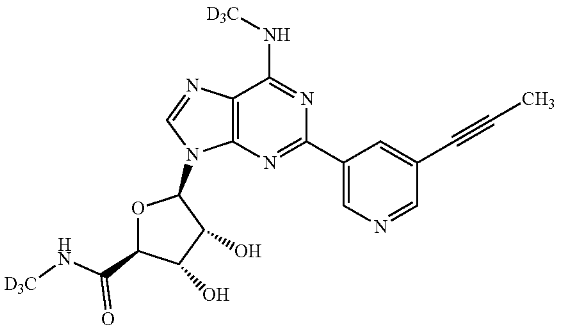 [SMILES: [2H]C([2H])([2H])NC(=O)[C@H]1O[C@@H](n2cnc3c(NC([2H])([2H])[2H])nc(-c4cncc(C#CC)c4)nc32)[C@H](O)[C@@H]1O] | (2S,3S,4R,5R)-3,4-dihydroxyl-N-(methyl-d3)-5-(6-((methyl-d3)-amino)-2-(5-(prop-1-yne-1-yl)pyridin-3-yl)-9H-purin-9-yl)tetrahydrofuran-2-carboxamide |
| 67 | 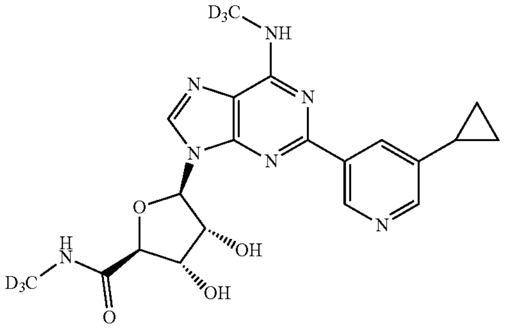 [SMILES: [2H]C([2H])([2H])NC(=O)[C@H]1O[C@@H](n2cnc3c(NC([2H])([2H])[2H])nc(-c4cncc(C5CC5)c4)nc32)[C@H](O)[C@@H]1O] | (2S,3S,4R,5R)-5-(2-(5-cyclopropylpyridin-3-yl)-6-((methyl-d3)amino)-9H-purin-9-yl)-3,4-dihydroxyl-N-(methyl-d3)-tetrahydrofuran-2-carboxamide |
| 68 | 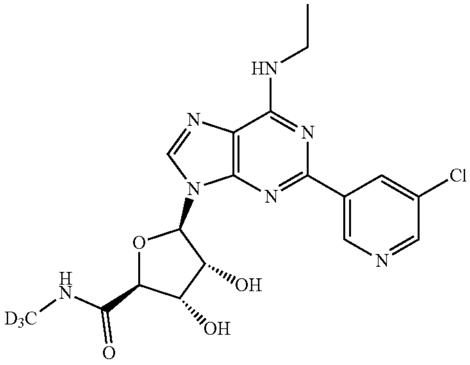 [SMILES: [2H]C([2H])([2H])NC(=O)[C@H]1O[C@@H](n2cnc3c(NCC)nc(-c4cncc(Cl)c4)nc32)[C@H](O)[C@@H]1O] | (2S,3S,4R,5R)-5-(2-(5-chloropyridin-3-yl)-6-(ethylamino)-9H-purin-9-yl)-3,4-dihydroxyl-N-(methyl-d3)-tetrahydrofuran-2-carboxamide |
| 69 | 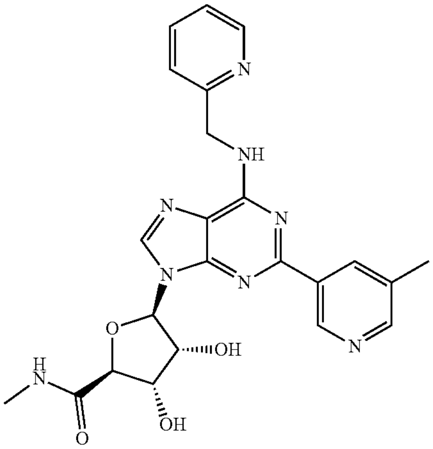 | (2S,3S,4R,5R)-3,4-dihydroxyl-N-methyl-5-(2-(5-methylpyridin-3-yl)-6-((pyridin-2-ylmethyl)amino)-9H-purin-9-yl)tetrahydrofuran-2-carboxamide |

-continued

| Compd. No. | Structural formula of compound | Compound name |
|---|---|---|
| 70 | 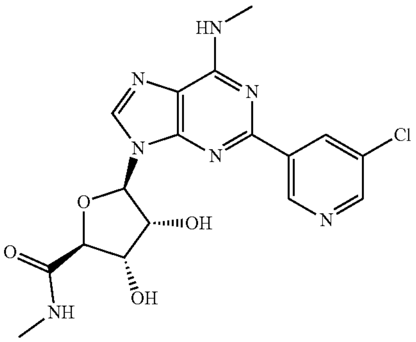 [SMILES: CNC(=O)[C@H]1O[C@@H](n2cnc3c(NC)nc(-c4cncc(Cl)c4)nc32)[C@H](O)[C@@H]1O] | (2S,3S,4R,5R)-5-(2-(5-chloropyridin-3-yl)-6-(methylamino)-9H-purin-9-yl)-3,4-dihydroxyl-N-methyltetrahydrofuran-2-carboxamide |
| 71 | 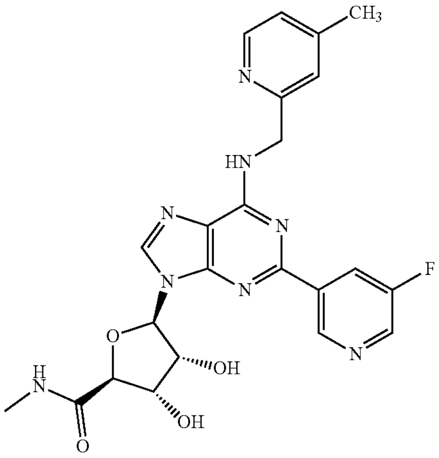 [SMILES: CNC(=O)[C@H]1O[C@@H](n2cnc3c(NCc4cc(C)ccn4)nc(-c4cncc(F)c4)nc32)[C@H](O)[C@@H]1O] | (2S,3S,4R,5R)-5-(2-(5-fluoropyridin-3-yl)-6-(((4-methylpyridin-2-yl)methyl)amino)-9H-purin-9-yl)-3,4-dihydroxyl-N-methyltetrahydrofuran-2-carboxamide |
| 72 | 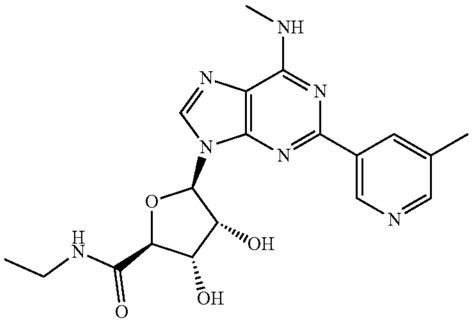 [SMILES: CCNC(=O)[C@H]1O[C@@H](n2cnc3c(NC)nc(-c4cncc(C)c4)nc32)[C@H](O)[C@@H]1O] | (2S,3S,4R,5R)-N-ethyl-3,4-dihydroxyl-5-(6-(methylamino)-2-(5-methylpyridin-3-yl)-9H-purin-9-yl)tetrahydrofuran-2-carboxamide |
| 73 | 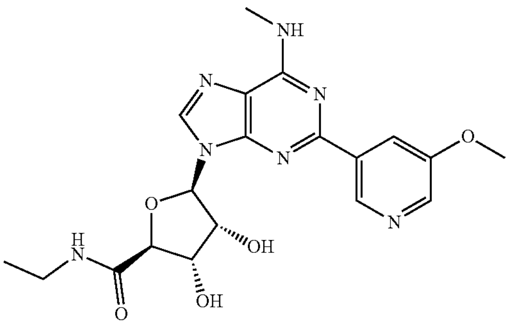 [SMILES: CCNC(=O)[C@H]1O[C@@H](n2cnc3c(NC)nc(-c4cncc(OC)c4)nc32)[C@H](O)[C@@H]1O] | (2S,3S,4R,5R)-N-ethyl-3,4-dihydroxyl-5-(2-(5-methoxypyridin-3-yl)-6-(methylamino)-9H-purin-9-yl)tetrahydrofuran-2-carboxamide |

-continued

| Compd. No. | Structural formula of compound | Compound name |
|---|---|---|
| 74 | 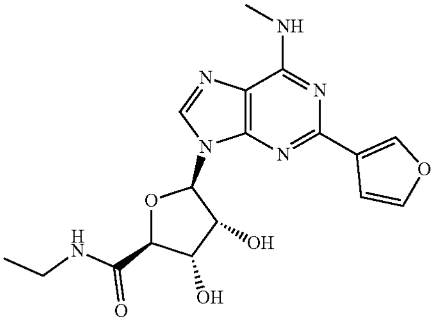 [SMILES: CCNC(=O)[C@H]1O[C@@H](n2cnc3c(NC)nc(-c4ccoc4)nc32)[C@H](O)[C@@H]1O] | (2S,3S,4R,5R)-N-ethyl-5-(2-(furan-3-yl)-6-(methylamino)-9H-purin-9-yl)-3,4-dihydroxyltetrahydrofuran-2-carboxamide |
| 75 | 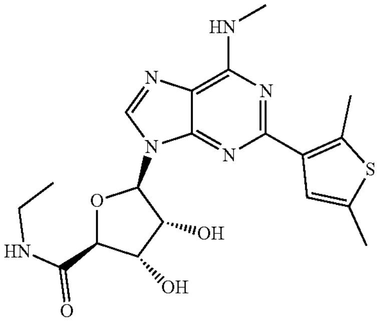 [SMILES: CCNC(=O)[C@H]1O[C@@H](n2cnc3c(NC)nc(-c4cc(C)sc4C)nc32)[C@H](O)[C@@H]1O] | (2S,3S,4R,5R)-5-(2-(2,5-dimethylthiophen-3-yl)-6-(methylamino)-9H-purin-9-yl)-N-ethyl-3,4-dihydroxyltetrahydrofuran-2-carboxamide |
| 76 | 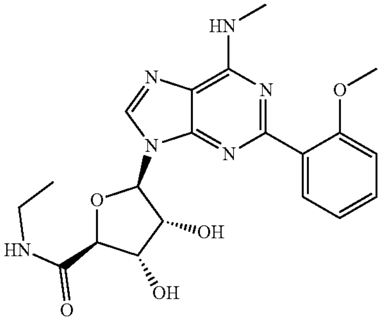 [SMILES: CCNC(=O)[C@H]1O[C@@H](n2cnc3c(NC)nc(-c4ccccc4OC)nc32)[C@H](O)[C@@H]1O] | (2S,3S,4R,5R)-N-ethyl-3,4-dihydroxyl-5-(2-(2-methoxyphenyl)-6-(methylamino)-9H-purin-9-yl)tetrahydrofuran-2-carboxamide |
| 77 | 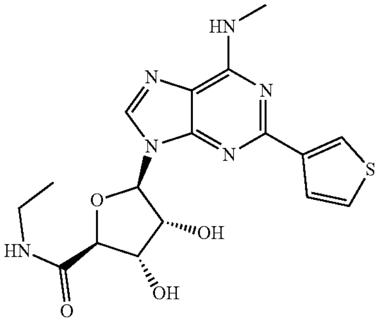 [SMILES: CCNC(=O)[C@H]1O[C@@H](n2cnc3c(NC)nc(-c4ccsc4)nc32)[C@H](O)[C@@H]1O] | (2S,3S,4R,5R)-N-ethyl-3,4-dihydroxyl-5-(6-(methylamino)-2-(thiophen-3-yl)-9H-purin-9-yl)tetrahydrofuran-2-carboxamide |

-continued

| Compd. No. | Structural formula of compound | Compound name |
|---|---|---|
| 78 | 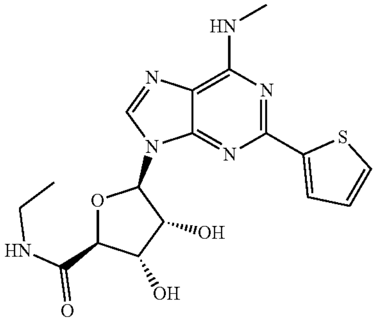 [SMILES: CCNC(=O)[C@H]1O[C@@H](n2cnc3c(NC)nc(-c4cccs4)nc32)[C@H](O)[C@@H]1O] | (2S,3S,4R,5R)-N-ethyl-3,4-dihydroxyl-5-(6-(methylamino)-2-(thiophen-2-yl)-9H-purin-9-yl)tetrahydrofuran-2-carboxamide |
| 79 | 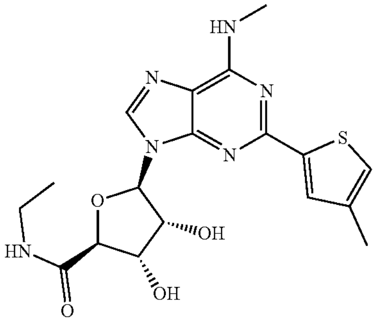 [SMILES: CCNC(=O)[C@H]1O[C@@H](n2cnc3c(NC)nc(-c4cc(C)cs4)nc32)[C@H](O)[C@@H]1O] | (2S,3S,4R,5R)-N-ethyl-3,4-dihydroxyl-5-(6-(methylamino)-2-(4-methylthiophen-2-yl)-9H-purin-9-yl)tetrahydrofuran-2-carboxamide |
| 80 | 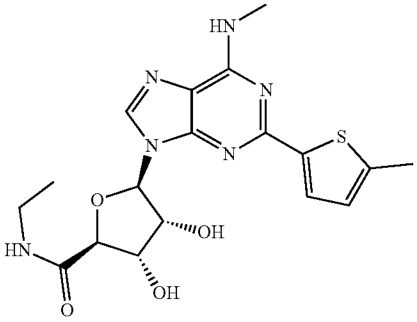 [SMILES: CCNC(=O)[C@H]1O[C@@H](n2cnc3c(NC)nc(-c4ccc(C)s4)nc32)[C@H](O)[C@@H]1O] | (2S,3S,4R,5R)-N-ethyl-3,4-dihydroxyl-5-(6-(methylamino)-2-(5-methylthiophen-2-yl)-9H-purin-9-yl)tetrahydrofuran-2-carboxamide |
| 81 | 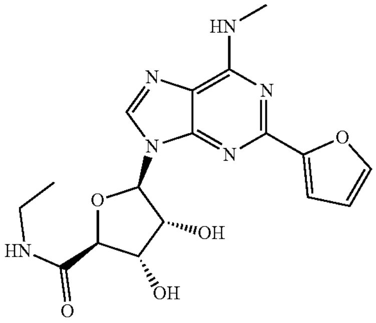 [SMILES: CCNC(=O)[C@H]1O[C@@H](n2cnc3c(NC)nc(-c4ccco4)nc32)[C@H](O)[C@@H]1O] | (2S,3S,4R,5R)-N-ethyl-5-(2-(furan-2-yl)-6-(methylamino)-9H-purin-9-yl)-3,4-dihydroxyltetrahydrofuran-2-carboxamide |

-continued

| Compd. No. | Structural formula of compound | Compound name |
|---|---|---|
| 82 | 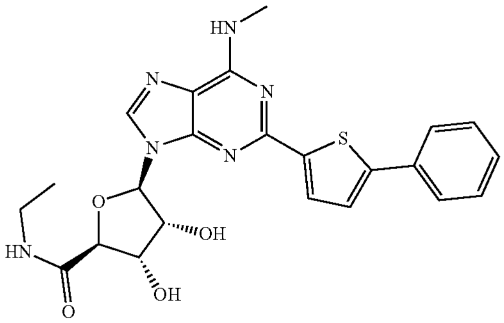 [SMILES: CCNC(=O)[C@H]1O[C@@H](n2cnc3c(NC)nc(-c4ccc(-c5ccccc5)s4)nc32)[C@H](O)[C@@H]1O] | (2S,3S,4R,5R)-N-ethyl-3,4-dihydroxyl-5-(6-(methylamino)-2-(5-phenylthiophen-2-yl)-9H-purin-9-yl)tetrahydrofuran-2-carboxamide |
| 83 | 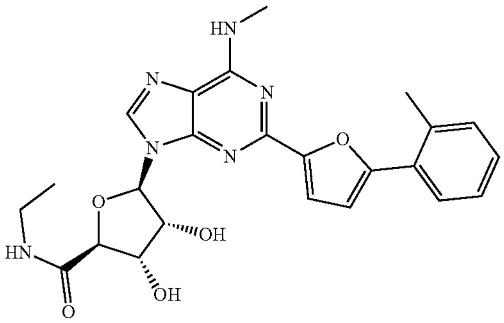 [SMILES: CCNC(=O)[C@H]1O[C@@H](n2cnc3c(NC)nc(-c4ccc(-c5ccccc5C)o4)nc32)[C@H](O)[C@@H]1O] | (2S,3S,4R,5R)-N-ethyl-3,4-dihydroxyl-5-(6-(methylamino)-2-(5-o-methylphenyl)furan-2-yl)-9H-purin-9-yl)tetrahydrofuran-2-carboxamide |
| 84 | 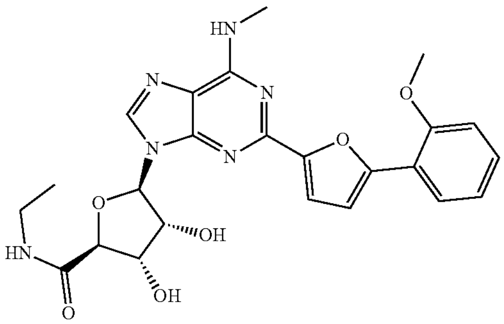 [SMILES: CCNC(=O)[C@H]1O[C@@H](n2cnc3c(NC)nc(-c4ccc(-c5ccccc5OC)o4)nc32)[C@H](O)[C@@H]1O] | (2S,3S,4R,5R)-N-ethyl-3,4-dihydroxyl-5-(2-(5-(2-methoxyphenyl)furan-2-yl)-6-(methylamino)-9H-purin-9-yl)tetrahydrofuran-2-carboxamide |
| 85 | 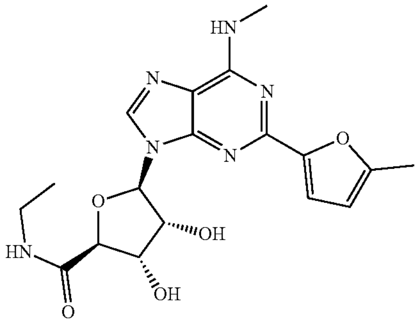 [SMILES: CCNC(=O)[C@H]1O[C@@H](n2cnc3c(NC)nc(-c4ccc(C)o4)nc32)[C@H](O)[C@@H]1O] | (2S,3S,4R,5R)-N-ethyl-3,4-dihydroxyl-5-(6-(methylamino)-2-(5-methylfuran-2-yl)-9H-purin-9-yl)tetrahydrofuran-2-carboxamide |

-continued

| Compd. No. | Structural formula of compound | Compound name |
|---|---|---|
| 86 | 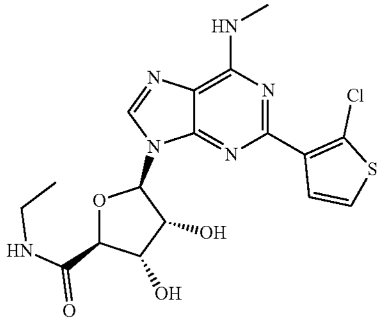 [SMILES: CCNC(=O)[C@H]1O[C@@H](n2cnc3c(NC)nc(-c4ccsc4Cl)nc32)[C@H](O)[C@@H]1O] | (2S,3S,4R,5R)-5-(2-(2-chlorothiophen-3-yl)-6-(methylamino)-9H-purin-9-yl)-N-ethyl-3,4-dihydroxyltetrahydrofuran-2-carboxamide |
| 87 | 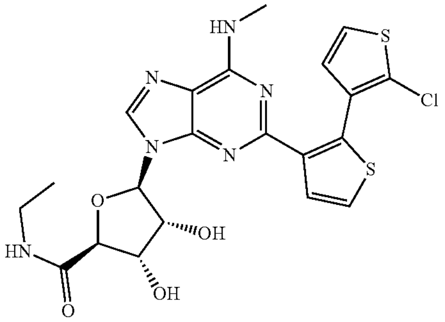 [SMILES: CCNC(=O)[C@H]1O[C@@H](n2cnc3c(NC)nc(-c4ccsc4-c4ccsc4Cl)nc32)[C@H](O)[C@@H]1O] | (2S,3S,4R,5R)-5-(2-(2'-chloro-(2,3'-bithiophen-3-yl)-6-(methylamino)-9H-purin-9-yl)-N-ethyl-3,4-dihydroxyltetrahydrofuran-2-carboxamide |
| 88 | 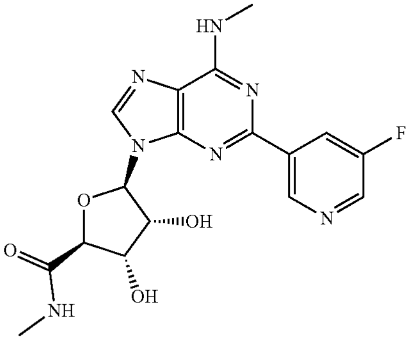 [SMILES: CNC(=O)[C@H]1O[C@@H](n2cnc3c(NC)nc(-c4cncc(F)c4)nc32)[C@H](O)[C@@H]1O] | (2S,3S,4R,5R)-5-(2-(5-fluoropyridin-3-yl)-6-(methylamino)-9H-purin-9-yl)-3,4-dihydroxyl-N-methyltetrahydrofuran-2-carboxamide |
| 89 | 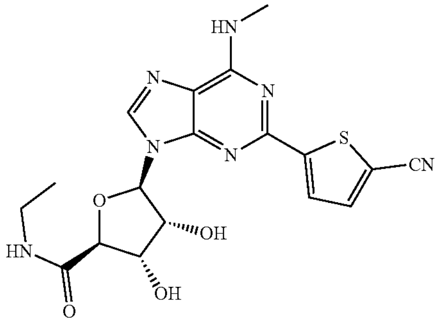 [SMILES: CCNC(=O)[C@H]1O[C@@H](n2cnc3c(NC)nc(-c4ccc(C#N)s4)nc32)[C@H](O)[C@@H]1O] | (2S,3S,4R,5R)-5-(2-(5-cyanothiophen-2-yl)-6-(methylamino)-9H-purin-9-yl)-N-ethyl-3,4-dihydroxyltetrahydrofuran-2-carboxamide |

-continued

| Compd. No. | Structural formula of compound | Compound name |
|---|---|---|
| 90 | 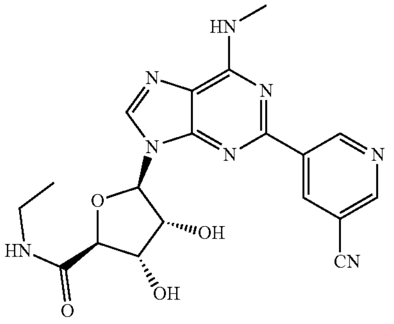 [SMILES: CCNC(=O)[C@H]1O[C@@H](n2cnc3c(NC)nc(-c4cncc(C#N)c4)nc32)[C@H](O)[C@@H]1O] | (2S,3S,4R,5R)-5-(2-(5-chloropyridin-3-yl)-6-(methylamino)-9H-purin-9-yl)-N-ethyl-3,4-dihydroxyltetrahydrofuran-2-carboxamide |
| 91 | 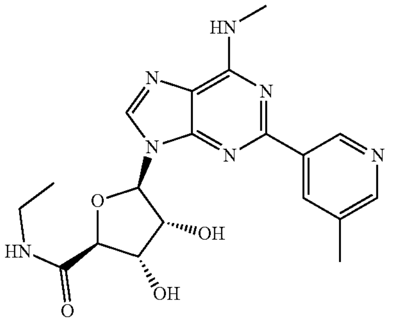 [SMILES: CCNC(=O)[C@H]1O[C@@H](n2cnc3c(NC)nc(-c4cncc(C)c4)nc32)[C@H](O)[C@@H]1O] | (2S,3S,4R,5R)-N-ethyl-3,4-dihydroxyl-5-(6-(methylamino)-2-(5-methylpyridin-3-yl)-9H-purin-9-yl)-tetrahydrofuran-2-carboxamide |
| 92 | 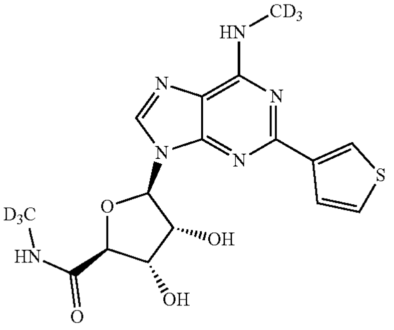 | (2S,3S,4R,5R)-3,4-dihydroxyl-N-((methyl-d3))-5-(6-((methyl-d3))amino)-2-(thiophen-3-yl)-9H-purin-9-yl)tetrahydrofuran-2-carboxamide |
| 93 | 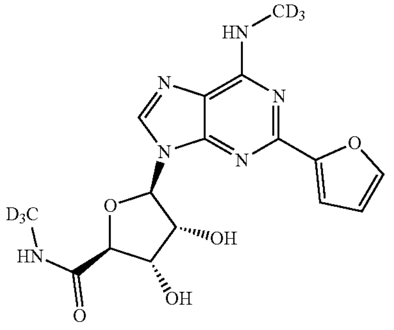 [SMILES: [2H]C([2H])([2H])NC(=O)[C@H]1O[C@@H](n2cnc3c(NC([2H])([2H])[2H])nc(-c4ccco4)nc32)[C@H](O)[C@@H]1O] | (2S,3S,4R,5R)-5-(2-(furan-2-yl)-6-(((methyl-d3))amino)-9H-purin-9-yl)-3,4-dihydroxyl-N-((methyl-d3))tetrahydrofuran-2-carboxamide |

-continued

| Compd. No. | Structural formula of compound | Compound name |
|---|---|---|
| 94 | 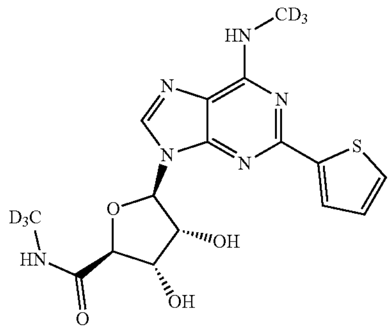 [SMILES: [2H]C([2H])([2H])NC(=O)[C@H]1O[C@@H](n2cnc3c(NC([2H])([2H])[2H])nc(-c4cccs4)nc32)[C@H](O)[C@@H]1O] | (2S,3S,4R,5R)-3,4-dihydroxyl-N-((methyl-d3))-5-(6-((methyl-d3)amino)-2-(thiophen-2-yl))-9H-purin-9-yl)tetrahydrofuran-2-carboxamide |
| 95 | 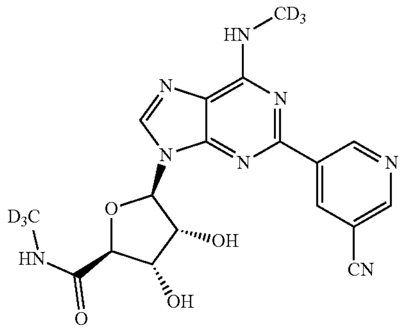 [SMILES: [2H]C([2H])([2H])NC(=O)[C@H]1O[C@@H](n2cnc3c(NC([2H])([2H])[2H])nc(-c4cncc(C#N)c4)nc32)[C@H](O)[C@@H]1O] | (2S,3S,4R,5R)-5-(2-(5-cyanopyridin-3-yl)-6-((methyl-d3)amino)-9H-purin-9-yl)-3,4-dihydroxyl-N-(methyl-d3)tetrahydrofuran-2-carboxamide |
| 96 | 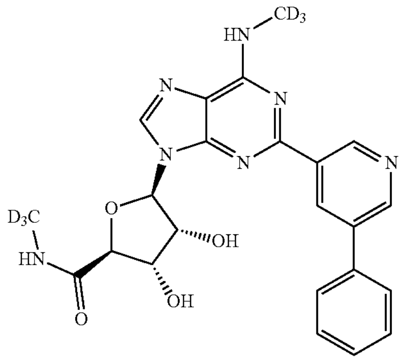 [SMILES: [2H]C([2H])([2H])NC(=O)[C@H]1O[C@@H](n2cnc3c(NC([2H])([2H])[2H])nc(-c4cncc(-c5ccccc5)c4)nc32)[C@H](O)[C@@H]1O] | (2S,3S,4R,5R)-3,4-dihydroxyl-N-methyl-d3))-5-(6-((methyl-d3)amino)-2-(5-phenylpyridin-3-yl)-9H-purin-9-yl)tetrahydrofuran-2-carboxamide |
| 97 | 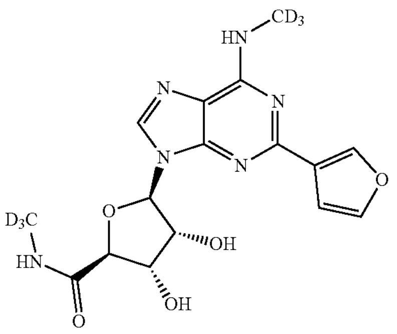 [SMILES: [2H]C([2H])([2H])NC(=O)[C@H]1O[C@@H](n2cnc3c(NC([2H])([2H])[2H])nc(-c4ccoc4)nc32)[C@H](O)[C@@H]1O] | (2S,3S,4R,5R)-5-(2-(furan-3-yl)-6-((methyl-d3)amino)-9H-purin-9-yl)-3,4-dihydroxyl-N-(methyl-d3)tetrahydrofuran-2-carboxamide |

-continued

| Compd. No. | Structural formula of compound | Compound name |
|---|---|---|
| 98 | 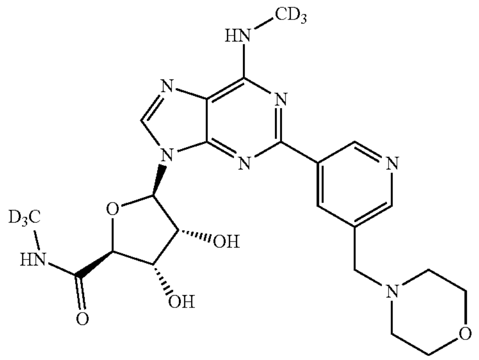 [SMILES: [2H]C([2H])([2H])NC(=O)[C@H]1O[C@@H](n2cnc3c(NC([2H])([2H])[2H])nc(-c4cncc(CN5CCOCC5)c4)nc32)[C@H](O)[C@@H]1O] | (2S,3S,4R,5R)-3,4-dihydroxyl-N-(methyl-d3)-5-(6-((methyl-d3)amino)-2-(5-(morpholinomethyl)pyridin-3-yl)-9H-purin-9-yl)tetrahydrofuran-2-carboxamide |
| 99 | 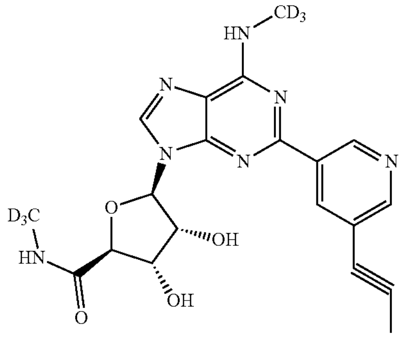 [SMILES: [2H]C([2H])([2H])NC(=O)[C@H]1O[C@@H](n2cnc3c(NC([2H])([2H])[2H])nc(-c4cncc(C#CC)c4)nc32)[C@H](O)[C@@H]1O] | (2S,3S,4R,5R)-3,4-dihydroxyl-N-((methyl-d3)-5-(6-((methyl-d3)-amino)-2-(5-(prop-1-yne-1-yl)pyridin-3-yl)-9H-purin-9-yl)tetrahydrofuran-2-carboxamide |
| 100 | 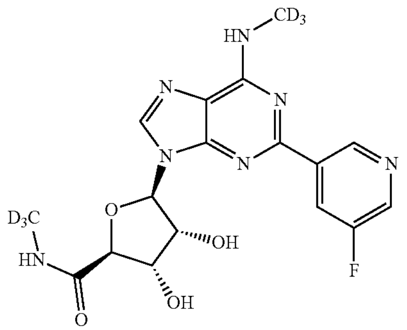 [SMILES: [2H]C([2H])([2H])NC(=O)[C@H]1O[C@@H](n2cnc3c(NC([2H])([2H])[2H])nc(-c4cncc(F)c4)nc32)[C@H](O)[C@@H]1O] | (2S,3S,4R,5R)-5-(2-(5-fluoropyridin-3-yl)-6-((methyl-d3)amino)-9H-purin-9-yl)-3,4-dihydroxyl-N-(methyl-d3)tetrahydrofuran-2-carboxamide |
| 101 | 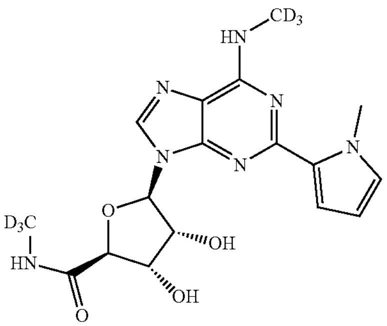 [SMILES: [2H]C([2H])([2H])NC(=O)[C@H]1O[C@@H](n2cnc3c(NC([2H])([2H])[2H])nc(-c4cccn4C)nc32)[C@H](O)[C@@H]1O] | (2S,3S,4R,5R)-3,4-dihydroxyl-N-(methyl-d3)-5-(2-(1-methyl-1H-pyrrol)-2-yl)-6-((methyl-d3)amino)-9H-purin-9-yl)tetrahydrofuran-2-carboxamide |

-continued
| Compd. No. | Structural formula of compound | Compound name |
|---|---|---|
| 102 | 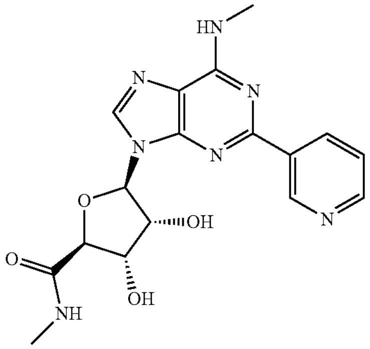 [SMILES: CNC(=O)[C@H]1O[C@@H](n2cnc3c(NC)nc(-c4cccnc4)nc32)[C@H](O)[C@@H]1O] | (2S,3S,4R,5R)-3,4-dihydroxyl-N-methyl-5-(6-(methylamino)-2-(pyridin-3-yl)-9H-purin-9-yl)tetrahydrofuran-2-carboxamide |
| 103 | 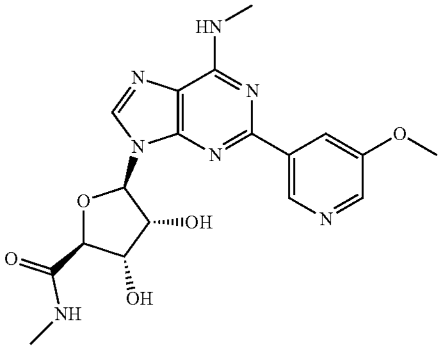 [SMILES: CNC(=O)[C@H]1O[C@@H](n2cnc3c(NC)nc(-c4cncc(OC)c4)nc32)[C@H](O)[C@@H]1O] | (2S,3S,4R,5R)-3,4-dihydroxyl-5-(2-(5-methoxypyridin-3-yl)-6-(methylamino)-9H-purin-9-yl)-N-methyltetrahydrofuran-2-carboxamide |
| 104 | 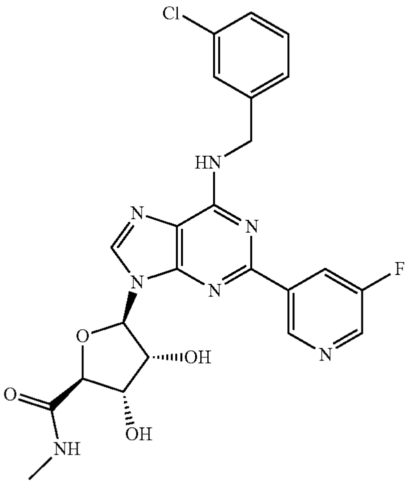 | (2S,3S,4R,5R)-5-(6-((3-chlorobenzyl)amino)-2-(5-fluoropyridin-3-yl)-9H-purin-9-yl)-3,4-dihydroxyl-N-methyltetrahydrofuran-2-carboxamide |

-continued

| Compd. No. | Structural formula of compound | Compound name |
|---|---|---|
| 105 | 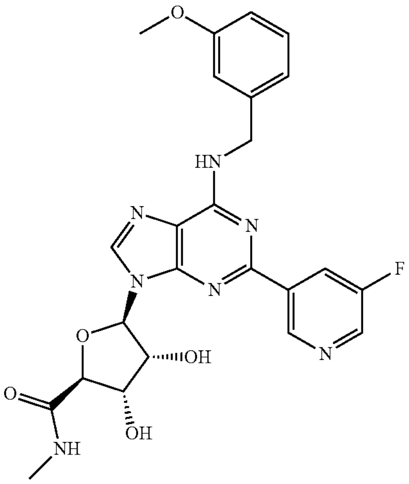 [SMILES: CNC(=O)[C@H]1O[C@@H](n2cnc3c(NCc4cccc(OC)c4)nc(-c4cncc(F)c4)nc32)[C@H](O)[C@@H]1O] | (2S,3S,4R,5R)-5-(2-(5-fluoropyridin-3-yl)-6-((3-methoxybenzyl)amino)-9H-purin-9-yl)-3,4-dihydroxyl-N-methyltetrahydrofuran-2-carboxamide |
| 106 | 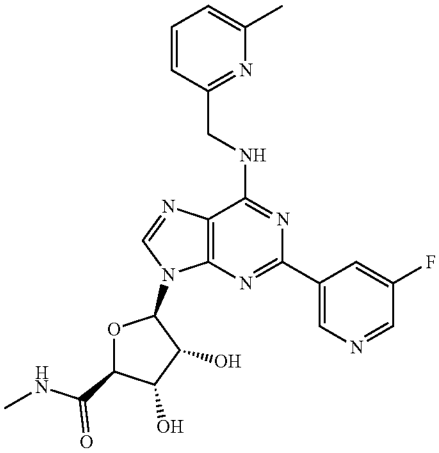 [SMILES: CNC(=O)[C@H]1O[C@@H](n2cnc3c(NCc4cccc(C)n4)nc(-c4cncc(F)c4)nc32)[C@H](O)[C@@H]1O] | (2S,3S,4R,5R)-5-(2-(5-fluoropyridin-3-yl)-6-((((6-methylpyridin-2-yl)methyl)amino)-9H-purin-9-yl)-3,4-dihydroxyl-N-methyltetrahydrofuran-2-carboxamide |
| 107 | 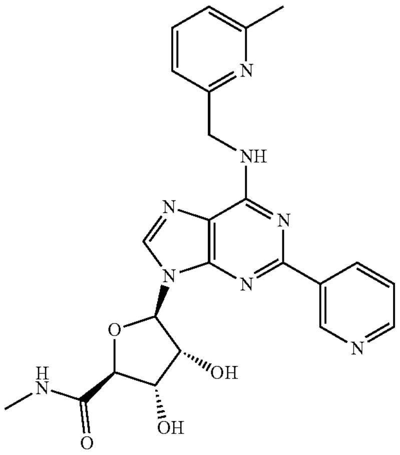 [SMILES: CNC(=O)[C@H]1O[C@@H](n2cnc3c(NCc4cccc(C)n4)nc(-c4cccnc4)nc32)[C@H](O)[C@@H]1O] | (2S,3S,4R,5R)-3,4-dihydroxyl-N-methyl-5-(6-((((6-methylpyridin-2-yl)methyl)amino)-2-(pyridin-3-yl)-9H-purin-9-yl)tetrahydrofuran-2-carboxamide |

-continued
| Compd. No. | Structural formula of compound | Compound name |
|---|---|---|
| 108 | 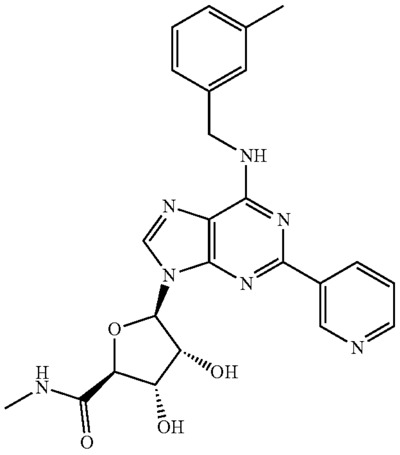 [SMILES: CNC(=O)[C@H]1O[C@@H](n2cnc3c(NCc4cccc(C)c4)nc(-c4cccnc4)nc32)[C@H](O)[C@@H]1O] | (2S,3S,4R,5R)-3,4-dihydroxyl-N-methyl-5-(6-((3-methylbenzyl)amino)-2-(pyridin-3-yl)-9H-purin-9-yl)tetrahydrofuran-2-carboxamide |
| 109 | 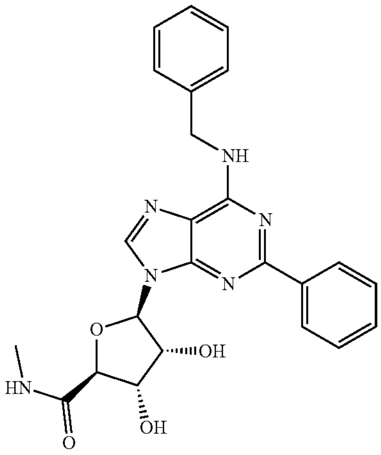 [SMILES: CNC(=O)[C@H]1O[C@@H](n2cnc3c(NCc4ccccc4)nc(-c4ccccc4)nc32)[C@H](O)[C@@H]1O] | (2S,3S,4R,5R)-5-(6-(benzylamino)-2-phenyl-9H-purin-9-yl)-3,4-dihydroxyl-N-methyltetrahydrofuran-2-carboxamide |
| 110 | 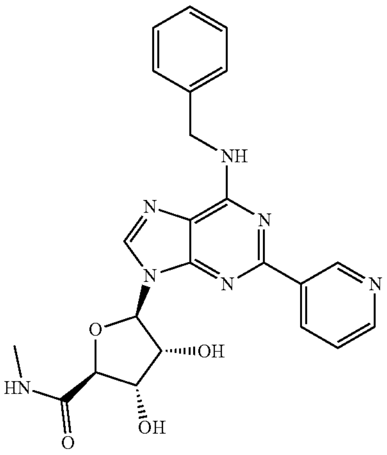 [SMILES: CNC(=O)[C@H]1O[C@@H](n2cnc3c(NCc4ccccc4)nc(-c4cccnc4)nc32)[C@H](O)[C@@H]1O] | (2S,3S,4R,5R)-5-(6-(benzylamino)-2-(pyridin-3-yl)-9H-purin-9-yl)-3,4-dihydroxyl-N-methyltetrahydrofuran-2-carboxamide |

-continued

| Compd. No. | Structural formula of compound | Compound name |
|---|---|---|
| 111 | 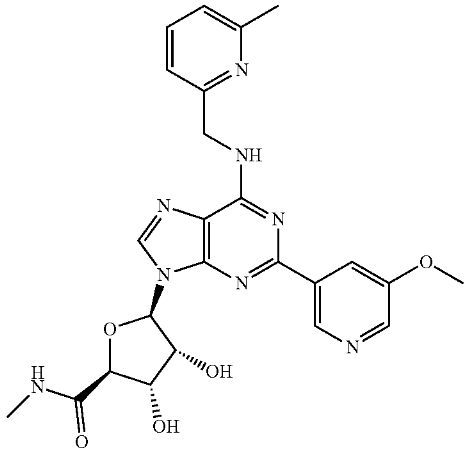 | (2S,3S,4R,5R)-3,4-dihydroxyl-5-(2-(5-methoxypyridin-3-yl)-6-((((6-methylpyridin-2-yl))methyl)amino)-9H-purin-9-yl)-N-methyltetrahydrofuran-2-carboxamide |
| 112 | 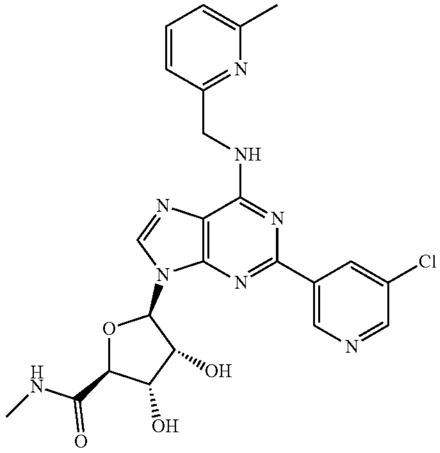 [SMILES: CNC(=O)[C@H]1O[C@@H](n2cnc3c(NCc4cccc(C)n4)nc(-c4cncc(Cl)c4)nc32)[C@H](O)[C@@H]1O] | ((2S,3S,4R,5R)-5-(2-(5-chloropyridin-3-yl)-6-((((6-methylpyridin-2-yl))methyl)amino)-9H-purin-9-yl)-3,4-dihydroxyl-N-methyltetrahydrofuran-2-carboxamide |
| 113 | 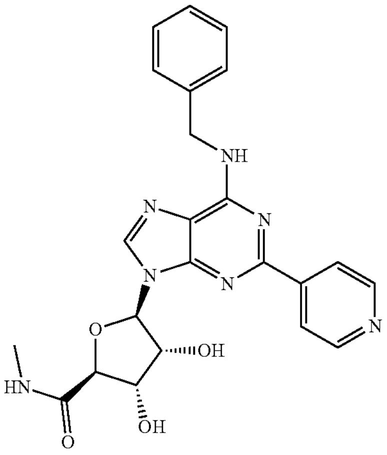 [SMILES: CNC(=O)[C@H]1O[C@@H](n2cnc3c(NCc4ccccc4)nc(-c4ccncc4)nc32)[C@H](O)[C@@H]1O] | (2S,3S,4R,5R)-5-(6-(benzylamino)-2-(pyridin-4-yl)-9H-purin-9-yl)-3,4-dihydroxyl-N-methyltetrahydrofuran-2-carboxamide |

-continued
| Compd. No. | Structural formula of compound | Compound name |
|---|---|---|
| 114 | 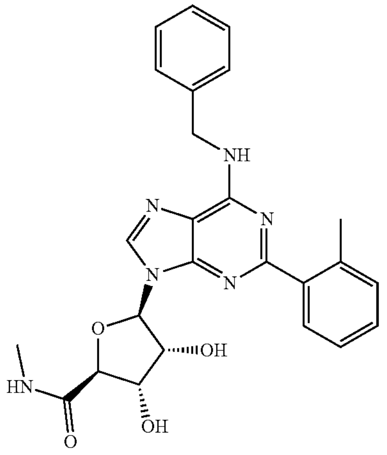 [SMILES: CNC(=O)[C@H]1O[C@@H](n2cnc3c(NCc4ccccc4)nc(-c4ccccc4C)nc32)[C@H](O)[C@@H]1O] | (2S,3S,4R,5R)-5-(6-(benzylamino)-2-o-methylphenyl-9H-purin-9-yl)-3,4-dihydroxyl-N-methyltetrahydrofuran-2-carboxamide |
| 115 | 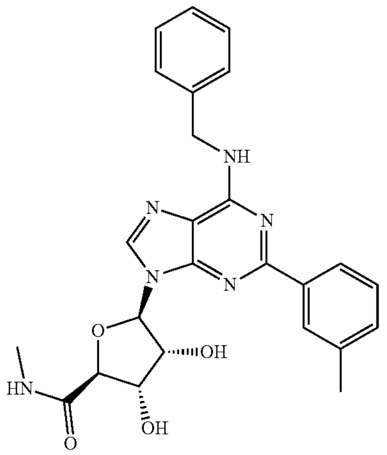 [SMILES: CNC(=O)[C@H]1O[C@@H](n2cnc3c(NCc4ccccc4)nc(-c4cccc(C)c4)nc32)[C@H](O)[C@@H]1O] | (2S,3S,4R,5R)-5-(6-(benzylamino)-2-m-methylphenyl-9H-purin-9-yl)-3,4-dihydroxyl-N-methyltetrahydrofuran-2-carboxamide |
| 116 | 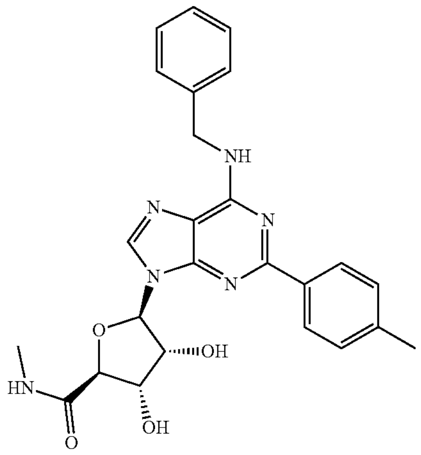 | (2S,3S,4R,5R)-5-(6-(benzylamino)-2-p-methylphenyl-9H-purin-9-yl)-3,4-dihydroxyl-N-methyltetrahydrofuran-2-carboxamide |

-continued
| Compd. No. | Structural formula of compound | Compound name |
|---|---|---|
| 117 | 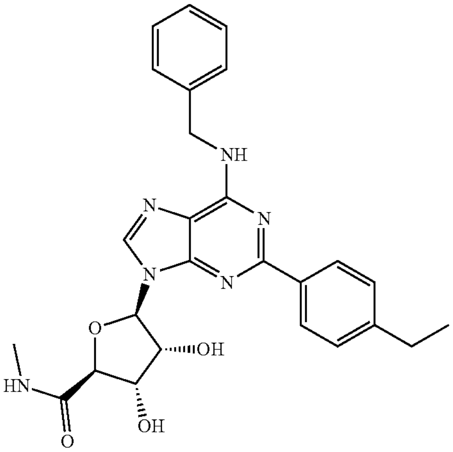 [SMILES: CCc1ccc(-c2nc(NCc3ccccc3)c3ncn([C@@H]4O[C@H](C(=O)NC)[C@@H](O)[C@H]4O)c3n2)cc1] | (2S,3S,4R,5R)-5-(6-(benzylamino)-2-(4-ethylphenyl)-9H-purin-9-yl)-3,4-dihydroxyl-N-methyltetrahydrofuran-2-carboxamide |
| 118 | 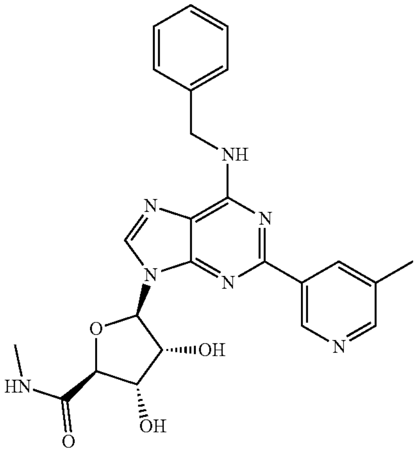 | (2S,3S,4R,5R)-5-(6-(benzylamino)-2-(5-methylpyridin-3-yl)-9/-purin-9-yl)-3,4-dihydroxyl-N-methyltetrahydrofuran-2-carboxamide |
| 119 | 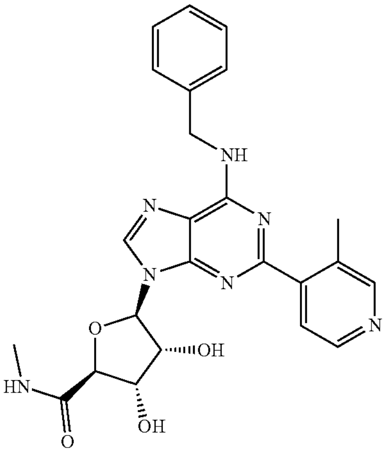 [SMILES: CNC(=O)[C@H]1O[C@@H](n2cnc3c(NCc4ccccc4)nc(-c4ccncc4C)nc32)[C@H](O)[C@@H]1O] | (2S,3S,4R,5R)-5-(6-(benzylamino)-2-(3-methylpyridin-4-yl)-9H-purin-9-yl)-3,4-dihydroxyl-N-methyltetrahydrofuran-2-carboxamide |

-continued
| Compd. No. | Structural formula of compound | Compound name |
|---|---|---|
| 120 | 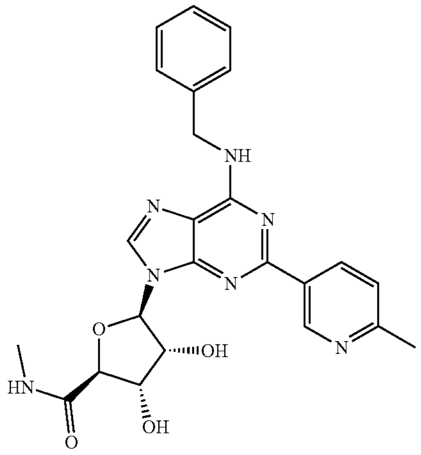 | (2S,3S,4R,5R)-5-(6-(benzylamino)-2-(6-methylpyridin-3-yl)-9H-purin-9-yl)-3,4-dihydroxyl-N-methyltetrahydrofuran-2-carboxamide |
| 121 | 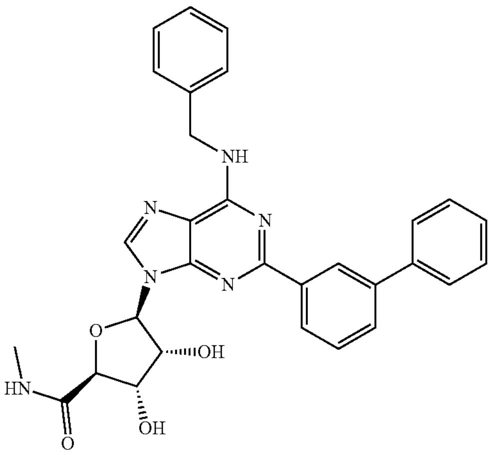 [SMILES: CNC(=O)[C@H]1O[C@@H](n2cnc3c(NCc4ccccc4)nc(-c4cccc(-c5ccccc5)c4)nc32)[C@H](O)[C@@H]1O] | (2S,3S,4R,5R)-5-(2-([1,1'-biphenyl]-3-yl)-6-(benzylamino)-9H-purin-9-yl)-3,4-dihydroxyl-N-methyltetrahydrofuran-2-carboxamide |
| 122 | 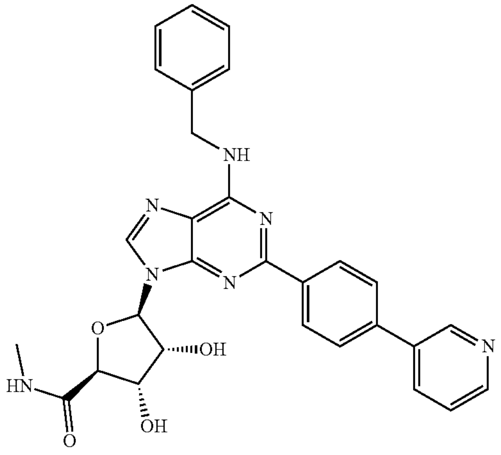 [SMILES: CNC(=O)[C@H]1O[C@@H](n2cnc3c(NCc4ccccc4)nc(-c4ccc(-c5cccnc5)cc4)nc32)[C@H](O)[C@@H]1O] | (2S,3S,4R,5R)-5-(6-(benzylamino)-2-(4-(pyridin-3-yl)phenyl)-9H-purin-9-yl)-3,4-dihydroxyl-N-methyltetrahydrofuran-2-carboxamide |

-continued
| Compd. No. | Structural formula of compound | Compound name |
|---|---|---|
| 123 | 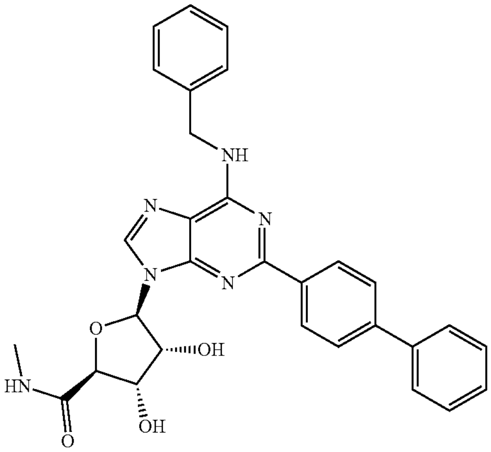 [SMILES: CNC(=O)[C@H]1O[C@@H](n2cnc3c(NCc4ccccc4)nc(-c4ccc(-c5ccccc5)cc4)nc32)[C@H](O)[C@@H]1O] | (2S,3S,4R,5R)-5-(2-([1,1'-biphenyl]-4-yl)-6-(benzylamino)-9H-purin-9-yl)-3,4-dihydroxyl-N-methyltetrahydrofuran-2-carboxamide |
| 124 | 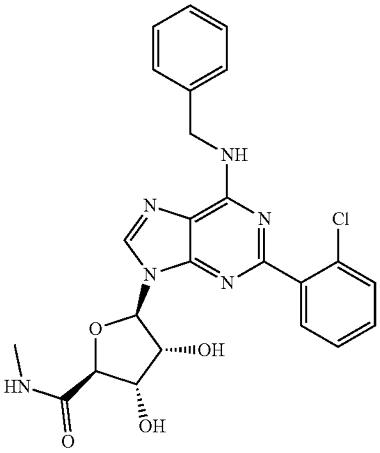 [SMILES: CNC(=O)[C@H]1O[C@@H](n2cnc3c(NCc4ccccc4)nc(-c4ccccc4Cl)nc32)[C@H](O)[C@@H]1O] | (2S,3S,4R,5R)-5-(6-(benzylamino)-2-(2-chlorophenyl)-9H-purin-9-yl)-3,4-dihydroxyl-N-methyltetrahydrofuran-2-carboxamide |
| 125 | 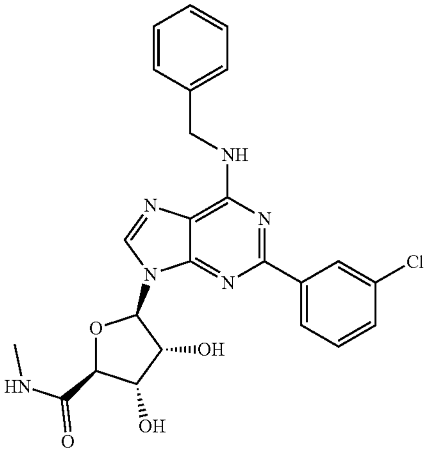 [SMILES: CNC(=O)[C@H]1O[C@@H](n2cnc3c(NCc4ccccc4)nc(-c4cccc(Cl)c4)nc32)[C@H](O)[C@@H]1O] | (2S,3S,4R,5R)-5-(6-(benzylamino)-2-(3-chlorophenyl)-9H-purin-9-yl)-3,4-dihydroxyl-N-methyltetrahydrofuran-2-carboxamide |

-continued
| Compd. No. | Structural formula of compound | Compound name |
|---|---|---|
| 126 | 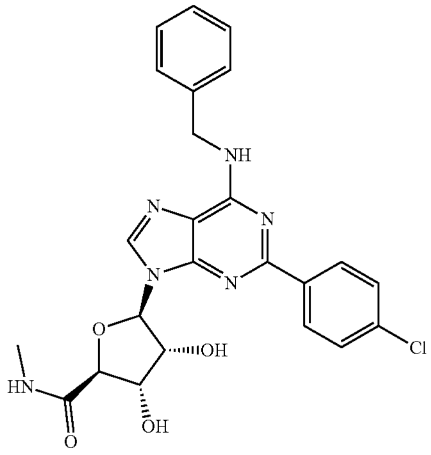 [SMILES: CNC(=O)[C@H]1O[C@@H](n2cnc3c(NCc4ccccc4)nc(-c4ccc(Cl)cc4)nc32)[C@H](O)[C@@H]1O] | (2S,3S,4R,5R)-5-(6-(benzylamino)-2-(4-chlorophenyl)-9H-purin-9-yl)-3,4-dihydroxoy-N-methyltetrahydrofuran-2-carboxamide |
| 127 | 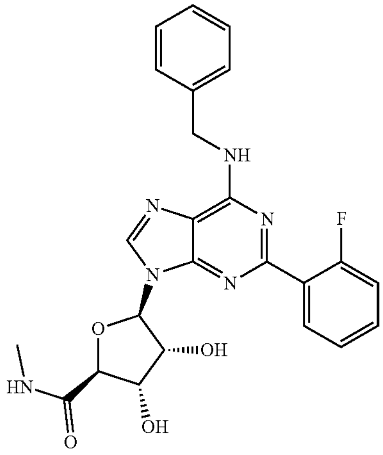 | (2S,3S,4R,5R)-5-(6-(benzylamino)-2-(2-fluorophenyl)-9H-purin-9-yl)-3,4-dihydroxyl-N-methyltetrahydrofuran-2-carboxamide |
| 128 | 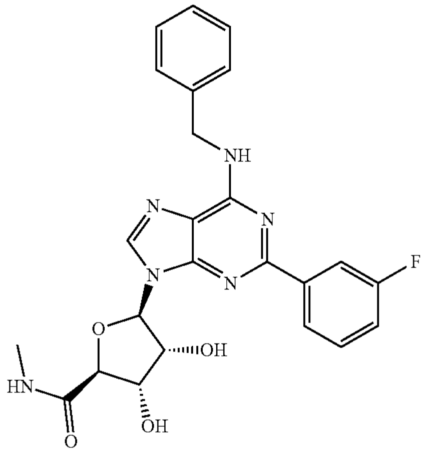 [SMILES: CNC(=O)[C@H]1O[C@@H](n2cnc3c(NCc4ccccc4)nc(-c4cccc(F)c4)nc32)[C@H](O)[C@@H]1O] | (2S,3S,4R,5R)-5-(6-(benzylamino)-2-(3-fluorophenyl)-9H-purin-9-yl)-3,4-dihydroxyl-N-methyltetrahydrofuran-2-carboxamide |

-continued
| Compd. No. | Structural formula of compound | Compound name |
|---|---|---|
| 129 | 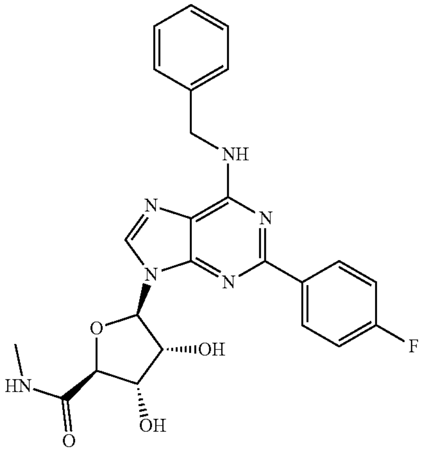 [SMILES: CNC(=O)[C@H]1O[C@@H](n2cnc3c(NCc4ccccc4)nc(-c4ccc(F)cc4)nc32)[C@H](O)[C@@H]1O] | (2S,3S,4R,5R)-5-(6-(benzylamino)-2-(4-fluorophenyl)-9H-purin-9-yl)-3,4-dihydroxyl-N-methyltetrahydrofuran-2-carboxamide |
| 130 | 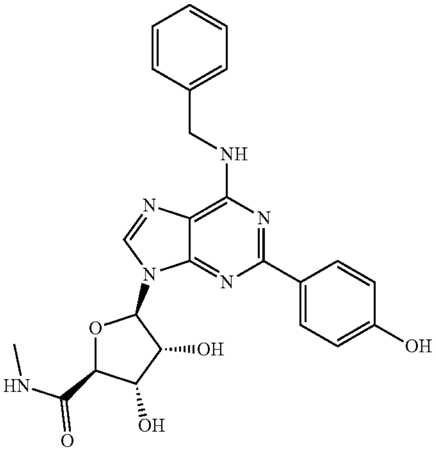 [SMILES: CNC(=O)[C@H]1O[C@@H](n2cnc3c(NCc4ccccc4)nc(-c4ccc(O)cc4)nc32)[C@H](O)[C@@H]1O] | (2S,3S,4R,5R)-5-(6-(benzylamino)-2-(4-hydroxylphenyl)-9H-purin-9-yl)-3,4-dihydroxyl-N-methyltetrahydrofuran-2-carboxamide |
| 131 | 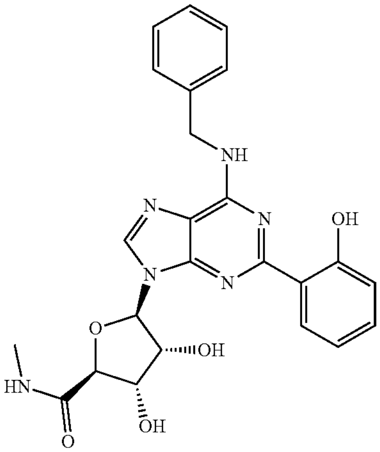 [SMILES: CNC(=O)[C@H]1O[C@@H](n2cnc3c(NCc4ccccc4)nc(-c4ccccc4O)nc32)[C@H](O)[C@@H]1O] | (2S,3S,4R,5R)-5-(6-(benzylamino)-2-(2-hydroxylphenyl)-9H-purin-9-yl)-3,4-dihydroxyl-N-methyltetrahydrofuran-2-carboxamide |

-continued
| Compd. No. | Structural formula of compound | Compound name |
|---|---|---|
| 132 | 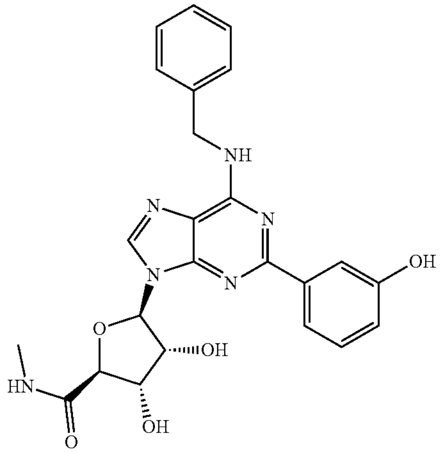 [SMILES: CNC(=O)[C@H]1O[C@@H](n2cnc3c(NCc4ccccc4)nc(-c4cccc(O)c4)nc32)[C@H](O)[C@@H]1O] | (2S,3S,4R,5R)-5-(6-(benzylamino)-2-(3-hydroxylphenyl)-9H-purin-9-yl)-3,4-dihydroxyl-N-methyltetrahydrofuran-2-carboxamide |
| 133 | 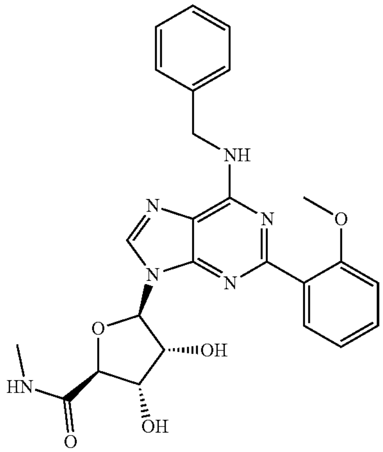 [SMILES: CNC(=O)[C@H]1O[C@@H](n2cnc3c(NCc4ccccc4)nc(-c4ccccc4OC)nc32)[C@H](O)[C@@H]1O] | (2S,3S,4R,5R)-5-(6-(benzylamino)-2-(2-methoxyphenyl)-9H-purin-9-yl)-3,4-dihydroxyl-N-methyltetrahydrofuran-2-carboxamide |
| 134 | 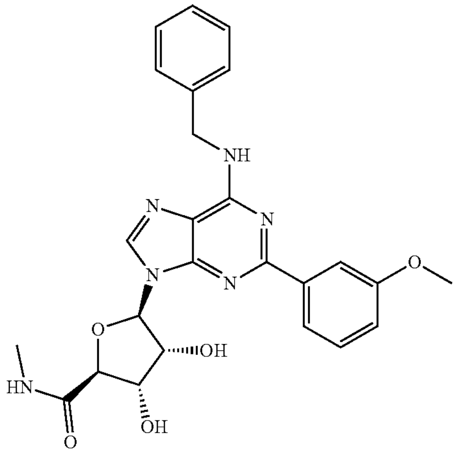 | (2S,3S,4R,5R)-5-(6-(benzylamino)-2-(3-methoxyphenyl)-9H-purin-9-yl)-3,4-dihydroxyl-N-methyltetrahydrofuran-2-carboxamide |

-continued

| Compd. No. | Structural formula of compound | Compound name |
|---|---|---|
| 135 | 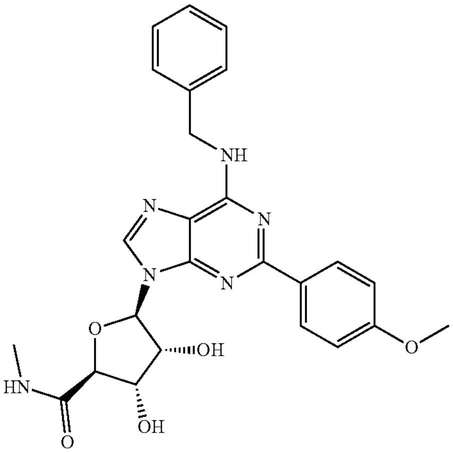 | (2S,3S,4R,5R)-5-(6-(benzylamino)-2-(4-methoxyphenyl)-9H-purin-9-yl)-3,4-dihydroxyl-N-methyltetrahydrofuran-2-carboxamide |
| 136 | 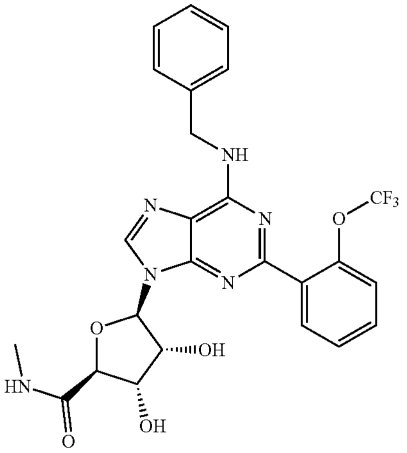 [SMILES: CNC(=O)[C@H]1O[C@@H](n2cnc3c(NCc4ccccc4)nc(-c4ccccc4OC(F)(F)F)nc32)[C@H](O)[C@@H]1O] | (2S,3S,4R,5R)-5-(6-(benzylamino)-2-(2-(trifluoromethoxy)phenyl)-9H-purin-9-yl)-3,4-dihydroxyl-N-methyltetrahydrofuran-2-carboxamide |
| 137 | 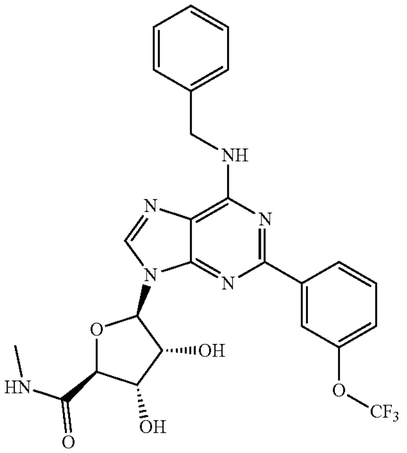 [SMILES: CNC(=O)[C@H]1O[C@@H](n2cnc3c(NCc4ccccc4)nc(-c4cccc(OC(F)(F)F)c4)nc32)[C@H](O)[C@@H]1O] | (2S,3S,4R,5R)-5-(6-(benzylamino)-2-(3-(trifluoromethoxy)phenyl)-9H-purin-9-yl)-3,4-dihydroxyl-N-methyltetrahydrofuran-2-carboxamide |

-continued

| Compd. No. | Structural formula of compound | Compound name |
| --- | --- | --- |
| 138 | 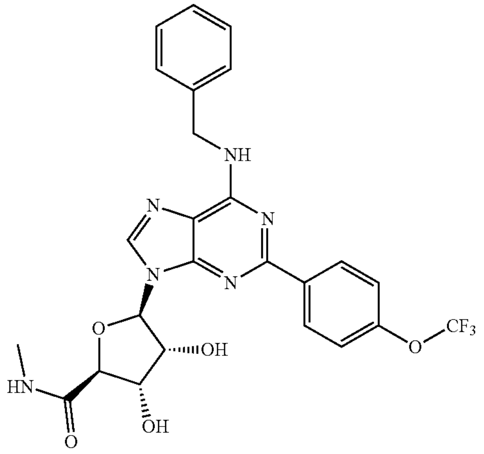 [SMILES: CNC(=O)[C@H]1O[C@@H](n2cnc3c(NCc4ccccc4)nc(-c4ccc(OC(F)(F)F)cc4)nc32)[C@H](O)[C@@H]1O] | (2S,3S,4R,5R)-5-(6-(benzylamino)-2-(4-(trifluoromethoxy)phenyl)-9H-purin-9-yl)-3,4-dihydroxyl-N-methyltetrahydrofuran-2-carboxamide |
| 139 | 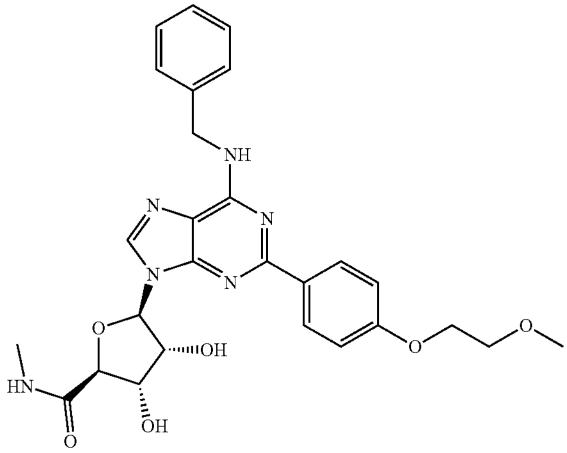 | (2S,3S,4R,5R)-5-(6-(benzylamino)-2-(4-(2-methoxyethoxy)phenyl)-9H-purin-9-yl)-3,4-dihydroxyl-N-methyltetrahydrofuran-2-carboxamide |
| 140 | 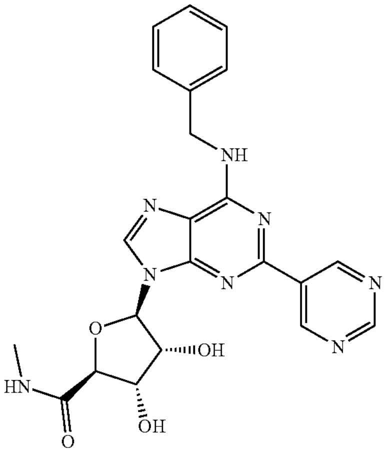 [SMILES: CNC(=O)[C@H]1O[C@@H](n2cnc3c(NCc4ccccc4)nc(-c4cncnc4)nc32)[C@H](O)[C@@H]1O] | (2S,3S,4R,5R)-5-(6-(benzylamino)-2-(pyrimidin-5-yl)-9H-purin-9-yl)-3,4-dihydroxyl-N-methyltetrahydrofuran-2-carboxamide |

-continued
| Compd. No. | Structural formula of compound | Compound name |
|---|---|---|
| 141 | 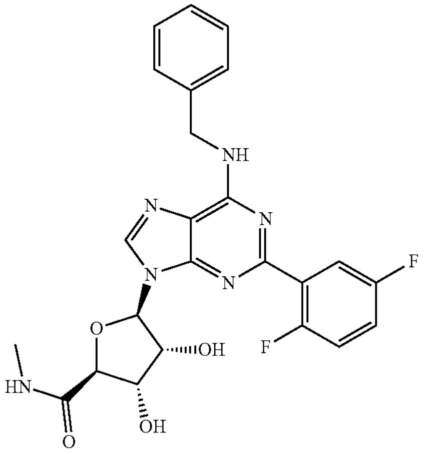 [SMILES: CNC(=O)[C@H]1O[C@@H](n2cnc3c(NCc4ccccc4)nc(-c4cc(F)ccc4F)nc32)[C@H](O)[C@@H]1O] | (2S,3S,4R,5R)-5-(6-(benzylamino)-2-(2,5-difluorophenyl)-9H-purin-9-yl)-3,4-dihydroxyl-N-methyltetrahydrofuran-2-carboxamide |
| 142 | 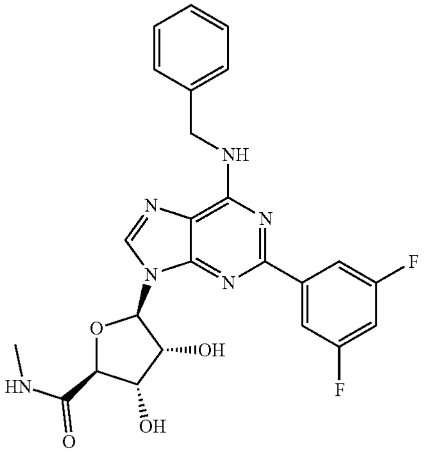 [SMILES: CNC(=O)[C@H]1O[C@@H](n2cnc3c(NCc4ccccc4)nc(-c4cc(F)cc(F)c4)nc32)[C@H](O)[C@@H]1O] | (2S,3S,4R,5R)-5-(6-(benzylamino)-2-(3,5-difluorophenyl)-9H-purin-9-yl)-3,4-dihydroxyl-N-methyltetrahydrofuran-2-carboxamide |
| 143 | 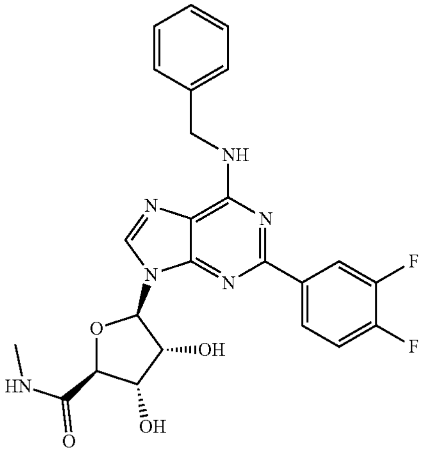 [SMILES: CNC(=O)[C@H]1O[C@@H](n2cnc3c(NCc4ccccc4)nc(-c4ccc(F)c(F)c4)nc32)[C@H](O)[C@@H]1O] | (2S,3S,4R,5R)-5-(6-(benzylamino)-2-(3,4-difluorophenyl)-9H-purin-9-yl)-3,4-dihydroxyl-N-methyltetrahydrofuran-2-carboxamide |

-continued
| Compd. No. | Structural formula of compound | Compound name |
|---|---|---|
| 144 | 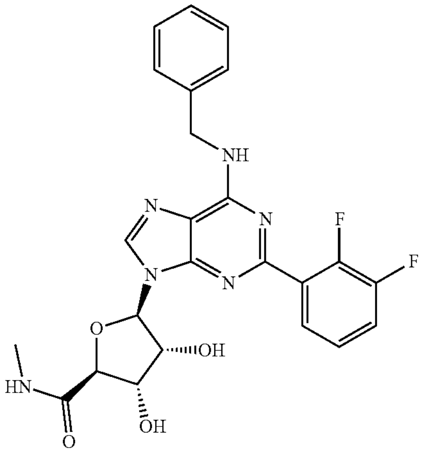 [SMILES: CNC(=O)[C@H]1O[C@@H](n2cnc3c(NCc4ccccc4)nc(-c4cccc(F)c4F)nc32)[C@H](O)[C@@H]1O] | (2S,3S,4R,5R)-5-(6-(benzylamino)-2-(2,3-difluorophenyl)-9H-purin-9-yl)-3,4-dihydroxyl-N-methyltetrahydrofuran-2-carboxamide |
| 145 | 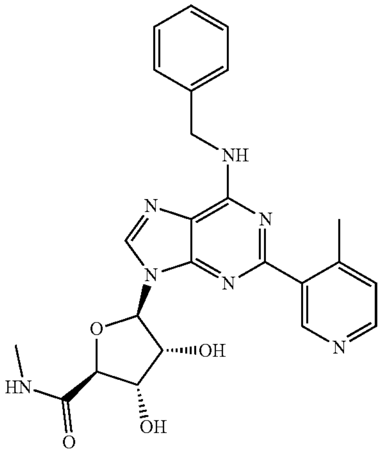 | (2S,3S,4R,5R)-5-(6-(benzylamino)-2-(4-methylpyridin-3-yl)-9H-purin-9-yl)-3,4-dihydroxyl-N-methyltetrahydrofuran-2-carboxamide |
| 146 | 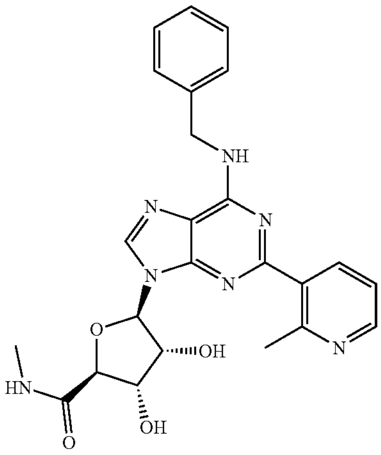 [SMILES: CNC(=O)[C@H]1O[C@@H](n2cnc3c(NCc4ccccc4)nc(-c4cccnc4C)nc32)[C@H](O)[C@@H]1O] | (2S,3S,4R,5R)-5-(6-(benzylamino)-2-(2-methylpyridin-3-yl)-9H-purin-9-yl)-3,4-dihydroxyl-N-methyltetrahydrofuran-2-carboxamide |

-continued
| Compd. No. | Structural formula of compound | Compound name |
|---|---|---|
| 147 | 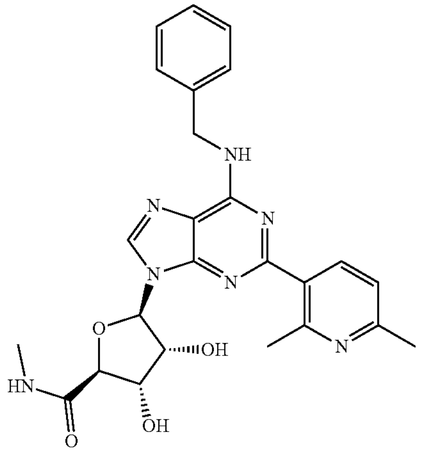 | (2S,3S,4R,5R)-5-(6-(benzylamino)-2-(2,6-dimethylpyridin-3-yl)-9H-purin-9-yl)-3,4-dihydroxyl-N-methyltetrahydrofuran-2-carboxamide |
| 148 | 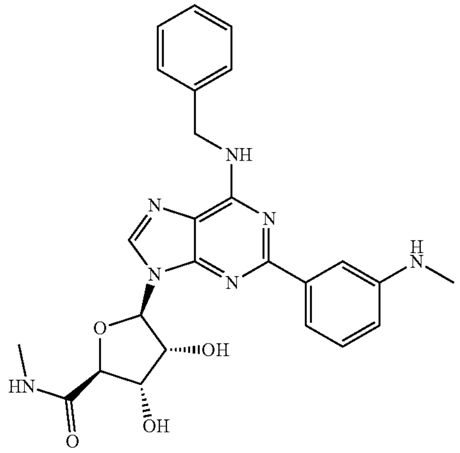 | (2S,3S,4R,5R)-5-(6-(benzylamino)-2-(3-(methylamino)phenyl)-9H-purin-9-yl)-3,4-dihydroxyl-N-methyltetrahydrofuran-2-carboxamide |
| 149 | 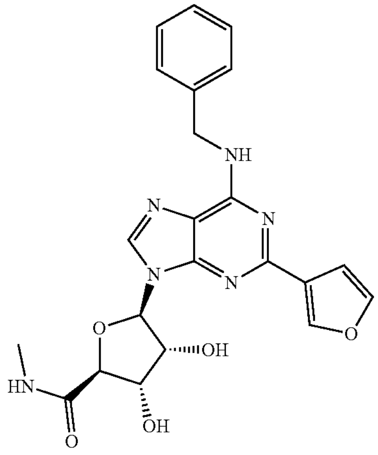 [SMILES: CNC(=O)[C@H]1O[C@@H](n2cnc3c(NCc4ccccc4)nc(-c4ccoc4)nc32)[C@H](O)[C@@H]1O] | (2S,3S,4R,5R)-5-(6-(benzylamino)-2-(furan-3-yl)-9H-purin-9-yl)-3,4-dihydroxyl-N-methyltetrahydrofuran-2-carboxamide |

-continued
| Compd. No. | Structural formula of compound | Compound name |
|---|---|---|
| 150 | 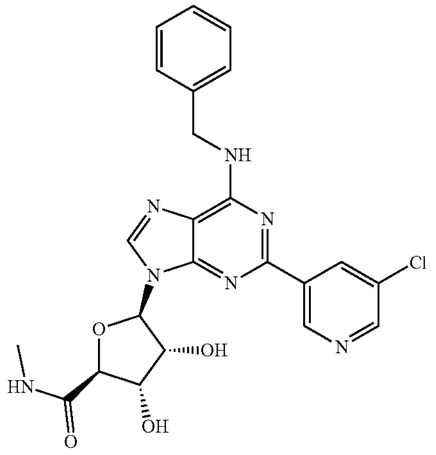 [SMILES: CNC(=O)[C@H]1O[C@@H](n2cnc3c(NCc4ccccc4)nc(-c4cncc(Cl)c4)nc32)[C@H](O)[C@@H]1O] | (2S,3S,4R,5R)-5-(6-(benzylamino)-2-(5-chloropyridin-3-yl)-9H-purin-9-yl)-3,4-dihydroxyl-N-methyltetrahydrofuran-2-carboxamide |
| 151 | 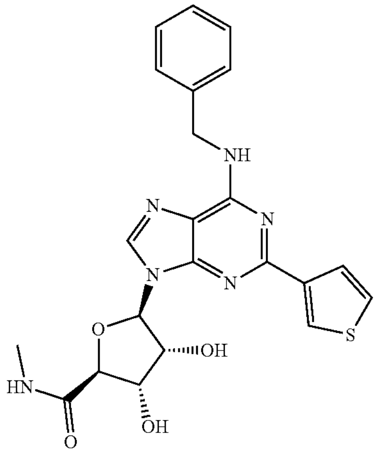 [SMILES: CNC(=O)[C@H]1O[C@@H](n2cnc3c(NCc4ccccc4)nc(-c4ccsc4)nc32)[C@H](O)[C@@H]1O] | (2S,3S,4R,5R)-5-(6-(benzylamino)-2-(thiophen-3-yl)-9H-purin-9-yl)-3,4-dihydroxyl-N-methyltetrahydrofuran-2-carboxamide |
| 152 | 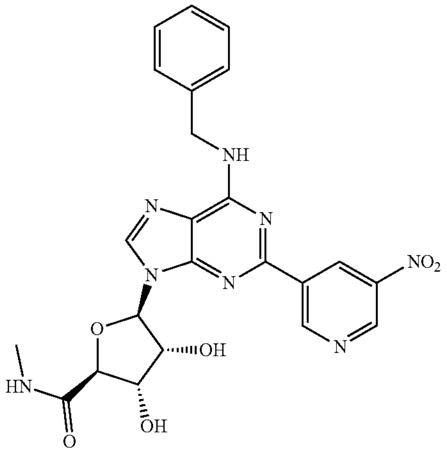 [SMILES: CNC(=O)[C@H]1O[C@@H](n2cnc3c(NCc4ccccc4)nc(-c4cncc([N+](=O)[O-])c4)nc32)[C@H](O)[C@@H]1O] | (2S,3S,4R,5R)-5-(6-(benzylamino)-2-(5-nitropyridin-3-yl)-9H-purin-9-yl)-3,4-dihydroxyl-N-methyltetrahydrofuran-2-carboxamide |

-continued
| Compd. No. | Structural formula of compound | Compound name |
| --- | --- | --- |
| 153 | 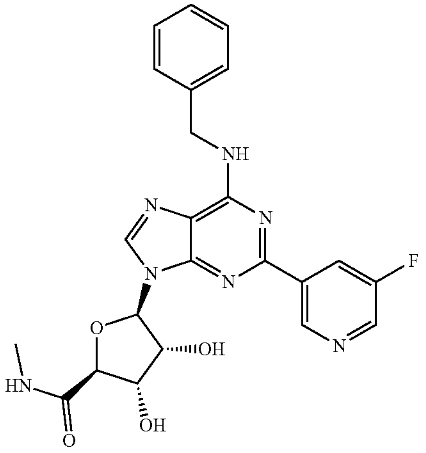 [SMILES: CNC(=O)[C@H]1O[C@@H](n2cnc3c(NCc4ccccc4)nc(-c4cncc(F)c4)nc32)[C@H](O)[C@@H]1O] | (2S,3S,4R,5R)-5-(6-(benzylamino)-2-(5-fluoropyridin-3-yl)-9H-purin-9-yl)-3,4-dihydroxyl-N-methyltetrahydrofuran-2-carboxamide |
| 154 | 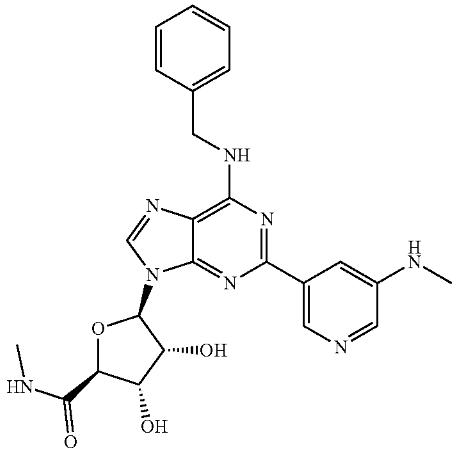 | (2S,3S,4R,5R)-5-(6-(benzylamino)-2-(5-(methylamino)pyridin-3-yl)-9H-purin-9-yl)-3,4-dihydroxyl-N-methyltetrahydrofuran-2-carboxamide |
| 155 | 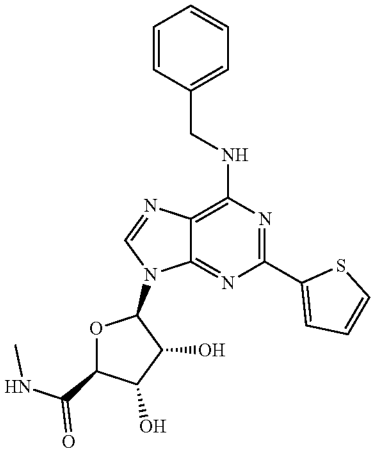 | (2S,3S,4R,5R)-5-(6-(benzylamino)-2-(thiophen-2-yl)-9H-purin-9-yl)-3,4-dihydroxyl-N-methyltetrahydrofuran-2-carboxamide |

-continued

| Compd. No. | Structural formula of compound | Compound name |
|---|---|---|
| 156 | 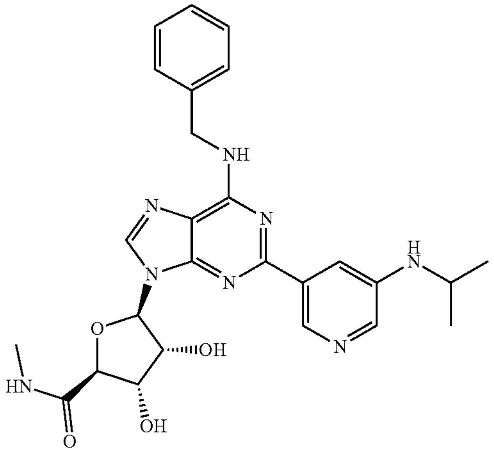 [SMILES: CNC(=O)[C@H]1O[C@@H](n2cnc3c(NCc4ccccc4)nc(-c4cncc(NC(C)C)c4)nc32)[C@H](O)[C@@H]1O] | (2S,3S,4R,5R)-5-(6-(benzylamino)-2-(5-(isopropylamino)pyridin-3-yl)-9H-purin-9-yl)-3,4-dihydroxyl-N-methyltetrahydrofuran-2-carboxamide |
| 157 | 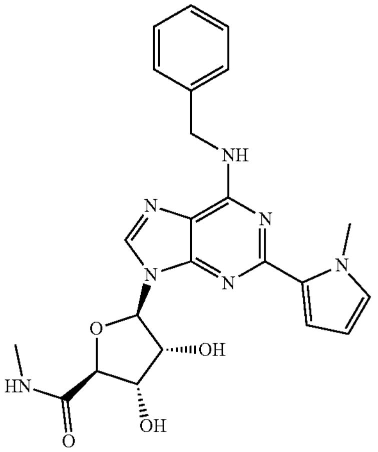 [SMILES: CNC(=O)[C@H]1O[C@@H](n2cnc3c(NCc4ccccc4)nc(-c4cccn4C)nc32)[C@H](O)[C@@H]1O] | (2S,3S,4R,5R)-5-(6-(benzylamino)-2-(1-methyl-1H-pyrrol-2-yl)-9H-purin-9-yl)-3,4-dihydroxyl-N-methyltetrahydrofuran-2-carboxamide |
| 158 | 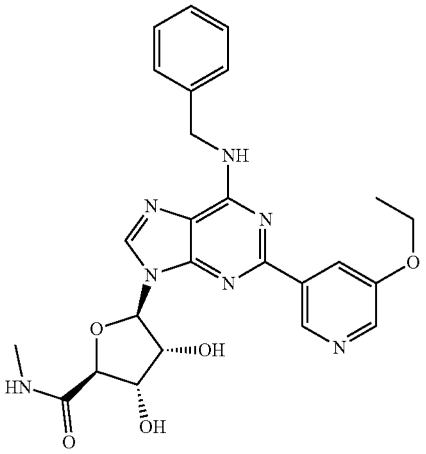 [SMILES: CCOc1cncc(-c2nc(NCc3ccccc3)c3ncn([C@@H]4O[C@H](C(=O)NC)[C@@H](O)[C@H]4O)c3n2)c1] | (2S,3S,4R,5R)-5-(6-(benzylamino)-2-(5-ethoxypyridin-3-yl)-9H-purin-9-yl)-3,4-dihydroxyl-N-methyltetrahydrofuran-2-carboxamide |

-continued

| Compd. No. | Structural formula of compound | Compound name |
|---|---|---|
| 159 | 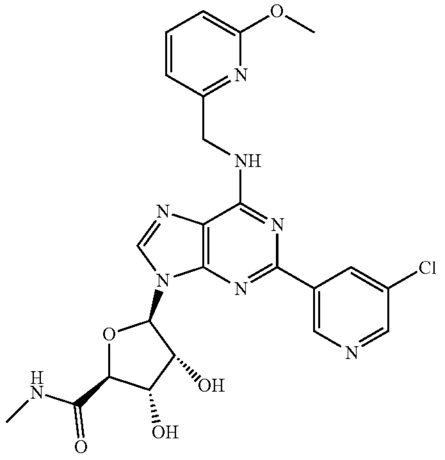 [SMILES: CNC(=O)[C@H]1O[C@@H](n2cnc3c(NCc4cccc(OC)n4)nc(-c4cncc(Cl)c4)nc32)[C@H](O)[C@@H]1O] | (2S,3S,4R,5R)-5-(2-(5-chloropyridin-3-yl)-6-((((6-methoxypyridin-2-yl)methyl)amino)-9H-purin-9-yl)-3,4-dihydroxyl-N-methyltetrahydrofuran-2-carboxamide |
| 160 | 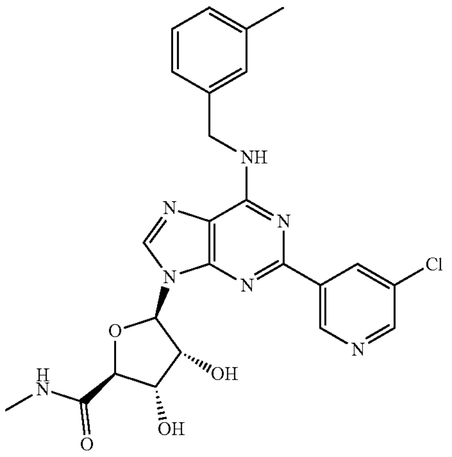 [SMILES: CNC(=O)[C@H]1O[C@@H](n2cnc3c(NCc4cccc(C)c4)nc(-c4cncc(Cl)c4)nc32)[C@H](O)[C@@H]1O] | (2S,3S,4R,5R)-5-(2-(5-chloropyridin-3-yl)-6-((3-methylbenzyl)amino)-9H-purin-9-yl)-3,4-dihydroxyl-N-methyltetrahydrofuran-2-carboxamide |
| 161 | 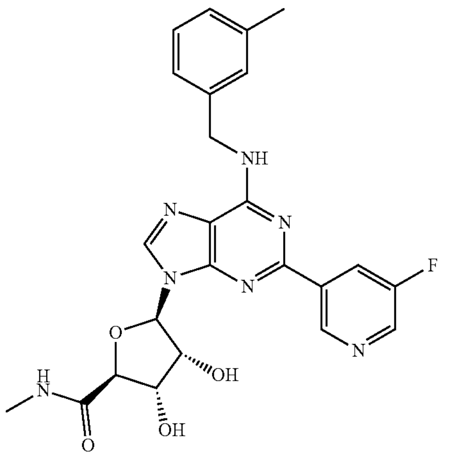 [SMILES: CNC(=O)[C@H]1O[C@@H](n2cnc3c(NCc4cccc(C)c4)nc(-c4cncc(F)c4)nc32)[C@H](O)[C@@H]1O] | (2S,3S,4R,5R)-5-(2-(5-fluoropyridin-3-yl)-6-((3-methylbenzyl)amino)-9H-purin-9-yl)-3,4-dihydroxyl-N-methyltetrahydrofuran-2-carboxamide |

-continued

| Compd. No. | Structural formula of compound | Compound name |
|---|---|---|
| 162 | 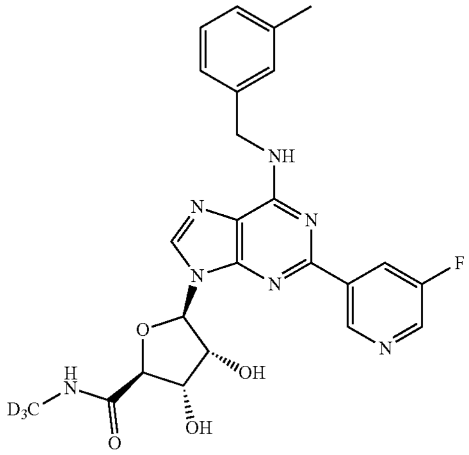 [SMILES: [2H]C([2H])([2H])NC(=O)[C@H]1O[C@@H](n2cnc3c(NCc4cccc(C)c4)nc(-c4cncc(F)c4)nc32)[C@H](O)[C@@H]1O] | (2S,3S,4R,5R)-5-(2-(5-fluoropyridin-3-yl)-6-((3-methylbenzyl)amino)-9H-purin-9-yl)-3,4-dihydroxyl-N-(methyl-d3)-tetrahydrofuran-2-carboxamide |
| 163 | 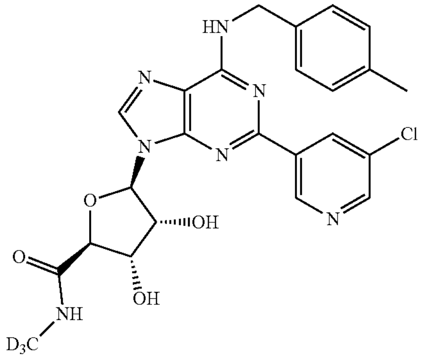 | (2S,3S,4R,5R)-5-(6-(p-methylphenylmethylamino)-2-(5-chloropyridin-3-yl)-9H-purin-9-yl)-3,4-dihydroxyl-N-(methyl-d3)-tetrahydrofuran-2-formamide |
| 164 | 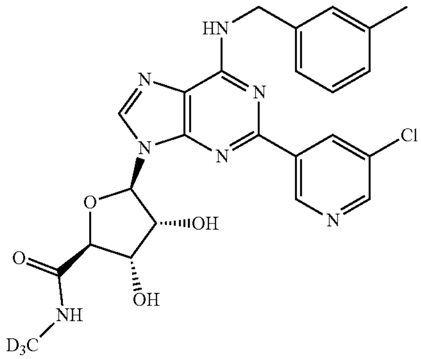 [SMILES: [2H]C([2H])([2H])NC(=O)[C@H]1O[C@@H](n2cnc3c(NCc4cccc(C)c4)nc(-c4cncc(Cl)c4)nc32)[C@H](O)[C@@H]1O] | (2S,3S,4R,5R)-5-(6-(m-methylphenylmethylamino)-2-(5-chloropyridin-3-yl)-9H-purin-9-yl)-3,4-dihydroxyl-N-(methyl-d3)-tetrahydrofuran-2-formamide |
| 165 | 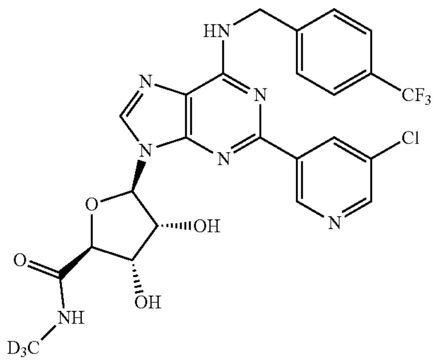 [SMILES: [2H]C([2H])([2H])NC(=O)[C@H]1O[C@@H](n2cnc3c(NCc4ccc(C(F)(F)F)cc4)nc(-c4cncc(Cl)c4)nc32)[C@H](O)[C@@H]1O] | (2S,3S,4R,5R)-5-(6-(4-(trifluoromethyl)benzylamino)-2-(5-chloropyridin-3-yl)-9H-purin-9-yl)-3,4-dihydroxyl-N-(methyl-d3)-tetrahydrofuran-2-formamide |

-continued

| Compd. No. | Structural formula of compound | Compound name |
|---|---|---|
| 166 | 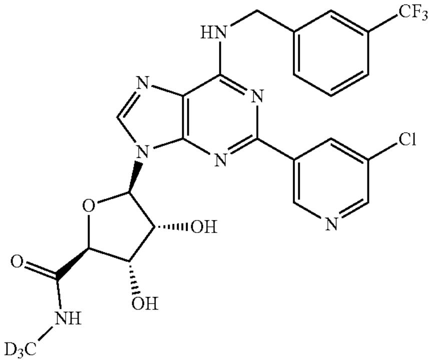 [SMILES: [2H]C([2H])([2H])NC(=O)[C@H]1O[C@@H](n2cnc3c(NCc4cccc(C(F)(F)F)c4)nc(-c4cncc(Cl)c4)nc32)[C@H](O)[C@@H]1O] | (2S,3S,4R,5R)-5-(6-(3-(trifluoromethyl)benzylamino)-2-(5-chloropyridin-3-yl)-9H-purin-9-yl)-3,4-dihydroxyl-N-(methyl-d3)-tetrahydrofuran-2-formamide |
| 167 | 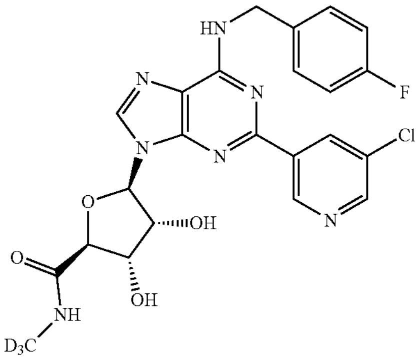 | (2S,3S,4R,5R)-5-(6-(4-fluorobenzylamino)-2-(5-chloropyridin-3-yl)-9H-purin-9-yl)-3,4-dihydroxyl-N-(methyl-d3)-tetrahydrofuran-2-formamide |
| 168 | 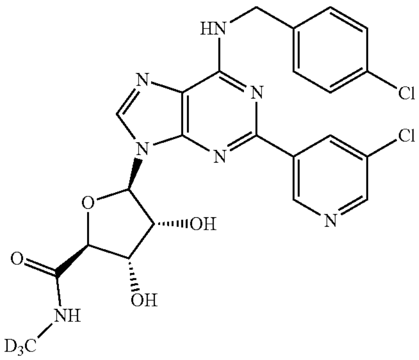 | (2S,3S,4R,5R)-5-(6-(4-chlorobenzylamino)-2-(5-chloropyridin-3-yl)-9H-purin-9-yl)-3,4-dihydroxyl-N-(methyl-d3)-tetrahydrofuran-2-formamide |
| 169 | 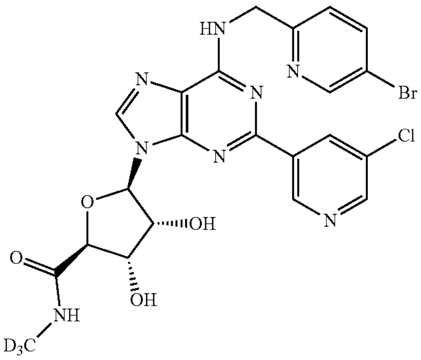 [SMILES: [2H]C([2H])([2H])NC(=O)[C@H]1O[C@@H](n2cnc3c(NCc4ccc(Br)cn4)nc(-c4cncc(Cl)c4)nc32)[C@H](O)[C@@H]1O] | (2S,3S,4R,5R)-5-(6-((5-bromopyridin-2-yl)methylamino)-2-(5-chloropyridin-3-yl)-9H-purin-9-yl)-3,4-dihydroxyl-N-(methyl-d3)-tetrahydrofuran-2-formamide |

-continued

| Compd. No. | Structural formula of compound | Compound name |
|---|---|---|
| 170 | 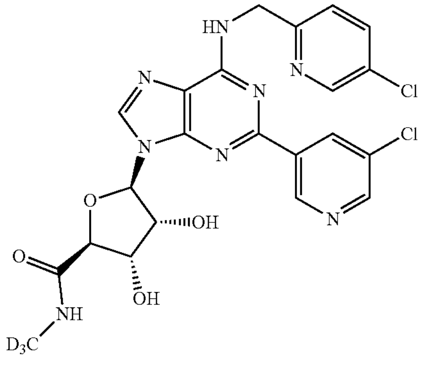 | (2S,3S,4R,5R)-5-(6-((5-chloropyridin-2-yl)methylamino)-2-(5-chloropyridin-3-yl)-9H-purin-9-yl)-3,4-dihydroxyl-N-(methyl-d3)-tetrahydrofuran-2-formamide |
| 171 | 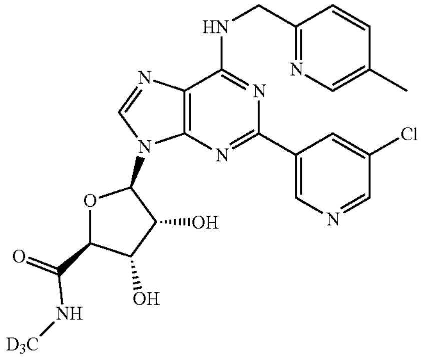 | (2S,3S,4R,5R)-5-(2-(5-chloropyridin-3-yl)-6-((5-methylpyridin-2-yl)methylamino)-9H-purin-9-yl)-3,4-dihydroxyl-N-(methyl-d3)-tetrahydrofuran-2-formamide |
| 172 | 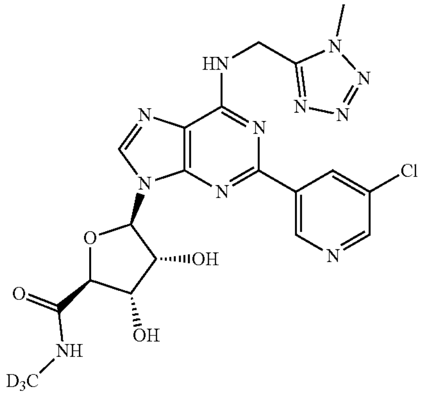 [SMILES: [2H]C([2H])([2H])NC(=O)[C@H]1O[C@@H](n2cnc3c(NCc4nnnn4C)nc(-c4cncc(Cl)c4)nc32)[C@H](O)[C@@H]1O] | (2S,3S,4R,5R)-5-(2-(5-chloropyridin-3-yl)-6-((1-methyl-1H-tetrazol-5-yl)methylamino)-9H-purin-9-yl)-3,4-dihydroxyl-N-(methyl-d3)-tetrahydrofuran-2-formamide |
| 173 | 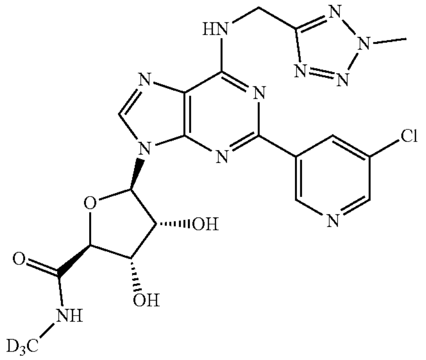 [SMILES: [2H]C([2H])([2H])NC(=O)[C@H]1O[C@@H](n2cnc3c(NCc4nnn(C)n4)nc(-c4cncc(Cl)c4)nc32)[C@H](O)[C@@H]1O] | (2S,3S,4R,5R)-5-(2-(5-chloropyridin-3-yl)-6-((2-methyl-2H-tetrazol-5-yl)methylamino)-9H-purin-9-yl)-3,4-dihydroxyl-N-(methyl-d3)-tetrahydrofuran-2-formamide |

-continued

| Compd. No. | Structural formula of compound | Compound name |
|---|---|---|
| 174 | 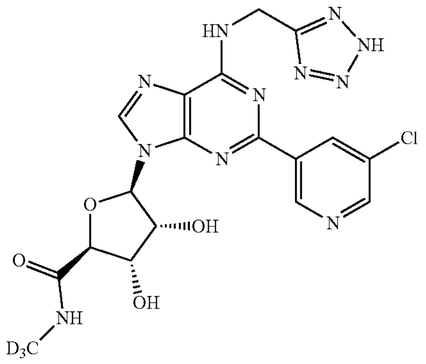 [SMILES: [2H]C([2H])([2H])NC(=O)[C@H]1O[C@@H](n2cnc3c(NCc4nn[nH]n4)nc(-c4cncc(Cl)c4)nc32)[C@H](O)[C@@H]1O] | (2S,3S,4R,5R)-5-(6-((1H-tetrazol-5-yl)methylamino)-2-(5-chloropyridin-3-yl)-9H-purin-9-yl)-3,4-dihydroxyl-N-(methyl-d3)-tetrahydrofuran-2-formamide |
| 175 | 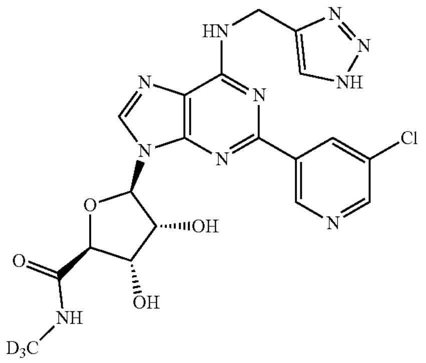 [SMILES: [2H]C([2H])([2H])NC(=O)[C@H]1O[C@@H](n2cnc3c(NCc4c[nH]nn4)nc(-c4cncc(Cl)c4)nc32)[C@H](O)[C@@H]1O] | (2S,3S,4R,5R)-5-(6-((1H-1,2,3-thiazol-4-yl)methylamino)-2-(5-chloropyridin-3-yl)-9H-purin-9-yl)-3,4-dihydroxyl-N-(methyl-d3)-tetrahydrofuran-2-formamide |
| 176 | 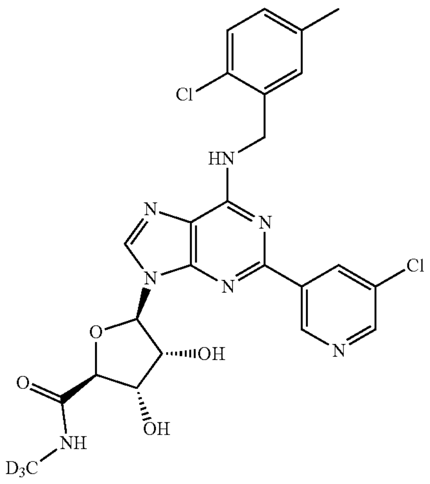 [SMILES: [2H]C([2H])([2H])NC(=O)[C@H]1O[C@@H](n2cnc3c(NCc4cc(C)ccc4Cl)nc(-c4cncc(Cl)c4)nc32)[C@H](O)[C@@H]1O] | (2S,3S,4R,5R)-5-(6-(2-chloro-5-methylbenzylamino)-2-(5-chloropyridin-3-yl)-9H-purin-9-yl)-3,4-dihydroxyl-N-(methyl-d3)-tetrahydrofuran-2-formamide |

-continued

| Compd. No. | Structural formula of compound | Compound name |
|---|---|---|
| 177 | 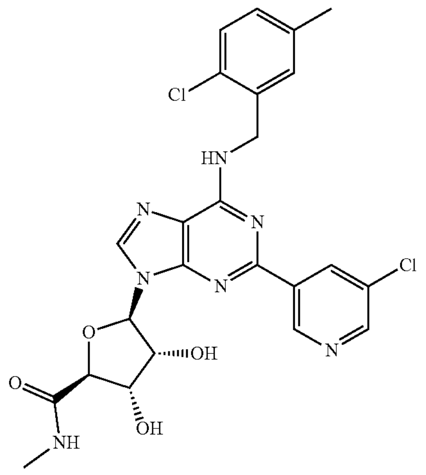 [SMILES: CNC(=O)[C@H]1O[C@@H](n2cnc3c(NCc4cc(C)ccc4Cl)nc(-c4cncc(Cl)c4)nc32)[C@H](O)[C@@H]1O] | (2S,3S,4R,5R)-5-(6-(2-chloro-5-methylbenzylamino)-2-(5-chloropyridin-3-yl)-9H-purin-9-yl)-3,4-dihydroxyl-N-methyl-tetrahydrofuran-2-formamide |
| 178 | 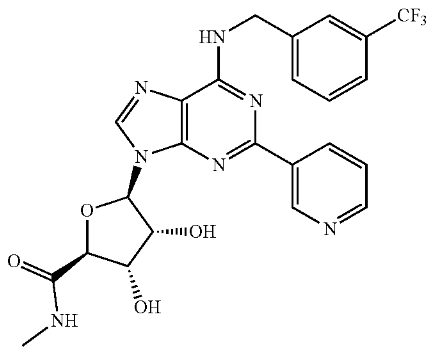 [SMILES: CNC(=O)[C@H]1O[C@@H](n2cnc3c(NCc4cccc(C(F)(F)F)c4)nc(-c4cccnc4)nc32)[C@H](O)[C@@H]1O] | (2S,3S,4R,5R)-5-(6-(3-(trifluoromethyl)benzylamino)-2-(pyridin-3-yl)-9H-purin-9-yl)-3,4-dihydroxyl-N-methyl-tetrahydrofuran-2-formamide |
| 179 | 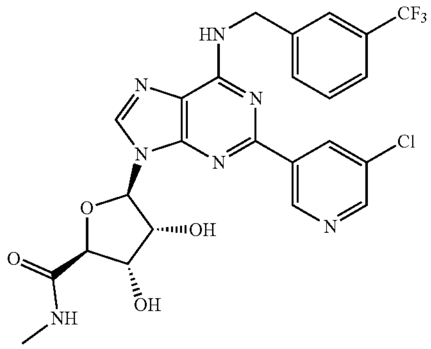 | (2S,3S,4R,5R)-5-(6-(3-(trifluoromethyl)benzylamino)-2-(5-chloropyridin-3-yl)-9H-purin-9-yl)-3,4-dihydroxyl-N-methyl-tetrahydrofuran-2-formamide |
| 180 | 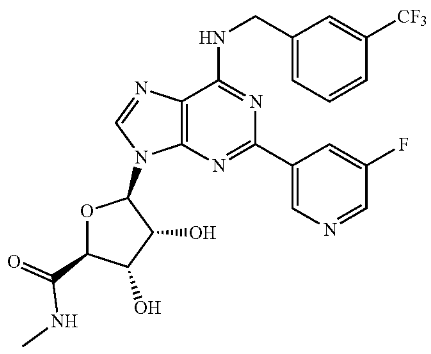 [SMILES: CNC(=O)[C@H]1O[C@@H](n2cnc3c(NCc4cccc(C(F)(F)F)c4)nc(-c4cncc(F)c4)nc32)[C@H](O)[C@@H]1O] | (2S,3S,4R,5R)-5-(6-(3-(trifluoromethyl)benzylamino)-2-(5-fluoropyridin-3-yl)-9H-purin-9-yl)-3,4-dihydroxyl-N-methyl-tetrahydrofuran-2-formamide |

-continued

| Compd. No. | Structural formula of compound | Compound name |
|---|---|---|
| 181 | 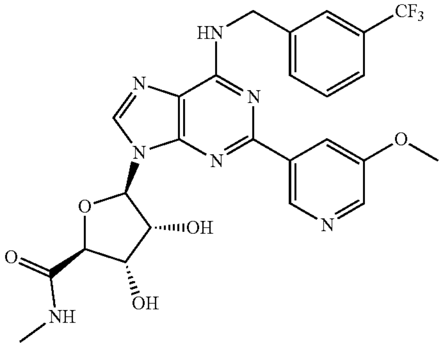 | (2S,3S,4R,5R)-5-(6-(3-(trifluoromethyl)benzylamino)-2-(5-methoxypyridin-3-yl)-9H-purin-9-yl)-3,4-dihydroxyl-N-methyl-tetrahydrofuran-2-formamide |
| 182 | 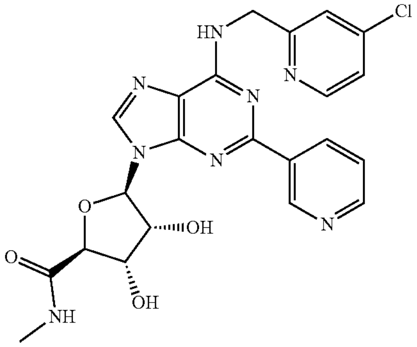 [SMILES: CNC(=O)[C@H]1O[C@@H](n2cnc3c(NCc4cc(Cl)ccn4)nc(-c4cccnc4)nc32)[C@H](O)[C@@H]1O] | (2S,3S,4R,5R)-5-(6-((4-chloropyridin-2-yl)methylamino)-2-(pyridin-3-yl)-9H-purin-9-yl)-3,4-dihydroxyl-N-methyl-tetrahydrofuran-2-formamide |
| 183 | 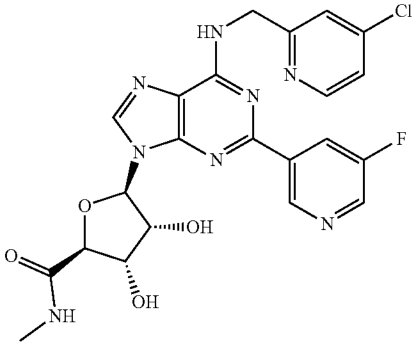 [SMILES: CNC(=O)[C@H]1O[C@@H](n2cnc3c(NCc4cc(Cl)ccn4)nc(-c4cncc(F)c4)nc32)[C@H](O)[C@@H]1O] | (2S,3S,4R,5R)-5-(6-((4-chloropyridin-2-yl)methylamino)-2-(5-fluoropyridin-3-yl)-9H-purin-9-yl)-3,4-dihydroxyl-N-methyl-tetrahydrofuran-2-formamide |
| 184 | 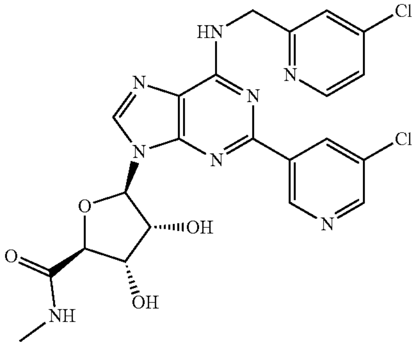 [SMILES: CNC(=O)[C@H]1O[C@@H](n2cnc3c(NCc4cc(Cl)ccn4)nc(-c4cncc(Cl)c4)nc32)[C@H](O)[C@@H]1O] | (2S,3S,4R,5R)-5-(6-((4-chloropyridin-2-yl)methylamino)-2-(5-chloropyridin-3-yl)-9H-purin-9-yl)-3,4-dihydroxyl-N-methyl-tetrahydrofuran-2-formamide |

-continued

| Compd. No. | Structural formula of compound | Compound name |
|---|---|---|
| 185 | 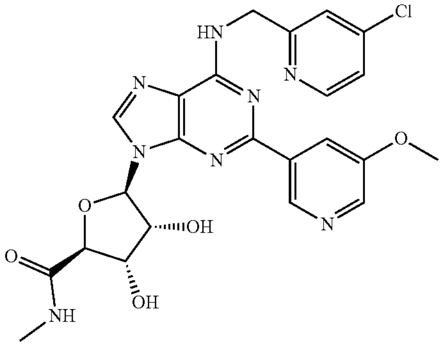 | (2S,3S,4R,5R)-5-(6-((4-chloropyridin-2-yl)methylamino)-2-(5-methoxypyridin-3-yl)-9H-purin-9-yl)-3,4-dihydroxyl-N-methyl-tetrahydrofuran-2-formamide |
| 186 | 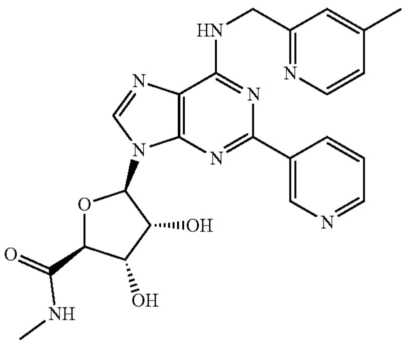 [SMILES: CNC(=O)[C@H]1O[C@@H](n2cnc3c(NCc4cc(C)ccn4)nc(-c4cccnc4)nc32)[C@H](O)[C@@H]1O] | (2S,3S,4R,5R)-3,4-dihydroxyl-N-methyl-5-(6-((4-methylpyridin-2-yl)methylamino)-2-(pyridin-3-yl)-9H-purin-9-yl)-tetrahydrofuran-2-formamide |
| 187 | 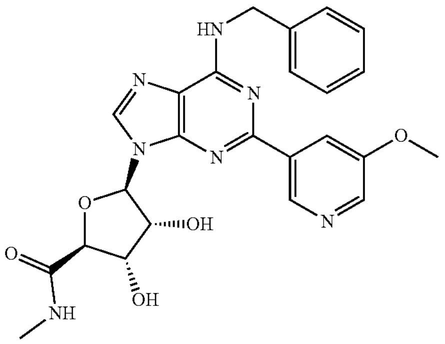 [SMILES: CNC(=O)[C@H]1O[C@@H](n2cnc3c(NCc4ccccc4)nc(-c4cncc(OC)c4)nc32)[C@H](O)[C@@H]1O] | (2S,3S,4R,5R)-5-(6-(benzylamino)-2-(5-methoxypyridin-3-yl)-9H-purin-9-yl)-3,4-dihydroxyl-N-methyl-tetrahydrofuran-2-formamide |
| 188 | 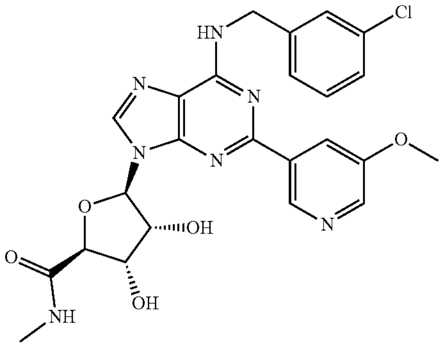 | (2S,3S,4R,5R)-5-(6-(3-chlorobenzylamino)-2-(5-methoxypyridin-3-yl)-9H-purin-9-yl)-3,4-dihydroxyl-N-methyl-tetrahydrofuran-2-formamide |

-continued

| Compd. No. | Structural formula of compound | Compound name |
|---|---|---|
| 189 | 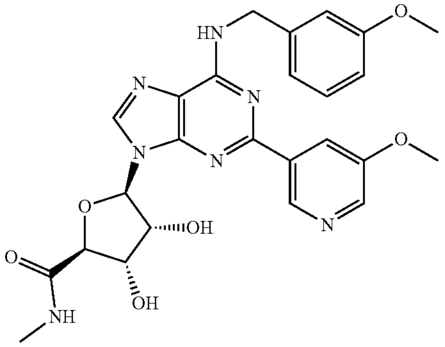 | (2S,3S,4R,5R)-5-(6-(3-methoxybenzylamino)-2-(5-methoxypyridin-3-yl)-9H-purin-9-yl)-3,4-dihydroxyl-N-methyl-tetrahydrofuran-2-formamide |
| 190 | 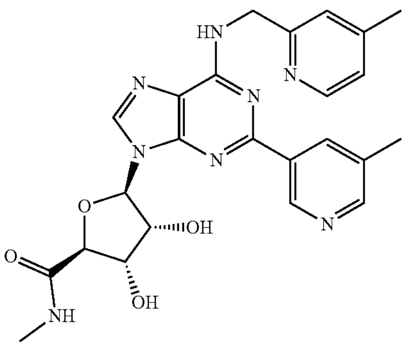 [SMILES: CNC(=O)[C@H]1O[C@@H](n2cnc3c(NCc4cc(C)ccn4)nc(-c4cncc(C)c4)nc32)[C@H](O)[C@@H]1O] | (2S,3S,4R,5R)-3,4-dihydroxyl-N-methyl-5-(6-((4-methylpyridin-2-yl)methylamino)-2-(5-methylpyridin-3-yl)-9H-purin-9-yl)-tetrahydrofuran-2-formamide |
| 191 | 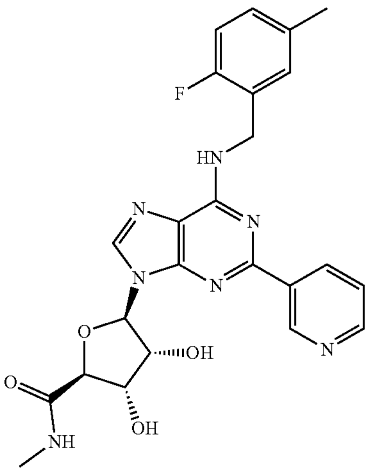 [SMILES: CNC(=O)[C@H]1O[C@@H](n2cnc3c(NCc4cc(C)ccc4F)nc(-c4cccnc4)nc32)[C@H](O)[C@@H]1O] | (2S,3S,4R,5R)-5-(6-(2-fluoro-5-methylbenzylamino)-2-(pyridin-3-yl)-9H-purin-9-yl)-3,4-dihydroxyl-N-methyl-tetrahydrofuran-2-formamide |

-continued

| Compd. No. | Structural formula of compound | Compound name |
|---|---|---|
| 192 | 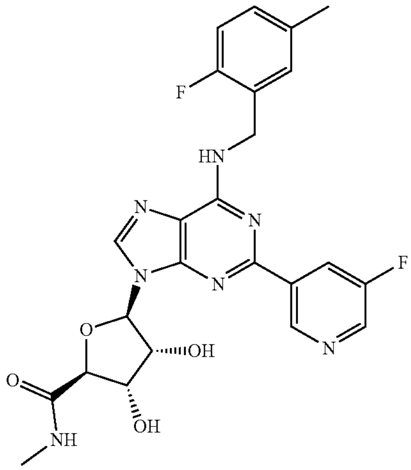 [SMILES: CNC(=O)[C@H]1O[C@@H](n2cnc3c(NCc4cc(C)ccc4F)nc(-c4cncc(F)c4)nc32)[C@H](O)[C@@H]1O] | (2S,3S,4R,5R)-5-(6-(2-fluoro-5-methylbenzylamino)-2-(5-fluoropyridin-3-yl)-9H-purin-9-yl)-3,4-dihydroxyl-N-methyl-tetrahydrofuran-2-formamide |
| 193 | 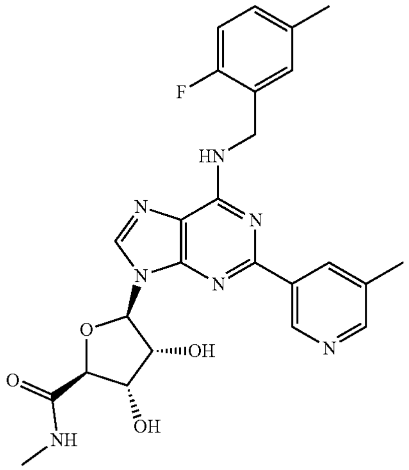 [SMILES: CNC(=O)[C@H]1O[C@@H](n2cnc3c(NCc4cc(C)ccc4F)nc(-c4cncc(C)c4)nc32)[C@H](O)[C@@H]1O] | (2S,3S,4R,5R)-5-(6-(2-fluoro-5-methylbenzylamino)-2-(5-methylpyridin-3-yl)-9H-purin-9-yl)-3,4-dihydroxyl-N-methyl-tetrahydrofuran-2-formamide |
| 194 | 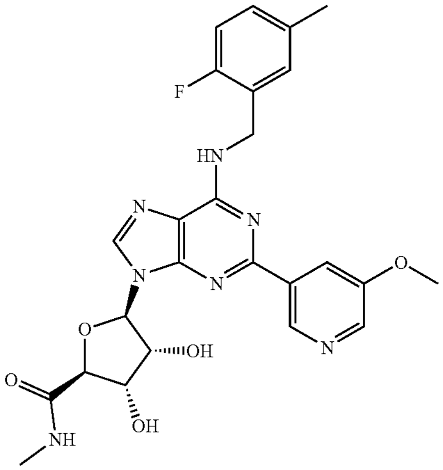 [SMILES: CNC(=O)[C@H]1O[C@@H](n2cnc3c(NCc4cc(C)ccc4F)nc(-c4cncc(OC)c4)nc32)[C@H](O)[C@@H]1O] | (2S,3S,4R,5R)-5-(6-(2-fluoro-5-methylbenzylamino)-2-(5-methoxypyridin-3-yl)-9H-purin-9-yl)-3,4-dihydroxyl-N-methyl-tetrahydrofuran-2-formamide |

-continued

| Compd. No. | Structural formula of compound | Compound name |
|---|---|---|
| 195 | 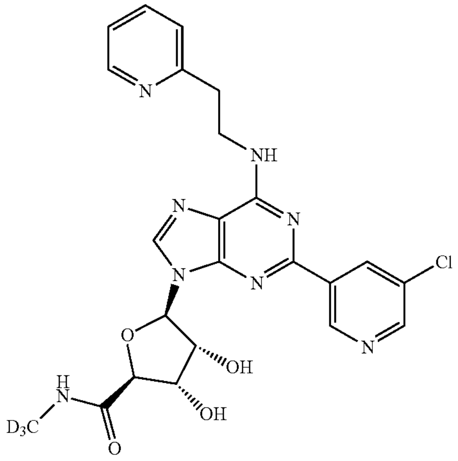 [SMILES: [2H]C([2H])([2H])NC(=O)[C@H]1O[C@@H](n2cnc3c(NCCc4ccccn4)nc(-c4cncc(Cl)c4)nc32)[C@H](O)[C@@H]1O] | (2S,3S,4R,5R)-5-(2-(5-chloropyridin-3-yl)-6-((2-(pyridin-2-yl)ethyl)amino)-9H-purin-9-yl)-3,4-dihydroxyl-N-(methyl-d3)-tetrahydrofuran-2-carboxamide |
| 196 | 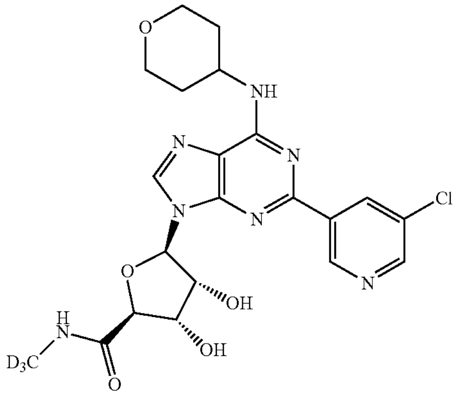 [SMILES: [2H]C([2H])([2H])NC(=O)[C@H]1O[C@@H](n2cnc3c(NC4CCOCC4)nc(-c4cncc(Cl)c4)nc32)[C@H](O)[C@@H]1O] | (2S,3S,4R,5R)-5-(2-(5-chloropyridin-3-yl)-6-((tetrahydro-2H-pyridin-4-yl)amino)-9H-purin-9-yl)-3,4-dihydroxyl-N-(methyl-d3)-tetrahydrofuran-2-carboxamide |
| 197 | 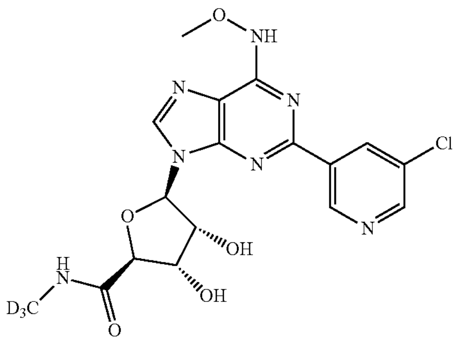 [SMILES: [2H]C([2H])([2H])NC(=O)[C@H]1O[C@@H](n2cnc3c(NOC)nc(-c4cncc(Cl)c4)nc32)[C@H](O)[C@@H]1O] | (2S,3S,4R,5R)-5-(2-(5-chloropyridin-3-yl)-6-(methoxyamino)-9H-purin-9-yl)-3,4-dihydroxyl-N-(methyl-d3)-tetrahydrofuran-2-carboxamide |

-continued

| Compd. No. | Structural formula of compound | Compound name |
|---|---|---|
| 198 | 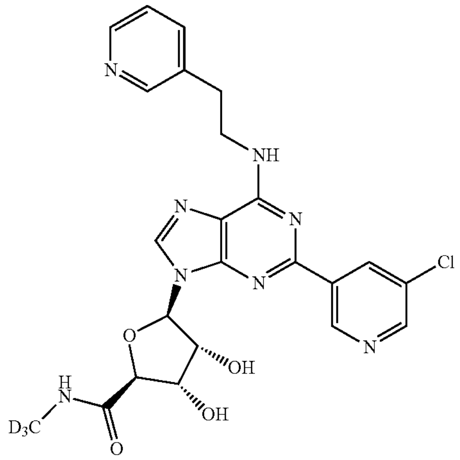 [SMILES: [2H]C([2H])([2H])NC(=O)[C@H]1O[C@@H](n2cnc3c(NCCc4cccnc4)nc(-c4cncc(Cl)c4)nc32)[C@H](O)[C@@H]1O] | (2S,3S,4R,5R)-5-(2-(5-chloropyridin-3-yl)-6-((2-(pyridin-3-yl)ethyl)amino)-9H-purin-9-yl)-3,4-dihydroxyl-N-(methyl-d3)-tetrahydrofuran-2-carboxamide |
| 199 | 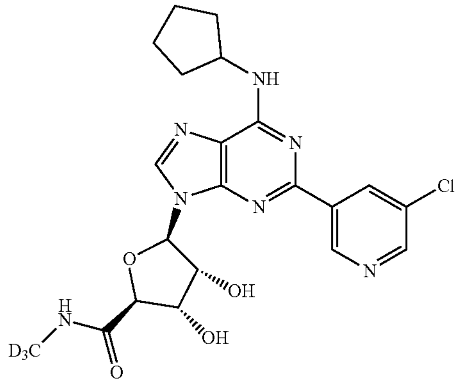 [SMILES: [2H]C([2H])([2H])NC(=O)[C@H]1O[C@@H](n2cnc3c(NC4CCCC4)nc(-c4cncc(Cl)c4)nc32)[C@H](O)[C@@H]1O] | (2S,3S,4R,5R)-5-(2-(5-chloropyridin-3-yl)-6-(cyclopentylamino)-9H-purin-9-yl)-3,4-dihydroxyl-N-(methyl-d3)-tetrahydrofuran-2-carboxamide |
| 200 | 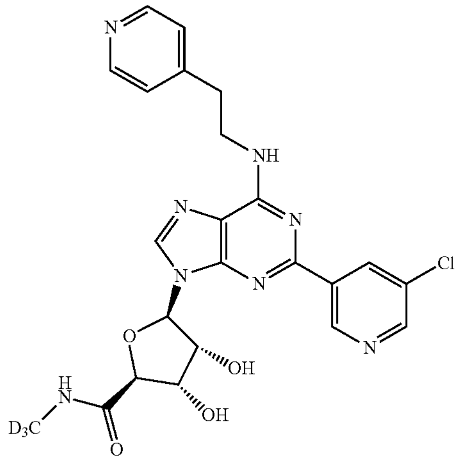 [SMILES: [2H]C([2H])([2H])NC(=O)[C@H]1O[C@@H](n2cnc3c(NCCc4ccncc4)nc(-c4cncc(Cl)c4)nc32)[C@H](O)[C@@H]1O] | (2S,3S,4R,5R)-5-(2-(5-chloropyridin-3-yl)-6-((2-(pyridin-4-yl)ethyl)amino)-9H-purin-9-yl)-3,4-dihydroxyl-N-(methyl-d3)-tetrahydrofuran-2-carboxamide |

-continued

| Compd. No. | Structural formula of compound | Compound name |
|---|---|---|
| 201 | 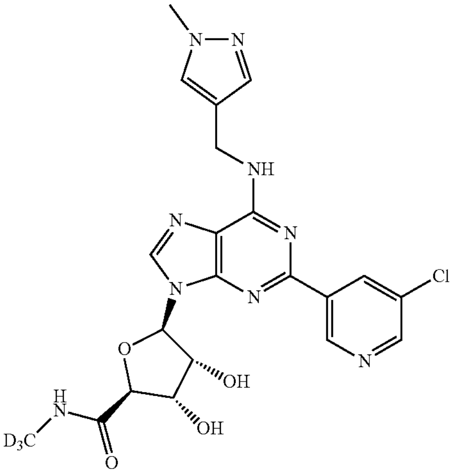 [SMILES: [2H]C([2H])([2H])NC(=O)[C@H]1O[C@@H](n2cnc3c(NCc4cnn(C)c4)nc(-c4cncc(Cl)c4)nc32)[C@H](O)[C@@H]1O] | (2S,3S,4R,5R)-5-(2-(5-chloropyridin-3-yl)-6-((((1-methyl-1H-pyrazol-4-yl)methyl)amino)-9H-purin-9-yl)-3,4-dihydroxyl-N-(methyl-d3)-tetrahydrofuran-2-carboxamide |
| 202 | 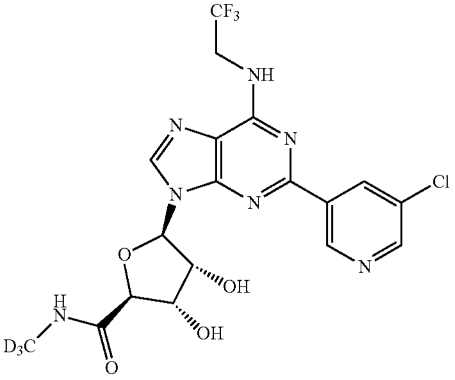 [SMILES: [2H]C([2H])([2H])NC(=O)[C@H]1O[C@@H](n2cnc3c(NCC(F)(F)F)nc(-c4cncc(Cl)c4)nc32)[C@H](O)[C@@H]1O] | (2S,3S,4R,5R)-5-(2-(5-chloropyridin-3-yl)-6-(((2,2,2-trifluoroethyl)amino)-9H-purin-9-yl)-3,4-dihydroxyl-N-(methyl-d3)-tetrahydrofuran-2-carboxamide |
| 203 | 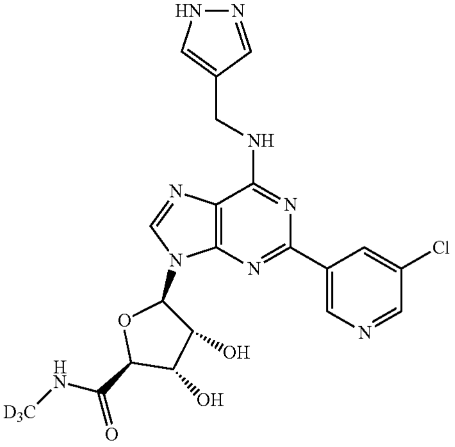 [SMILES: [2H]C([2H])([2H])NC(=O)[C@H]1O[C@@H](n2cnc3c(NCc4cn[nH]c4)nc(-c4cncc(Cl)c4)nc32)[C@H](O)[C@@H]1O] | (2S,3S,4R,5R)-5-(6-((((1H-pyrazol-4-yl)methyl)amino)amino)-2-(5-chloropyridin-3-yl)-9H-purin-9-yl)-3,4-dihydroxyl-N-(methyl-d3)-tetrahydrofuran-2-carboxamide |

-continued

| Compd. No. | Structural formula of compound | Compound name |
|---|---|---|
| 204 | 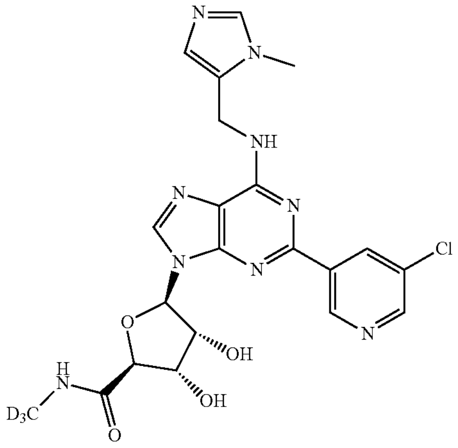 [SMILES: [2H]C([2H])([2H])NC(=O)[C@H]1O[C@@H](n2cnc3c(NCc4cncn4C)nc(-c4cncc(Cl)c4)nc32)[C@H](O)[C@@H]1O] | (2S,3S,4R,5R)-5-(2-(5-chloropyridin-3-yl)-6-((((1-methyl-1H-imidazol-5-yl)methyl)amino)-9H-purin-9-yl)-3,4-dihydroxyl-N-(methyl-d3)-tetrahydrofuran-2-carboxamide |
| 205 | 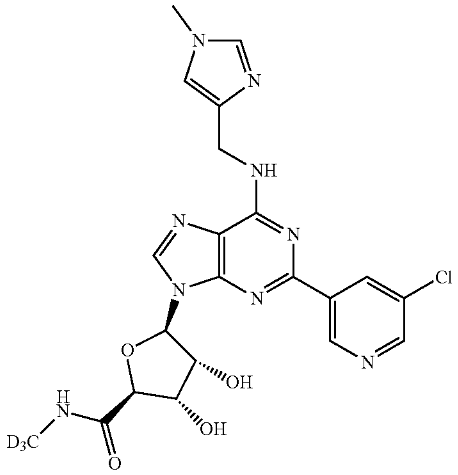 [SMILES: [2H]C([2H])([2H])NC(=O)[C@H]1O[C@@H](n2cnc3c(NCc4cn(C)cn4)nc(-c4cncc(Cl)c4)nc32)[C@H](O)[C@@H]1O] | (2S,3S,4R,5R)-5-(2-(5-chloropyridin-3-yl)-6-((((1-methyl-1H-imidazol-4-yl)methyl)amino)-9H-purin-9-yl)-3,4-dihydroxyl-N-(methyl-d3)-tetrahydrofuran-2-carboxamide |
| 206 | 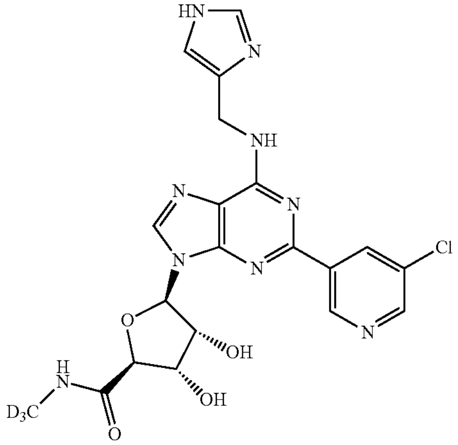 [SMILES: [2H]C([2H])([2H])NC(=O)[C@H]1O[C@@H](n2cnc3c(NCc4c[nH]cn4)nc(-c4cncc(Cl)c4)nc32)[C@H](O)[C@@H]1O] | (2S,3S,4R,5R)-5-(6-((((1H-imidazol-4-yl)methyl)amino-2-(5-chloropyridin-3-yl)-9H-purin-9-yl)-3,4-dihydroxyl-N-(methyl-d3)-tetrahydrofuran-2-carboxamide |

-continued

| Compd. No. | Structural formula of compound | Compound name |
|---|---|---|
| 207 | 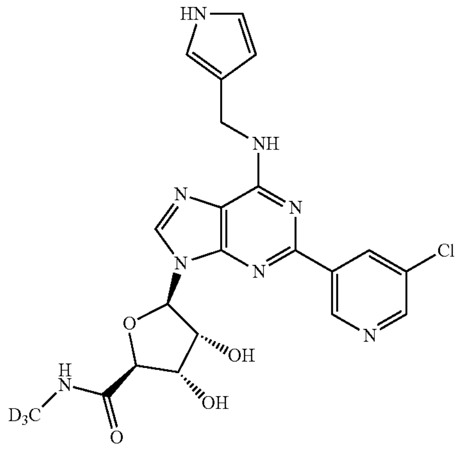 [SMILES: [2H]C([2H])([2H])NC(=O)[C@H]1O[C@@H](n2cnc3c(NCc4cc[nH]c4)nc(-c4cncc(Cl)c4)nc32)[C@H](O)[C@@H]1O] | (2S,3S,4R,5R)-5-(6-((((1H-pyrrol-3-yl)methyl)amino-2-(5-chloropyridin-3-yl)-9H-purin-9-yl)-3,4-dihydroxyl-N-(methyl-d3)-tetrahydrofuran-2-carboxamide |
| 208 | 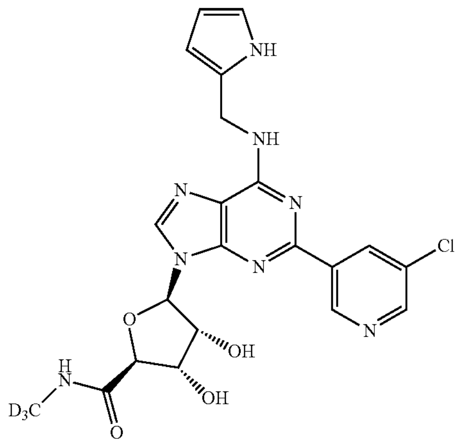 [SMILES: [2H]C([2H])([2H])NC(=O)[C@H]1O[C@@H](n2cnc3c(NCc4ccc[nH]4)nc(-c4cncc(Cl)c4)nc32)[C@H](O)[C@@H]1O] | (2S,3S,4R,5R)-5-(6-((((1H-pyrrol-2-yl)methyl)amino-2-(5-chloropyridin-3-yl)-9H-purin-9-yl)-3,4-dihydroxyl-N-(methyl-d3)-tetrahydrofuran-2-carboxamide |
| 209 | 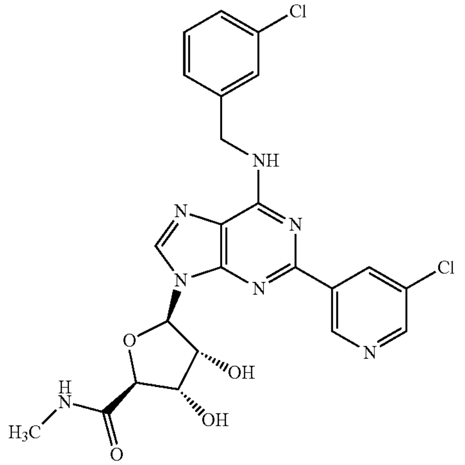 | (2S,3S,4R,5R)-5-(6-((3-chlorobenzyl))amino-2-(5-chloropyridin-3-yl)-9H-purin-9-yl)-3,4-dihydroxyl-N-methyltetrahydrofuran-2-carboxamide |

-continued

| Compd. No. | Structural formula of compound | Compound name |
|---|---|---|
| 210 | 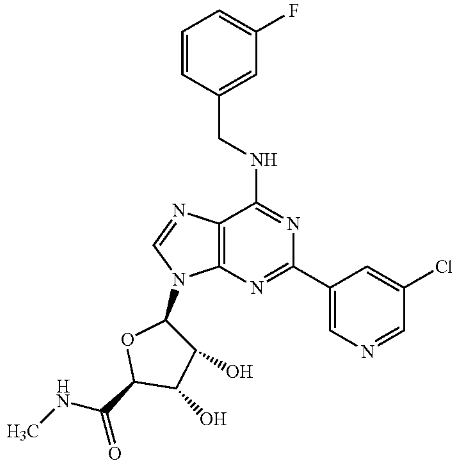 [SMILES: CNC(=O)[C@H]1O[C@@H](n2cnc3c(NCc4cccc(F)c4)nc(-c4cncc(Cl)c4)nc32)[C@H](O)[C@@H]1O] | (2S,3S,4R,5R)-5-(2-(5-chloropyridin-3-yl)-6-((3-fluorobenzyl))amino-9H-purin-9-yl)-3,4-dihydroxyl-N-methyltetrahydrofuran-2-carboxamide |
| 211 | 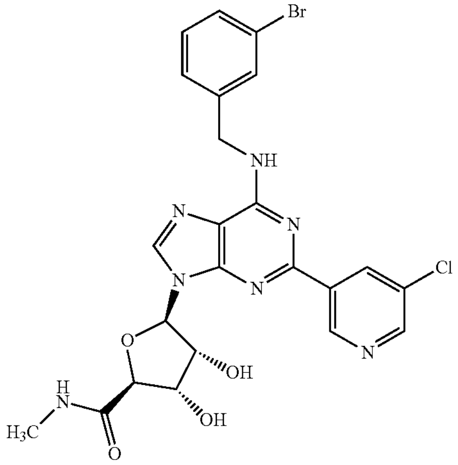 [SMILES: CNC(=O)[C@H]1O[C@@H](n2cnc3c(NCc4cccc(Br)c4)nc(-c4cncc(Cl)c4)nc32)[C@H](O)[C@@H]1O] | (2S,3S,4R,5R)-5-(6-((3-bromobenzyl))amino-2-(5-chloropyridin-3-yl)-9H-purin-9-yl)-3,4-dihydroxyl-N-methyltetrahydrofuran-2-carboxamide |
| 212 | 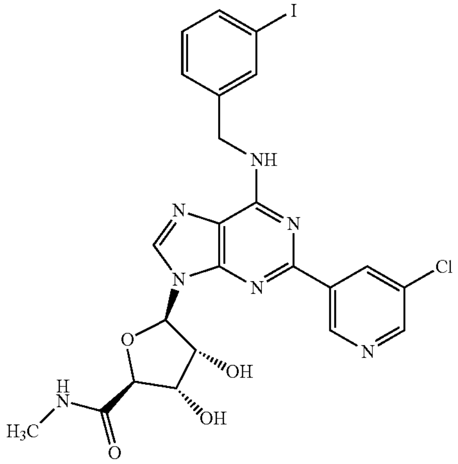 [SMILES: CNC(=O)[C@H]1O[C@@H](n2cnc3c(NCc4cccc(I)c4)nc(-c4cncc(Cl)c4)nc32)[C@H](O)[C@@H]1O] | (3aS,4S,6R,6aR)-6-(2-(5-chloropyridin-3-yl)-6-((3-iodobenzyl)amino)-9H-purin-9-yl)-N,2,2-trimethyltetrahydrofuran[3,4-d][1,3]dioxazol-4-carboxamide |

-continued

| Compd. No. | Structural formula of compound | Compound name |
| --- | --- | --- |
| 213 | 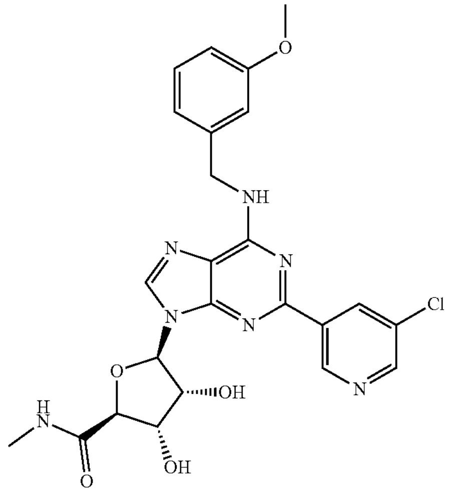 [SMILES: CNC(=O)[C@H]1O[C@@H](n2cnc3c(NCc4cccc(OC)c4)nc(-c4cncc(Cl)c4)nc32)[C@H](O)[C@@H]1O] | (2S,3S,4R,5S)-5-(2-(5-chloropyridin-3-yl)-6-((3-methoxybenzyl)amino)-9H-purin-9-yl)-3,4-dihydroxyl-N-methyltetrahydrofuran-2-carboxamide |
| 214 | 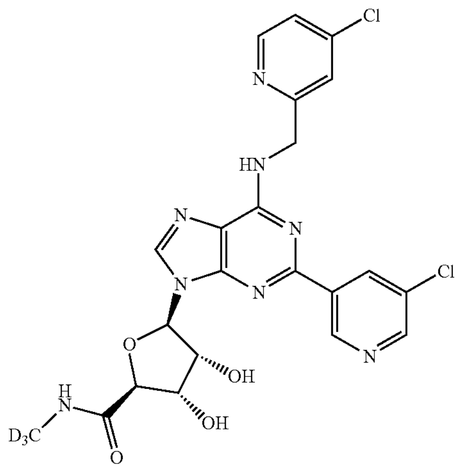 [SMILES: [2H]C([2H])([2H])NC(=O)[C@H]1O[C@@H](n2cnc3c(NCc4cc(Cl)ccn4)nc(-c4cncc(Cl)c4)nc32)[C@H](O)[C@@H]1O] | (2S,3S,4R,5R)-5-(6-(((4-chloropyridin-2-yl)methyl)amino-2-(5-chloropyridin-3-yl)-9H-purin-9-yl)-3,4-dihydroxyl-N-(methyl-d3)-tetrahydrofuran-2-carboxamide |
| 215 | 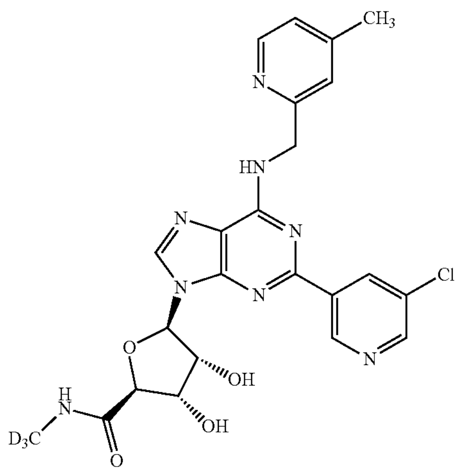 [SMILES: [2H]C([2H])([2H])NC(=O)[C@H]1O[C@@H](n2cnc3c(NCc4cc(C)ccn4)nc(-c4cncc(Cl)c4)nc32)[C@H](O)[C@@H]1O] | (2S,3S,4R,5R)-5-(2-(5-chloropyridin-3-yl)-6-(((4-methylpyridin-2-yl)methyl)amino)-9H-purin-9-yl)-3,4-dihydroxyl-N-(methyl-d3)-tetrahydrofuran-2-carboxamide |

-continued

| Compd. No. | Structural formula of compound | Compound name |
| --- | --- | --- |
| 216 | 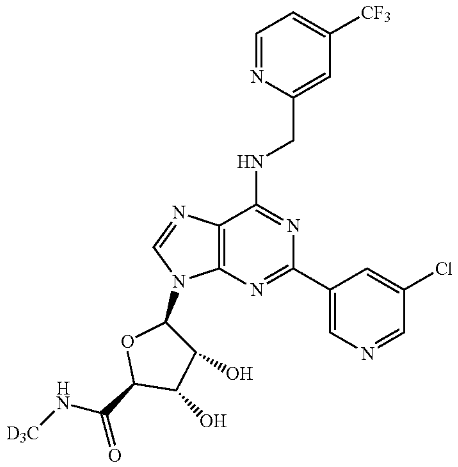 [SMILES: [2H]C([2H])([2H])NC(=O)[C@H]1O[C@@H](n2cnc3c(NCc4cc(C(F)(F)F)ccn4)nc(-c4cncc(Cl)c4)nc32)[C@H](O)[C@@H]1O] | (2S,3S,4R,5R)-5-(2-(5-chloropyridin-3-yl)-6-((((4-(trifluoromethyl)pyridin-2-yl)methyl)amino)-9H-purin-9-yl)-3,4-dihydroxyl-N-(methyl-d3)-tetrahydrofuran-2-carboxamide |
| 217 | 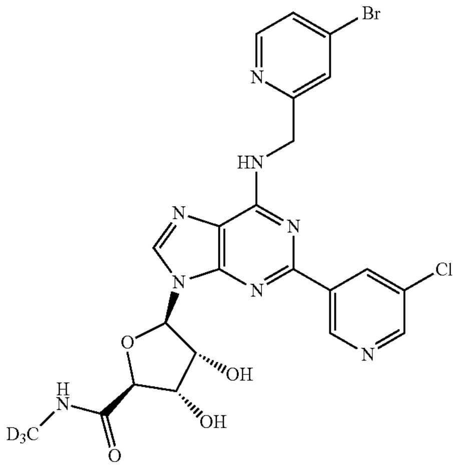 [SMILES: [2H]C([2H])([2H])NC(=O)[C@H]1O[C@@H](n2cnc3c(NCc4cc(Br)ccn4)nc(-c4cncc(Cl)c4)nc32)[C@H](O)[C@@H]1O] | (2S,3S,4R,5R)-5-(6-(((4-bromopyridin-2-yl)methyl)amino)-2-(5-chloropyridin-3-yl)-9H-purin-9-yl)-3,4-dihydroxyl-N-(methyl-d3)-tetrahydrofuran-2-carboxamide |
| 218 | 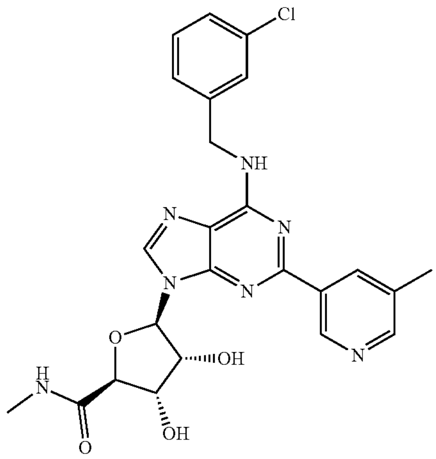 | (2S,3S,4R,5S)-5-(6-((3-chlorobenzyl)amino)-2-(5-methylpyridin-3-yl)-9H-purin-9-yl)-3,4-dihydroxyl-N-methyltetrahydrofuran-2-carboxamide |

-continued

| Compd. No. | Structural formula of compound | Compound name |
|---|---|---|
| 219 | 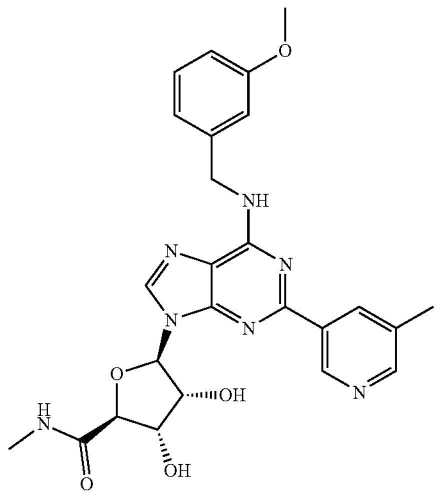 | (2S,3S,4R,5S)-3,4-dihydroxyl-5-(6-((3-methoxybenzyl)amino)-2-(5-methylpyridin-3-yl)-9H-purin-9-yl)-N-methyltetrahydrofuran-2-carboxamide |
| 220 | 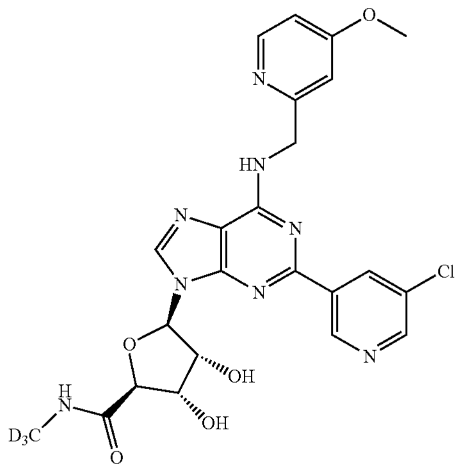 [SMILES: [2H]C([2H])([2H])NC(=O)[C@H]1O[C@@H](n2cnc3c(NCc4cc(OC)ccn4)nc(-c4cncc(Cl)c4)nc32)[C@H](O)[C@@H]1O] | (2S,3S,4R,5R)-5-(2-(5-chloropyridin-3-yl)-6-((3-methoxybenzyl)amino)-9H-purin-9-yl)-3,4-dihydroxyl-N-(methyl-d3)-tetrahydrofuran-2-carboxamide |
| 221 | 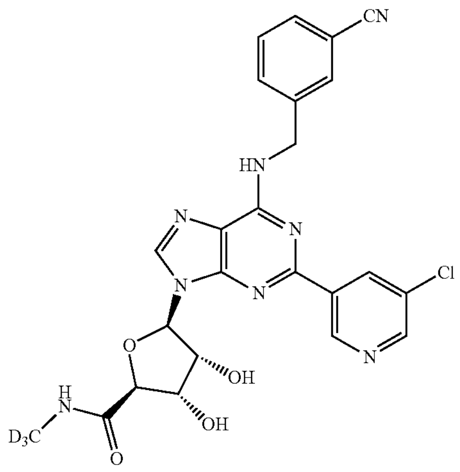 [SMILES: [2H]C([2H])([2H])NC(=O)[C@H]1O[C@@H](n2cnc3c(NCc4cccc(C#N)c4)nc(-c4cncc(Cl)c4)nc32)[C@H](O)[C@@H]1O] | (2S,3S,4R,5R)-5-(2-(5-chloropyridin-3-yl)-6-((3-cyanobenzyl)amino)-9H-purin-9-yl)-3,4-dihydroxyl-N-(methyl-d3)-tetrahydrofuran-2-carboxamide |

-continued

| Compd. No. | Structural formula of compound | Compound name |
|---|---|---|
| 222 | 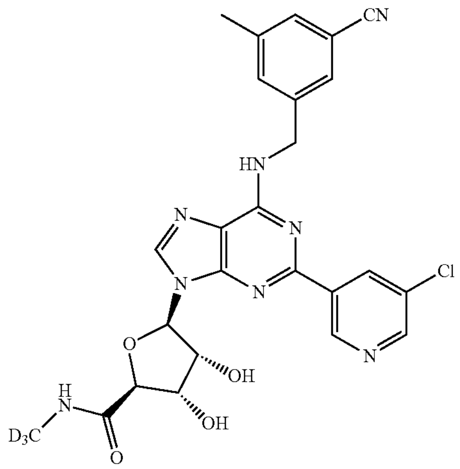 [SMILES: [2H]C([2H])([2H])NC(=O)[C@H]1O[C@@H](n2cnc3c(NCc4cc(C)cc(C#N)c4)nc(-c4cncc(Cl)c4)nc32)[C@H](O)[C@@H]1O] | (2S,3S,4R,5R)-5-(6-((3-chloro-5-methylbenzyl)amino)-2-(5-chloropyridin-3-yl)-9H-purin-9-yl)-3,4-dihydroxyl-N-(methyl-d3)-tetrahydrofuran-2-carboxamide |
| 223 | 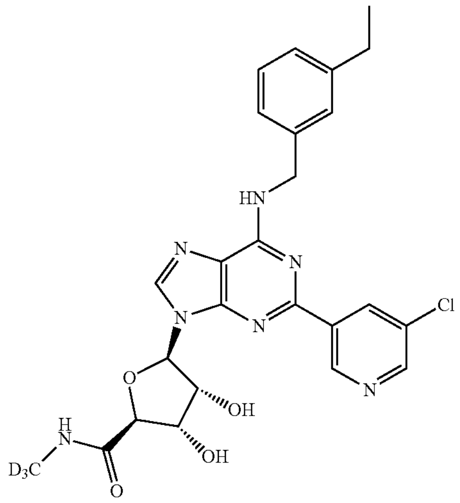 [SMILES: [2H]C([2H])([2H])NC(=O)[C@H]1O[C@@H](n2cnc3c(NCc4cccc(CC)c4)nc(-c4cncc(Cl)c4)nc32)[C@H](O)[C@@H]1O] | (2S,3S,4R,5R)-5-(2-(5-chloropyridin-3-yl)-6-((3-ethylbenzyl)amino)-9H-purin-9-yl)-3,4-dihydroxyl-N-(methyl-d3)-tetrahydrofuran-2-carboxamide |
| 224 | 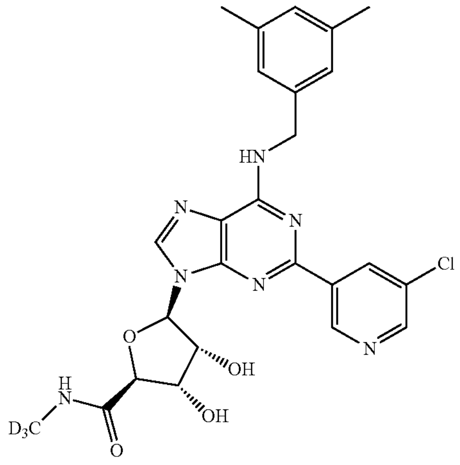 [SMILES: [2H]C([2H])([2H])NC(=O)[C@H]1O[C@@H](n2cnc3c(NCc4cc(C)cc(C)c4)nc(-c4cncc(Cl)c4)nc32)[C@H](O)[C@@H]1O] | (2S,3S,4R,5R)-5-(2-(5-chloropyridin-3-yl)-6-((3,5-dimethylbenzyl)amino)-9H-purin-9-yl)-3,4-dihydroxyl-N-(methyl-d3)-tetrahydrofuran-2-carboxamide |

-continued

| Compd. No. | Structural formula of compound | Compound name |
| --- | --- | --- |
| 225 | 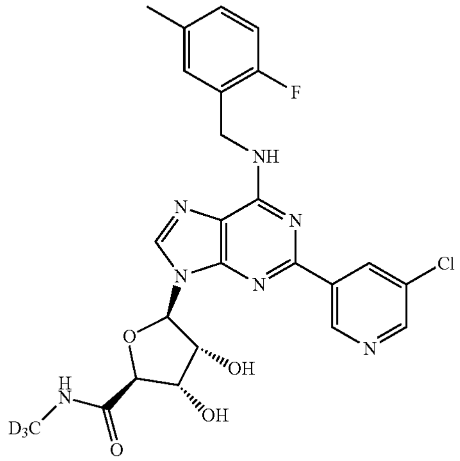 [SMILES: [2H]C([2H])([2H])NC(=O)[C@H]1O[C@@H](n2cnc3c(NCc4cc(C)ccc4F)nc(-c4cncc(Cl)c4)nc32)[C@H](O)[C@@H]1O] | (2S,3S,4R,5R)-5-(2-(5-chloropyridin-3-yl)-6-((2-fluoro-5-methylbenzyl)amino)-9H-purin-9-yl)-3,4-dihydroxyl-N-(methyl-d3)-tetrahydrofuran-2-carboxamide |
| 226 | 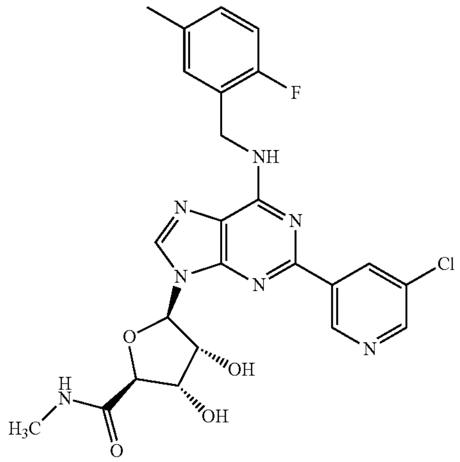 | (2S,3S,4R,5R)-5-(2-(5-chloropyridin-3-yl)-6-((2-fluoro-5-methylbenzyl)amino)-9H-purin-9-yl)-3,4-dihydroxyl-N-methyltetrahydrofuran-2-carboxamide |
| 227 | 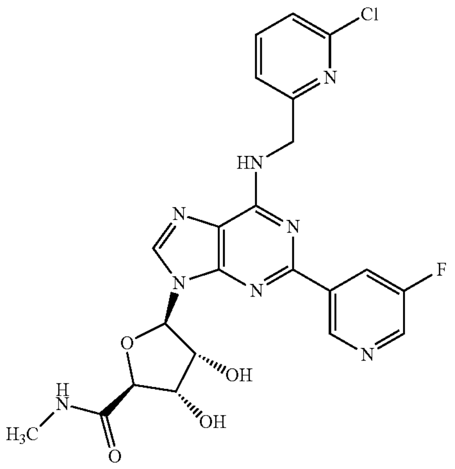 [SMILES: CNC(=O)[C@H]1O[C@@H](n2cnc3c(NCc4cccc(Cl)n4)nc(-c4cncc(F)c4)nc32)[C@H](O)[C@@H]1O] | (2S,3S,4R,5R)-5-(6-(((6-chloropyridin-2-yl)methyl)amino)-2-(5-pyridin-3-yl)-9H-purin-9-yl)-3,4-dihydroxyl-N-methyltetrahydrofuran-2-carboxamide |

-continued

| Compd. No. | Structural formula of compound | Compound name |
|---|---|---|
| 228 | 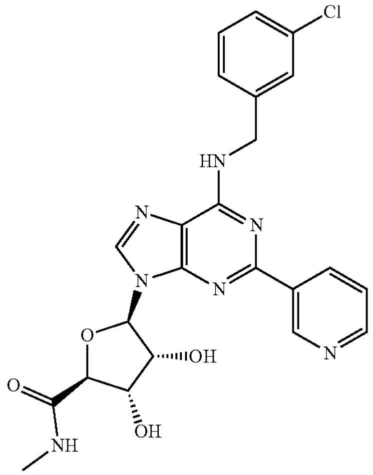 [SMILES: CNC(=O)[C@H]1O[C@@H](n2cnc3c(NCc4cccc(Cl)c4)nc(-c4cccnc4)nc32)[C@H](O)[C@@H]1O] | (2S,3S,4R,5R)-5-(6-((3-chlorobenzyl)amino)-2-(pyridin-3-yl)-9H-purin-9-yl)-3,4-dihydroxyl-N-methyltetrahydrofuran-2-carboxamide |
| 229 | 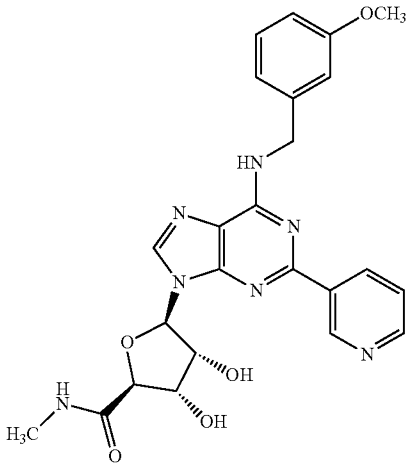 [SMILES: CNC(=O)[C@H]1O[C@@H](n2cnc3c(NCc4cccc(OC)c4)nc(-c4cccnc4)nc32)[C@H](O)[C@@H]1O] | (2S,3S,4R,5R)-3,4-dihydroxyl-5-(6-((3-methoxybenzyl)amino)-2-(pyridin-3-yl)-9H-purin-9-yl)-N-methyltetrahydrofuran-2-carboxamide |
| 230 | 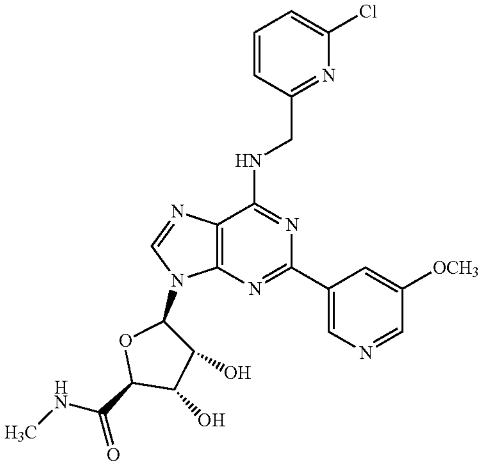 [SMILES: CNC(=O)[C@H]1O[C@@H](n2cnc3c(NCc4cccc(Cl)n4)nc(-c4cncc(OC)c4)nc32)[C@H](O)[C@@H]1O] | (2S,3S,4R,5R)-5-(6-(((6-chloropyridin-2-yl)methyl)amino)-2-(5-methoxypyridin-3-yl)-9H-purin-9-yl)-3,4-dihydroxyl-N-methyltetrahydrofuran-2-carboxamide |

-continued

| Compd. No. | Structural formula of compound | Compound name |
|---|---|---|
| 231 | 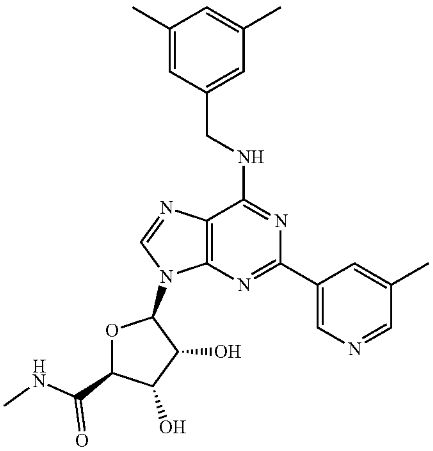 | (2S,3S,4R,5R)-5-(6-((3,5-dimethylbenzyl)amino)-2-(5-methylpyridin-3-yl)-9H-purin-9-yl)-3,4-dihydroxyl-N-methyltetrahydrofuran-2-carboxamide |
| 232 | 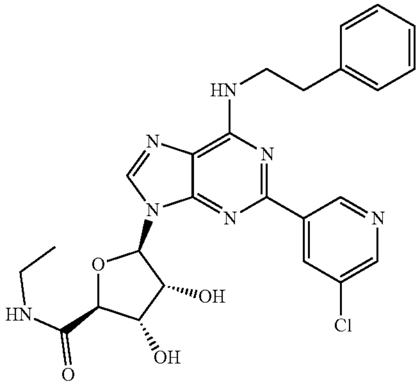 [SMILES: CCNC(=O)[C@H]1O[C@@H](n2cnc3c(NCCc4ccccc4)nc(-c4cncc(Cl)c4)nc32)[C@H](O)[C@@H]1O] | (2S,3S,4R,5R)-5-(2-(5-chloropyridin-3-yl)-6-(phenethylamino)-9H-purin-9-yl)-N-ethyl-3,4-dihydroxyltetrahydrofuran-2-carboxamide |
| 233 | 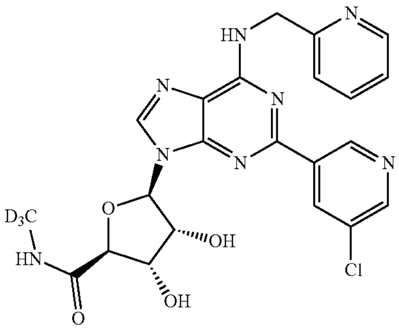 [SMILES: [2H]C([2H])([2H])NC(=O)[C@H]1O[C@@H](n2cnc3c(NCc4ccccn4)nc(-c4cncc(Cl)c4)nc32)[C@H](O)[C@@H]1O] | (2S,3S,4R,5R)-5-(2-(5-chloropyridin-3-yl)-6-(pyridin-2-methylamino)-9H-purin-9-yl)-3,4-dihydroxyl-N-(methyl-d3)-tetrahydrofuran-2-carboxamide |
| 234 | 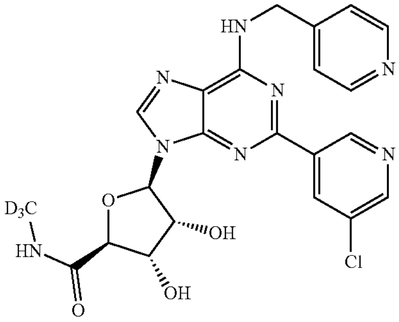 [SMILES: [2H]C([2H])([2H])NC(=O)[C@H]1O[C@@H](n2cnc3c(NCc4ccncc4)nc(-c4cncc(Cl)c4)nc32)[C@H](O)[C@@H]1O] | (2S,3S,4R,5R)-5-(2-(5-chloropyridin-3-yl)-6-(pyridin-4-ylmethylamino)-9H-purin-9-yl)-3,4-dihydroxyl-N-(methyl-d3)-tetrahydrofuran-2-carboxamide |

-continued

| Compd. No. | Structural formula of compound | Compound name |
|---|---|---|
| 235 | 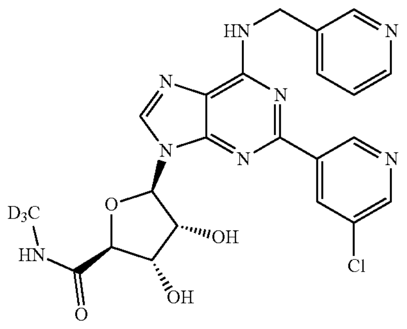 [SMILES: [2H]C([2H])([2H])NC(=O)[C@H]1O[C@@H](n2cnc3c(NCc4cccnc4)nc(-c4cncc(Cl)c4)nc32)[C@H](O)[C@@H]1O] | (2S,3S,4R,5R)-5-(2-(5-chloropyridin-3-yl)-6-(pyridin-3-ylmethylamino)-9H-purin-9-yl)-3,4-dihydroxyl-N-(methyl-d3)-tetrahydrofuran-2-carboxamide |
| 236 | 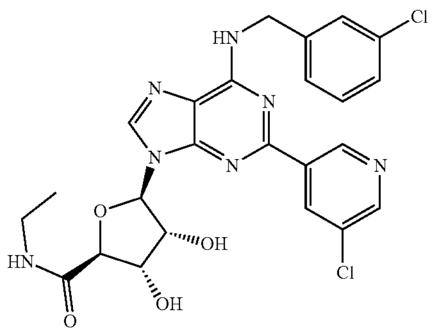 | (2S,3S,4R,5R)-5-(6-(3-chlorobenzylamino)-2-(5-chloropyridin-3-yl)-9H-purin-9-yl)-N-ethyl-3,4-dihydroxyltetrahydrofuran-2-carboxamide |
| 237 | 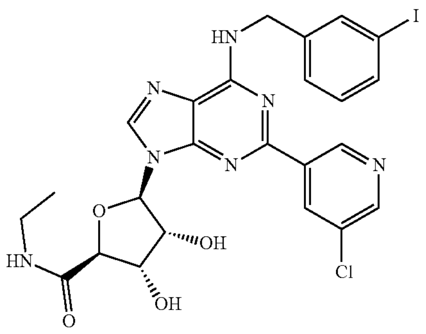 [SMILES: CCNC(=O)[C@H]1O[C@@H](n2cnc3c(NCc4cccc(I)c4)nc(-c4cncc(Cl)c4)nc32)[C@H](O)[C@@H]1O] | (2S,3S,4R,5R)-5-(2-(5-chloropyridin-3-yl)-6-(3-iodobenzylamino)-9H-purin-9-yl)-N-ethyl-3,4-dihydroxyltetrahydrofuran-2-carboxamide |
| 238 | 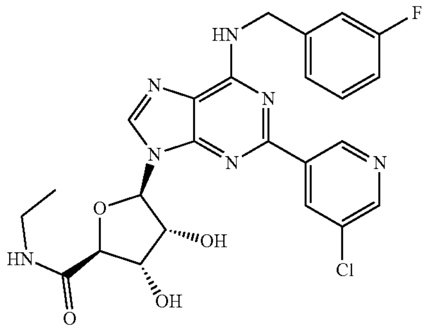 [SMILES: CCNC(=O)[C@H]1O[C@@H](n2cnc3c(NCc4cccc(F)c4)nc(-c4cncc(Cl)c4)nc32)[C@H](O)[C@@H]1O] | (2S,3S,4R,5R)-5-(2-(5-chloropyridin-3-yl)-6-(3-fluorobenzylamino)-9H-purin-9-yl)-N-ethyl-3,4-dihydroxyltetrahydrofuran-2-carboxamide |

-continued

| Compd. No. | Structural formula of compound | Compound name |
|---|---|---|
| 239 | 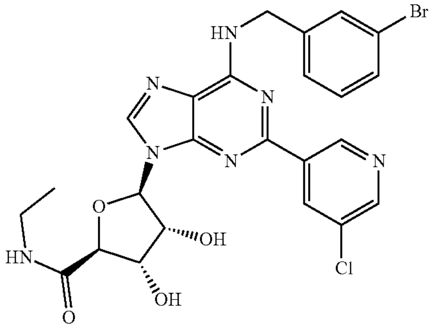 [SMILES: CCNC(=O)[C@H]1O[C@@H](n2cnc3c(NCc4cccc(Br)c4)nc(-c4cncc(Cl)c4)nc32)[C@H](O)[C@@H]1O] | (2S,3S,4R,5R)-5-(6-(3-bromobenzylamino)-2-(5-chloropyridin-3-yl)-9H-purin-9-yl)-N-ethyl-3,4-dihydroxyltetrahydrofuran-2-carboxamide |
| 240 | 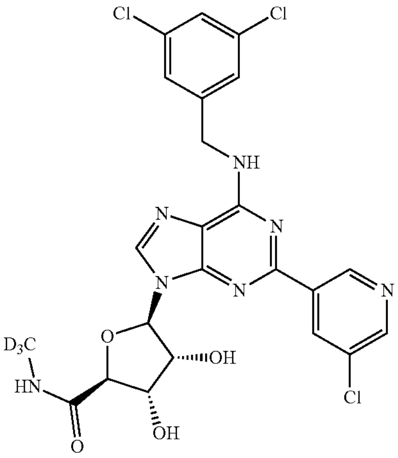 [SMILES: [2H]C([2H])([2H])NC(=O)[C@H]1O[C@@H](n2cnc3c(NCc4cc(Cl)cc(Cl)c4)nc(-c4cncc(Cl)c4)nc32)[C@H](O)[C@@H]1O] | (2S,3S,4R,5R)-5-(2-(5-chloropyridin-3-yl)-6-(3,5-dichlorobenzylamino)-9H-purin-9-yl)-3,4-dihydroxyl-N-(methyl-d3)-tetrahydrofuran-2-carboxamide |
| 241 | 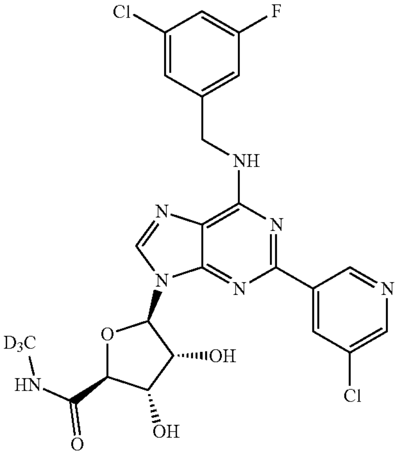 [SMILES: [2H]C([2H])([2H])NC(=O)[C@H]1O[C@@H](n2cnc3c(NCc4cc(F)cc(Cl)c4)nc(-c4cncc(Cl)c4)nc32)[C@H](O)[C@@H]1O] | (2S,3S,4R,5R)-5-(6-(3-chloro-5-fluorobenzylamino)-2-(5-chloropyridin-3-yl)-9H-purin-9-yl)-3,4-dihydroxyl-N-(methyl-d3)-tetrahydrofuran-2-carboxamide |
| 242 | 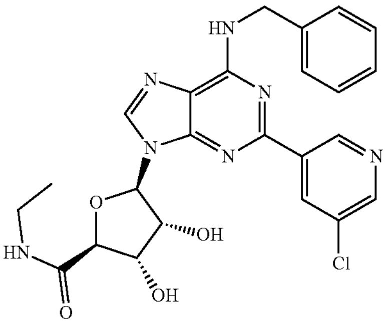 [SMILES: CCNC(=O)[C@H]1O[C@@H](n2cnc3c(NCc4ccccc4)nc(-c4cncc(Cl)c4)nc32)[C@H](O)[C@@H]1O] | (2S,3S,4R,5R)-5-(6-(benzylamino)-2-(5-chloropyridin-3-yl)-9H-purin-9-yl)-N-ethyl-3,4-dihydroxyltetrahydrofuran-2-carboxamide |

-continued

| Compd. No. | Structural formula of compound | Compound name |
|---|---|---|
| 243 | 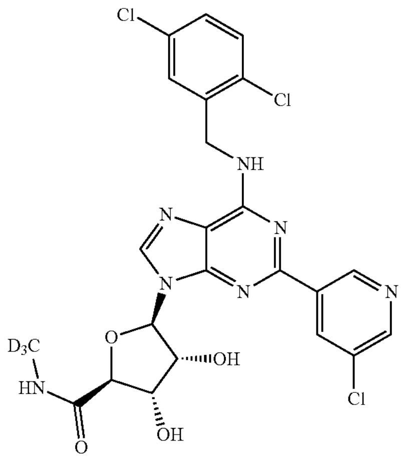 [SMILES: [2H]C([2H])([2H])NC(=O)[C@H]1O[C@@H](n2cnc3c(NCc4cc(Cl)ccc4Cl)nc(-c4cncc(Cl)c4)nc32)[C@H](O)[C@@H]1O] | (2S,3S,4R,5R)-5-(2-(5-chloropyridin-3-yl)-6-(2,5-dichlorobenzylamino)-9H-purin-9-yl)-3,4-dihydroxyl-N-((methyl-d3))-tetrahydrofuran-2-carboxamide |
| 244 | 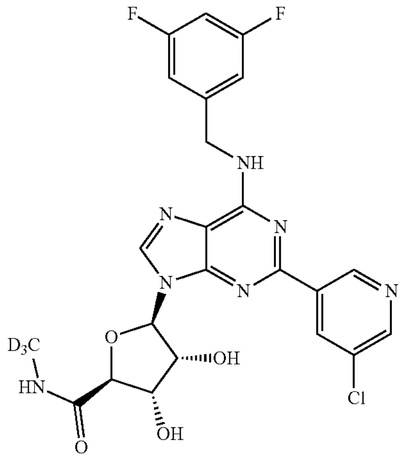 [SMILES: [2H]C([2H])([2H])NC(=O)[C@H]1O[C@@H](n2cnc3c(NCc4cc(F)cc(F)c4)nc(-c4cncc(Cl)c4)nc32)[C@H](O)[C@@H]1O] | (2S,3S,4R,5R)-5-(2-(5-chloropyridin-3-yl)-6-(3,5-difluorobenzylamino)-9H-purin-9-yl)-3,4-dihydroxyl-N-((methyl-d3))-tetrahydrofuran-2-carboxamide |
| 245 | 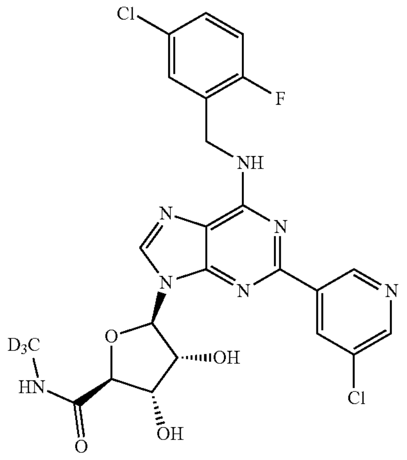 [SMILES: [2H]C([2H])([2H])NC(=O)[C@H]1O[C@@H](n2cnc3c(NCc4cc(Cl)ccc4F)nc(-c4cncc(Cl)c4)nc32)[C@H](O)[C@@H]1O] | (2S,3S,4R,5R)-5-(6-(5-chloro-2-fluorobenzylamino)-2-(5-chloropyridin-3-yl)-9H-purin-9-yl)-3,4-dihydroxyl-N-((methyl-d3))-tetrahydrofuran-2-carboxamide |

-continued

| Compd. No. | Structural formula of compound | Compound name |
|---|---|---|
| 246 | 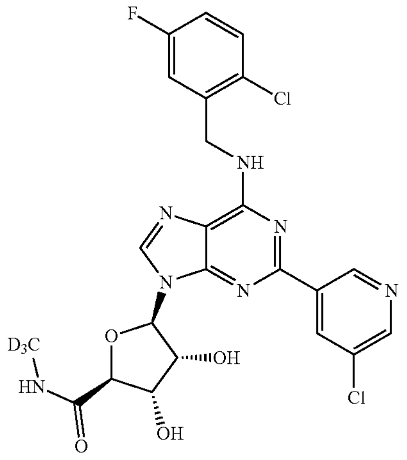 [SMILES: [2H]C([2H])([2H])NC(=O)[C@H]1O[C@@H](n2cnc3c(NCc4cc(F)ccc4Cl)nc(-c4cncc(Cl)c4)nc32)[C@H](O)[C@@H]1O] | (2S,3S,4R,5R)-5-(6-(2-chloro-5-fluorobenzylamino)-2-(5-chloropyridin-3-yl)-9H-purin-9-yl)-3,4-dihydroxyl-N-(methyl-d3)-tetrahydrofuran-2-carboxamide |
| 247 | 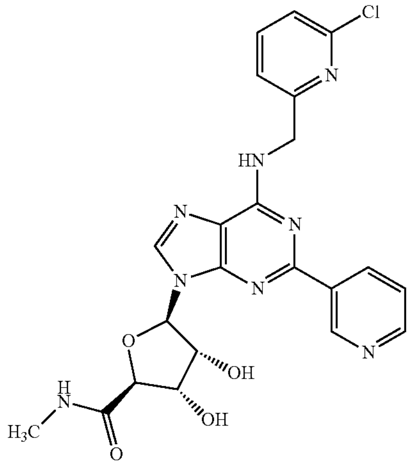 [SMILES: CNC(=O)[C@H]1O[C@@H](n2cnc3c(NCc4cccc(Cl)n4)nc(-c4cccnc4)nc32)[C@H](O)[C@@H]1O] | (2S,3S,4R,5R)-5-(6-((((6-chloropyridin-2-yl)methyl)amino)-2-(pyridin-3-yl)-9H-purin-9-yl)-3,4-dihydroxyl-N-methyltetrahydrofuran-2-carboxamide |
| 248 | 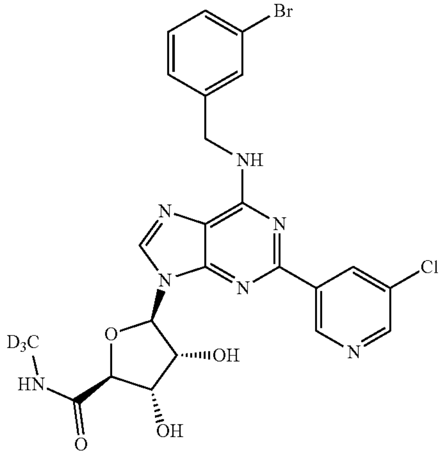 [SMILES: [2H]C([2H])([2H])NC(=O)[C@H]1O[C@@H](n2cnc3c(NCc4cccc(Br)c4)nc(-c4cncc(Cl)c4)nc32)[C@H](O)[C@@H]1O] | (2S,3S,4R,5R)-5-(6-((3-bromobenzyl)amino)-2-(5-chloropyridin-3-yl)-9H-purin-9-yl)-3,4-dihydroxyl-N-(methyl-d3)tetrahydrofuran-2-carboxamide |

-continued

| Compd. No. | Structural formula of compound | Compound name |
|---|---|---|
| 249 | 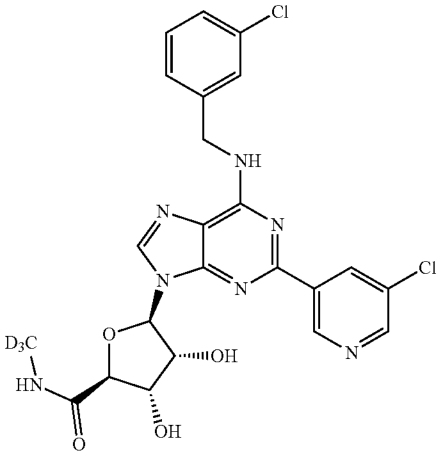 [SMILES: [2H]C([2H])([2H])NC(=O)[C@H]1O[C@@H](n2cnc3c(NCc4cccc(Cl)c4)nc(-c4cncc(Cl)c4)nc32)[C@H](O)[C@@H]1O] | (2S,3S,4R,5R)-5-(6-((3-chlorobenzyl)amino)-2-(5-chloropyridin-3-yl)-9H-purin-9-yl)-3,4-dihydroxyl-N-(methyl-d3)tetrahydrofuran-2-carboxamide |
| 250 | 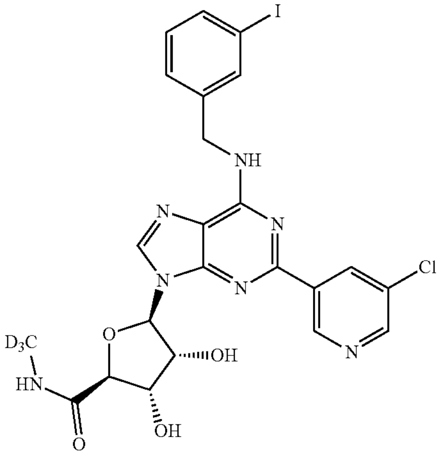 [SMILES: [2H]C([2H])([2H])NC(=O)[C@H]1O[C@@H](n2cnc3c(NCc4cccc(I)c4)nc(-c4cncc(Cl)c4)nc32)[C@H](O)[C@@H]1O] | (2S,3S,4R,5R)-5-(2-(5-chloropyridin-3-yl)-6-((3-iodobenzyl)amino)-9H-purin-9-yl)-3,4-dihydroxyl-N-(methyl-d3)tetrahydrofuran-2-carboxamide |
| 251 | 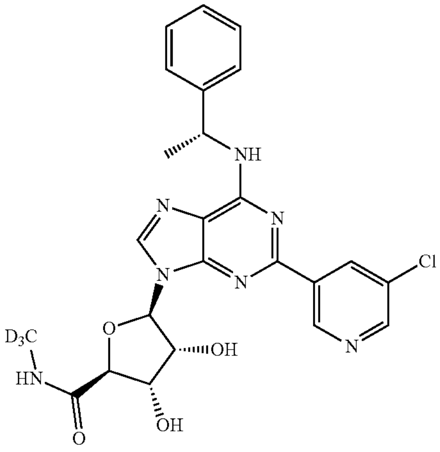 [SMILES: [2H]C([2H])([2H])NC(=O)[C@H]1O[C@@H](n2cnc3c(N[C@H](C)c4ccccc4)nc(-c4cncc(Cl)c4)nc32)[C@H](O)[C@@H]1O] | (2S,3S,4R,5R)-5-(2-(5-chloropyridin-3-yl)-6-((((R)-1-phenethyl)amino)-9H-purin-9-yl)-3,4-dihydroxyl-N-(methyl-d3)tetrahydrofuran-2-carboxamide |

-continued

| Compd. No. | Structural formula of compound | Compound name |
|---|---|---|
| 252 | 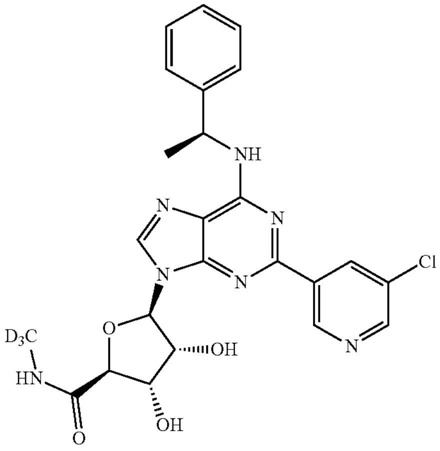 [SMILES: [2H]C([2H])([2H])NC(=O)[C@H]1O[C@@H](n2cnc3c(N[C@@H](C)c4ccccc4)nc(-c4cncc(Cl)c4)nc32)[C@H](O)[C@@H]1O] | (2S,3S,4R,5R)-5-(2-(5-chloropyridin-3-yl)-6-((((S)-1-phenethyl)amino)-9H-purin-9-yl)-3,4-dihydroxyl-N-(methyl-d3)tetrahydrofuran-2-carboxamide |
| 253 | 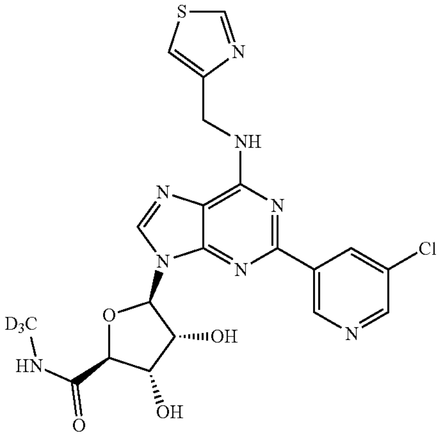 [SMILES: [2H]C([2H])([2H])NC(=O)[C@H]1O[C@@H](n2cnc3c(NCc4cscn4)nc(-c4cncc(Cl)c4)nc32)[C@H](O)[C@@H]1O] | (2S,3S,4R,5R)-5-(2-(5-chloropyridin-3-yl)-6-((thiazol-4-ylmethyl)amino)-9H-purin-9-yl)-3,4-dihydroxyl-N-(methyl-d3)tetrahydrofuran-2-carboxamide |
| 254 | 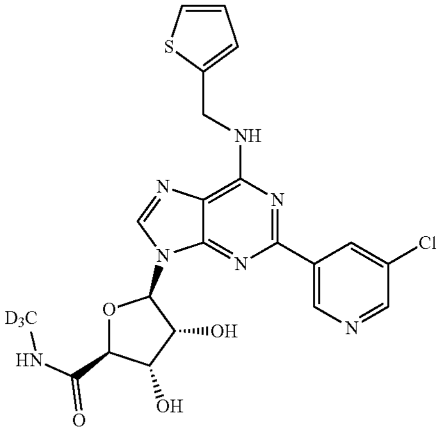 [SMILES: [2H]C([2H])([2H])NC(=O)[C@H]1O[C@@H](n2cnc3c(NCc4cccs4)nc(-c4cncc(Cl)c4)nc32)[C@H](O)[C@@H]1O] | (2S,3S,4R,5R)-5-(2-(5-chloropyridin-3-yl)-6-((thiophen-2-ylmethyl)amino)-9H-purin-9-yl)-3,4-dihydroxyl-N-(methyl-d3)tetrahydrofuran-2-carboxamide |

-continued

| Compd. No. | Structural formula of compound | Compound name |
|---|---|---|
| 255 | 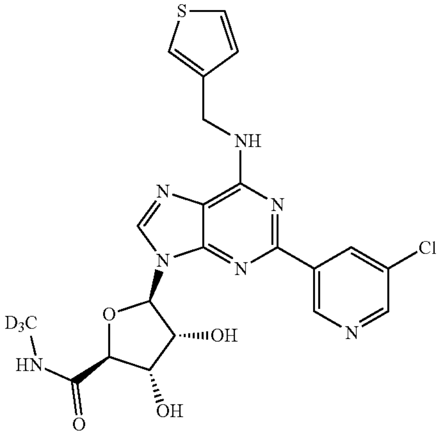 [SMILES: [2H]C([2H])([2H])NC(=O)[C@H]1O[C@@H](n2cnc3c(NCc4ccsc4)nc(-c4cncc(Cl)c4)nc32)[C@H](O)[C@@H]1O] | (2S,3S,4R,5R)-5-(2-(5-chloropyridin-3-yl)-6-((thiophen-3-ylmethyl)amino)-9H-purin-9-yl)-3,4-dihydroxyl-N-(methyl-d3)tetrahydrofuran-2-carboxamide |
| 256 | 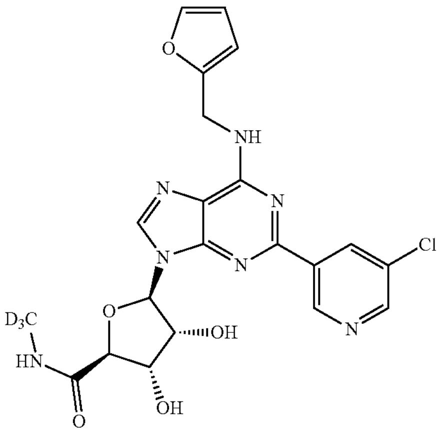 [SMILES: [2H]C([2H])([2H])NC(=O)[C@H]1O[C@@H](n2cnc3c(NCc4ccco4)nc(-c4cncc(Cl)c4)nc32)[C@H](O)[C@@H]1O] | (2S,3S,4R,5R)-5-(2-(5-chloropyridin-3-yl)-6-((furan-2-ylmethyl)amino)-9H-purin-9-yl)-3,4-dihydroxyl-N-(methyl-d3)tetrahydrofuran-2-carboxamide; |
| 257 | 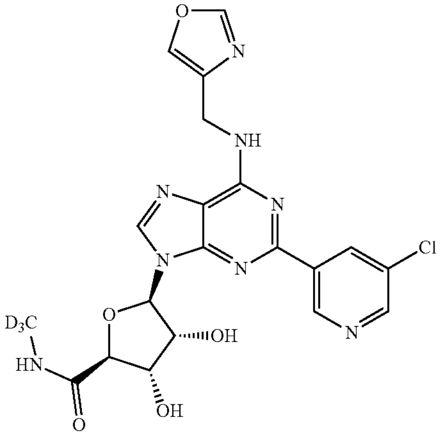 [SMILES: [2H]C([2H])([2H])NC(=O)[C@H]1O[C@@H](n2cnc3c(NCc4cocn4)nc(-c4cncc(Cl)c4)nc32)[C@H](O)[C@@H]1O] | (2S,3S,4R,5R)-5-(2-(5-chloropyridin-3-yl)-6-((oxazol-4-ylmethyl)amino)-9H-purin-9-yl)-3,4-dihydroxyl-N-(methyl-d3)tetrahydrofuran-2-carboxamide |

-continued

| Compd. No. | Structural formula of compound | Compound name |
|---|---|---|
| 258 | 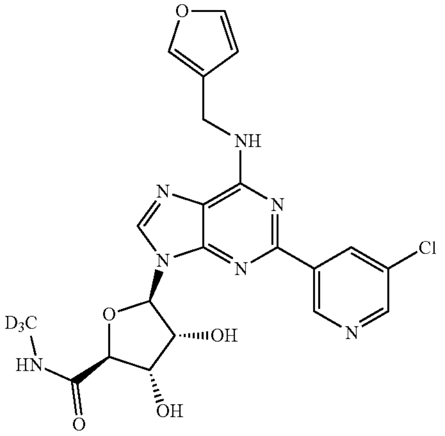 [SMILES: [2H]C([2H])([2H])NC(=O)[C@H]1O[C@@H](n2cnc3c(NCc4ccoc4)nc(-c4cncc(Cl)c4)nc32)[C@H](O)[C@@H]1O] | (2S,3S,4R,5R)-5-(2-(5-chloropyridin-3-yl)-6-((furan-3-ylmethyl)amino)-9H-purin-9-yl)-3,4-dihydroxyl-N-(methyl-d3)tetrahydrofuran-2-carboxamide |
| 259 | 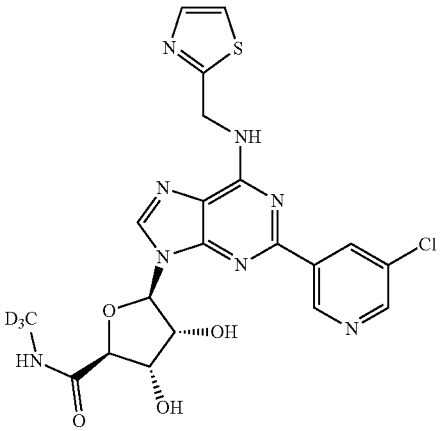 [SMILES: [2H]C([2H])([2H])NC(=O)[C@H]1O[C@@H](n2cnc3c(NCc4nccs4)nc(-c4cncc(Cl)c4)nc32)[C@H](O)[C@@H]1O] | (2S,3S,4R,5R)-5-(2-(5-chloropyridin-3-yl)-6-((thiazol-2-ylmethyl)amino)-9H-purin-9-yl)-3,4-dihydroxyl-N-(methyl-d3)tetrahydrofuran-2-carboxamide |
| 260 | 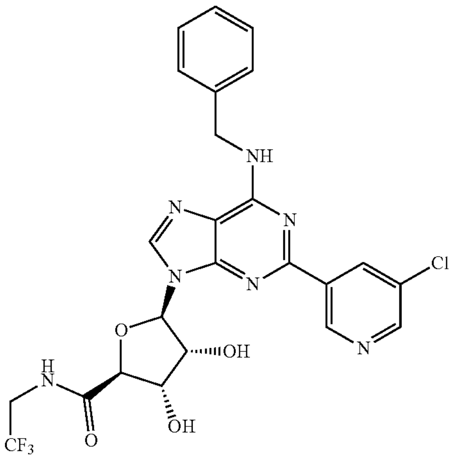 [SMILES: O=C(NCC(F)(F)F)[C@H]1O[C@@H](n2cnc3c(NCc4ccccc4)nc(-c4cncc(Cl)c4)nc32)[C@H](O)[C@@H]1O] | (2S,3S,4R,5R)-5-(6-(benzylamino)-2-(5-chloropyridin-3-yl)-9H-purin-9-yl)-3,4-dihydroxyl-N-(2,2,2-trifluoroethyl)tetrahydrofuran-2-carboxamide |

-continued

| Compd. No. | Structural formula of compound | Compound name |
|---|---|---|
| 261 | 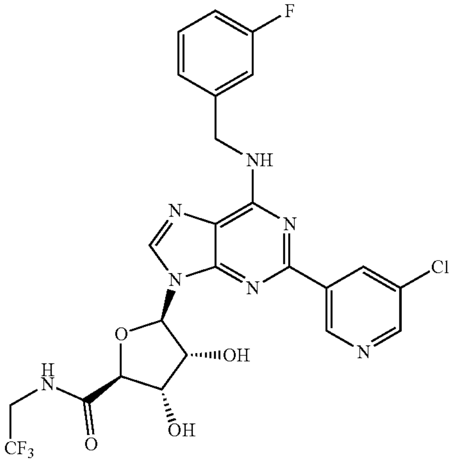 | (2S,3S,4R,5R)-5-(2-(5-chloropyridin-3-yl)-6-(3-fluorobenzylamino)-9H-purin-9-yl)-3,4-dihydroxyl-N-(2,2,2-trifluoroethyl)tetrahydrofuran-2-carboxamide |
| 262 | 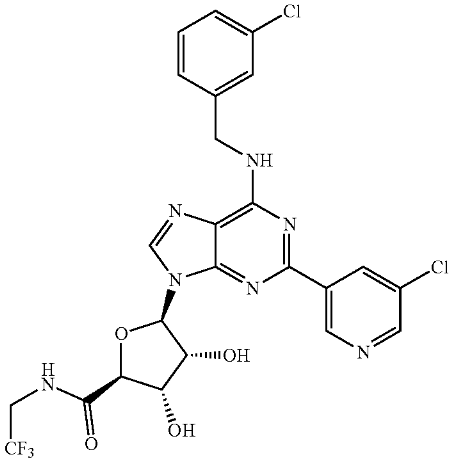 [SMILES: O=C(NCC(F)(F)F)[C@H]1O[C@@H](n2cnc3c(NCc4cccc(Cl)c4)nc(-c4cncc(Cl)c4)nc32)[C@H](O)[C@@H]1O] | (2S,3S,4R,5R)-5-(6-(3-chlorobenzylamino)-2-(5-chloropyridin-3-yl)-9H-purin-9-yl)-3,4-dihydroxyl-N-(2,2,2-trifluoroethyl)tetrahydrofuran-2-carboxamide |
| 263 | 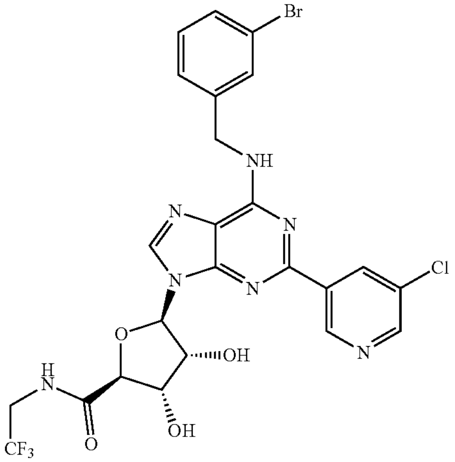 [SMILES: O=C(NCC(F)(F)F)[C@H]1O[C@@H](n2cnc3c(NCc4cccc(Br)c4)nc(-c4cncc(Cl)c4)nc32)[C@H](O)[C@@H]1O] | (2S,3S,4R,5R)-5-(6-(3-bromobenzylamino)-2-(5-chloropyridin-3-yl)-9H-purin-9-yl)-3,4-dihydroxyl-N-(2,2,2-trifluoroethyl)tetrahydrofuran-2-carboxamide |

-continued

| Compd. No. | Structural formula of compound | Compound name |
|---|---|---|
| 264 | 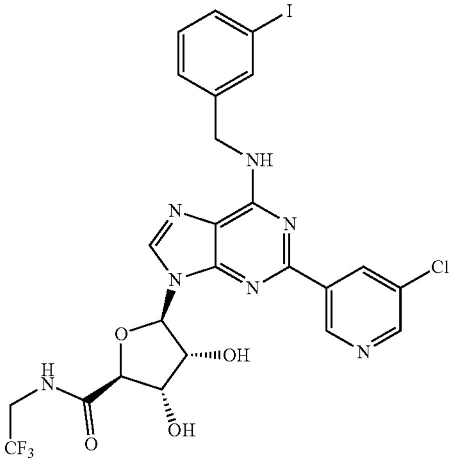 [SMILES: O=C(NCC(F)(F)F)[C@H]1O[C@@H](n2cnc3c(NCc4cccc(I)c4)nc(-c4cncc(Cl)c4)nc32)[C@H](O)[C@@H]1O] | (2S,3S,4R,5R)-5-(2-(5-chloropyridin-3-yl)-6-(3-iodobenzylamino)-9/-purin-9-yl)-3,4-dihydroxyl-N-(2,2,2-trifluoroethyl)tetrahydrofuran-2-carboxamide |
| 265 | 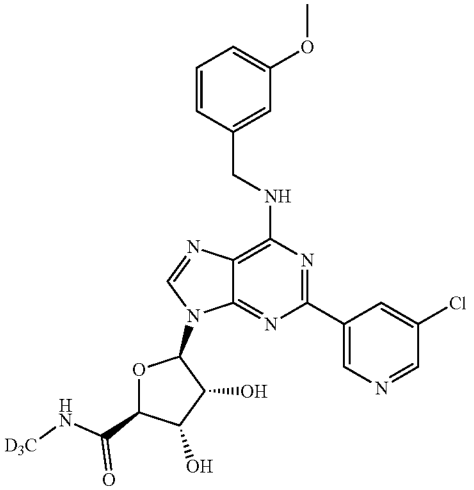 | (2S,3S,4R,5R)-5-(2-(5-chloropyridin-3-yl)-6-(3-methoxybenzylamino)-9H-purin-9-yl)-3,4-dihydroxyl-N-(methyl-d3)-tetrahydrofuran-2-carboxamide |
| 266 | 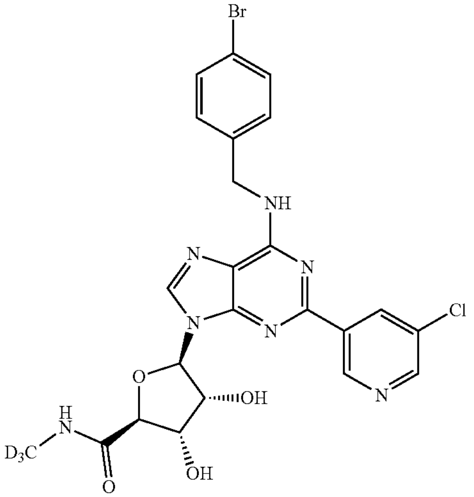 | (2S,3S,4R,5R)-5-(6-(4-bromobenzylamino)-2-(5-chloropyridin-3-yl)-9H-purin-9-yl)-3,4-dihydroxyl-N-(methyl-d3)-tetrahydrofuran-2-carboxamide |

-continued

| Compd. No. | Structural formula of compound | Compound name |
|---|---|---|
| 267 | 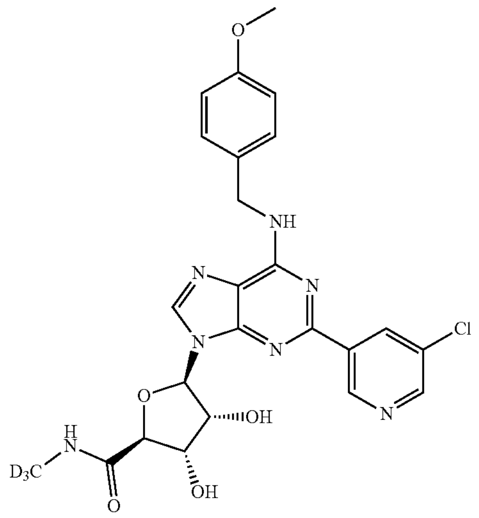 [SMILES: [2H]C([2H])([2H])NC(=O)[C@H]1O[C@@H](n2cnc3c(NCc4ccc(OC)cc4)nc(-c4cncc(Cl)c4)nc32)[C@H](O)[C@@H]1O] | (2S,3S,4R,5R)-5-(2-(5-chloropyridin-3-yl)-6-(4-methoxybenzylamino)-9H-purin-9-yl)-3,4-dihydroxyl-N-(methyl-d3)-tetrahydrofuran-2-carboxamide |
| 268 | 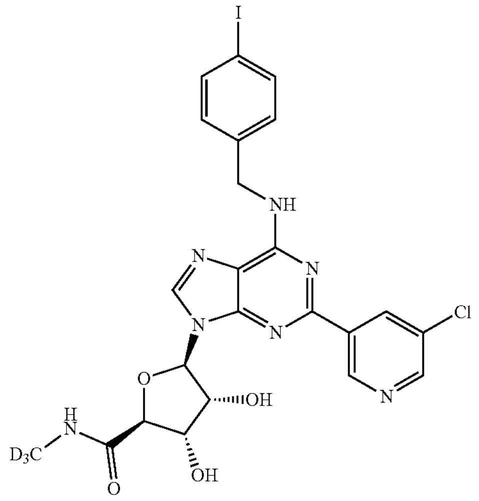 | (2S,3S,4R,5R)-5-(2-(5-chloropyridin-3-yl)-6-(4-iodobenzylamino)-9H-purin-9-yl)-3,4-dihydroxyl-N-(methyl-d3)-tetrahydrofuran-2-carboxamide |
| 269 | 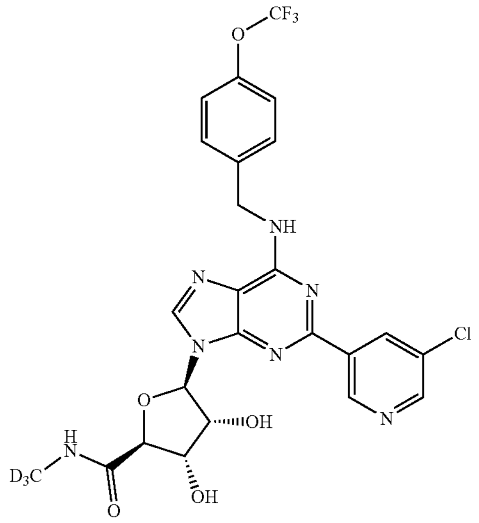 [SMILES: [2H]C([2H])([2H])NC(=O)[C@H]1O[C@@H](n2cnc3c(NCc4ccc(OC(F)(F)F)cc4)nc(-c4cncc(Cl)c4)nc32)[C@H](O)[C@@H]1O] | (2S,3S,4R,5R)-5-(2-(5-chloropyridin-3-yl)-6-(4-(trifluoromethoxy)benzylamino)-9H-purin-9-yl)-3,4-dihydroxyl-N-(methyl-d3)-tetrahydrofuran-2-carboxamide |

-continued

| Compd. No. | Structural formula of compound | Compound name |
|---|---|---|
| 270 | 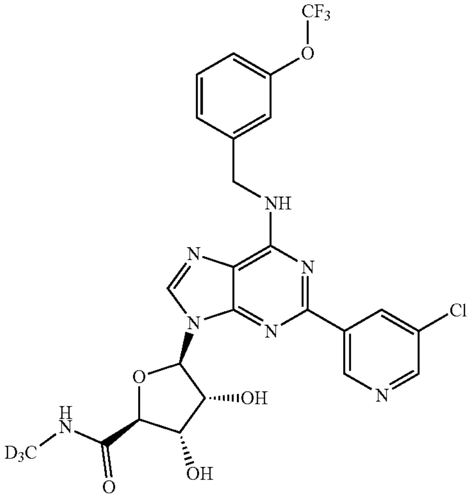 [SMILES: [2H]C([2H])([2H])NC(=O)[C@H]1O[C@@H](n2cnc3c(NCc4cccc(OC(F)(F)F)c4)nc(-c4cncc(Cl)c4)nc32)[C@H](O)[C@@H]1O] | (2S,3S,4R,5R)-5-(2-(5-chloropyridin-3-yl)-6-(3-(trifluoromethoxy)benzylamino)-9H-purin-9-yl)-3,4-dihydroxyl-N-(methyl-d3)-tetrahydrofuran-2-carboxamide |
| 271 | 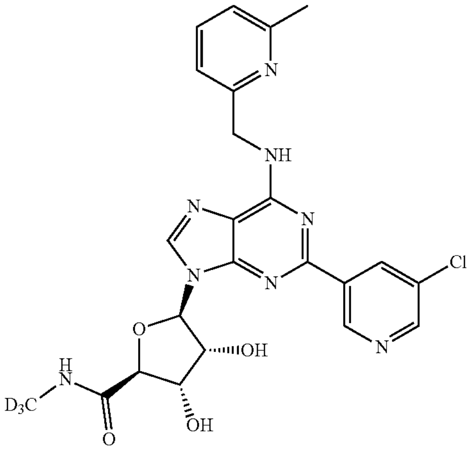 [SMILES: [2H]C([2H])([2H])NC(=O)[C@H]1O[C@@H](n2cnc3c(NCc4cccc(C)n4)nc(-c4cncc(Cl)c4)nc32)[C@H](O)[C@@H]1O] | (2S,3S,4R,5R)-5-(2-(5-chloropyridin-3-yl)-6-((6-methylpyridin-2-yl)methylamino)-9H-purin-9-yl)-3,4-dihydroxyl-N-(methyl-d3)-tetrahydrofuran-2-carboxamide |
| 272 | 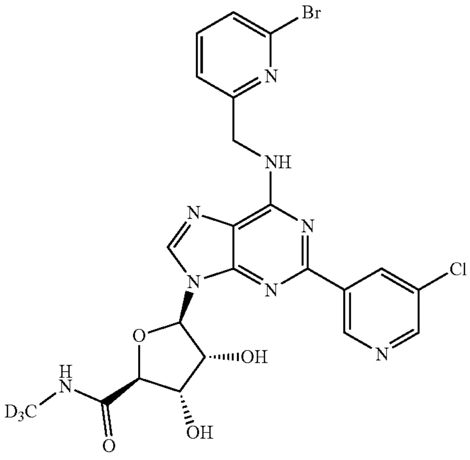 | (2S,3S,4R,5R)-5-(6-((6-bromopyridin-2-yl)methylamino)-2-(5-chloropyridin-3-yl)-9H-purin-9-yl)-3,4-dihydroxyl-N-(methyl-d3)-tetrahydrofuran-2-carboxamide |

-continued

| Compd. No. | Structural formula of compound | Compound name |
|---|---|---|
| 273 | 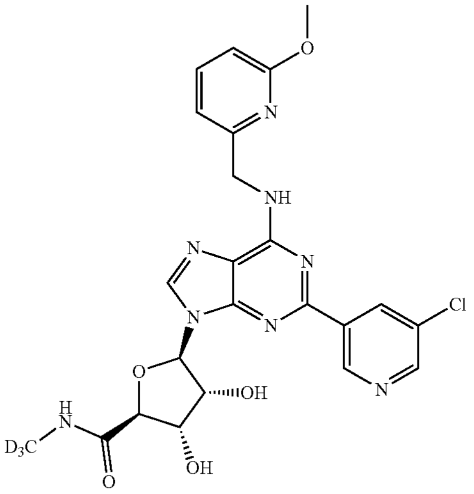 | (2S,3S,4R,5R)-5-(2-(5-chloropyridin-3-yl)-6-((6-methoxypyridin-2-yl)methylamino)-9H-purin-9-yl)-3,4-dihydroxyl-N-(methyl-d3)-tetrahydrofuran-2-carboxamide |
| 274 | 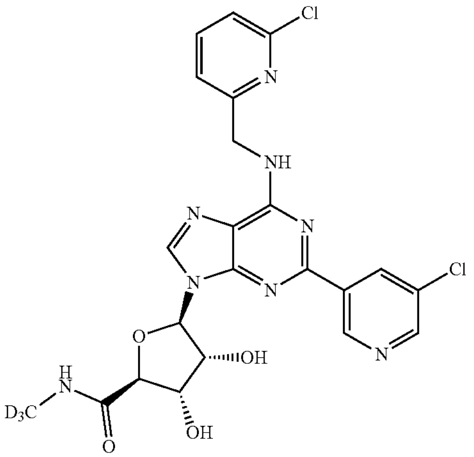 | (2S,3S,4R,5R)-5-(6-((6-chloropyridin-2-yl)methylamino)-2-(5-chloropyridin-3-yl)-9H-purin-9-yl)-3,4-dihydroxyl-N-(methyl-d3)-tetrahydrofuran-2-carboxamide |
| 275 | 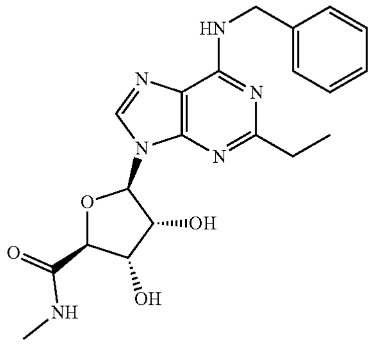 [SMILES: CCc1nc(NCc2ccccc2)c2ncn([C@@H]3O[C@H](C(=O)NC)[C@@H](O)[C@H]3O)c2n1] | (2S,3S,4R,5R)-5-(6-(benzylamino)-2-ethyl-9H-purin-9-yl)-3,4-dihydroxyl-N-methyl-tetrahydrofuran-2-formamide |

-continued

| Compd. No. | Structural formula of compound | Compound name |
|---|---|---|
| 276 | 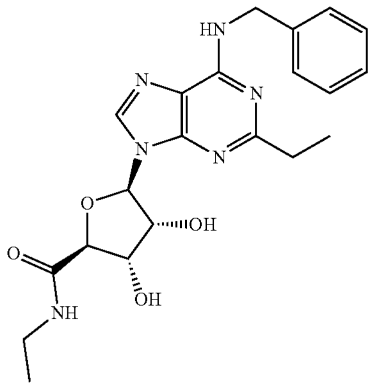 [SMILES: CCNC(=O)[C@H]1O[C@@H](n2cnc3c(NCc4ccccc4)nc(CC)nc32)[C@H](O)[C@@H]1O] | (2S,3S,4R,5R)-5-(6-(benzylamino)-2-ethyl-9H-purin-9-yl)-N-ethyl-3,4-dihydroxyltetrahydrofuran-2-formamide |
| 277 | 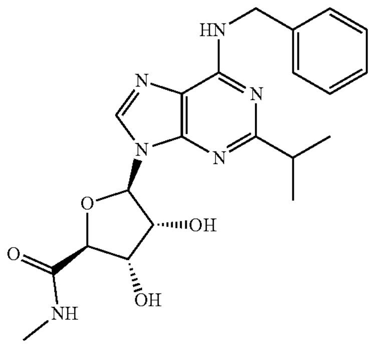 [SMILES: CNC(=O)[C@H]1O[C@@H](n2cnc3c(NCc4ccccc4)nc(C(C)C)nc32)[C@H](O)[C@@H]1O] | (2S,3S,4R,5R)-5-(6-(benzylamino)-2-isopropyl-9H-purin-9-yl)-3,4-dihydroxyl-N-methyl-tetrahydrofuran-2-formamide |
| 278 | 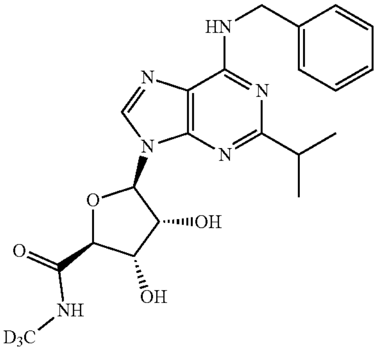 [SMILES: [2H]C([2H])([2H])NC(=O)[C@H]1O[C@@H](n2cnc3c(NCc4ccccc4)nc(C(C)C)nc32)[C@H](O)[C@@H]1O] | (2S,3S,4R,5R)-5-(6-(benzylamino)-2-isopropyl-9H-purin-9-yl)-3,4-dihydroxyl-N-(methyl-d3)-tetrahydrofuran-2-formamide |
| 279 | 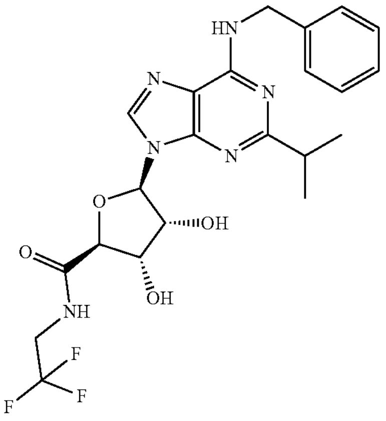 [SMILES: CC(C)c1nc(NCc2ccccc2)c2ncn([C@@H]3O[C@H](C(=O)NCC(F)(F)F)[C@@H](O)[C@H]3O)c2n1] | (2S,3S,4R,5R)-5-(6-(benzylamino)-2-isopropyl-9H-purin-9-yl)-3,4-dihydroxyl-N-(2,2,2-trifluoroethyl)-tetrahydrofuran-2-formamide |

-continued

| Compd. No. | Structural formula of compound | Compound name |
|---|---|---|
| 280 | 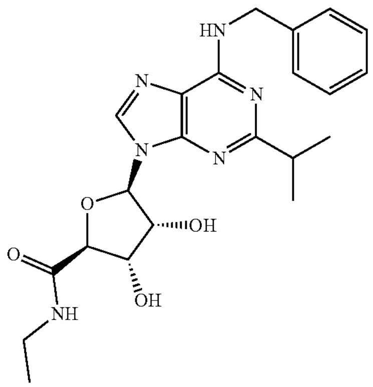 [SMILES: CCNC(=O)[C@H]1O[C@@H](n2cnc3c(NCc4ccccc4)nc(C(C)C)nc32)[C@H](O)[C@@H]1O] | (2S,3S,4R,5R)-5-(6-(benzylamino)-2-isopropyl-9H-purin-9-yl)-N-ethyl-3,4-dihydroxyltetrahydrofuran-2-formamide |
| 281 | 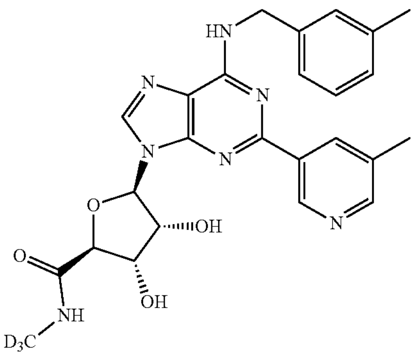 [SMILES: [2H]C([2H])([2H])NC(=O)[C@H]1O[C@@H](n2cnc3c(NCc4cccc(C)c4)nc(-c4cncc(C)c4)nc32)[C@H](O)[C@@H]1O] | (2S,3S,4R,5R)-5-(6-(3-methylbenzylamino)-2-(5-methylpyridin-3-yl)-9H-purin-9-yl)-3,4-dihydroxyl-N-(methyl-d3)-tetrahydrofuran-2-formamide |
| 282 | 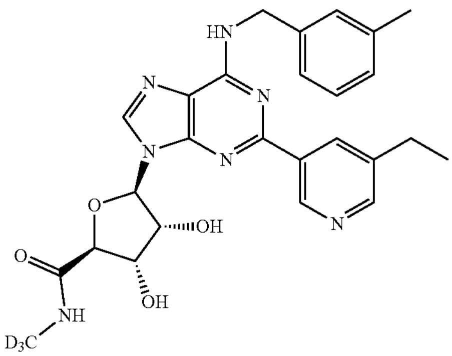 [SMILES: [2H]C([2H])([2H])NC(=O)[C@H]1O[C@@H](n2cnc3c(NCc4cccc(C)c4)nc(-c4cncc(CC)c4)nc32)[C@H](O)[C@@H]1O] | (2S,3S,4R,5R)-5-(2-(5-ethylpyridin-3-yl)-6-((3-methylbenzyl)amino)-9H-purin-9-yl)-3,4-dihydroxyl-N-(methyl-d3)tetrahydrofuran-2-formamide |
| 283 | 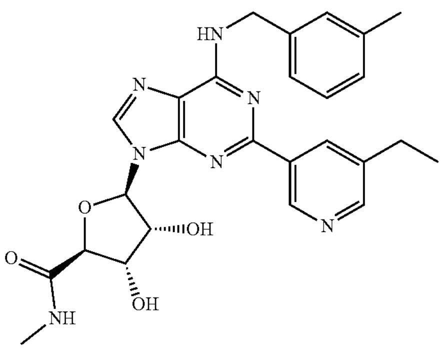 [SMILES: CCc1cncc(-c2nc(NCc3cccc(C)c3)c3ncn([C@@H]4O[C@H](C(=O)NC)[C@@H](O)[C@H]4O)c3n2)c1] | (2S,3S,4R,5R)-5-(6-((3-methylbenzylamino)-2-(5-ethylpyridin-3-yl)-9H-purin-9-yl)-3,4-dihydroxyl-N-methyl-tetrahydrofuran-2-formamide |

-continued

| Compd. No. | Structural formula of compound | Compound name |
|---|---|---|
| 284 | 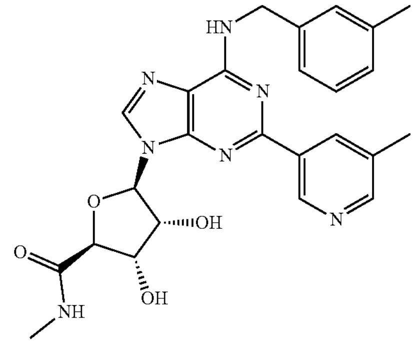 [SMILES: CNC(=O)[C@H]1O[C@@H](n2cnc3c(NCc4cccc(C)c4)nc(-c4cncc(C)c4)nc32)[C@H](O)[C@@H]1O] | (2S,3S,4R,5R)-5-(6-(3-methylbenzylamino)-2-(5-methylpyridin-3-yl)-9H-purin-9-yl)-3,4-dihydroxyl-N-methyl-tetrahydrofuran-2-formamide |
| 285 | 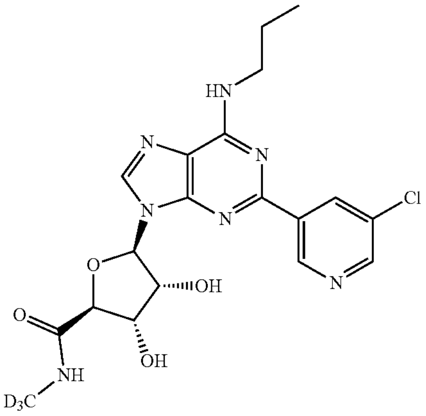 [SMILES: [2H]C([2H])([2H])NC(=O)[C@H]1O[C@@H](n2cnc3c(NCCC)nc(-c4cncc(Cl)c4)nc32)[C@H](O)[C@@H]1O] | (2S,3S,4R,5R)-5-(2-(5-chloropyridin-3-yl)-6-(propylamino)-9H-purin-9-yl)-3,4-dihydroxyl-N-(methyl-d3)-tetrahydrofuran-2-carboxamide |
| 286 | 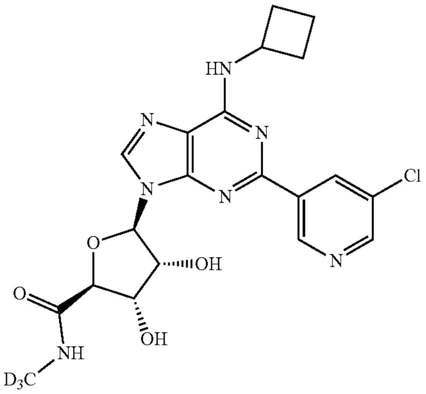 [SMILES: [2H]C([2H])([2H])NC(=O)[C@H]1O[C@@H](n2cnc3c(NC4CCC4)nc(-c4cncc(Cl)c4)nc32)[C@H](O)[C@@H]1O] | (2S,3S,4R,5R)-5-(2-(5-chloropyridin-3-yl)-6-(cyclobutylamino)-9H-purin-9-yl)-3,4-dihydroxyl-N-(methyl-d3)-tetrahydrofuran-2-carboxamide |
| 287 | 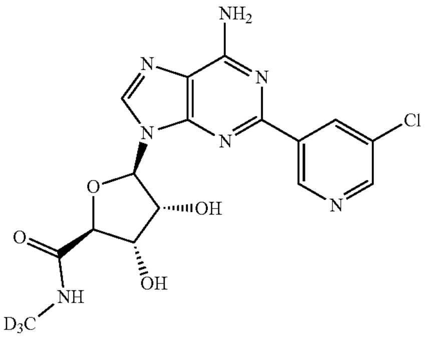 [SMILES: [2H]C([2H])([2H])NC(=O)[C@H]1O[C@@H](n2cnc3c(N)nc(-c4cncc(Cl)c4)nc32)[C@H](O)[C@@H]1O] | (2S,3S,4R,5R)-5-(6-amino-2-(5-chloropyridin-3-yl)-9H-purin-9-yl)-3,4-dihydroxyl-N-(methyl-d3)-tetrahydrofuran-2-carboxamide |

-continued

| Compd. No. | Structural formula of compound | Compound name |
|---|---|---|
| 288 | 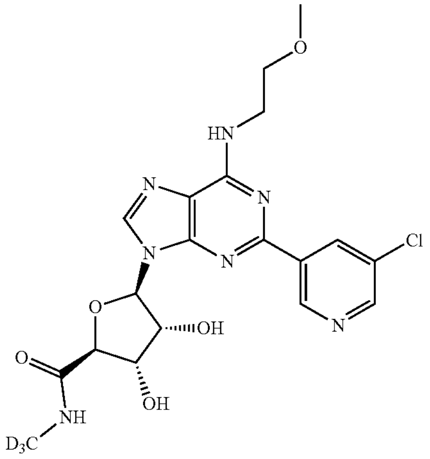 [SMILES: [2H]C([2H])([2H])NC(=O)[C@H]1O[C@@H](n2cnc3c(NCCOC)nc(-c4cncc(Cl)c4)nc32)[C@H](O)[C@@H]1O] | (2S,3S,4R,5R)-5-(2-(5-chloropyridin-3-yl)-6-((2-methoxyethyl)amino)-9H-purin-9-yl)-3,4-dihydroxyl-N-(methyl-d3)-tetrahydrofuran-2-carboxamide |
| 289 | 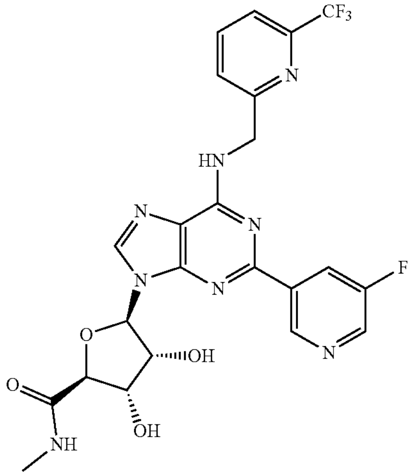 [SMILES: CNC(=O)[C@H]1O[C@@H](n2cnc3c(NCc4cccc(C(F)(F)F)n4)nc(-c4cncc(F)c4)nc32)[C@H](O)[C@@H]1O] | (2S,3S,4R,5R)-5-(2-(5-fluoropyridin-3-yl)-6-(((6-(trifluoromethyl)pyridin-2-yl)methyl)amino)-9H-purin-9-yl)-3,4-dihydroxyl-N-methyltetrahydrofuran-2-carboxamide |
| 290 | 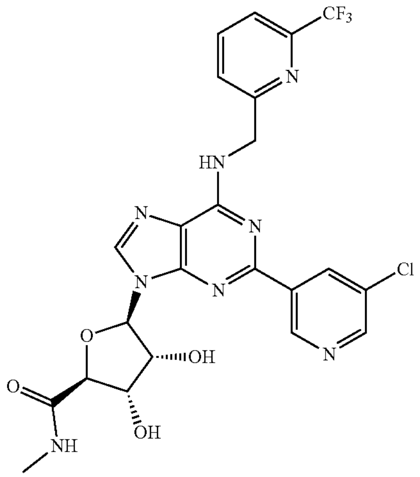 [SMILES: CNC(=O)[C@H]1O[C@@H](n2cnc3c(NCc4cccc(C(F)(F)F)n4)nc(-c4cncc(Cl)c4)nc32)[C@H](O)[C@@H]1O] | (2S,3S,4R,5R)-5-(2-(5-chloropyridin-3-yl)-6-(((6-(trifluoromethyl)pyridin-2-yl)methyl)amino)-9H-purin-9-yl)-3,4-dihydroxyl-N-methyltetrahydrofuran-2-carboxamide |

-continued

| Compd. No. | Structural formula of compound | Compound name |
| --- | --- | --- |
| 291 | 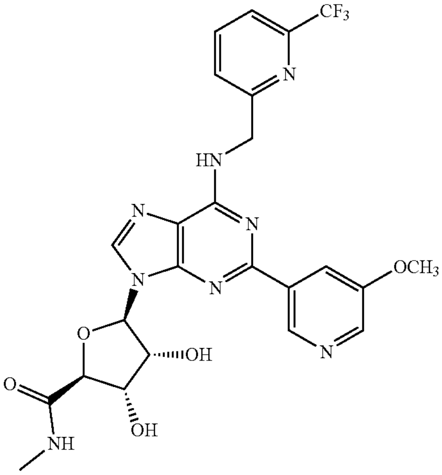 [SMILES: CNC(=O)[C@H]1O[C@@H](n2cnc3c(NCc4cccc(C(F)(F)F)n4)nc(-c4cncc(OC)c4)nc32)[C@H](O)[C@@H]1O] | (2S,3S,4R,5R)-3,4-dihydroxyl-5-(2-(5-methoxypyridin-3-yl)-6-(((6-(trifluoromethyl)pyridin-2-yl)methyl)amino)-9H-purin-9-yl)-N-methyltetrahydrofuran-2-carboxamide |
| 292 | 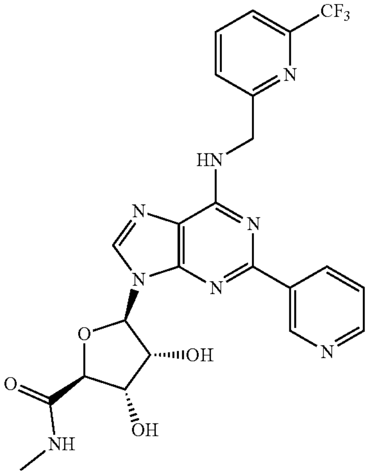 [SMILES: CNC(=O)[C@H]1O[C@@H](n2cnc3c(NCc4cccc(C(F)(F)F)n4)nc(-c4cccnc4)nc32)[C@H](O)[C@@H]1O] | (2S,3S,4R,5R)-3,4-dihydroxyl-N-methyl-5-(2-pyridin-3-yl)-6-(((6-(trifluoromethyl)pyridin-2-yl)methyl)amino)-9/-purin-9-yl)tetrahydrofuran-2-carboxamide |
| 293 | 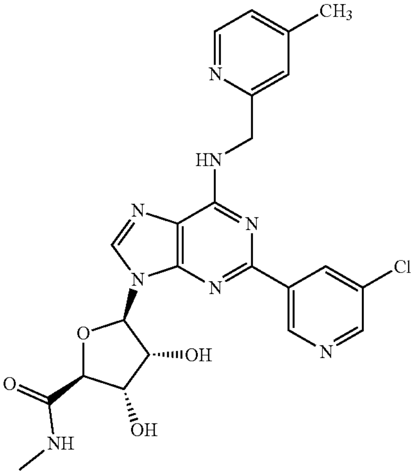 [SMILES: CNC(=O)[C@H]1O[C@@H](n2cnc3c(NCc4cc(C(F)(F)F)ccn4)nc(-c4cncc(Cl)c4)nc32)[C@H](O)[C@@H]1O] | (2S,3S,4R,5R)-5-(2-(5-chloropyridin-3-yl)-6-(((4-methylpyridin-2-yl)methyl)amino)-9H-purin-9-yl)-3,4-dihydroxyl-N-methyltetrahydrofuran-2-carboxamide |

-continued

| Compd. No. | Structural formula of compound | Compound name |
|---|---|---|
| 294 | 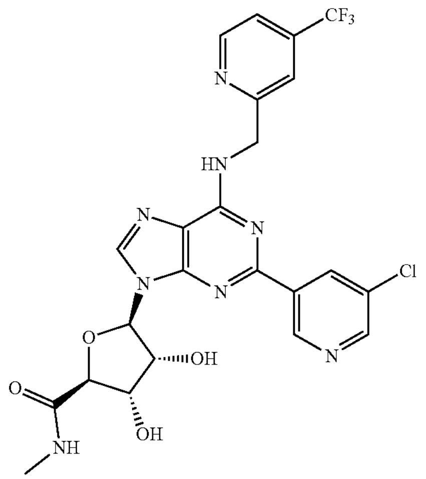 | (2S,3S,4R,5R)-5-(2-(5-chloropyridin-3-yl)-6-(((4-(trifluoromethyl)pyridin-2-yl)methyl)amino)-9H-purin-9-yl)-3,4-dihydroxyl-N-methyltetrahydrofuran-2-carboxamide |
| 295 | 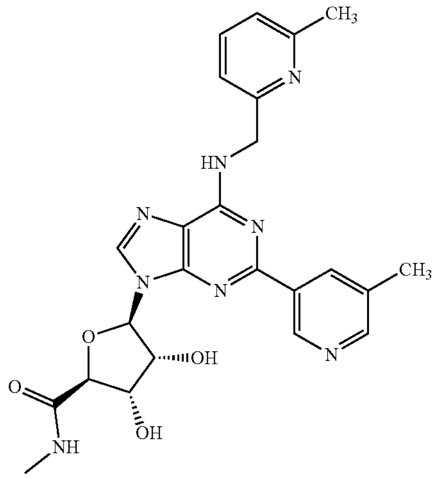 [SMILES: CNC(=O)[C@H]1O[C@@H](n2cnc3c(NCc4cccc(C)n4)nc(-c4cncc(C)c4)nc32)[C@H](O)[C@@H]1O] | (2S,3S,4R,5R)-3,4-dihydroxyl-N-methyl-5-(6-(((6-methylpyridin-2-yl)methyl)amino)-2-(5-methylpyridin-3-yl)-9H-purin-9-yl)tetrahydrofuran-2-carboxamide |
| 296 | 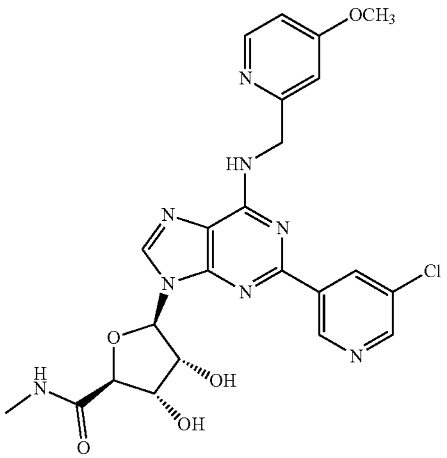 [SMILES: CNC(=O)[C@H]1O[C@@H](n2cnc3c(NCc4cc(OC)ccn4)nc(-c4cncc(Cl)c4)nc32)[C@H](O)[C@@H]1O] | (2S,3S,4R,5R)-5-(2-(5-chloropyridin-3-yl)-6-(((4-methoxypyridin-2-yl)methyl)amino)-9H-purin-9-yl)-3,4-dihydroxyl-N-methyltetrahydrofuran-2-carboxamide |

-continued

| Compd. No. | Structural formula of compound | Compound name |
|---|---|---|
| 297 | 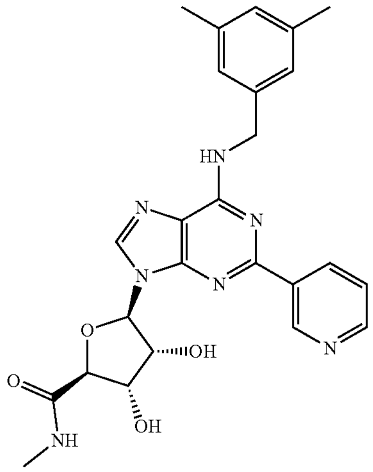 [SMILES: CNC(=O)[C@H]1O[C@@H](n2cnc3c(NCc4cc(C)cc(C)c4)nc(-c4cccnc4)nc32)[C@H](O)[C@@H]1O] | (2S,3S,4R,5S)-5-(6-((3,5-dimethylbenzyl)amino)-2-(pyridin-3-yl)-9H-purin-9-yl)-3,4-dihydroxyl-N-methyltetrahydrofuran-2-carboxamide |
| 298 | 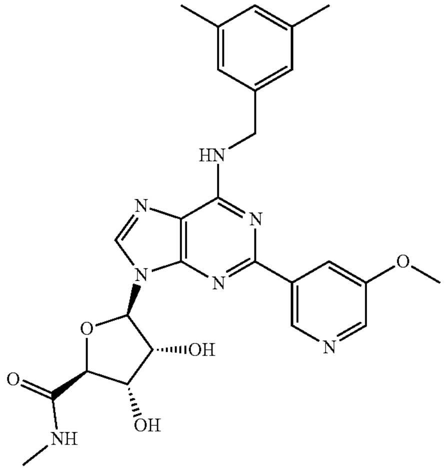 [SMILES: CNC(=O)[C@H]1O[C@@H](n2cnc3c(NCc4cc(C)cc(C)c4)nc(-c4cncc(OC)c4)nc32)[C@H](O)[C@@H]1O] | (2S,3S,4R,5S)-5-(6-((3,5-dimethylbenzyl)amino)-2-(5-methoxypyridin-3-yl)-9H-purin-9-yl)-3,4-dihydroxyl-N-methyltetrahydrofuran-2-carboxamide |
| 299 | 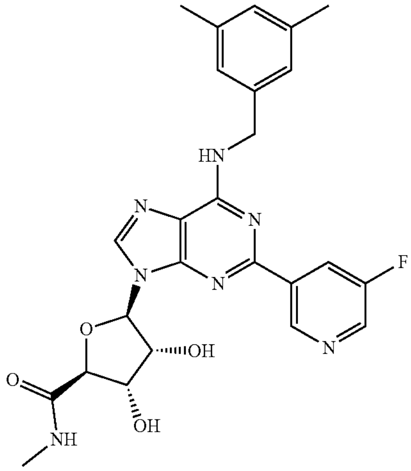 [SMILES: CNC(=O)[C@H]1O[C@@H](n2cnc3c(NCc4cc(C)cc(C)c4)nc(-c4cncc(F)c4)nc32)[C@H](O)[C@@H]1O] | (2S,3S,4R,5S)-5-(6-((3,5-dimethylbenzyl)amino)-2-(5-fluoropyridin-3-yl)-9H-purin-9-yl)-3,4-dihydroxyl-N-methyltetrahydrofuran-2-carboxamide |

-continued

| Compd. No. | Structural formula of compound | Compound name |
|---|---|---|
| 300 | 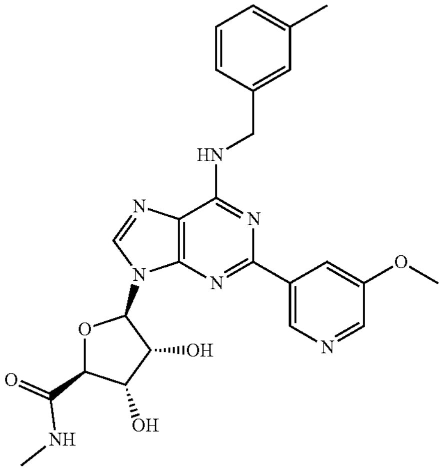 [SMILES: CNC(=O)[C@H]1O[C@@H](n2cnc3c(NCc4cccc(C)c4)nc(-c4cncc(OC)c4)nc32)[C@H](O)[C@@H]1O] | (2S,3S,4R,5S)-3,4-dihydroxyl-5-(2-(5-methoxypyridin-3-yl)-6-((3-methylbenzylamino)-9H-purin-9-yl)-N-methyltetrahydrofuran-2-carboxamide |
| 301 | 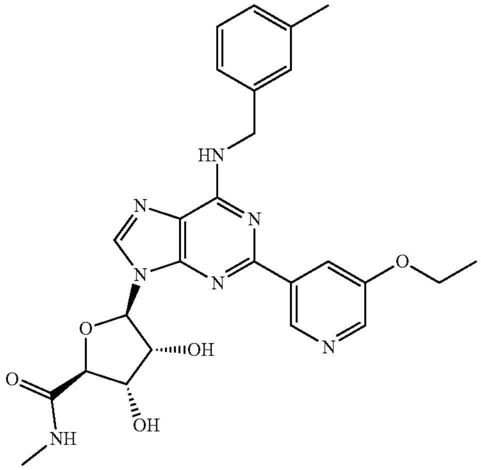 [SMILES: CCOc1cncc(-c2nc(NCc3cccc(C)c3)c3ncn([C@@H]4O[C@H](C(=O)NC)[C@@H](O)[C@H]4O)c3n2)c1] | (2S,3S,4R,5S)-5-(2-(5-ethoxypyridin-3-yl)-6-((3-methylbenzyl)amino)-9H-purin-9-yl)-3,4-dihydroxyl-N-methyltetrahydrofuran-2-carboxamide |
| 302 | 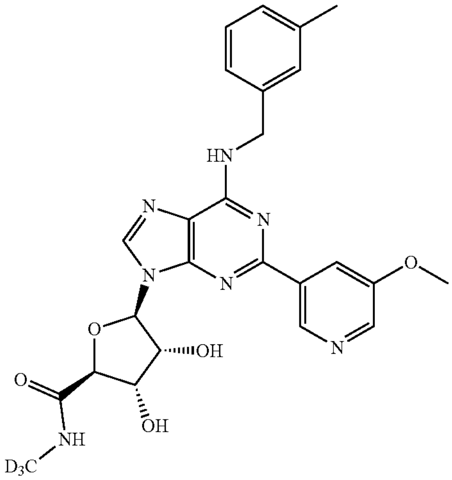 [SMILES: [2H]C([2H])([2H])NC(=O)[C@H]1O[C@@H](n2cnc3c(NCc4cccc(C)c4)nc(-c4cncc(OC)c4)nc32)[C@H](O)[C@@H]1O] | (2S,3S,4R,5S)-3,4-dihydroxyl-5-(2-(5-methoxypyridin-3-yl)-6-((3-methylbenzylamino)-9H-purin-9-yl)-N-methyl-D3-tetrahydrofuran-2-carboxamide |

-continued

| Compd. No. | Structural formula of compound | Compound name |
|---|---|---|
| 303 | 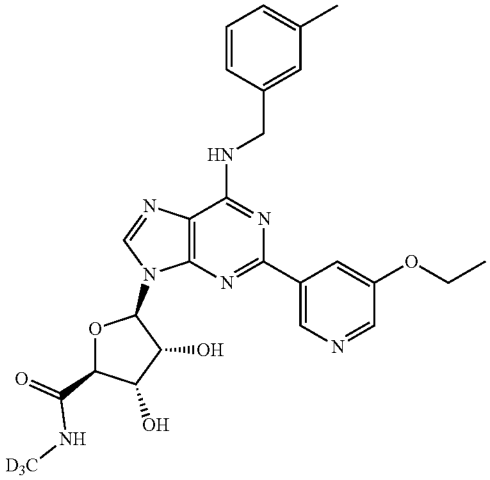 [SMILES: [2H]C([2H])([2H])NC(=O)[C@H]1O[C@@H](n2cnc3c(NCc4cccc(C)c4)nc(-c4cncc(OCC)c4)nc32)[C@H](O)[C@@H]1O] | (2S,3S,4R,5S)-5-(2-(5-ethoxypyridin-3-yl)-6-((3-methylbenzyl)amino)-9H-purin-9-yl)-3,4-dihydroxyl-N-(methyl-d3)-tetrahydrofuran-2-carboxamide |
| 304 | 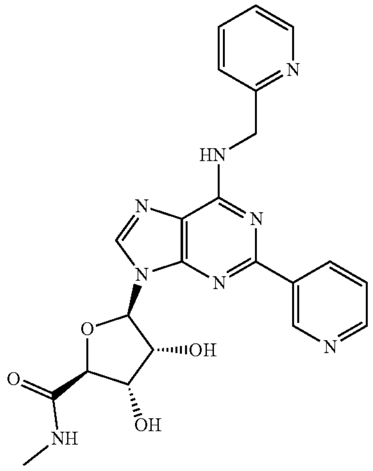 [SMILES: CNC(=O)[C@H]1O[C@@H](n2cnc3c(NCc4ccccn4)nc(-c4cccnc4)nc32)[C@H](O)[C@@H]1O] | (2S,3S,4R,5S)-3,4-dihydroxyl-N-methyl-5-(6-((pyridin-2-ylmethyl)amino)-2-(pyridin-3-yl)-9H-purin-9-yl)tetrahydrofuran-2-carboxamide |
| 305 | 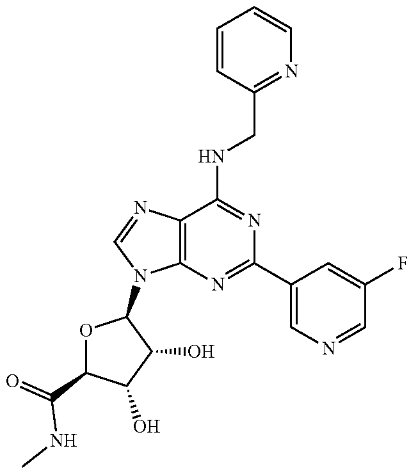 [SMILES: CNC(=O)[C@H]1O[C@@H](n2cnc3c(NCc4ccccn4)nc(-c4cncc(F)c4)nc32)[C@H](O)[C@@H]1O] | (2S,3S,4R,5S)-5-(2-(5-fluoropyridin-3-yl)-6-((pyridin-2-ylmethyl)amino)-9/-purin-9-yl)-3,4-dihydroxyl-N-methyltetrahydrofuran-2-carboxamide |

-continued

| Compd. No. | Structural formula of compound | Compound name |
|---|---|---|
| 306 | 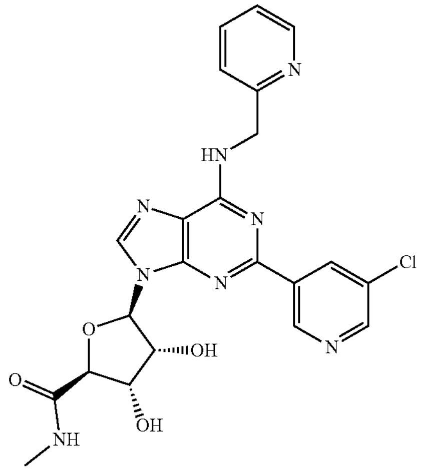 [SMILES: CNC(=O)[C@H]1O[C@@H](n2cnc3c(NCc4ccccn4)nc(-c4cncc(Cl)c4)nc32)[C@H](O)[C@@H]1O] | (2S,3S,4R,5S)-5-(2-(5-chloropyridin-3-yl)-6-((pyridin-2-lymethyl)amino)-9H-purin-9-yl)-3,4-dihydroxyl-N-methyltetrahydrofuran-2-carboxamide |
| 307 | 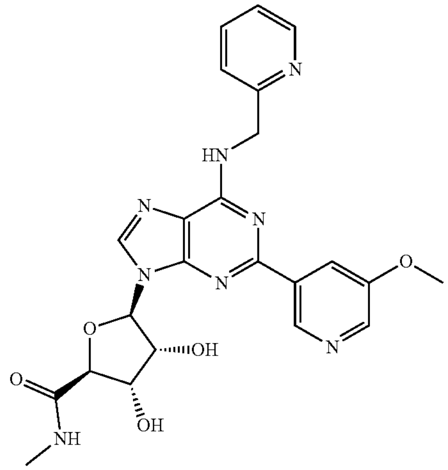 [SMILES: CNC(=O)[C@H]1O[C@@H](n2cnc3c(NCc4ccccn4)nc(-c4cncc(OC)c4)nc32)[C@H](O)[C@@H]1O] | (2S,3S,4R,5S)-3,4-dihydroxyl-5-(2-(5-methoxypyridin-3-yl)-6-((pyridin-2-ylmethyl)amino)-9H-purin-9-yl)-N-methyltetrahydrofuran-2-carboxamide |
| 308 | 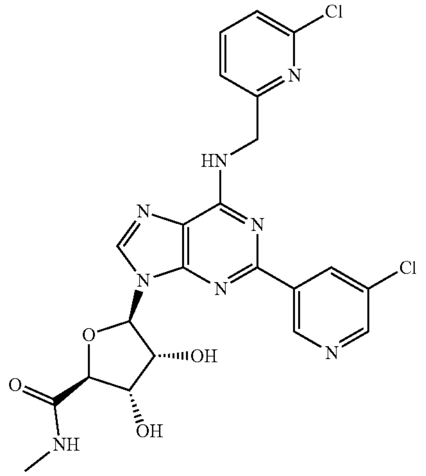 [SMILES: CNC(=O)[C@H]1O[C@@H](n2cnc3c(NCc4cccc(Cl)n4)nc(-c4cncc(Cl)c4)nc32)[C@H](O)[C@@H]1O] | (2S,3S,4R,5S)-5-(6-((((6-chloropyridin-2-yl)methyl)amino)-2-(5-chloropyridin-3-ly)-9H-purin-9-yl)-3,4-dihydroxyl-N-methyltetrahydrofuran-2-carboxamide |

-continued

| Compd. No. | Structural formula of compound | Compound name |
|---|---|---|
| 309 | 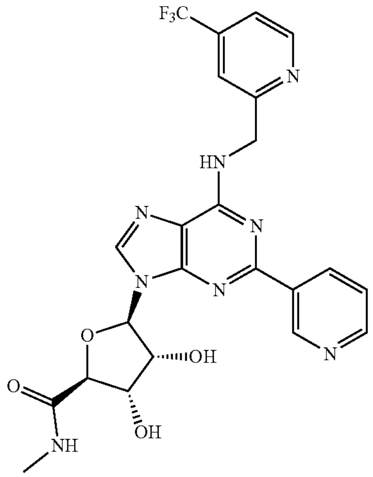 [SMILES: CNC(=O)[C@H]1O[C@@H](n2cnc3c(NCc4cc(C(F)(F)F)ccn4)nc(-c4cccnc4)nc32)[C@H](O)[C@@H]1O] | (2S,3S,4R,5S)-3,4-dihydroxyl-N-methyl-5-(2-(pyridin-3-yl)-6-((((4-(trifluoromethyl)pyridin-2-yl]methyl)amino)-9H-purin-9-yl)tetrahydrofuran-2-carboxamide |
| 310 | 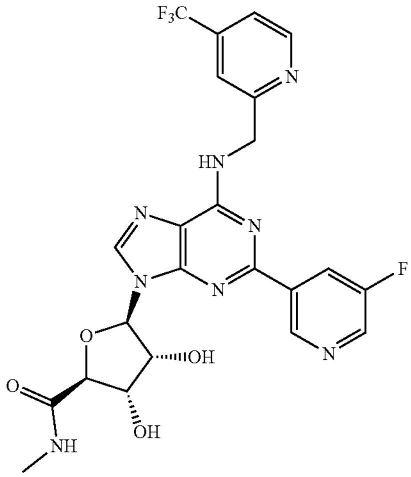 [SMILES: CNC(=O)[C@H]1O[C@@H](n2cnc3c(NCc4cc(C(F)(F)F)ccn4)nc(-c4cncc(F)c4)nc32)[C@H](O)[C@@H]1O] | (2S,3S,4R,5S)-5-(2-(5-fluoropyridin-3-yl)-6-((((4-(trifluoromethyl)pyridin-2-yl)methyl)amino)-9H-purin-9-yl)-3,4-dihydroxyl-N-methyltetrahydrofuran-2-carboxamide |
| 311 | 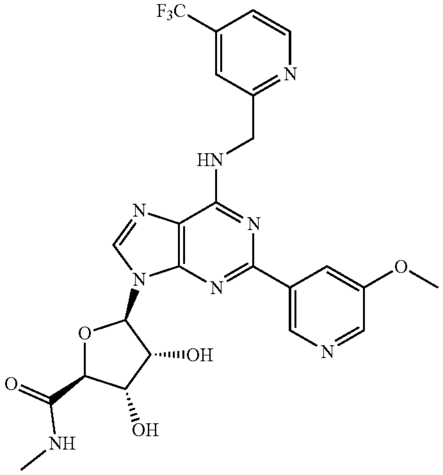 [SMILES: CNC(=O)[C@H]1O[C@@H](n2cnc3c(NCc4cc(C(F)(F)F)ccn4)nc(-c4cncc(OC)c4)nc32)[C@H](O)[C@@H]1O] | (2S,3S,4R,5S)-3,4-dihydroxyl-5-(2-(5-methoxypyridin-3-yl)-6-((((4-(trifluoromethyl)pyridin-2-yl)methyl)amino)-9H-purin-9-yl)-N-methyltetrahydrofuran-2-carboxamide |

-continued

| Compd. No. | Structural formula of compound | Compound name |
|---|---|---|
| 312 | 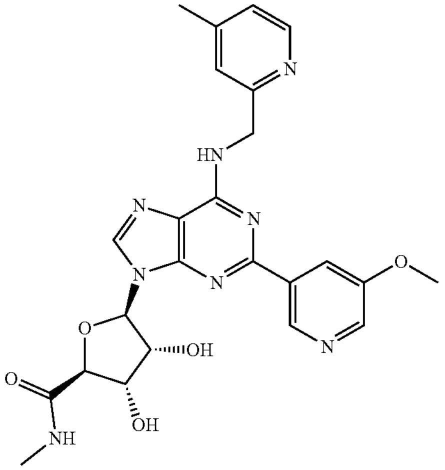 [SMILES: CNC(=O)[C@H]1O[C@@H](n2cnc3c(NCc4cc(C)ccn4)nc(-c4cncc(OC)c4)nc32)[C@H](O)[C@@H]1O] | (2S,3S,4R,5S)-3,4-dihydroxyl-5-(2-(5-methoxypyridin-3-yl)-6-((((4-(methylpyridin-2-yl)methyl)amino)-9H-purin-9-yl)-N-methyltetrahydrofuran-2-carboxamide |
| 313 | 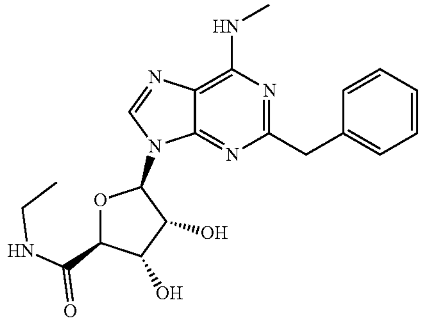 [SMILES: CCNC(=O)[C@H]1O[C@@H](n2cnc3c(NC)nc(Cc4ccccc4)nc32)[C@H](O)[C@@H]1O] | (2S,3S,4R,5R)-5-(2-benzyl-6-(methylamino)-9H-purin-9-yl)-N-ethyl-3,4-dihydroxyltetrahydrofuran-2-carboxamide |
| 314 | 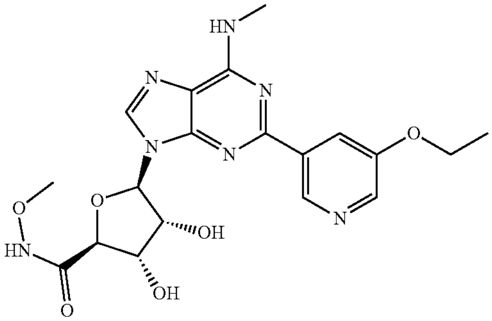 [SMILES: CCOc1cncc(-c2nc(NC)c3ncn([C@@H]4O[C@H](C(=O)NOC)[C@@H](O)[C@H]4O)c3n2)c1] | (2S,3S,4R,5R)-5-(2-(5-ethoxypyridin-3-yl)-6-(methylamino)-9H-purin-9-yl)-3,4-dihydroxyl-N-methoxytetrahydrofuran-2-carboxamide |
| 315 | 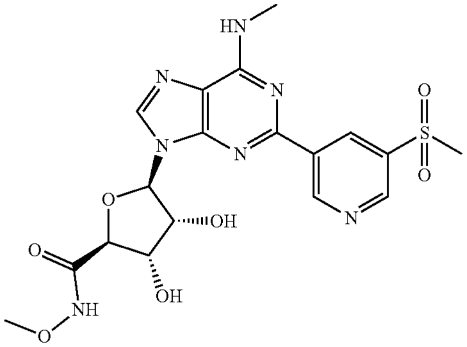 | (2S,3S,4R,5R)-3,4-dihydroxyl-N-methoxy-5-(6-(methylamino)-2-(5-(methylsulfonyl)pyridin-3-yl)-9H-purin-9-yl)tetrahydrofuran-2-carboxamide |

-continued

| Compd. No. | Structural formula of compound | Compound name |
| --- | --- | --- |
| 316 | 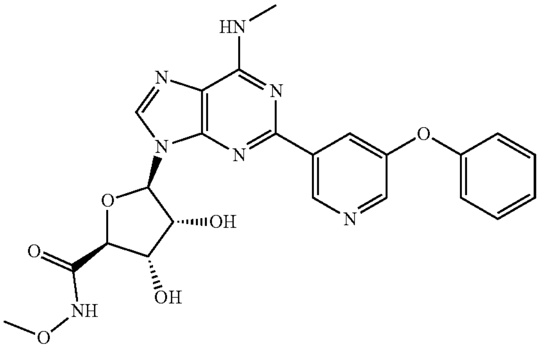 [SMILES: CNc1nc(-c2cncc(Oc3ccccc3)c2)nc2c1ncn2[C@@H]1O[C@H](C(=O)NOC)[C@@H](O)[C@H]1O] | (2S,3S,4R,5R)-3,4-dihydroxyl-N-methoxy-5-(6-(methylamino)-2-(5-phenoxypyridin-3-yl)-9H-purin-9-yl)tetrahydrofuran-2-carboxamide |
| 317 | 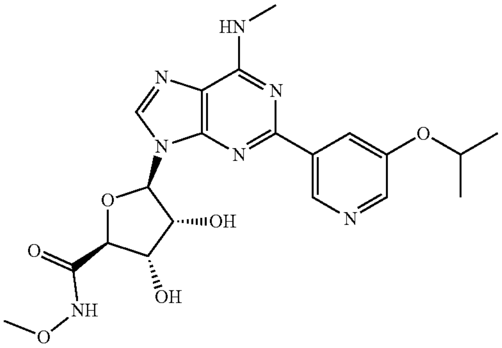 [SMILES: CNc1nc(-c2cncc(OC(C)C)c2)nc2c1ncn2[C@@H]1O[C@H](C(=O)NOC)[C@@H](O)[C@H]1O] | (2S,3S,4R,5R)-3,4-dihydroxyl-5-(2-(5-isopropoxypyridin-3-yl)-6-(methylamino)-9H-purin-9-yl)-N-methoxytetrahydrofuran-2-carboxamide |
| 318 | 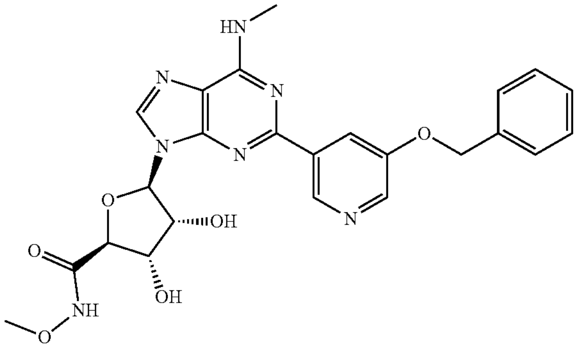 [SMILES: CNc1nc(-c2cncc(OCc3ccccc3)c2)nc2c1ncn2[C@@H]1O[C@H](C(=O)NOC)[C@@H](O)[C@H]1O] | (2S,3S,4R,5R)-5-(2-(5-(benzyloxy)pyridin-3-yl)-6-(methylamino)-9H-purin-9-yl)-3,4-dihydroxyl-N-methoxytetrahydrofuran-2-carboxamide |
| 319 | 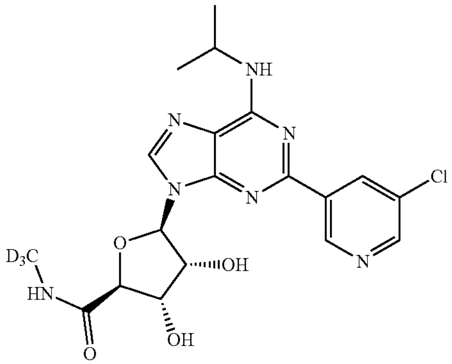 [SMILES: [2H]C([2H])([2H])NC(=O)[C@H]1O[C@@H](n2cnc3c(NC(C)C)nc(-c4cncc(Cl)c4)nc32)[C@H](O)[C@@H]1O] | (2S,3S,4R,5R)-5-(2-(5-chloropyridin-3-yl)-6-(isopropylamino)-9H-purin-9-yl)-3,4-dihydroxyl-N-(methyl-d3)tetrahydrofuran-2-carboxamide |

-continued

| Compd. No. | Structural formula of compound | Compound name |
|---|---|---|
| 320 | 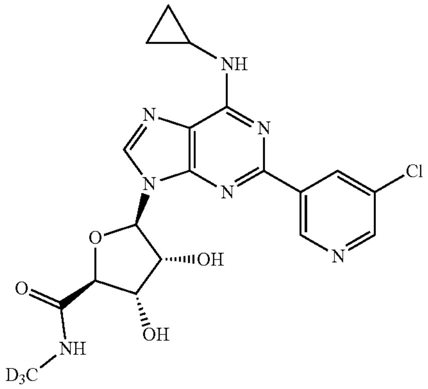 [SMILES: [2H]C([2H])([2H])NC(=O)[C@H]1O[C@@H](n2cnc3c(NC4CC4)nc(-c4cncc(Cl)c4)nc32)[C@H](O)[C@@H]1O] | (2S,3S,4R,5R)-5-(2-(5-chloropyridin-3-yl)-6-(cyclopropylamino)-9H-purin-9-yl)-3,4-dihydroxyl-N-(methyl-d3)tetrahydrofuran-2-carboxamide |
| 321 | 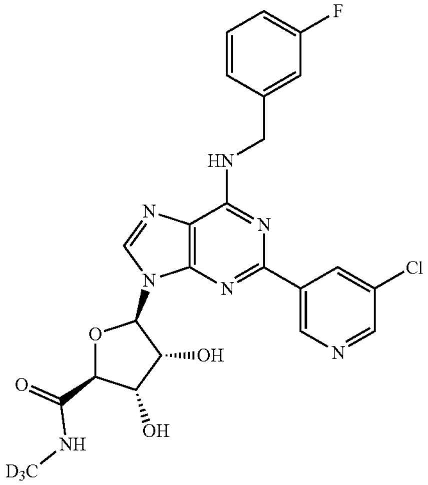 [SMILES: [2H]C([2H])([2H])NC(=O)[C@H]1O[C@@H](n2cnc3c(NCc4cccc(F)c4)nc(-c4cncc(Cl)c4)nc32)[C@H](O)[C@@H]1O] | (2S,3S,4R,5R)-5-(2-(5-chloropyridin-3-yl)-6-((3-fluorobenzylamino)-9H-purin-9-yl)-3,4-dihydroxyl-N-(methyl-d3)-tetrahydrofuran-2-carboxamide |
| 322 | 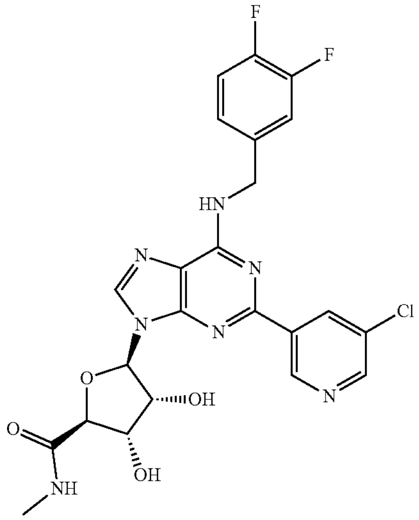 [SMILES: CNC(=O)[C@H]1O[C@@H](n2cnc3c(NCc4ccc(F)c(F)c4)nc(-c4cncc(Cl)c4)nc32)[C@H](O)[C@@H]1O] | (2S,3S,4R,5R)-5-(2-(5-chloropyridin-3-yl)-6-((3,4-difluorobenzyl)amino)-9H-purin-9-yl)-3,4-dihydroxyl-N-methyltetrahydrofuran-2-carboxamide |

-continued
| Compd. No. | Structural formula of compound | Compound name |
|---|---|---|
| 323 | 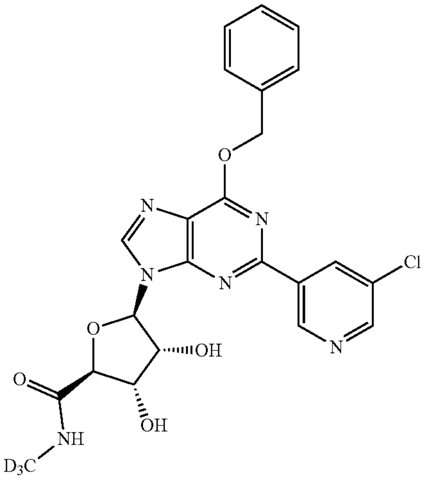 [SMILES: [2H]C([2H])([2H])NC(=O)[C@H]1O[C@@H](n2cnc3c(OCc4ccccc4)nc(-c4cncc(Cl)c4)nc32)[C@H](O)[C@@H]1O] | (2S,3S,4R,5R)-5-(6-(benzyloxy)-2-(5-chloropyridin-3-yl)-9H-purin-9-yl)-3,4-dihydroxyl-N-(methyl-d3)-tetrahydrofuran-2-formamide |
| 324 | 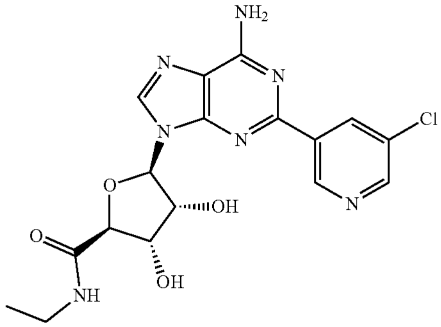 [SMILES: CCNC(=O)[C@H]1O[C@@H](n2cnc3c(N)nc(-c4cncc(Cl)c4)nc32)[C@H](O)[C@@H]1O] | (2S,3S,4R,5R)-5-(6-amino-2-(5-chloropyridin-3-yl)-9H-purin-9-yl)-N-ethyl-3,4-dihydroxyltetrahydrofuran-2-formamide |
| 325 | 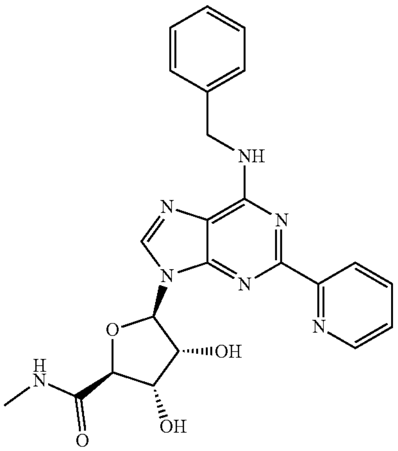 [SMILES: CNC(=O)[C@H]1O[C@@H](n2cnc3c(NCc4ccccc4)nc(-c4ccccn4)nc32)[C@H](O)[C@@H]1O] | (2S,3S,4R,5S)-5-(6-(benzylamino)-2-(pyridin-2-yl)-9H-purin-9-yl)-3,4-dihydroxyl-N-methyltetrahydrofuran-2-carboxamide |

In other embodiments, the compound of formula I may be selected from the following compounds:

| Compd. No | Structural formula of compound | Name |
|---|---|---|
| 326 | 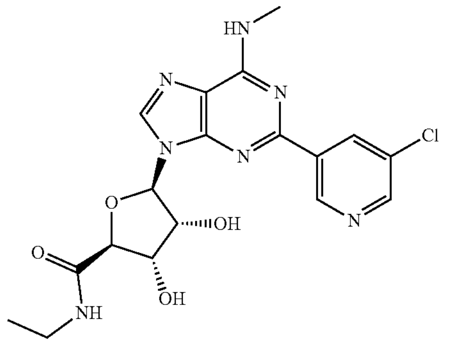 | (2S,3S,4R,5R)-5-(2-(5-chloropyridin-3-yl)-6-(methylamino)-9H-purin-9-yl)-N-ethyl-3,4-dihydroxyltetrahydrofuran-2-formamide |
| 327 | 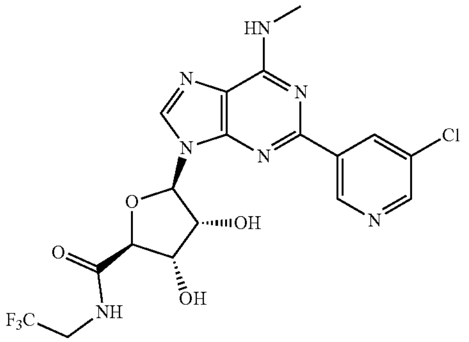 [SMILES: CNc1nc(-c2cncc(Cl)c2)nc2c1ncn2[C@@H]1O[C@H](C(=O)NCC(F)(F)F)[C@@H](O)[C@H]1O] | (2S,3S,4R,5R)-5-(2-(5-chloropyridin-3-yl)-6-(methylamino)-9H-purin-9-yl)-3,4-dihydroxyl-N-(2,2,2-trifluoroethyl)tetrahydrofuran-2-formamide |
| 328 | 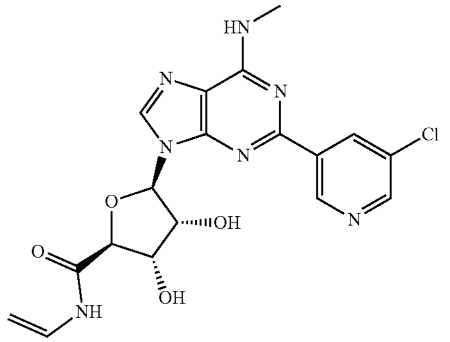 [SMILES: C=CNC(=O)[C@H]1O[C@@H](n2cnc3c(NC)nc(-c4cncc(Cl)c4)nc32)[C@H](O)[C@@H]1O] | (2S,3S,4R,5R)-5-(2-(5-chloropyridin-3-yl)-6-(methylamino)-9H-purin-9-yl)-3,4-dihydroxyl-N-vinyltetrahydrofuran-2-formamide |
| 329 | 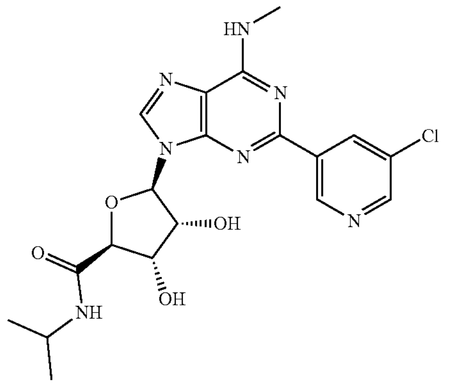 [SMILES: CNc1nc(-c2cncc(Cl)c2)nc2c1ncn2[C@@H]1O[C@H](C(=O)NC(C)C)[C@@H](O)[C@H]1O] | (2S,3S,4R,5R)-5-(2-(5-chloropyridin-3-yl)-6-(methylamino)-9H-purin-9-yl)-3,4-dihydroxyl-N-isopropyltetrahydrofuran-2-formamide |

-continued

| Compd. No | Structural formula of compound | Name |
|---|---|---|
| 330 | 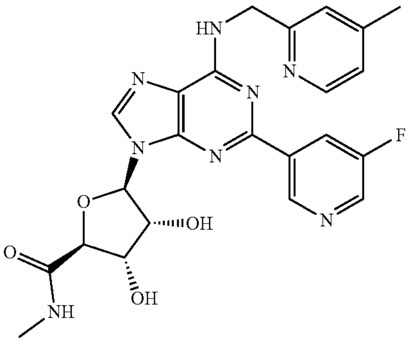 [SMILES: CNC(=O)[C@H]1O[C@@H](n2cnc3c(NCc4cc(C)ccn4)nc(-c4cncc(F)c4)nc32)[C@H](O)[C@@H]1O] | (2S,3S,4R,5R)-5-(2-(5-fluoropyridin-3-yl)-6-(((4-methylpyridin-2-yl)methyl)amino)-9H-purin-9-yl)-3,4-dihydroxyl-N-methyltetrahydrofuran-2-formamide |
| 331 | 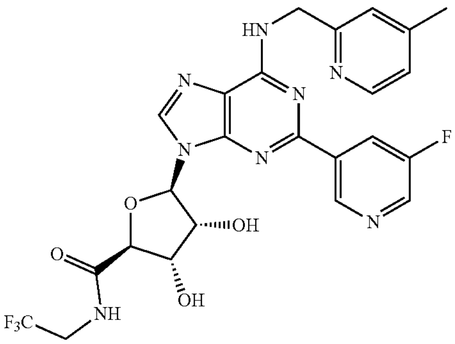 [SMILES: Cc1ccnc(CNc2nc(-c3cncc(F)c3)nc3c2ncn3[C@@H]2O[C@H](C(=O)NCC(F)(F)F)[C@@H](O)[C@H]2O)c1] | (2S,3S,4R,5R)-5-(2-(5-fluoropyridin-3-yl)-6-(((6-methylpyridin-2-yl)methyl)amino)-9H-purin-9-yl)-3,4-dihydroxyl-N-(2,2,2-trifluoroethyl)tetrahydrofuran-2-formamide |
| 332 | 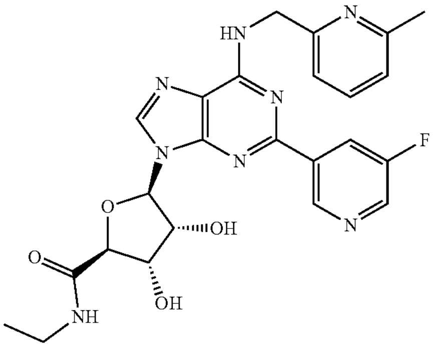 [SMILES: CCNC(=O)[C@H]1O[C@@H](n2cnc3c(NCc4cccc(C)n4)nc(-c4cncc(F)c4)nc32)[C@H](O)[C@@H]1O] | (2S,3S,4R,5R)-N-ethyl-5-(2-(5-fluoropyridin-3-yl)-6-(((6-methylpyridin-2-yl)methyl)amino)-9H-purin-9-yl)-3,4-dihydroxyltetrahydrofuran-2-formamide |
| 333 | 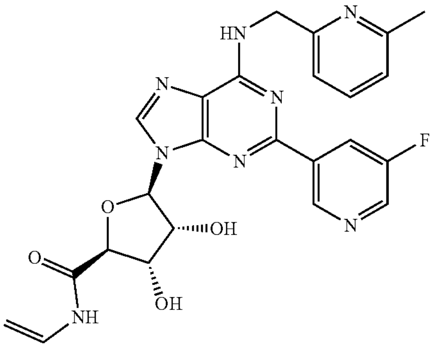 [SMILES: C=CNC(=O)[C@H]1O[C@@H](n2cnc3c(NCc4cccc(C)n4)nc(-c4cncc(F)c4)nc32)[C@H](O)[C@@H]1O] | (2S,3S,4R,5R)-5-(2-(5-fluoropyridin-3-yl)-6-(((6-methylpyridin-2-yl)methyl)amino)-9H-purin-9-yl)-3,4-dihydroxyl-N-vinyltetrahydrofuran-2-formamide |

-continued

| Compd. No | Structural formula of compound | Name |
|---|---|---|
| 334 | 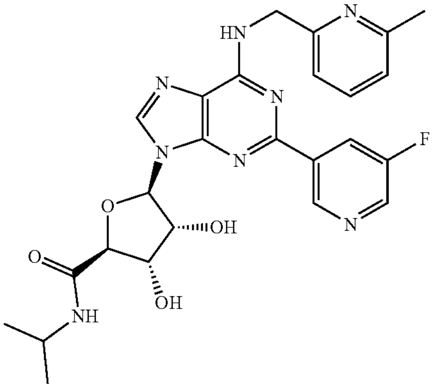 [SMILES: Cc1cccc(CNc2nc(-c3cncc(F)c3)nc3c2ncn3[C@@H]2O[C@H](C(=O)NC(C)C)[C@@H](O)[C@H]2O)n1] | (2S,3S,4R,5R)-5-(2-(5-fluoropyridin-3-yl)-6-(((6-methylpyridin-2-yl)methyl)amino)-9H-purin-9-yl)3,4-dihydroxyl-N-isopropyltetrahydrofuran-2-formamide |
| 335 | 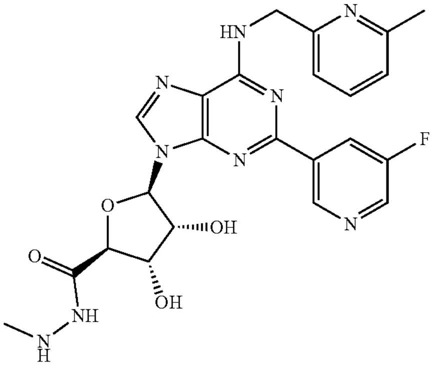 | (2S,3S,4R,5R)-5-(2-(5-fluoropyridin-3-yl)-6-(((6-methylpyridin-2-yl)methyl)amino)-9H-purin-9-yl)3,4-dihydroxyl-N'-methyltetrahydrofuran-2-carbohydrazide |
| 336 | 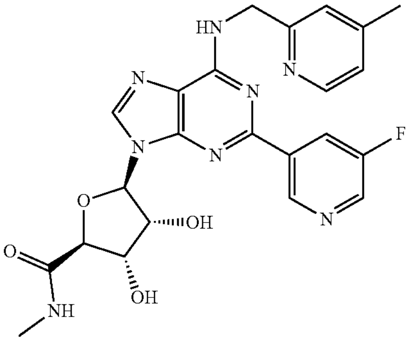 [SMILES: CNC(=O)[C@H]1O[C@@H](n2cnc3c(NCc4cc(C)ccn4)nc(-c4cncc(F)c4)nc32)[C@H](O)[C@@H]1O] | (2S,3S,4R,5R)-5-(2-(5-fluoropyridin-3-yl)-6-(((4-methylpyridin-2-yl)methyl)amino)-9H-purin-9-yl)-3,4-dihydroxyl-N-methyltetrahydrofuran-2-formamide |
| 337 | 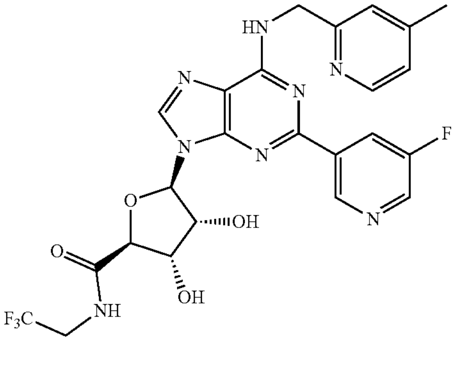 [SMILES: Cc1ccnc(CNc2nc(-c3cncc(F)c3)nc3c2ncn3[C@@H]2O[C@H](C(=O)NCC(F)(F)F)[C@@H](O)[C@H]2O)c1] | (2S,3S,4R,5R)-5-(2-(5-fluoropyridin-3-yl)-6-(((4-methylpyridin-2-yl)methyl)amino)-9H-purin-9-yl)-3,4-dihydroxyl-N-(2,2,2-trifluoroethyl)tetrahydrofuran-2-formamide |

-continued

| Compd. No | Structural formula of compound | Name |
|---|---|---|
| 338 | 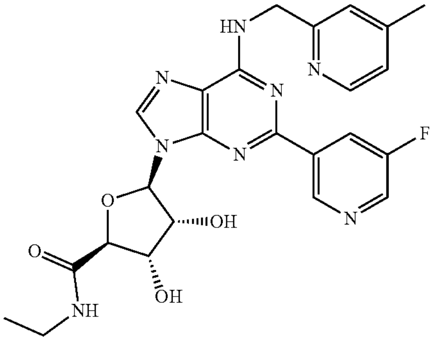 [SMILES: CCNC(=O)[C@H]1O[C@@H](n2cnc3c(NCc4cc(C)ccn4)nc(-c4cncc(F)c4)nc32)[C@H](O)[C@@H]1O] | (2S,3S,4R,5R)-N-ethyl-5-(2-(5-fluoropyridin-3-yl)-6-(((4-methylpyridin-2-yl)methyl)amino)-9H-purin-9-yl)-3,4-dihydroxyltetrahydrofuran-2-formamide |
| 339 | 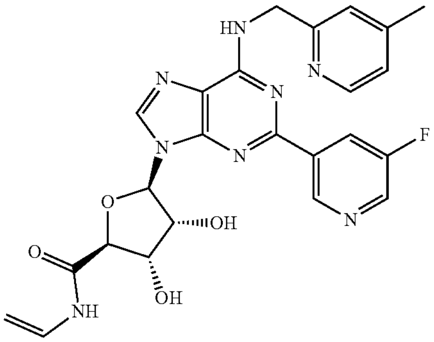 [SMILES: C=CNC(=O)[C@H]1O[C@@H](n2cnc3c(NCc4cc(C)ccn4)nc(-c4cncc(F)c4)nc32)[C@H](O)[C@@H]1O] | (2S,3S,4R,5R)-5-(2-(5-fluoropyridin-3-yl)-6-(((4-methylpyridin-2-yl)methyl)amino)-9H-purin-9-yl)-3,4-dihydroxyl-N-vinyltetrahydrofuran-2-formamide |
| 340 | 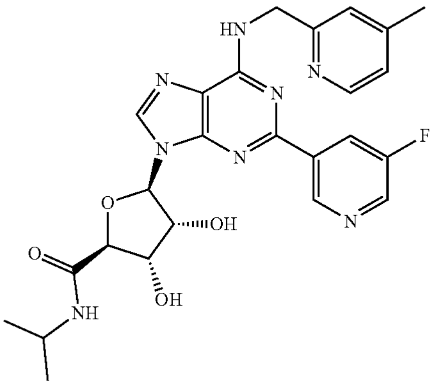 [SMILES: Cc1ccnc(CNc2nc(-c3cncc(F)c3)nc3c2ncn3[C@@H]2O[C@H](C(=O)NC(C)C)[C@@H](O)[C@H]2O)c1] | (2S,3S,4R,5R)-5-(2-(5-fluoropyridin-3-yl)-6-(((4-methylpyridin-2-yl)methyl)amino)-9H-purin-9-yl)-3,4-dihydroxyl-N-isopropyltetrahydrofuran-2-formamide |
| 341 | 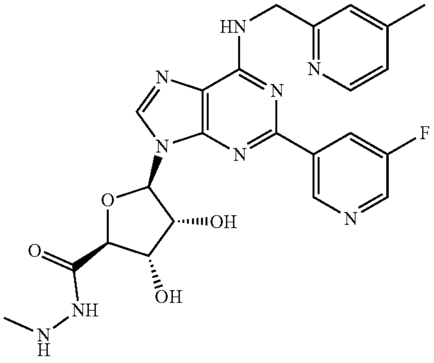 | (2S,3S,4R,5R)-5-(2-(5-fluoropyridin-3-yl)-6-(((4-methylpyridin-2-yl)methyl)amino)-9H-purin-9-yl)-3,4-dihydroxyl-N'-methyltetrahydrofuran-2-carbohydrazide |

-continued

| Compd. No | Structural formula of compound | Name |
|---|---|---|
| 342 | 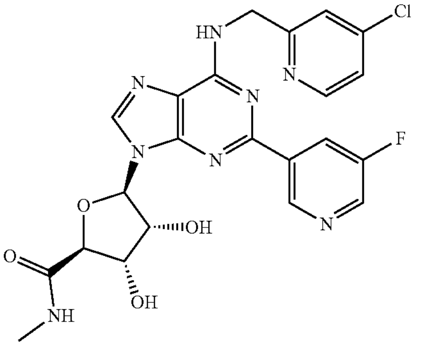 | (2S,3S,4R,5R)-5-(6-(((4-chloropyridin-2-yl)methyl)amino)-2-(5-fluoropyridin-3-yl)-9H-purin-9-yl)-3,4-dihydroxyl-N-methyltetrahydrofuran-2-formamide |
| 343 | 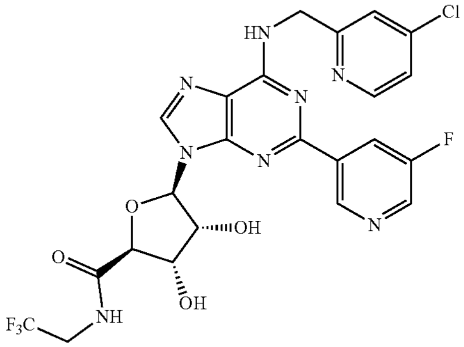 [SMILES: O=C(NCC(F)(F)F)[C@H]1O[C@@H](n2cnc3c(NCc4cc(Cl)ccn4)nc(-c4cncc(F)c4)nc32)[C@H](O)[C@@H]1O] | (2S,3S,4R,5R)-5-(6-(((4-chloropyridin-2-yl)methyl)amino)-2-(5-fluoropyridin-3-yl)-9H-purin-9-yl)-3,4-dihydroxyl-N-(2,2,2-trifluoroethyl)tetrahydrofuran-2-formamide |
| 344 | 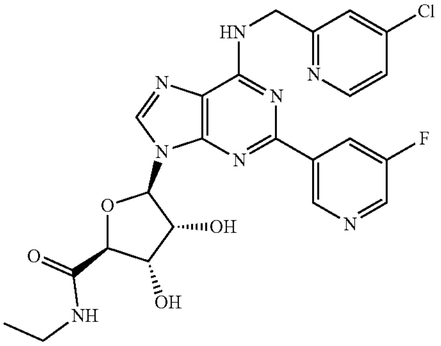 [SMILES: CCNC(=O)[C@H]1O[C@@H](n2cnc3c(NCc4cc(Cl)ccn4)nc(-c4cncc(F)c4)nc32)[C@H](O)[C@@H]1O] | (2S,3S,4R,5R)-5-(6-(((4-chloropyridin-2-yl)methyl)amino)-2-(5-fluoropyridin-3-yl)-9H-purin-9-yl)-N-ethyl-3,4-dihydroxyltetrahydrofuran-2-formamide |
| 345 | 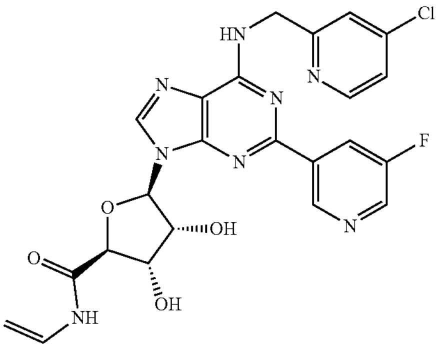 [SMILES: C=CNC(=O)[C@H]1O[C@@H](n2cnc3c(NCc4cc(Cl)ccn4)nc(-c4cncc(F)c4)nc32)[C@H](O)[C@@H]1O] | (2S,3S,4R,5R)-5-(6-(((4-chloropyridin-2-yl)methyl)amino)-2-(5-fluoropyridin-3-yl)-9H-purin-9-yl)-3,4-dihydroxyl-N-vinyltetrahydrofuran-2-formamide |

-continued

| Compd. No | Structural formula of compound | Name |
|---|---|---|
| 346 | 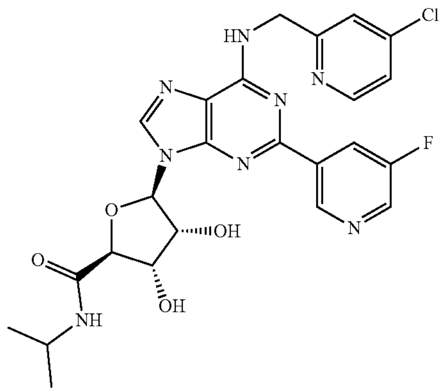 [SMILES: CC(C)NC(=O)[C@H]1O[C@@H](n2cnc3c(NCc4cc(Cl)ccn4)nc(-c4cncc(F)c4)nc32)[C@H](O)[C@@H]1O] | (2S,3S,4R,5R)-5-(6-(((4-chloropyridin-2-yl)methyl)amino)-2-(5-fluoropyridin-3-yl)-9H-purin-9-yl)-3,4-dihydroxyl-N-isopropyltetrahydrofuran-2-formamide |
| 347 | 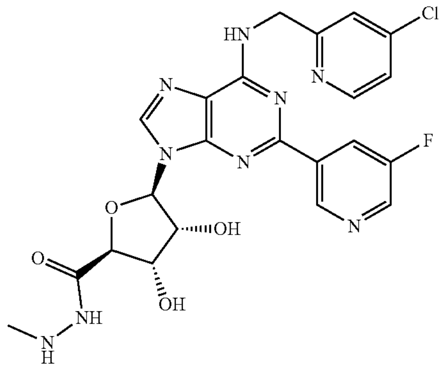 [SMILES: CNNC(=O)[C@H]1O[C@@H](n2cnc3c(NCc4cc(Cl)ccn4)nc(-c4cncc(F)c4)nc32)[C@H](O)[C@@H]1O] | (2S,3S,4R,5R)-5-(6-(((4-chloropyridin-2-yl)methyl)amino)-2-(5-fluoropyridin-3-yl)-9H-purin-9-yl)-3,4-dihydroxyl-N-methyltetrahydrofuran-2-carbohydrazide |
| 348 | 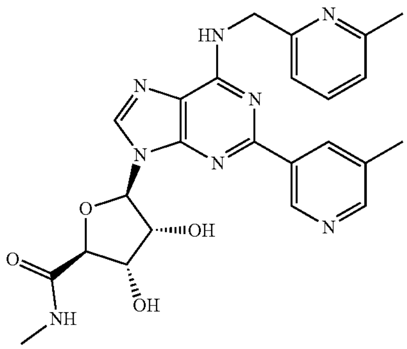 [SMILES: CNC(=O)[C@H]1O[C@@H](n2cnc3c(NCc4cccc(C)n4)nc(-c4cncc(C)c4)nc32)[C@H](O)[C@@H]1O] | (2S,3S,4R,5R)-3,4-dihydroxyl-N-methyl-5-(6-(((6-methylpyridin-2-yl)methyl)amino)-2-(5-methylpyridin-3-yl)-9H-purin-9-yl)tetrahydrofuran-2-formamide |
| 349 | 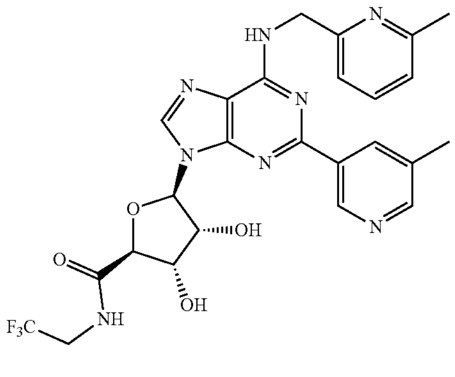 [SMILES: Cc1cncc(-c2nc(NCc3cccc(C)n3)c3ncn([C@@H]4O[C@H](C(=O)NCC(F)(F)F)[C@@H](O)[C@H]4O)c3n2)c1] | (2S,3S,4R,5R)-3,4-dihydroxyl-5-(6-(((6-methylpyridin-2-yl)methyl)amino)-2-(5-methylpyridin-3-yl)-9H-purin-9-yl)-N-(2,2,2-trifluoroethyl)tetrahydrofuran-2-formamide |

-continued

| Compd. No | Structural formula of compound | Name |
|---|---|---|
| 350 | 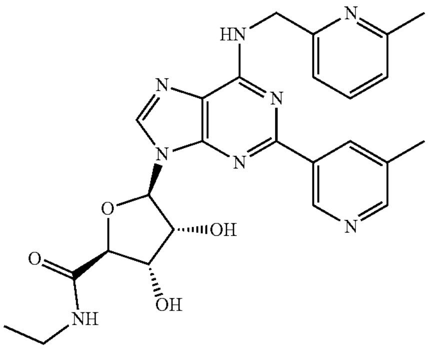 [SMILES: CCNC(=O)[C@H]1O[C@@H](n2cnc3c(NCc4cccc(C)n4)nc(-c4cncc(C)c4)nc32)[C@H](O)[C@@H]1O] | (2S,3S,4R,5R)-N-ethyl-3,4-dihydroxyl-5-(6-(((6-methylpyridin-2-yl)methyl)amino)-2-(5-methylpyridin-3-yl)-9H-purin-9-yl)tetrahydrofuran-2-formamide |
| 351 | 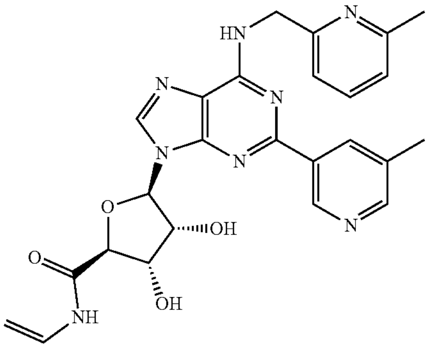 [SMILES: C=CNC(=O)[C@H]1O[C@@H](n2cnc3c(NCc4cccc(C)n4)nc(-c4cncc(C)c4)nc32)[C@H](O)[C@@H]1O] | (2S,3S,4R,5R)-3,4-dihydroxyl-5-(6-(((6-methylpyridin-2-yl)methyl)amino)-2-(5-methylpyridin-3-yl)-9H-purin-9-yl)-N-vinyltetrahydrofuran-2-formamide |
| 352 | 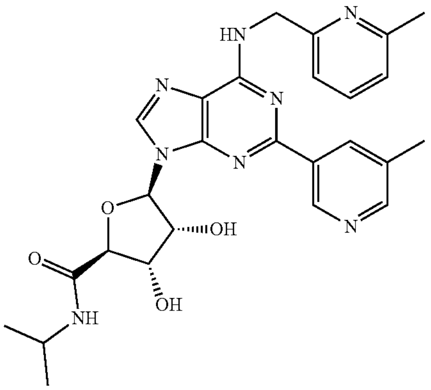 [SMILES: Cc1cncc(-c2nc(NCc3cccc(C)n3)c3ncn([C@@H]4O[C@H](C(=O)NC(C)C)[C@@H](O)[C@H]4O)c3n2)c1] | (2S,3S,4R,5R)-3,4-dihydroxyl-N-isopropyl-5-(6-(((6-methylpyridin-2-yl)methyl)amino)-2-(5-methylpyridin-3-yl)-9H-purin-9-yl)tetrahydrofuran-2-formamide |
| 353 | 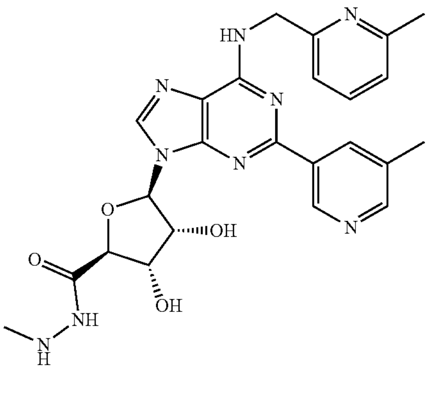 | (2S,3S,4R,5R)-3,4-dihydroxyl-N'-methyl-5-(6-(((6-methylpyridin-2-yl)methyl)amino)-2-(5-methylpyridin-3-yl)-9H-purin-9-yl)tetrahydrofuran-2-carbohydrazide |

-continued

| Compd. No | Structural formula of compound | Name |
|---|---|---|
| 354 | 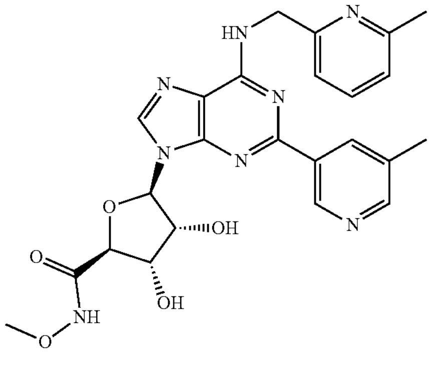 | ((2S,3S,4R,5R)-3,4-dihydroxyl-N-methoxy-5-(6-(((6-methylpyridin-2-yl)methyl)amino)-2-(5-methylpyridin-3-yl)-9H-purin-9-yl)tetrahydrofuran-2-formamide |
| 355 | 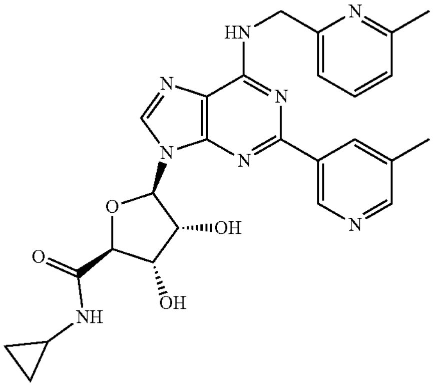 [SMILES: Cc1cncc(-c2nc(NCc3cccc(C)n3)c3ncn([C@@H]4O[C@H](C(=O)NC5CC5)[C@@H](O)[C@H]4O)c3n2)c1] | ((2S,3S,4R,5R)-N-cyclopropyl-3,4-dihydroxyl-5-(6-(((6-methylpyridin-2-yl)methyl)amino)-2-(5-methylpyridin-3-yl)-9H-purin-9-yl)tetrahydrofuran-2-formamide |
| 356 | 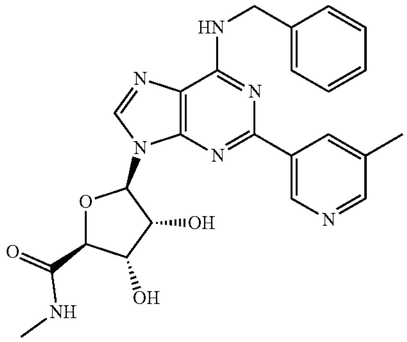 | (2S,3S,4R,5R)-5-(6-(benzylamino)-2-(5-methylpyridin-3-yl)-9H-purin-9-yl)-3,4-dihydroxyl-N-methyltetrahydrofuran-2-formamide |
| 357 | 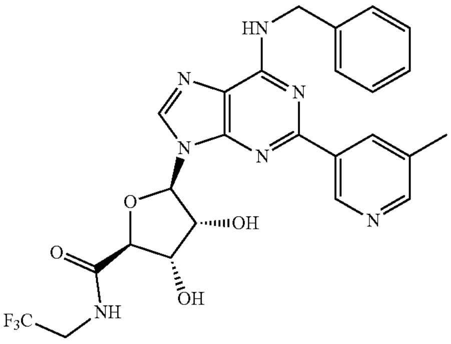 [SMILES: Cc1cncc(-c2nc(NCc3ccccc3)c3ncn([C@@H]4O[C@H](C(=O)NCC(F)(F)F)[C@@H](O)[C@H]4O)c3n2)c1] | (2S,3S,4R,5R)-5-(6-(benzylamino)-2-(5-methylpyridin-3-yl)-9H-purin-9-yl)-3,4-dihydroxyl-N-(2,2,2-trifluoroethyl)tetrahydrofuran-2-formamide |

-continued

| Compd. No | Structural formula of compound | Name |
|---|---|---|
| 358 | 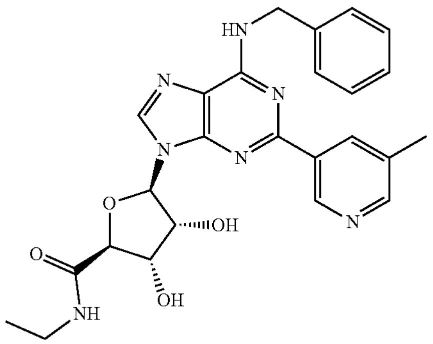 [SMILES: CCNC(=O)[C@H]1O[C@@H](n2cnc3c(NCc4ccccc4)nc(-c4cncc(C)c4)nc32)[C@H](O)[C@@H]1O] | (2S,3S,4R,5R)-5-(6-(benzylamino)-2-(5-methylpyridin-3-yl)-9H-purin-9-yl)-N-ethyl-3,4-dihydroxyltetrahydrofuran-2-formamide |
| 359 | 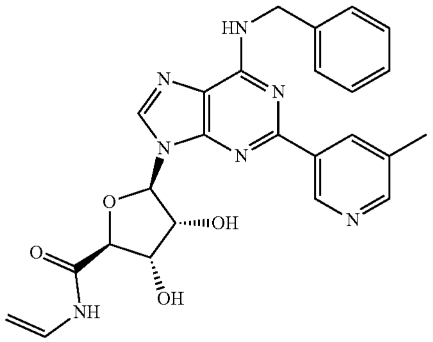 [SMILES: C=CNC(=O)[C@H]1O[C@@H](n2cnc3c(NCc4ccccc4)nc(-c4cncc(C)c4)nc32)[C@H](O)[C@@H]1O] | (2S,3S,4R,5R)-5-(6-(benzylamino)-2-(5-methylpyridin-3-yl)-9H-purin-9-yl)-3,4-dihydroxyl-N-vinyltetrahydrofuran-2-formamide |
| 360 | 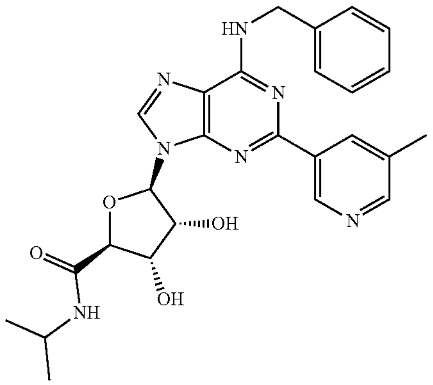 [SMILES: Cc1cncc(-c2nc(NCc3ccccc3)c3ncn([C@@H]4O[C@H](C(=O)NC(C)C)[C@@H](O)[C@H]4O)c3n2)c1] | (2S,3S,4R,5R)-5-(6-(benzylamino)-2-(5-methylpyridin-3-yl)-9H-purin-9-yl)-3,4-dihydroxyl-N-isopropyltetrahydrofuran-2-formamide |
| 361 | 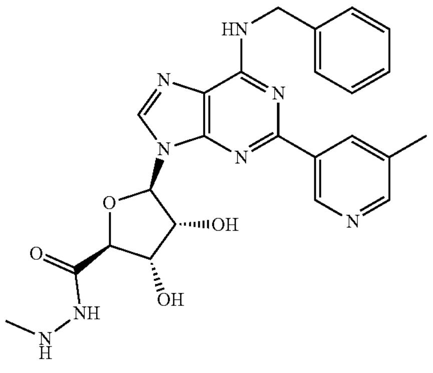 | (2S,3S,4R,5R)-5-(6-(benzylamino)-2-(5-methylpyridin-3-yl)-9H-purin-9-yl)-3,4-dihydroxyl-N'-methyltetrahydrofuran-2-carbohydrazide |

-continued

| Compd. No | Structural formula of compound | Name |
| --- | --- | --- |
| 362 | 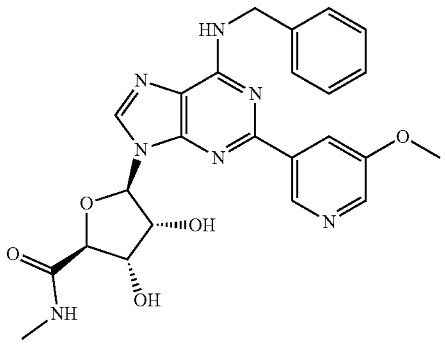 [SMILES: CNC(=O)[C@H]1O[C@@H](n2cnc3c(NCc4ccccc4)nc(-c4cncc(OC)c4)nc32)[C@H](O)[C@@H]1O] | (2S,3S,4R,5R)-5-(6-(benzylamino)-2-(5-methoxypyridin-3-yl)-9H-purin-9-yl)-3,4-dihydroxyl-N-methyltetrahydrofuran-2-formamide |
| 363 | 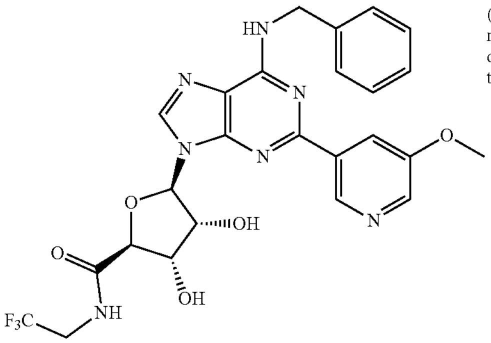 | (2S,3S,4R,5R)-5-(6-(benzylamino)-2-(5-methoxypyridin-3-yl)-9H-purin-9-yl)-3,4-dihydroxyl-N-(2,2,2-trifluoroethyl)tetrahydrofuran-2-formamide |
| 364 | 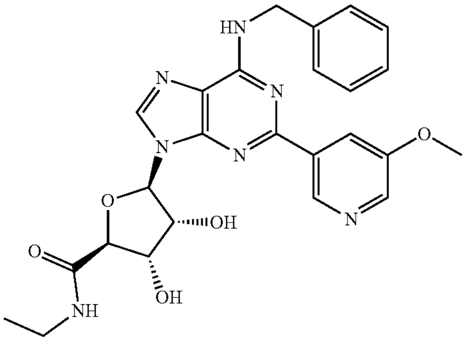 [SMILES: CCNC(=O)[C@H]1O[C@@H](n2cnc3c(NCc4ccccc4)nc(-c4cncc(OC)c4)nc32)[C@H](O)[C@@H]1O] | (2S,3S,4R,5R)-5-(6-(benzylamino)-2-(5-methoxypyridin-3-yl)-9H-purin-9-yl)-N-ethyl-3,4-dihydroxyltetrahydrofuran-2-formamide |
| 365 | 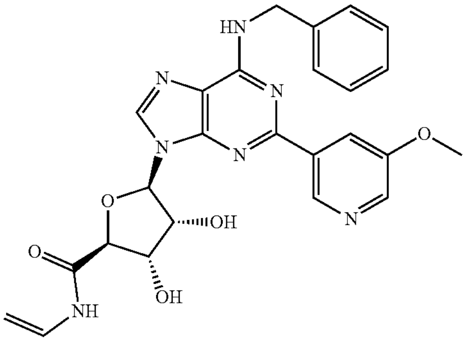 | (2S,3S,4R,5R)-5-(6-(benzylamino)-2-(5-methoxypyridin-3-yl)-9H-purin-9-yl)-3,4-dihydroxyl-N-vinyltetrahydrofuran-2-formamide |

-continued

| Compd. No | Structural formula of compound | Name |
| --- | --- | --- |
| 366 | 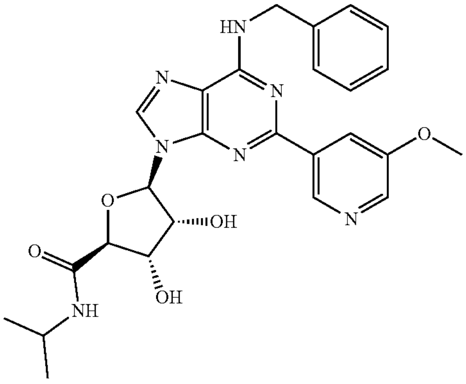 [SMILES: COc1cncc(-c2nc(NCc3ccccc3)c3ncn([C@@H]4O[C@H](C(=O)NC(C)C)[C@@H](O)[C@H]4O)c3n2)c1] | (2S,3S,4R,5R)-5-(6-(benzylamino)-2-(5-methoxypyridin-3-yl)-9H-purin-9-yl)-3,4-dihydroxyl-N-isopropyltetrahydrofuran-2-formamide |
| 367 | 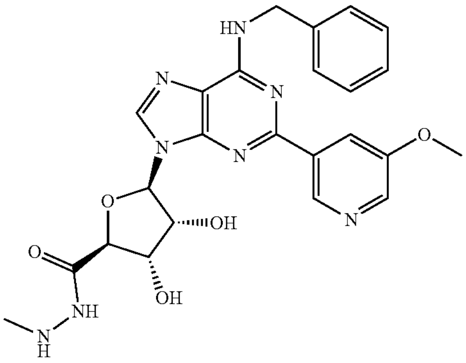 | (2S,3S,4R,5R)-5-(6-(benzylamino)-2-(5-methoxypyridin-3-yl)-9H-purin-9-yl)-3,4-dihydroxyl-N'-methyltetrahydrofuran-2-carbohydrazide |
| 368 | 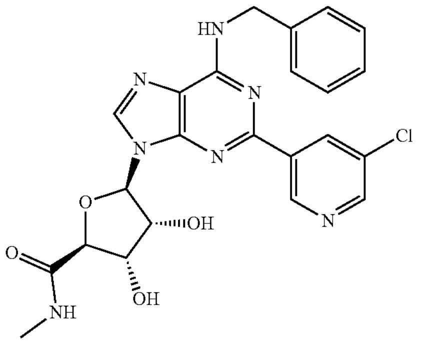 [SMILES: CNC(=O)[C@H]1O[C@@H](n2cnc3c(NCc4ccccc4)nc(-c4cncc(Cl)c4)nc32)[C@H](O)[C@@H]1O] | (2S,3S,4R,5R)-5-(6-(benzylamino)-2-(5-chloropyridin-3-yl)-9H-purin-9-yl)-3,4-dihydroxyl-N-methyltetrahydrofuran-2-formamide |
| 369 | 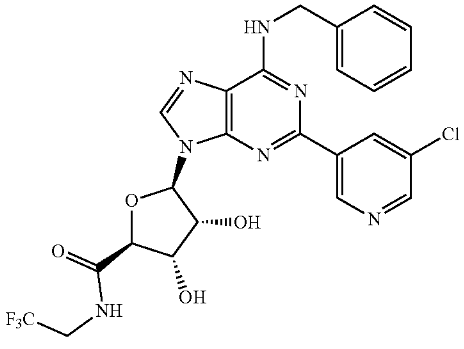 [SMILES: O=C(NCC(F)(F)F)[C@H]1O[C@@H](n2cnc3c(NCc4ccccc4)nc(-c4cncc(Cl)c4)nc32)[C@H](O)[C@@H]1O] | (2S,3S,4R,5R)-5-(6-(benzylamino)-2-(5-chloropyridin-3-yl)-9H-purin-9-yl)-3,4-dihydroxyl-N-(2,2,2-trifluoroethyl)tetrahydrofuran-2-formamide |

-continued

| Compd. No | Structural formula of compound | Name |
|---|---|---|
| 370 | 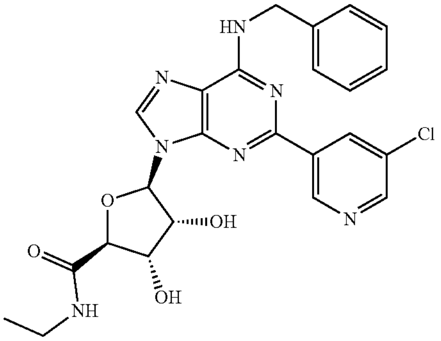 [SMILES: CCNC(=O)[C@H]1O[C@@H](n2cnc3c(NCc4ccccc4)nc(-c4cncc(Cl)c4)nc32)[C@H](O)[C@@H]1O] | (2S,3S,4R,5R)-5-(6-(benzylamino)-2-(5-chloropyridin-3-yl)-9H-purin-9-yl)-N-ethyl-3,4-dihydroxyltetrahydrofuran-2-formamide |
| 371 | 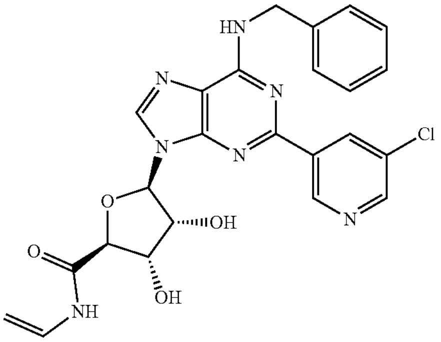 [SMILES: C=CNC(=O)[C@H]1O[C@@H](n2cnc3c(NCc4ccccc4)nc(-c4cncc(Cl)c4)nc32)[C@H](O)[C@@H]1O] | (2S,3S,4R,5R)-5-(6-(benzylamino)-2-(5-chloropyridin-3-yl)-9H-purin-9-yl)-3,4-dihydroxyl-N-vinyltetrahydrofuran-2-formamide |
| 372 | 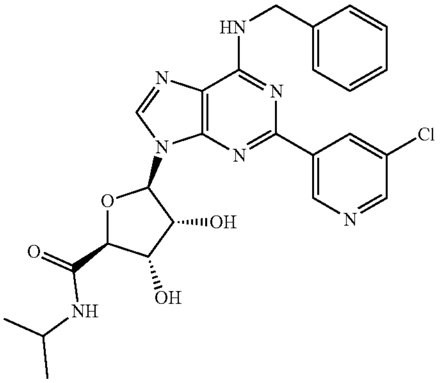 [SMILES: CC(C)NC(=O)[C@H]1O[C@@H](n2cnc3c(NCc4ccccc4)nc(-c4cncc(Cl)c4)nc32)[C@H](O)[C@@H]1O] | (2S,3S,4R,5R)-5-(6-(benzylamino)-2-(5-chloropyridin-3-yl)-9H-purin-9-yl)-3,4-dihydroxyl-N-isopropyltetrahydrofuran-2-formamide |
| 373 | 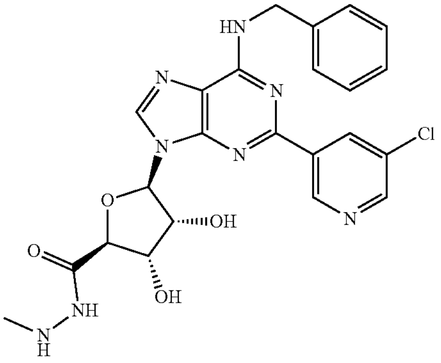 [SMILES: CNNC(=O)[C@H]1O[C@@H](n2cnc3c(NCc4ccccc4)nc(-c4cncc(Cl)c4)nc32)[C@H](O)[C@@H]1O] | (2S,3S,4R,5R)-5-(6-(benzylamino)-2-(5-chloropyridin-3-yl)-9H-purin-9-yl)-3,4-dihydroxyl-N'-methyltetrahydrofuran-2-carbohydrazide |

-continued

| Compd. No | Structural formula of compound | Name |
|---|---|---|
| 374 | 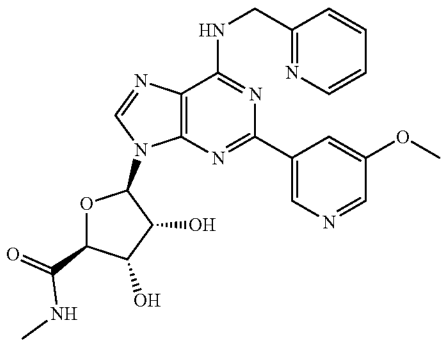 | (2S,3S,4R,5R)-3,4-dihydroxyl-5-(2-(5-methoxypyridin-3-yl)-6-((pyridin-2-ylmethyl)amino)-9H-purin-9-yl)-N-methyltetrahydrofuran-2-formamide |
| 375 | 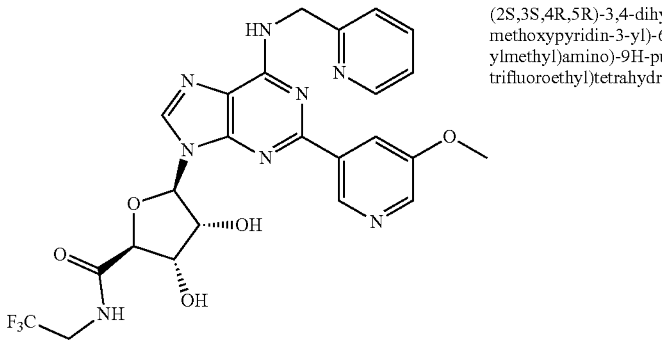 | (2S,3S,4R,5R)-3,4-dihydroxyl-5-(2-(5-methoxypyridin-3-yl)-6-((pyridin-2-ylmethyl)amino)-9H-purin-9-yl)-N-(2,2,2-trifluoroethyl)tetrahydrofuran-2-formamide |
| 376 | 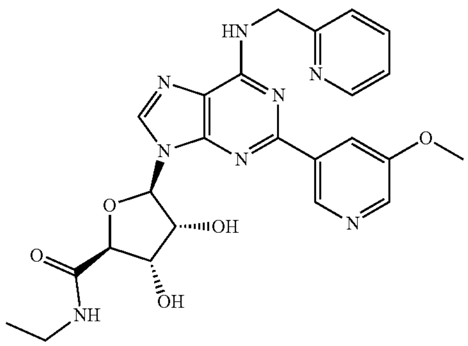 [SMILES: CCNC(=O)[C@H]1O[C@@H](n2cnc3c(NCc4ccccn4)nc(-c4cncc(OC)c4)nc32)[C@H](O)[C@@H]1O] | (2S,3S,4R,5R)-N-ethyl-3,4-dihydroxyl-5-(2-(5-methoxypyridin-3-yl)-6-((pyridin-2-ylmethyl)amino)-9H-purin-9-yl)tetrahydrofuran-2-formamide |
| 377 | 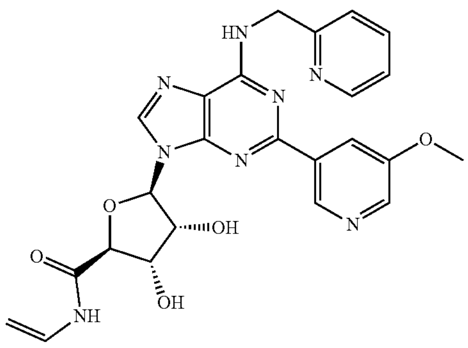 [SMILES: C=CNC(=O)[C@H]1O[C@@H](n2cnc3c(NCc4ccccn4)nc(-c4cncc(OC)c4)nc32)[C@H](O)[C@@H]1O] | (2S,3S,4R,5R)-3,4-dihydroxyl-5-(2-(5-methoxypyridin-3-yl)-6-((pyridin-2-ylmethyl)amino)-9H-purin-9-yl)-N-vinyltetrahydrofuran-2-formamide |

-continued

| Compd. No | Structural formula of compound | Name |
| --- | --- | --- |
| 378 | 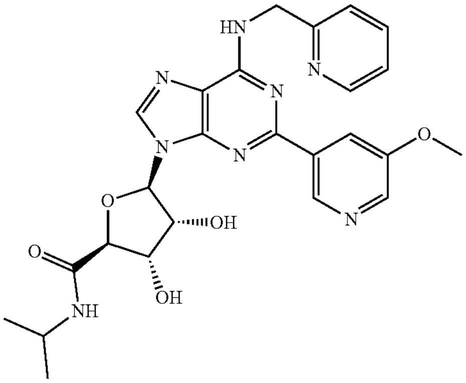 [SMILES: COc1cncc(-c2nc(NCc3ccccn3)c3ncn([C@@H]4O[C@H](C(=O)NC(C)C)[C@@H](O)[C@H]4O)c3n2)c1] | (2S,3S,4R,5R)-3,4-dihydroxyl-N-isopropyl-5-(2-(5-methoxypyridin-3-yl)-6-((pyridin-2-ylmethyl)amino)-9H-purin-9-yl)tetrahydrofuran-2-formamide |
| 379 | 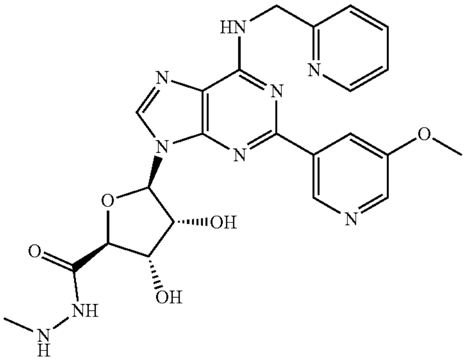 | (2S,3S,4R,5R)-3,4-dihydroxyl-5-(2-(5-methoxypyridin-3-yl)-6-((pyridin-2-ylmethyl)amino)-9H-purin-9-yl)-N'-methyltetrahydrofuran-2-carbohydrazide |
| 380 | 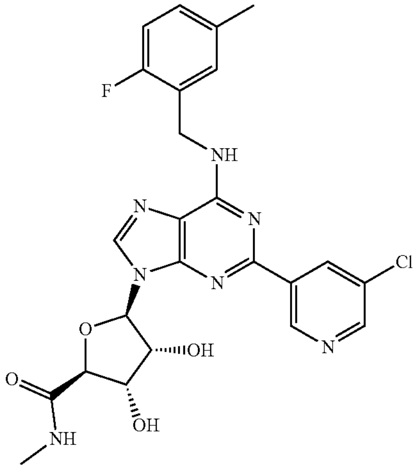 [SMILES: CNC(=O)[C@H]1O[C@@H](n2cnc3c(NCc4cc(C)ccc4F)nc(-c4cncc(Cl)c4)nc32)[C@H](O)[C@@H]1O] | (2S,3S,4R,5R)-5-(2-(5-chloropyridin-3-yl)-6-((2-fluoro-5-methylbenzyl)amino)-9H-purin-9-yl)-3,4-dihydroxyl-N-methyltetrahydrofuran-2-formamide |

-continued

| Compd. No | Structural formula of compound | Name |
|---|---|---|
| 381 | 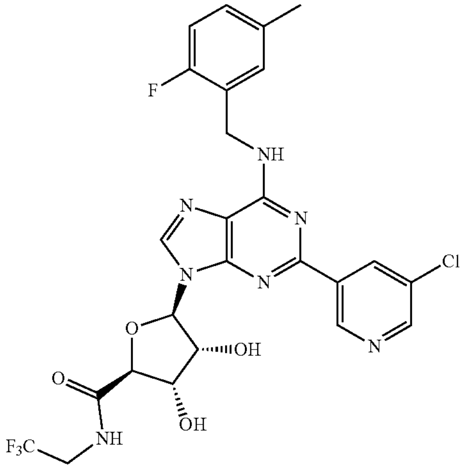 [SMILES: Cc1ccc(F)c(CNc2nc(-c3cncc(Cl)c3)nc3c2ncn3[C@@H]2O[C@H](C(=O)NCC(F)(F)F)[C@@H](O)[C@H]2O)c1] | (2S,3S,4R,5R)-5-(2-(5-chloropyridin-3-yl)-6-((2-fluoro-5-methylbenzyl)amino)-9H-purin-9-yl)-3,4-dihydroxyl-N-(2,2,2-trifluoroethyl)tetrahydrofuran-2-formamide |
| 382 | 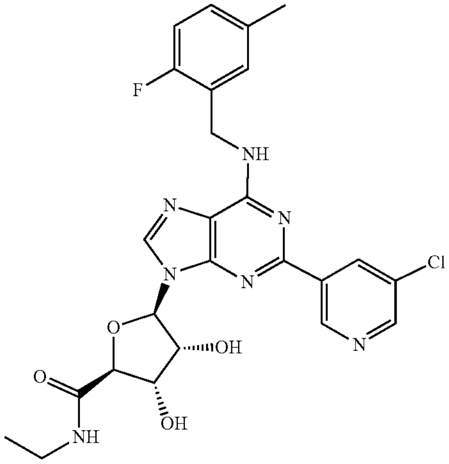 [SMILES: CCNC(=O)[C@H]1O[C@@H](n2cnc3c(NCc4cc(C)ccc4F)nc(-c4cncc(Cl)c4)nc32)[C@H](O)[C@@H]1O] | (2S,3S,4R,5R)-5-(2-(5-chloropyridin-3-yl)-6-((2-fluoro-5-methylbenzyl)amino)-9H-purin-9-yl)-N-ethyl-3,4-dihydroxyltetrahydrofuran-2-formamide |
| 383 | 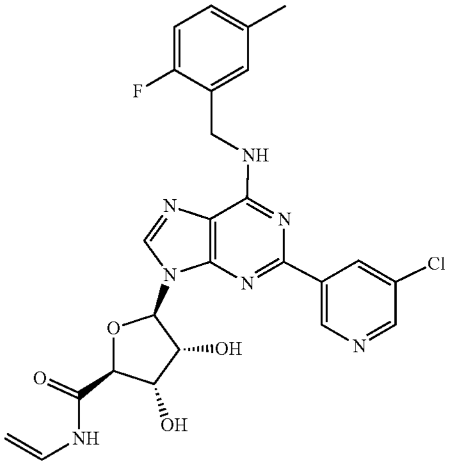 [SMILES: C=CNC(=O)[C@H]1O[C@@H](n2cnc3c(NCc4cc(C)ccc4F)nc(-c4cncc(Cl)c4)nc32)[C@H](O)[C@@H]1O] | (2S,3S,4R,5R)-5-(2-(5-chloropyridin-3-yl)-6-((2-fluoro-5-methylbenzyl)amino)-9H-purin-9-yl)-3,4-dihydroxyl-N-vinyltetrahydrofuran-2-formamide |

-continued

| Compd. No | Structural formula of compound | Name |
|---|---|---|
| 384 | 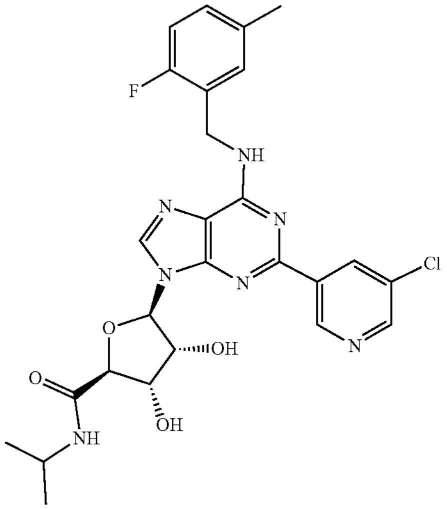 [SMILES: Cc1ccc(F)c(CNc2nc(-c3cncc(Cl)c3)nc3c2ncn3[C@@H]2O[C@H](C(=O)NC(C)C)[C@@H](O)[C@H]2O)c1] | (2S,3S,4R,5R)-5-(2-(5-chloropyridin-3-yl)-6-((2-fluoro-5-methylbenzyl)amino)-9H-purin-9-yl)-3,4-dihydroxyl-N-isopropyl tetrahydrofuran-2-formamide |
| 385 | 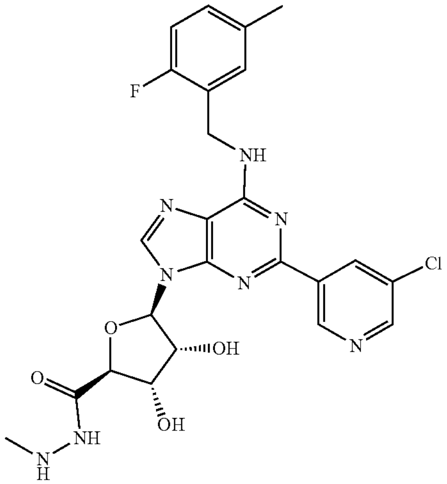 [SMILES: CNNC(=O)[C@H]1O[C@@H](n2cnc3c(NCc4cc(C)ccc4F)nc(-c4cncc(Cl)c4)nc32)[C@H](O)[C@@H]1O] | (2S,3S,4R,5R)-5-(2-(5-chloropyridin-3-yl)-6-((2-fluoro-5-methylbenzyl)amino)-9H-purin-9-yl)-3,4-dihydroxyl-N'-methyltetrahydrofuran-2-carbohydrazide |
| 386 | 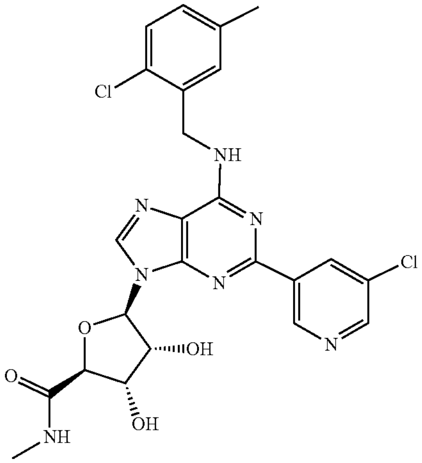 [SMILES: CNC(=O)[C@H]1O[C@@H](n2cnc3c(NCc4cc(C)ccc4Cl)nc(-c4cncc(Cl)c4)nc32)[C@H](O)[C@@H]1O] | (2S,3S,4R,5R)-5-(6-((2-chloro-5-methylbenzyl)amino)-2-(5-chloropyridin-3-yl)-9H-purin-9-yl)-3,4-dihydroxyl-N-methyltetrahydrofuran-2-formamide |

-continued

| Compd. No | Structural formula of compound | Name |
|---|---|---|
| 387 | 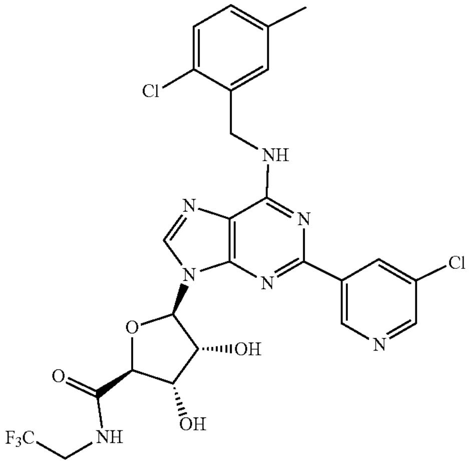 [SMILES: Cc1ccc(Cl)c(CNc2nc(-c3cncc(Cl)c3)nc3c2ncn3[C@@H]2O[C@H](C(=O)NCC(F)(F)F)[C@@H](O)[C@H]2O)c1] | (2S,3S,4R,5R)-5-(6-((2-chloro-5-methylbenzyl)amino)-2-(5-chloropyridin-3-yl)-9H-purin-9-yl)-3,4-dihydroxyl-N-(2,2,2-trifluoroethyl)tetrahydrofuran-2-formamide |
| 388 | 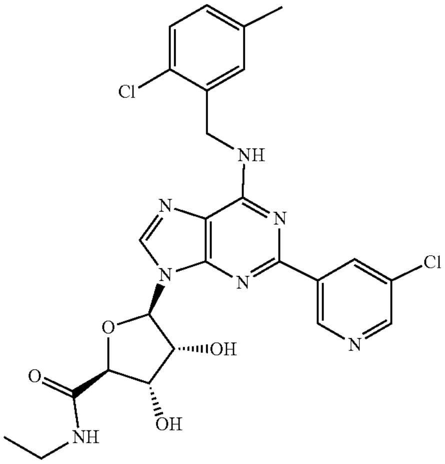 [SMILES: CCNC(=O)[C@H]1O[C@@H](n2cnc3c(NCc4cc(C)ccc4Cl)nc(-c4cncc(Cl)c4)nc32)[C@H](O)[C@@H]1O] | (2S,3S,4R,5R)-5-(6-((2-chloro-5-methylbenzyl)amino)-2-(5-chloropyridin-3-yl)-9H-purin-9-yl)-N-ethyl-3,4-dihydroxyltetrahydrofuran-2-formamide |
| 389 | 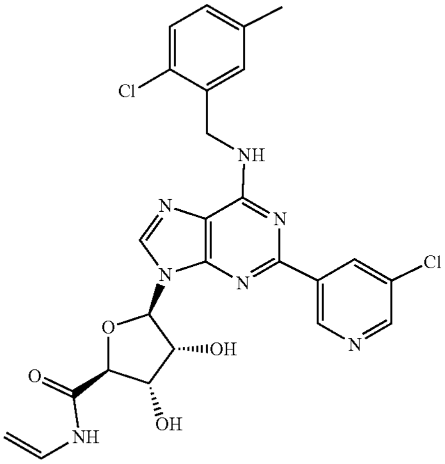 [SMILES: C=CNC(=O)[C@H]1O[C@@H](n2cnc3c(NCc4cc(C)ccc4Cl)nc(-c4cncc(Cl)c4)nc32)[C@H](O)[C@@H]1O] | (2S,3S,4R,5R)-5-(6-((2-chloro-5-methylbenzyl)amino)-2-(5-chloropyridin-3-yl)-9H-purin-9-yl)-3,4-dihydroxyl-N-vinyltetrahydrofuran-2-formamide |

-continued

| Compd. No | Structural formula of compound | Name |
|---|---|---|
| 390 | 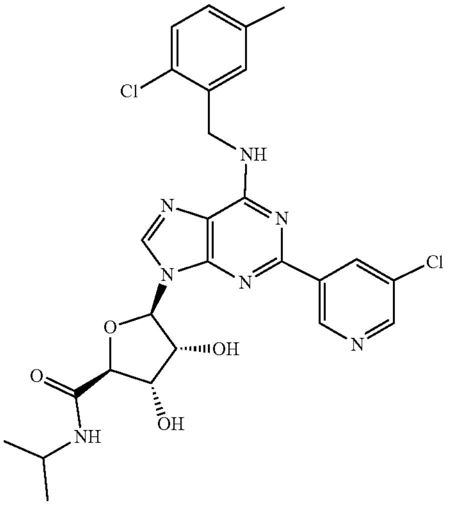 [SMILES: Cc1ccc(Cl)c(CNc2nc(-c3cncc(Cl)c3)nc3c2ncn3[C@@H]2O[C@H](C(=O)NC(C)C)[C@@H](O)[C@H]2O)c1] | (2S,3S,4R,5R)-5-(6-((2-chloro-5-methylbenzyl)amino)-2-(5-chloropyridin-3-yl)-9H-purin-9-yl)-3,4-dihydroxyl-N-isopropyltetrahydrofuran-2-formamide |
| 391 | 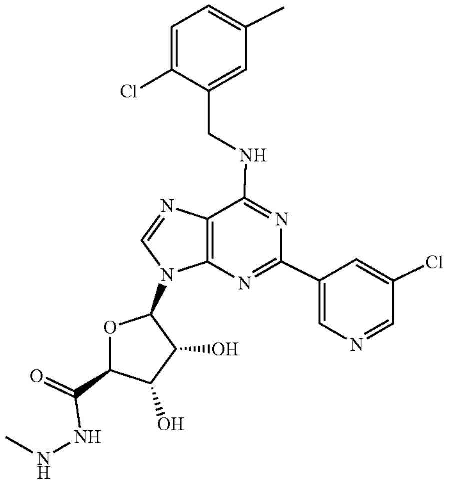 [SMILES: CNNC(=O)[C@H]1O[C@@H](n2cnc3c(NCc4cc(C)ccc4Cl)nc(-c4cncc(Cl)c4)nc32)[C@H](O)[C@@H]1O] | (2S,3S,4R,5R)-5-(6-((2-chloro-5-methylbenzyl)amino)-2-(5-chloropyridin-3-yl)-9H-purin-9-yl)-3,4-dihydroxyl-N'-methyltetrahydrofuran-2-carbohydrazide |
| 392 | 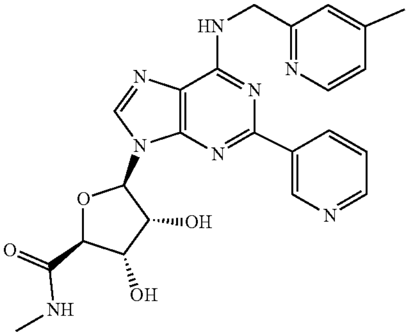 [SMILES: CNC(=O)[C@H]1O[C@@H](n2cnc3c(NCc4cc(C)ccn4)nc(-c4cccnc4)nc32)[C@H](O)[C@@H]1O] | (2S,3S,4R,5R)-3,4-dihydroxyl-N-methyl-5-(6-(((4-methylpyridin-2-yl)methyl)amino)-2-(pyridin-3-yl)-9H-purin-9-yl)tetrahydrofuran-2-formamide |

-continued

| Compd. No | Structural formula of compound | Name |
|---|---|---|
| 393 | 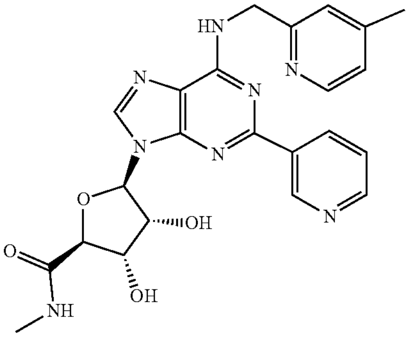 [SMILES: CNC(=O)[C@H]1O[C@@H](n2cnc3c(NCc4cc(C)ccn4)nc(-c4cccnc4)nc32)[C@H](O)[C@@H]1O] | (2S,3S,4R,5R)-3,4-dihydroxyl-5-(6-(((4-methylpyridin-2-yl)methyl)amino)-2-(pyridin-3-yl)-9H-purin-9-yl)-N-(2,2,2-trifluoroethyl)tetrahydrofuran-2-formamide |
| 394 | 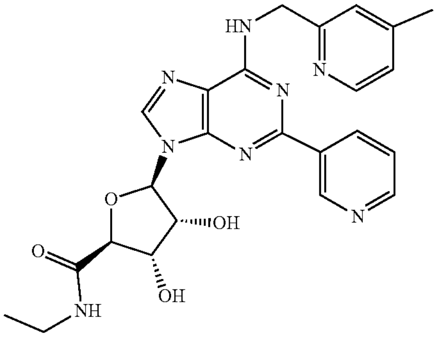 [SMILES: CCNC(=O)[C@H]1O[C@@H](n2cnc3c(NCc4cc(C)ccn4)nc(-c4cccnc4)nc32)[C@H](O)[C@@H]1O] | (2S,3S,4R,5R)-N-ethyl-3,4-dihydroxyl-5-(6-(((4-methylpyridin-2-yl)methyl)amino)-2-(pyridin-3-yl)-9H-purin-9-yl)tetrahydrofuran-2-formamide |
| 395 | 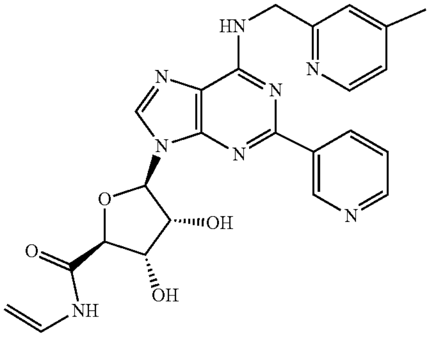 [SMILES: C=CNC(=O)[C@H]1O[C@@H](n2cnc3c(NCc4cc(C)ccn4)nc(-c4cccnc4)nc32)[C@H](O)[C@@H]1O] | (2S,3S,4R,5R)-3,4-dihydroxyl-5-(6-(((4-methylpyridin-2-yl)methyl)amino)-2-(pyridin-3-yl)-9H-purin-9-yl)-N-vinyltetrahydrofuran-2-formamide |
| 396 | 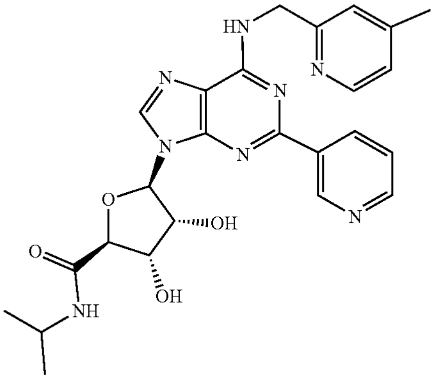 [SMILES: Cc1ccnc(CNc2nc(-c3cccnc3)nc3c2ncn3[C@@H]2O[C@H](C(=O)NC(C)C)[C@@H](O)[C@H]2O)c1] | (((4-methylpyridin-2-yl)methyl)amino)-2-(pyridin-3-yl)-9H-purin-9-yl)tetrahydrofuran-2-formamide |

-continued

| Compd. No | Structural formula of compound | Name |
| --- | --- | --- |
| 397 | 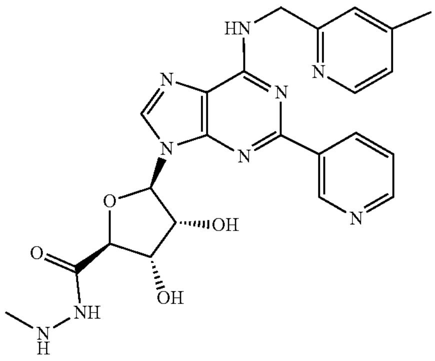 | (2S,3S,4R,5R)-3,4-dihydroxyl-N'-methyl-5-(6-(((4-methylpyridin-2-yl)methyl)amino)-2-(pyridin-3-yl)-9H-purin-9-yl)tetrahydrofuran-2-carbohydrazide |
| 398 | 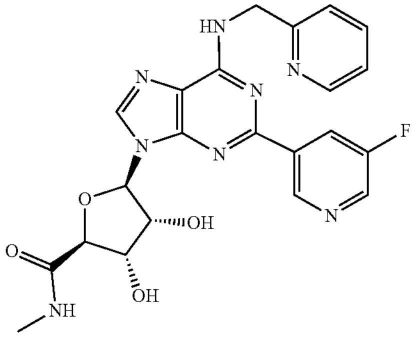 [SMILES: CNC(=O)[C@H]1O[C@@H](n2cnc3c(NCc4ccccn4)nc(-c4cncc(F)c4)nc32)[C@H](O)[C@@H]1O] | (2S,3S,4R,5R)-5-(2-(5-fluoropyridin-3-yl)-6-((pyridin-2-ylmethyl)amino)-9H-purin-9-yl)-3,4-dihydroxyl-N-methyltetrahydrofuran-2-formamide |
| 399 | 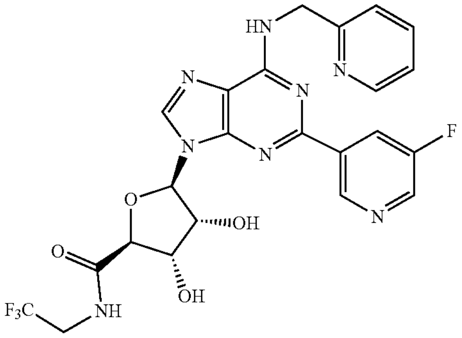 [SMILES: O=C(NCC(F)(F)F)[C@H]1O[C@@H](n2cnc3c(NCc4ccccn4)nc(-c4cncc(F)c4)nc32)[C@H](O)[C@@H]1O] | (2S,3S,4R,5R)-5-(2-(5-fluoropyridin-3-yl)-6-((pyridin-2-ylmethyl)amino)-9H-purin-9-yl)-3,4-dihydroxyl-N-(2,2,2-trifluoroethyl )tetrahydrofuran-2-formamide |
| 400 | 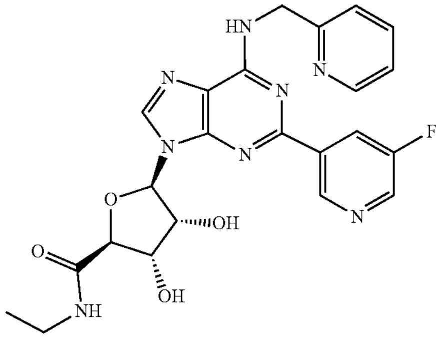 [SMILES: CCNC(=O)[C@H]1O[C@@H](n2cnc3c(NCc4ccccn4)nc(-c4cncc(F)c4)nc32)[C@H](O)[C@@H]1O] | (2S,3S,4R,5R)-N-ethyl-5-(2-(5-fluoropyridin-3-yl)-6-((pyridin-2-ylmethyl)amino)-9H-purin-9-yl)-3,4-dihydroxyltetrahydrofuran-2-formamide |

-continued

| Compd. No | Structural formula of compound | Name |
|---|---|---|
| 401 | 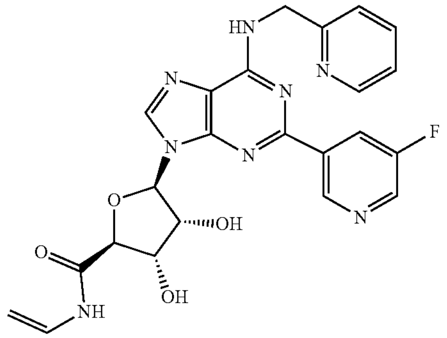 [SMILES: C=CNC(=O)[C@H]1O[C@@H](n2cnc3c(NCc4ccccn4)nc(-c4cncc(F)c4)nc32)[C@H](O)[C@@H]1O] | (2S,3S,4R,5R)-5-(2-(5-fluoropyridin-3-yl)-6-((pyridin-2-ylmethyl)amino)-9H-purin-9-yl)-3,4-dihydroxyl-N-vinyltetrahydrofuran-2-formamide |
| 402 | 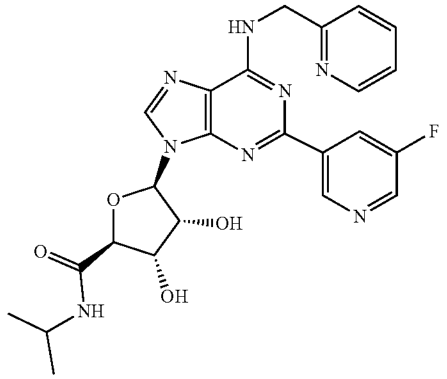 [SMILES: CC(C)NC(=O)[C@H]1O[C@@H](n2cnc3c(NCc4ccccn4)nc(-c4cncc(F)c4)nc32)[C@H](O)[C@@H]1O] | (2S,3S,4R,5R)-5-(2-(5-fluoropyridin-3-yl)-6-((pyridin-2-ylmethyl)amino)-9H-purin-9-yl)-3,4-dihydroxyl-N-isopropyltetrahydrofuran-2-formamide |
| 403 | 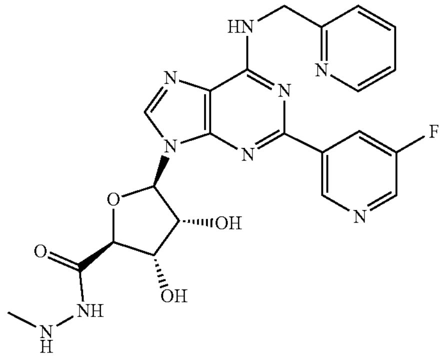 [SMILES: CNNC(=O)[C@H]1O[C@@H](n2cnc3c(NCc4ccccn4)nc(-c4cncc(F)c4)nc32)[C@H](O)[C@@H]1O] | (2S,3S,4R,5R)-5-(2-(5-fluoropyridin-3-yl)-6-((pyridin-2-ylmethyl)amino)-9H-purin-9-yl)-3,4-dihydroxyl-N'-methyltetrahydrofuran-2-carbohydrazide |
| 404 | 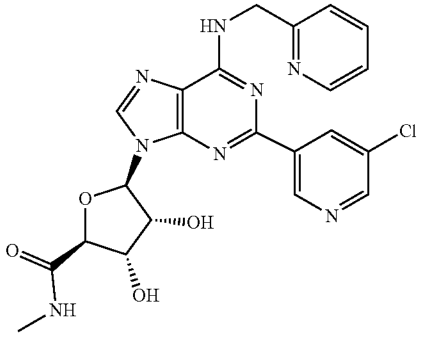 [SMILES: CNC(=O)[C@H]1O[C@@H](n2cnc3c(NCc4ccccn4)nc(-c4cncc(Cl)c4)nc32)[C@H](O)[C@@H]1O] | (2S,3S,4R,5R)-5-(2-(5-chloropyridin-3-yl)-6-((pyridin-2-ylmethyl)amino)-9H-purin-9-yl)-3,4-dihydroxyl-N-methyltetrahydrofuran-2-formamide |

-continued

| Compd. No | Structural formula of compound | Name |
|---|---|---|
| 405 | 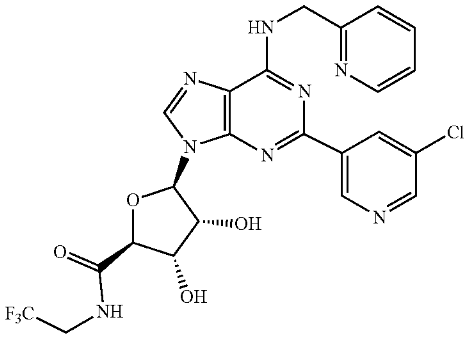 [SMILES: O=C(NCC(F)(F)F)[C@H]1O[C@@H](n2cnc3c(NCc4ccccn4)nc(-c4cncc(Cl)c4)nc32)[C@H](O)[C@@H]1O] | (2S,3S,4R,5R)-5-(2-(5-chloropyridin-3-yl)-6-((pyridin-2-ylmethyl)amino)-9H-purin-9-yl)-3,4-dihydroxyl-N-(2,2,2-trifluoroethyl)tetrahydrofuran-2-formamide |
| 406 | 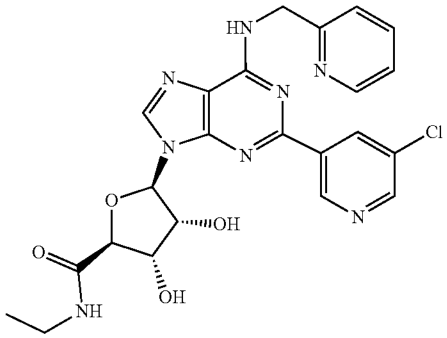 [SMILES: CCNC(=O)[C@H]1O[C@@H](n2cnc3c(NCc4ccccn4)nc(-c4cncc(Cl)c4)nc32)[C@H](O)[C@@H]1O] | (2S,3S,4R,5R)-5-(2-(5-chloropyridin-3-yl)-6-((pyridin-2-ylmethyl)amino)-9H-purin-9-yl)-N-ethyl-3,4-dihydroxyltetrahydrofuran-2-formamide |
| 407 | 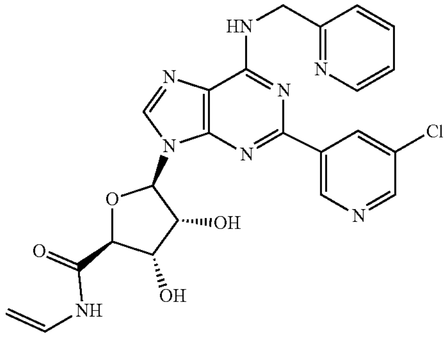 [SMILES: C=CNC(=O)[C@H]1O[C@@H](n2cnc3c(NCc4ccccn4)nc(-c4cncc(Cl)c4)nc32)[C@H](O)[C@@H]1O] | (2S,3S,4R,5R)-5-(2-(5-chloropyridin-3-yl)-6-((pyridin-2-ylmethyl)amino)-9H-purin-9-yl)-3,4-dihydroxyl-N-vinyltetrahydrofuran-2-formamide |
| 408 | 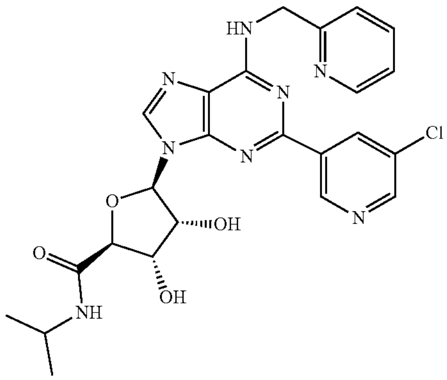 [SMILES: CC(C)NC(=O)[C@H]1O[C@@H](n2cnc3c(NCc4ccccn4)nc(-c4cncc(Cl)c4)nc32)[C@H](O)[C@@H]1O] | (2S,3S,4R,5R)-5-(2-(5-chloropyridin-3-yl)-6-((pyridin-2-ylmethyl)amino)-9H-purin-9-yl)-3,4-dihydroxyl-N-isopropyltetrahydrofuran-2-formamide |

-continued

| Compd. No | Structural formula of compound | Name |
| --- | --- | --- |
| 409 | 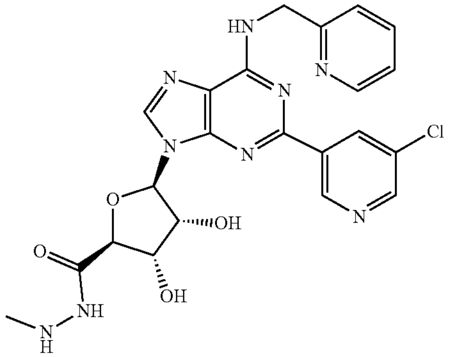 [SMILES: CNNC(=O)[C@H]1O[C@@H](n2cnc3c(NCc4ccccn4)nc(-c4cncc(Cl)c4)nc32)[C@H](O)[C@@H]1O] | (2S,3S,4R,5R)-5-(2-(5-chloropyridin-3-yl)-6-((pyridin-2-ylmethyl)amino)-9H-purin-9-yl)-3,4-dihydroxyl-N'-methyltetrahydrofuran-2-carbohydrazide |
| 410 | 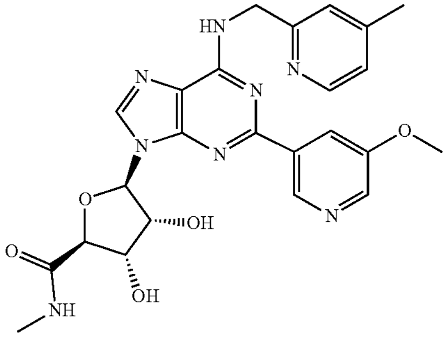 [SMILES: CNC(=O)[C@H]1O[C@@H](n2cnc3c(NCc4cc(C)ccn4)nc(-c4cncc(OC)c4)nc32)[C@H](O)[C@@H]1O] | (2S,3S,4R,5R)-3,4-dihydroxyl-5-(2-(5-methoxypyridin-3-yl)-6-(((methylpyridin-2-yl)methyl)amino)-9H-purin-9-yl)-N-methyltetrahydrofuran-2-formamide |
| 411 | 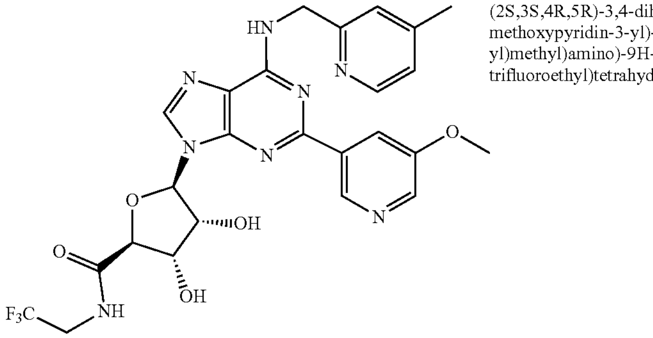 | (2S,3S,4R,5R)-3,4-dihydroxyl-5-(2-(5-methoxypyridin-3-yl)-6-(((methylpyridin-2-yl)methyl)amino)-9H-purin-9-yl)-N-(2,2,2-trifluoroethyl)tetrahydrofuran-2-formamide |
| 412 | 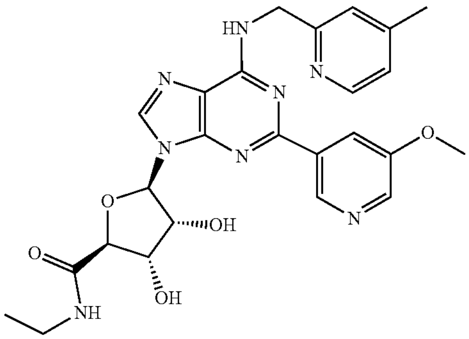 [SMILES: CCNC(=O)[C@H]1O[C@@H](n2cnc3c(NCc4cc(C)ccn4)nc(-c4cncc(OC)c4)nc32)[C@H](O)[C@@H]1O] | (2S,3S,4R,5R)-N-ethyl-3,4-dihydroxyl-5-(2-(5-methoxypyridin-3-yl)-6-(((4-methylpyridin-2-yl)methyl)amino)-9H-purin-9-yl)tetrahydrofuran-2-formamide |

-continued

| Compd. No | Structural formula of compound | Name |
|---|---|---|
| 413 | 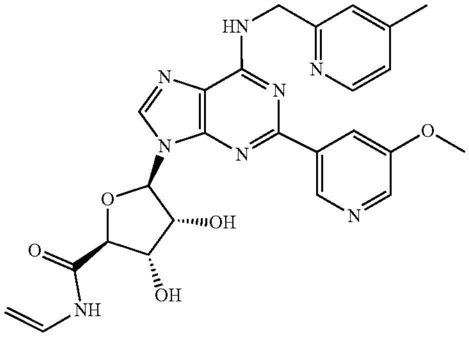 [SMILES: C=CNC(=O)[C@H]1O[C@@H](n2cnc3c(NCc4cc(C)ccn4)nc(-c4cncc(OC)c4)nc32)[C@H](O)[C@@H]1O] | (2S,3S,4R,5R)-3,4-dihydroxyl-5-(2-(5-methoxypyridin-3-yl)-6-(((4-methylpyridin-2-yl)methyl)amino)-9/-purin-9-yl)-N-vinyltetrahydrofuran-2-formamide |
| 414 | 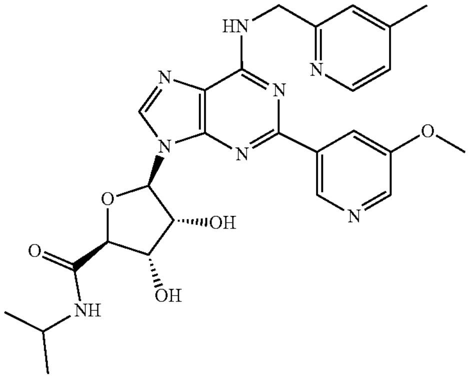 [SMILES: COc1cncc(-c2nc(NCc3cc(C)ccn3)c3ncn([C@@H]4O[C@H](C(=O)NC(C)C)[C@@H](O)[C@H]4O)c3n2)c1] | (2S,3S,4R,5R)-3,4-dihydroxyl-N-isopropyl-5-(2-(5-methoxypyridin-3-yl)-6-(((4-methylpyridin-2-yl)methyl)amino)-9H-purin-9-yl)tetrahydrofuran-2-formamide |
| 415 | 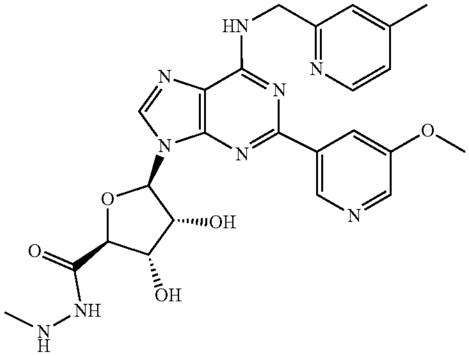 | (2S,3S,4R,5R)-3,4-dihydroxyl-5-(2-(5-methoxypyridin-3-yl)-6-(((4-methylpyridin-2-yl)methyl)amino)-9H-purin-9-yl)-N-methyltetrahydrofuran-2-carbohydrazide |
| 416 | 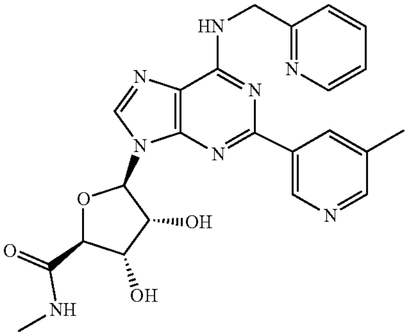 [SMILES: CNC(=O)[C@H]1O[C@@H](n2cnc3c(NCc4ccccn4)nc(-c4cncc(C)c4)nc32)[C@H](O)[C@@H]1O] | (2S,3S,4R,5R)-3,4-dihydroxyl-N-methyl-5-(2-(5-methylpyridin-3-yl)-6-(((4-methylpyridin-2-yl)methyl)amino)-9H-purin-9-yl)tetrahydrofuran-2-formamide |

-continued

| Compd. No | Structural formula of compound | Name |
|---|---|---|
| 417 | 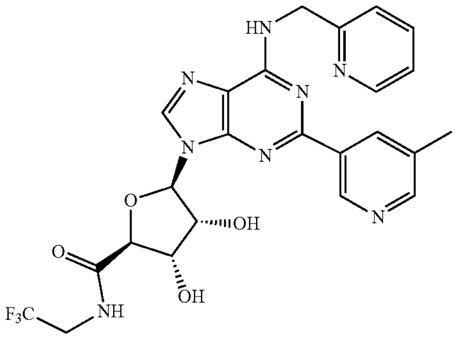 | (2S,3S,4R,5R)-3,4-dihydroxyl-5-(2-(5-methylpyridin-3-yl)-6-(((4-methylpyridin-2-yl)methyl)amino)-9H-purin-9-yl)-N-(2,2,2-trifluoroethyl)tetrahydrofuran-2-formamide |
| 418 | 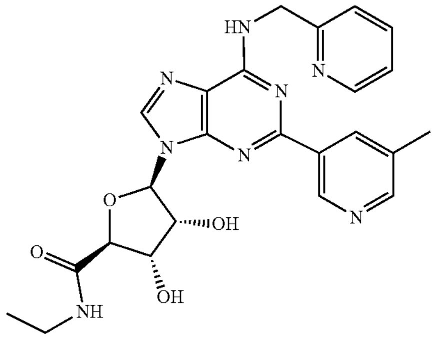 [SMILES: CCNC(=O)[C@H]1O[C@@H](n2cnc3c(NCc4ccccn4)nc(-c4cncc(C)c4)nc32)[C@H](O)[C@@H]1O] | (2S,3S,4R,5R)-N-ethyl-3,4-dihydroxyl-5-(2-(5-methylpyridin-3-yl)-6-(((4-methylpyridin-2-yl)methyl)amino)-9H-purin-9-yl)-tetrahydrofuran-2-formamide |
| 419 | 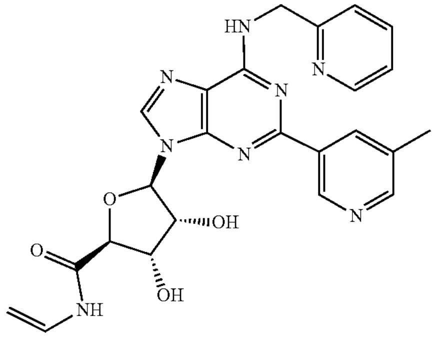 [SMILES: C=CNC(=O)[C@H]1O[C@@H](n2cnc3c(NCc4ccccn4)nc(-c4cncc(C)c4)nc32)[C@H](O)[C@@H]1O] | (2S,3S,4R,5R)-3,4-dihydroxyl-5-(2-(5-methylpyridin-3-yl)-6-(((4-methylpyridin-2-yl)methyl)amino)-9H-purin-9-yl)-N-vinyltetrahydrofuran-2-formamide |
| 420 | 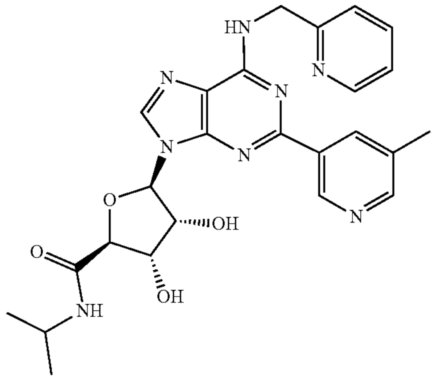 [SMILES: Cc1cncc(-c2nc(NCc3ccccn3)c3ncn([C@@H]4O[C@H](C(=O)NC(C)C)[C@@H](O)[C@H]4O)c3n2)c1] | (2S,3S,4R,5R)-3,4-dihydroxyl-N-isopropyl-5-(2-(5-methylpyridin-3-yl)-6-((pyridin-2-ylmethyl)amino)-9H-purin-9-yl)tetrahydrofuran-2-formamide |

-continued

| Compd. No | Structural formula of compound | Name |
|---|---|---|
| 421 | 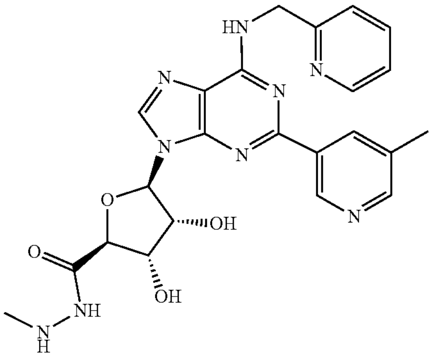 | (2S,3S,4R,5R)-3,4-dihydroxyl-N'-methyl-5-(2-(5-methylpyridin-3-yl)-6-((pyridin-2-ylmethyl)amino)-9H-purin-9-yl)tetrahydrofuran-2-carbohydrazide |
| 422 | 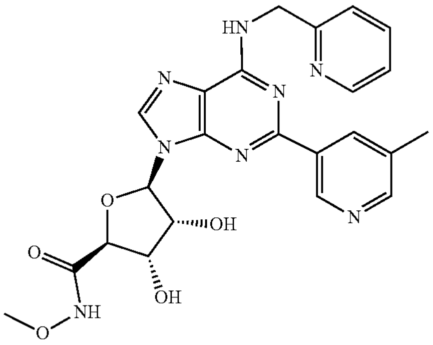 | (2S,3S,4R,5R)-3,4-dihydroxyl-N-methoxy-5-(2-(5-methylpyridin-3-yl)-6-((pyridin-2-ylmethyl)amino)-9H-purin-9-yl)tetrahydrofuran-2-formamide |
| 423 | 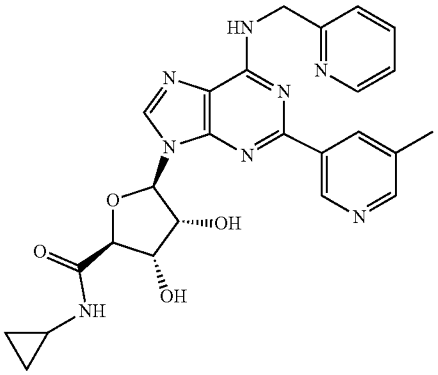 [SMILES: Cc1cncc(-c2nc(NCc3ccccn3)c3ncn([C@@H]4O[C@H](C(=O)NC5CC5)[C@@H](O)[C@H]4O)c3n2)c1] | (2S,3S,4R,5R)-N-cyclopropyl-3,4-dihydroxyl-5-(2-(5-methylpyridin-3-yl)-6-((pyridin-2-ylmethyl)amino)-9H-purin-9-yl)tetrahydrofuran-2-formamide |
| 424 | 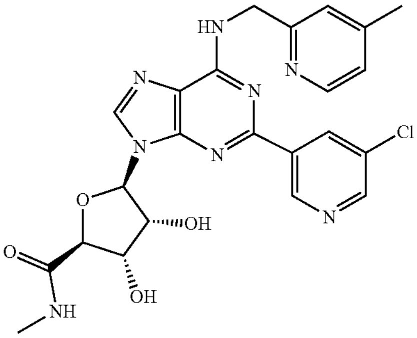 [SMILES: CNC(=O)[C@H]1O[C@@H](n2cnc3c(NCc4cc(C)ccn4)nc(-c4cncc(Cl)c4)nc32)[C@H](O)[C@@H]1O] | (2S,3S,4R,5R)-5-(2-(5-methylpyridin-3-yl)-6-((pyridin-2-ylmethyl)amino)-9H-purin-9-yl)-3,4-dihydroxyl-N-methyltetrahydrofuran-2-formamide |

-continued

| Compd. No | Structural formula of compound | Name |
|---|---|---|
| 425 | 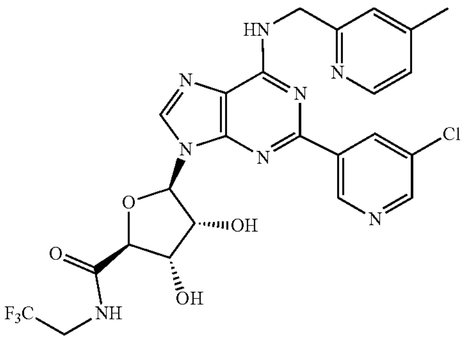 [SMILES: Cc1ccnc(CNc2nc(-c3cncc(Cl)c3)nc3c2ncn3[C@@H]2O[C@H](C(=O)NCC(F)(F)F)[C@@H](O)[C@H]2O)c1] | (2S,3S,4R,5R)-5-(2-(5-chloropyridin-3-yl)-6-(((4-methylpyridin-2-yl)methyl)amino)-9H-purin-9-yl)-3,4-dihydroxyl-N-(2,2,2-trifluoroethyl)tetrahydrofuran-2-formamide |
| 426 | 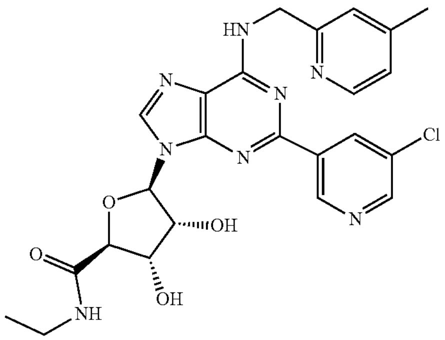 [SMILES: CCNC(=O)[C@H]1O[C@@H](n2cnc3c(NCc4cc(C)ccn4)nc(-c4cncc(Cl)c4)nc32)[C@H](O)[C@@H]1O] | (2S,3S,4R,5R)-5-(2-(5-chloropyridin-3-yl)-6-(((4-methylpyridin-2-yl)methyl)amino)-9H-purin-9-yl)-N-ethyl-3,4-dihydroxyltetrahydrofuran-2-formamide |
| 427 | 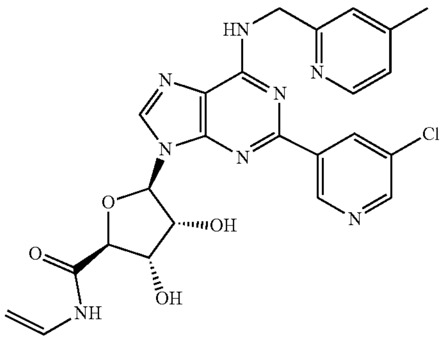 [SMILES: C=CNC(=O)[C@H]1O[C@@H](n2cnc3c(NCc4cc(C)ccn4)nc(-c4cncc(Cl)c4)nc32)[C@H](O)[C@@H]1O] | (2S,3S,4R,5R)-5-(2-(5-chloropyridin-3-yl)-6-(((4-methylpyridin-2-yl)methyl)amino)-9H-purin-9-yl)-3,4-dihydroxyl-N-vinyltetrahydrofuran-2-formamide |
| 428 | 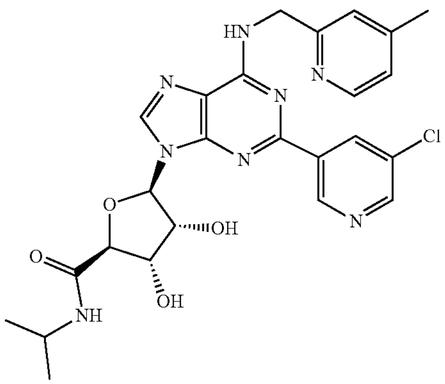 [SMILES: Cc1ccnc(CNc2nc(-c3cncc(Cl)c3)nc3c2ncn3[C@@H]2O[C@H](C(=O)NC(C)C)[C@@H](O)[C@H]2O)c1] | (2S,3S,4R,5R)-5-(2-(5-chloropyridin-3-yl)-6-(((4-methylpyridin-2-yl)methyl)amino)-9H-purin-9-yl)-3,4-dihydroxyl-N-isopropyltetrahydrofuran-2-formamide |

-continued

| Compd. No | Structural formula of compound | Name |
|---|---|---|
| 429 | 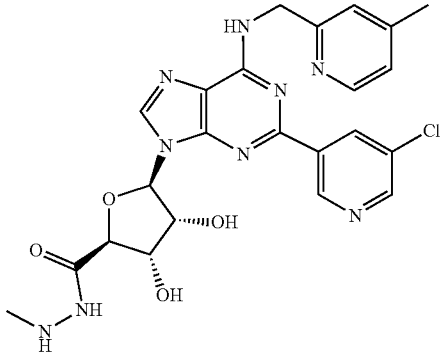 [SMILES: CNNC(=O)[C@H]1O[C@@H](n2cnc3c(NCc4cc(C)ccn4)nc(-c4cncc(Cl)c4)nc32)[C@H](O)[C@@H]1O] | (2S,3S,4R,5R)-5-(2-(5-chloropyridin-3-yl)-6-(((4-methylpyridin-2-yl)methyl)amino)-9H-purin-9-yl)-3,4-dihydroxyl-N'-methyltetrahydrofuran-2-carbohydrazide |
| 430 | 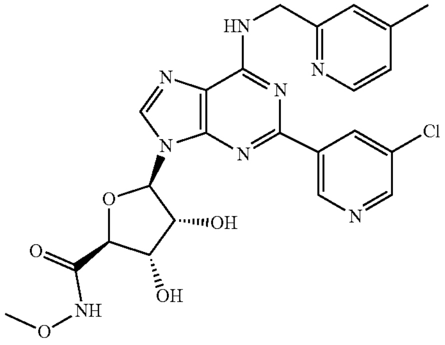 [SMILES: CONC(=O)[C@H]1O[C@@H](n2cnc3c(NCc4cc(C)ccn4)nc(-c4cncc(Cl)c4)nc32)[C@H](O)[C@@H]1O] | (2S,3S,4R,5R)-5-(2-(5-chloropyridin-3-yl)-6-(((4-methylpyridin-2-yl)methyl)amino)-9H-purin-9-yl)-3,4-dihydroxyl-N-methoxytetrahydrofuran-2-formamide |
| 431 | 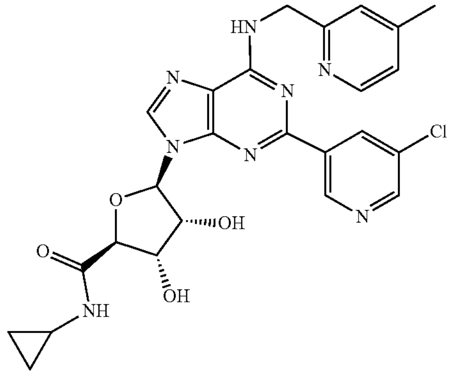 [SMILES: Cc1ccnc(CNc2nc(-c3cncc(Cl)c3)nc3c2ncn3[C@@H]2O[C@H](C(=O)NC3CC3)[C@@H](O)[C@H]2O)c1] | (2S,3S,4R,5R)-5-(2-(5-chloropyridin-3-yl)-6-(((4-methylpyridin-2-yl)methyl)amino)-9H-purin-9-yl)-N-cyclopropyl-3,4-dihydroxyltetrahydrofuran-2-formamide |
| 432 | 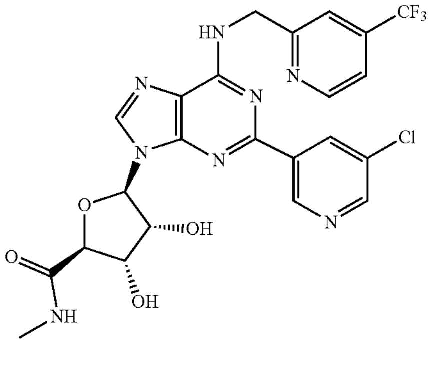 [SMILES: CNC(=O)[C@H]1O[C@@H](n2cnc3c(NCc4cc(C(F)(F)F)ccn4)nc(-c4cncc(Cl)c4)nc32)[C@H](O)[C@@H]1O] | (2S,3S,4R,5R)-5-(2-(5-chloropyridin-3-yl)-6-(((4-(trifluoromethyl)pyridin-2-yl)methyl)amino)-9H-purin-9-yl)-3,4-dihydroxyl-N-methyltetrahydrofuran-2-formamide |

-continued

| Compd. No | Structural formula of compound | Name |
|---|---|---|
| 433 | 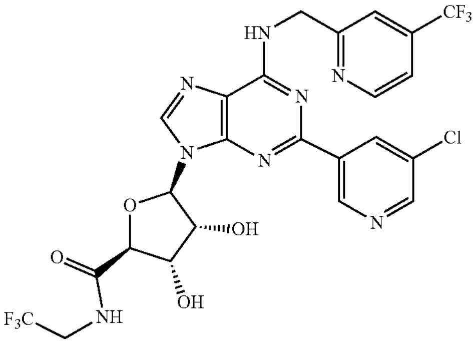 [SMILES: O=C(NCC(F)(F)F)[C@H]1O[C@@H](n2cnc3c(NCc4cc(C(F)(F)F)ccn4)nc(-c4cncc(Cl)c4)nc32)[C@H](O)[C@@H]1O] | (2S,3S,4R,5R)-5-(2-(5-chloropyridin-3-yl)-6-(((4-(trifluoromethyl)pyridin-2-yl)methyl)amino)-9H-purin-9-yl)-3,4-dihydroxyl-N(2,2,2-trifluoroethyl)tetrahydrofuran-2-formamide |
| 434 | 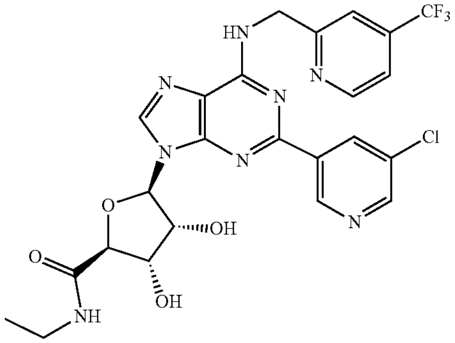 [SMILES: CCNC(=O)[C@H]1O[C@@H](n2cnc3c(NCc4cc(C(F)(F)F)ccn4)nc(-c4cncc(Cl)c4)nc32)[C@H](O)[C@@H]1O] | (2S,3S,4R,5R)-5-(2-(5-chloropyridin-3-yl)-6-(((4-(trifluoromethyl)pyridin-2-yl)methyl)amino)-9H-purin-9-yl)-N-ethyl-3,4-dihydroxyltetrahydrofuran-2-formamide |
| 435 | 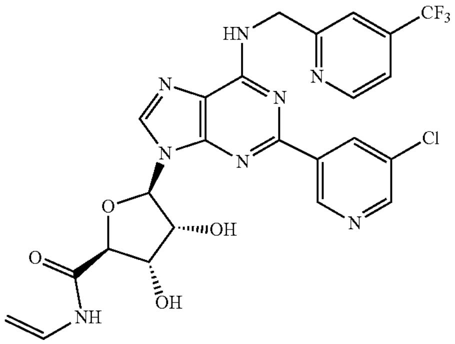 [SMILES: C=CNC(=O)[C@H]1O[C@@H](n2cnc3c(NCc4cc(C(F)(F)F)ccn4)nc(-c4cncc(Cl)c4)nc32)[C@H](O)[C@@H]1O] | (2S,3S,4R,5R)-5-(2-(5-chloropyridin-3-yl)-6-(((4-(trifluoromethyl)pyridin-2-yl)methyl)amino)-9H-purin-9-yl)-3,4-dihydroxyl-N-vinyltetrahydrofuran-2-formamide |
| 436 | 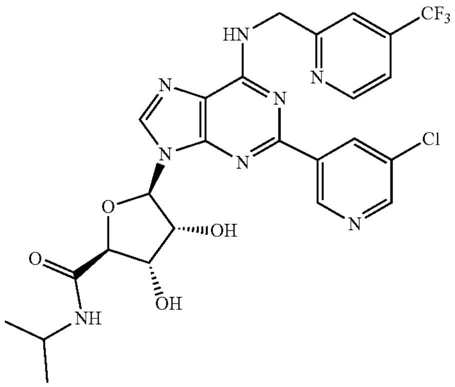 [SMILES: CC(C)NC(=O)[C@H]1O[C@@H](n2cnc3c(NCc4cc(C(F)(F)F)ccn4)nc(-c4cncc(Cl)c4)nc32)[C@H](O)[C@@H]1O] | (2S,3S,4R,5R)-5-(2-(5-chloropyridin-3-yl)-6-(((4-(trifluoromethyl)pyridin-2-yl)methyl)amino)-9H-purin-9-yl)-3,4-dihydroxyl-N-isopropyltetrahydrofuran-2-formamide |

-continued

| Compd. No | Structural formula of compound | Name |
|---|---|---|
| 437 | 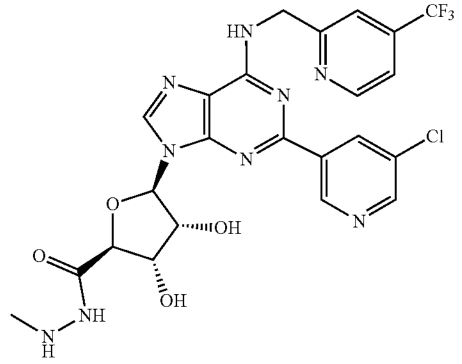 [SMILES: CNNC(=O)[C@H]1O[C@@H](n2cnc3c(NCc4cc(C(F)(F)F)ccn4)nc(-c4cncc(Cl)c4)nc32)[C@H](O)[C@@H]1O] | (2S,3S,4R,5R)-5-(2-(5-chloropyridin-3-yl)-6-(((4-(trifluoromethyl)pyridin-2-yl)methyl)amino)-9H-purin-9-yl)-3,4-dihydroxyl-N'-methyltetrahydrofuran-2-carbohydrazide |
| 438 | 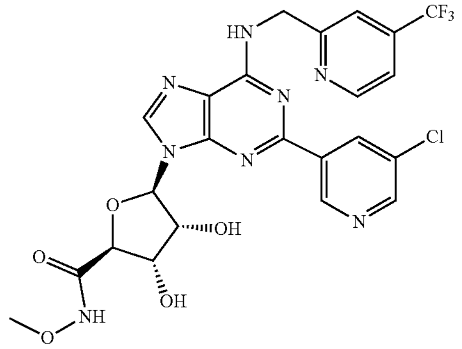 [SMILES: CONC(=O)[C@H]1O[C@@H](n2cnc3c(NCc4cc(C(F)(F)F)ccn4)nc(-c4cncc(Cl)c4)nc32)[C@H](O)[C@@H]1O] | (2S,3S,4R,5R)-5-(2-(5-chloropyridin-3-yl)-6-(((4-(trifluoromethyl)pyridin-2-yl)methyl)amino)-9H-purin-9-yl)-3,4-dihydroxyl-N-methoxytetrahydrofuran-2-formamide |
| 439 | 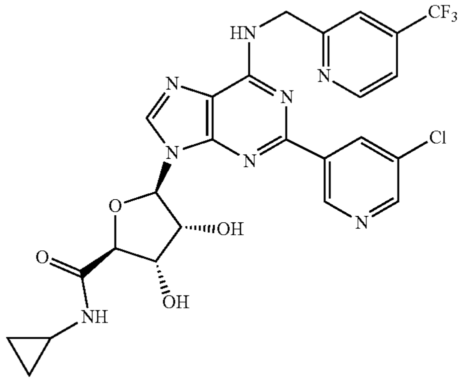 [SMILES: O=C(NC1CC1)[C@H]1O[C@@H](n2cnc3c(NCc4cc(C(F)(F)F)ccn4)nc(-c4cncc(Cl)c4)nc32)[C@H](O)[C@@H]1O] | (2S,3S,4R,5R)-5-(2-(5-chloropyridin-3-yl)-6-(((4-(trifluoromethyl)pyridin-2-yl)methyl)amino)-9H-purin-9-yl)-N-cyclopropyl-3,4-dihydroxyltetrahydrofuran-2-formamide |
| 440 | 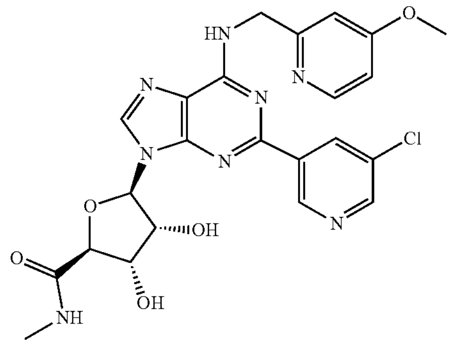 [SMILES: CNC(=O)[C@H]1O[C@@H](n2cnc3c(NCc4cc(OC)ccn4)nc(-c4cncc(Cl)c4)nc32)[C@H](O)[C@@H]1O] | (2S,3S,4R,5R)-5-(2-(5-chloropyridin-3-yl)-6-((((4-methoxypyridin-2-yl)methyl)amino)-9//-purin-9-yl)-3,4-dihydroxyl-N-methyltetrahydrofuran-2-formamide |

-continued

| Compd. No | Structural formula of compound | Name |
|---|---|---|
| 441 | 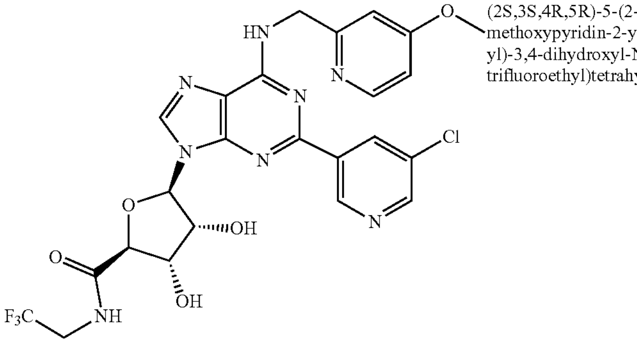 | (2S,3S,4R,5R)-5-(2-(5-chloropyridin-3-yl)-6-((((4-methoxypyridin-2-yl)methyl)amino)-9H-purin-9-yl)-3,4-dihydroxyl-N-(2,2,2-trifluoroethyl)tetrahydrofuran-2-formamide |
| 442 | 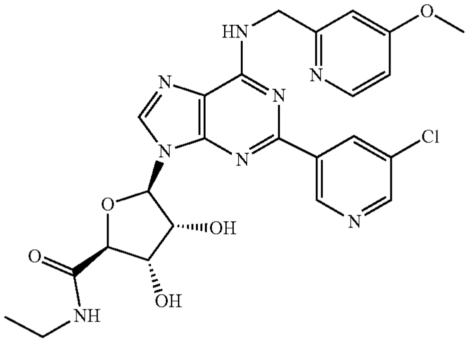 [SMILES: CCNC(=O)[C@H]1O[C@@H](n2cnc3c(NCc4cc(OC)ccn4)nc(-c4cncc(Cl)c4)nc32)[C@H](O)[C@@H]1O] | (2S,3S,4R,5R)-5-(2-(5-chloropyridin-3-yl)-6-((((4-methoxypyridin-2-yl)methyl)amino)-9H-purin-9-yl)-N-ethyl-3,4-dihydroxyltetrahydrofuran-2-formamide |
| 443 | 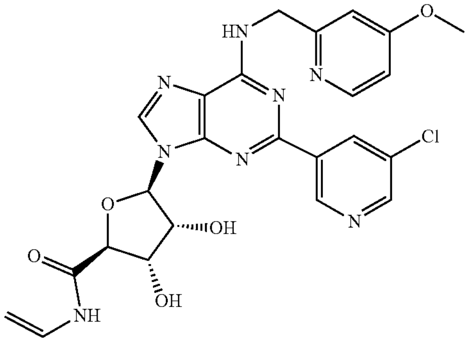 [SMILES: C=CNC(=O)[C@H]1O[C@@H](n2cnc3c(NCc4cc(OC)ccn4)nc(-c4cncc(Cl)c4)nc32)[C@H](O)[C@@H]1O] | (2S,3S,4R,5R)-5-(2-(5-chloropyridin-3-yl)-6-((((4-methoxypyridin-2-yl)methyl)amino)-9H-purin-9-yl)-3,4-dihydroxyl-N-vinyltetrahydrofuran-2-formamide |
| 444 | 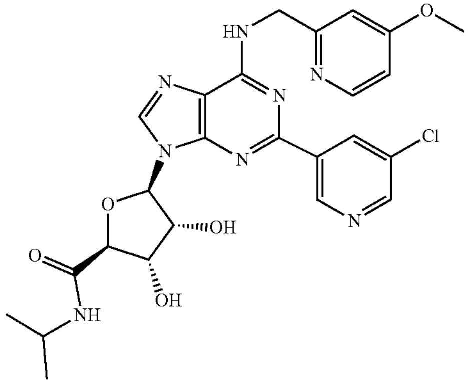 [SMILES: COc1ccnc(CNc2nc(-c3cncc(Cl)c3)nc3c2ncn3[C@@H]2O[C@H](C(=O)NC(C)C)[C@@H](O)[C@H]2O)c1] | (2S,3S,4R,5R)-5-(2-(5-chloropyridin-3-yl)-6-((((4-methoxypyridin-2-yl)methyl)amino)-9/-purin-9-yl)-3,4-dihydroxyl-N-isopropyltetrahydrofuran-2-formamide |

-continued

| Compd. No | Structural formula of compound | Name |
|---|---|---|
| 445 | 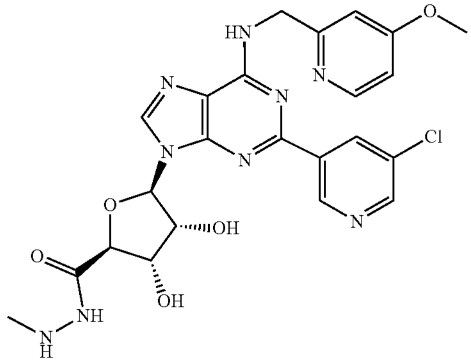 | (2S,3S,4R,5R)-5-(2-(5-chloropyridin-3-yl)-6-((((4-methoxypyridin-2-yl)methyl)amino)-9H-purin-9-yl)-3,4-dihydroxyl-N'-methyltetrahydrofuran-2-carbohydrazide |
| 446 | 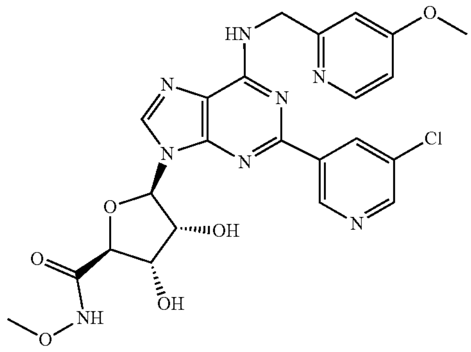 | (2S,3S,4R,5R)-5-(2-(5-chloropyridin-3-yl)-6-((((4-methoxypyridin-2-yl)methyl)amino)-9H-purin-9-yl)-3,4-dihydroxyl-N-methoxytetrahydrofuran-2-formamide |
| 447 | 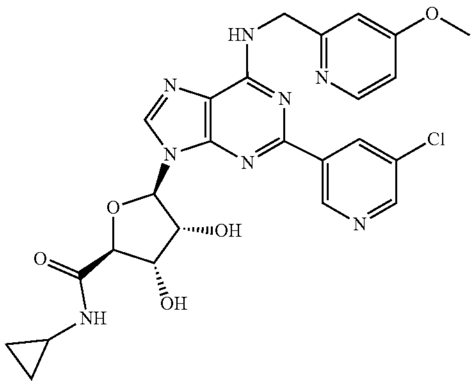 [SMILES: COc1ccnc(CNc2nc(-c3cncc(Cl)c3)nc3c2ncn3[C@@H]2O[C@H](C(=O)NC3CC3)[C@@H](O)[C@H]2O)c1] | (2S,3S,4R,5R)-5-(2-(5-chloropyridin-3-yl)-6-((((4-methoxypyridin-2-yl)methyl)amino)-9H-purin-9-yl)-N-cyclopropyl-3,4-dihydroxyltetrahydrofuran-2-formamide |
| 448 | 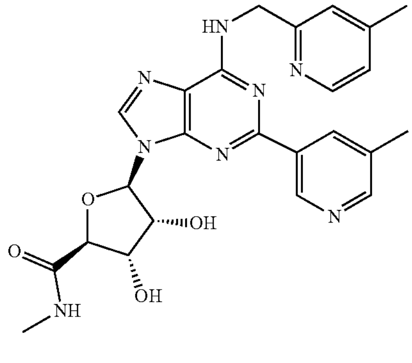 [SMILES: CNC(=O)[C@H]1O[C@@H](n2cnc3c(NCc4cc(C)ccn4)nc(-c4cncc(C)c4)nc32)[C@H](O)[C@@H]1O] | (2S,3S,4R,5R)-3,4-dihydroxyl-N-methyl-5-(6-((4-methylpyridin-2-yl)methylamino)-2-(5-methylpyridin-3-yl)-9H-purin-9-yl)-tetrahydrofuran-2-formamide |

-continued

| Compd. No | Structural formula of compound | Name |
|---|---|---|
| 449 | 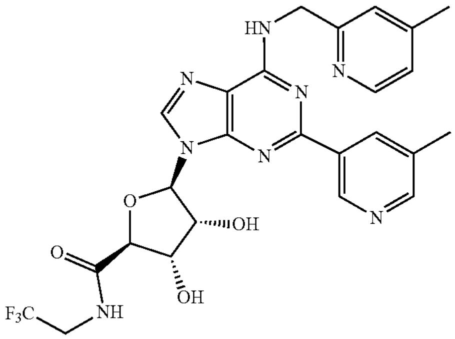 [SMILES: Cc1cncc(-c2nc(NCc3cc(C)ccn3)c3ncn([C@@H]4O[C@H](C(=O)NCC(F)(F)F)[C@@H](O)[C@H]4O)c3n2)c1] | (2S,3S,4R,5R)-3,4-dihydroxyl-5-(6-(((4-methylpyridin-2-yl)methyl)amino)-2-(5-methylpyridin-3-yl)-9H-purin-9-yl)-N-(2,2,2-trifluoroethyl)tetrahydrofuran-2-formamide |
| 450 | 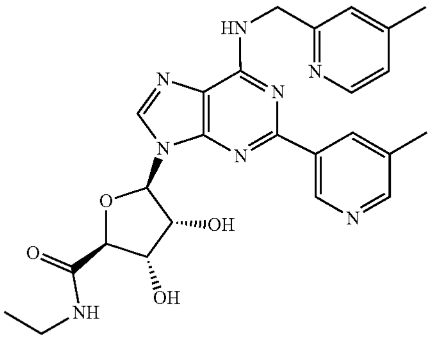 [SMILES: CCNC(=O)[C@H]1O[C@@H](n2cnc3c(NCc4cc(C)ccn4)nc(-c4cncc(C)c4)nc32)[C@H](O)[C@@H]1O] | (2S,3S,4R,5R)-N-ethyl-3,4-dihydroxyl-5-(6-(((4-methylpyridin-2-yl)methyl)amino)-2-(5-methylpyridin-3-yl)-9H-purin-9-yl)tetrahydrofuran-2-formamide |
| 451 | 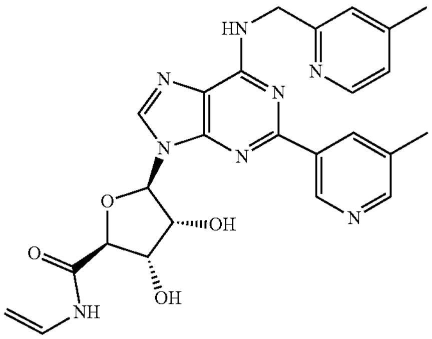 [SMILES: C=CNC(=O)[C@H]1O[C@@H](n2cnc3c(NCc4cc(C)ccn4)nc(-c4cncc(C)c4)nc32)[C@H](O)[C@@H]1O] | (2S,3S,4R,5R)-3,4-dihydroxyl-5-(6-(((4-methylpyridin-2-yl)methyl)amino)-2-(5-methylpyridin-3-yl)-9H-purin-9-yl)-N-vinyltetrahydrofuran-2-formamide |
| 452 | 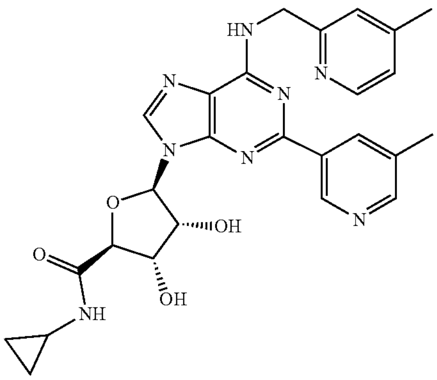 [SMILES: Cc1cncc(-c2nc(NCc3cc(C)ccn3)c3ncn([C@@H]4O[C@H](C(=O)NC5CC5)[C@@H](O)[C@H]4O)c3n2)c1] | (2S,3S,4R,5R)-N-cyclopropyl-3,4-dihydroxyl-5-(6-(((4-methylpyridin-2-yl)methyl)amino)-2-(5-methylpyridin-3-yl)-9H-purin-9-yl)tetrahydrofuran-2-formamide |

-continued

| Compd. No | Structural formula of compound | Name |
| --- | --- | --- |
| 453 | 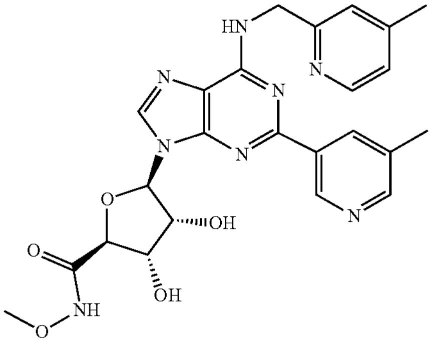 | (2S,3S,4R,5R)-3,4-dihydroxyl-N-methoxy-5-(6-(((4-methylpyridin-2-yl)methyl)amino)-2-(5-methylpyridin-3-yl)-9H-purin-9-yl)tetrahydrofuran-2-formamide |
| 454 | 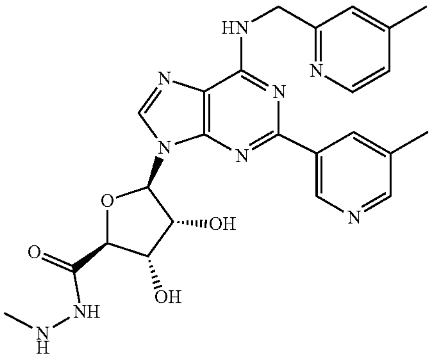 | (2S,3S,4R,5R)-3,4-dihydroxyl-N' -methyl-5-(6-(((4-methylpyridin-2-yl)methyl)amino)-2-(5-methylpyridin-3-yl)-9H-purin-9-yl)tetrahydrofuran-2-carbohydrazide |
| 455 | 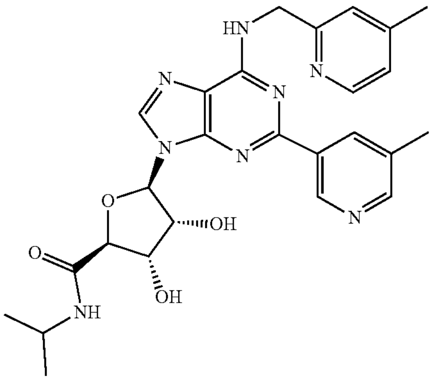 [SMILES: Cc1cncc(-c2nc(NCc3cc(C)ccn3)c3ncn([C@@H]4O[C@H](C(=O)NC(C)C)[C@@H](O)[C@H]4O)c3n2)c1] | (2S,3S,4R,5R)-3,4-dihydroxyl-N'-isopropyl-5-(6-(((4-methylpyridin-2-yl)methyl)amino)-2-(5-methylpyridin-3-yl)-9H-purin-9-yl)tetrahydrofuran-2-carbamide |
| 456 | 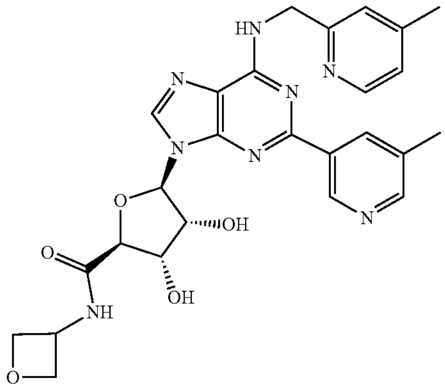 [SMILES: Cc1cncc(-c2nc(NCc3cc(C)ccn3)c3ncn([C@@H]4O[C@H](C(=O)NC5COC5)[C@@H](O)[C@H]4O)c3n2)c1] | (2S,3S,4R,5R)-3,4-dihydroxyl-5-(6-(((4-methylpyridin-2-yl)methyl)amino)-2-(5-methyl-9-pyridin-3-yl)-9H-purin-9-yl)-N'-(oxetane-3-yl)tetrahydrofuran-2-carbamide |

The present application further comprise A3 receptor agonists obtained by further non-substantial modification or replacement of functional groups of the compounds in formulas I-IX shown above. As specific examples, the compound of the present application further comprises but are not limited to:

| Compd. No. | Structural formula of compound | Name |
|---|---|---|
| 457 | 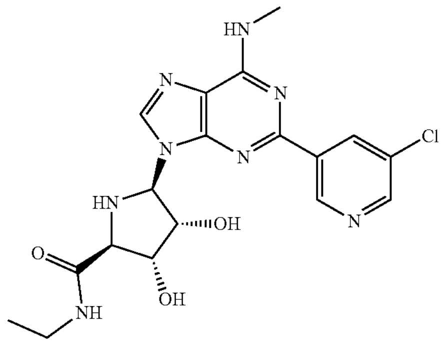 [SMILES: CCNC(=O)[C@H]1N[C@@H](n2cnc3c(NC)nc(-c4cncc(Cl)c4)nc32)[C@H](O)[C@@H]1O] | (2S,3R,4S,5S)-5-(2-(5-chloropyridin-3-yl)-6-(methylamino)-9H-purin-9-yl)-N-ethyl-3,4-dihydroxylpyrrolidin-2-form-amide |
| 458 | 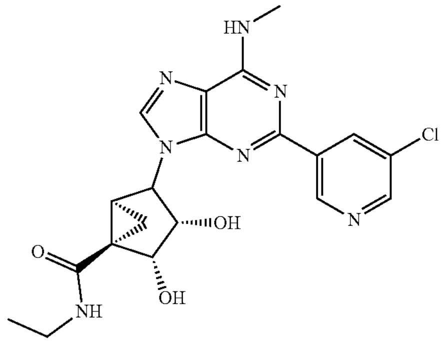 [SMILES: CCNC(=O)[C@]12C[C@@H]1C(n1cnc3c(NC)nc(-c4cncc(Cl)c4)nc31)[C@H](O)[C@@H]2O] | (1S,2R,3S,5S)-4-(2-(5-chloropyridin-3-yl)-6-(methylamino)-9H-purin-9-yl)-N-ethyl-2,3-dihydroxylbicyclo[3.1.0]-hexane-1-formamide |
| 459 | 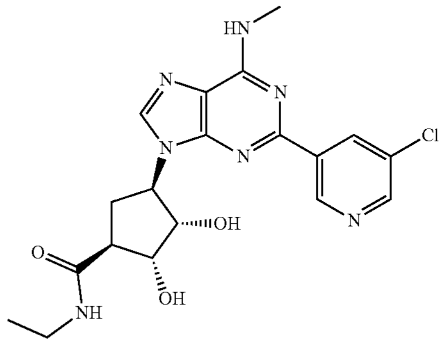 [SMILES: CCNC(=O)[C@H]1C[C@@H](n2cnc3c(NC)nc(-c4cncc(Cl)c4)nc32)[C@H](O)[C@@H]1O] | (1S,2R,3S,4R)-4-(2-(5-chloropyridin-3-yl)-6-(methylamino)-9H-purin-9-yl)-N-ethyl-2,3-dihydroxylcyclopentaneform-amide |
| 460 | 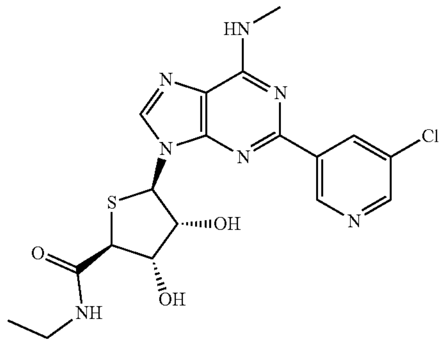 [SMILES: CCNC(=O)[C@H]1S[C@@H](n2cnc3c(NC)nc(-c4cncc(Cl)c4)nc32)[C@H](O)[C@@H]1O] | (2S,3S,4R,5R)-5-(2-(5-chloropyridin-3-yl)-6-(methylamino)-9H-purin-9-yl)-N-ethyl-3,4-dihydroxyltetrahydrothio-phen-2-formamide |

-continued

| Compd. No. | Structural formula of compound | Name |
|---|---|---|
| 461 | 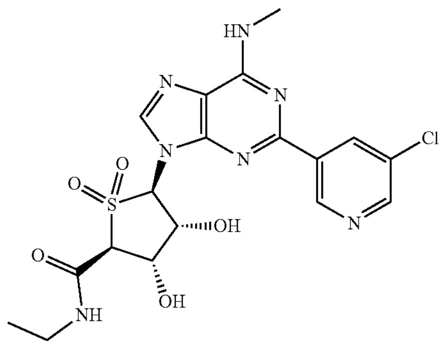 [SMILES: CCNC(=O)[C@@H]1[C@@H](O)[C@@H](O)[C@H](n2cnc3c(NC)nc(-c4cncc(Cl)c4)nc32)S1(=O)=O] | (2S,3S,4R,5R)-5-(2-(5-chloropyridin-3-yl)-6-(methylamino)-9H-purin-9-yl)-N-ethyl-3,4-dihydroxyltetrahydrothiophen-2-formamide 1,1-dioxide |
| 462 | 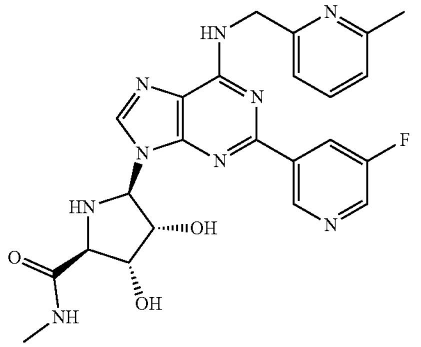 [SMILES: CNC(=O)[C@H]1N[C@@H](n2cnc3c(NCc4cccc(C)n4)nc(-c4cncc(F)c4)nc32)[C@H](O)[C@@H]1O] | (2S,3R,4S,5S)-5-(2-(5-fluoropyridin-3-yl)-6-(((6-methylpyridin-2-yl)methyl)-amino)-9H-purin-9-yl)-3,4-dihydroxyl-N-methylpyrrolidin-2-formamide |
| 463 | 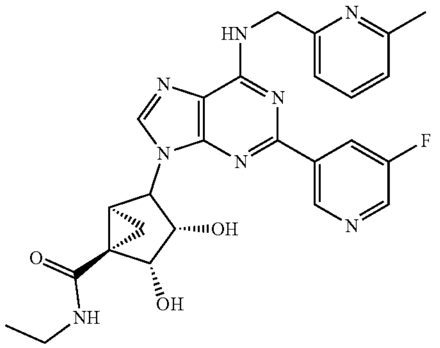 [SMILES: CCNC(=O)[C@]12C[C@@H]1C(n1cnc3c(NCc4cccc(C)n4)nc(-c4cncc(F)c4)nc31)[C@H](O)[C@@H]2O] | (1S,2R,3S,5S)-4-(2-(5-fluoropyridin-3-yl)-6-(((6-methylpyridin-2-yl)methyl)-amino)-9H-purin-9-yl)-2,3-dihydroxyl-N-methylbicyclo[3.1.0]hexane-1-formamide |
| 464 | 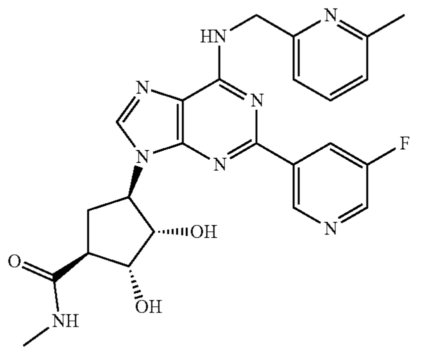 [SMILES: CNC(=O)[C@H]1C[C@@H](n2cnc3c(NCc4cccc(C)n4)nc(-c4cncc(F)c4)nc32)[C@H](O)[C@@H]1O] | (1S,2R,3S,4R)-4-(2-(5-fluoropyridin-3-yl)-6-(((6-methylpyridin-2-yl)methyl)-amino)-9H-purin-9-yl)-2,3-dihydroxyl-N-methylcyclopentaneformamide |

-continued

| Compd. No. | Structural formula of compound | Name |
|---|---|---|
| 465 | 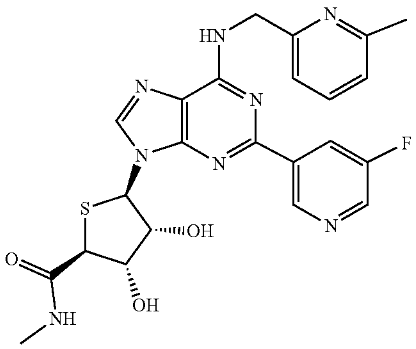 [SMILES: CNC(=O)[C@H]1S[C@@H](n2cnc3c(NCc4cccc(C)n4)nc(-c4cncc(F)c4)nc32)[C@H](O)[C@@H]1O] | (2S,3S,4R,5R)-5-(2-(5-fluoropyridin-3-yl)-6-(((6-methylpyridin-2-yl)methyl)-amino)-9H-purin-9-yl)-3,4-dihydroxyl-N-methyltetrahydrothiophen-2-form-amide |
| 466 | 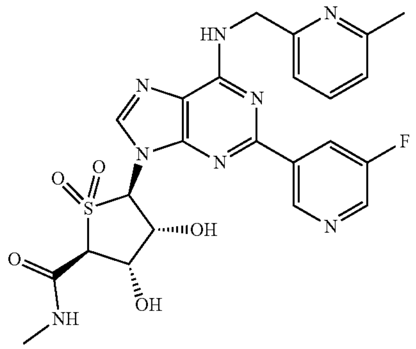 [SMILES: CNC(=O)[C@@H]1[C@@H](O)[C@@H](O)[C@H](n2cnc3c(NCc4cccc(C)n4)nc(-c4cncc(F)c4)nc32)S1(=O)=O] | (2S,3S,4R,5R)-5-(2-(5-fluoropyridin-3-yl)-6-(((6-methylpyridin-2-yl)methyl)-amino)-9H-purin-9-yl)-3,4-dihydroxyl-N-methyltetrahydrothiophen-2-form-amide 1,1-dioxide |
| 467 | 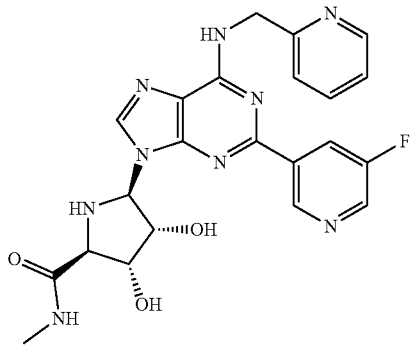 [SMILES: CNC(=O)[C@H]1N[C@@H](n2cnc3c(NCc4ccccn4)nc(-c4cncc(F)c4)nc32)[C@H](O)[C@@H]1O] | (2S,3R,4S,5S)-5-(2-(5-fluoropyridin-3-yl)-6-((pyridin-2-ylmethyl)amino)-9H-purin-9-yl)-3,4-dihydroxyl-N-methyl-pyrrolidin-2-formamide |
| 468 | 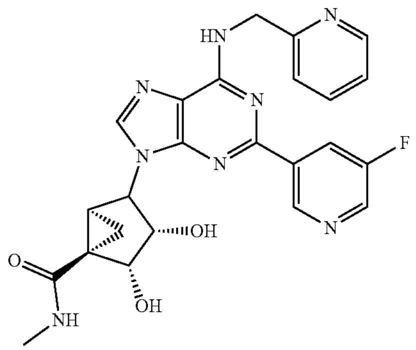 [SMILES: CNC(=O)[C@]12C[C@@H]1C(n1cnc3c(NCc4ccccn4)nc(-c4cncc(F)c4)nc31)[C@H](O)[C@@H]2O] | (1S,2R,3S,5S)-4-(2-(5-fluoropyridin-3-yl)-6-((pyridin-2-ylmethyl)amino)-9H-purin-9-yl)-2,3-dihydroxyl-N-methyl-bicyclo[3.1.0]hexane-1-formamide |

-continued

| Compd. No. | Structural formula of compound | Name |
|---|---|---|
| 469 | 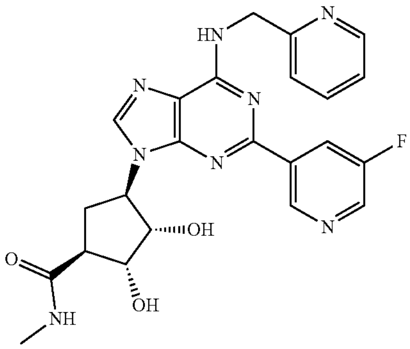 [SMILES: CNC(=O)[C@H]1C[C@@H](n2cnc3c(NCc4ccccn4)nc(-c4cncc(F)c4)nc32)[C@H](O)[C@@H]1O] | (1S,2R,3S,4R)-4-(2-(5-fluoropyridin-3-yl)-6-((pyridin-2-ylmethyl)amino)-9H-purin-9-yl)-2,3-dihydroxyl-N-methyl-cyclopentaneformamide |
| 470 | 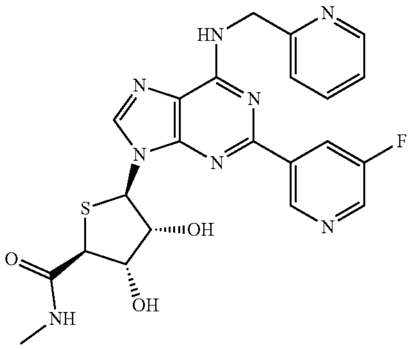 [SMILES: CNC(=O)[C@H]1S[C@@H](n2cnc3c(NCc4ccccn4)nc(-c4cncc(F)c4)nc32)[C@H](O)[C@@H]1O] | (2S,3S,4R,5R)-5-(2-(5-fluoropyridin-3-yl)-6-((pyridin-2-ylmethyl)amino)-9H-purin-9-yl)-3,4-dihydroxyl-N-methyl-tetrahydrothiophen-2-formamide |
| 471 | 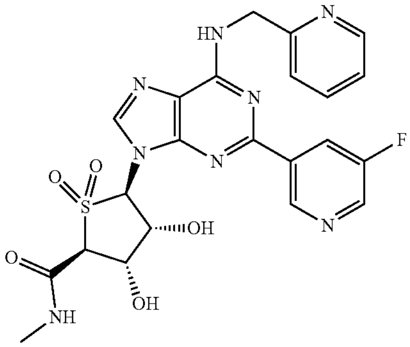 [SMILES: CNC(=O)[C@@H]1[C@@H](O)[C@@H](O)[C@H](n2cnc3c(NCc4ccccn4)nc(-c4cncc(F)c4)nc32)S1(=O)=O] | (2S,3S,4R,5R)-5-(2-(5-fluoropyridin-3-yl)-6-((pyridin-2-ylmethyl)amino)-9H-purin-9-yl)-3,4-dihydroxyl-N-methyl-tetrahydrothiophen-2-formamide 1,1-dioxide |
| 472 | 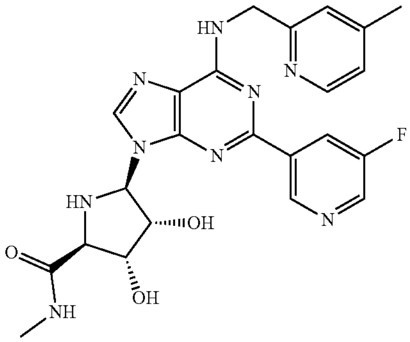 [SMILES: CNC(=O)[C@H]1N[C@@H](n2cnc3c(NCc4cc(C)ccn4)nc(-c4cncc(F)c4)nc32)[C@H](O)[C@@H]1O] | (2S,3R,4S,5S)-5-(2-(5-fluoropyridin-3-yl)-6-(((4-methylpyridin-2-yl)methyl)-amino)-9H-purin-9-yl)-3,4-dihydroxyl-N-methylpyrrolidin-2-formamide |

-continued

| Compd. No. | Structural formula of compound | Name |
|---|---|---|
| 473 | 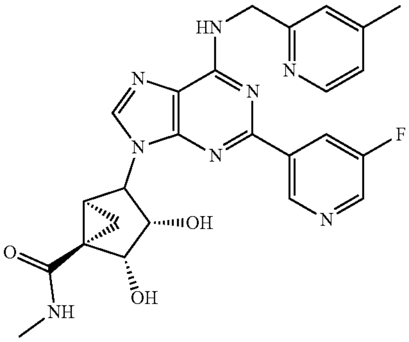 [SMILES: CNC(=O)[C@]12C[C@@H]1C(n1cnc3c(NCc4cc(C)ccn4)nc(-c4cncc(F)c4)nc31)[C@H](O)[C@@H]2O] | (1S,2R,3S,5S)-4-(2-(5-fluoropyridin-3-yl)-6-(((4-methylpyridin-2-yl)methyl)-amino)-9H-purin-9-yl)-2,3-dihydroxyl-N-methylbicyclo[3.1.0]hexane-1-form-amide |
| 474 | 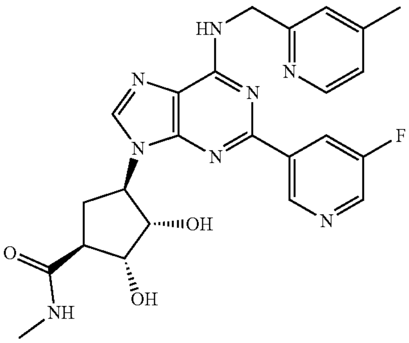 [SMILES: CNC(=O)[C@H]1C[C@@H](n2cnc3c(NCc4cc(C)ccn4)nc(-c4cncc(F)c4)nc32)[C@H](O)[C@@H]1O] | (1S,2R,3S,4R)-4-(2-(5-fluoropyridin-3-yl)-6-(((4-methylpyridin-2-yl)methyl)-amino)-9H-purin-9-yl)-2,3-dihydroxyl-N-methylcyclopentaneformamide |
| 475 | 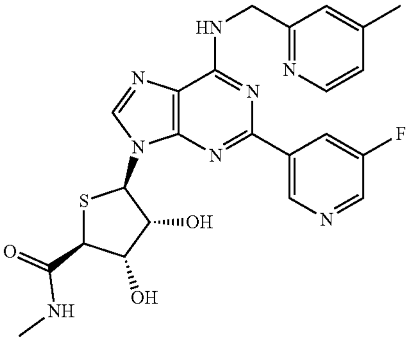 [SMILES: CNC(=O)[C@H]1S[C@@H](n2cnc3c(NCc4cc(C)ccn4)nc(-c4cncc(F)c4)nc32)[C@H](O)[C@@H]1O] | (2S,3S,4R,5R)-5-(2-(5-fluoropyridin-3-yl)-6-(((4-methylpyridin-2-yl)methyl)-amino)-9H-purin-9-yl)-3,4-dihydroxyl-N-methyltetrahydrothiophen-2-form-amide |
| 476 | 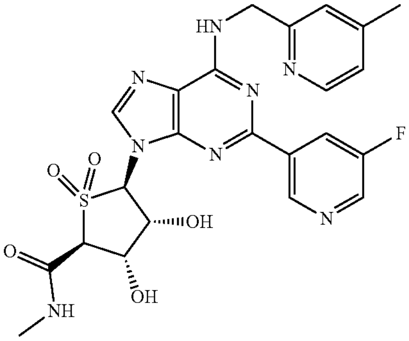 [SMILES: CNC(=O)[C@@H]1[C@@H](O)[C@@H](O)[C@H](n2cnc3c(NCc4cc(C)ccn4)nc(-c4cncc(F)c4)nc32)S1(=O)=O] | (2S,3S,4R,5R)-5-(2-(5-fluoropyridin-3-yl)-6-(((4-methylpyridin-2-yl)methyl)-amino)-9H-purin-9-yl)-3,4-dihydroxyl-N-methyltetrahydrothiophen-2-form-amide 1,1-dioxide |

-continued

| Compd. No. | Structural formula of compound | Name |
|---|---|---|
| 477 | 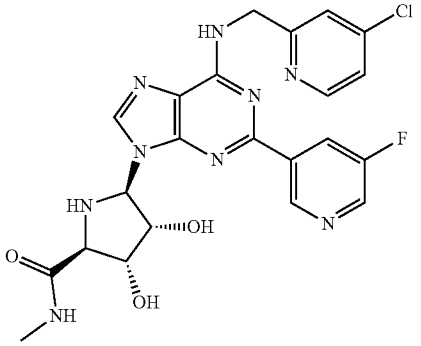 [SMILES: CNC(=O)[C@H]1N[C@@H](n2cnc3c(NCc4cc(Cl)ccn4)nc(-c4cncc(F)c4)nc32)[C@H](O)[C@@H]1O] | (2S,3R,4S,5S)-5-(6-(((4-chloropyridin-2-yl)methyl)amino)-2-(5-fluoropyridin-3-yl)-9H-purin-9-yl)-3,4-dihydroxyl-N-methylpyrrolidin-2-formamide |
| 478 | 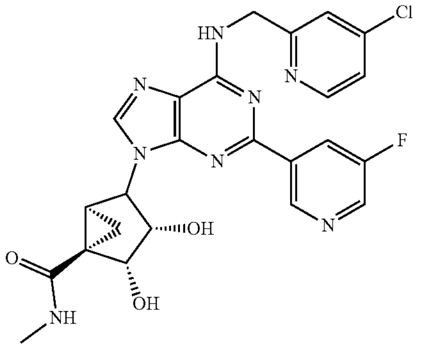 [SMILES: CNC(=O)[C@]12C[C@@H]1C(n1cnc3c(NCc4cc(Cl)ccn4)nc(-c4cncc(F)c4)nc31)[C@H](O)[C@@H]2O] | (1S,2R,3S,5S)-4-(6-(((4-chloropyridin-2-yl)methyl)amino)-2-(5-fluoropyridin-3-yl)-9H-purin-9-yl)-2,3-dihydroxyl-N-methylbicyclo[3.1.0]hexane-1-formamide |
| 479 | 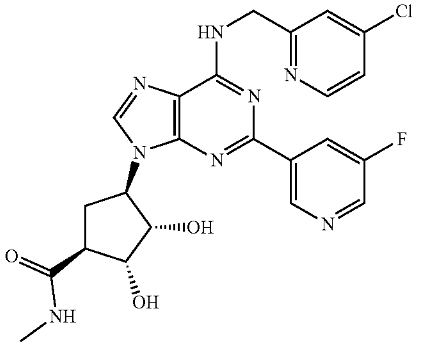 [SMILES: CNC(=O)[C@H]1C[C@@H](n2cnc3c(NCc4cc(Cl)ccn4)nc(-c4cncc(F)c4)nc32)[C@H](O)[C@@H]1O] | (1S,2R,3S,4R)-4-(6-(((4-chloropyridin-2-yl)methyl)amino)-2-(5-fluoropyridin-3-yl)-9H-purin-9-yl)-2,3-dihydroxyl-N-methylcyclopentaneformamide |
| 480 | 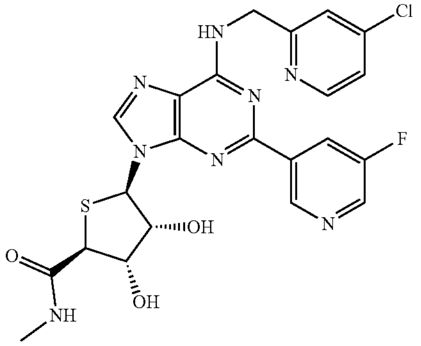 [SMILES: CNC(=O)[C@H]1S[C@@H](n2cnc3c(NCc4cc(Cl)ccn4)nc(-c4cncc(F)c4)nc32)[C@H](O)[C@@H]1O] | (2S,3S,4R,5R)-5-(6-(((4-chloropyridin-2-yl)methyl)amino)-2-(5-fluoropyridin-3-yl)-9H-purin-9-yl)-3,4-dihydroxyl-N-methyltetrahydrothiophen-2-formamide |

-continued

| Compd. No. | Structural formula of compound | Name |
|---|---|---|
| 481 | 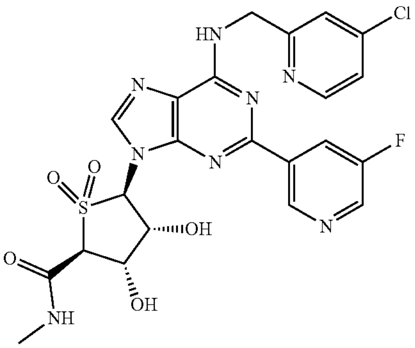 [SMILES: CNC(=O)[C@@H]1[C@@H](O)[C@@H](O)[C@H](n2cnc3c(NCc4cc(Cl)ccn4)nc(-c4cncc(F)c4)nc32)S1(=O)=O] | (2S,3S,4R,5R)-5-(6-(((4-chloropyridin-2-yl)methyl)amino)-2-(5-fluoropyridin-3-yl)-9H-purin-9-yl)-3,4-dihydroxyl-N-methyltetrahydrothiophen-2-formamide 1,1-dioxide |
| 482 | 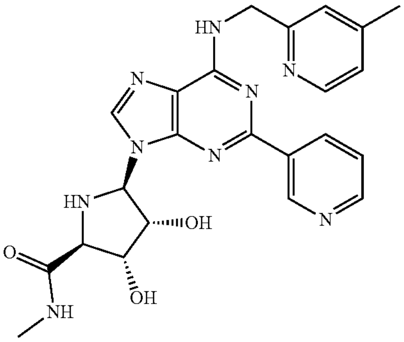 [SMILES: CNC(=O)[C@H]1N[C@@H](n2cnc3c(NCc4cc(C)ccn4)nc(-c4cccnc4)nc32)[C@H](O)[C@@H]1O] | (2S,3R,4S,5S)-3,4-dihydroxyl-N-methyl-5-(6-(((4-methylpyridin-2-yl)methyl)amino)-2-(pyridin-3-yl)-9H-purin-9-yl)-pyrrolidin-2-formamide |
| 483 | 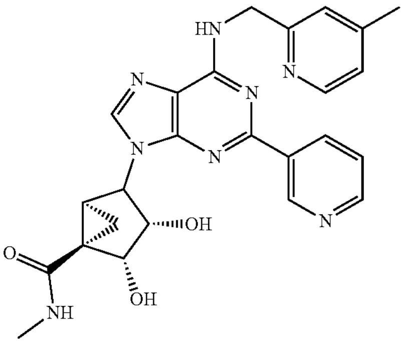 [SMILES: CNC(=O)[C@]12C[C@@H]1C(n1cnc3c(NCc4cc(C)ccn4)nc(-c4cccnc4)nc31)[C@H](O)[C@@H]2O] | (1S,2R,3S,5S)-2,3-dihydroxyl-N-methyl-4-(6-(((4-methylpyridin-2-yl)methyl)amino)-2-(pyridin-3-yl)-9H-purin-9-yl)bicyclo[3.1.0]hexane-1-formamide |
| 484 | 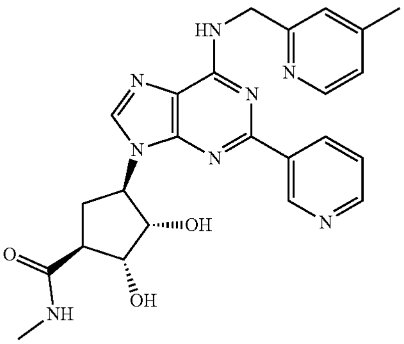 [SMILES: CNC(=O)[C@H]1C[C@@H](n2cnc3c(NCc4cc(C)ccn4)nc(-c4cccnc4)nc32)[C@H](O)[C@@H]1O] | (1S,2R,3S,4R)-2,3-dihydroxyl-N-methyl-4-(6-(((4-methylpyridin-2-yl)methyl)amino)-2-(pyridin-3-yl)-9H-purin-9-yl)cyclopentaneformamide |

-continued

| Compd. No. | Structural formula of compound | Name |
|---|---|---|
| 485 | 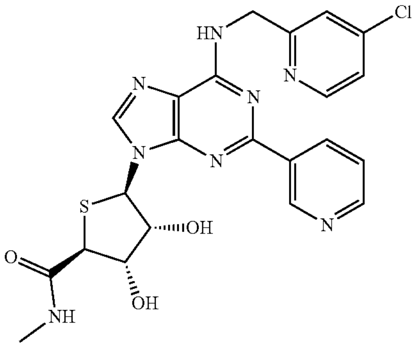 [SMILES: CNC(=O)[C@H]1S[C@@H](n2cnc3c(NCc4cc(Cl)ccn4)nc(-c4cccnc4)nc32)[C@H](O)[C@@H]1O] | (2S,3S,4R,5R)-5-(6-(((4-methylpyridin-2-yl)methyl)amino)-2-(pyridin-3-yl)-9H-purin-9-yl)-3,4-dihydroxyl-N-methyl-tetrahydrothiophen-2-formamide |
| 486 | 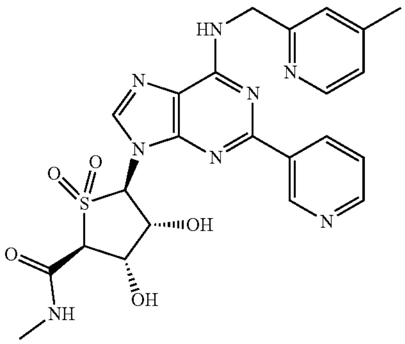 [SMILES: CNC(=O)[C@@H]1[C@@H](O)[C@@H](O)[C@H](n2cnc3c(NCc4cc(C)ccn4)nc(-c4cccnc4)nc32)S1(=O)=O] | (2S,3S,4R,5R)-3,4-dihydroxyl-N-methyl-5-(6-(((4-methylpyridin-2-yl)methyl)amino)-2-(pyridin-3-yl)-9H-purin-9-yl)tetrahydrothiophen-2-formamide 1,1-dioxide |
| 487 | 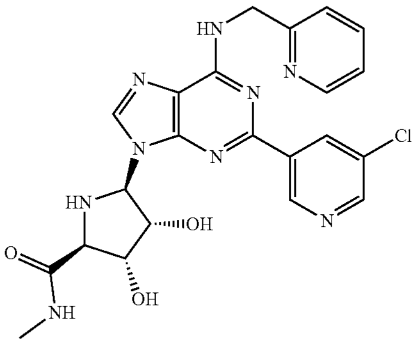 [SMILES: CNC(=O)[C@H]1N[C@@H](n2cnc3c(NCc4ccccn4)nc(-c4cncc(Cl)c4)nc32)[C@H](O)[C@@H]1O] | (2S,3R,4S,5S)-5-(2-(5-chloropyridin-3-yl)-6-((pyridin-2-ylmethyl)amino-9H-purin-9-yl)-3,4-dihydroxyl-N-methyl-pyrrolidin-2-formamide |
| 488 | 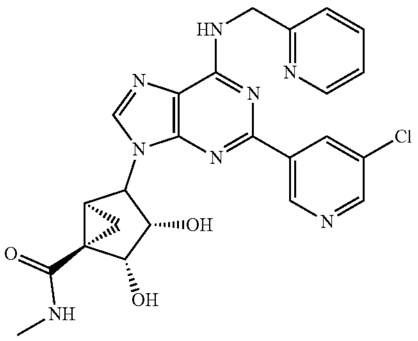 [SMILES: CNC(=O)[C@@]12C[C@@H]1C(n1cnc3c(NCc4ccccn4)nc(-c4cncc(Cl)c4)nc31)[C@H](O)[C@@H]2O] | (1S,2R,3S,5S)-4-(2-(5-chloropyridin-3-yl)-6-((pyridin-2-ylmethyl)amino-9H-purin-9-yl)-2,3-dihydroxyl-N-methyl-bicyclo[3.1.0]hexane-1-formamide |

-continued

| Compd. No. | Structural formula of compound | Name |
|---|---|---|
| 489 | 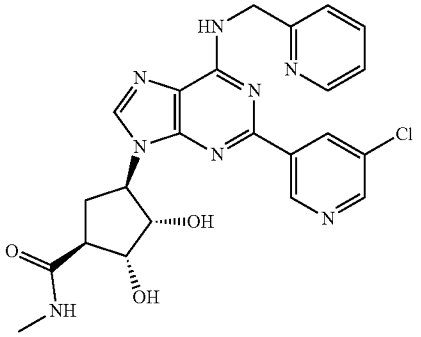 [SMILES: CNC(=O)[C@H]1C[C@@H](n2cnc3c(NCc4ccccn4)nc(-c4cncc(Cl)c4)nc32)[C@H](O)[C@@H]1O] | (1S,2R,3S,4R)-4-(2-(5-chloropyridin-3-yl)-6-((pyridin-2-ylmethyl)amino-9H-purin-9-yl)-2,3-dihydroxyl-N-methyl-cyclopentaneformamide |
| 490 | 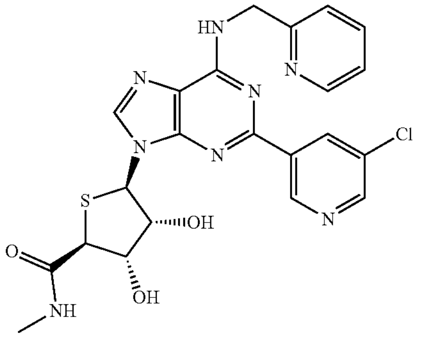 | (2S,3S,4R,5R)-5-(2-(5-chloropyridin-3-yl)-6-((pyridin-2-ylmethyl)amino-9H-purin-9-yl)-3,4-dihydroxyl-N-methyl-tetrahydrothiophen-2-formamide |
| 491 | 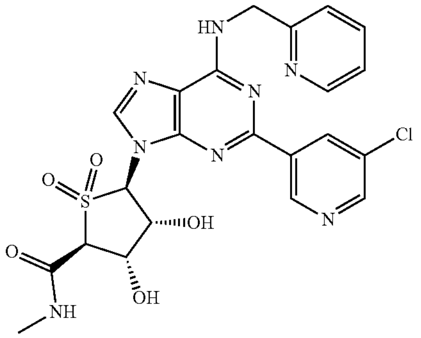 [SMILES: CNC(=O)[C@@H]1[C@@H](O)[C@@H](O)[C@H](n2cnc3c(NCc4ccccn4)nc(-c4cncc(Cl)c4)nc32)S1(=O)=O] | (2S,3S,4R,5R)-5-(2-(5-chloropyridin-3-yl)-6-((pyridin-2-ylmethyl)amino-9H-purin-9-yl)-3,4-dihydroxyl-N-methyl-tetrahydrothiophen-2-formamide 1,1-dioxide |
| 492 | 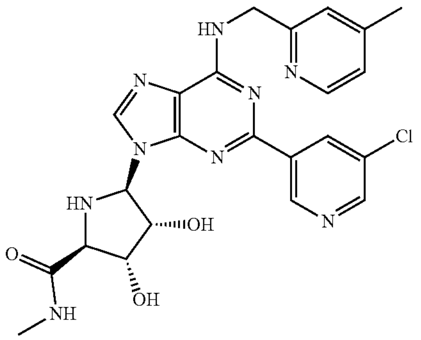 [SMILES: CNC(=O)[C@H]1N[C@@H](n2cnc3c(NCc4cc(C)ccn4)nc(-c4cncc(Cl)c4)nc32)[C@H](O)[C@@H]1O] | (2S,3R,4S,5S)-5-(2-(5-chloropyridin-3-yl)-6-(((4-methylpyridin-2-yl)methyl)-amino)-9H-purin-9-yl)-3,4-dihydroxyl-N-methylpyrrolidin-2-formamide |

-continued

| Compd. No. | Structural formula of compound | Name |
|---|---|---|
| 493 | 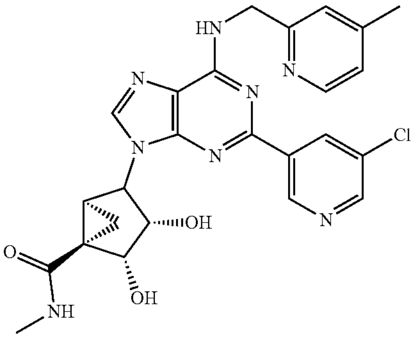 [SMILES: CNC(=O)[C@]12C[C@@H]1C(n1cnc3c(NCc4cc(C)ccn4)nc(-c4cncc(Cl)c4)nc31)[C@H](O)[C@@H]2O] | (1S,2R,3S,5S)-4-(2-(5-chloropyridin-3-yl)-6-(((4-methylpyridin-2-yl)methyl)-amino)-9H-purin-9-yl)-2,3-dihydroxyl-N-methylbicyclo[3.1.0]hexane-1-form-amide |
| 494 | 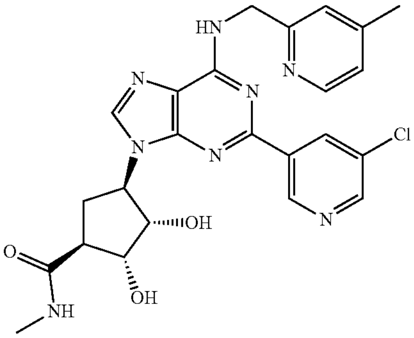 [SMILES: CNC(=O)[C@H]1C[C@@H](n2cnc3c(NCc4cc(C)ccn4)nc(-c4cncc(Cl)c4)nc32)[C@H](O)[C@@H]1O] | (1S,2R,3S,4R)-4-(2-(5-chloropyridin-3-yl)-6-(((4-methylpyridin-2-yl)methyl)-amino)-9H-purin-9-yl)-2,3-dihydroxyl-N-methylcyclopentaneformamide |
| 495 | 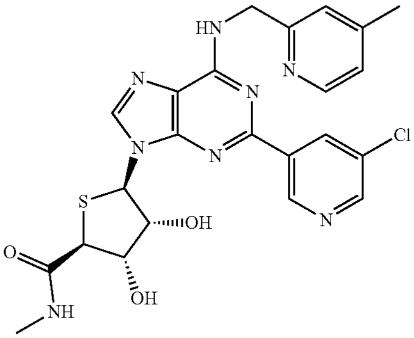 [SMILES: CNC(=O)[C@H]1S[C@@H](n2cnc3c(NCc4cc(C)ccn4)nc(-c4cncc(Cl)c4)nc32)[C@H](O)[C@@H]1O] | (2S,3S,4R,5R)-5-(2-(5-chloropyridin-3-yl)-6-(((4-methylpyridin-2-yl)methyl)-amino)-9H-purin-9-yl)-3,4-dihydroxyl-N-methyltetrahydrothiophen-2-form-amide |
| 496 | 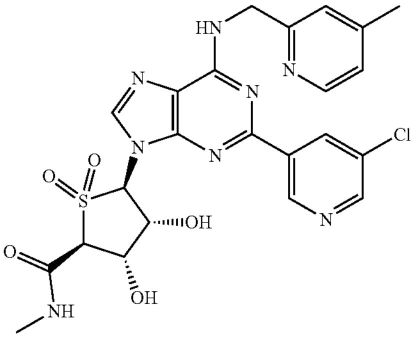 [SMILES: CNC(=O)[C@@H]1[C@@H](O)[C@@H](O)[C@H](n2cnc3c(NCc4cc(C)ccn4)nc(-c4cncc(Cl)c4)nc32)S1(=O)=O] | (2S,3S,4R,5R)-5-(2-(5-chloropyridin-3-yl)-6-(((4-methylpyridin-2-yl)methyl)-amino)-9H-purin-9-yl)-3,4-dihydroxyl-N-methyltetrahydrothiophen-2-form-amide 1,1-dioxide |

-continued

| Compd. No. | Structural formula of compound | Name |
|---|---|---|
| 497 | 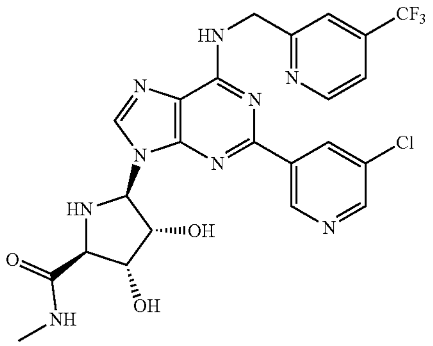 [SMILES: CNC(=O)[C@H]1N[C@@H](n2cnc3c(NCc4cc(C(F)(F)F)ccn4)nc(-c4cncc(Cl)c4)nc32)[C@H](O)[C@@H]1O] | (2S,3R,4S,5S)-5-(2-(5-chloropyridin-3-yl)-6-(((4-(trifluoromethyl)pyridin-2-yl)methyl)amino)-9H-purin-9-yl)-3,4-dihydroxyl-N-methylpyrrolidin-2-formamide |
| 498 | 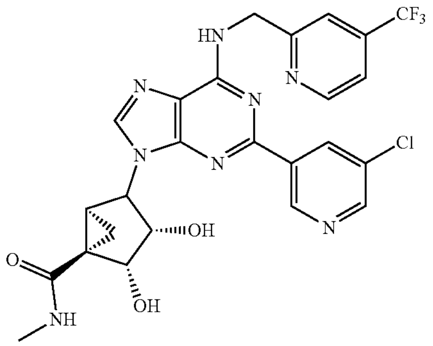 | (1S,2R,3S,5S)-4-(2-(5-chloropyridin-3-yl)-6-(((4-(trifluoromethyl)pyridin-2-yl)methyl)amino)-9H-purin-9-yl)-2,3-dihydroxyl-N-methylbicyclo[3.1.0]-hexane-1-formamide |
| 499 | 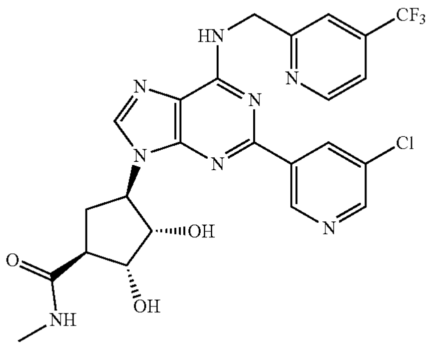 [SMILES: CNC(=O)[C@H]1C[C@@H](n2cnc3c(NCc4cc(C(F)(F)F)ccn4)nc(-c4cncc(Cl)c4)nc32)[C@H](O)[C@@H]1O] | (1S,2R,3S,4R)-4-(2-(5-chloropyridin-3-yl)-6-(((4-(trifluoromethyl)pyridin-2-yl)methyl)amino)-9H-purin-9-yl)-2,3-dihydroxyl-N-methylcyclopentane-formamide |
| 500 | 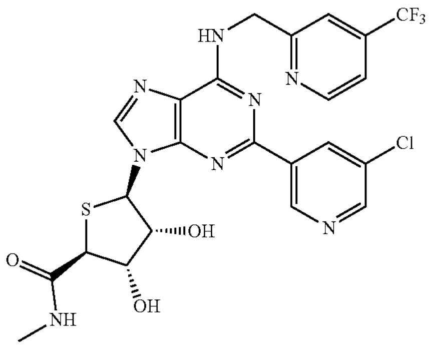 | (2S,3S,4R,5R)-5-(2-(5-chloropyridin-3-yl)-6-(((4-(trifluoromethyl)pyridin-2-yl)methyl)amino)-9H-purin-9-yl)-3,4-dihydroxyl-N-methyltetrahydrothiophen-2-formamide |

-continued

| Compd. No. | Structural formula of compound | Name |
|---|---|---|
| 501 | 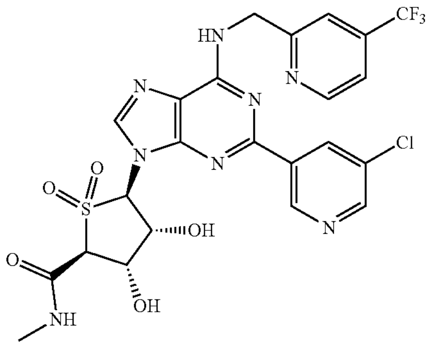 [SMILES: CNC(=O)[C@@H]1[C@@H](O)[C@@H](O)[C@H](n2cnc3c(NCc4cc(C(F)(F)F)ccn4)nc(-c4cncc(Cl)c4)nc32)S1(=O)=O] | (2S,3S,4R,5R)-5-(2-(5-chloropyridin-3-yl)-6-(((4-(trifluoromethyl)pyridin-2-yl)methyl)amino)-9H-purin-9-yl)-3,4-dihydroxyl-N-methyltetrahydrothiophen-2-formamide 1,1-dioxide |
| 502 | 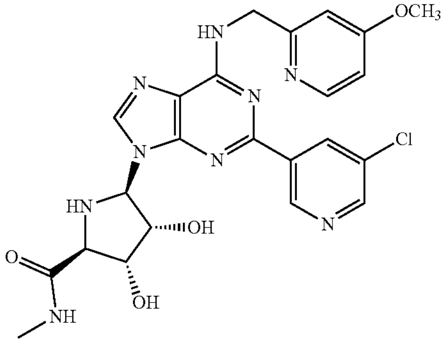 | (2S,3R,4S,5S)-5-(2-(5-chloropyridin-3-yl)-6-(((4-methoxypyridin-2-yl)methyl)-amino)-9H-purin-9-yl)-3,4-dihydroxyl-N-methylpyrrolidin-2-formamide |
| 503 | 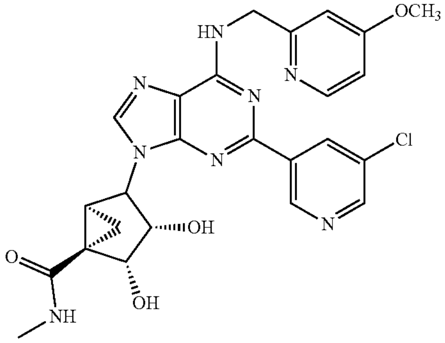 [SMILES: CNC(=O)[C@]12C[C@@H]1C(n1cnc3c(NCc4cc(OC)ccn4)nc(-c4cncc(Cl)c4)nc31)[C@H](O)[C@@H]2O] | (1S,2R,3S,5S)-4-(2-(5-chloropyridin-3-yl)-6-(((4-methoxypyridin-2-yl)methyl)amino)-9H-purin-9-yl)-2,3-dihydroxyl-N-methylbicyclo[3.1.0]hexane-1-formamide |
| 504 | 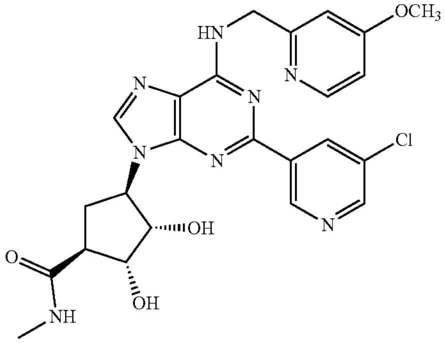 [SMILES: CNC(=O)[C@H]1C[C@@H](n2cnc3c(NCc4cc(OC)ccn4)nc(-c4cncc(Cl)c4)nc32)[C@H](O)[C@@H]1O] | (1S,2R,3S,4R)-4-(2-(5-chloropyridin-3-yl)-6-(((4-methoxypyridin-2-yl)methyl)amino)-9H-purin-9-yl)-2,3-dihydroxyl-N-methylcyclopentaneformamide |

-continued

| Compd. No. | Structural formula of compound | Name |
|---|---|---|
| 505 | 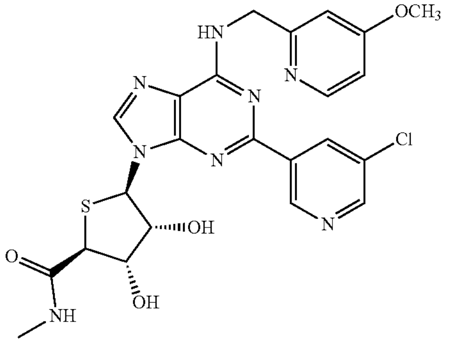 [SMILES: CNC(=O)[C@H]1S[C@@H](n2cnc3c(NCc4cc(OC)ccn4)nc(-c4cncc(Cl)c4)nc32)[C@H](O)[C@@H]1O] | (2S,3S,4R,5R)-5-(2-(5-chloropyridin-3-yl)-6-(((4-methoxypyridin-2-yl)methyl)amino)-9H-purin-9-yl)-3,4-dihydroxyl-N-methyltetrahydrothiophen-2-formamide |
| 506 | 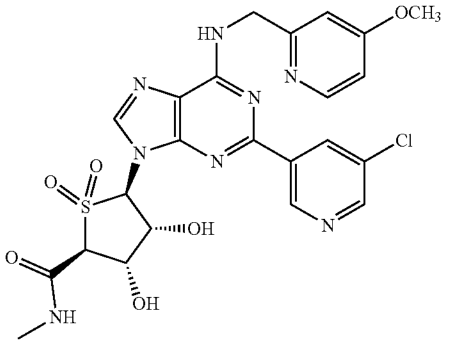 [SMILES: CNC(=O)[C@@H]1[C@@H](O)[C@@H](O)[C@H](n2cnc3c(NCc4cc(OC)ccn4)nc(-c4cncc(Cl)c4)nc32)S1(=O)=O] | (2S,3S,4R,5R)-5-(2-(5-chloropyridin-3-yl)-6-(((4-methoxypyridin-2-yl)methyl)amino)-9H-purin-9-yl)-3,4-dihydroxyl-N-methyltetrahydrothiophen-2-formamide 1,1-dioxide |
| 507 | 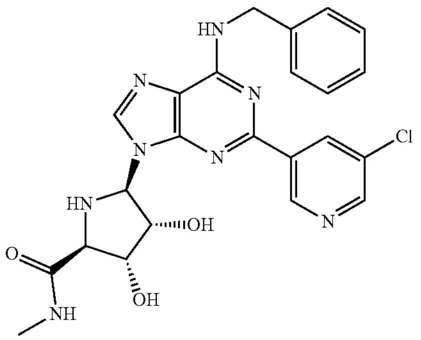 [SMILES: CNC(=O)[C@H]1N[C@@H](n2cnc3c(NCc4ccccc4)nc(-c4cncc(Cl)c4)nc32)[C@H](O)[C@@H]1O] | (2S,3R,4S,5S)-5-(6-(benzylamino)-2-(5-chloropyridin-3-yl)-9H-purin-9-yl)-3,4-dihydroxyl-N-methylpyrrolidin-2-formamide |
| 508 | 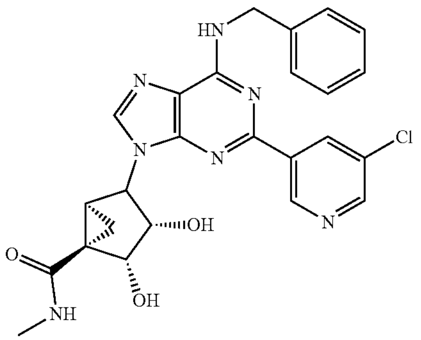 | (1S,2R,3S,5S)-4-(6-(benzylamino)-2-(5-chloropyridin-3-yl)-9H-purin-9-yl)-2,3-dihydroxyl-N-methylbicyclo-[3.1.0]hexane-1-formamide |

-continued

| Compd. No. | Structural formula of compound | Name |
|---|---|---|
| 509 | 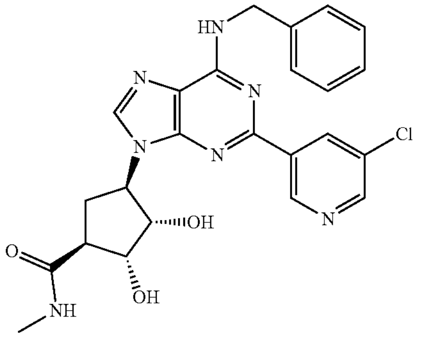 [SMILES: CNC(=O)[C@H]1C[C@@H](n2cnc3c(NCc4ccccc4)nc(-c4cncc(Cl)c4)nc32)[C@H](O)[C@@H]1O] | (1S,2R,3S,4R)-4-(6-(benzylamino)-2-(5-chloropyridin-3-yl)-9H-purin-9-yl)-2,3-dihydroxyl-N-methylcyclopentane-formamide |
| 510 | 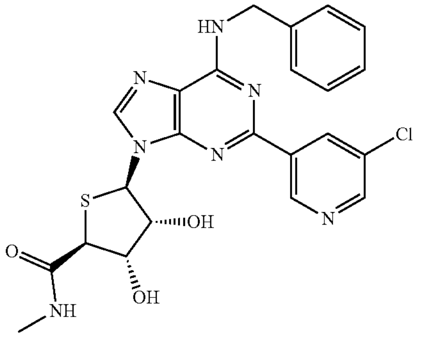 | (2S,3S,4R,5R)-5-(6-(benzylamino)-2-(5-chloropyridin-3-yl)-9H-purin-9-yl)-3,4-dihydroxyl-N-methyltetrahydro-thiophen-2-formamide |
| 511 | 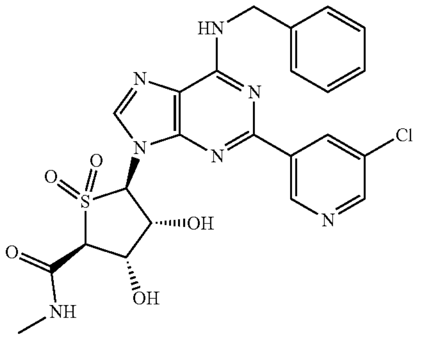 [SMILES: CNC(=O)[C@@H]1[C@@H](O)[C@@H](O)[C@H](n2cnc3c(NCc4ccccc4)nc(-c4cncc(Cl)c4)nc32)S1(=O)=O] | (2S,3S,4R,5R)-5-(6-(benzylamino)-2-(5-chloropyridin-3-yl)-9H-purin-9-yl)-3,4-dihydroxyl-N-methyltetrahydro-thiophen-2-formamide 1,1-dioxide |
| 512 | 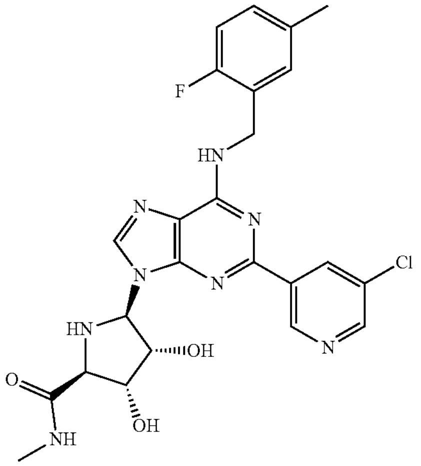 [SMILES: CNC(=O)[C@H]1N[C@@H](n2cnc3c(NCc4cc(C)ccc4F)nc(-c4cncc(Cl)c4)nc32)[C@H](O)[C@@H]1O] | (2S,3R,4S,5S)-5-(2-(5-chloropyridin-3-yl)-6-((2-fluoro-5-methylbenzyl)amino-9H-purin-9-yl)-3,4-dihydroxyl-N-methylpyrrolidin-2-formamide |

-continued

| Compd. No. | Structural formula of compound | Name |
|---|---|---|
| 513 | 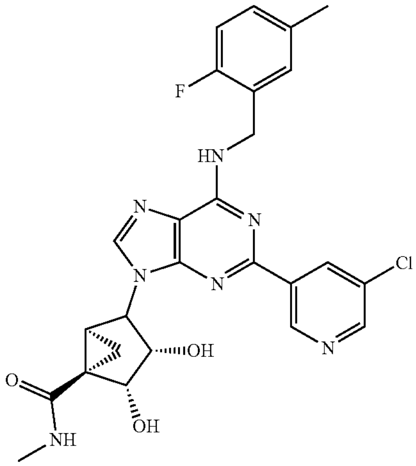 [SMILES: CNC(=O)[C@]12C[C@@H]1C(n1cnc3c(NCc4cc(C)ccc4F)nc(-c4cncc(Cl)c4)nc31)[C@H](O)[C@@H]2O] | (1S,2R,3S,5S)-4-(2-(5-chloropyridin-3-yl)-6-((2-fluoro-5-methylbenzyl)amino)-9H-purin-9-yl)-2,3-dihydroxyl-N-methylbicyclo[3.1.0]hexane-1-formamide |
| 514 | 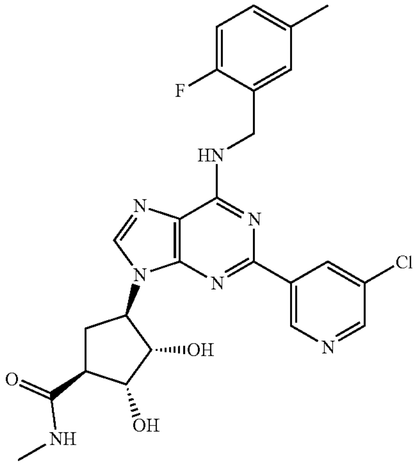 [SMILES: CNC(=O)[C@H]1C[C@@H](n2cnc3c(NCc4cc(C)ccc4F)nc(-c4cncc(Cl)c4)nc32)[C@H](O)[C@@H]1O] | (1S,2R,3S,4R)-4-(2-(5-chloropyridin-3-yl)-6-((2-fluoro-5-methylbenzyl)amino)-9H-purin-9-yl)-2,3-dihydroxyl-N-methylcyclopentaneformamide |
| 515 | 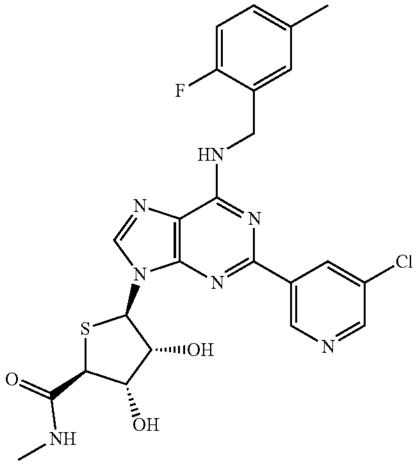 [SMILES: CNC(=O)[C@H]1S[C@@H](n2cnc3c(NCc4cc(C)ccc4F)nc(-c4cncc(Cl)c4)nc32)[C@H](O)[C@@H]1O] | (2S,3S,4R,5R)-5-(2-(5-chloropyridin-3-yl)-6-((2-fluoro-5-methylbenzyl)amino-9H-purin-9-yl)-3,4-dihydroxyl-N-methyltetrahydrothiophen-2-formamide |

-continued

| Compd. No. | Structural formula of compound | Name |
| --- | --- | --- |
| 516 | 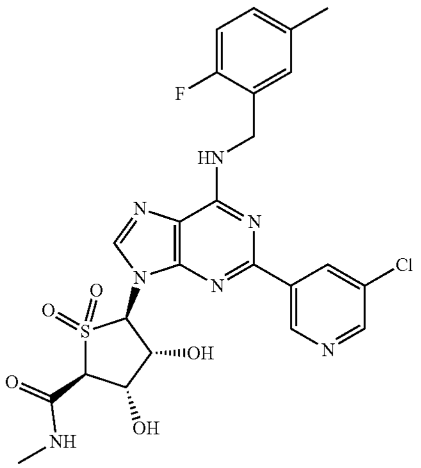 [SMILES: CNC(=O)[C@@H]1[C@@H](O)[C@@H](O)[C@H](n2cnc3c(NCc4cc(C)ccc4F)nc(-c4cncc(Cl)c4)nc32)S1(=O)=O] | (2S,3S,4R,5R)-5-(2-(5-chloropyridin-3-yl)-6-((2-fluoro-5-methylbenzyl)amino)-9H-purin-9-yl)-3,4-dihydroxyl-N-methyltetrahydrothiophen-2-formamide 1,1-dioxide |
| 517 | 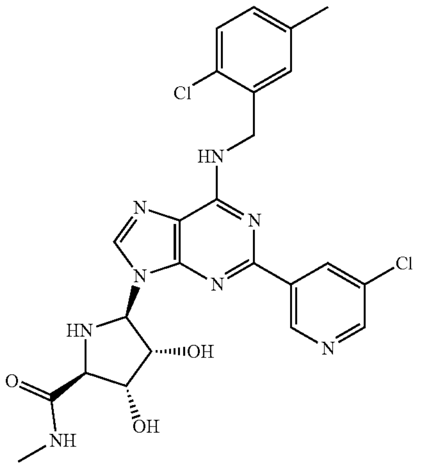 [SMILES: CNC(=O)[C@H]1N[C@@H](n2cnc3c(NCc4cc(C)ccc4Cl)nc(-c4cncc(Cl)c4)nc32)[C@H](O)[C@@H]1O] | (2S,3R,4S,5S)-5-(6-((2-chloro-5-methylbenzyl)amino)-2-(5-chloropyridin-3-yl)-9H-purin-9-yl)-3,4-dihydroxyl-N-methylpyrrolidin-2-formamide |
| 518 | 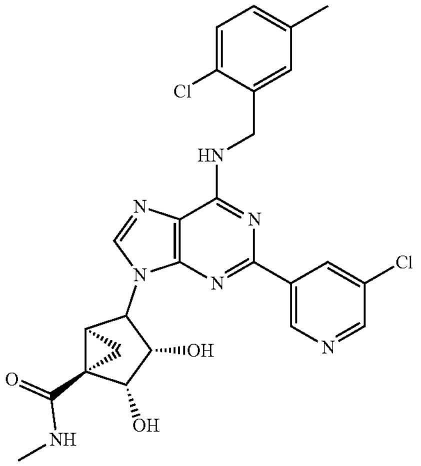 [SMILES: CNC(=O)[C@]12C[C@@H]1C(n1cnc3c(NCc4cc(C)ccc4Cl)nc(-c4cncc(Cl)c4)nc31)[C@H](O)[C@@H]2O] | (1S,2R,3S,5S)-4-(6-((2-chloro-5-methylbenzyl)amino)-2-(5-chloropyridin-3-yl)-9H-purin-9-yl)-2,3-dihydroxyl-N-methylbicyclo[3.1.0]hexane-1-formamide |

-continued

| Compd. No. | Structural formula of compound | Name |
|---|---|---|
| 519 | 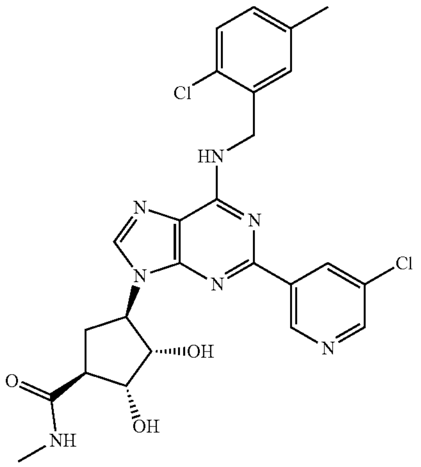 [SMILES: CNC(=O)[C@H]1C[C@@H](n2cnc3c(NCc4cc(C)ccc4Cl)nc(-c4cncc(Cl)c4)nc32)[C@H](O)[C@@H]1O] | (1S,2R,3S,4R)-4-(6-((2-chloro-methyl-benzyl)amino)-2-(5-chloropyridin-3-yl)-9H-purin-9-yl)-2,3-dihydroxyl-N-methylcyclopentaneformamide |
| 520 | 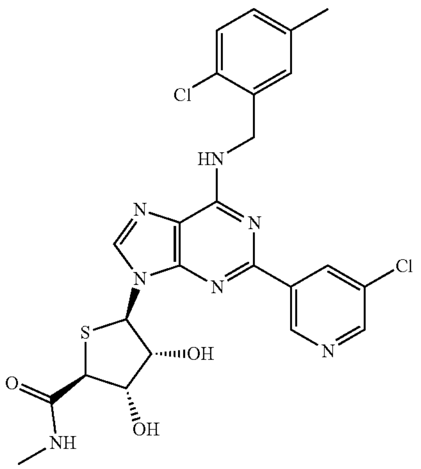 [SMILES: CNC(=O)[C@H]1S[C@@H](n2cnc3c(NCc4cc(C)ccc4Cl)nc(-c4cncc(Cl)c4)nc32)[C@H](O)[C@@H]1O] | (2S,3S,4R,5R)-5-(6-((2-chloro-5-methylbenzyl)amino)-2-(5-chloropyridin-3-yl)-9H-purin-9-yl)-3,4-dihydroxyl-N-methyltetrahydrothiophen-2-formamide |
| 521 | 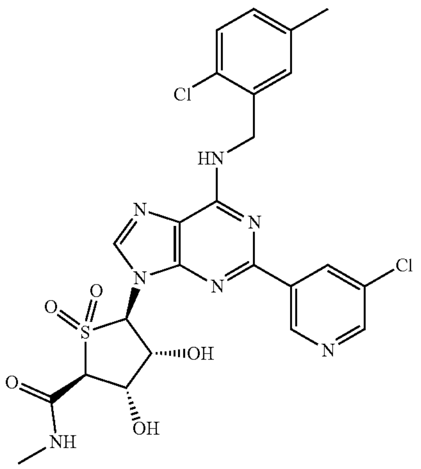 [SMILES: CNC(=O)[C@@H]1[C@@H](O)[C@@H](O)[C@H](n2cnc3c(NCc4cc(C)ccc4Cl)nc(-c4cncc(Cl)c4)nc32)S1(=O)=O] | (2S,3S,4R,5R)-5-(6-((2-chloro-5-methylbenzyl)amino)-2-(5-chloropyridin-3-yl)-9H-purin-9-yl)-3,4-dihydroxyl-N-methyltetrahydrothiophen-2-methoxylated-1,1-dioxide |

-continued

| Compd. No. | Structural formula of compound | Name |
|---|---|---|
| 522 | 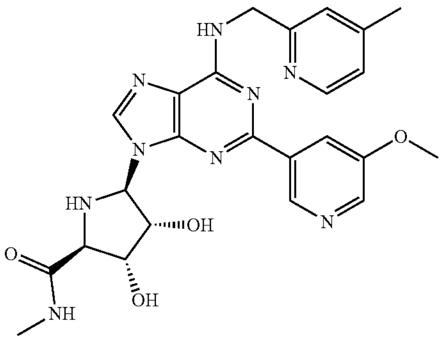 | (2S,3R,4S,4S)-3,4-dihydroxyl-5-(2-(5-methoxypyridin-3-yl)-6-(((4-methyl-pyridin-2-yl)methyl)amino)-9H-purin-9-yl)-N-methylpyrrolidin-2-formamide |
| 523 | 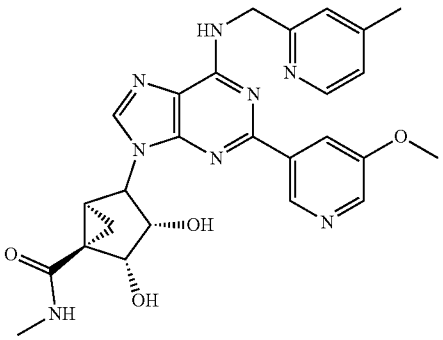 | (1S,2R,3S,5S)-2,3-dihydroxyl-4-(2-(5-methoxypyridin-3-yl)-6-(((4-methyl-pyridin-2-yl)methyl)amino)-9H-purin-9-yl)-N-methylbicyclo[3.1.0]hexane-1-formamide |
| 524 | 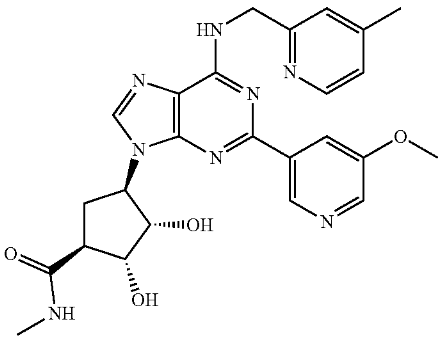 | (1S,2R,3S,4R)-2,3-dihydroxyl-4-(2-(5-methoxypyridin-3-yl)-6-(((4-methyl-pyridin-2-yl)methyl)amino)-9H-purin-9-yl)-N-methylcyclopentaneformamide |
| 525 | 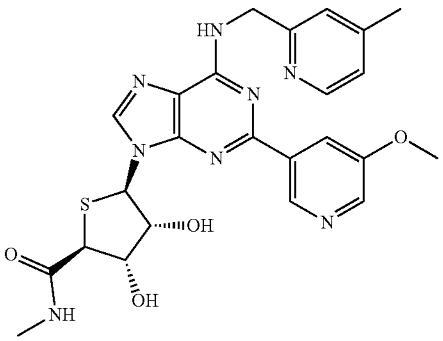 [SMILES: CNC(=O)[C@H]1S[C@@H](n2cnc3c(NCc4cc(C)ccn4)nc(-c4cncc(OC)c4)nc32)[C@H](O)[C@@H]1O] | (2S,3S,4R,5R)-3,4-dihydroxyl-5-(2-(5-methoxypyridin-3-yl)-6-(((4-methyl-pyridin-2-yl)methyl)amino)-9H-purin-9-yl)-N-methyltetrahydrothiophen-2-formamide |

-continued

| Compd. No. | Structural formula of compound | Name |
|---|---|---|
| 526 | 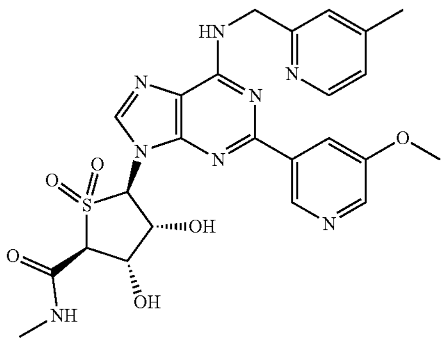 [SMILES: CNC(=O)[C@@H]1[C@@H](O)[C@@H](O)[C@H](n2cnc3c(NCc4cc(C)ccn4)nc(-c4cncc(OC)c4)nc32)S1(=O)=O] | (2S,3S,4R,5R)-3,4-dihydroxyl-5-(2-(5-methoxypyridin-3-yl)-6-(((4-methyl-pyridin-2-yl)methyl)amino)-9H-purin-9-yl)-N-methyltetrahydrothiophen-2-formamide 1,1-dioxide |
| 527 | 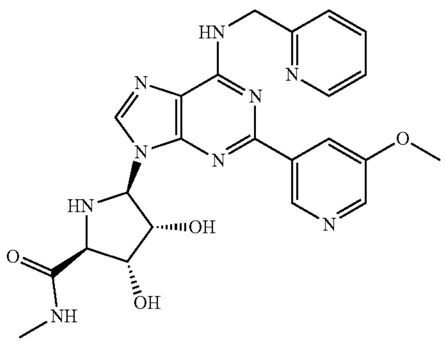 [SMILES: CNC(=O)[C@H]1N[C@@H](n2cnc3c(NCc4ccccn4)nc(-c4cncc(OC)c4)nc32)[C@H](O)[C@@H]1O] | (2S,3R,4S,5S)-3,4-dihydroxyl-5-(2-(5-methoxypyridin-3-yl)-6-((pyridin-2-ylmethyl)amino)-9H-purin-9-yl)-N-methylpyrrolidin-2-formamide |
| 528 | 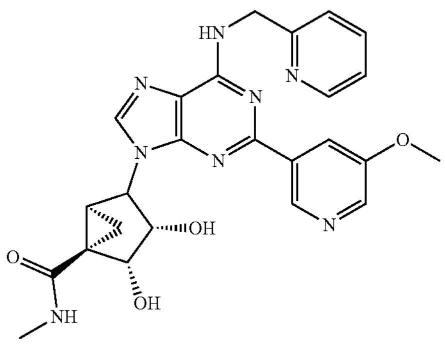 | (1S,2R,3S,5S)-2,3-dihydroxyl-4-(2-(5-methoxypyridin-3-yl)-6-((pyridin-2-ylmethyl)amino)-9H-purin-9-yl)-N-methylbicyclo[3.1.0]hexane-1-formamide |
| 529 | 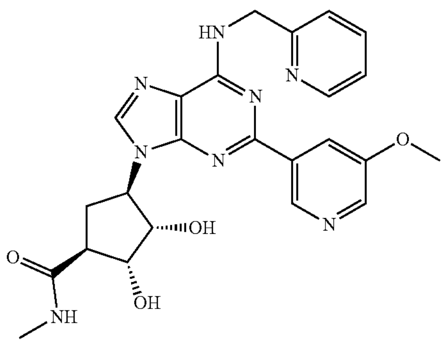 | (1S,2R,3S,4R)-2,3-dihydroxyl-4-(2-(5-methoxypyridin-3-yl)-6-((pyridin-2-ylmethyl)amino)-9H-purin-9-yl)-N-methylcyclopentaneformamide |

-continued

| Compd. No. | Structural formula of compound | Name |
|---|---|---|
| 530 | 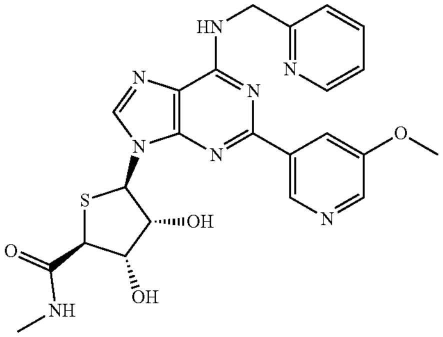 | (2S,3S,4R,5R)-3,4-dihydroxyl-5-(2-(5-methoxypyridin-3-yl)-6-((pyridin-2-ylmethyl)amino)-9H-purin-9-yl)-N-methyltetrahydrothiophen-2-formamide |
| 531 | 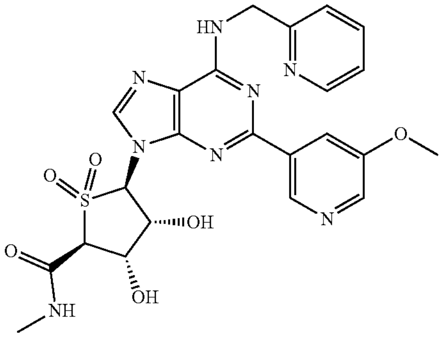 [SMILES: CNC(=O)[C@@H]1[C@@H](O)[C@@H](O)[C@H](n2cnc3c(NCc4ccccn4)nc(-c4cncc(OC)c4)nc32)S1(=O)=O] | (2S,3S,4R,5R)-3,4-dihydroxyl-5-(2-(5-methoxypyridin-3-yl)-6-((pyridin-2-ylmethyl)amino)-9H-purin-9-yl)-N-methyltetrahydrothiophen-2-formamide 1,1-dioxide |
| 532 | 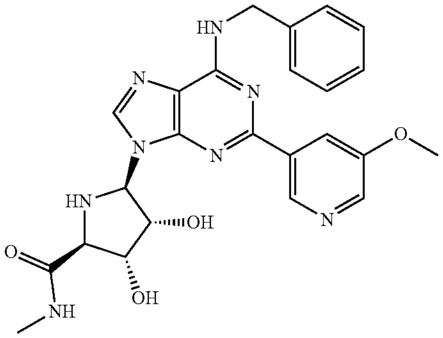 [SMILES: CNC(=O)[C@H]1N[C@@H](n2cnc3c(NCc4ccccc4)nc(-c4cncc(OC)c4)nc32)[C@H](O)[C@@H]1O] | (2S,3R,4S,5S)-5-(6-((2-benzylamino)-2-(5-methoxypyridin-3-yl)-9H-purin-9-yl)-3,4-dihydroxyl-N-methylpyrrolidin-2-formamide |
| 533 | 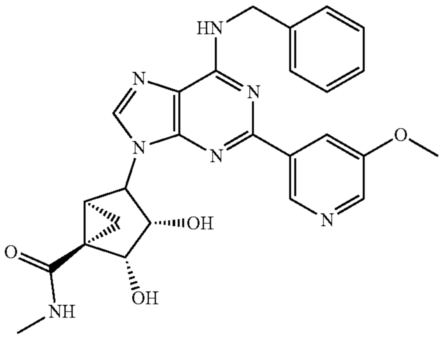 [SMILES: CNC(=O)[C@]12C[C@@H]1C(n1cnc3c(NCc4ccccc4)nc(-c4cncc(OC)c4)nc31)[C@H](O)[C@@H]2O] | (1S,2R,3S,5S)-4-(6-(benzylamino)-2-(5-methoxypyridin-3-yl)-9H-purin-9-yl)-2,3-dihydroxyl-N-methylbicyclo-[3.1.0]hexane-1-formamide |

-continued

| Compd. No. | Structural formula of compound | Name |
|---|---|---|
| 534 | 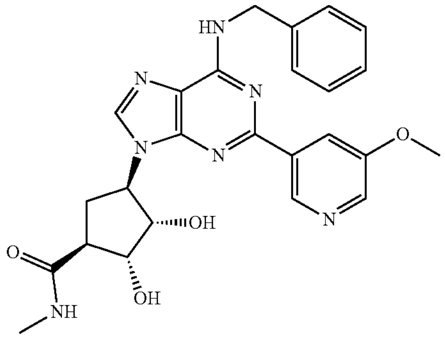 [SMILES: CNC(=O)[C@H]1C[C@@H](n2cnc3c(NCc4ccccc4)nc(-c4cncc(OC)c4)nc32)[C@H](O)[C@@H]1O] | (1S,2R,3S,4R)-4-(6-(benzylamino)-2-(5-methoxypyridin-3-yl)-9H-purin-9-yl)-2,3-dihydroxyl-N-methylcyclopentaneformamide |
| 535 | 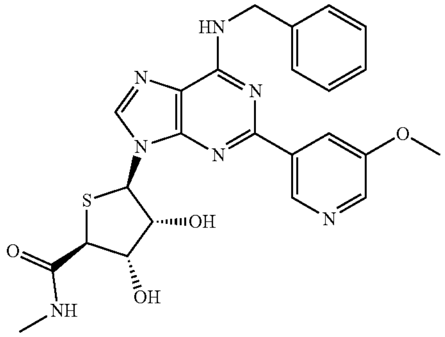 | (2S,3S,4R,5R)-5-(6-(benzylamino)-2-(5-methoxypyridin-3-yl)-9H-purin-9-yl)-3,4-dihydroxyl-N-methyltetrahydrothiophen-2-formamide |
| 536 | 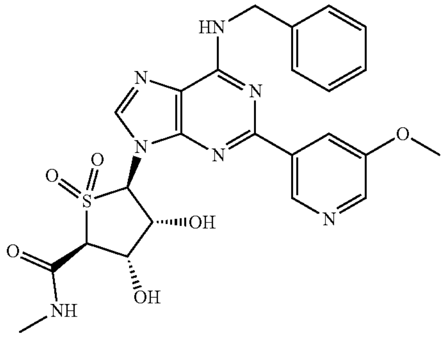 | (2S,3S,4R,5R)-5-(6-(benzylamino)-2-(5-methoxypyridin-3-yl)-9H-purin-9-yl)-3,4-dihydroxyl-N-methyltetrahydrothiophen-2-formamide 1,1-dioxide |
| 537 | 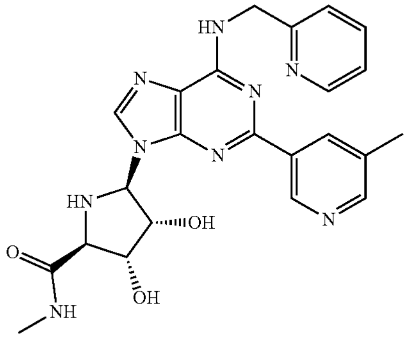 [SMILES: CNC(=O)[C@H]1N[C@@H](n2cnc3c(NCc4ccccn4)nc(-c4cncc(C)c4)nc32)[C@H](O)[C@@H]1O] | (2S,3R,4S,5S)-3,4-dihydroxyl-N-methyl-5-(2-(5-methoxypyridin-3-yl)-6-((pyridin-2-ylmethyl)amino)-9H-purin-9-yl)pyrrolidin-2-formamide |

-continued

| Compd. No. | Structural formula of compound | Name |
|---|---|---|
| 538 | 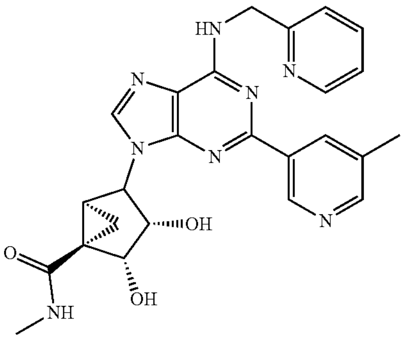 [SMILES: CNC(=O)[C@]12C[C@@H]1C(n1cnc3c(NCc4ccccn4)nc(-c4cncc(C)c4)nc31)[C@H](O)[C@@H]2O] | (1S,2R,3S,5S)-2,3-dihydroxyl-N-methyl-4-(2-(5-methoxypyridin-3-yl)-6-((pyridin-2-ylmethyl)amino)-9H-purin-9-yl)bicyclo[3.1.0]hexane-1-formamide |
| 539 | 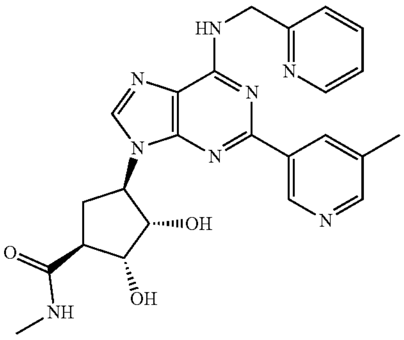 | (1S,2R,3S,4R)-2,3-dihydroxyl-N-methyl-4-(2-(5-methoxypyridin-3-yl)-6-((pyridin-2-ylmethyl)amino)-9H-purin-9-yl)cyclopentaneformamide |
| 540 | 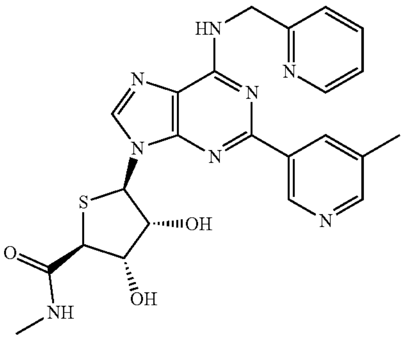 [SMILES: CNC(=O)[C@H]1S[C@@H](n2cnc3c(NCc4ccccn4)nc(-c4cncc(C)c4)nc32)[C@H](O)[C@@H]1O] | (2S,3S,4R,5R)-3,4-dihydroxyl-N-methyl-5-(2-(5-methoxypyridin-3-yl)-6-((pyridin-2-ylmethyl)amino)-9H-purin-9-yl)tetrahydrothiophen-2-formamide |
| 541 | 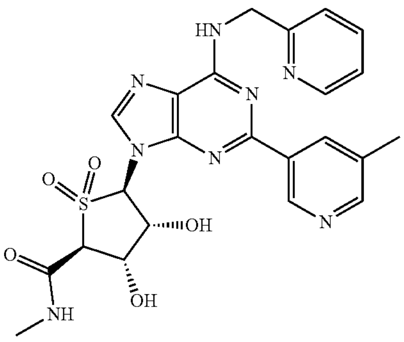 [SMILES: CNC(=O)[C@@H]1[C@@H](O)[C@@H](O)[C@H](n2cnc3c(NCc4ccccn4)nc(-c4cncc(C)c4)nc32)S1(=O)=O] | (2S,3S,4R,5R)-3,4-dihydroxyl-N-methyl-5-(2-(5-methoxypyridin-3-yl)-6-((pyridin-2-ylmethyl)amino)-9H-purin-9-yl)tetrahydrothiophen-2-formamide 1,1-dioxide |

-continued

| Compd. No. | Structural formula of compound | Name |
|---|---|---|
| 542 | 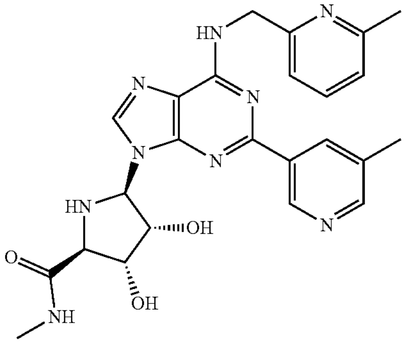 [SMILES: CNC(=O)[C@H]1N[C@@H](n2cnc3c(NCc4cccc(C)n4)nc(-c4cncc(C)c4)nc32)[C@H](O)[C@@H]1O] | (2S,3R,4S,5S)-3,4-dihydroxyl-N-methyl-5-(6-(((6-methylpyridin-2-yl)methyl)amino)-2-(5-methylpyridin-3-yl)-9H-purin-9-yl)pyrrolidin-2-formamide |
| 543 | 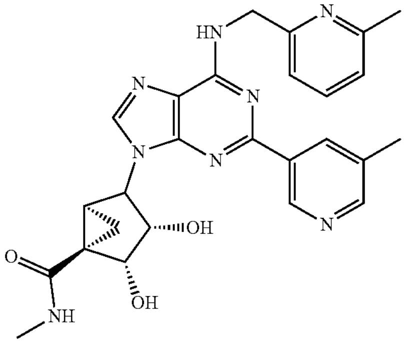 [SMILES: CNC(=O)[C@]12C[C@@H]1C(n1cnc3c(NCc4cccc(C)n4)nc(-c4cncc(C)c4)nc31)[C@H](O)[C@@H]2O] | (1S,2R,3S,5S)-2,3-dihydroxyl-N-methyl-4-(6-(((6-methylpyridin-2-yl)methyl)amino)-2-(5-methylpyridin-3-yl)-9H-purin-9-yl)bicyclo[3.1.0]hexane-1-formamide |
| 544 | 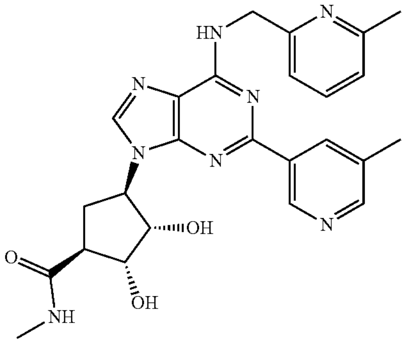 [SMILES: CNC(=O)[C@H]1S[C@@H](n2cnc3c(NCc4cccc(C)n4)nc(-c4cncc(C)c4)nc32)[C@H](O)[C@@H]1O] | (1S,2R,3S,4R)-2,3-dihydroxyl-N-methyl-4-(6-(((6-methylpyridin-2-yl)methyl)amino)-2-(5-methylpyridin-3-yl)-9H-purin-9-yl)cyclopentaneformamide |
| 545 | 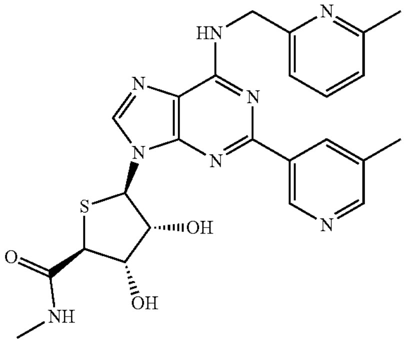 | (2S,3S,4R,5R)-3,4-dihydroxyl-N-methyl-5-(6-(((6-methylpyridin-2-yl)methyl)amino)-2-(5-methylpyridin-3-yl)-9H-purin-9-yl)tetrahydrothiophen-2-formamide |

-continued

| Compd. No. | Structural formula of compound | Name |
|---|---|---|
| 546 | 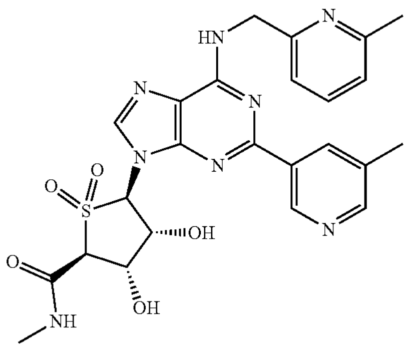 [SMILES: CNC(=O)[C@@H]1[C@@H](O)[C@@H](O)[C@H](n2cnc3c(NCc4cccc(C)n4)nc(-c4cncc(C)c4)nc32)S1(=O)=O] | (2S,3S,4R,5R)-3,4-dihydroxyl-N-methyl-5-(6-(((6-methylpyridin-2-yl)methyl)amino)-2-(5-methylpyridin-3-yl)-9H-purin-9-yl)tetrahydrothiophen-2-formamide 1,1-dioxide |
| 547 | 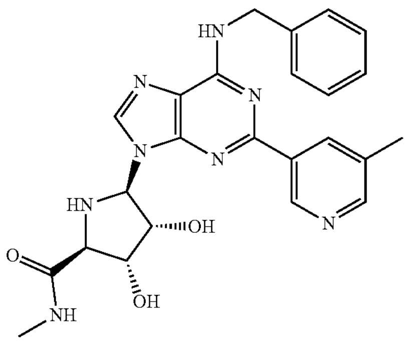 | (2S,3R,4S,5S)-5-(6-(benzylamino)-2-(5-methylpyridin-3-yl)-9H-purin-9-yl)-3,4-dihydroxyl-N-methylpyrrolidin-2-formamide |
| 548 | 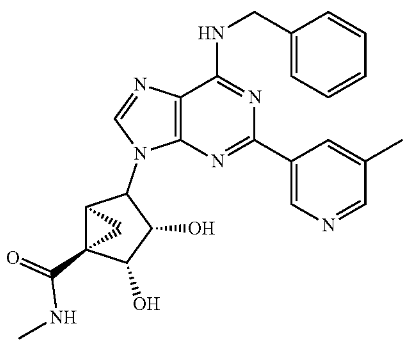 [SMILES: CNC(=O)[C@]12C[C@@H]1C(n1cnc3c(NCc4ccccc4)nc(-c4cncc(C)c4)nc31)[C@H](O)[C@@H]2O] | (1S,2R,3S,5S)-4-(6-(benzylamino)-2-(5-methylpyridin-3-yl)-9H-purin-9-yl)-2,3-dihydroxyl-N-methylbicyclo[3.1.0]-hexane-1-formamide |
| 549 | 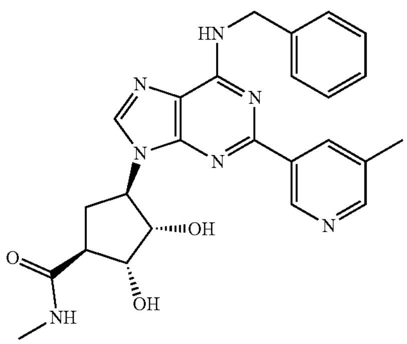 [SMILES: CNC(=O)[C@H]1C[C@@H](n2cnc3c(NCc4ccccc4)nc(-c4cncc(C)c4)nc32)[C@H](O)[C@@H]1O] | (1S,2R,3S,4R)-4-(6-(benzylamino)-2-(5-methylpyridin-3-yl)-9H-purin-9-yl)-2,3-dihydroxyl-N-methylcyclopentane-formamide |

-continued

| Compd. No. | Structural formula of compound | Name |
|---|---|---|
| 550 | 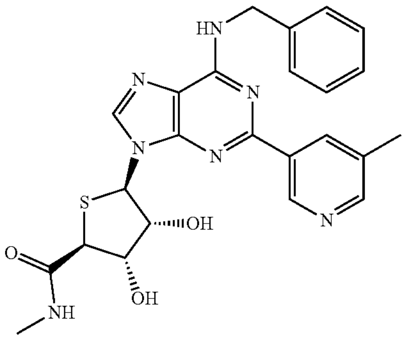 | (2S,3S,4R,5R)-5-(6-(benzylamino)-2-(5-methylpyridin-3-yl)-9H-purin-9-yl)-3,4-dihydroxyl-N-methyltetrahydro-thiophen-2-formamide |
| 551 | 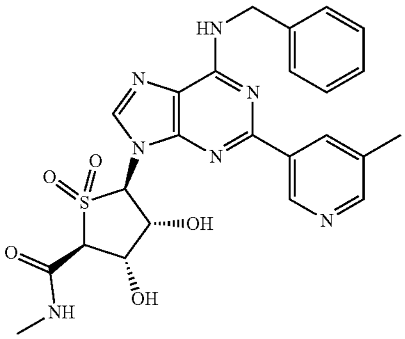 [SMILES: CNC(=O)[C@@H]1[C@@H](O)[C@@H](O)[C@H](n2cnc3c(NCc4ccccc4)nc(-c4cncc(C)c4)nc32)S1(=O)=O] | (2S,3S,4R,5R)-5-(6-(benzylamino)-2-(5-methylpyridin-3-yl)-9H-purin-9-yl)-3,4-dihydroxyl-N-methyltetrahydro-thiophen-2-formamide |
| 552 | 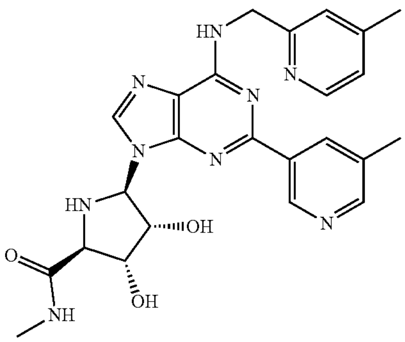 [SMILES: CNC(=O)[C@H]1N[C@@H](n2cnc3c(NCc4cc(C)ccn4)nc(-c4cncc(C)c4)nc32)[C@H](O)[C@@H]1O] | (2S,3R,4S,5S)-3,4-dihydroxyl-N-methyl-5-(6-(((4-methylpyridin-2-yl)methyl)amino)-2-(5-methylpyridin-3-yl)-9H-purin-9-yl)pyrrolidin-2-formamide |
| 553 | 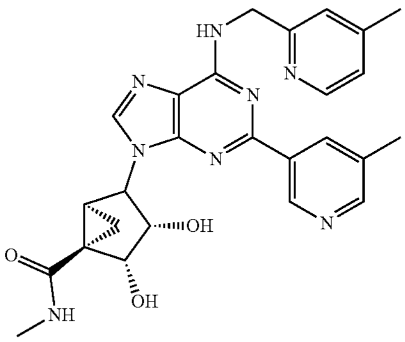 [SMILES: CNC(=O)[C@]12C[C@@H]1C(n1cnc3c(NCc4cc(C)ccn4)nc(-c4cncc(C)c4)nc31)[C@H](O)[C@@H]2O] | (1S,2R,3S,5S)-2,3-dihydroxyl-N-methyl-4-(6-(((4-methylpyridin-2-yl)methyl)amino)-2-(5-methylpyridin-3-yl)-9H-purin-9-yl)bicyclo[3.1.0]hexane-1-formamide |

-continued

| Compd. No. | Structural formula of compound | Name |
|---|---|---|
| 554 | 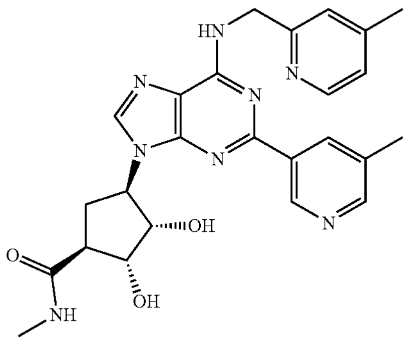 [SMILES: CNC(=O)[C@H]1C[C@@H](n2cnc3c(NCc4cc(C)ccn4)nc(-c4cncc(C)c4)nc32)[C@H](O)[C@@H]1O] | (1S,2R,3S,4R)-2,3-dihydroxyl-N-methyl-4-(6-(((4-methylpyridin-2-yl)methyl)amino)-2-(5-methylpyridin-3-yl)-9H-purin-9-yl)cyclopentaneformamide |
| 555 | 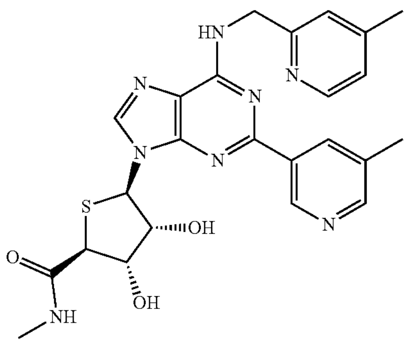 [SMILES: CNC(=O)[C@H]1S[C@@H](n2cnc3c(NCc4cc(C)ccn4)nc(-c4cncc(C)c4)nc32)[C@H](O)[C@@H]1O] | (2S,3S,4R,5R)-3,4-dihydroxyl-N-methyl-5-(6-(((4-methylpyridin-2-yl)methyl)amino)-2-(5-methylpyridin-3-yl)-9H-purin-9-yl)tetrahydrothiophen-2-formamide |
| 556 | 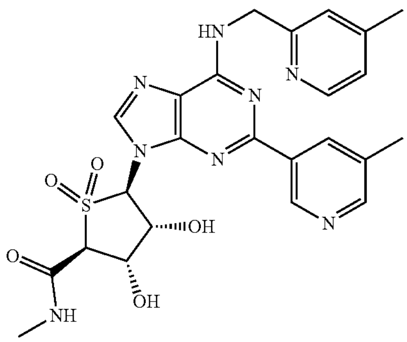 [SMILES: CNC(=O)[C@@H]1[C@@H](O)[C@@H](O)[C@H](n2cnc3c(NCc4cc(C)ccn4)nc(-c4cncc(C)c4)nc32)S1(=O)=O] | (2S,3S,4R,5R)-3,4-dihydroxyl-N-methyl-5-(6-(((4-methylpyridin-2-yl)methyl)amino)-2-(5-methylpyridin-3-yl)-9H-purin-9-yl)tetrahydrothiophen-2-formamide 1,1-dioxide |
| 557 | 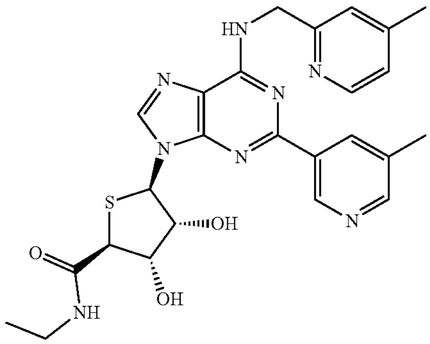 [SMILES: CCNC(=O)[C@H]1S[C@@H](n2cnc3c(NCc4cc(C)ccn4)nc(-c4cncc(C)c4)nc32)[C@H](O)[C@@H]1O] | (2S,3S,4R,5R)-N-ethyl-3,4-dihydroxyl-5-(6-(((4-methylpyridin-2-yl)methyl)amino)-2-(5-methylpyridin-3-yl)-9H-purin-9-yl)tetrahydrothiophen-2-formamide |

-continued

| Compd. No. | Structural formula of compound | Name |
| --- | --- | --- |
| 558 | 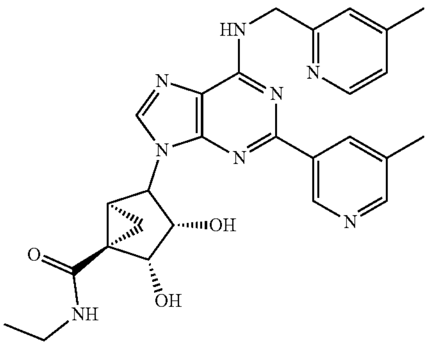 [SMILES: CCNC(=O)[C@]12C[C@@H]1C(n1cnc3c(NCc4cc(C)ccn4)nc(-c4cncc(C)c4)nc31)[C@H](O)[C@@H]2O] | (1S,2R,3S,5S)-N-ethyl-2,3-dihydroxyl-4-(6-(((4methylpyridin-2-yl)methyl)-amino)-2-(5-methylpyridin-3-yl)-9H-purin-9-yl)bicyclo[3.1.0]hexane-1-formamide |
| 559 | 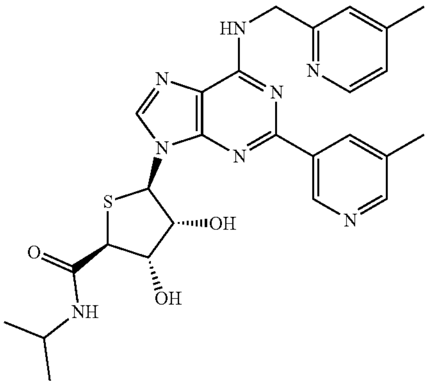 [SMILES: Cc1cncc(-c2nc(NCc3cc(C)ccn3)c3ncn([C@@H]4S[C@H](C(=O)NC(C)C)[C@@H](O)[C@H]4O)c3n2)c1] | (2S,3S,4R,5R)-3,4-dihydroxyl-N-iso-propyl-5-(6-(((4-methylpyridin-2-yl)-methyl)amino)-2-(5-methylpyridin-3-yl)-9H-purin-9-yl)tetrahydrothiophen-2-formamide |
| 560 | 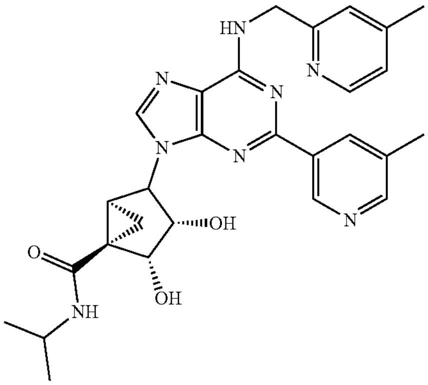 [SMILES: Cc1cncc(-c2nc(NCc3cc(C)ccn3)c3ncn(C4[C@H]5C[C@]5(C(=O)NC(C)C)[C@@H](O)[C@H]4O)c3n2)c1] | (1S,2R,3S,5S)-2,3-dihydroxyl-N-iso-propyl-4-(6-(((4-methylpyridin-2-yl)-methyl)amino)-2-(5-methylpyridin-3-yl)-9H-purin-9-yl)bicyclo[3.1.0]hexane-1-formamide |
| 561 | 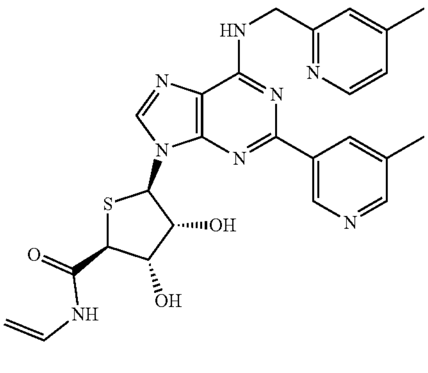 [SMILES: C=CNC(=O)[C@H]1S[C@@H](n2cnc3c(NCc4cc(C)ccn4)nc(-c4cncc(C)c4)nc32)[C@H](O)[C@@H]1O] | (2S,3S,4R,5R)-3,4-dihydroxyl-5-(6-(((4-methylpyridin-2-yl)methyl)amino)-2-(5-methylpyridin-3-yl)-9H-purin-9-yl)-N-vinyltetrahydrothiophen-2-formamide |

-continued

| Compd. No. | Structural formula of compound | Name |
| --- | --- | --- |
| 562 | 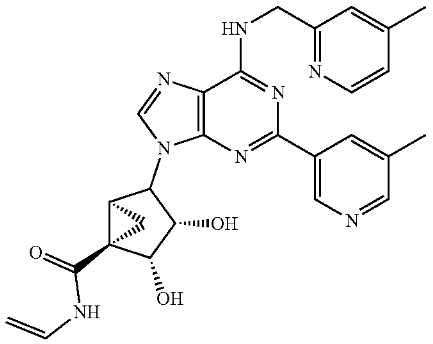 [SMILES: C=CNC(=O)[C@]12C[C@@H]1C(n1cnc3c(NCc4cc(C)ccn4)nc(-c4cncc(C)c4)nc31)[C@H](O)[C@@H]2O] | (1S,2R,3S,5S)-2,3-dihydroxyl-4-(6-(((4-methylpyridin-2-yl)methyl)amino)-2-(5-methylpyridin-3-yl)-9H-purin-9-yl)-N-vinylbicyclo[3.1.0]hexane-1-formamide |

In another aspect, the present application provides a solvate, a hydrate, a stereoisomer, a tautomer, an isotopic compound, a metabolite, or a prodrug of the compound of the present application or a pharmaceutically acceptable salt thereof.

In another aspect, the present application provides a pharmaceutical composition, comprises said compound of the present application, the pharmaceutically acceptable salt thereof, the solvate thereof, the hydrate thereof, the stereoisomer thereof, the tautomer thereof, the isotopic compound thereof, the metabolite thereof, or the prodrug thereof, and optionally a pharmaceutically acceptable carrier.

In another aspect, the present application provides the compound of the present application or the pharmaceutically acceptable salt thereof, and the solvate thereof, the hydrate thereof, the stereoisomer thereof, the tautomer thereof, the isotopic compound thereof, the metabolite thereof, or the prodrug thereof, or the pharmaceutical composition thereof for use in the preparation of an adenosine A3 receptor agonist.

In another aspect, the present application provides the compound of the present application or the pharmaceutically acceptable salt thereof, and the solvate thereof, the hydrate thereof, the stereoisomer thereof, the tautomer thereof, the isotopic compound thereof, the metabolite thereof, or the prodrug thereof, or the pharmaceutical composition of the present application for use in preparation of a drug for preventing and/or treating an adenosine A3 receptor agonist-mediated or an adenosine A3 receptor agonist-related disease.

Other aspects and advantages of the present application will be readily apparent to a person skilled in the art from the following detailed description. Only exemplary embodiments of the present application are shown and described in the following detailed description. As a person skilled in the art will recognize, the content of the present application enables a person skilled in the art to make changes to the specific embodiments disclosed without departing from the spirit and scope of the invention disclosed by the present application. Accordingly, the description of the present application is to be regarded as exemplary but not as restrictive.

Implementation of the Invention

The embodiments of the present application will be described by specific examples below, and other advantages and benefits of the present application will be easily understood by a person skilled in the art from the disclosure of the description.

Definitions of Terms

The term "adenosine A3 receptor agonist" (A3AR agonist) refers to any molecule capable of specifically binding to adenosine A3 receptor (A3AR) to fully or partially activate the receptor. In other words, the A3AR agonist is a molecule that exerts its primary effect by binding and activating the A3AR. It should be noted that some A3AR agonists may also interact with other receptors with a lower affinity and activate the receptors accordingly.

The term "alkyl" generally refers to a straight-chain or saturated branched-chain hydrocarbon moiety only consisting of carbon and hydrogen atoms. Non-limiting examples of alkyl include: methyl, ethyl, propyl (including n-propyl and isopropyl), butyl (including n-butyl, isobutyl, sec-butyl, and tert-butyl), pentyl, isopentyl or hexyl, etc. As appropriate, the alkyl may optionally be substituted on each carbon as defined in the claims. Typical substituents include, but are not limited to: fluoro, chloro, OH, cyano, (optionally substituted) alkyl, cycloalkyl, etc.

In some cases, the number of carbon atoms in a hydrocarbon substituent (i.e., alkyl, cycloalkyl, etc.) is indicated by a prefix "$C_x$-$C_y$" or "$C_{x-y}$", where x is the minimum and y is the maximum number of carbon atoms in the substituent. Thus, "$C_1$-$C_6$ alkyl" or "$C_{1-6}$ alkyl" refers to the alkyl substituent containing 1 to 6 carbon atoms. As a further example, $C_3$-$C_6$ cycloalkyl or $C_{3-6}$ cycloalkyl means saturated cycloalkyl group containing from 3 to 6 carbon ring atoms.

The term "aminoalkyl" generally refers to an alkyl substituted by a primary, secondary, or tertiary amino. In some embodiments, the aminoalkyl may include those aminoalkyls having one or more primary, secondary, and/or tertiary amine groups, and those aminoalkyls with 1 to about 12 carbon atoms, 1 to about 10 carbon atoms, 1 to about 8 carbon atoms, and 1, 2, 3, 4, 5, or 6 carbon atoms. Non-limiting examples of such aminoalkyls include aminomethyl, aminoethyl, etc.

The term "cycloalkyl" generally refers to a fully hydrogenated, mono-, di- or tricyclic non-aromatic ring containing 3 to 10 carbons. Accordingly, the cycloalkyl may be monocyclic, typically containing 3 to 7 ring atoms. Examples include, but are not limited to: cyclopropyl, cyclobutyl, cyclopentyl, and cyclohexyl. Alternatively, 2 or 3 rings may be fused together, for example, bicyclodecyl and naphthylalkyl. The term "cycloalkyl" further includes a bridged bicycloalkyl system, such as, including but not limited to: bicyclo[2.2.1]heptane and bicyclo[1.1.1]pentane. The cycloalkyl may be optionally substituted by 1 to 5 suitable substituents as described herein, as appropriate, such as, fluoro, chloro, deuterium, cyano, trifluoromethyl, $C_1$-$C_6$ alkoxy, trifluoromethoxy, difluoromethoxy, or $C_1$-$C_6$ alkyl.

The term "heterocycloalkyl" generally refers to a monovalent saturated moiety consisting of one to three rings having one, two, three, or four heteroatoms (selected from N, O, or S), and 3 to 10 carbon atoms. The heterocycloalkyl may be optionally substituted in the manner as defined herein. Examples of the heterocycloalkyl moiety include, but are not limited to: optionally substituted piperidinyl, piperazinyl, homopiperazinyl, azazepine, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolidinyl, benzothiazolinyl, benzoazolidinyl, dihydrofuranyl, tetrahydrofuranyl, dihydropyranyl, tetrahydropyranyl, thiomorpholinyl, thiomorpholinyl sulfoxide, thiomorpholinyl sulfone, dihydroquinolinyl, tetrahydroquinolinyl, tetrahydroisoquinolinyl, etc. The heterocycloalkyl may be optionally substituted by 1 to 5 suitable substituents as defined herein, as appropriate, such as, fluoro, chloro, deuterium, cyano, trifluoromethyl, $C_1$-$C_6$ alkoxy, $C_6$-$C_{10}$ aryloxy, trifluoromethoxy, difluoromethoxy or $C_1$-$C_6$ alkyl.

The terms "alkoxy" and "alkyloxy" generally refer to a moiety of a formula —OR, wherein R is a straight-chain or saturated branched-chain alkyl moiety as defined herein, bonded through an oxygen atom. The alkoxy may be optionally substituted in the manner as defined herein. Non-limiting examples of such alkoxy include methoxy, ethoxy, propoxy, isopropoxy, butoxy, isobutoxy, tert-butoxy, pentoxy, etc.

The term "halogenated alkyl" generally refers to an alkyl substituted by one or more halogen substituents.

The term "halogen" or "halo" generally refers to —F, —Cl, —Br, or —I.

In the present application, the term "alkenyl" generally refers to a branched-chain or straight-chain hydrocarbon partially unsaturated having at least one carbon-carbon double bond. The alkenyl may be optionally substituted. In the present application, the terms "$C_2$-$C_3$ alkenyl", "$C_2$-$C_4$ alkenyl", "$C_2$-$C_5$ alkenyl", "$C_2$-$C_6$ alkenyl", "$C_2$-$C_7$ alkenyl", and "$C_2$-$C_8$ alkenyl" typically refer to the alkenyl containing at least 2 and at most 3, 4, 5, 6, 7 or 8 carbon atoms respectively. Unless stated otherwise, the alkenyl generally refers to $C_2$-$C_6$ alkenyl. In the present application, non-limiting examples of alkenyl include ethenyl, propenyl, butenyl, pentenyl, hexenyl, heptenyl, octenyl, nonenyl, decenyl, etc.

The term "alkynyl" generally refers to a branched-chain or straight-chain hydrocarbon partially unsaturated having at least one carbon-carbon triple bond. The alkynyl may be optionally substituted. In the present application, the terms "$C_2$-$C_3$ alkynyl", "$C_2$-$C_4$ alkynyl", "$C_2$-$C_5$ alkynyl", "$C_2$-$C_6$ alkynyl", "$C_2$-$C_7$ alkynyl", and "$C_2$-$C_8$ alkynyl" typically refer to the alkynyl containing at least 2 and at most 3, 4, 5, 6, 7 or 8 carbon atoms respectively. Unless stated otherwise, the alkynyl is typically $C_2$-$C_6$ alkynyl. In the present application, non-limiting examples of the alkynyl include ethynyl, propynyl, butynyl, pentynyl, hexynyl, heptynyl, octynyl, nonynyl, decynyl, etc.

The term "cycloalkyl" generally refers to a 3-10, or 3-9, or 3-8, or 3-7, or 3-6, or 3-5, or 3-4 membered hydrocarbon and may be monocyclic or bicyclic. The ring may be saturated or may have a certain degree of unsaturation. The cycloalkyl may be optionally substituted by one or more substituents. In one embodiment, 0, 1, 2, 3, or 4 atoms of each ring of the cycloalkyl may be substituted by a substituent. Non-limiting examples of the cycloalkyl include cyclopropyl, cyclopentyl, cyclohexyl, cyclobutyl, cycloheptyl, cyclopentenyl, cyclopentadienyl, cyclohexenyl, cyclohexadienyl, etc.

The term "aryl" generally refers to a hydrocarbon monocyclic or bicyclic aromatic ring system, wherein the rings may be fused. If the rings are fused, one of the rings must be fully unsaturated, and the fused rings may be fully saturated, partially unsaturated, or fully unsaturated. The term "fused" means that a second ring is present (i.e., connected or formed) with two adjacent atoms in common (i.e., shared) with the first ring. The term "aryl" includes an aromatic group such as phenyl, naphthyl, tetrahydronaphthyl, indanyl, biphenyl, 4-(pyridin-3-yl)phenyl, 2,3-dihydro-1H indenyl, and 1,2,3,4-tetrahydronaphthyl. The aryl may be optionally substituted by 1 to 5 suitable substituents as described above, as appropriate.

The term "heteroaryl" generally refers to an aromatic 5-10 membered ring system, wherein a heteroatom is selected from O, N, or S, and the remaining ring atoms are carbons (with appropriate number of hydrogen atoms unless stated otherwise). The heteroaryl may be optionally substituted by one or more substituents. In one embodiment, 0, 1, 2, 3, or 4 atoms of each ring of the heteroaryl may be substituted by a substituent. Non-limiting examples of the heteroaryl include pyridyl, furyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, isoquinolinyl, indazolyl, etc.

In some embodiments, the number of atoms in a ring substituent containing one or more heteroatoms (i.e., the heteroaryl or heterocycloalkyl) is indicated by a prefix "x- to y-membered", where x is the minimum number and y is the maximum number of atoms forming a ring moiety of the substituent. Thus, for example, a "5- to 6-membered heteroaryl" refers to a heteroaryl containing 5 to 6 atoms in a ring moiety of the heteroaryl, including one or more heteroatoms, which may be selected from nitrogen, oxygen, and sulfur.

The term "fused-ring" generally refers to saturated or unsaturated fused-ring system, and relates to a non-aromatic bicyclic ring system with at least one non-aromatic ring. Such systems may comprise an independent or conjugated unsaturated state. Each ring in the fused bicyclic ring may be either a carbon ring or a heteroalicyclic group. Examples include, but are not limited to, hexahydro-furo[3,2-b]furanyl, 2,3,3a,4,7,7a-hexahydro-1H-indenyl, 7-azabicyclo[2.2.1]heptanyl, fused bicyclo[3.3.0]octanyl, fused bicyclo[3.1.0]hexanyl, 1,2,3,4,4a,5,8,8a-octahydronaphthyl, 1,2,3,4-tetrahydronaphthalene, and 2,3-indane, all of which are included in the fused bicyclic system.

The term "spiro" generally refers to a polycyclic group in which two carbon rings share a common carbon atom. The term "heterospiro" generally refers to a polycyclic group in which two monocyclic rings share a common carbon atom, where the two rings may contain 1 or more heteroatoms.

The term "bridged-ring" generally refers to a ring group in which any two carbon rings in the group share two carbon atoms that are not directly connected, and is classified into bicyclic, tricyclic, tetracyclic, etc., according to the number of constituent rings. The term "heterobridged-ring" generally refers to a polycyclic heterocyclyl in which two rings share two non-adjacent carbon atoms or heteroatoms.

The term "independently" or "independent" generally means that when a substituent has one or more variables, each example of the substituent is selected independently of the others in the appropriate variables listed. Thus, each substituent may be the same or different from the other substituents.

The term "optionally substituted" generally means that the group may be unsubstituted or substituted by one or more additional groups which may be individually and independently selected from, without limitation, alkyl, alkenyl, alkynyl, cycloalkyl, aryl, heteroaryl, heterocycloalkyl, hydroxyl, alkoxy, mercapto, cyano, acetyl, deuterium, halogen, carbonyl, thiocarbonyl, isocyanato, thiocyanato, isothiocyanato, nitro, acylamino, sulfonyl, phosphoryl, halogenated alkyl, fluoroalkyl, and amino including mono- and di-substituted amino groups, and derivatives with protecting groups thereof. Non-limiting examples of the optional substituents comprise deuterium, halogen, —CN, =O, =N—OH, =N—OR, =N—R, OR, —C(O)R, —C(O)OR, —OC(O)R, —OC(O)OR, —C(O)NHR, —C(O)$NR_2$, —OC(O)NHR, —OC(O)$NR_2$, —SR—, —S(O)R, —S$(O)_2$R, —NHR, —N$(R)_2$, —NHC(O)R, —NRC(O)R, —NHC(O)OR, —NRC(O)OR, S$(O)_2$NHR, —S$(O)_2$N$(R)_2$, —NHS$(O)_2$$NR_2$, —NRS$(O)_2$$NR_2$, —NHS$(O)_2$$R_2$, —NRS$(O)_2$R, $C_1$-$C_8$ alkyl, $C_1$-$C_8$ alkoxy, aryl, heteroaryl, cycloalkyl, heterocycloalkyl, $C_1$-$C_8$ alkyl substituted by halogen, and $C_1$-$C_8$ alkoxy substituted by halogen, wherein each R is independently selected from hydrogen, deuterium, halogen, $C_1$-$C_8$ alkyl, $C_1$-$C_8$ alkoxy, aryl, heteroaryl, cycloalkyl, heterocycloalkyl, $C_1$-$C_8$ alkyl substituted by halogen, and $C_1$-$C_8$ alkoxy substituted by halogen. The position and number of such substituent groups are determined by well-known valence restrictions of the respective groups, for example, =O is a suitable substitution of alkyl.

The terms "formula I" and "formulas II to VII" as used herein may be referred to hereinafter as "compound of the present application" and are collectively referred to as "compound of formula I". Accordingly, the term "compound of formula I" comprises compounds of "formulas II to VII". It is also defined that the term comprises all forms of the compound of formula I, comprising a solvate, a hydrate, a stereoisomer, a tautomer, an isotopic compound, a metabolite, or a prodrug. For example, the compound of the present application or the pharmaceutically acceptable salt thereof may exist in an unsolvated and solvated form.

The term "pharmaceutically acceptable salt" generally refers to a pharmaceutically acceptable organic or inorganic salt of the compound of the present application. The exemplary salt include, but is not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisate, fumarate, gluconate, glucuronate, saccharate, formate, benzoate, glutamate, methanesulfonate, ethanesulfonate, benzenesulfonate, p-toluenesulfonate, pamoate (i.e., 1,1'-methylene-bis-(2-hydroxyl-3-naphthoic acid)salt), alkali metal (e.g., sodium and potassium) salts, alkaline earth metal (e.g., magnesium) salts, and ammonium salts. A pharmaceutically acceptable salt may involve the inclusion of another molecule, such as an acetate, succinate or other counter ion. The counter ion may be any organic or inorganic moiety that stabilizes the charge on the parent compound. Furthermore, the pharmaceutically acceptable salt may have more than one charged atom in its structure. Instances where multiple charged atoms are part of the pharmaceutically acceptable salt, the salt may have multiple counter ions. Hence, the pharmaceutically acceptable salt may have one or more charged atoms and/or one or more counter ion.

The term "solvate" generally refers to an associated matter (association) or a complex of one or more solvent molecules with the compound of the present application. Non-limiting examples of the solvent that form the solvate include, but are not limited to, water, isopropanol, ethanol, methanol, DMSO, ethyl acetate, acetic acid, and ethanolamine. The term "hydrate" refers to a complex in which the solvent molecule is water.

The term "isomer" or "stereoisomer" generally refers to a compound having the same chemical composition but different arrangements of atoms or groups in a space.

The term "tautomer" generally refers to a structural isomer having different energies that may be interconverted through a low energy barrier. For example, a proton tautomer comprises an interconversion by a proton migration, such as keto-enol and imine-enamine isomerizations. A valence tautomer comprises an interconversion by recombining some bonding electrons.

The subject matter disclosed by the present application further comprises isotopic forms of the compounds described herein. An isotope comprises atoms having the same atomic number but different mass number. Examples of isotopes that may be incorporated into the compounds and the pharmaceutically acceptable salts described herein comprise isotopes of hydrogen, carbon, nitrogen, oxygen, phosphorus, sulfur, fluorine, iodine, and chlorine. For example, $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

The term "metabolite" generally refers to a product produced by metabolizing a particular compound or a salt thereof in vivo. The metabolites of the compound may be identified using a conventional technique known in the art, and the activity is determined by using the test described herein. Such products may result, for example, from oxidation, hydroxylation, reduction, hydrolysis, amidation, deamidation, esterification, deesterification, enzymatic cleavage, etc., of the administered compound. Accordingly, the present application comprises the metabolites of the compounds of the present application, and the compound produced by the following method: The method comprises administration of the compound of the present application to a mammal for a period of time sufficient to produce a metabolite thereof.

The term "prodrug" generally refers to a compound of a drug precursor. When administered to a subject, the prodrug is subjected to a chemical transformation, either by metabolic or chemical processes, to obtain the compound or the salt thereof of the present application. The content of the prodrug is well-known in the art (see, e.g., Berge et al (1977) "Pharmaceutical Salts", J. Pharm. Sci. 66:1-19).

Non-limiting examples of the prodrug moiety comprise a substituted and unsubstituted, branched or unbranched lower alkyl ester moiety (e.g., propionate), a lower alkenyl ester, a di-lower alkyl-amino lower alkyl ester), (e.g., dimethylaminoethyl ester), an acylamino lower alkyl ester (e.g., acetoxymethyl ester), an acyloxy lower alkyl ester (e.g., pivaloyloxymethyl ester), an aryl ester (phenyl ester), an aryl-lower alkyl ester (e.g., benzyl ester), a substituted (e.g., substituted by a methyl, halogen, or methoxy substituent) aryl and aryl-lower alkyl ester, amide, a lower alkyl amide, a di-lower alkyl amide, and hydroxyamide. The prodrug that is converted to an active form by other mechanisms in vivo is also included.

The term "lower" when used in conjunction with an organic group or a compound generally means that the compound or the group may be branched or unbranched, having less than or equal to 7 carbon atoms, e.g., 1-6 carbon atoms, 1-5 carbon atoms, or 1-4 carbon atoms.

The compound of the present application may form esters, which are also within the scope of the present application. The term "ester" generally refers to those esters that hydrolyze in vivo and comprises those that break down readily in human body to leave a parent compound or a salt thereof. A suitable ester comprises, for example, those derived from a pharmaceutically acceptable aliphatic carboxylic acid. Representative examples of the specific ester include, but are not limited to, formate, acetate, propionate, butyrate, acrylate, and ethyl succinate.

The compounds of the present invention have asymmetric carbon atoms. The present application may use solid line (-), solid wedge ( ), or dotted wedge ( ), to depict a carbon-carbon bond of the compound of the present invention. The use of the solid line to depict bonds to asymmetric carbon atoms is generally meant to indicate that all possible stereoisomers (e.g., specific enantiomers, racemic mixtures, etc.) at that carbon atom are included. The use of either a solid wedge or dotted wedge to depict bonds to asymmetric carbon atoms is generally meant to indicate stereoisomers. The compounds of formula I may contain one or more asymmetric carbon atoms. In those compounds, the use of the solid line to depict bonds to asymmetric carbons atom is meant to indicate that all possible stereoisomers are meant to be included. For example, unless stated otherwise, it is intended that the compounds of formula I may exist as enantiomers and diastereomers or as racemates and mixtures thereof. The use of the solid line to depict bonds to one or more asymmetric carbon atoms in the compound of formula I and the use of the solid or dotted wedge to depict a bond to other asymmetric carbon atoms of the same compound generally is meant to indicate that a mixture of diastereomers is present.

The term "carrier" may comprise pharmaceutically acceptable carriers, excipients, or stabilizers which are nontoxic to cells or mammals being exposed thereto at the dosages and concentrations employed. Often the physiologically acceptable carrier is an aqueous pH buffered solution. Non-limiting examples of the physiologically acceptable carrier comprise buffers such as phosphate, citrate, and other organic acids; antioxidants, including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; a monosaccharide, disaccharides, and other carbohydrates including glucose, mannose, or dextrins; chelating agents, such as EDTA; sugar alcohols such as mannitol or sorbitol; salt-forming counterions such as sodium; and/or a nonionic surfactant such as TWEEN™, polyethylene glycol (PEG), and PLURONI-DSTM. In certain embodiments, the pharmaceutically acceptable carrier is a non-naturally occurring pharmaceutically acceptable carrier.

The term "preventing and/or treating" comprises preventing and/or treating a disease, also generally comprises preventing the onset of the disease, slowing or reversing the progression of the disease, preventing or slowing the onset of one or more symptoms associated with the disease, reducing and/or alleviating one or more symptoms associated with the disease, reducing severity and/or duration of the disease and/or any symptoms associated therewith, and/or preventing further increase of the severity of the disease and/or any symptoms associated therewith, and preventing, reducing or reversing any physiological injury caused by the disease, and comprises any pharmacological effect which is generally beneficial to a patient being treated. The composition of the present application does not have to achieve complete cure or eradication of any symptom or manifestation of the disease to be a feasible therapeutic agent. As recognized in the relevant art, a drug used as a therapeutic agent may reduce the severity of a given disease state, but need not eliminate every manifestation of the disease to be considered a useful therapeutic agent. Similarly, treatments administered prophylactically need not be completely effective in preventing the onset of the condition to constitute a viable prophylactic. It is sufficient to simply reduce the impact of the disease (e.g., by reducing the number or severity of its symptoms, or by increasing the effectiveness of another treatment, or by producing another beneficial effect), or reduce the likelihood of the disease progressing or worsening in the subject.

The term "administration" or "administering" comprises the means by which the compound is introduced into a subject to achieve its intended function. Non-limiting examples of the route of administration that may be used comprise injection (subcutaneous, intravenous, parenteral, intraperitoneal, and intrathecal injection), and topical, oral, inhaled, rectal, and transdermal administration.

The term "effective amount" comprises an amount effectively achieving a desired result at a necessary dosage during a period of time. The effective amount of a compound may vary depending on factors such as a disease state, age, and weight of the subject, and the ability of the compound to elicit a desired response in the subject. The dosage regimen may be adjusted to provide an optimal therapeutic response. The "therapeutically effective amount" refers to an amount of the compound of the present application that (i) treats or prevents a particular disease, condition, or disorder, (ii) attenuates, ameliorates, or eliminates one or more symptoms of a particular disease, condition, or disorder, or (iii) prevents or delays the onset of one or more symptoms of a particular disease, condition, or disorder described herein. In the case of cancer, the therapeutically effective amount of a drug may reduce the number of cancer cells, reduce the size of a tumor, inhibit (i.e., slow to some extent and preferably stop) cancer cell infiltration into peripheral organs, inhibit (i.e., slow to some extent and preferably stop) tumor metastasis, inhibit tumor growth to some extent, and/or relieve one or more symptoms associated with cancer to some extent. To the extent that the drug may prevent and/or kill the growth of existing cancer cells, it may be cytostatic and/or cytotoxic. For cancer treatment, efficacy may be measured, for example, by assessing the time to progression (TTP) of a disease and/or assessing the response rate (RR).

The term "interacting" generally means that two or more different types of substances are brought into together to interact in any order, in any manner, and for any length of time, for example, an interaction between an A3R agonist and A3R. In some embodiments, the interaction comprises one or more hydrogen bonds, covalent bonds, ionic bonds, hydrophobic interaction, and/or van der Waals interaction.

The term "subject" or "patient" generally refers to an animal, such as a mammal, including, but not limited to, primates (e.g., human), cows, sheep, goats, horses, dogs, cats, rabbits, rats, mice, etc. In certain embodiments, the subject is a human.

Preparation Method
In another aspect, the present application provides a preparation method of the compound of formula I, which comprises the following steps:
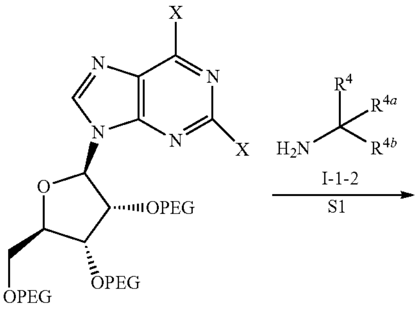
I-1-1
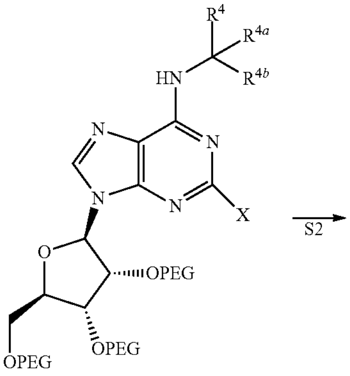
I-1-3
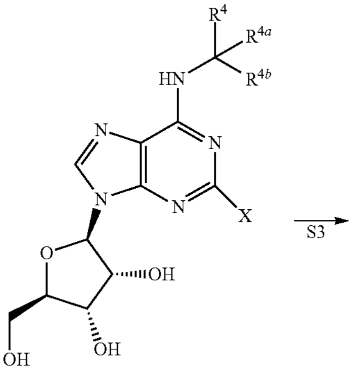
I-1-4
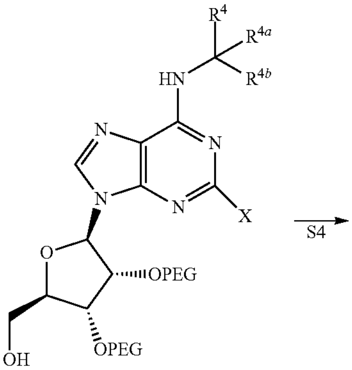
I-1-5
-continued
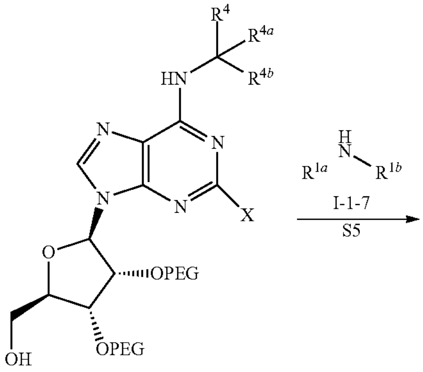
I-1-6
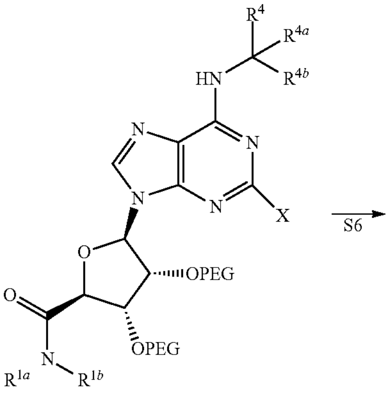
I-1-8
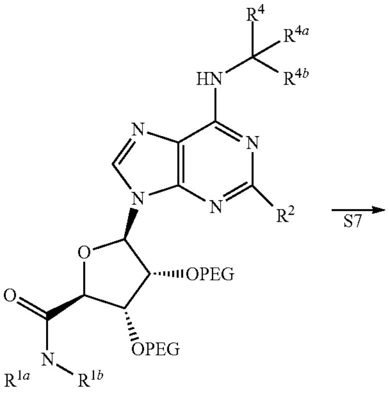
I-1-9
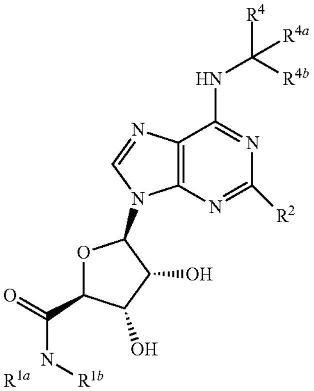
I
S1: compound I-1-1 reacts with compound I-1-2 to form compound I-1-3;

S2: deprotection of hydroxyl groups of compound I-1-3 to form compound I-1-4;

S3: protection of hydroxyls of compound I-1-4 to form compound I-1-5;

S4: oxidization of the hydroxyl of compound I-1-5 to form compound I-1-6;

S5: condensation reaction of compound I-1-6 with compound I-1-7 to form compound I-1-8;

S6: coupling reaction of compound I-1-8 to form compound I-1-9; and

S7: deprotection of hydroxyls of compound I-1-9 to form the compound of formula I, wherein X is chlorine, bromine or iodine; PEG is a protecting group of a hydroxy. The 2 PEG protecting groups on compound I-1-6 may be connected to form 1 protecting group, so that the two hydroxyls are protected at the same time; $R^{1a}$, $R^{1b}$, $R^2$, $R^4$, $R^{4a}$, and $R^{4b}$ are as defined in the compound of formula I.

In another aspect, the present application provides a preparation method of the compound of formula I, which comprises the following steps:

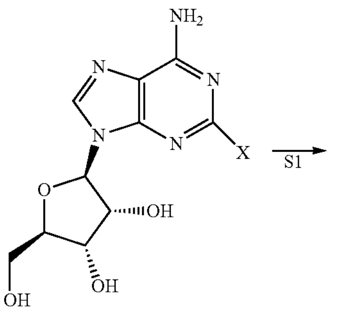

I-2-1

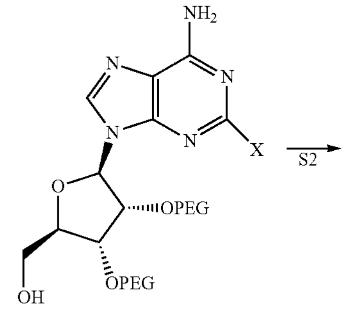

I-2-2

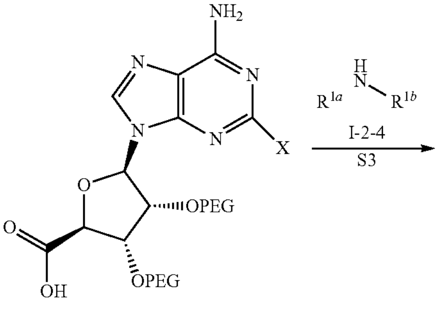

I-2-3

-continued

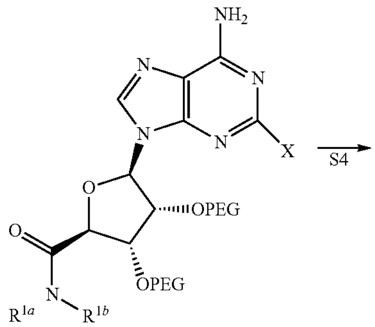

I-2-5

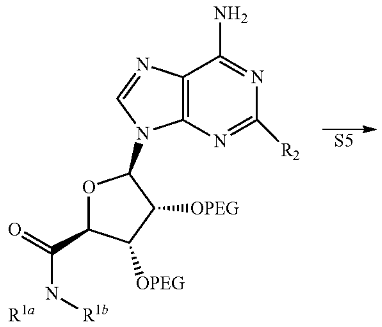

I-2-6

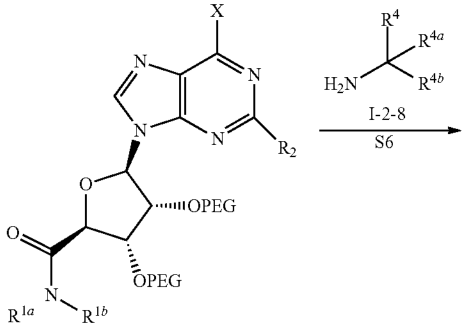

I-2-7

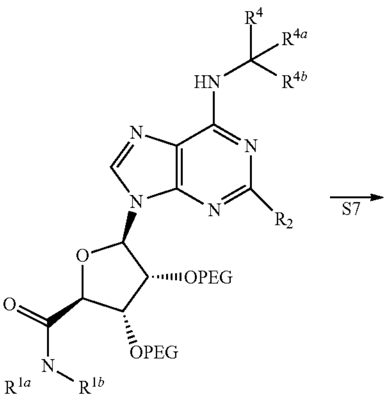

I-2-9

-continued

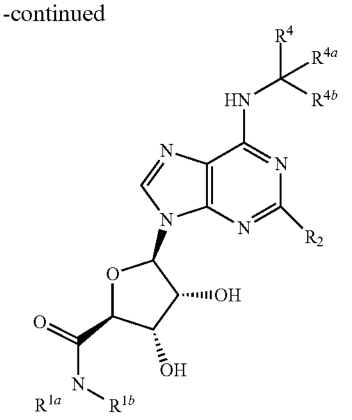

I

S1: protection of hydroxyls of compound I-2-1 to form compound I-2-2;

S2: oxidization of the hydroxyl of compound I-2-2 to obtain compound I-2-3;

S3: condensation reaction of compound I-2-3 with compound I-2-4 to form compound I-2-5;

S4: coupling reaction of compound I-2-5 to form compound I-2-6;

S5: converting the amino on compound I-2-6 to a halogen to form compound I-2-7;

S6: compound I-2-7 reacts with compound I-2-8 to form compound I-2-9; and

S7: deprotection of hydroxyls of compound I-2-9 to form the compound of formula I, wherein X is chlorine, bromine or iodine; PEG is a protecting group of a hydroxyl. The 2 PEG protecting groups on compound I-2-2 may be connected to form 1 protecting group, so that the two hydroxyls are protected at the same time; $R^{1a}$, $R^{1b}$, $R^2$, $R^4$, $R^{4a}$, and $R^{4b}$ are as defined in the compound of formula I.

In another aspect, the present application provides a preparation method of the compound of formula I, which comprises the following steps:

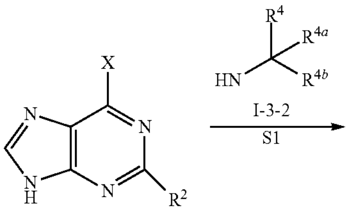

I-3-1

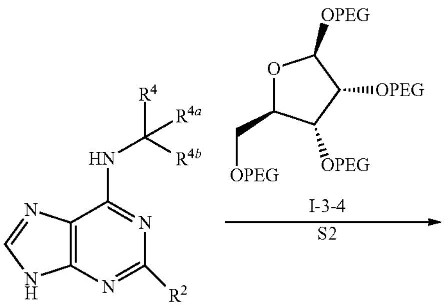

I-3-3

-continued

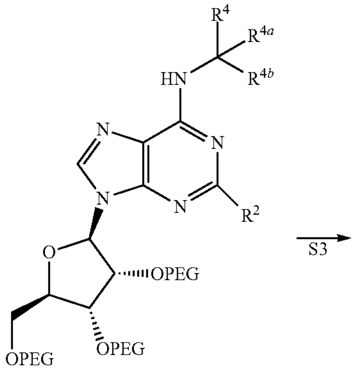

I-3-5

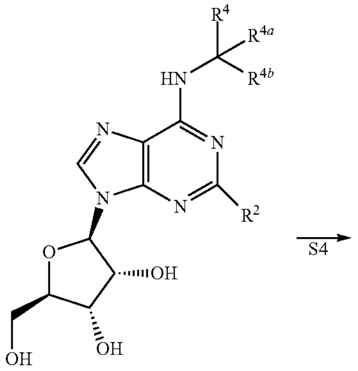

I-3-6

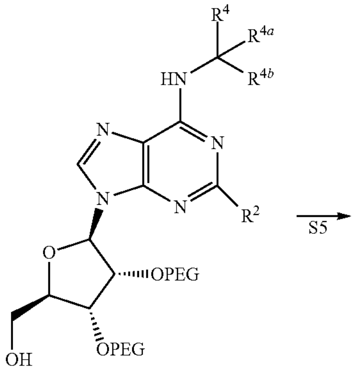

I-3-7

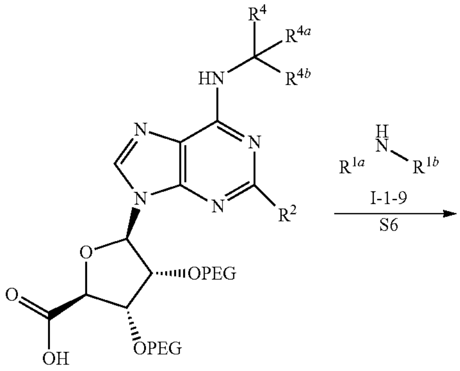

I-3-8

-continued

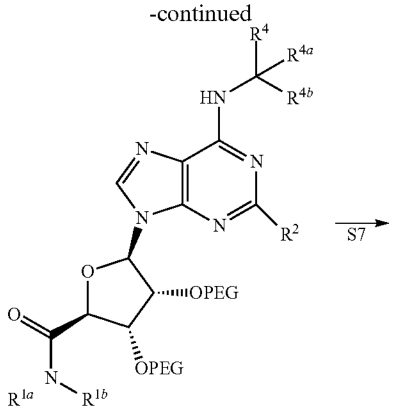

I-3-10

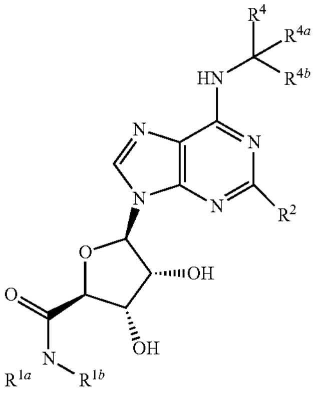

I

S1: compound I-3-1 reacts with compound I-3-2 to form compound I-3-3;

S2: compound I-3-3 reacts with compound I-3-4 to form compound I-3-5;

S3: deprotection of hydroxyls of compound I-3-5 to form compound I-3-6;

S4: protection of hydroxyls of compound I-3-6 to form compound I-3-7;

S5: oxidization of the hydroxyl of compound I-3-7 to form compound I-3-8;

S6: condensation reaction of compound I-3-8 with compound I-3-9 to form compound I-3-10; and S7: deprotection of hydroxyls of compound I-3-10 to form the compound of formula I, wherein X is chlorine, bromine or iodine; PEG is a protecting group of a hydroxyl. The 2 PEG protecting groups on compound I-3-7 may be connected to form 1 protecting group, so that the two hydroxyls are protected at the same time; $R^{1a}$, $R^{1b}$, $R^2$, $R^4$, $R^{4a}$, and $R^{4b}$ are as defined in the compound of formula I.

In another aspect, the present application provides a preparation method of the compound of formula I, which comprises the following steps:

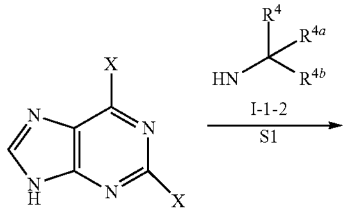

I-4-1

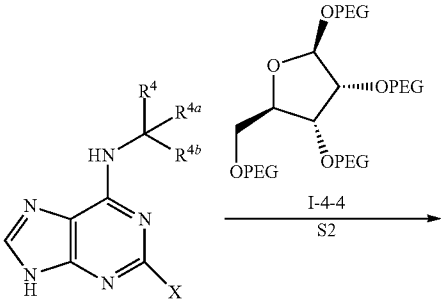

I-4-3

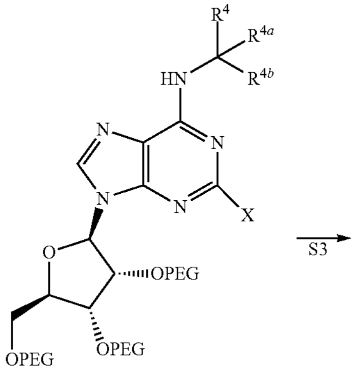

I-4-5

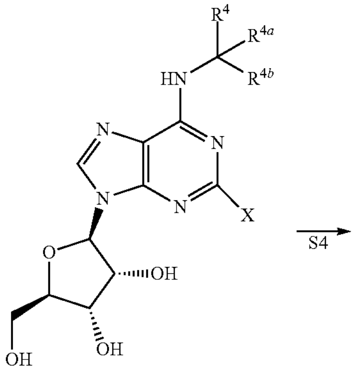

I-4-6

-continued

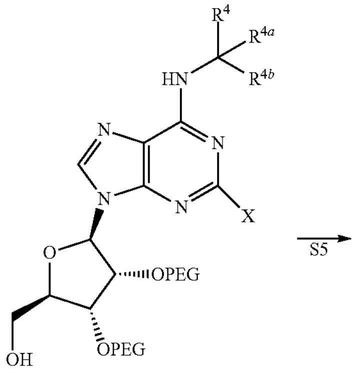

I-4-7

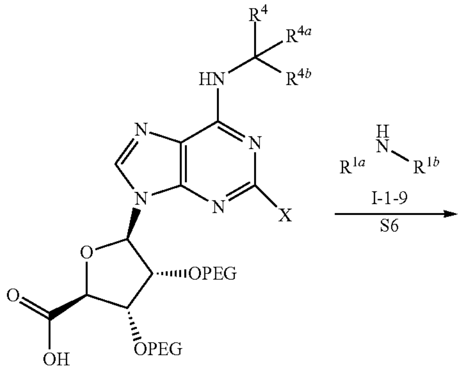

I-4-8

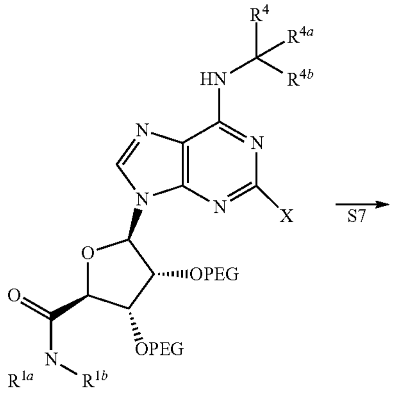

I-4-10

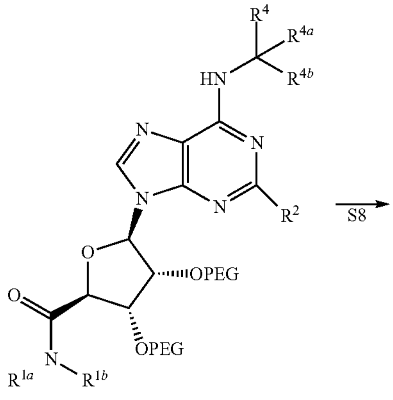

I-4-11

-continued

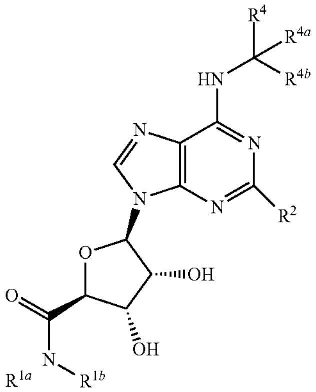

I

S1: compound I-4-1 reacts with compound I-4-2 to form compound I-4-3;

S2: compound I-4-3 reacts with compound I-4-4 to form compound I-4-5;

S3: deprotection of hydroxyls of compound I-4-5 to form compound I-4-6;

S4: protection of hydroxyls of compound I-4-6 to form compound I-4-7;

S5: oxidization of the hydroxyl of compound I-4-7 to form compound I-4-8;

S6: condensation reaction of compound I-4-8 with compound I-4-9 to form compound I-4-10;

S7: coupling reaction of compound I-4-10 to form compound I-4-11; and

S8: deprotection of hydroxyls of compound I-4-11 to form the compound of formula I, wherein X is chlorine, bromine or iodine; PEG is a protecting group of a hydroxyl. The 2 PEG protecting groups on compound I-4-7 may be connected to form 1 protecting group, so that the two hydroxyls are protected at the same time; $R^{1a}$, $R^{1b}$, $R^2$, $R^4$, $R^{4a}$, and $R^{4b}$ are as defined in the compound of formula I.

In another aspect, the present application provides a preparation method of the compound of formula I, which comprises the following steps:

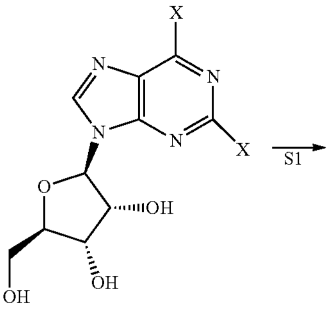

I-5-1

-continued

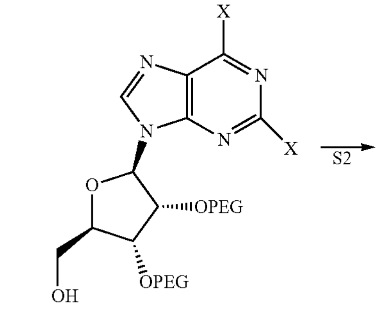

I-5-2

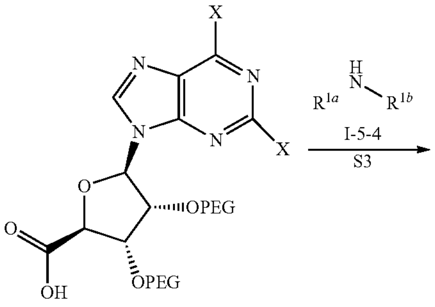

I-5-3

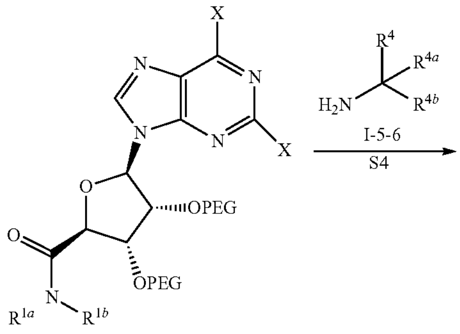

I-5-5

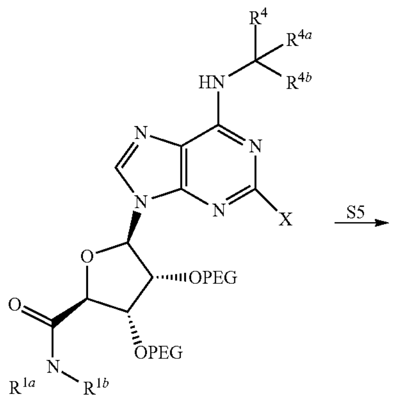

I-5-7

-continued

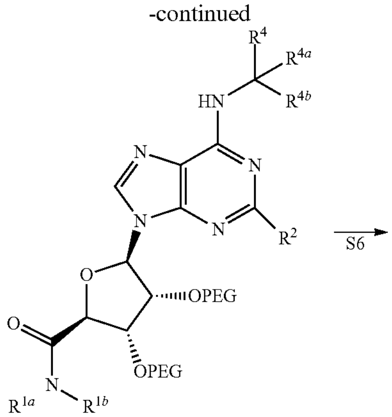

I-5-8

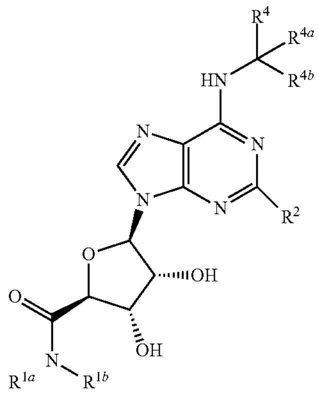

I

S1: protection of hydroxyls of compound I-5-1 to form compound I-5-2;

S2: oxidization of the hydroxyl of compound I-5-2 to form compound I-5-3;

S3: condensation reaction of compound I-5-3 with compound I-5-4 to form compound I-5-5;

S4: compound I-5-5 reacts with compound I-5-6 to form compound I-5-7;

S5: coupling reaction of compound I-5-7 to form compound I-5-8; and

S6: deprotection of hydroxyls of compound I-5-8 to form the compound of formula I, wherein X is chlorine, bromine or iodine; PEG is a protecting group of a hydroxyl. The 2 PEG protecting groups on compound I-5-2 may be connected to form 1 protecting group, so that the two hydroxyls are protected at the same time; $R^{1a}$, $R^{1b}$, $R^2$, $R^4$, $R^{4a}$, and $R^{4b}$ are as defined in the compound of formula I.

In another aspect, the present application provides a preparation method of the compound of formula I, which comprises the following steps:

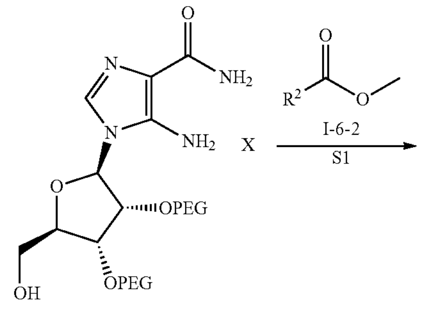

I-6-1

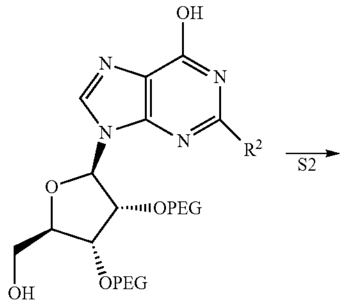

I-6-3

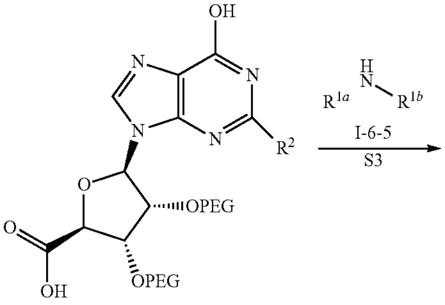

I-6-4

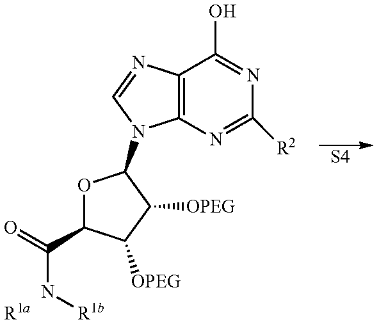

I-6-6

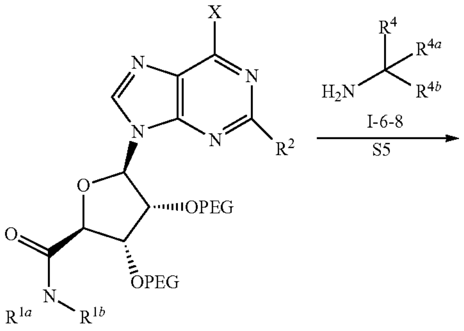

I-6-7

-continued

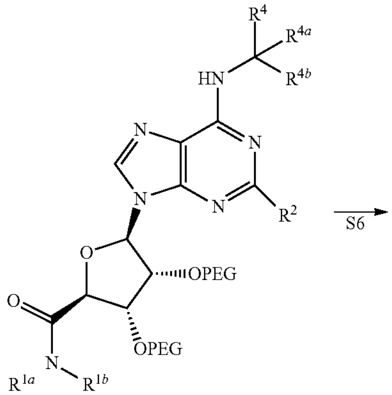

I-6-9

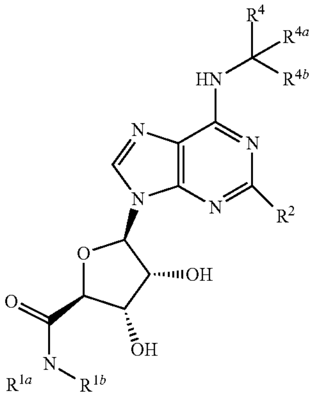

I

S1: cyclization of compound I-6-1 with compound I-6-2 to form compound I-6-3;

S2: oxidization of the hydroxyl of compound I-6-3 to form compound I-6-4;

S3: condensation reaction of compound I-6-4 with compound I-6-5 to form compound I-6-6;

S4: converting compound I-6-6 into a halide to form compound I-6-7;

S5: compound I-6-7 reacts with compound I-6-8 to form compound I-6-9; and

S6: deprotection of hydroxyls of compound I-6-9 to form the compound of formula I, wherein X is chlorine, bromine or iodine; PEG is a protecting group of a hydroxyl. The 2 PEG protecting groups on compound I-6-1 may be connected to form 1 protecting group, so that the two hydroxyls are protected at the same time; $R^{1a}$, $R^{1b}$, $R^2$, $R^4$, $R^{4a}$, and $R^{4b}$ are as defined in the compound of formula I.

In another aspect, the present application provides a preparation method of the compound of formula I, which comprises the following steps:

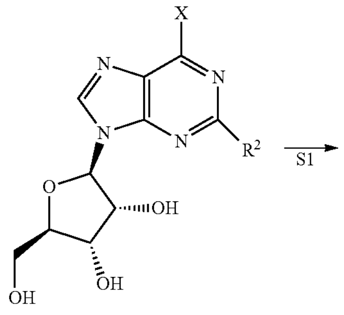

I-7-1

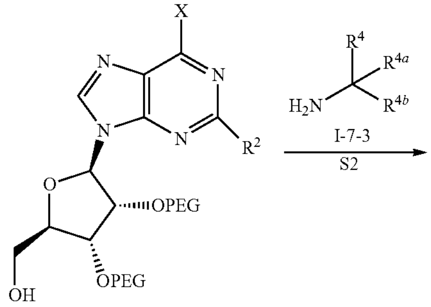

I-7-2

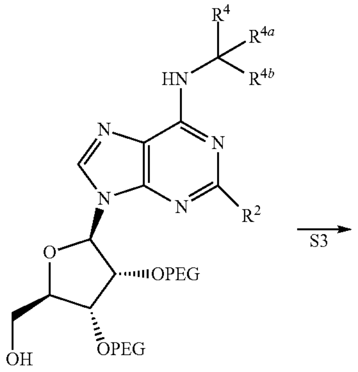

I-7-4

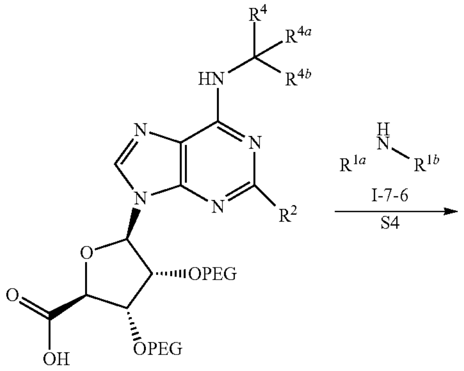

I-7-5

-continued

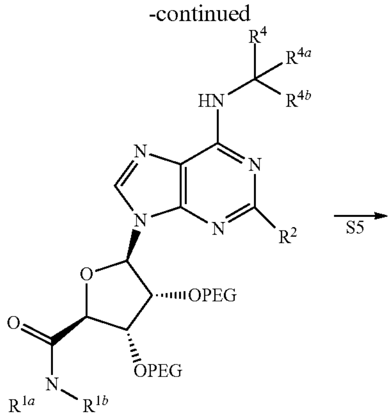

I-7-7

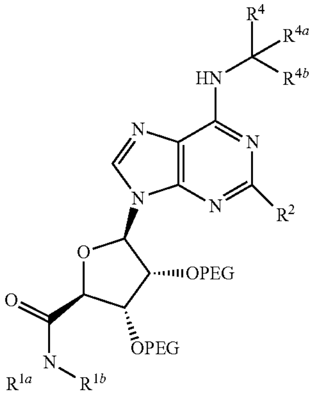

I

S1: protection of hydroxyls of compound I-7-1 to form compound I-7-2;

S2: compound I-7-2 reacts with compound I-7-3 to form compound I-7-4;

S3: oxidization of the hydroxyl of compound I-7-4 to form compound I-7-5;

S4: condensation reaction of compound I-7-5 with compound I-7-6 to form compound I-7-7; and S5: deprotection of hydroxyls of compound I-7-7 to form the compound of formula I, wherein X is chlorine, bromine or iodine; PEG is a protecting group of a hydroxyl. The 2 PEG protecting groups on compound I-6-1 may be connected to form 1 protecting group, so that the two hydroxyls are protected at the same time; $R^{1a}$, $R^{1b}$, $R^2$, $R^4$, $R^{4a}$, and $R^{4b}$ are as defined in the compound of formula I.

Use

The present application provides a method of preventing and/or treating adenosine A3 receptor mediated or adenosine A3 receptor associated diseases, comprising: administering to a subject in need a therapeutically effective amount of the compound, the pharmaceutically acceptable salt, the solvate, the hydrate, the stereoisomer, the tautomer, the isotopic compound, the metabolite, or the prodrug thereof, or the pharmaceutical composition of the present application.

In some embodiments, the diseases treatable with adenosine A3 receptor agonists may comprise:

cancers such as non-small cell lung cancer, small cell lung cancer, gastric cancer, liver cancer, thyroid cancer, cervical cancer, ovarian cancer, breast cancer, colon cancer, pancreatic cancer, prostate cancer, and kidney cancer;

autoimmune diseases such as plaque psoriasis and psoriasis;

neuropathic pains such as chemotherapy-induced neuropathic pain;

neurodegenerative diseases such as rheumatoid arthritis and osteoarthritis of a knee joint;

ischemia reperfusion injury; local ischemia, such as ischemic tissue resulting from the local ischemia, and irreversible organ injury caused by ischemic or hypoxic tissue subjected to ischemic necrosis or infarction, these tissues include, but are not limited to muscle, brain, kidneys, and lungs; local ischemic diseases comprising cerebral thrombosis, renal ischemia, pulmonary ischemia, ischemic cardiomyopathy, myocardial ischemia reperfusion, and other related disorders;

viral infections (inhibiting replication of relevant viruses in cells), such as COVID-19 coronavirus infection and chronic hepatitis C;

nonalcoholic steatohepatitis (NASH); and eye diseases such as keratoconjunctivitis sicca, uveitis, increased intraocular pressure, and glaucoma.

In certain embodiments, the method may further comprise administering to a subject in need at least one additional treatment such as other therapeutic agents for cancers or immune diseases.

In another aspect, the present application provides a drug for preventing and/or treating adenosine A3 receptor mediated or adenosine A3 receptor associated disease, the drug of the present application comprises the compound of the present application or the pharmaceutically acceptable salt thereof, the solvate thereof, the hydrate thereof, the stereoisomer thereof, the tautomer thereof, the isotopic compound thereof, the metabolite thereof, or the prodrug thereof, or the pharmaceutical composition of the present application.

In another aspect, the present application provides a method for regulating the activity of adenosine A3 receptor, which may comprise letting the compound of the present application or the pharmaceutically acceptable salt thereof, the solvate thereof, the hydrate thereof, the stereoisomer thereof, the tautomer thereof, the isotopic compound thereof, the metabolite thereof, or the prodrug thereof, or the pharmaceutical composition of the present application interact with the adenosine A3 receptor.

In some embodiments, the regulation of the activity of the adenosine A3 receptor may comprise activating the activity of the adenosine A3 receptor.

It is not intended to be limited by any theory. The following examples are only intended to illustrate the compound, the preparation method and the use of the present application, and are not intended to limit the scope of the present application.

EXAMPLES

Example 1: Synthesis of (2S,3S,4R,5R)-5-(6-(3-iodobenzylamino)-9H-purin-9-yl)-3,4-dihydroxyl-N-(methyl-d3)-tetrahydrofuran-2-formamide (compound 1)

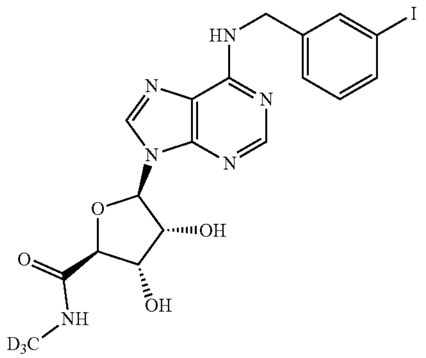 [SMILES: [2H]C([2H])([2H])NC(=O)[C@H]1O[C@@H](n2cnc3c(NCc4cccc(I)c4)ncnc32)[C@H](O)[C@@H]1O]

S1: Synthesis of ((3aR,4R,6R,6aR)-6-(6-chloro-9H-purin-9-yl)-2,2-dimethyltetrahydrofuran[3,4-d][1,3]dioxo-4-yl)methanol

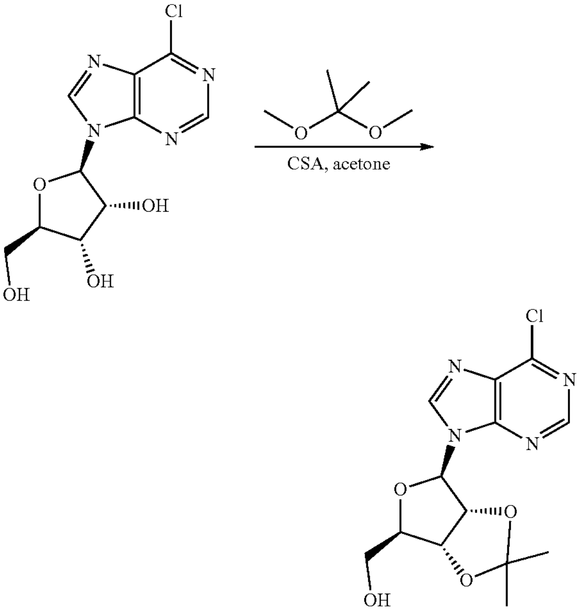

(2R,3R,4S,5R)-2-(6-chloro-9H-purin-9-yl)-5-(hydroxylmethyl)-tetrahydrofuran-3,4-diol (10 g, 34.88 mmol) was dissolved in acetone (60 mL) solvent, and 2,2-dimethoxypropane (14.5 g, 139 mmol) and dexcamphorsulfonic acid (8.1 g, 34.8 mmol) were added sequentially. The materials were stirred at room temperature overnight, and the completion of the reaction was detected by TLC. The reaction solution was concentrated in vacuum, water was added to quench the reaction, an extraction was performed with ethyl acetate, organic layers were mixed, the organic layer was washed with water and saturated saline solution, collected the organic layer, dried with anhydrous sodium sulfate, and filtered, and the residue was concentrated under reduced pressure to obtain the crude product. The crude product was purified by column chromatography (ethyl acetate) to obtain the target compound as a white solid (8.9 g, yield of 64%).

S2: Synthesis of ((3aR,4R,6R,6aR)-6-(6-(3-iodobenzylamino)-9H-purin-9-yl)-2,2-dimethyltetrahydrofuran[3,4-d][1,3]dioxo-4-yl)methanol

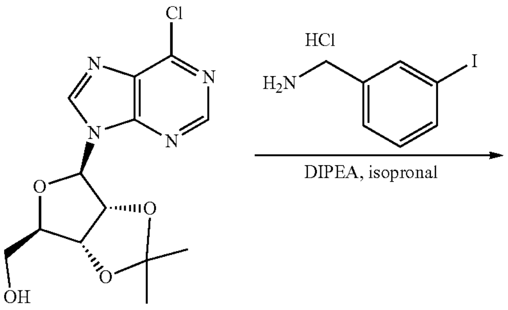

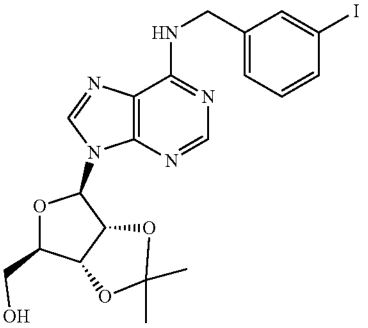

((3aR,4R,6R,6aR)-6-(6-chloro-9H-purin-9-yl)-2,2-dimethyltetrahydrofuran[3,4-d][1,3]dioxo-4-yl)methanol (6.5 g, 16.3 mmol) was dissolved in isopropanol (50 mL) solvent, and N,N'-diisopropylethylamine (6.3 g, 48.8 mmol) and (3-iodophenyl)formamide hydrochloride (5.0 g, 18.5 mmol) were added sequentially. The materials were heated to 80° C. and reacted overnight, and the completion of the reaction was detected by TLC. The reaction solution was concentrated in vacuum, water was added to quench the reaction, an extraction was performed with ethyl acetate, organic layers were mixed, the organic layer was washed with water and saturated saline solution, collected, dried with anhydrous sodium sulfate, and filtered, and the residue was concentrated under reduced pressure to obtain the crude product. The crude product was purified by column chromatography (ethyl acetate) to obtain the target compound as a white solid (8.5 g, yield of 100%). LC-MS m/z $[M+H]^+$: 524.

S3: Synthesis of (3aS,4S,6R,6aR)-6-(6-(3-iodobenzylamino)-9H-purin-9-yl)-2,2-dimethyltetrahydrofuran[3,4-d][1,3]dioxo-4-carboxylic acid

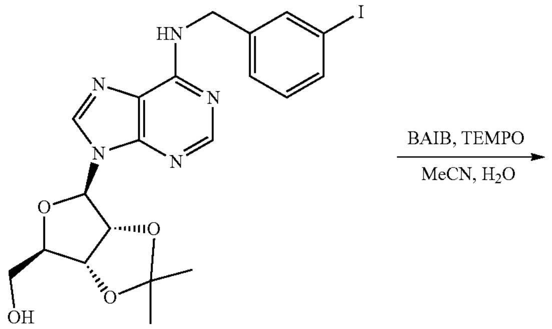

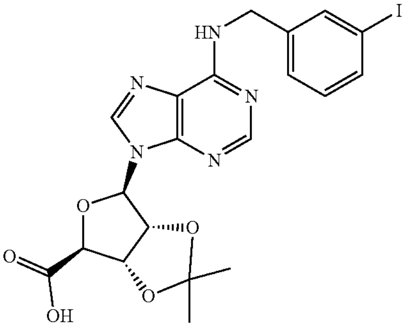

((3aR,4R,6R,6aR)-6-(6-(3-iodobenzylamino)-9H-purin-9-yl)-2,2-dimethyltetrahydrofuran[3,4-d][1,3]dioxo-4-yl)methanol (8.5 g, 16.2 mmol) was dissolved in a mixed solvent of acetonitrile (40 mL) and water (40 mL), and iodobenzene diacetate (11.5 g, 35.7 mmol) and 2,2,6,6-tetramethylpiperidine oxide (500 mg, 3.2 mmol) were added sequentially. The materials were stirred at room temperature overnight, and the completion of the reaction was detected by TLC. A suspended substance of the reaction solution was filtered, a filter cake was then pulped with (ethyl acetate:n-hexane=30 mL:20 mL) and filtered, and the filter cake was dried to obtain the target compound as a white solid (5.9 g, yield of 68%). $^1H$ NMR (500 MHz, DMSO-$d_6$) δ 12.81 (s, 1H), 8.42 (d, J=34.2 Hz, 1H), 8.30 (s, 1H), 8.12 (d, J=38.0 Hz, 1H), 7.74 (d, J=14.9 Hz, 1H), 7.58 (d, J=7.8 Hz, 1H), 7.37 (t, J=13.5 Hz, 1H), 7.14 (dt, J=15.5, 7.8 Hz, 1H), 6.35 (s, 1H), 5.54 (d, J=4.5 Hz, 1H), 5.47 (d, J=5.9 Hz, 1H), 4.68 (t, J=14.6 Hz, 3H), 1.56-1.46 (m, 3H), 1.34 (d, J=11.8 Hz, 3H).

S4: Synthesis of (3aS,4S,6R,6aR)-6-(6-(3-iodobenzylamino)-9H-purin-9-yl)-N-methyl-D3,2,2-dimethyltetrahydrofuran[3,4-d][1,3]dioxo-4-formamide S5: Synthesis of (2S,3S,4R,5R)-5-(6-(3-iodobenzylamino)-9H-purin-9-yl)-3,4-dihydroxyl-N-(methyl-d3)-tetrahydrofuran-2-formamide (compound 1)

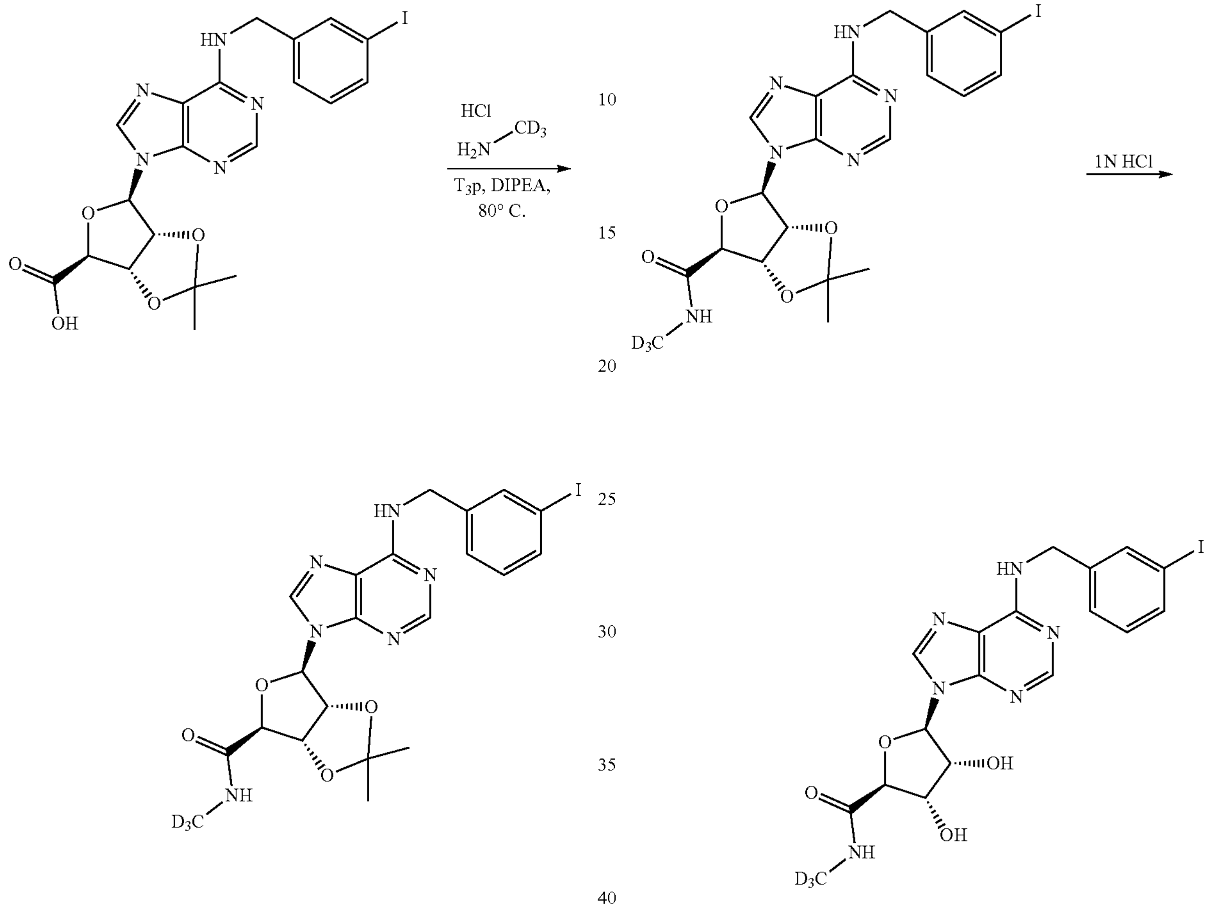

(3aS,4S,6R,6aR)-6-(6-(3-iodobenzylamino)-9H-purin-9-yl)-2,2-dimethyltetrahydrofuran[3,4-d][1,3]dioxo-4-carboxylic acid (400 mg, 0.74 mmol) was dissolved in anhydrous DMF (15 mL) solvent, and N,N'-diisopropylethylamine (288 mg, 2.23 mmol), deuterated methylamine hydrochloride (105 mg, 1.48 mmol), and T3P (473 mg, 1.48 mmol) were added sequentially. The materials were heated to 80° C. and reacted overnight, and the completion of the reaction was detected by TLC. Water was added to quench the reaction, an extraction was performed with ethyl acetate, organic layers were mixed, the organic layer was respectively washed with water and saturated saline solution, collected, dried with anhydrous sodium sulfate, and filtered, and the residue was concentrated under reduced pressure to obtain the crude product. The crude product was purified by column chromatography (ethyl acetate) to obtain the target compound as a white solid (200 mg, yield of 49%). $^1$H NMR (500 MHz, DMSO-$d_6$) δ 8.48 (s, 1H), 8.31 (s, 1H), 8.18 (s, 1H), 7.69 (s, 1H), 7.58 (d, J=7.8 Hz, 1H), 7.49 (s, 1H), 7.34 (d, J=7.5 Hz, 1H), 7.10 (t, J=7.8 Hz, 1H), 6.34 (s, 1H), 5.46-5.28 (m, 2H), 4.66 (s, 2H), 4.55 (d, J=1.7 Hz, 1H), 1.53 (s, 3H), 1.39-1.29 (m, 3H).

(3aS,4S,6R,6aR)-6-(6-(3-iodobenzylamino)-9H-purin-9-yl)-N-methyl-D3,2,2-dimethyltetrahydrofuran[3,4-d][1,3]dioxo-4-formamide (200 mg, 0.36 mmol) was dissolved in THF (1 mL) solvent, and then 1N dilute hydrochloric acid (2 mL) was added. The materials were heated to 50° C. and reacted for 2 hours, and the completion of the reaction was detected by TLC. The reaction solution was adjusted to a pH=7 with sodium bicarbonate aqueous solution and filtered, a filter cake was then pulped with (ethyl acetate) and filtered, and the filter cake was dried to obtain the target compound as a white solid (115 mg, yield of 62%). LC-MS m/z $[M+1]^+$: 514.1; $^1$H NMR (500 MHz, DMSO-$d_6$) δ 8.86 (s, 1H), 8.61 (s, 1H), 8.46 (s, 1H), 8.31 (s, 1H), 7.73 (s, 1H), 7.59 (d, J=7.8 Hz, 1H), 7.37 (d, J=7.5 Hz, 1H), 7.12 (t, J=7.7 Hz, 1H), 5.98 (d, J=6.5 Hz, 1H), 5.52 (d, J=194.7 Hz, 2H), 4.64 (d, J=35.6 Hz, 3H), 4.32 (s, 1H), 4.16 (s, 1H).

Example 2: Following Reactions S1-S5 Shown in Example 1, the Compounds in the Table Below were Obtained

| No. | Compound structure and name | Characterization data |
|---|---|---|
| 2 | 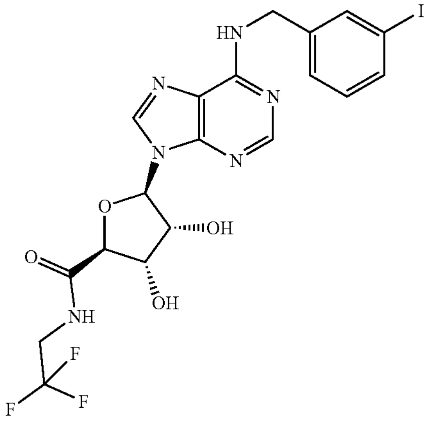 [SMILES: O=C(NCC(F)(F)F)[C@H]1O[C@@H](n2cnc3c(NCc4cccc(I)c4)ncnc32)[C@H](O)[C@@H]1O] (2S,3S,4R,5R)-5-(6-(3-iodophenylamino)-9H-purin-9-yl)-3,4-dihydroxyl-N-(2,2,2-trifluoroethyl)-tetrahydrofuran-2-formamide | LC-MS m/z $[M + 1]^+$: 579.3; $^1H$ NMR (500 MHz, DMSO-$d_6$) δ 9.94 (s, 1H), 8.66 (s, 1H), 8.39 (s, 1H), 8.31 (s, 1H), 7.74 (s, 1H), 7.59 (d, J = 7.7 Hz, 1H), 7.37 (d, J = 7.3 Hz, 1H), 7.12 (t, J = 7.7 Hz, 1H), 6.00 (d, J = 7.7 Hz, 1H), 5.91 (s, 1H), 5.65 (s, 1H), 4.67 (s, 2H), 4.56 (s, 1H), 4.44 (s, 1H), 4.25-3.92 (m, 3H). |
| 3 | 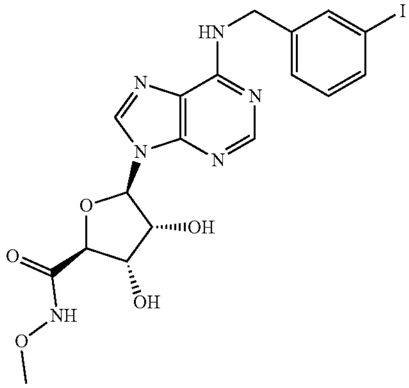 [SMILES: CONC(=O)[C@H]1O[C@@H](n2cnc3c(NCc4cccc(I)c4)ncnc32)[C@H](O)[C@@H]1O] (2S,3S,4R,5R)-5-(6-(3-iodobenzylamino)-9H-purin-9-yl)-3,4-dihydroxyl-N-methoxy-tetrahydrofuran-2-formamide | LC-MS m/z $[M + 1]^+$: 527.2; $^1H$ NMR (500 MHz, DMSO-$d_6$) δ 12.17 (s, 1H), 8.67 (s, 1H), 8.48 (s, 1H), 8.27 (s, 1H), 7.73 (s, 1H), 7.59 (d, J = 7.5 Hz, 1H), 7.37 (d, J = 6.9 Hz, 1H), 7.12 (t, J = 7.7 Hz, 1H), 6.00 (d, J = 6.7 Hz, 1H), 5.63 (t, J = 142.0 Hz, 2H), 4.68 (s, 2H), 4.58 (d, J = 5.1 Hz, 1H), 4.30 (s, 1H), 4.24 (s, 1H), 3.66 (s, 3H). |
| 4 | 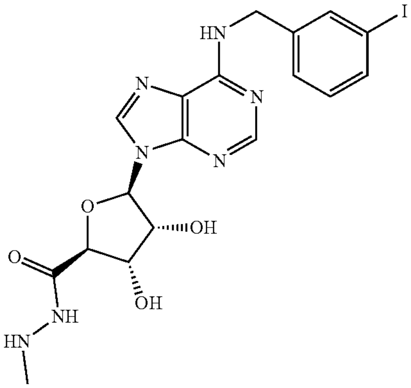 [SMILES: CNNC(=O)[C@H]1O[C@@H](n2cnc3c(NCc4cccc(I)c4)ncnc32)[C@H](O)[C@@H]1O] (2S,3S,4R,5R)-5-(6-(3-iodobenzylamino)-9H-purin-9-yl)-3,4-dihydroxyl-N'-methyl-tetrahydrofuran-2-carbohydrazide | LC-MS m/z $[M + 1]^+$: 526.2; $^1H$ NMR (500 MHz, DMSO-$d_6$) δ 8.83 (s, 1H), 8.50 (s, 1H), 8.21 (d, J = 14.4 Hz, 1H), 7.73 (s, 1H), 7.58 (d, J = 7.7 Hz, 1H), 7.36 (d, J = 7.2 Hz, 1H), 7.11 (t, J = 7.7 Hz, 1H), 6.10 (t, J = 8.7 Hz, 1H), 5.63 (d, J = 4.1 Hz, 1H), 5.56 (d, J = 6.4 Hz, 1H), 5.37 (s, 1H), 4.85 (s, 2H), 4.68 (s, 2H), 4.40 (dd, J = 10.8, 6.7 Hz, 1H), 4.20 (s, 1H), 3.05 (d, J = 16.6 Hz, 3H). |

Example 3: Synthesis of (2S,3S,4R,5R)-5-(6-(3-iodobenzylamino)-9H-purin-9-yl)-3,4-dihydroxyltetrahydrofuran-2-carbohydrazide (compound 5)

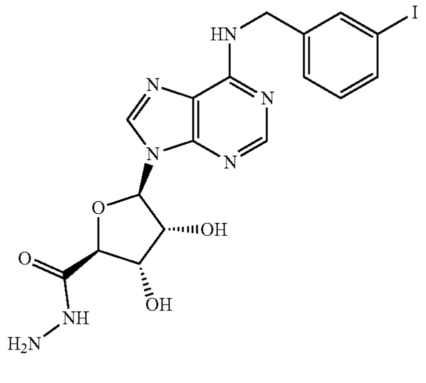 [SMILES: NNC(=O)[C@H]1O[C@@H](n2cnc3c(NCc4cccc(I)c4)ncnc32)[C@H](O)[C@@H]1O]

S1-S3: please referred to the specific reactions in example 1.

S4: Synthesis of (2S,3S,4R,5R)-methyl-5-(6-(3-iodobenzylamino)-9H-purin-9-yl)-3,4-dihydroxyltetrahydrofuran-2-carboxylic ester

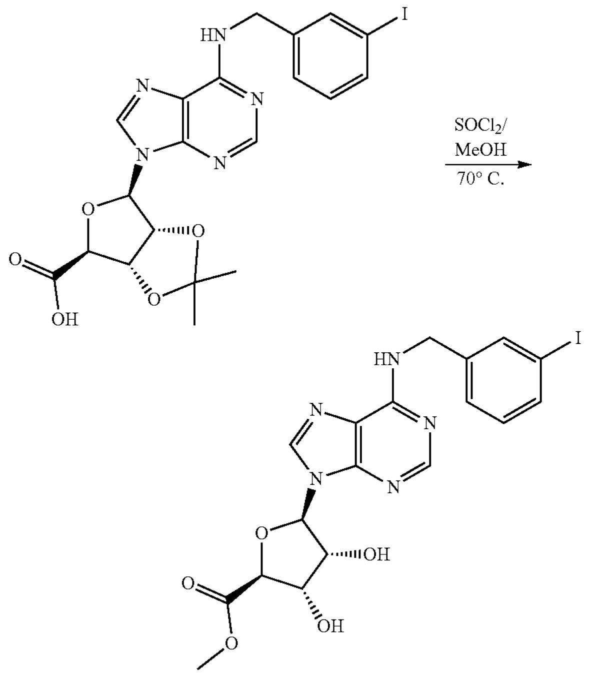

(3aS,4S,6R,6aR)-6-(6-(3-iodobenzylamino)-9H-purin-9-yl)-2,2-dimethyltetrahydrofuran[3,4-d][1,3]dioxo-4-carboxylic acid (1.0 g, 1.86 mmol) was dissolved in MeOH (10 mL) solvent, and thionyl chloride (2 mL) was added. The materials were heated to 80° C. and reacted for 2 h, and the completion of the reaction was detected by TLC. The reaction solution was concentrated in vacuum, water was added to quench the reaction, an extraction was performed with ethyl acetate, organic layers were mixed, the organic layer was washed with water and saturated saline solution respectively, collected, dried with anhydrous sodium sulfate, and filtered, and the residue was concentrated under reduced pressure to obtain the crude product. The crude product was purified by column chromatography (ethyl acetate) to obtain the target compound as a white solid (250 mg, yield of 26%). $^1$H NMR (500 MHz, DMSO-$d_6$) δ 8.48 (d, J=24.3 Hz, 2H), 8.24 (s, 1H), 7.73 (s, 1H), 7.59 (d, J=7.8 Hz, 1H), 7.36 (d, J=7.6 Hz, 1H), 7.11 (t, J=7.8 Hz, 1H), 6.07 (d, J=6.3 Hz, 1H), 5.86 (d, J=5.2 Hz, 1H), 5.71 (d, J=6.3 Hz, 1H), 4.70-4.62 (m, 2H), 4.50 (d, J=2.7 Hz, 1H), 4.40 (d, J=2.6 Hz, 1H), 3.72 (s, 3H).

S5: Synthesis of (2S,3S,4R,5R)-5-(6-(3-iodobenzylamino)-9H-purin-9-yl)-3,4-dihydroxyltetrahydrofuran-2-carbohydrazide (compound 5)

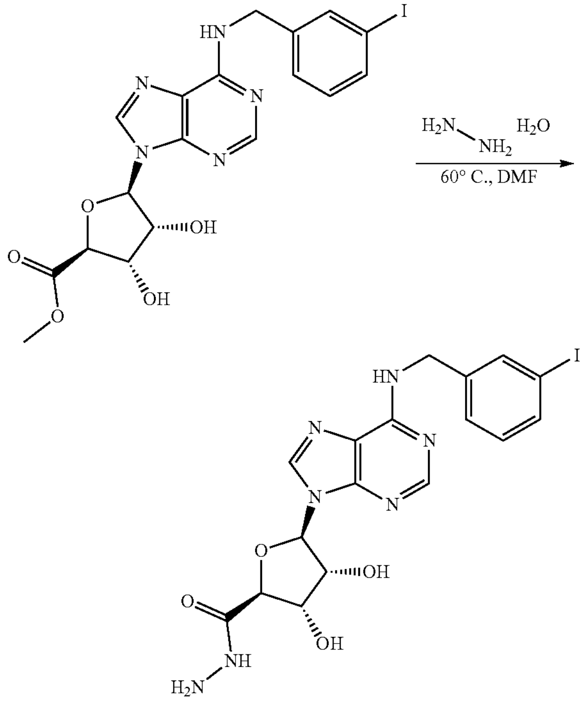

(2S,3S,4R,5R)-methyl-5-(6-(3-iodobenzylamino)-9H-purin-9-yl)-3,4-dihydroxyltetrahydrofuran-2-carboxylic ester (100 mg, 0.19 mmol) was dissolved in DMF (20 mL) solvent, and hydrazine hydrate was added (3 mL). The materials were heated to 60° C. and reacted for 2 h, and the completion of the reaction was detected by TLC. The reaction solution was concentrated in vacuum, water was added to quench the reaction, an extraction was performed with ethyl acetate, organic layers were mixed, the organic layer was washed with water and saturated saline solution respectively, collected, dried with anhydrous sodium sulfate, and filtered, and the residue was concentrated under reduced pressure to obtain the crude product. The crude product was purified by column chromatography (ethyl acetate:methanol=20:1) to obtain the target compound as a white solid (57 mg, yield of 57%). LC-MS m/z $[M+1]^+$: 512.2; $^1$H NMR (500 MHz, DMSO-$d_6$) δ 10.14 (s, 1H), 8.60 (s, 1H), 8.52 (s, 1H), 8.25 (s, 1H), 7.73 (s, 1H), 7.59 (d, J=7.8 Hz, 1H), 7.37 (d, J=7.5 Hz, 1H), 7.12 (t, J=7.8 Hz, 1H), 5.99 (d, J=6.9 Hz, 1H), 5.74 (d, J=4.5 Hz, 1H), 5.64 (d, J=6.2 Hz, 1H), 4.68 (s, 2H), 4.59 (dd, J=11.1, 6.6 Hz, 1H), 4.44 (s, 2H), 4.36 (d, J=1.8 Hz, 1H), 4.17 (d, J=1.7 Hz, 1H).

Example 4: Synthesis of (2S,3S,4R,5R)-5-(6-(3-iodobenzylamino)-9H-purin-9-yl)-N,3,4-trihydroxyltetrahydrofuran-2-formamide (compound 6)

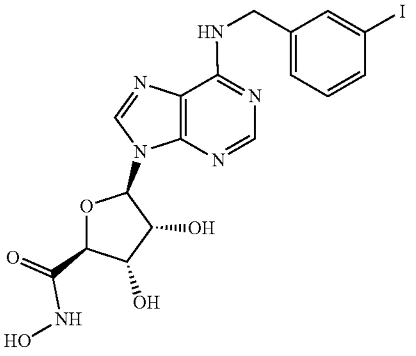 [SMILES: O=C(NO)[C@H]1O[C@@H](n2cnc3c(NCc4cccc(I)c4)ncnc32)[C@H](O)[C@@H]1O]

Referring to example 3, the target compound as a white solid was obtained (47 mg, yield of 47%). LC-MS m/z $[M+1]^+$: 513.2; $^1H$ NMR (500 MHz, DMSO-$d_6$) δ 11.53 (s, 1H), 9.14 (s, 1H), 8.61 (s, 1H), 8.52 (s, 1H), 8.24 (s, 1H), 7.73 (s, 1H), 7.59 (d, J=7.8 Hz, 1H), 7.36 (d, J=7.5 Hz, 1H), 7.12 (t, J=7.8 Hz, 1H), 6.00 (d, J=6.5 Hz, 1H), 5.76 (d, J=4.7 Hz, 1H), 5.67 (d, J=6.1 Hz, 1H), 4.67 (s, 2H), 4.56 (dd, J=10.9, 6.2 Hz, 1H), 4.30 (d, J=2.2 Hz, 1H), 4.20 (d, J=2.2 Hz, 1H).

Example 5: Synthesis of (2S,3S,4R,5R)-2-(6-(benzylamino)-9H-purin-9-yl)-3,4-dihydroxyltetrahydrofuran-5-carbonylaminoethyl formate (compound 7)

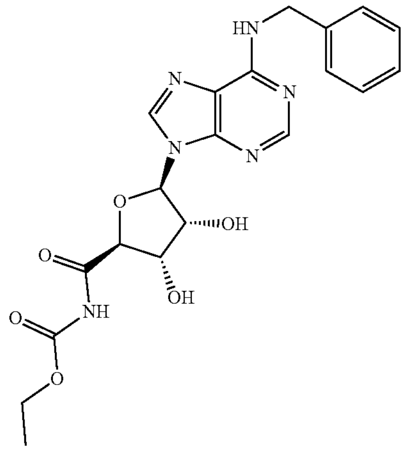 [SMILES: CCOC(=O)NC(=O)[C@H]1O[C@@H](n2cnc3c(NCc4ccccc4)ncnc32)[C@H](O)[C@@H]1O]

S1-S3: Synthesis of (3aS,4S,6R,6aR)-6-(6-chloro-9H-purin-9-yl)-2,2-dimethyltetrahydrofuran[3,4-d][1,3]dioxo-4-carboxylic acid

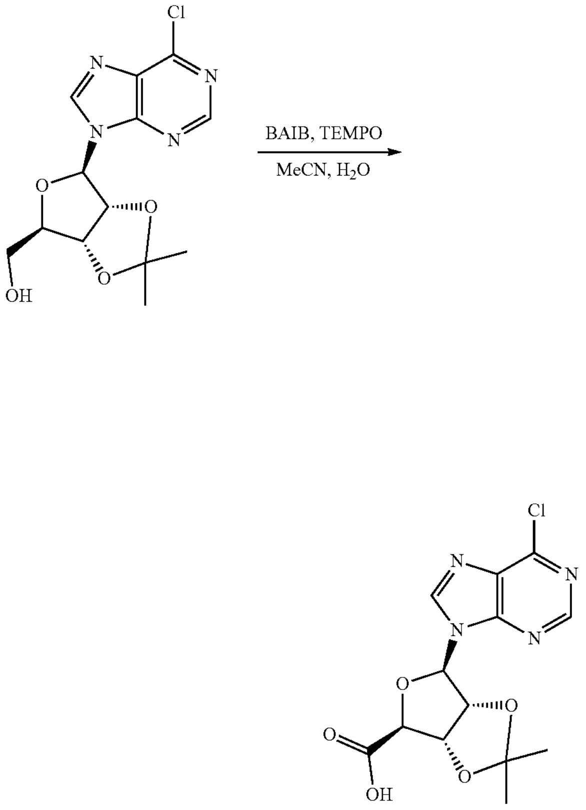

The reaction was performed according to the corresponding steps in example 1 to obtain the title compound as a white solid (8 g, yield of 100%). $^1H$ NMR (500 MHz, DMSO-$d_6$) δ 12.91 (s, 1H), 8.79 (d, J=34.4 Hz, 2H), 6.51 (s, 1H), 5.59 (dd, J=30.3, 5.8 Hz, 2H), 4.79 (s, 1H), 1.53 (s, 3H), 1.37 (s, 3H).

S4: Synthesis of (3aS,4S,6R,6aR)-6-(6-chloro-9H-purin-9-yl)-2,2-dimethyltetrahydrofuran[3,4-d][1,3]dioxo-4-formamide

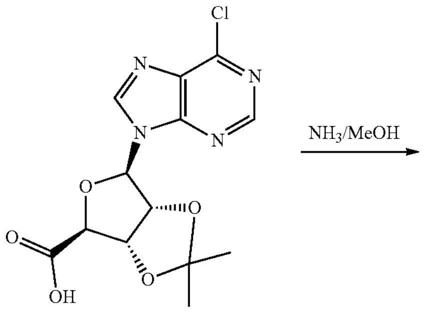

-continued

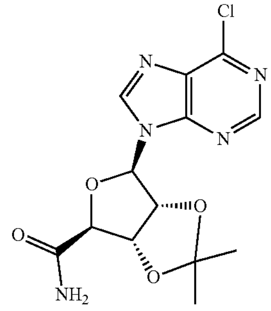

(3aS,4S,6R,6aR)-6-(6-chloro-9H-purin-9-yl)-2,2-dimethyltetrahydrofuran[3,4-d][1,3]dioxo-4-carboxylic acid (2 g, 4.9 mmol) was dissolved in THF (40 mL) solvent, and triethylamine (1.4 g, 12 mmol), CDI (1.8 g, 7.3 mmol), and ammonia (2 mL, 7.0 M in MeOH) were added sequentially. After the materials were reacted at a room temperature overnight, it was concentrated under reduced pressure to remove the solvent, water was added to quench the reaction, an extraction was performed with ethyl acetate, organic layers were mixed, the organic layer was washed with water and saturated saline solution respectively, collected, dried with anhydrous sodium sulfate, and filtered, and the residue was concentrated under reduced pressure to obtain the crude product. The crude product was purified by column chromatography (ethyl acetate) to obtain the target compound as a white solid (413 mg, yield of 26%). $^1H$ NMR (500 MHz, DMSO-$d_6$) δ 8.81 (s, 1H), 8.76 (s, 1H), 7.12 (s, 1H), 7.04 (s, 1H), 6.51 (d, J=38.7 Hz, 1H), 5.52 (d, J=6.0 Hz, 1H), 5.43 (dd, J=6.0, 2.1 Hz, 1H), 4.60 (d, J=2.1 Hz, 1H), 1.55 (s, 3H), 1.36 (s, 3H).

S5: Synthesis of (3aS,4S,6R,6aR)-6-(6-(benzylamino)-9H-purin-9-yl)-2,2-dimethyltetrahydrofuran [3,4-d][1,3]dioxo-4-formamide

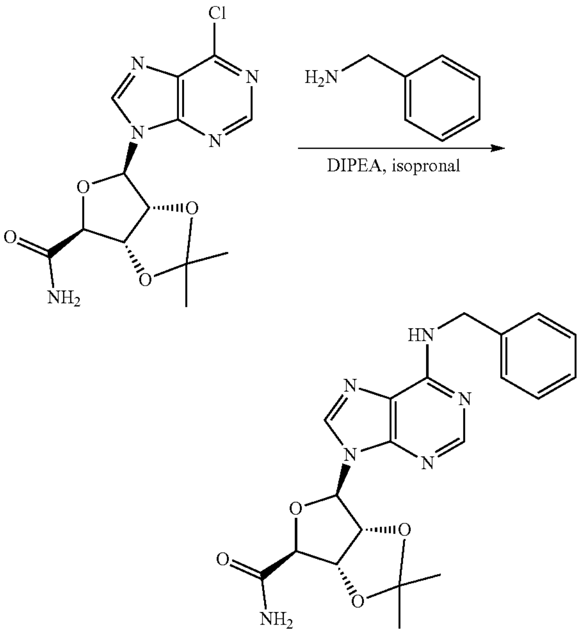

The reaction was performed according to the corresponding steps in example 1 to obtain the title compound as a white solid (1.3 g, yield of 68%). $^1H$ NMR (500 MHz, DMSO-$d_6$) δ 8.45 (d, J=0.8 Hz, 1H), 8.32 (s, 1H), 8.19 (s, 1H), 7.39-7.26 (m, 4H), 7.19 (dd, J=24.1, 12.2 Hz, 3H), 6.31 (s, 1H), 5.37 (d, J=24.6 Hz, 2H), 4.70 (s, 2H), 4.52 (s, 1H), 1.54 (d, J=10.9 Hz, 3H), 1.34 (s, 3H).

S6: Synthesis of (3aR,4R,6S,6aS)-4-(6-(benzylamino)-9H-purin-9-yl)-2,2-dimethyltetrahydrofuran [3,4-d][1,3]dioxo-6-carbonylamino ethyl formate

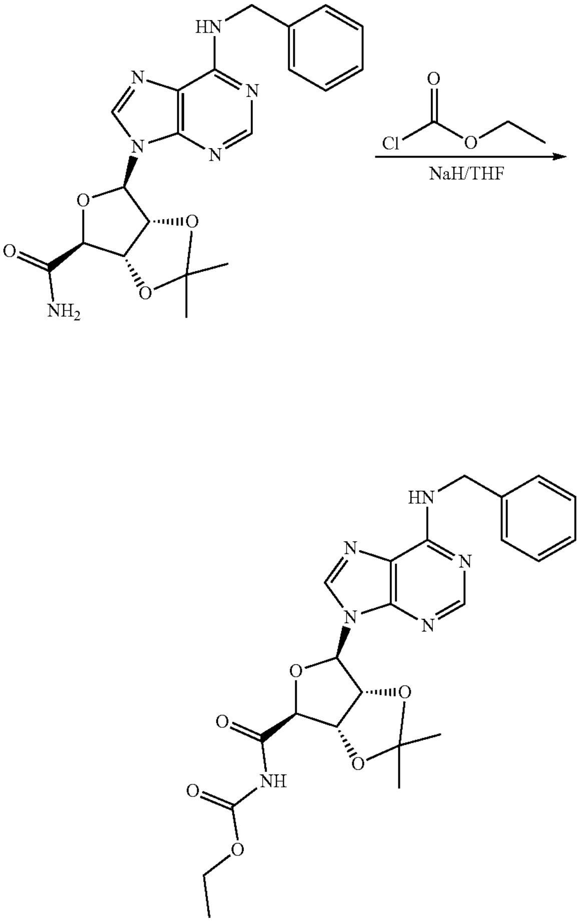

(3aS,4S,6R,6aR)-6-(6-(benzylamino)-9H-purin-9-yl)-2,2-dimethyltetrahydrofuran[3,4-d][1,3]dioxo-4-formamide (400 mg, 0.97 mmol) was dissolved in anhydrous THE (15 mL) solvent, and sodium hydride (78 mg, 1.9 mmol) and ethyl chloroacetate (160 mg, 1.46 mmol) were added sequentially at 0° C. The materials were reacted at a room temperature for 3 hours, and the completion of the reaction was detected by TLC. Water was added to quench the reaction, an extraction was performed with ethyl acetate, organic layers were mixed, the organic layer was washed with water and saturated saline solution, collected, dried with anhydrous sodium sulfate, and filtered, and the residue was concentrated under reduced pressure to obtain the crude product. The crude product was purified by column chromatography (ethyl acetate:n-hexane=2:1) to obtain the target compound as a white solid (300 mg, yield of 64%). LC-MS m/z $[M+H]^+$: 483.

S7: Synthesis of (2R,3R,4S,5S)-2-(6-(benzylamino)-9H-purin-9-yl)-3,4-dihydroxyltetrahydrofuran-5-carbonylamino ethyl formate (compound 7)

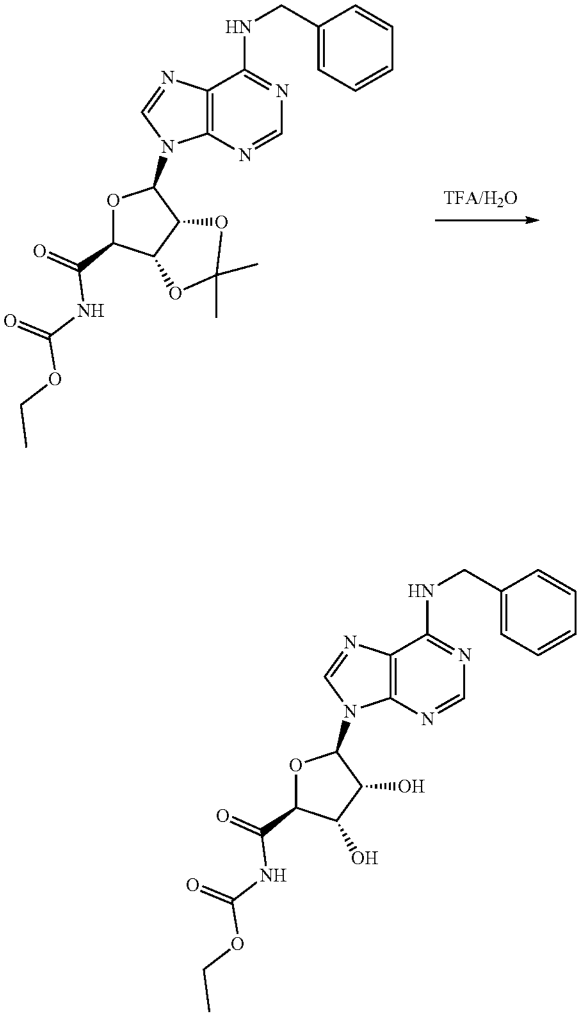 [SMILES: CCOC(=O)NC(=O)[C@H]1O[C@@H](n2cnc3c(NCc4ccccc4)ncnc32)[C@@H]2OC(C)(C)O[C@@H]21 ; CCOC(=O)NC(=O)[C@H]1O[C@@H](n2cnc3c(NCc4ccccc4)ncnc32)[C@H](O)[C@@H]1O]

(3aR,4R,6S,6aS)-4-(6-(benzylamino)-9H-purin-9-yl)-2,2-dimethyltetrahydrofuran[3,4-d][1,3]dioxo-6-carbonylamino ethyl formate (100 mg, 0.20 mmol) was dissolved in water (2 mL) solvent, TFA (3 mL) was added, the materials were reacted at a room temperature for 3 hours, and the completion of the reaction was detected by TLC. It was concentrated under reduced pressure to remove the solvent, water was added to quench the reaction, an extraction was performed with ethyl acetate, organic layers were mixed, the organic layer was washed with water and saturated saline solution respectively, collected, dried with anhydrous sodium sulfate, and filtered, and the residue was concentrated under reduced pressure to obtain the crude product. The crude product was purified by column chromatography (ethyl acetate:n-hexane=2:1) to obtain the target compound as a white solid (25 mg, yield of 27%). $^1H$ NMR (500 MHz, DMSO-$d_6$) δ 11.70 (s, 1H), 8.62 (s, 1H), 8.39 (s, 1H), 8.28 (s, 1H), 7.37-7.19 (m, 5H), 6.00 (d, J=7.5 Hz, 1H), 5.91 (d, J=3.9 Hz, 1H), 5.64 (d, J=6.2 Hz, 1H), 4.73 (s, 2H), 4.52 (d, J=11.2 Hz, 2H), 4.26 (s, 1H), 4.23-4.16 (m, 2H), 1.25 (dd, J=14.3, 7.2 Hz, 3H).

Example 6: Synthesis of (2S,3S,4R,5R)-5-(6-(3-iodobenzylamino)-2-chloro-9H-purin-9-yl)-3,4-dihydroxyl-N-(methyl-d3)-tetrahydrofuran-2-formamide (compound 8)

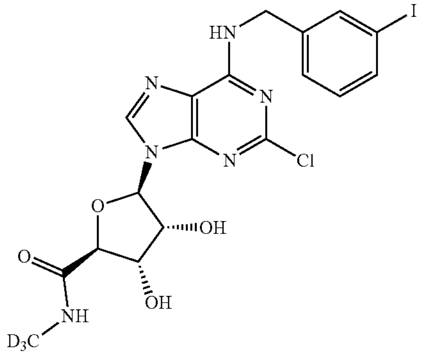 [SMILES: [2H]C([2H])([2H])NC(=O)[C@H]1O[C@@H](n2cnc3c(NCc4cccc(I)c4)nc(Cl)nc32)[C@H](O)[C@@H]1O]

S1: Synthesis of 2',3',5'-tri-O-acetyl-2,6-dichloropurine nucleoside

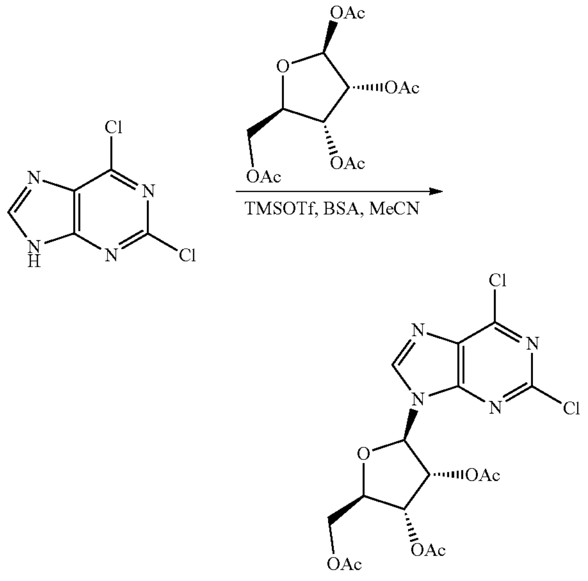

2,6-dichloro-9H-purine (10 g, 53 mmol) was dissolved in anhydrous acetonitrile (60 mL) solvent, trimethylsilicyl trifluoromesulfonate (12.9 g, 58.2 mmol) and N,O-bistrimethylsilicyl acetamide (11.8 g, 58.2 mmol) were added sequentially, the materials were stirred at a room temperature for 2 hours, a compound 1,2,3,5-tetra-O-acetyl-β-L-furanoribose was added to a reaction solution, the materials were heated to 80° C. for 3 hours, and the completion of the reaction was detected by TLC. It was concentrated under reduced pressure to remove the solvent, water was added to quench the reaction, an extraction was performed with ethyl acetate, organic layers were mixed, the organic layer was washed with water and saturated saline solution respectively, collected, dried with anhydrous sodium sulfate, and filtered, and the residue was concentrated under reduced pressure to obtain the crude product. The crude product was purified by column chromatography (ethyl acetate:n-hexane=2:1) to obtain the target compound as a yellow solid (23 g, yield of 57%). $^1$H NMR (500 MHz, DMSO-$d_6$) δ 8.76 (s, 1H), 6.16 (d, J=5.0 Hz, 1H), 5.80-5.70 (m, 1H), 5.46 (t, J=5.6 Hz, 1H), 4.32-4.20 (m, 2H), 4.17-4.09 (m, 1H), 1.98-1.93 (m, 3H), 1.91-1.88 (m, 3H), 1.86 (d, J=6.3 Hz, 3H).

S2: Synthesis of 2',3',5'-tri-O-acetyl-6-(3-iodobenzylamino)-2-chloropurine ribose

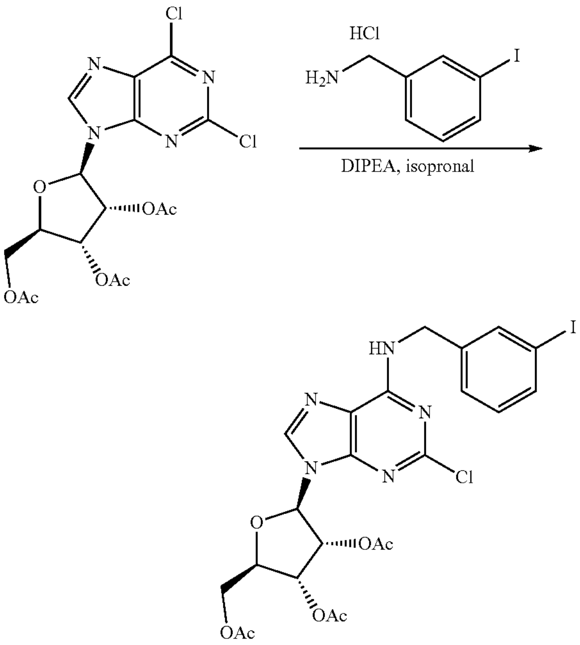

The reaction was performed according to the corresponding steps in example 1 to obtain the title compound as a yellow solid (8.1 g, yield of 100%).

S3: Synthesis of (2R,3R,4S,5R)-2-(6-(3-iodobenzylamino)-2-chloro-9H-purin-9-yl)-5-(hydroxylmethyl)-tetrahydrofuran-3,4-diol

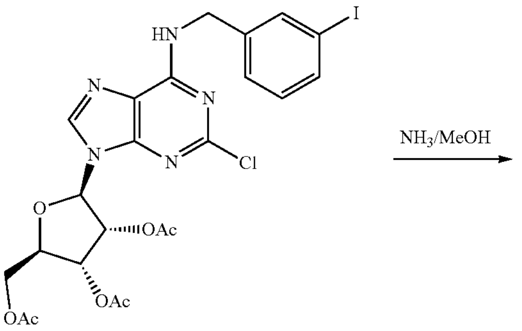

-continued

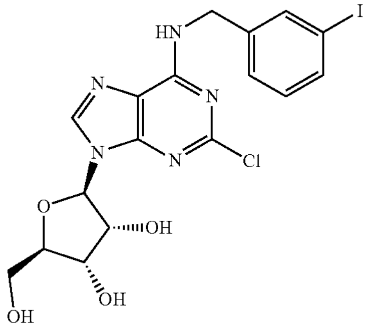

2',3',5'-tri-O-acetyl-6-(3-iodobenzylamino)-2-chloropurine ribose (8 g, 12.6 mmol) was dissolved in a methanol (50 mL) solvent, ammonia (5 mL, 7.0 M in MeOH) was added, the materials were stirred at a room temperature overnight, and the completion of the reaction was detected by TLC. It was concentrated under reduced pressure to remove the solvent, water was added to quench the reaction, an extraction was performed with ethyl acetate, organic layers were mixed, the organic layer was washed with water and saturated saline solution respectively, collected, dried with anhydrous sodium sulfate, and filtered, and the residue was concentrated under reduced pressure to obtain the crude product as a yellow oily substance (5.2 g, yield of 91%). LC-MS m/z [M+H]$^+$: 518.

S4: Synthesis of ((3aR,4R,6R,6aR)-2-(6-(3-iodophenylamino)-2-chloro-9H-purin-9-yl)-2,2-dimethyltetrahydrofuran[3,4-d][1,3]dioxo-4-yl)methanol

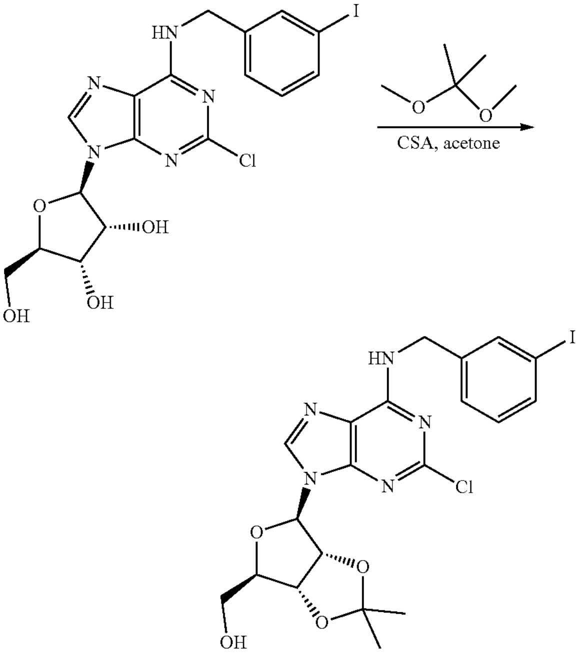

The reaction was performed according to the corresponding steps in example 1 to obtain the title compound as a white solid (5.5 g, yield of 64%).

S5: Synthesis of (3aS,4S,6R,6aR)-6-(6-(3-iodobenzylamino)-2-chloro-9H-purin-9-yl)-2,2-dimethyltetrahydrofuran[3,4-d][1,3]dioxo-4-carboxylic acid

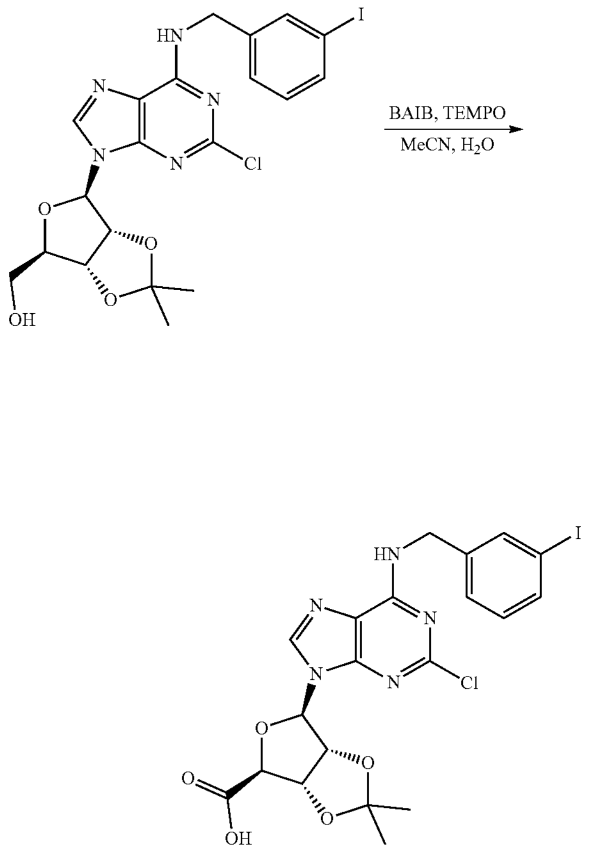

((3aR,4R,6R,6aR)-6-(6-(3-iodophenylamino)-2-chloro-9H-purin-9-yl)-2,2-dimethyltetrahydrofuran[3,4-d][1,3]dioxo-4-yl)methanol (5.5 g, 9.9 mmol) was dissolved in a mixed solvent of acetonitrile (40 mL) and water (40 mL), and iodophenyldiacetic acid (7.0 g, 21.7 mmol) and 2,2,6,6-tetramethylpiperidine oxide (308 mg, 2.0 mmol) were added sequentially. The materials were stirred at room temperature overnight, and the completion of the reaction was detected by TLC. It was concentrated under reduced pressure to remove the solvent, water was added to quench the reaction, pH was adjusted to be >7 by using sodium hydroxide solution, an extraction was performed with ethyl acetate, after an aqueous layer was collected, the aqueous layer was then adjusted to have a pH<7 by using concentrated hydrochloric acid, an extraction was performed with ethyl acetate, the organic layer was washed with water and saturated saline solution, collected, dried with anhydrous sodium sulfate, and filtered, and the residue was concentrated under reduced pressure to obtain the crude product as a yellow solid (3.5 g, yield of 63%). $^1$H NMR (500 MHz, DMSO-$d_6$) δ 8.33-8.18 (m, 1H), 7.74 (s, 1H), 7.61 (d, J=7.7 Hz, 1H), 7.43-7.31 (m, 1H), 7.14 (t, J=7.7 Hz, 1H), 6.37-6.28 (m, 1H), 5.55-5.46 (m, 1H), 5.42 (d, J=5.9 Hz, 1H), 5.16-4.92 (m, 1H), 4.75 (d, J=33.0 Hz, 1H), 4.58 (d, J=6.1 Hz, 1H), 1.95 (d, J=40.0 Hz, 3H), 1.50 (d, J=13.1 Hz, 3H), 1.35 (s, 2H).

S6: Synthesis of (3aS,4S,6R,6aR)-6-(6-(3-iodobenzylamino)-2-chloro-9H-purin-9-yl)-N-methyl-D3,2,2-dimethyl-tetrahydrofuran[3,4-d][1,3]dioxo-formamide

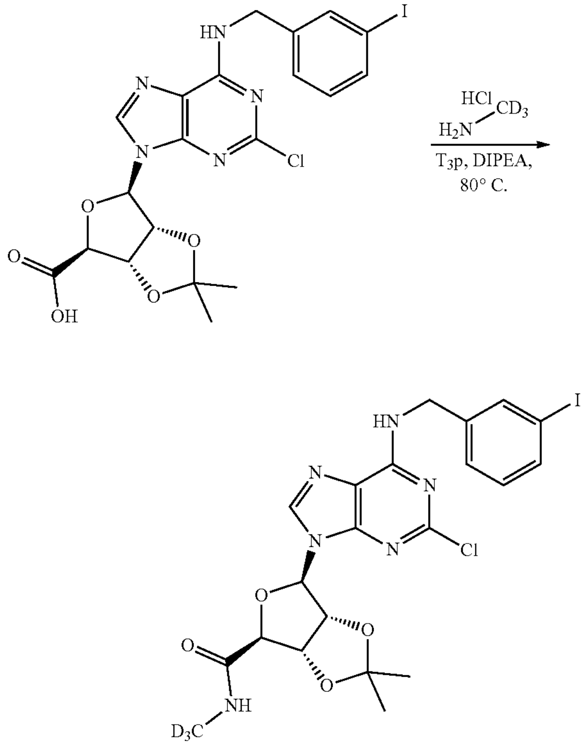

The reaction was performed according to the corresponding steps in example 1 to obtain the title compound as a yellow solid (1.0 g, yield of 50%). LC-MS m/z [M+H]$^+$: 588.

S7: Synthesis of (2S,3S,4R,5R)-5-(6-(3-iodobenzylamino)-2-chloro-9H-purin-9-yl)-3,4-dihydroxy-N-(methyl-d3)-tetrahydrofuran-2-formamide (compound 8)

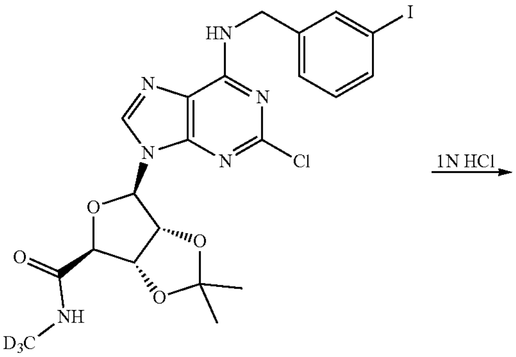

-continued

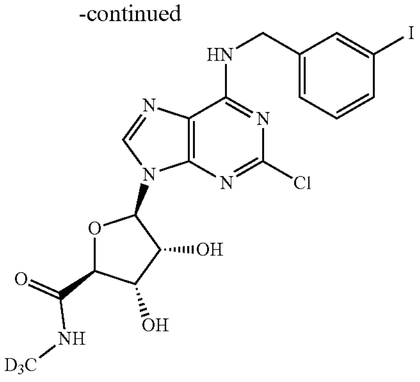

The reaction was performed according to the corresponding steps in example 1 to obtain the title compound as a white solid (1.0 g, yield of 50%). LC-MS m/z $[M+1]^+$: 548.2; $^1H$ NMR (500 MHz, DMSO-$d_6$) δ 9.05 (t, J=6.1 Hz, 1H), 8.51 (s, 1H), 8.28 (s, 1H), 7.76 (s, 1H), 7.62 (d, J=7.7 Hz, 1H), 7.36 (d, J=7.6 Hz, 1H), 7.14 (t, J=7.7 Hz, 1H), 5.93 (d, J=7.3 Hz, 1H), 5.76 (d, J=4.2 Hz, 1H), 5.61 (d, J=6.2 Hz, 1H), 4.62 (d, J=5.9 Hz, 2H), 4.59-4.53 (m, 1H), 4.33 (s, 1H), 4.17 (s, 1H).

Example 7: Synthesis of (2S,3S,4R,5R)-5-(2-chloro-6-((methyl-d3)-amino)-9H-purin-9-yl)-3,4-dihydroxyl-N-methyl-tetrahydrofuran-2-formamide (compound 9)

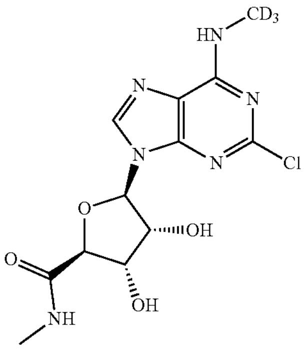 [SMILES: [2H]C([2H])([2H])Nc1nc(Cl)nc2c1ncn2[C@@H]1O[C@H](C(=O)NC)[C@@H](O)[C@H]1O]

Referring to specific operations of example 6, the title compound as a white solid was obtained (55 mg, yield of 10%). LC-MS m/z $[M+1]^+$: 346.2; $^1H$ NMR (500 MHz, DMSO-$d_6$) δ 8.45 (s, 1H), 8.37 (s, 1H), 8.33 (d, J=4.6 Hz, 1H), 5.92 (d, J=7.4 Hz, 1H), 5.74 (d, J=4.5 Hz, 1H), 5.59 (d, J=6.4 Hz, 1H), 4.55 (dd, J=11.5, 6.8 Hz, 1H), 4.33 (d, J=1.4 Hz, 1H), 4.16 (td, J=4.5, 1.7 Hz, 1H), 2.74 (d, J=4.7 Hz, 3H).

Example 8: Synthesis of (2S,3S,4R,5R)-5-(6-(benzylamino)-2-(pyridin-3-yl)-9H-purin-9-yl)-3,4-dihydroxyl-N-(methyl-d3)-tetrahydrofuran-2-formamide (compound 10)

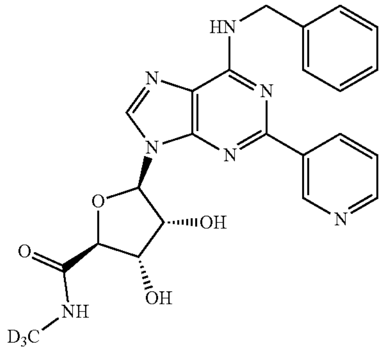 [SMILES: [2H]C([2H])([2H])NC(=O)[C@H]1O[C@@H](n2cnc3c(NCc4ccccc4)nc(-c4cccnc4)nc32)[C@H](O)[C@@H]1O]

S1: Synthesis of 2',3',5'-tri-O-acetyl-6-(benzylamino)-2-chloropurine ribose

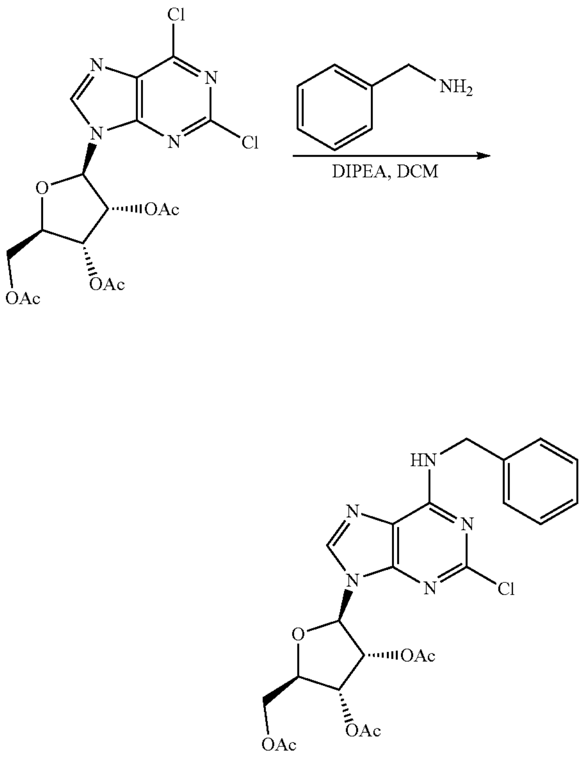

Referring an operation of S2 in example 6, the target compound as a white solid was obtained (21 g, yield of 83%).

S2: Synthesis of (2R,3R,4S,5R)-2-(6-(benzylamino)-2-chloro-9H-purin-9-yl)-5-(hydroxylmethyl)-tetrahydrofuran-3,4-diol

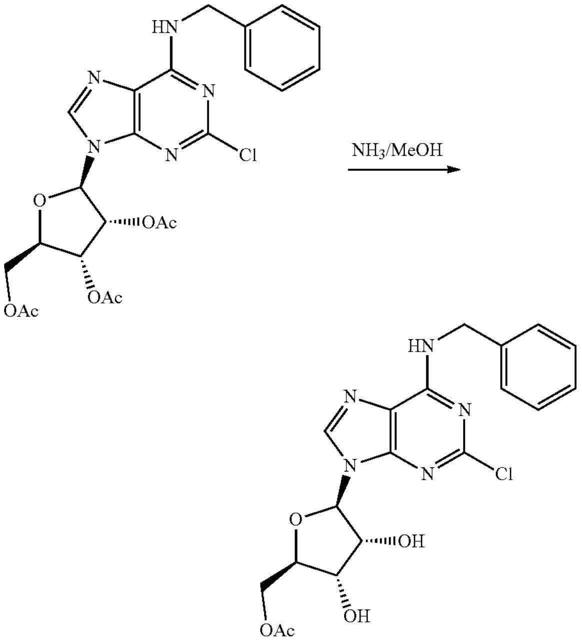

Referring an operation of S3 in example 6, the title compound as a yellow oily substance was obtained (16 g, yield of 100%).

S4: Synthesis of (((3aR,4R,6R,6aR)-6-(6-(benzylamino)-2-chloro-9H-purin-9-yl)-2,2-dimethyltetrahydrofuran[3,4-d][1,3]-dioxazol-4-yl)methanol

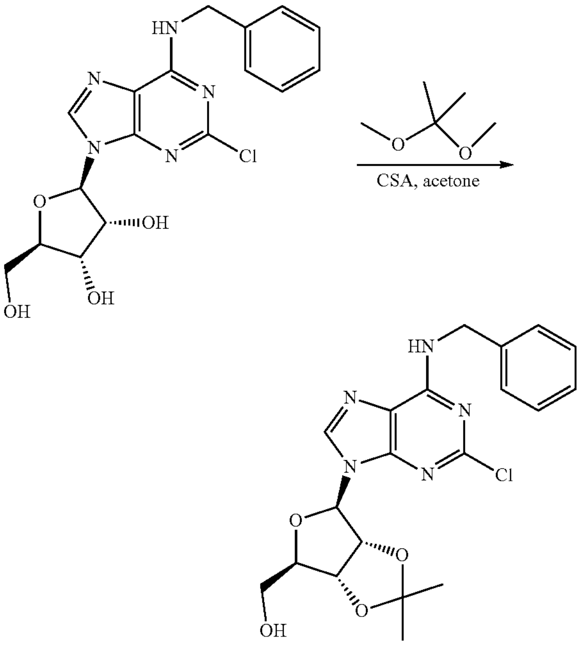

Referring an operation of S4 in example 6, the title compound as a yellow solid was obtained (18 g, yield of 100%). $^1$H NMR (500 MHz, DMSO-$d_6$) δ 8.89 (dd, J=49.2, 43.1 Hz, 1H), 8.38 (s, 1H), 7.40-7.28 (m, 4H), 7.23 (t, J=6.7 Hz, 1H), 6.07 (d, J=2.5 Hz, 1H), 5.34-5.22 (m, 1H), 5.08 (t, J=5.4 Hz, 1H), 4.93 (dd, J=6.0, 2.5 Hz, 1H), 4.65 (d, J=6.1 Hz, 2H), 4.26-4.17 (m, 1H), 3.60-3.50 (m, 2H), 1.54 (s, 3H), 1.33 (s, 3H).

S5: Synthesis of (3aS,4S,6R,6aR)-6-(6-(benzylamino)-2-chloro-9H-purin-9-yl)-2,2-dimethyltetrahydrofuran[3,4-d][1,3]dioxo-4-carboxylic acid

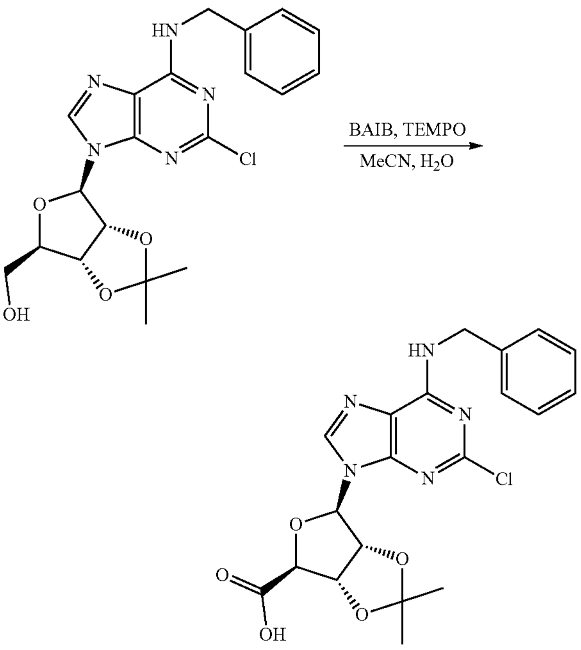

Referring an operation of S5 in example 6, the title compound as a white solid was obtained (14 g, yield of 88%). $^1$H NMR (500 MHz, DMSO-$d_6$) δ 12.87 (s, 1H), 8.85 (dd, J=51.9, 45.8 Hz, 1H), 8.29 (s, 1H), 7.39-7.28 (m, 4H), 7.24 (dt, J=8.4, 2.0 Hz, 1H), 6.31 (d, J=9.1 Hz, 1H), 5.50 (d, J=5.8 Hz, 1H), 5.42 (d, J=5.9 Hz, 1H), 4.71 (t, J=2.2 Hz, 1H), 4.63 (d, J=6.1 Hz, 2H), 1.52 (s, 3H), 1.36 (s, 3H).

S6: Synthesis of (3aS,4S,6R,6aR)-6-(6-(benzylamino)-2-chloro-9H-purin-9-yl)-N-methyl-D3,2,2-dimethyl-tetrahydrofuran[3,4-d][1,3]dioxo-4-formamide

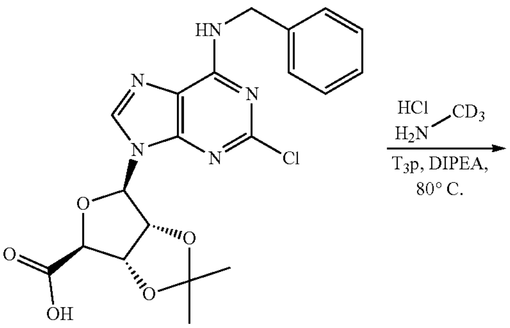

-continued

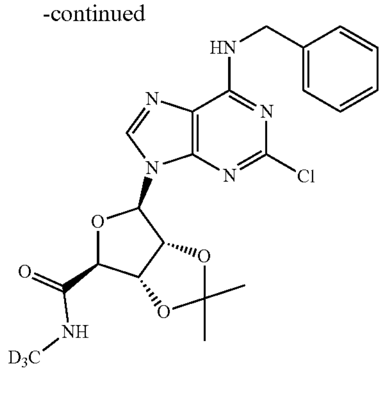

Referring an operation of S6 in example 6, the title compound as a white solid was obtained (4.4 g, yield of 61%). $^1$H NMR (500 MHz, DMSO-$d_6$) δ 8.87 (dd, J=52.1, 46.3 Hz, 1H), 8.29 (s, 1H), 7.52 (d, J=15.7 Hz, 1H), 7.36-7.30 (m, 4H), 7.27-7.20 (m, 1H), 6.27 (s, 1H), 5.39-5.30 (m, 2H), 4.67 (dd, J=24.2, 7.9 Hz, 2H), 4.57 (d, J=1.2 Hz, 1H), 1.53 (d, J=10.5 Hz, 3H), 1.34 (s, 3H).

S7: Synthesis of (3aS,4S,6R,6aR)-6-(6-(benzylamino)-2-(pyridin-3-yl)-9H-purin-9-yl)-N-methyl-D3,2,2-dimethyl-tetrahydrofuran[3,4-d][1,3]dioxin-4-formamide

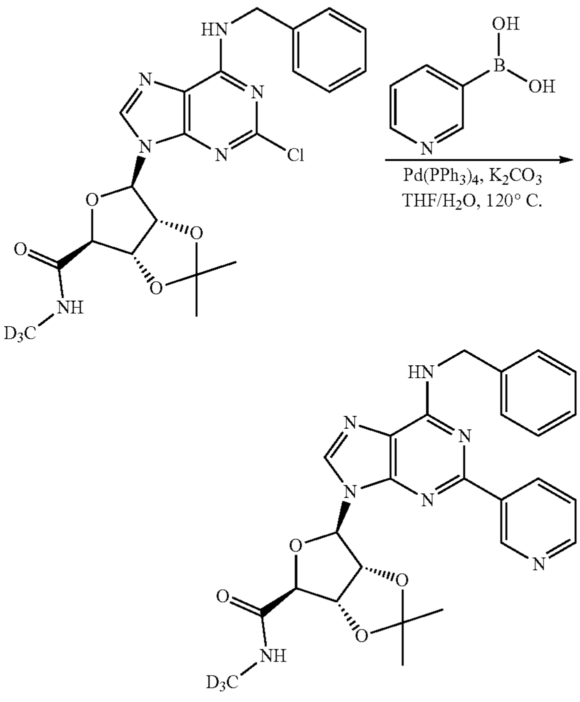

(3aS,4S,6R,6aR)-6-(6-(benzylamino)-2-chloro-9H-purin-9-yl)-N-methyl-D3,2,2-dimethyl-tetrahydrofuran[3,4-d][1,3]dioxo-4-formamide (200 mg, 0.4 mmol) was dissolved in a mixed solvent of tetrahydrofuran (10 mL) and water (5 mL), and potassium carbonate (180 mg, 1.3 mmol), pyridin-3-yl boric acid (136 mg, 0.9 mmol), and Pd($PPh_3$)$_4$ (50 mg, 0.04 mmol) were added sequentially. Under the protection of nitrogen, the materials were heated to 120° C. and stirred under high pressure overnight, and the completion of the reaction was detected by TLC. Water was added to quench the reaction, an extraction was performed with ethyl acetate, organic layers were mixed, the organic layer was washed with water and saturated saline solution, collected, dried with anhydrous sodium sulfate, and filtered, and the residue was concentrated under reduced pressure to obtain the crude product. The crude product was purified by column chromatography (ethyl acetate:n-hexane=2:1) to obtain the target compound as a white solid (90 mg, yield of 42%). $^1$H NMR (500 MHz, DMSO-$d_6$) δ 9.41 (s, 1H), 8.68-8.53 (m, 3H), 8.34 (s, 1H), 7.55-7.18 (m, 7H), 6.46 (s, 1H), 5.59 (dd, J=6.0, 1.8 Hz, 1H), 5.50 (d, J=6.0 Hz, 1H), 4.77 (d, J=36.5 Hz, 2H), 4.62 (d, J=2.0 Hz, 1H), 1.56 (s, 3H), 1.35 (d, J=8.7 Hz, 3H).

S8: Synthesis of (2S,3S,4R,5R)-5-(6-(benzylamino)-2-(pyridin-3-yl)-9H-purin-9-yl)-3,4-dihydroxyl-N-(methyl-d3)-tetrahydrofuran-2-formamide (compound 10)

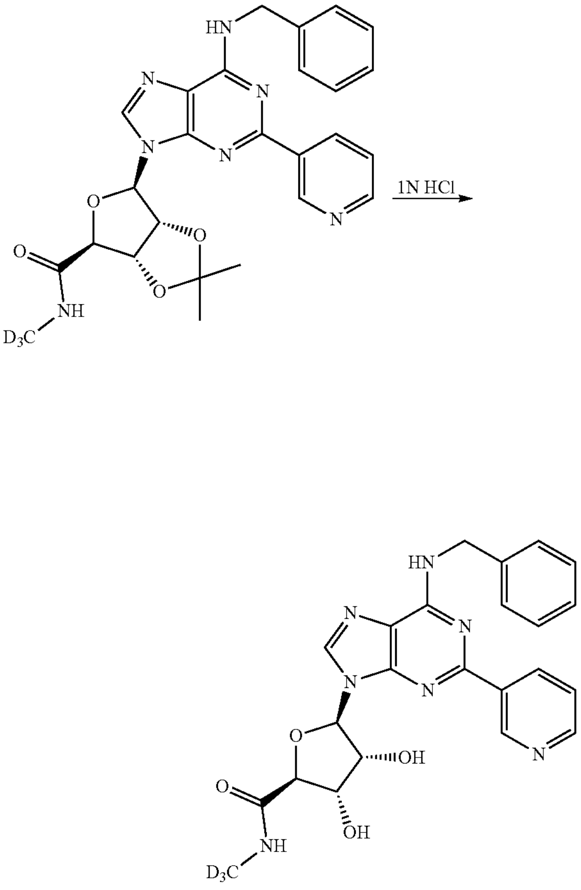

The reaction was performed according to the corresponding steps in example 6 to obtain the title compound as a white solid (51 mg, yield of 61%). LC-MS m/z $[M+1]^+$: 465.3; $^1$H NMR (500 MHz, DMSO-$d_6$) δ 9.44 (s, 1H), 8.77-8.50 (m, 4H), 7.92 (s, 1H), 7.51 (dd, J=7.7, 4.9 Hz, 1H), 7.45 (d, J=7.4 Hz, 2H), 7.32 (t, J=7.6 Hz, 2H), 7.22 (t, J=7.2 Hz, 1H), 6.09 (d, J=6.8 Hz, 1H), 5.69 (s, 2H), 4.95-4.88 (m, 1H), 4.83 (s, 2H), 4.34 (d, J=6.9 Hz, 2H).

Example 9: Following the Reactions Shown in Example 8, the Compounds in the Table Below were Obtained

| No. | Compound structure and name | Characterization data |
|---|---|---|
| 11 | 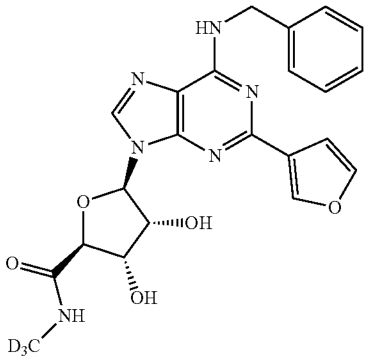 [SMILES: [2H]C([2H])([2H])NC(=O)[C@H]1O[C@@H](n2cnc3c(NCc4ccccc4)nc(-c4ccoc4)nc32)[C@H](O)[C@@H]1O] (2S,3S,4R,5R)-5-(6-(benzylamino)-2-(furan-3-yl)-9H-purin-9-yl)-3,4-dihydroxyl-N-(methyl-d3)-tetrahydrofuran-2-formamide | LC-MS m/z $[M + 1]^+$: 454.3; $^1H$ NMR (500 MHz, DMSO-$d_6$) δ: 8.45 (s, 2H), 8.25 (s, 1H), 7.91 (s, 1H), 7.74 (s, 1H), 7.45 (s, 2H), 7.31 (s, 2H), 7.22 (s, 1H), 6.96 (s, 1H), 6.03 (d, J = 5.2 Hz, 1H), 5.67 (s, 1H), 5.58 (s, 1H), 4.80 (d, J = 44.9 Hz, 3H), 4.33 (s, 2H). |
| 12 | 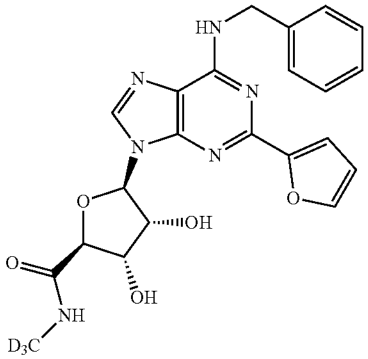 [SMILES: [2H]C([2H])([2H])NC(=O)[C@H]1O[C@@H](n2cnc3c(NCc4ccccc4)nc(-c4ccco4)nc32)[C@H](O)[C@@H]1O] (2S,3S,4R,5R)-5-(6-(benzylamino)-2-(furan-2-yl)-9H-purin-9-yl)-3,4-dihydroxyl-N-(methyl-d3)-tetrahydrofuran-2-formamide | LC-MS m/z $[M + 1]^+$: 454.3; $^1H$ NMR (500 MHz, DMSO-$d_6$) δ: 8.57 (s, 1H), 8.47 (s, 1H), 8.06 (s, 1H), 7.84 (s, 1H), 7.44 (d, J = 6.8 Hz, 2H), 7.31 (t, J = 7.5 Hz, 2H), 7.21 (t, J = 7.2 Hz, 1H), 7.14 (s, 1H), 6.64 (s, 1H), 6.02 (d, J = 7.2 Hz, 1H), 5.72 (d, J = 4.2 Hz, 1H), 5.59 (d, J = 6.2 Hz, 1H), 4.78 (dd, J = 11.7, 6.4 Hz, 3H), 4.33 (s, 1H), 4.24 (s, 1H). |
| 13 | 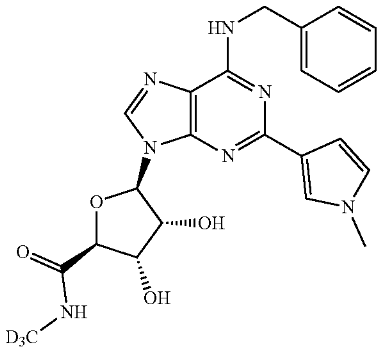 (2S,3S,4R,5R)-5-(6-(benzylamino)-2-(1-methyl-1H-pyrrol-3-yl)-9H-purin-9-yl)-3,4-dihydroxyl-N-(methyl-d3)-tetrahydrofuran-2-formamide | LC-MS m/z $[M + 1]^+$: 467.3; $^1H$ NMR (500 MHz, DMSO-$d_6$) δ: 8.38 (s, 1H), 8.27 (s, 1H), 8.00 (d, J = 10.8 Hz, 1H), 7.49 (d, J = 7.3 Hz, 2H), 7.42 (s, 1H), 7.36 (t, J = 7.5 Hz, 2H), 7.26 (t, J = 7.2 Hz, 1H), 6.76 (s, 1H), 6.63 (s, 1H), 6.04 (d, J = 7.0 Hz, 1H), 5.72 (d, J = 4.1 Hz, 1H), 5.61 (d, J = 6.3 Hz, 1H), 4.91 (dd, J = 11.1, 6.3 Hz, 1H), 4.81 (s, 2H), 4.36 (s, 2H), 3.72 (s, 3H). |

-continued

| No. | Compound structure and name | Characterization data |
| --- | --- | --- |
| 14 | 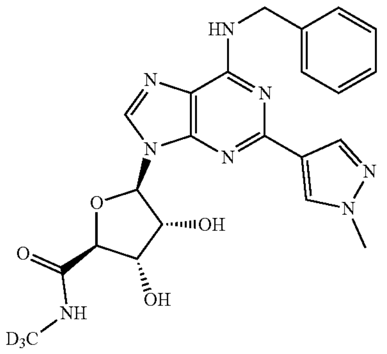 (2S,3S,4R,5R)-5-(6-(benzylamino)-2-(1-methyl-1H-pyrazolyl-4-yl)-9H-purin-9-yl)-3,4-dihydroxyl-N-(methyl-d3)-tetrahydrofuran-2-formamide | LC-MS m/z $[M+1]^+$: 468.3; $^1H$ NMR (500 MHz, DMSO-$d_6$) δ: 8.40 (s, 2H), 8.21 (s, 1H), 7.92 (d, J = 6.0 Hz, 2H), 7.44 (d, J = 6.6 Hz, 2H), 7.31 (t, J = 7.4 Hz, 2H), 7.21 (t, J = 7.1 Hz, 1H), 6.01 (d, J = 6.8 Hz, 1H), 5.67 (d, J = 3.4 Hz, 1H), 5.56 (d, J = 6.1 Hz, 1H), 5.16 - 4.53 (m, 3H), 4.31 (s, 2H), 3.89 (s, 3H). |
| 15 | 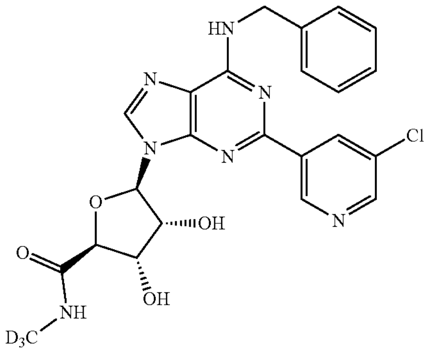 (2S,3S,4R,5R)-5-(6-(benzylamino)-2-(5-chloropyridin-3-yl)-9H-purin-9-yl)-3,4-dihydroxyl-N-(methyl-d3)-tetrahydrofuran-2-formamide | LC-MS m/z $[M+1]^+$: 499.2; $^1H$ NMR (400 MHz, DMSO-$d_6$) δ: 9.37 (s, 1H), 8.80 (s, 1H), 8.71 (s, 1H), 8.61 (s, 1H), 8.56 (s, 1H), 7.94 (s, 1H), 7.44 (d, J = 7.4 Hz, 2H), 7.32 (t, J = 7.5 Hz, 2H), 7.22 (t, J = 7.3 Hz, 1H), 6.10 (d, J = 6.8 Hz, 1H), 4.99 - 4.86 (m, 1H), 4.81 (d, J = 4.8 Hz, 2H), 4.36 (d, J = 1.9 Hz, 1H), 4.34 - 4.29 (m, 1H), 4.11 - 3.95 (m, 2H). |
| 16 | 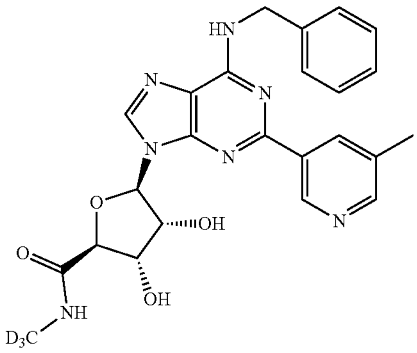 [SMILES: [2H]C([2H])([2H])NC(=O)[C@H]1O[C@@H](n2cnc3c(NCc4ccccc4)nc(-c4cncc(C)c4)nc32)[C@H](O)[C@@H]1O] (2S,3S,4R,5R)-5-(6-(benzylamino)-2-(5-methylpyridin-3-yl)-9H-purin-9-yl)-3,4-dihydroxyl-N-(methyl-d3)-tetrahydrofuran-2-formamide | LC-MS m/z $[M+1]^+$: 479.3; $^1H$ NMR (400 MHz, DMSO-$d_6$) δ: 9.24 (s, 1H), 8.68 (s, 1H), 8.54 (s, 1H), 8.47 (s, 1H), 8.37 (s, 1H), 7.94 (s, 1H), 7.44 (d, J = 7.4 Hz, 2H), 7.31 (t, J = 7.5 Hz, 2H), 7.21 (t, J = 7.3 Hz, 1H), 6.09 (d, J = 7.0 Hz, 1H), 5.72 (d, J = 4.5 Hz, 1H), 5.62 (d, J = 6.4 Hz, 1H), 4.89 (dd, J = 11.3, 6.6 Hz, 1H), 4.80 (s, 2H), 4.39 - 4.28 (m, 2H), 2.39 (s, 3H). |

-continued

| No. | Compound structure and name | Characterization data |
|---|---|---|
| 17 | 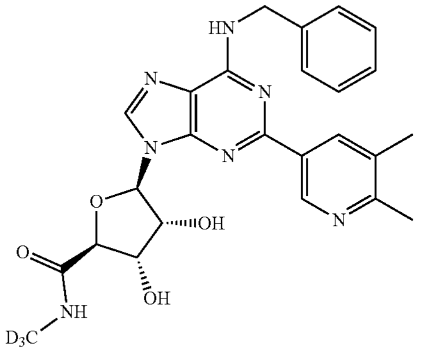 (2S,3S,4R,5R)-5-(6-(benzylamino)-2-(5,6-dimethylpyridin-3-yl)-9/-purin-9-yl)-3,4-dihydroxyl-N-(methyl-d3)-tetrahydrofuran-2-formamide | LC-MS m/z $[M + 1]^+$: 493.3; $^1H$ NMR (500 MHz, DMSO-$d_6$) δ: 9.11 (s, 1H), 8.60 (s, 1H), 8.50 (s, 1H), 8.27 (s, 1H), 7.91 (s, 1H), 7.44 (d, J = 7.1 Hz, 2H), 7.31 (t, J = 7.5 Hz, 2H), 7.21 (t, J = 7.1 Hz, 1H), 6.08 (d, J = 6.8 Hz, 1H), 5.73 (s, 1H), 5.63 (s, 1H), 4.88 (s, 1H), 4.79 (s, 2H), 4.34 (s, 2H), 2.47 (s, 3H), 2.33 (s, 3H). |
| 18 | 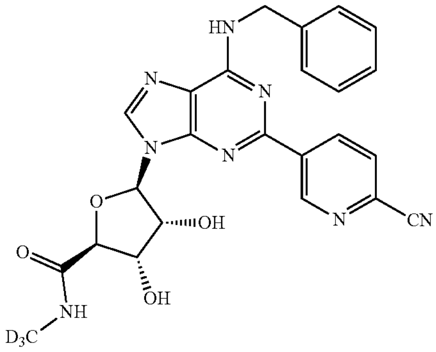 [SMILES: [2H]C([2H])([2H])NC(=O)[C@H]1O[C@@H](n2cnc3c(NCc4ccccc4)nc(-c4ccc(C#N)nc4)nc32)[C@H](O)[C@@H]1O] (2S,3S,4R,5R)-5-(6-(benzylamino)-2-(6-cyanopyridin-3-yl)-9H-purin-9-yl)-3,4-dihydroxyl-N-(methyl-d3)-tetrahydrofuran-2-formamide | LC-MS m/z $[M + 1]^+$: 490.3; $^1H$ NMR (500 MHz, DMSO-$d_6$) δ: 9.55 (s, 1H), 8.92 - 8.69 (m, 2H), 8.61 (s, 1H), 8.15 (d, J = 8.1 Hz, 1H), 7.91 (s, 1H), 7.44 (d, J = 7.5 Hz, 2H), 7.31 (t, J = 7.6 Hz, 2H), 7.21 (t, J = 7.3 Hz, 1H), 6.10 (d, J = 6.7 Hz, 1H), 5.68 (s, 2H), 4.90 - 4.86 (m, 1H), 4.82 (s, 2H), 4.34 (dd, J = 7.8, 3.2 Hz, 2H). |
| 19 | 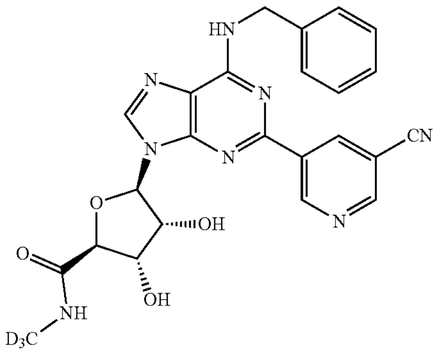 [SMILES: [2H]C([2H])([2H])NC(=O)[C@H]1O[C@@H](n2cnc3c(NCc4ccccc4)nc(-c4cncc(C#N)c4)nc32)[C@H](O)[C@@H]1O] (2S,3S,4R,5R)-5-(6-(benzylamino)-2-(5-cyanopyridin-3-yl)-9H-purin-9-yl)-3,4-dihydroxyl-N-(methyl-d3)-tetrahydrofuran-2-formamide | LC-MS m/z $[M + 1]^+$: 490.3; $^1H$ NMR (500 MHz, DMSO-$d_6$) δ: 9.65 (s, 1H), 9.09 (s, 1H), 8.94 (d, J = 1.8 Hz, 1H), 8.79 (s, 1H), 8.59 (s, 1H), 7.93 (s, 1H), 7.45 (d, J = 7.4 Hz, 2H), 7.31 (t, J = 7.6 Hz, 2H), 7.22 (t, J = 7.3 Hz, 1H), 6.10 (d, J = 6.7 Hz, 1H), 5.71 (s, 2H), 4.93 - 4.86 (m, 1H), 4.83 (d, J = 4.6 Hz, 2H), 4.43 - 4.26 (m, 2H). |

-continued

| No. | Compound structure and name | Characterization data |
|---|---|---|
| 20 | 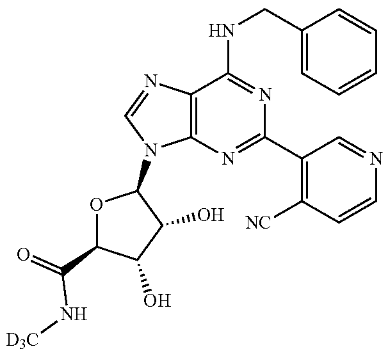 [SMILES: [2H]C([2H])([2H])NC(=O)[C@H]1O[C@@H](n2cnc3c(NCc4ccccc4)nc(-c4cnccc4C#N)nc32)[C@H](O)[C@@H]1O] (2S,3S,4R,5R)-5-(6-(benzylamino)-2-(4-cyanopyridin-3-yl)-9H-purin-9-yl)-3,4-dihydroxyl-N-(methyl-d3)-tetrahydrofuran-2-formamide | LC-MS m/z $[M + 1]^+$: 490.3; $^1H$ NMR (500 MHz, DMSO-$d_6$) δ: 9.52 (s, 1H), 8.95 – 8.77 (m, 2H), 8.61 (s, 1H), 8.11 – 7.83 (m, 2H), 7.41 (d, J = 7.4 Hz, 2H), 7.29 (t, J = 7.5 Hz, 2H), 7.20 (t, J = 7.2 Hz, 1H), 6.08 (d, J = 6.9 Hz, 1H), 5.69 (d, J = 4.4 Hz, 1H), 5.55 (d, J = 6.2 Hz, 1H), 5.02 – 4.84 (m, 3H), 4.33 (s, 1H), 4.29 (s, 1H). |
| 21 | 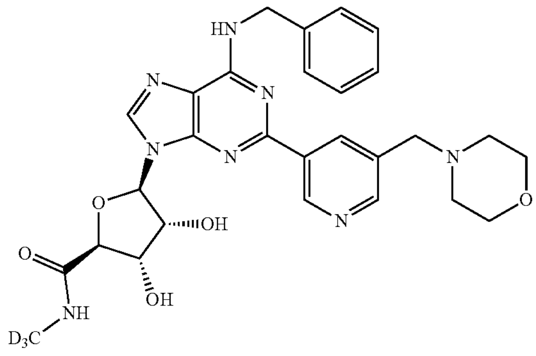 [SMILES: [2H]C([2H])([2H])NC(=O)[C@H]1O[C@@H](n2cnc3c(NCc4ccccc4)nc(-c4cncc(CN5CCOCC5)c4)nc32)[C@H](O)[C@@H]1O] (2S,3S,4R,5R)-5-(6-(benzylamino)-2-(5-morpholinomethyl)pyridin-3-yl)-9H-purin-9-yl)-3,4-dihydroxyl-N-(methyl-d3)-tetrahydrofuran-2-formamide | LC-MS m/z $[M + 1]^+$: 564.4; $^1H$ NMR (500 MHz, DMSO-$d_6$) δ: 9.32 (s, 1H), 8.70 (s, 1H), 8.53 (dd, J = 11.2, 9.2 Hz, 3H), 7.92 (s, 1H), 7.46 (d, J = 7.3 Hz, 2H), 7.31 (t, J = 7.6 Hz, 2H), 7.21 (t, J = 7.3 Hz, 1H), 6.12 (dd, J = 27.2, 7.1 Hz, 1H), 5.67 (d, J = 43.9 Hz, 2H), 4.96 – 4.88 (m, 1H), 4.80 (s, 2H), 4.34 (dd, J = 12.2, 3.2 Hz, 2H), 3.64 – 3.54 (m, 6H), 2.38 (d, J = 18.0 Hz, 4H). |
| 22 | 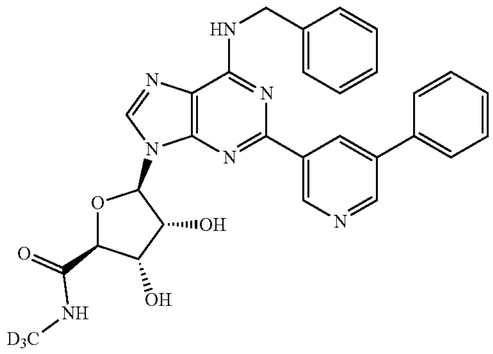 [SMILES: [2H]C([2H])([2H])NC(=O)[C@H]1O[C@@H](n2cnc3c(NCc4ccccc4)nc(-c4cncc(-c5ccccc5)c4)nc32)[C@H](O)[C@@H]1O] (2S,3S,4R,5R)-5-(6-(benzylamino)-2-(5-phenylpyridin-3-yl)-9H-purin-9-yl)-3,4-dihydroxyl-N-(methyl-d3)-tetrahydrofuran-2-formamide | LC-MS m/z $[M + 1]^+$: 541.4; $^1H$ NMR (500 MHz, DMSO-$d_6$)) δ 9.41 (s, 1H), 8.95 (s, 1H), 8.74 (s, 2H), 8.57 (s, 1H), 7.94 (s, 1H), 7.77 (d, J = 7.3 Hz, 2H), 7.57 (t, J = 7.5 Hz, 2H), 7.48 (dd, J = 11.9, 7.1 Hz, 3H), 7.31 (t, J = 7.5 Hz, 2H), 7.22 (d, J = 7.2 Hz, 1H), 6.11 (d, J = 6.8 Hz, 1H), 5.65 (d, J = 34.9 Hz, 2H), 4.99 – 4.89 (m, 1H), 4.80 (s, 2H), 4.36 (s, 2H). |

-continued

| No. | Compound structure and name | Characterization data |
|---|---|---|
| 23 | 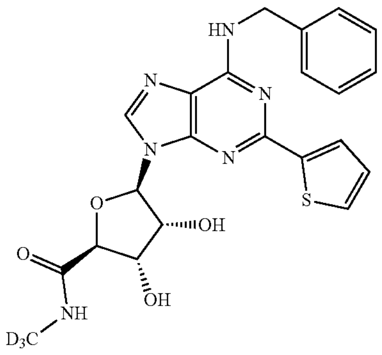 (2S,3S,4R,5R)-5-(6-(benzylamino)-2-(thiophen-2-yl)-9H-purin-9-yl)-3,4-dihydroxyl-N-(methyl-d3)-tetrahydrofuran-2-formamide | LC-MS m/z $[M+1]^+$: 470.3; $^1H$ NMR (500 MHz, DMSO-$d_6$) δ: 8.57 (s, 1H), 8.47 (s, 1H), 7.88 (s, 1H), 7.82 - 7.77 (m, 1H), 7.62 (d, J = 4.9 Hz, 1H), 7.46 (d, J = 7.0 Hz, 2H), 7.30 (t, J = 7.6 Hz, 2H), 7.21 (t, J = 7.3 Hz, 1H), 7.16 - 7.11 (m, 1H), 6.02 (d, J = 6.8 Hz, 1H), 5.67 (d, J = 4.5 Hz, 1H), 5.58 (d, J = 6.2 Hz, 1H), 4.86 - 4.68 (m, 3H), 4.32 (s, 2H). |
| 24 | 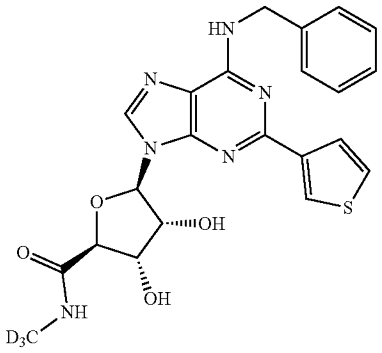 (2S,3S,4R,5R)-5-(6-(benzylamino)-2-(thiophen-3-yl)-9H-purin-9-yl)-3,4-dihydroxyl-N-(methyl-d3)-tetrahydrofuran-2-formamide | LC-MS m/z $[M+1]^+$: 470.3; $^1H$ NMR (500 MHz, DMSO-$d_6$) δ: 8.45 (s, 2H), 8.17 (s, 1H), 7.89 (s, 1H), 7.73 (d, J = 4.7 Hz, 1H), 7.62 - 7.53 (m, 1H), 7.44 (d, J = 6.9 Hz, 2H), 7.30 (t, J = 7.4 Hz, 2H), 7.21 (d, J = 7.2 Hz, 1H), 6.04 (d, J = 6.8 Hz, 1H), 5.65 (d, J = 4.0 Hz, 1H), 5.56 (d, J = 6.2 Hz, 1H), 4.97 - 4.66 (m, 3H), 4.32 (s, 2H). |
| 25 | 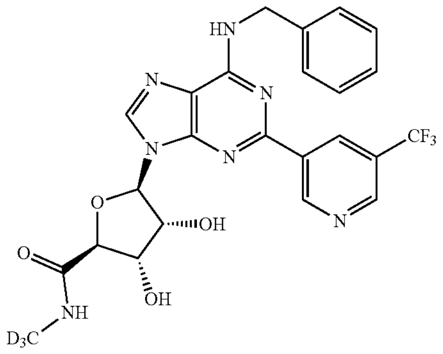 [SMILES: [2H]C([2H])([2H])NC(=O)[C@H]1O[C@@H](n2cnc3c(NCc4ccccc4)nc(-c4cncc(C(F)(F)F)c4)nc32)[C@H](O)[C@@H]1O] (2S,3S,4R,5R)-5-(6-(benzylamino)-2-(5-trifluoromethyl)pyridin-3-yl)-9H-purin-9-yl)-3,4-dihydroxyl-N-(methyl-d3)-tetrahydrofuran-2-formamide | LC-MS m/z $[M+1]^+$: 533.4; $^1H$ NMR (500 MHz, DMSO-$d_6$) δ: 9.66 (d, J = 21.2 Hz, 1H), 9.05 (s, 1H), 8.80 (dd, J = 9.7, 9.2 Hz, 2H), 8.60 (s, 1H), 7.91 (s, 1H), 7.45 (d, J = 7.4 Hz, 2H), 7.31 (t, J = 7.6 Hz, 2H), 7.22 (d, J = 7.2 Hz, 1H), 6.11 (d, J = 6.8 Hz, 1H), 5.69 (d, J = 4.4 Hz, 1H), 5.60 (d, J = 5.9 Hz), 4.89 (d, J = 5.1 Hz, 1H), 4.79 (s, 2H), 4.34 (dd, J = 14.4, 2.1 Hz, 2H). |

-continued

| No. | Compound structure and name | Characterization data |
|---|---|---|
| 26 | 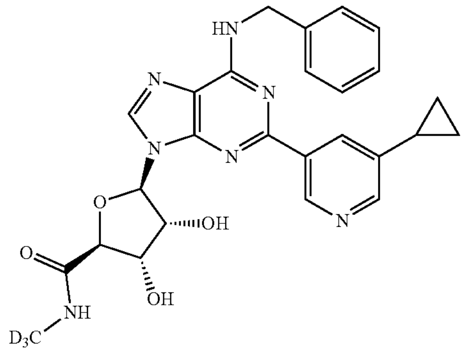 [SMILES: [2H]C([2H])([2H])NC(=O)[C@H]1O[C@@H](n2cnc3c(NCc4ccccc4)nc(-c4cncc(C5CC5)c4)nc32)[C@H](O)[C@@H]1O] (2S,3S,4R,5R)-5-(6-(benzylamino)-2-(5-cyclopropylpyridin-3-yl)-9H-purin-9-yl)-3,4-dihydroxyl-N-methyl-3-tetrahydrofuran-2-formamide | LC-MS m/z $[M+1]^+$: 505.4; $^1H$ NMR (500 MHz, DMSO-$d_6$) δ: 9.19 (s, 1H), 8.67 (d, J = 0.9 Hz, 1H), 8.52 (s, 1H), 8.44 (s, 1H), 8.13 (s, 1H), 7.89 (s, 1H), 7.44 (d, J = 6.8 Hz, 2H), 7.31 (t, J = 7.3 Hz, 2H), 7.22 (d, J = 7.0 Hz, 1H), 6.08 (d, J = 6.7 Hz, 1H), 5.67 (d, J = 3.5 Hz, 1H), 5.58 (d, J = 6.2 Hz, 1H), 4.92 (d, J = 4.3 Hz, 1H), 4.78 (s, 2H), 4.34 (s, 2H), 2.04 (d, J = 4.3 Hz, 1H), 1.06 (d, J = 7.6 Hz, 2H), 0.83 − 0.73 (m, 2H). |
| 27 | 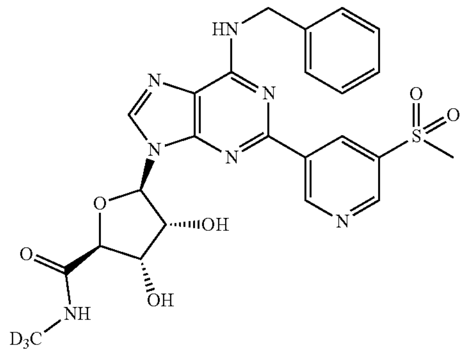 [SMILES: [2H]C([2H])([2H])NC(=O)[C@H]1O[C@@H](n2cnc3c(NCc4ccccc4)nc(-c4cncc(S(C)(=O)=O)c4)nc32)[C@H](O)[C@@H]1O] (2S,3S,4R,5R)-5-(6-(benzylamino)-2-(5-(methylsulfo)pyridin-3-yl)-9H-purin-9-yl)-3,4-dihydroxyl-N-(methyl-d3)-tetrahydrofuran-2-formamide | LC-MS m/z $[M+1]^+$: 543.3; $^1H$ NMR (500 MHz, DMSO-$d_6$) δ: 9.70 (s, 1H), 9.15 (d, J = 1.9 Hz, 1H), 9.02 (s, 1H), 8.83 (s, 1H), 8.61 (s, 1H), 7.94 (s, 1H), 7.47 (d, J = 7.2 Hz, 2H), 7.31 (t, J = 7.6 Hz, 2H), 7.21 (t, J = 7.2 Hz, 1H), 6.13 (d, J = 6.8 Hz, 1H), 5.77 − 5.56 (m, 2H), 4.94 − 4.74 (m, 3H), 4.40 − 4.28 (m, 2H), 3.41 (s, 3H). |
| 28 | 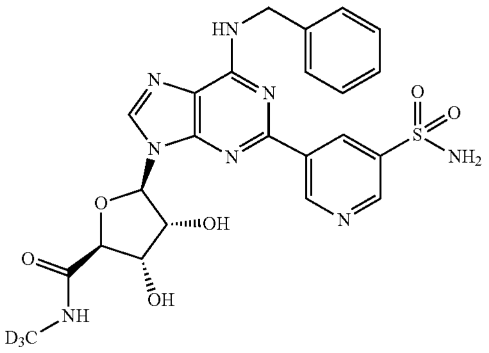 [SMILES: [2H]C([2H])([2H])NC(=O)[C@H]1O[C@@H](n2cnc3c(NCc4ccccc4)nc(-c4cncc(S(N)(=O)=O)c4)nc32)[C@H](O)[C@@H]1O] (2S,3S,4R,5R)-5-(6-(benzylamino)-2-(5-(sulfamide)pyridin-3-yl)-9/-purin-9-yl)-3,4-dihydroxyl-N-(methyl-d3)-tetrahydrofuran-2-formamide | LC-MS m/z $[M+1]^+$: 544.3; $^1H$ NMR (500 MHz, DMSO-$d_6$) δ: 9.60 (s, 1H), 9.02 (s, 2H), 8.89 − 8.76 (m, 1H), 8.61 (s, 1H), 7.99 (s, 1H), 7.75 (s, 2H), 7.53 − 7.42 (m, 2H), 7.32 (t, J = 7.5 Hz, 2H), 7.22 (d, J = 7.0 Hz, 1H), 6.13 (d, J = 6.8 Hz, 1H), 5.74 (d, J = 4.0 Hz, 1H), 5.64 (d, J = 6.2 Hz, 1H), 4.94 − 4.77 (m, 3H), 4.34 (d, J = 22.0 Hz, 2H). |

-continued

| No. | Compound structure and name | Characterization data |
|---|---|---|
| 29 | 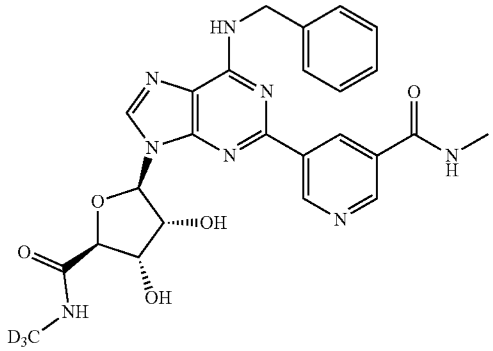 [SMILES: [2H]C([2H])([2H])NC(=O)[C@H]1O[C@@H](n2cnc3c(NCc4ccccc4)nc(-c4cncc(C(=O)NC)c4)nc32)[C@H](O)[C@@H]1O] 5-(6-(benzylamino)-9-((2S,3S,4R,5R)-3,4-dihydroxyl-5-((methyl-d3)-aminobenzyl)-tetrahydrofuran-2-yl)-9H-purin-2-yl)-N-methylnicotinamide | LC-MS m/z [M + 1]$^+$: 522.3; $^1$H NMR (500 MHz, DMSO-$d_6$) δ: 9.52 (s, 1H), 9.03 (d, J = 2.1 Hz, 1H), 8.97 (t, J = 2.0 Hz, 1H), 8.79 (d, J = 4.5 Hz, 1H), 8.72 (s, 1H), 8.57 (s, 1H), 7.96 (s, 1H), 7.46 (d, J = 7.4 Hz, 2H), 7.31 (t, J = 7.6 Hz, 2H), 7.22 (d, J = 7.3 Hz, 1H), 6.12 (d, J = 6.9 Hz, 1H), 5.66 (s, 2H), 5.00 − 4.67 (m, 3H), 4.41 − 4.29 (m, 2H), 2.86 (d, J = 4.4 Hz, 3H). |
| 30 | 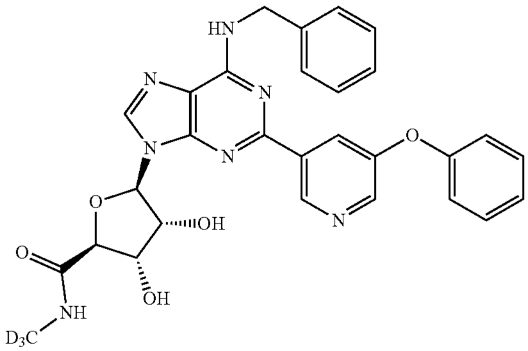 (2S,3S,4R,5R)-5-(6-(benzylamino)-2-(5-phenoxypyridin-3-yl)-9H-purin-9-yl)-3,4-dihydroxyl-N-(methyl-d3)-tetrahydrofuran-2-formamide | LC-MS m/z [M + 1]$^+$: 557.4; $^1$H NMR (500 MHz, DMSO-$d_6$) δ: 9.21 (s, 1H), 8.71 (s, 1H), 8.54 (s, 1H), 8.45 (d, J = 2.8 Hz, 1H), 8.12 (s, 1H), 7.87 (s, 1H), 7.47 (t, J = 7.9 Hz, 2H), 7.23 (m, , 8H), 6.05 (d, J = 6.9 Hz, 1H), 5.66 (d, J = 4.7 Hz, 1H), 5.56 (d, J = 6.4 Hz, 1H), 4.86 (dd, J = 11.4, 6.5 Hz, 1H), 4.66 (s, 2H), 4.35 − 4.25 (m, 2H). |
| 31 | 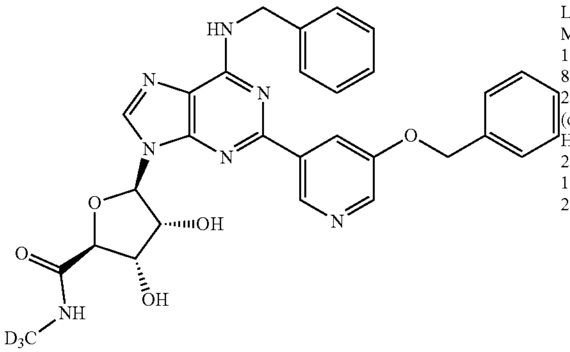 (2S,3S,4R,5R)-5-(6-(benzylamino)-2-(5-(benzyloxy)pyridin-3-yl)-9H-purin-9-yl)-3,4-dihydroxyl-N-(methyl-d3)-tetrahydrofuran-2-formamide | LC-MS m/z [M + 1]$^+$: 571.4; $^1$H NMR (500 MHz, DMSO-$d_6$) δ: 9.05 (s, 1H), 8.66 (s, 1H), 8.54 (s, 1H), 8.41 (d, J = 2.8 Hz, 1H), 8.15 (s, 1H), 7.91 (s, 1H), 7.54 − 7.48 (m, 2H), 7.42 (dd, J = 17.4, 7.7 Hz, 4H), 7.32 (dt, J = 21.5, 7.5 Hz, 3H), 7.21 (t, J = 7.3 Hz, 1H), 6.08 (d, J = 6.8 Hz, 1H), 5.68 (s, 2H), 5.26 (s, 2H), 4.92 (dd, J = 6.8, 4.5 Hz, 1H), 4.79 (s, 2H), 4.36 (dd, J = 7.4, 2.2 Hz, 2H). |

-continued

| No. | Compound structure and name | Characterization data |
|---|---|---|
| 32 | 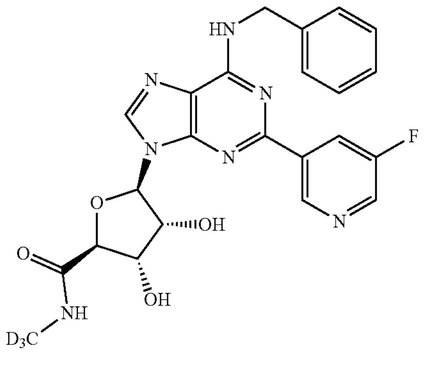 [SMILES: [2H]C([2H])([2H])NC(=O)[C@H]1O[C@@H](n2cnc3c(NCc4ccccc4)nc(-c4cncc(F)c4)nc32)[C@H](O)[C@@H]1O] (2S,3S,4R,5R)-5-(6-(benzylamino)-2-(5-fluoropyridin-3-yl)-9H-purin-9-yl)-3,4-dihydroxyl-N-(methyl-d3)-tetrahydrofuran-2-formamide | LC-MS m/z $[M+1]^+$: 483.3; $^1H$ NMR (500 MHz, DMSO-$d_6$) δ: 9.31 (s, 1H), 8.83 - 8.61 (m, 2H), 8.57 (s, 1H), 8.34 (d, J = 9.5 Hz, 1H), 7.90 (s, 1H), 7.44 (d, J = 7.3 Hz, 2H), 7.31 (t, J = 7.5 Hz, 2H), 7.21 (t, J = 7.2 Hz, 1H), 6.09 (d, J = 6.7 Hz, 1H), 5.68 (d, J = 4.4 Hz, 1H), 5.59 (d, J = 6.2 Hz, 1H), 4.98 - 4.64 (m, 3H), 4.35 (s, 2H). |
| 33 | 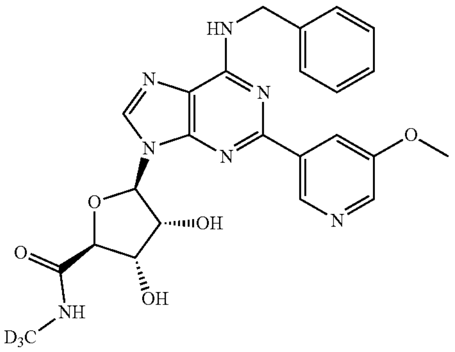 [SMILES: [2H]C([2H])([2H])NC(=O)[C@H]1O[C@@H](n2cnc3c(NCc4ccccc4)nc(-c4cncc(CC)c4)nc32)[C@H](O)[C@@H]1O] (2S,3S,4R,5R)-5-(6-(benzylamino)-2-(5-methoxypyridin-3-yl)-9H-purin-9-yl)-3,4-dihydroxyl-N-(methyl-d3)-tetrahydrofuran-2-formamide | LC-MS m/z $[M+1]^+$: 495.2; $^1H$ NMR (500 MHz, DMSO-$d_6$) δ: 9.05 (s, 1H), 8.69 (s, 1H), 8.54 (s, 1H), 8.35 (s, 1H), 8.06 (s, 1H), 7.89 (s, 1H), 7.45 (d, J = 7.2 Hz, 2H), 7.31 (t, J = 7.5 Hz, 2H), 7.22 (d, J = 7.2 Hz, 1H), 6.08 (d, J = 6.7 Hz, 1H), 5.62 (dd, J = 41.8, 5.2 Hz, 2H), 4.93 (d, J = 4.6 Hz, 1H), 4.79 (s, 3H), 4.34 (s, 2H), 3.91 (s, 3H). |
| 34 | 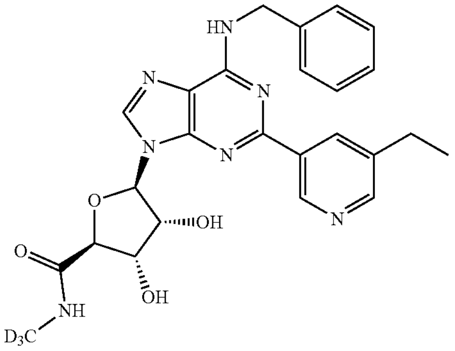 (2S,3S,4R,5R)-5-(6-(benzylamino)-2-(5-ethylpyridin-3-yl)-9H-purin-9-yl)-3,4-dihydroxyl-N-(methyl-d3)-tetrahydrofuran-2-formamide; | LC-MS m/z $[M+1]^+$: 493.3; $^1H$ NMR (500 MHz, DMSO-$d_6$) δ: 9.25 (s, 1H), 8.66 (s, 1H), 8.52 (d, J = 17.9 Hz, 2H), 8.38 (s, 1H), 7.91 (s, 1H), 7.45 (d, J = 7.2 Hz, 2H), 7.31 (t, J = 7.5 Hz, 2H), 7.22 (d, J = 7.2 Hz, 1H), 6.09 (d, J = 6.8 Hz, 1H), 5.68 (d, J = 4.1 Hz, 1H), 5.59 (d, J = 6.2 Hz, 1H), 5.05 - 4.67 (m, 3H), 4.35 (s, 2H), 2.77 - 2.64 (m, 2H), 1.25 (t, J = 7.6 Hz, 3H). |

-continued

| No. | Compound structure and name | Characterization data |
|---|---|---|
| 35 | 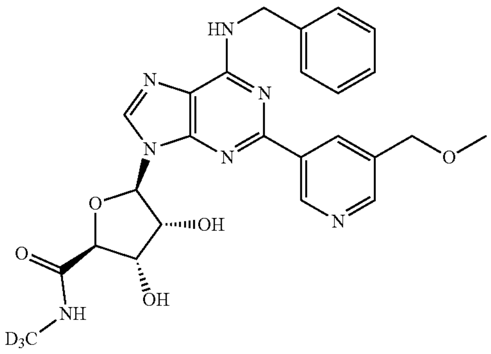 [SMILES: [2H]C([2H])([2H])NC(=O)[C@H]1O[C@@H](n2cnc3c(NCc4ccccc4)nc(-c4cncc(COC)c4)nc32)[C@H](O)[C@@H]1O] (2S,3S,4R,5R)-5-(6-(benzylamino)-2-(5-(methoxymethyl)pyridin-3-yl)-9H-purin-9-yl)-3,4-dihydroxyl-N-(methyl-d3)-tetrahydrofuran-2-formamide | LC-MS m/z $[M + 1]^+$: 509.3; $^1H$ NMR (500 MHz, DMSO-$d_6$) δ: 9.36 (s, 1H), 8.68 (s, 1H), 8.55 (t, J = 14.5 Hz, 3H), 7.92 (s, 1H), 7.45 (d, J = 7.1 Hz, 2H), 7.31 (t, J = 7.6 Hz, 2H), 7.22 (d, J = 7.3 Hz, 1H), 6.10 (d, J = 6.9 Hz, 1H), 5.69 (d, J = 4.6 Hz, 1H), 5.59 (d, J = 6.3 Hz, 1H), 4.95 - 4.73 (m, 3H), 4.55 (s, 2H), 4.33 (dd, J = 16.9, 2.0 Hz, 2H), 3.36 (s, 3H). |
| 36 | 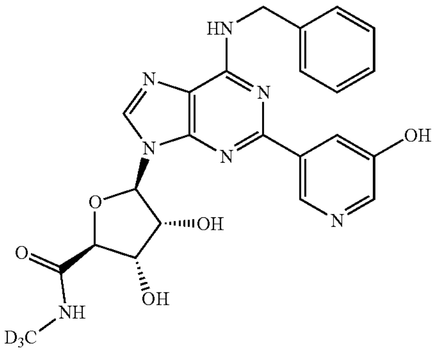 (2S,3S,4R,5R)-5-(6-(benzylamino)-2-(5-hydroxylpyridin-3-yl)-9H-purin-9-yl)-3,4-dihydroxyl-N-(methyl-d3)-tetrahydrofuran-2-formamide | LC-MS m/z $[M + 1]^+$: 481.3; $^1H$ NMR (500 MHz, DMSO-$d_6$) δ: 8.90 (s, 1H), 8.62 (s, 1H), 8.52 (s, 1H), 8.16 (d, J = 2.3 Hz, 1H), 8.00 (s, 1H), 7.91 (s, 1H), 7.44 (d, J = 7.3 Hz, 2H), 7.31 (t, J = 7.5 Hz, 2H), 7.22 (d, J = 7.2 Hz, 1H), 6.08 (d, J = 7.0 Hz, 1H), 5.68 (d, J = 46.0 Hz, 2H), 4.86 (dd, J = 24.2, 18.2 Hz, 3H), 4.43 - 4.23 (m, 2H). |
| 37 | 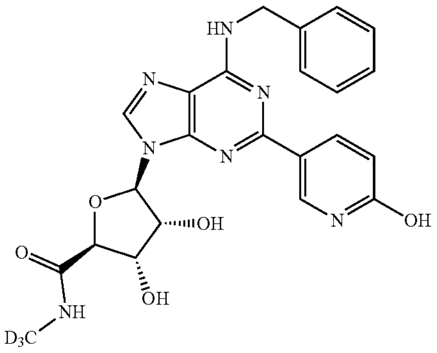 (2S,3S,4R,5R)-5-(6-(benzylamino)-2-(6-hydroxylpyridin-3-yl)-9H-purin-9-yl)-3,4-dihydroxyl-N-(methyl-d3)-tetrahydrofuran-2-formamide | LC-MS m/z $[M + 1]^+$: 481.3; $^1H$ NMR (500 MHz, DMSO-$d_6$) δ: 8.57 - 8.37 (m, 2H), 8.29 (s, 1H), 8.22 (d, J = 9.4 Hz, 1H), 7.91 (s, 1H), 7.40 (d, J = 7.4 Hz, 2H), 7.30 (t, J = 7.5 Hz, 2H), 7.21 (d, J = 7.3 Hz, 1H), 6.34 (d, J = 9.5 Hz, 1H), 6.03 (d, J = 6.9 Hz, 1H), 4.95 - 4.61 (m, 3H), 4.44 - 4.24 (m, 2H). |

-continued

| No. | Compound structure and name | Characterization data |
|---|---|---|
| 38 | 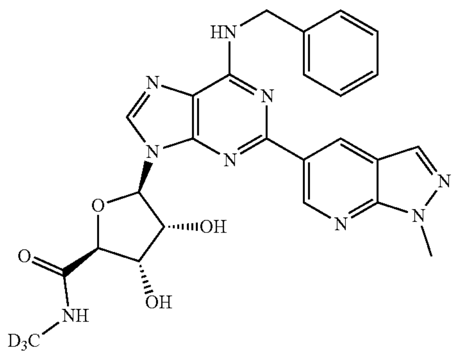 [SMILES: [2H]C([2H])([2H])NC(=O)[C@H]1O[C@@H](n2cnc3c(NCc4ccccc4)nc(-c4cnc5c(cnn5C)c4)nc32)[C@H](O)[C@@H]1O]<br>(2S,3S,4R,5R)-5-(6-(benzylamino)-2-(1-methyl-1H-pyrazolin[3,4-b]pyridin-5-yl)-9H-purin-9-yl)-3,4-dihydroxyl-N-(methyl-d3)-tetrahydrofuran-2-formamide | LC-MS m/z $[M + 1]^+$: 519.3; $^1H$ NMR (500 MHz, DMSO-$d_6$) δ: 9.49 (s, 1H), 9.05 (s, 1H), 8.64 (d, J = 0.7 Hz, 1H), 8.52 (s, 1H), 8.28 (s, 1H), 7.94 (s, 1H), 7.47 (d, J = 6.6 Hz, 2H), 7.34 (s, 2H), 7.22 (t, J = 7.0 Hz, 1H), 6.11 (d, J = 6.7 Hz, 1H), 5.70 (d, J = 3.7 Hz, 1H), 5.60 (d, J = 6.1 Hz, 1H), 5.04 - 4.68 (m, 3H), 4.36 (s, 2H), 4.10 (s, 3H). |
| 39 | 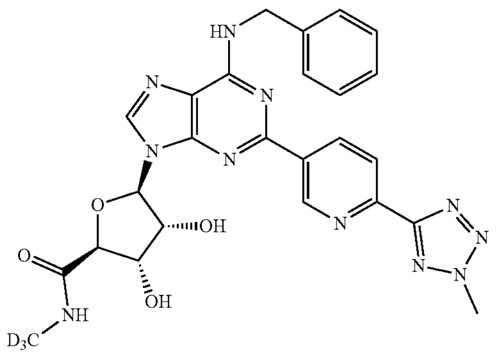 [SMILES: [2H]C([2H])([2H])NC(=O)[C@H]1O[C@@H](n2cnc3c(NCc4ccccc4)nc(-c4ccc(-c5nnn(C)n5)nc4)nc32)[C@H](O)[C@@H]1O]<br>(2S,3S,4R,5R)-5-(6-(benzylamino)-2-(6-(2-methyl-2H-tetrazol-5-yl)pyridin-3-yl)-9H-purin-9-yl)-3,4-dihydroxyl-N-(methyl-d3)-tetrahydrofuran-2-formamide | LC-MS m/z $[M + 1]^+$: 547.4; $^1H$ NMR (500 MHz, DMSO-$d_6$) δ: 9.58 (s, 1H), 8.79 (dd, J = 8.2, 2.0 Hz, 2H), 8.60 (s, 1H), 8.26 (s, 1H), 7.94 (s, 1H), 7.48 (d, J = 7.2 Hz, 2H), 7.33 (t, J = 7.6 Hz, 2H), 7.22 (s, 1H), 6.13 (d, J = 6.8 Hz, 1H), 4.95 - 4.76 (m, 3H), 4.48 (s, 3H), 4.39 - 4.32 (m, 2H), 4.21 (s, 2H). |
| 40 | 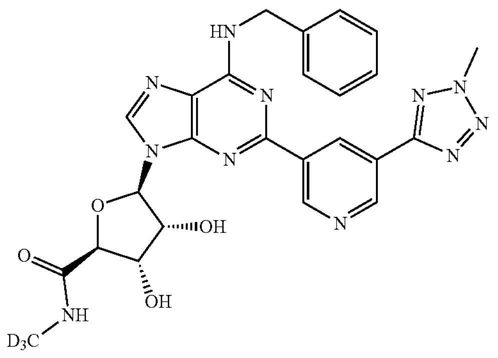 [SMILES: [2H]C([2H])([2H])NC(=O)[C@H]1O[C@@H](n2cnc3c(NCc4ccccc4)nc(-c4cncc(-c5nnn(C)n5)c4)nc32)[C@H](O)[C@@H]1O]<br>(2S,3S,4R,5R)-5-(6-(benzylamino)-2-(5-(2-methyl-2H-tetrazol-5-yl)pyridin-3-yl)-9H-purin-9-yl)-3,4-dihydroxyl-N-(methyl-d3)-tetrahydrofuran-2-formamide | LC-MS m/z $[M + 1]^+$: 547.4; $^1H$ NMR (500 MHz, DMSO-$d_6$) δ: 9.56 (s, 1H), 9.25 (d, J = 29.7 Hz, 2H), 8.78 (s, 1H), 8.60 (s, 1H), 7.96 (s, 1H), 7.50 (d, J = 6.0 Hz, 2H), 7.33 (t, J = 7.5 Hz, 2H), 7.21 (s, 1H), 6.14 (d, J = 6.9 Hz, 1H), 5.73 (d, J = 4.5 Hz, 1H), 5.63 (d, J = 6.3 Hz, 1H), 4.85 (dd, J = 14.3, 7.7 Hz, 3H), 4.51 (s, 3H), 4.37 (s, 1H), 4.31 (s, 1H) |

-continued

| No. | Compound structure and name | Characterization data |
|---|---|---|
| 41 | 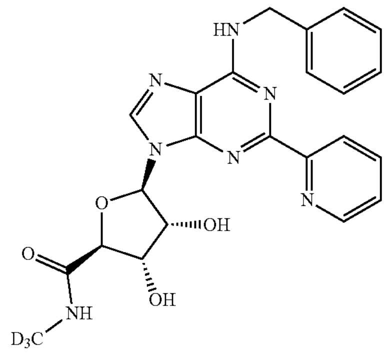 (2S,3S,4R,5R)-5-(6-(benzylamino)-2-(pyridin-2-yl)-9H-purin-9-yl)-3,4-dihydroxyl-N-(methyl-d3)-tetrahydrofuran-2-formamide | LC-MS m/z $[M+1]^+$: 465.3; $^1H$ NMR (500 MHz, DMSO-$d_6$) δ: 8.72 (d, J = 2.1 Hz, 1H), 8.66 (s, 1H), 8.54 (s, 1H), 8.36 - 8.28 (m, 1H), 8.21 (s, 1H), 7.97 (d, J = 0.9 Hz, 1H), 7.50 (dd, J = 1.7, 0.9 Hz, 1H), 7.44 (d, J = 6.9 H, 2Hz), 7.32 (s, 2H), 7.21 (s, 1H), 6.08 (d, J = 7.1 Hz, 1H), 5.81 - 5.70 (m, 1H), 5.69 - 5.56 (m, 1H), 4.83 (dd, J = 2.2, 1.1 Hz, 3H), 4.33 (s, 1H), 4.23 (d, J = 1.0 Hz, 1H). |
| 42 | 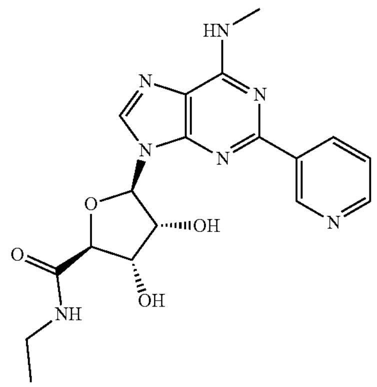 [SMILES: CCNC(=O)[C@H]1O[C@@H](n2cnc3c(NC)nc(-c4cccnc4)nc32)[C@H](O)[C@@H]1O] (2S,3S,4R,5R)-N-ethyl-3,4-dihydroxyl-5-(6-(methylamino)-2-(pyridin-3-yl)-9H-purin-9-yl)-tetrahydrofuran-2-formamide | LC-MS m/z $[M+1]^+$: 400.5; $^1H$ NMR (500 MHz, DMSO-$d_6$) δ: 9.52 (s, 1H), 8.65 (d, J = 5.0 Hz, 2H), 8.52 (s, 1H), 7.99 (t, J = 5.4 Hz, 1H), 7.56 - 7.48 (m, 1H), 6.11 (d, J = 6.7 Hz, 1H), 5.69 (d, J = 4.5 Hz, 1H), 5.61 (d, J = 6.3 Hz, 1H), 4.87 (dd, J = 10.9, 6.4 Hz, 1H), 4.40 - 4.28 (m, 2H), 3.12 (dd, J = 17.0, 9.9 Hz, 4H), 3.03 - 2.92 (m, 1H), 0.88 (t, J = 7.2 Hz, 3H). |
| 43 | 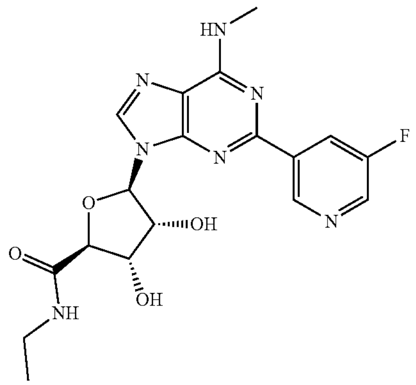 [SMILES: CCNC(=O)[C@H]1O[C@@H](n2cnc3c(NC)nc(-c4cncc(F)c4)nc32)[C@H](O)[C@@H]1O] (2S,3S,4R,5R)-N-ethyl-5-(2-(5-fluoropyridin-3-yl)-6-(methylamino)-9H-purin-9-yl)-3,4-dihydroxyl-tetrahydrofuran-2-formamide | LC-MS m/z $[M+1]^+$: 418.5; $^1H$ NMR (500 MHz, DMSO-$d_6$) δ: 9.40 (s, 1H), 8.67 (d, J = 2.9 Hz, 1H), 8.55 (s, 1H), 8.44 (d, J = 9.3 Hz, 1H), 8.06 (d, J = 3.5 Hz, 1H), 8.00 (t, J = 5.6 Hz, 1H), 6.11 (d, J = 6.6 Hz, 1H), 5.68 (d, J = 4.7 Hz, 1H), 5.61 (d, J = 6.3 Hz, 1H), 4.86 (dd, J = 10.8, 6.4 Hz, 1H), 4.39 - 4.32 (m, 2H), 3.14 t, 6.2 Hz, 4H), 3.03 - 2.94 (m, 1H), 0.90 (t, J = 7.2 Hz, 3H). |

-continued

| No. | Compound structure and name | Characterization data |
|---|---|---|
| 44 | 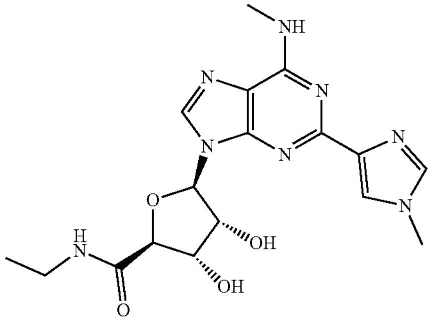 [SMILES: CCNC(=O)[C@H]1O[C@@H](n2cnc3c(NC)nc(-c4cn(C)cn4)nc32)[C@H](O)[C@@H]1O] (2S,3S,4R,5R)-N-ethyl-3,4-dihydroxyl-5-(2-(1-methyl-1/-imidazol-4-yl)-6-(methylamino)-9H-purin-9-yl)tetrahydrofuran-2-carboxamide | $^1$H NMR (500 MHz, DMSO-$d_6$) δ: 8.38 (s, 1H), 8.23 (s, 1H), 7.97 (dd, J = 17.4, 12.1 Hz, 2H), 7.70 (s, 1H), 6.03 (d, J = 6.7 Hz, 1H), 5.67 (s, 1H), 5.58 (d, J = 4.7 Hz, 1H), 4.78 (s, 1H), 4.31 (s, 2H), 3.89 (s, 3H), 3.15 (dd, J = 13.5, 6.6 Hz, 2H), 3.03 (d, J = 5.4 Hz, 3H), 0.93 (t, J = 7.2 Hz, 3H). LC-MS m/z [M + H]$^+$: 403. |
| 45 | 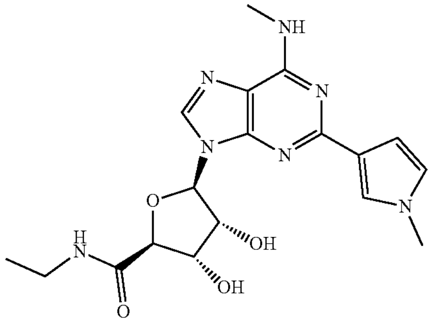 [SMILES: CCNC(=O)[C@H]1O[C@@H](n2cnc3c(NC)nc(-c4ccn(C)c4)nc32)[C@H](O)[C@@H]1O] (2S,3S,4R,5R)-N-ethyl-3,4-dihydroxyl-5-(2-(1-methyl-1H-pyrrol-3-yl)-6-(methylamino)-9H-purin-9-yl)tetrahydrofuran-2-carboxamide | $^1$H NMR (500 MHz, DMSO-$d_6$) δ: 8.31 (s, 1H), 7.99 (s, 1H), 7.54 (s, 1H), 7.40 (s, 1H), 6.71 (s, 1H), 6.61 (s, 1H), 6.01 (d, J = 6.8 Hz, 1H), 5.65 (s, 2H), 4.81 (dd, J = 6.6, 4.2 Hz, 1H), 4.30 (d, J = 4.2 Hz, 2H), 3.67 (s, 3H), 3.17 (td, J = 13.4, 6.9 Hz, 2H), 3.03 (d, J = 5.3 Hz, 3H), 0.92 (t, J = 7.2 Hz, 3H). LC-MS m/z [M + H]$^+$: 402. |
| 46 | 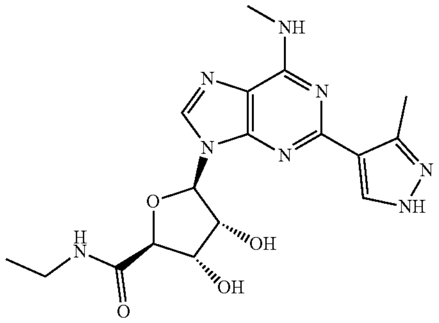 [SMILES: CCNC(=O)[C@H]1O[C@@H](n2cnc3c(NC)nc(-c4c[nH]nc4C)nc32)[C@H](O)[C@@H]1O] (2S,3S,4R,5R)-N-ethyl-3,4-dihydroxyl-5-(2-(3-methyl-1H-pyrazol-4-yl)-6-(methylamino)-9H-purin-9-yl)tetrahydrofuran-2-formamide | $^1$H NMR (500 MHz, DMSO-$d_6$) δ: 12.71 (s, 1H), 8.37 (s, 1H), 7.98 (dd, J = 16.4, 10.8 Hz, 2H), 7.70 (s, 1H), 6.02 (d, J = 6.7 Hz, 1H), 5.67 (d, J = 3.9 Hz, 1H), 5.59 (d, J = 6.1 Hz, 1H), 4.85 (d, J = 4.4 Hz, 1H), 4.31 (d, J = 4.3 Hz, 2H), 3.19 - 3.08 (m, 2H), 3.03 (s, 3H), 2.63 (s, 3H), 0.91 (t, J = 7.2 Hz, 3H). LC-MS m/z [M + H]$^+$: 403. |

-continued

| No. | Compound structure and name | Characterization data |
|---|---|---|
| 47 | 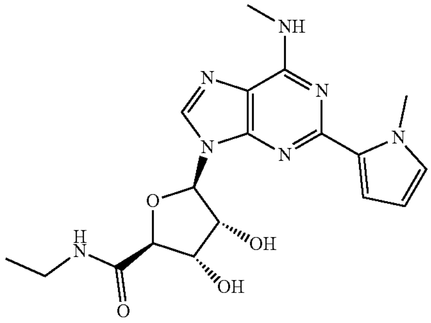 [SMILES: CCNC(=O)[C@H]1O[C@@H](n2cnc3c(NC)nc(-c4cccn4C)nc32)[C@H](O)[C@@H]1O] (2S,3S,4R,5R)-N-ethyl-3,4-dihydroxyl-5-(2-(1-methyl-1H-pyrrol-2-yl)-6-(methylamino)-9H-purin-9-yl)tetrahydrofuran-2-carboxamide | $^1$H NMR (500 MHz, DMSO-$d_6$) δ: 8.35 (s, 1H), 8.03 (s, 1H), 7.73 (s, 1H), 6.85 (s, 2H), 6.00 (d, J = 21.4 Hz, 1H), 5.59 (d, J = 36.4 Hz, 2H), 4.79 (s, 1H), 4.27 (s, 3H), 4.00 (s, 3H), 3.04 (d, J = 57.9 Hz, 5H), 0.85 (d, J = 6.3 Hz, 3H). LC-MS m/z [M + H]$^+$: 402. |
| 48 | 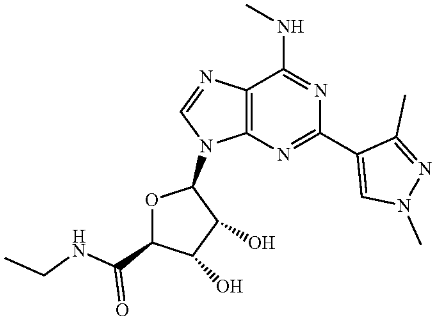 [SMILES: CCNC(=O)[C@H]1O[C@@H](n2cnc3c(NC)nc(-c4cn(C)nc4C)nc32)[C@H](O)[C@@H]1O] (2S,3S,4R,5R)-5-(2-(1,3-dimethyl-1H-pyrazol-4-yl)-6-(methylamino)-9H-purin-9-yl)-N-ethyl-3,4-dihydroxyltetrahydrofuran-2-carboxamide | $^1$H NMR (500 MHz, DMSO-$d_6$) δ: 8.38 (s, 1H), 8.16 (s, 1H), 8.02 (t, J = 5.4 Hz, 1H), 7.71 (s, 1H), 6.02 (d, J = 6.8 Hz, 1H), 5.68 (d, J = 4.4 Hz, 1H), 5.59 (d, J = 6.3 Hz, 1H), 4.83 (dd, J = 11.3, 6.3 Hz, 1H), 4.31 (s, 1H), 4.26 (d, J = 1.7 Hz, 1H), 3.81 (s, 3H), 3.16 - 3.11 (m, 1H), 3.00 (d, J = 12.8 Hz, 3H), 2.97 (d, J = 5.8 Hz, 1H), 2.52 (s, 3H), 0.92 (t, J = 7.2 Hz, 3H). LC-MS m/z [M + H]$^+$: 417. |
| 49 | 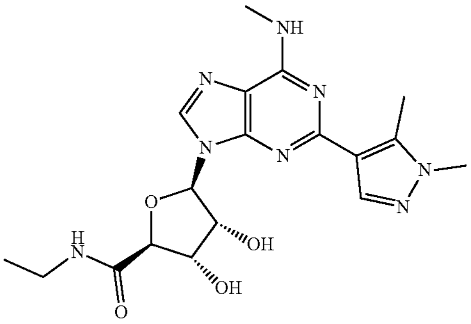 [SMILES: CCNC(=O)[C@H]1O[C@@H](n2cnc3c(NC)nc(-c4cnn(C)c4C)nc32)[C@H](O)[C@@H]1O] (2S,3S,4R,5R)-5-(2-(1,5-dimethyl-1H-pyrazol-4-yl)-6-(methylamino)-9H-purin-9-yl)-N-ethyl-3,4-dihydroxyltetrahydrofuran-2-carboxamide | $^1$H NMR (500 MHz, DMSO-$d_6$) δ: 8.39 (s, 1H), 8.00 (t, J = 5.6 Hz, 1H), 7.91 (s, 1H), 7.72 (s, 1H), 6.02 (d, J = 6.7 Hz, 1H), 5.66 (d, J = 4.6 Hz, 1H), 5.59 (d, J = 6.3 Hz, 1H), 4.82 (dd, J = 11.2, 6.4 Hz, 1H), 4.33 - 4.26 (m, 2H), 3.77 (d, J = 16.6 Hz, 3H), 3.14 (dd, J = 13.7, 6.6 Hz, 1H), 2.98 (ddd, J = 14.3, 12.4, 7.0 Hz, 4H), 2.72 (s, 3H), 0.92 (t, J = 7.2 Hz, 3H). LC-MS m/z [M + H]$^+$: 417. |

-continued

| No. | Compound structure and name | Characterization data |
|---|---|---|
| 50 | 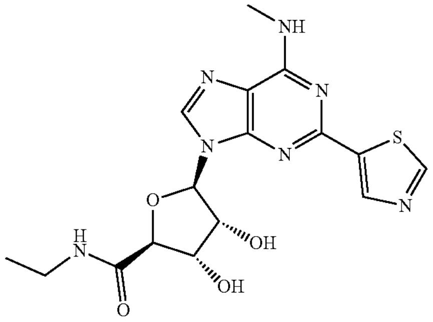 [SMILES: CCNC(=O)[C@H]1O[C@@H](n2cnc3c(NC)nc(-c4cncs4)nc32)[C@H](O)[C@@H]1O] (2S,3S,4R,5R)-N-ethyl-3,4-dihydroxyl-5-(6-(methylamino)-2-(thiazol-5-yl)-9H-purin-9-yl)tetrahydrofuran-2-carboxamide | $^1H$ NMR (500 MHz, DMSO-$d_6$) δ: 9.14 (s, 1H), 8.53 (d, J = 5.6 Hz, 2H), 8.02 (d, J = 5.4 Hz, 2H), 6.06 (d, J = 6.6 Hz, 1H), 5.72 (d, J = 4.6 Hz, 1H), 5.63 (d, J = 6.2 Hz, 1H), 4.79 (dd, J = 10.8, 6.3 Hz, 1H), 4.34 (s, 2H), 3.20 – 2.99 (m, 5H), 0.95 (t, J = 7.2 Hz, 3H). LC-MS m/z $[M + H]^+$: 406. |
| 51 | 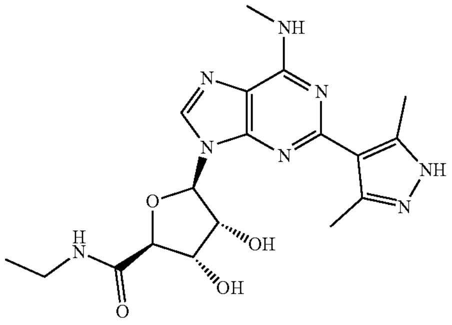 [SMILES: CCNC(=O)[C@H]1O[C@@H](n2cnc3c(NC)nc(-c4c(C)n[nH]c4C)nc32)[C@H](O)[C@@H]1O] (2S,3S,4R,5R)-5-(2-(3,5-dimethyl-1H-pyrazol-4-yl)-6-(methylamino)-9H-purin-9-yl)-N-ethyl-3,4-dihydroxyltetrahydrofuran-2-carboxamide | $^1H$ NMR (500 MHz, DMSO-$d_6$) δ: 12.33 (s, 1H), 8.38 (s, 1H), 8.04 (t, J = 5.4 Hz, 1H), 7.67 (s, 1H), 6.00 (d, J = 6.9 Hz, 1H), 5.71 – 5.55 (m, 2H), 4.89 (d, J = 4.9 Hz, 1H), 4.31 (d, J = 2.0 Hz, 1H), 4.22 (s, 1H), 3.16 – 3.09 (m, 1H), 2.96 (d, J = 55.4 Hz, 3H), 2.86 (dt, J = 19.9, 6.3 Hz, 1H), 2.51 (s, 6H), 0.86 (t, J = 7.2 Hz, 3H). LC-MS mlz $[M + H]^+$: 417. |
| 52 | 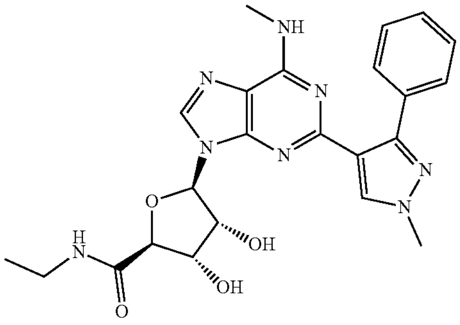 [SMILES: CCNC(=O)[C@H]1O[C@@H](n2cnc3c(NC)nc(-c4cn(C)nc4-c4ccccc4)nc32)[C@H](O)[C@@H]1O] (2S,3S,4R,5R)-N-ethyl-3,4-dihydroxyl-5-(2-(1-methyl-3-phenyl-1H-pyrazol-4-yl)-6-(methylamino)-9H-purin-9-yl)tetrahydrofuran-2-carboxamide | $^1H$ NMR (500 MHz, DMSO-$d_6$) δ: 8.36 (s, 1H), 8.26 (s, 1H), 8.11 (t, J = 5.3 Hz, 1H), 7.67 (dd, J = 13.8, 12.5 Hz, 3H), 7.31 (dt, J = 27.1, 7.2 Hz, 3H), 5.92 (d, J = 7.3 Hz, 1H), 5.67 (d, J = 4.3 Hz, 1H), 5.50 (d, J = 6.3 Hz, 1H), 4.64 (d, J = 4.4 Hz, 1H), 4.24 (s, 1H), 4.08 (s, 1H), 3.94 (s, 3H), 3.13 (dt, J = 13.6, 6.9 Hz, 1H), 2.81 (s, 1H), 2.71 (s, 3H), 0.82 (t, J = 7.1 Hz, 3H). LC-MS m/z $[M + H]^+$: 479. |

-continued

| No. | Compound structure and name | Characterization data |
|---|---|---|
| 53 | 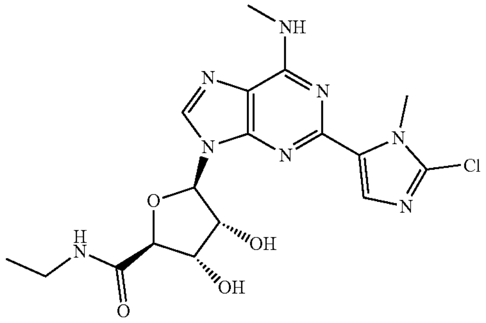 [SMILES: CCNC(=O)[C@H]1O[C@@H](n2cnc3c(NC)nc(-c4cnc(Cl)n4C)nc32)[C@H](O)[C@@H]1O] (2S,3S,4R,5R)-5-(2-(2-chloro-1-methyl-1H-imidazol-5-yl)-6-(methylamino)-9H-purin-9-yl)-N-ethyl-3,4-dihydroxyltetrahydrofuran-2-carboxamide | $^1$H NMR (500 MHz, DMSO-$d_6$) δ: 8.50 (s, 1H), 8.07 (t, J = 5.6 Hz, 1H), 8.00 (s, 1H), 7.58 (s, 1H), 6.03 (d, J = 6.6 Hz, 1H), 5.71 (d, J = 4.3 Hz, 1H), 5.63 (d, J = 5.7 Hz, 1H), 4.77 (d, J = 4.9 Hz, 1H), 4.33 (d, J = 2.4 Hz, 1H), 4.29 (s, 1H), 4.06 (s, 3H), 3.12 (td, J = 13.4, 6.7 Hz, 1H), 3.08 − 2.89 (m, 4H), 0.92 (t, J = 7.2 Hz, 3H). LC-MS m/z [M + H]$^+$: 437. |
| 54 | 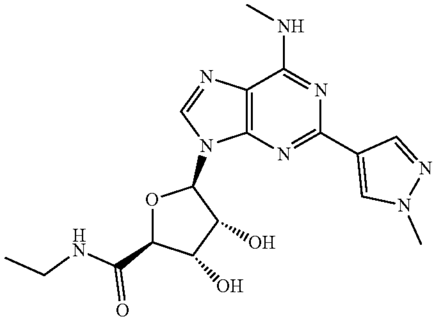 [SMILES: CCNC(=O)[C@H]1O[C@@H](n2cnc3c(NC)nc(-c4cnn(C)c4)nc32)[C@H](O)[C@@H]1O] (2S,3S,4R,5R)-N-ethyl-3,4-dihydroxyl-5-(2-(1-methyl-1H-pyrazol-4-yl)-6-(methylamino)-9H-purin-9-yl)tetrahydrofuran-2-carboxamide | $^1$H NMR (500 MHz, DMSO-$d_6$) δ: 8.39 (s, 1H), 8.24 (s, 1H), 8.01 (t, J = 5.5 Hz, 1H), 7.94 (s, 1H), 7.73 (s, 1H), 6.03 (d, J = 6.8 Hz, 1H), 5.69 (d, J = 4.0 Hz, 1H), 5.60 (d, J = 6.0 Hz, 1H), 4.79 (d, J = 4.4 Hz, 1H), 4.31 (s, 2H), 3.90 (s, 3H), 3.16 (dt, J = 13.4, 5.3 Hz, 2H), 3.03 (dd, J = 15.3, 10.0 Hz, 3H), 0.93 (t, J = 7.2 Hz, 3H). LC-MS m/z [M + H]$^+$: 403. |
| 55 | 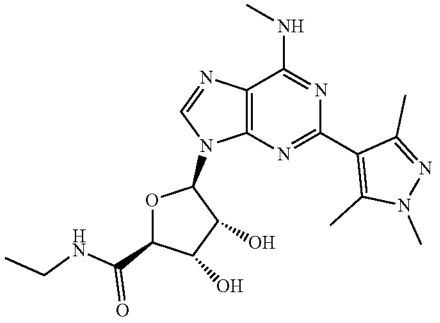 [SMILES: CCNC(=O)[C@H]1O[C@@H](n2cnc3c(NC)nc(-c4c(C)nn(C)c4C)nc32)[C@H](O)[C@@H]1O] (2S,3S,4R,5R)-N-ethyl-3,4-dihydroxyl-5-(6-(methylamino)-2-(1,3,5-trimethyl-1H-pyrazol-4-yl)-9H-purin-9-yl)tetrahydrofuran-2-carboxamide | $^1$H NMR (500 MHz, DMSO-$d_6$) δ: 8.39 (s, 1H), 8.08 (t, J = 5.5 Hz, 1H), 7.73 (s, 1H), 6.00 (d, J = 6.9 Hz, 1H), 5.66 (d, J = 22.5 Hz, 2H), 4.89 − 4.79 (m, 1H), 4.30 (d, J = 2.0 Hz, 1H), 4.21 (d, J = 2.4 Hz, 1H), 3.71 (s, 3H), 3.17 − 3.09 (m, 1H), 3.05 (d, J = 41.7 Hz, 3H), 2.87 − 2.76 (m, 1H), 2.59 (s, 3H), 2.42 (s, 3H), 0.85 (t, J = 7.2 Hz, 3H). LC-MS m/z [M + H]$^+$: 431. |

-continued

| No. | Compound structure and name | Characterization data |
|---|---|---|
| 56 | 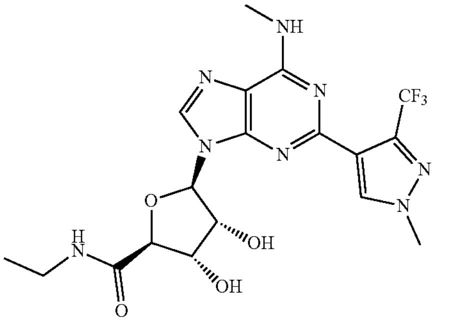 [SMILES: CCNC(=O)[C@H]1O[C@@H](n2cnc3c(NC)nc(-c4cn(C)nc4C(F)(F)F)nc32)[C@H](O)[C@@H]1O]<br>(2S,3S,4R,5R)-N-ethyl-3,4-dihydroxyl-5-(2-(1-methyl-3-(trifluoromethyl)-1H-pyrazol-4-yl)-6-(methylamino)-9H-purin-9-yl)tetrahydrofuran-2-carboxamide | $^1$H NMR (500 MHz, DMSO-$d_6$) δ: 8.47 (s, 2H), 8.07 (t, J = 5.5 Hz, 1H), 7.88 (d, J = 3.8 Hz, 1H), 6.04 (d, J = 6.9 Hz, 1H), 5.69 (d, J = 4.4 Hz, 1H), 5.58 (d, J =6.2 Hz, 1H), 4.78 (dd, J = 11.3, 6.5 Hz, 1H), 4.32 (d, J = 2.1 Hz, 1H), 4.27 (dd, J = 6.5, 4.4 Hz, 1H), 3.98 (s, 3H), 3.21 - 2.94 (m, 5H), 0.92 (t, J = 7.2 Hz, 3H). LC-MS m/z [M + H]$^+$: 471. |
| 57 | 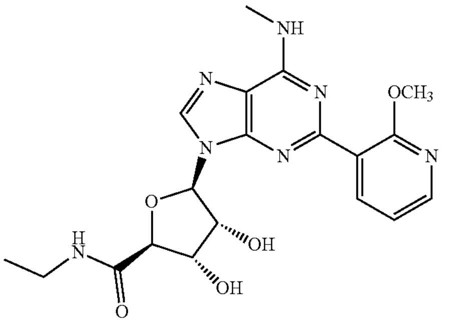 [SMILES: CCNC(=O)[C@H]1O[C@@H](n2cnc3c(NC)nc(-c4cccnc4OC)nc32)[C@H](O)[C@@H]1O]<br>(2S,3S,4R,5R)-N-ethyl-3,4-dihydroxyl-5-(2-(2-methoxypyridin-3-yl)-6-(methylamino)-9H-purin-9-yl)tetrahydrofuran-2-carboxamide | $^1$H NMR (500 MHz, DMSO-$d_6$) δ: 8.46 (s, 1H), 8.42 (s, 1H), 8.27 (dd, J = 4.9, 1.9 Hz, 1H), 7.97 (d, J = 15.6 Hz, 2H), 7.11 (dd, J = 7.2, 5.0 Hz, 1H), 5.97 (d, J = 7.6 Hz, 1H), 5.73 (d, J = 4.3 Hz, 1H), 5.59 (d, J = 6.5 Hz, 1H), 4.75 (dd, J = 11.8, 6.9 Hz, 1H), 4.28 (d, J = 1.6 Hz, 1H), 4.15 (s, 1H), 3.86 (s, 3H), 3.07 - 2.83 (m, 4H), 2.54 (d, J = 6.0 Hz, 1H), 0.66 (t, J = 7.2 Hz, 3H). LC-MS m/z [M + H]$^+$: 430. |
| 58 | 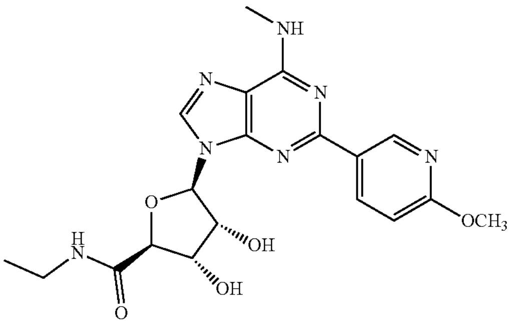 [SMILES: CCNC(=O)[C@H]1O[C@@H](n2cnc3c(NC)nc(-c4ccc(OC)nc4)nc32)[C@H](O)[C@@H]1O]<br>(2S,3S,4R,5R)-N-ethyl-3,4-dihydroxyl-5-(2-(6-methoxypyridin-3-yl)-6-(methylamino)-9H-purin-9-yl)tetrahydrofuran-2-carboxamide | $^1$H NMR (500 MHz, DMSO-$d_6$) δ: 9.14 (s, 1H), 8.57 (d, J = 7.3 Hz, 1H), 8.47 (s, 1H), 7.99 (s, 1H), 7.91 (s, 1H), 6.92 (d, J = 8.5 Hz, 1H), 6.08 (d, J = 6.4 Hz, 1H), 5.70 (s, 1H), 5.63 (s, 1H), 4.87 (s, 1H), 4.34 (s, 2H), 3.93 (s, 3H), 3.20 - 2.94 (m, 5H), 0.89 (t, J = 7.0 Hz, 3H). LC-MS m/z [M + H]$^+$: 430. |

-continued

| No. | Compound structure and name | Characterization data |
|---|---|---|
| 59 | 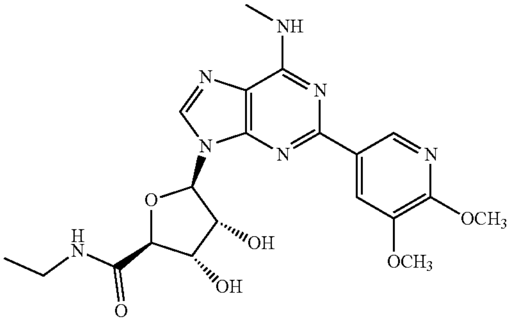 [SMILES: CCNC(=O)[C@H]1O[C@@H](n2cnc3c(NC)nc(-c4cnc(OC)c(OC)c4)nc32)[C@H](O)[C@@H]1O] (2S,3S,4R,5R)-5-(2-(5,6-dimethoxypyridin-3-yl)-6-(methylamino)-9H-purin-9-yl)-N-ethyl-3,4-dihydroxyltetrahydrofuran-2-carboxamide | $^1$H NMR (500 MHz, DMSO-$d_6$) δ: 8.71 (s, 1H), 8.47 (s, 1H), 8.10 (s, 1H), 7.97 (t, J = 5.5 Hz, 1H), 7.89 (s, 1H), 6.08 (d, J = 6.4 Hz, 1H), 5.66 (d, J = 4.7 Hz, 1H), 5.61 (d, J = 6.1 Hz, 1H), 4.91 (dd, J = 11.1, 6.0 Hz, 1H), 4.40 − 4.35 (m, 1H), 4.34 (d, J = 2.4 Hz, 1H), 3.92 (d, J = 17.5 Hz, 6H), 3.19 − 2.85 (m, 5H), 0.88 (t, J = 7.2 Hz, 3H). LC-MS m/z [M + H]$^+$: 460. |
| 60 | 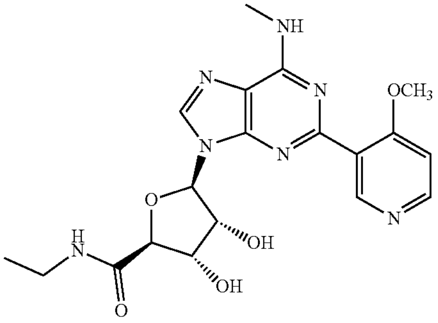 [SMILES: CCNC(=O)[C@H]1O[C@@H](n2cnc3c(NC)nc(-c4cnccc4OC)nc32)[C@H](O)[C@@H]1O] (2S,3S,4R,5R)-N-ethyl-3,4-dihydroxyl-5-(2-(4-methoxypyridin-3-yl)-6-(methylamino)-9H-purin-9-yl)tetrahydrofuran-2-carboxamide | $^1$H NMR (500 MHz, DMSO-$d_6$) δ: 8.52 (d, J = 5.8 Hz, 1H), 8.43 (d, J = 9.6 Hz, 2H), 7.96 (s, 1H), 7.19 (d, J = 5.9 Hz, 1H), 5.97 (d, J = 7.5 Hz, 1H), 5.73 (d, J = 4.4 Hz, 1H), 5.57 (d, J = 6.5 Hz, 1H), 4.76 − 4.70 (m, 1H), 4.28 (d, J = 1.6 Hz, 1H), 4.16 (s, 1H), 3.84 (s, 3H), 2.92 (dd, J = 22.7, 15.9 Hz, 4H), 2.54 (d, J = 6.7 Hz, 1H), 0.68 (t, J = 7.2 Hz, 3H). LC-MS m/z [M + H]$^+$: 430. |
| 61 | 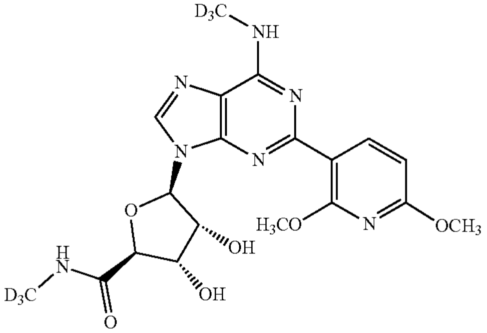 [SMILES: [2H]C([2H])([2H])NC(=O)[C@H]1O[C@@H](n2cnc3c(NC([2H])([2H])[2H])nc(-c4ccc(OC)nc4OC)nc32)[C@H](O)[C@@H]1O] (2S,3S,4R,5R)-5-(2-(2,6-dimethoxypyridin-3-yl)-6-((methyl-d3)-amino)-9/-purin-9-yl)-3,4-dihydroxyl-N-methyl-D3-tetrahydrofuran-2-carboxamide | $^1$H NMR (500 MHz, DMSO-$d_6$) δ: 8.50 (s, 1H), 8.36 (s, 1H), 8.11 (d, J = 6.3 Hz, 1H), 7.84 (s, 1H), 6.49 (d, J = 8.1 Hz, 1H), 5.95 (d, J = 7.6 Hz, 1H), 5.73 (d, J = 4.2 Hz, 1H), 5.59 (d, J = 6.5 Hz, 1H), 4.88 (dd, J = 11.9, 6.8 Hz, 1H), 4.30 (d, J = 1.4 Hz, 1H), 4.19 (t, J = 3.7 Hz, 1H), 3.91 (d, J = 18.2 Hz, 6H). LC-MS m/z [M + H]$^+$: 452. |

-continued

| No. | Compound structure and name | Characterization data |
| --- | --- | --- |
| 62 | 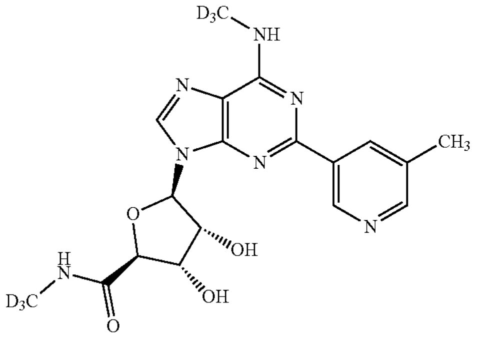 [SMILES: [2H]C([2H])([2H])NC(=O)[C@H]1O[C@@H](n2cnc3c(NC([2H])([2H])[2H])nc(-c4cncc(C)c4)nc32)[C@H](O)[C@@H]1O] (2S,3S,4R,5R)-3,4-dihydroxyl-N-(methyl-d3)-5-(6-((methyl-d3)-amino)-2-(5-methylpyridin-3-yl)-9H-purin-9-yl)tetrahydrofuran-2-carboxamide | $^1$H NMR (500 MHz, DMSO-$d_6$) δ: 9.32 (s, 2H), 8.58 − 8.42 (m, 6H), 7.94 (s, 4H), 6.09 (d, J = 6.9 Hz, 2H), 5.76 − 5.52 (m, 4H), 4.88 (s, 2H), 4.34 (t, J = 5.8 Hz, 4H), 2.41 (s, 7H). LC-MS m/z [M + H]$^+$: 406. |
| 63 | 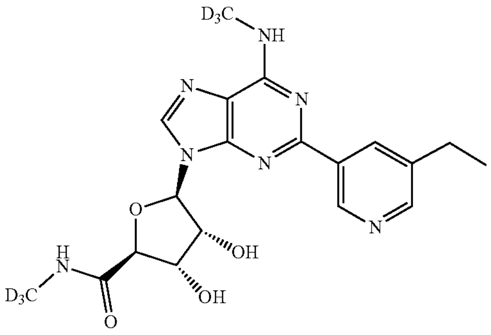 [SMILES: [2H]C([2H])([2H])NC(=O)[C@H]1O[C@@H](n2cnc3c(NC([2H])([2H])[2H])nc(-c4cncc(CC)c4)nc32)[C@H](O)[C@@H]1O] (2S,3S,4R,5R)-5-(2-(5-ethylpyridin-3-yl)-6-((methyl-d3)-amino)-9H-purin-9-yl)-3,4-dihydroxyl-N-(methyl-d3)-tetrahydrofuran-2-carboxamide | $^1$H NMR (500 MHz, DMSO-$d_6$) δ: 9.34 (s, 1H), 8.61 − 8.40 (m, 3H), 7.94 (s, 2H), 6.10 (d, J = 6.3 Hz, 1H), 5.69 (s, 2H), 4.91 (s, 1H), 4.36 (s, 2H), 2.74 (dd, J = 15.0, 7.4 Hz, 2H), 1.27 (t, J = 7.6 Hz, 3H). LC-MS m/z [M + H]$^+$: 420. |
| 64 | 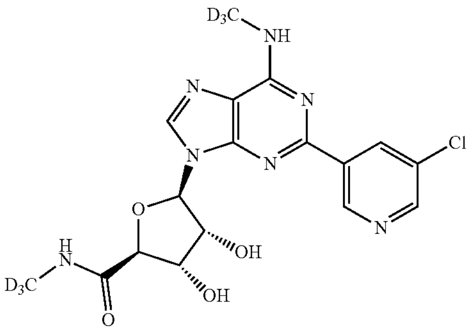 [SMILES: [2H]C([2H])([2H])NC(=O)[C@H]1O[C@@H](n2cnc3c(NC([2H])([2H])[2H])nc(-c4cncc(Cl)c4)nc32)[C@H](O)[C@@H]1O] (2S,3S,4R,5R)-5-(2-(5-chloropyridin-3-yl)-6-((methyl-d3)-amino)-9H-purin-9-yl)-3,4-dihydroxyl-N-(methyl-d3)-tetrahydrofuran-2-carboxamide | $^1$H NMR (500 MHz, DMSO-$d_6$) : 9.45 (s, 1H), 8.72 (d, J = 2.4 Hz, 1H), 8.65 (s, 1H), 8.54 (s, 1H), 8.04 (s, 1H), 7.92 (s, 1H), 6.10 (d, J = 6.8 Hz, 1H), 5.69 (d, J = 4.7 Hz, 1H), 5.60 (d, J = 6.4 Hz, 1H), 4.89 (dd, J = 11.3, 6.5 Hz, 1H), 4.37 − 4.29 (m, 2H). LC-MS m/z [M + H]$^+$: 426. |

-continued

| No. | Compound structure and name | Characterization data |
|---|---|---|
| 65 | 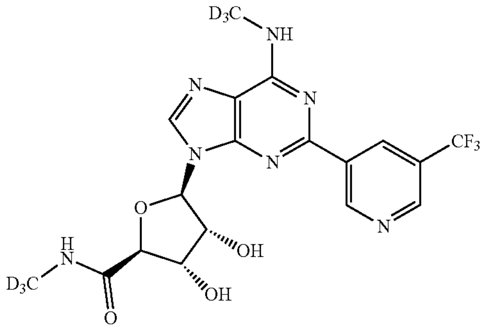 [SMILES: [2H]C([2H])([2H])NC(=O)[C@H]1O[C@@H](n2cnc3c(NC([2H])([2H])[2H])nc(-c4cncc(C(F)(F)F)c4)nc32)[C@H](O)[C@@H]1O] (2S,3S,4R,5R)-3,4-dihydroxyl-N-(methyl-d3)-5-(6-((methyl-d3)-amino)-2-(5-(trifluoromethyl)pyridin-3-yl)-9/-purin-9-yl)tetrahydrofuran-2-carboxamide | $^1$H NMR (500 MHz, DMSO-$d_6$) δ: 9.79 (s, 1H), 9.08 (s, 1H), 8.89 (s, 1H), 8.57 (s, 1H), 8.08 (s, 1H), 7.94 (s, 1H), 6.12 (d, J = 6.8 Hz, 1H), 5.70 (d, J = 4.7 Hz, 1H), 5.62 (d, J = 6.4 Hz, 1H), 4.90 (d, J = 4.9 Hz, 1H), 4.41 - 4.27 (m, 2H). LC-MS m/z [M + H]$^+$: 460. |
| 66 | 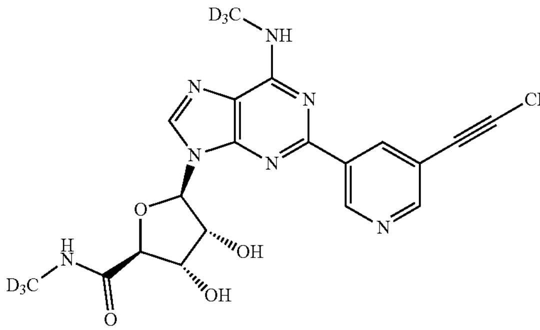 (2S,3S,4R,5R)-3,4-dihydroxyl-N-(methyl-d3)-5-(6-((methyl-d3)-amino)-2-(5-(prop-1-yne-1-yl)pyridin-3-yl)-9H-purin-9-yl)tetrahydrofuran-2-carboxamide | $^1$H NMR (500 MHz, DMSO-$d_6$) δ: 9.42 (s, 1H), 8.66 (d, J = 1.6 Hz, 1H), 8.58 (s, 1H), 8.53 (s, 1H), 7.97 (d, J = 27.4 Hz, 2H), 6.10 (d, J = 6.9 Hz, 1H), 5.70 (d, J = 4.7 Hz, 1H), 5.61 (d, J = 6.4 Hz, 1H), 4.86 (dd, J = 11.3, 6.5 Hz, 1H), 4.32 (ddd, J = 12.3, 6.9, 2.3 Hz, 2H), 2.13 (s, 3H). LC-MS m/z [M + H]$^+$: 430. |
| 67 | 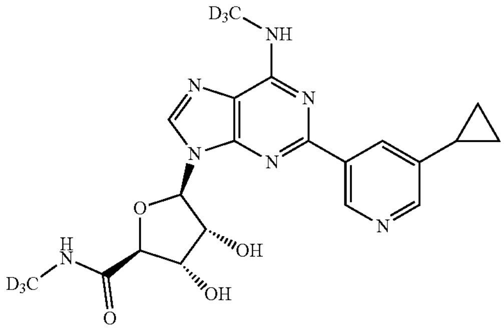 [SMILES: [2H]C([2H])([2H])NC(=O)[C@H]1O[C@@H](n2cnc3c(NC([2H])([2H])[2H])nc(-c4cncc(C5CC5)c4)nc32)[C@H](O)[C@@H]1O] (2S,3S,4R,5R)-5-(2-(5-cyclopropylpyridin-3-yl)-6-((methyl-d3)amino)-9H-purin-9-yl)-3,4-dihydroxyl-N-(methyl-d3)-tetrahydrofuran-2-carboxamide | $^1$H NMR (500 MHz, DMSO-$d_6$) δ: 9.28 (s, 1H), 8.50 (s, 1H), 8.44 (d, J = 1.8 Hz, 1H), 8.27 (s, 1H), 7.92 (s, 2H), 6.08 (d, J = 6.8 Hz, 1H), 5.69 (d, J = 4.4 Hz, 1H), 5.60 (d, J = 6.4 Hz, 1H), 4.93 (d, J = 4.8 Hz, 1H), 4.35 (s, 2H), 2.12 - 2.02 (m, 1H), 1.11 - 1.03 (m, 2H), 0.89 - 0.80 (m, 2H). LC-MS m/z [M + H]$^+$: 432. |

-continued

| No. | Compound structure and name | Characterization data |
|---|---|---|
| 68 | 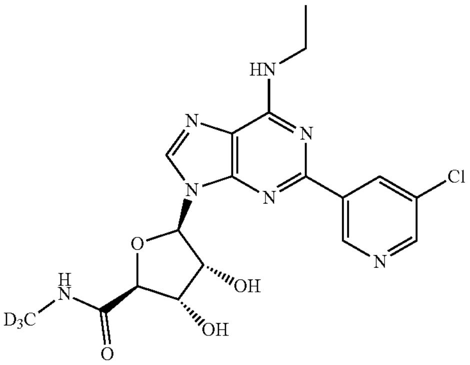 [SMILES: [2H]C([2H])([2H])NC(=O)[C@H]1O[C@@H](n2cnc3c(NCC)nc(-c4cncc(Cl)c4)nc32)[C@H](O)[C@@H]1O] (2S,3S,4R,5R)-5-(2-(5-chloropyridin-3-yl)-6-(ethylamino)-9H-purin-9-yl)-3,4-dihydroxyl-N-(methyl-d3)-tetrahydrofuran-2-carboxamide | $^1$H NMR (500 MHz, DMSO-$d_6$) δ: 9.43 (s, 1H), 8.72 (d, J = 2.3 Hz, 1H), 8.62 (s, 1H), 8.54 (s, 1H), 8.12 (s, 1H), 7.92 (s, 1H), 6.09 (d, J = 6.7 Hz, 1H), 5.71 (s, 2H), 4.98 - 4.86 (m, 1H), 4.45 - 4.28 (m, 2H), 3.65 (s, 2H), 1.26 (t, J = 7.1 Hz, 3H). LC-MS m/z [M + H]$^+$: 437. |
| 69 | 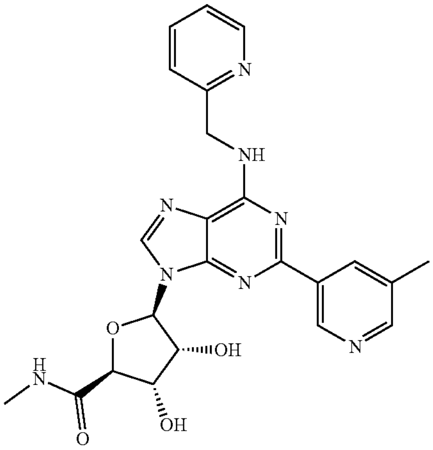 (2S,3S,4R,5R)-3,4-dihydroxyl-N-methyl-5-(2-(5-methylpyridin-3-yl)-6-((pyridin-2-ylmethyl)amino)-9H-purin-9-yl)tetrahydrofuran-2-carboxamide | $^1$H NMR (500 MHz, DMSO-$d_6$) δ: 9.14 (s, 1H), 8.56 (dd, J = 25.2, 13.1 Hz, 3H), 8.44 (s, 1H), 8.28 (s, 1H), 7.96 (d, J = 4.7 Hz, 1H), 7.72 (td, J = 7.7, 1.8 Hz, 1H), 7.38 (d, J = 7.9 Hz, 1H), 7.25 (dd, J = 6.7, 5.0 Hz, 1H), 6.10 (d, J = 7.0 Hz, 1H), 5.71 (d, J = 4.6 Hz, 1H), 5.61 (d, J = 6.4 Hz, 1H), 4.90 (d, J = 4.6 Hz, 3H), 4.34 (dd, J = 7.6, 3.3 Hz, 2H), 2.53 (d, J = 4.7 Hz, 3H), 2.36 (s, 3H).LC-MS(m/z): 477.2.2 [M + H]$^+$. |
| 70 | 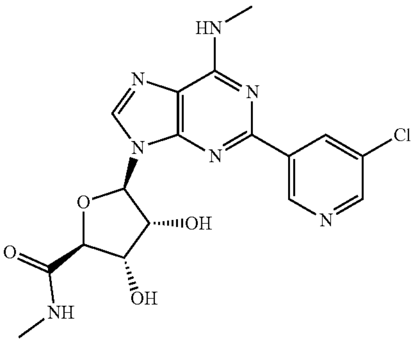 [SMILES: CNC(=O)[C@H]1O[C@@H](n2cnc3c(NC)nc(-c4cncc(Cl)c4)nc32)[C@H](O)[C@@H]1O] (2S,3S,4R,5R)-5-(2-(5-chloropyridin-3-yl)-6-(methylamino)-9H-purin-9-yl)-3,4-dihydroxyl-N-methyltetrahydrofuran-2-carboxamide | LC-MS m/z [M + 1]$^+$: 420.2; $^1$H NMR (500 MHz, DMSO-$d_6$) δ: 9.46 (s, 1H), 8.73 (d, J = 2.3 Hz, 1H), 8.65 (s, 1H), 8.55 (s, 1H), 8.10 (d, J = 4.1 Hz, 1H), 7.97 (d, J = 4.6 Hz, 1H), 6.10 (d, J = 6.8 Hz, 1H), 5.72 (d, J = 4.7 Hz, 1H), 5.62 (d, J = 6.4 Hz, 1H), 4.93 - 4.85 (m, 1H), 4.36 (d, J = 1.9 Hz, 1H), 4.34 - 4.30 (m, 1H), 3.09 (d, J = 3.7 Hz, 3H), 2.55 (d, J = 4.6 Hz, 3H). |

-continued

| No. | Compound structure and name | Characterization data |
|---|---|---|
| 71 | 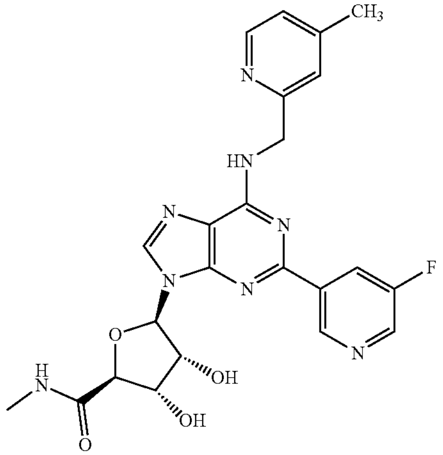 [SMILES: CNC(=O)[C@H]1O[C@@H](n2cnc3c(NCc4cc(C)ccn4)nc(-c4cncc(F)c4)nc32)[C@H](O)[C@@H]1O] (2S,3S,4R,5R)-5-(2-(5-fluoropyridin-3-yl)-6-(((4-methylpyridin-2-yl)methyl)amino)-9H-purin-9-yl)-3,4-dihydroxyl-N-methyltetrahydrofuran-2-carboxamide | $^1$H NMR (500 MHz, DMSO-$d_6$) δ: 9.17 (s, 1H), 8.57 (s, 2H), 8.53 (s, 1H), 8.31 (d, J = 5.0 Hz, 1H), 8.21 (d, J = 9.4 Hz, 1H), 7.88 (d, J = 4.7 Hz, 1H), 7.17 (s, 1H), 7.01 (d, J = 5.1 Hz, 1H), 6.03 (d, J = 6.8 Hz, 1H), 5.61 (s, 2H), 4.88 - 4.72 (m, 3H), 4.28 (d, J = 5.6 Hz, 2H), 2.47 (d, J = 4.7 Hz, 3H), 2.19 (s, 3H). LC-MS m/z [M + H]$^+$: 495. |
| 72 | 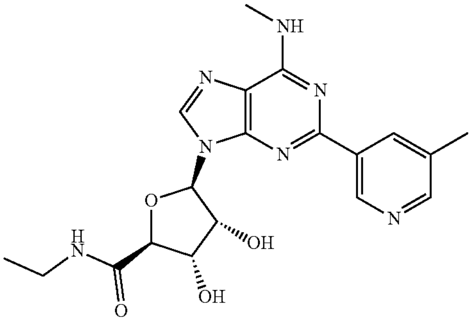 [SMILES: CCNC(=O)[C@H]1O[C@@H](n2cnc3c(NC)nc(-c4cncc(C)c4)nc32)[C@H](O)[C@@H]1O] (2S,3S,4R,5R)-N-ethyl-3,4-dihydroxyl-5-(6-(methylamino)-2-(5-methylpyridin-3-yl)-9H-purin-9-yl)tetrahydrofuran-2-carboxamide | $^1$H NMR (500 MHz, DMSO-$d_6$) δ: 9.33 (s, 1H), 8.61 - 8.39 (m, 3H), 8.00 (dd, J = 17.1, 11.5 Hz, 2H), 6.11 (d, J = 6.7 Hz, 1H), 5.70 (d, J = 4.7 Hz, 1H), 5.62 (d, J = 6.4 Hz, 1H), 4.86 (dd, J = 11.2, 6.5 Hz, 1H), 4.39 - 4.27 (m, 2H), 3.16 (dd, J = 13.4, 7.1 Hz, 1H), 3.11 (d, J = 13.3 Hz, 3H), 3.01 - 2.93 (m, 1H), 2.41 (s, 3H), 0.90 (t, J = 7.2 Hz, 3H). LC-MS m/z [M + H]$^+$: 414. |
| 73 | 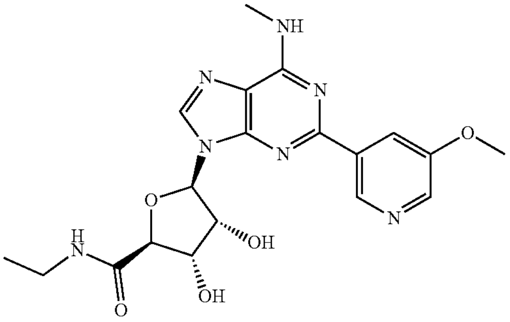 [SMILES: CCNC(=O)[C@H]1O[C@@H](n2cnc3c(NC)nc(-c4cncc(OC)c4)nc32)[C@H](O)[C@@H]1O] (2S,3S,4R,5R)-N-ethyl-3,4-dihydroxyl-5-(2-(5-methoxypyridin-3-yl)-6-(methylamino)-9H-purin-9-yl)tetrahydrofuran-2-carboxamide | $^1$H NMR (500 MHz, DMSO-$d_6$) δ: 9.14 (s, 1H), 8.52 (s, 1H), 8.38 (d, J = 2.8 Hz, 1H), 8.17 (s, 1H), 7.98 (t, J = 5.5 Hz, 2H), 6.10 (d, J = 6.6 Hz, 1H), 5.68 (d, J = 4.7 Hz, 1H), 5.62 (d, J = 6.3 Hz, 1H), 4.89 (dd, J = 10.8, 6.4 Hz, 1H), 4.35 (dd, J = 5.3, 2.7 Hz, 2H), 3.94 (s, 3H), 3.18 - 3.12 (m, 1H), 3.10 (d, J = 6.3 Hz, 3H), 3.01 - 2.93 (m, 1H), 0.88 (t, J = 7.2 Hz, 3H). LC-MS m/z [M + H]$^+$: 430. |

-continued

| No. | Compound structure and name | Characterization data |
|---|---|---|
| 74 | 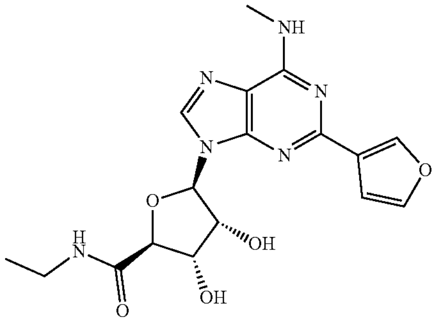 [SMILES: CCNC(=O)[C@H]1O[C@@H](n2cnc3c(NC)nc(-c4ccoc4)nc32)[C@H](O)[C@@H]1O] (2S,3S,4R,5R)-N-ethyl-5-(2-(furan-3-yl)-6-(methylamino)-9H-purin-9-yl)-3,4-dihydroxyltetrahydrofuran-2-carboxamide | $^{1}H$ NMR (500 MHz, DMSO-$d_6$): δ: 8.42(s, 1H), 8.26(s, 1H), 7.96 (t, 1H), 7.77 (s, 1H), 7.73 (s, 1H), 6.99 (s, 1H), 6.03 (d, 1H), 5.65 (d, 1H), 5.56 (d, 1H), 4.80 (d, 1H), 4.31 (t, 2H),3.15 (m, 2H), 3.03 (m, 3H), 0.94 (t, 3H). |
| 75 | 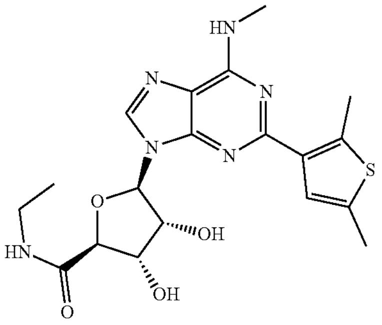 [SMILES: CCNC(=O)[C@H]1O[C@@H](n2cnc3c(NC)nc(-c4cc(C)sc4C)nc32)[C@H](O)[C@@H]1O] (2S,3S,4R,5R)-5-(2-(2,5-dimethylthiophen-3-yl)-6-(methylamino)-9H-purin-9-yl)-N-ethyl-3,4-dihydroxyltetrahydrofuran-2-carboxamide | $^{1}H$ NMR (500 MHz, DMSO-$d_6$): δ: 8.44(s, 1H), 8.05 (t, 1H), 7.80 (s, 1H), 7.33 (s, 1H),6.02 (d, 1H), 5.67 (d, 2H), 4.81 (t, 1H), 4.31 (d, 1H), 4.24 (q, 1H), 3.13 (m, 1H), 3.01 (s, 3H), 2.94 (m, 1H), 2.75 (s, 3H), 2.39 (s, 3H), 0.88 (t, 3H). |
| 76 | 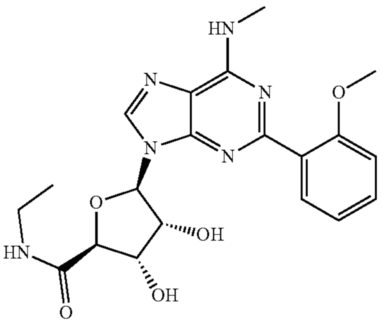 [SMILES: CCNC(=O)[C@H]1O[C@@H](n2cnc3c(NC)nc(-c4ccccc4OC)nc32)[C@H](O)[C@@H]1O] (2S,3S,4R,5R)-N-ethyl-3,4-dihydroxyl-5-(2-(2-methoxyphenyl)-6-(methylamino)-9H-purin-9-yl)tetrahydrofuran-2-carboxamide | $^{1}H$ NMR (500 MHz, DMSO-$d_6$): δ: 8.68(d, 1H), 8.37 (s, 1H), 7.89 (t, 1H), 7.46 (d, 1H),7.40 (t, 1H), 7.12 (d, 1H), 7.02 (t, 1H), 5.95 (d, 1H), 5.74 (d, 1H), 5.56 (d, 1H), 4.70 (q, 1H), 4.26 (d, 1H), 4.09 (s, 1H), 3.73 (s, 3H), 2.95 (s, 3H), 2.79 (m, 1H)), 2.36 (m, 1H), 0.61 (t, 3H). |

-continued

| No. | Compound structure and name | Characterization data |
| --- | --- | --- |
| 77 | 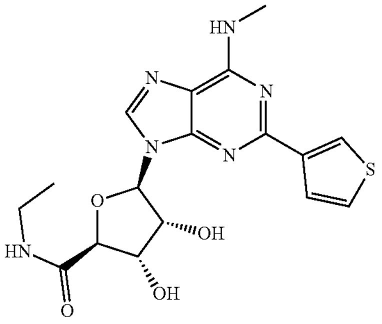 [SMILES: CCNC(=O)[C@H]1O[C@@H](n2cnc3c(NC)nc(-c4ccsc4)nc32)[C@H](O)[C@@H]1O] (2S,3S,4R,5R)-N-ethyl-3,4-dihydroxyl-5-(6-(methylamino)-2-(thiophen-3-yl)-9H-purin-9-yl)tetrahydrofuran-2-carboxamide | $^1$H NMR (500 MHz, DMSO-$d_6$): δ: 8.44(s, 1H), 8.22 (s, 1H), 7.98 (t, 1H), 7.80 (s, 1H), 7.78 (d, 1H), 7.58 (q, 1H), 6.05 (d, 1H), 5.67 (d, 1H), 5.58 (d, 1H), 4.84 (q, 1H), 4.33 (m, 2H), 3.16 (m, 1H), 3.05 (s, 3H), 2.98 (m, 1H), 0.89 (t, 3H). |
| 78 | 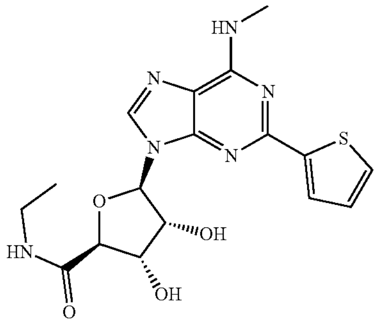 (2S,3S,4R,5R)-N-ethyl-3,4-dihydroxyl-5-(6-(methylamino)-2-(thiophen-2-yl)-9H-purin-9-yl)tetrahydrofuran-2-carboxamide | $^1$H NMR (500 MHz, DMSO-$d_6$): δ: 8.23(s, 1H), 7.84 (s, 1H), 7.80 (s, 1H), 7.57 (q, 1H), 7.31 (d, 1H), 7.15 (q, 1H), 6.43 (s, 1H), 5.67 (q, 1H), 5.48 (d, 1H), 4.57 (s, 1H), 3.01 (s, 3H), 2.72 (m, 1H), 2.63 (m, 1H), 1.55 (s, 3H), 1.37 (s, 3H), 0.44 (t, 3H). |
| 79 | 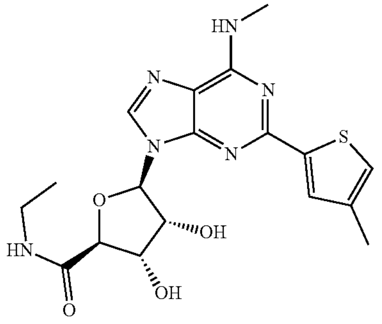 [SMILES: CCNC(=O)[C@H]1O[C@@H](n2cnc3c(NC)nc(-c4cc(C)cs4)nc32)[C@H](O)[C@@H]1O] (2S,3S,4R,5R)-N-ethyl-3,4-dihydroxyl-5-(6-(methylamino)-2-(4-methylthiophen-2-yl)-9H-purin-9-yl)tetrahydrofuran-2-carboxamide | $^1$H NMR (500 MHz, DMSO-$d_6$): δ: 8.21(s, 1H), 7.77 (s, 1H), 7.56 (m, 1H), 7.30 (t, 1H), 7.19 (s, 1H), 6.41 (s, 1H), 5.64 (d, 1H), 5.48 (d, 1H), 4.55 (d, 1H), 3.00 (s, 3H), 2.72 (m, 2H), 2.26 (s, 3H), 1.55 (s, 3H), 1.37 (s, 3H), 0.47 (t, 3H). |

-continued

| No. | Compound structure and name | Characterization data |
|---|---|---|
| 80 | 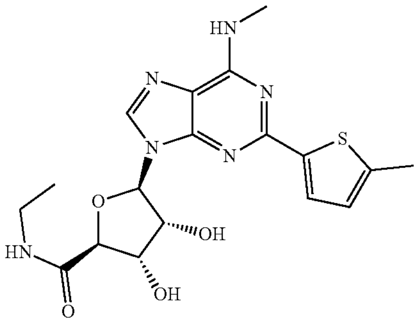 (2S,3S,4R,5R)-N-ethyl-3,4-dihydroxyl-5-(6-(methylamino)-2-(5-methylthiophen-2-yl)-9H-purin-9-yl)tetrahydrofuran-2-carboxamide | $^1H$ NMR (500 MHz, DMSO-$d_6$): δ: 8.20(s, 1H), 7.75 (s, 1H), 7.63 (d, 1H), 7.30 (d, 1H), 6.84 (q, 1H), 6.41 (s, 1H), 5.65 (dd, 1H), 5.45 (d, 1H), 4.55 (d, 1H), 2.99 (s, 3H), 2.72 (m, 2H), 2.48 (s, 3H), 1.55 (s, 3H), 1.36 (s, 3H), 0.43 (t, 3H). |
| 81 | 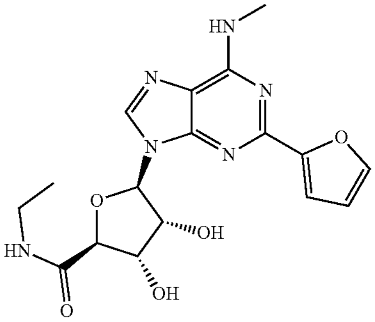 (2S,3S,4R,5R)-N-ethyl-5-(2-(furan-2-yl)-6-(methylamino)-9H-purin-9-yl)-3,4-dihydroxyltetrahydrofuran-2-carboxamide | $^1H$ NMR (500 MHz, DMSO-$d_6$): δ: 8.45(s, 1H), 8.08 (t, 1H), 7.89 (s, 1H), 7.83 (s, 1H), 7.16 (s, 1H), 6.64 (q, 1H), 6.03 (d, 1H), 5.70 (d, 1H), 5.60 (d, 1H), 4.78 (q, 1H), 4.32 (d, 2H), 4.25 (q, 1H), 3.19 (m, 1H), 3.09 (m, 1H), 3.03 (s, 3H), 0.93 (t, 3H). |
| 82 | 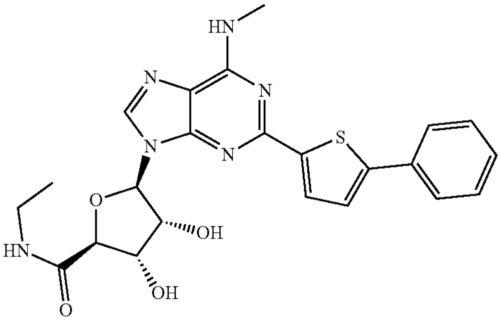 [SMILES: CCNC(=O)[C@H]1O[C@@H](n2cnc3c(NC)nc(-c4ccc(-c5ccccc5)s4)nc32)[C@H](O)[C@@H]1O] (2S,3S,4R,5R)-N-ethyl-3,4-dihydroxyl-5-(6-(methylamino)-2-(5-phenylthiophen-2-yl)-9H-purin-9-yl)tetrahydrofuran-2-carboxamide | $^1H$ NMR (500 MHz, DMSO-$d_6$): δ: 8.48(s, 1H), 8.02 (t, 1H), 7.79 (s, 1H), 7.83 (d, 1H), 7.75 (d, 2H), 7.56 (d, 1H), 7.45 (t, 2H), 7.33 (t, 1H), 6.06 (d, 1H), 5.70 (d, 1H), 5.62 (d, 1H), 4.78 (q, 1H), 4.32 (m, 2H), 3.16 (m, 2H), 0.95 (t, 3H). |

-continued

| No. | Compound structure and name | Characterization data |
|---|---|---|
| 83 | 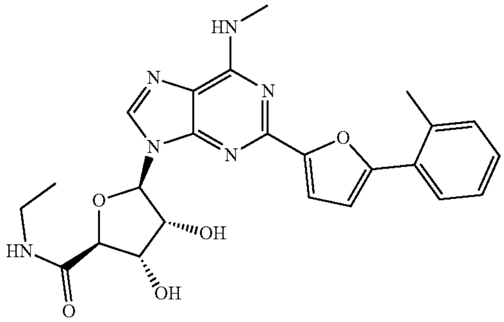 [SMILES: CCNC(=O)[C@H]1O[C@@H](n2cnc3c(NC)nc(-c4ccc(-c5ccccc5C)o4)nc32)[C@H](O)[C@@H]1O] (2S,3S,4R,5R)-N-ethyl-3,4-dihydroxyl-5-(6-(methylamino)-2-(5-o-methylphenyl) furan-2-yl)-9H-purin-9-yl)tetrahydrofuran-2-carboxamide | $^1$H NMR (500 MHz, DMSO-$d_6$): δ: 8.48(s, 1H), 8.02 (t, 1H), 7.90 (s, 1H), 7.79 (d, 1H), 7.34 (d, 2H), 7.27 (q, 2H), 6.94 (d, 1H), 6.06 (d, 1H), 5.70 (d, 1H), 5.63 (d, 1H), 4.88 (q, 1H), 4.32 (m, 2H), 3.11 (m, 1H), 3.06 (s, 3H), 2.95 (m, 1H), 2.56 (s, 3H) , 0.87 (t, 3H). |
| 84 | 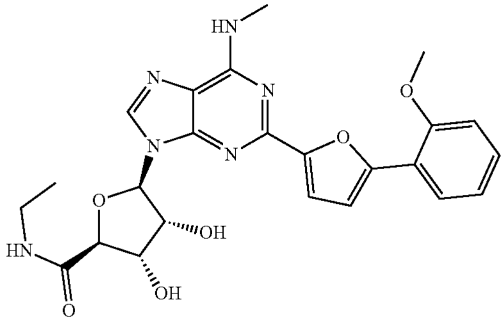 [SMILES: CCNC(=O)[C@H]1O[C@@H](n2cnc3c(NC)nc(-c4ccc(-c5ccccc5OC)o4)nc32)[C@H](O)[C@@H]1O] (2S,3S,4R,5R)-N-ethyl-3,4-dihydroxyl-5-(2-(5-(2-methoxyphenyl)furan-2-yl)-6-(methylamino)-9H-purin-9-yl)tetrahydrofuran-2-carboxamide | $^1$H NMR (500 MHz, DMSO-$d_6$): δ: 8.24(s, 1H), 8.01 (d, 1H), 7.79 (s, 1H), 7.62 (m, 1H), 7.34 (td, 1H), 7.27 (t, 2H), 7.17 (d, 1H), 7.06 (d, 1H), 6.45 (s, 1H), 5.83 (dd, 1H), 5.51 (d, 1H), 4.56 (d, 1H), 3.95 (s, 3H), 3.03 (s, 3H), 2.63 (m, 2H), 1.56 (s, 3H), 1.38 (s, 3H), 0.41 (t, 3H). |
| 85 | 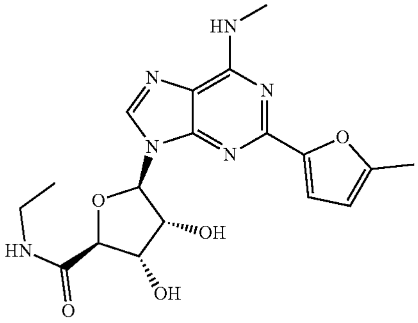 (2S,3S,4R,5R)-N-ethyl-3,4-dihydroxyl-5-(6-(methylamino)-2-(5-methylfuran-2-yl)-9H-purin-9-yl)tetrahydrofuran-2-carboxamide | $^1$H NMR (500 MHz, DMSO-$d_6$): δ: 8.45(s, 1H), 8.09 (t, 1H), 7.82 (s, 1H), 7.06 (s, 1H), 6.26 (d, 1H), 6.06 (d, 1H), 5.72 (d, 1H), 5.62 (d, 1H), 4.76 (q, 1H), 4.32 (d, 1H), 4.24 (d, 1H), 3.14 (m, 2H), 3.01 (s, 3H), 2.38(s, 3H), 0.95 (t, 3H). |

-continued

| No. | Compound structure and name | Characterization data |
|---|---|---|
| 86 | 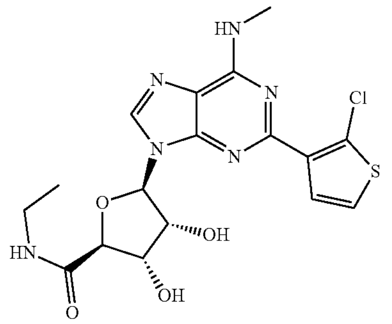 [SMILES: CCNC(=O)[C@H]1O[C@@H](n2cnc3c(NC)nc(-c4ccsc4Cl)nc32)[C@H](O)[C@@H]1O] (2S,3S,4R,5R)-5-(2-(2-chlorothiophen-3-yl)-6-(methylamino)-9H-purin-9-yl)-N-ethyl-3,4-dihydroxyltetrahydrofuran-2-carboxamide | $^{1}H$ NMR (500 MHz, DMSO-$d_6$): δ: 8.48(s, 1H), 8.04 (t, 1H), 7.94 (s, 1H), 7.60 (d, 1H), 7.48 (d, 1H), 6.03 (d, 1H), 5.68 (d, 1H), 5.57 (d, 1H), 4.90 (q, 1H), 4.30 (d, 1H), 4.25 (q, 1H), 3.14 (m, 1H), 3.04 (s, 3H), 2.88 (m, 1H), 0.84 (t, 3H). |
| 87 | 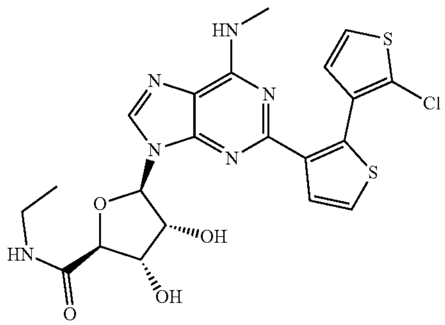 [SMILES: CCNC(=O)[C@H]1O[C@@H](n2cnc3c(NC)nc(-c4ccsc4-c4ccsc4Cl)nc32)[C@H](O)[C@@H]1O] (2S,3S,4R,5R)-5-(2-(2'-chloro-(2,3'-bithiophen-3-yl)-6-(methylamino)-9H-purin-9-yl)-N-ethyl-3,4-dihydroxyltetrahydrofuran-2-carboxamide | $^{1}H$ NMR (500 MHz, DMSO-$d_6$): δ: 8.40 (s, 1H), 8.06 (t, 1H), 7.68 (s, 3H), 7.46 (d, 1H), 7.02 (d, 1H), 5.95 (d, 1H), 5.68 (d, 1H), 5.50 (s, 1H), 4.69 (s, 1H), 4.28 (s, 1H), 4.21 (s, 1H), 3.14 (m, 1H), 2.85 (m, 1H), 2.60 (s, 3H), 0.84 (t, 3H). |
| 88 | 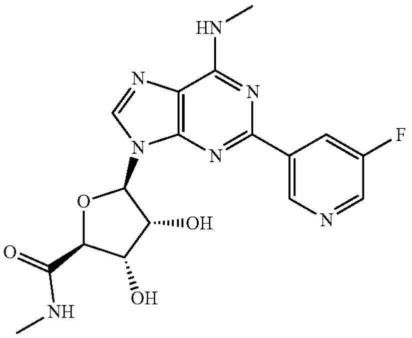 [SMILES: CNC(=O)[C@H]1O[C@@H](n2cnc3c(NC)nc(-c4cncc(F)c4)nc32)[C@H](O)[C@@H]1O] (2S,3S,4R,5R)-5-(2-(5-fluoropyridin-3-yl)-6-(methylamino)-9H-purin-9-yl)-3,4-dihydroxyl-N-methyltetrahydrofuran-2-carboxamide | LC-MS m/z $[M + 1]^+$: 404.2; $^{1}H$ NMR (500 MHz, DMSO-$d_6$) δ: 9.39 (s, 1H), 8.68 (s, 1H), 8.55 (s, 1H), 8.43 (d, J = 8.0 Hz, 1H), 8.07 (d, J = 1.0 Hz, 1H), 7.96 (d, J = 3.1 Hz, 1H), 6.09 (d, J = 6.2 Hz, 1H), 5.71 (d, J = 3.5 Hz, 1H), 5.61 (d, J = 6.1 Hz, 1H), 4.90 (d, J = 3.9 Hz, 1H), 4.35 (s, 2H), 3.09 (s, 3H), 2.54 (d, J = 3.2 Hz, 3H). |

-continued

| No. | Compound structure and name | Characterization data |
|---|---|---|
| 89 | 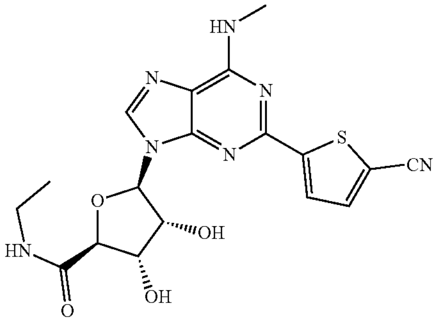 [SMILES: CCNC(=O)[C@H]1O[C@@H](n2cnc3c(NC)nc(-c4ccc(C#N)s4)nc32)[C@H](O)[C@@H]1O] (2S,3S,4R,5R)-5-(2-(5-cyanothiophen-2-yl)-6-(methylamino)-9H-purin-9-yl)-N-ethyl-3,4-dihydroxyltetrahydrofuran-2-carboxamide | $^{1}H$ NMR (500 MHz, DMSO-$d_6$): δ: 8.49 (s, 1H), 8.05 (d, 1H), 7.96 (t, 1H), 7.91 (d, 1H), 7.81 (d, 1H), 5.98 (d, 1H), 5.64 (d, 1H), 5.55 (d, 1H), 4.71 (q, 1H), 4.26 (s, 2H), 3.06 (m, 2H), 2.94 (s, 3H), 0.87 (t, 3H). |
| 90 | 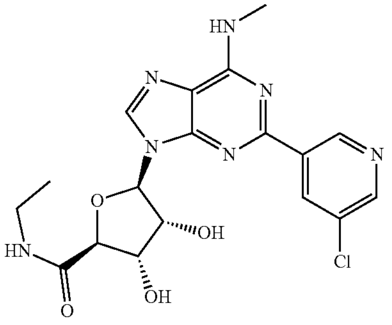 [SMILES: CCNC(=O)[C@H]1O[C@@H](n2cnc3c(NC)nc(-c4cncc(Cl)c4)nc32)[C@H](O)[C@@H]1O] (2S,3S,4R,5R)-5-(2-(5-chloropyridin-3-yl)-6-(methylamino)-9H-purin-9-yl)-N-ethyl-3,4-dihydroxyltetrahydrofuran-2-carboxamide | $^{1}H$ NMR (500 MHz, DMSO-$d_6$): δ: 9.46 (s, 1H), 8.73 (d, 1H), 8.67 (s, 1H), 8.56 (s, 1H), 8.08 (d, 1H), 8.00 (t, 1H), 6.11 (s, 1H), 5.69 (d, 1H), 5.61 (d, 1H), 4.86 (q, 1H), 4.35 (d, 1H), 4.31 (q, 1H), 3.14 (m, 1H), 3.09 (s, 3H), 3.00 (m, 1H), 0.90 (t, 3H). |
| 91 | 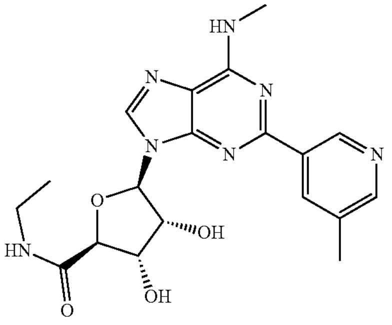 [SMILES: CCNC(=O)[C@H]1O[C@@H](n2cnc3c(NC)nc(-c4cncc(C)c4)nc32)[C@H](O)[C@@H]1O] (2S,3S,4R,5R)-N-ethyl-3,4-dihydroxyl-5-(6-(methylamino)-2-(5-methylpyridin-3-yl)-9H-purin-9-yl)-tetrahydrofuran-2-carboxamide | $^{1}H$ NMR (500 MHz, DMSO-$d_6$): δ: 9.28 (s, 1H), 8.48 (d, 2H), 8.29 (s, 1H), 7.91 (s, 1H), 7.41 (t, 1H), 6.48 (s, 1H), 5.66 (dd, 1H), 5.50 (d, 1H), 4.61 (s, 1H), 3.06 (s, 3H), 2.61 (m, 2H), 2.41 (s, 3H), 1.55 (s, 3H), 1.36 (s, 3H), 0.38 (t, 3H). |

-continued

| No. | Compound structure and name | Characterization data |
|---|---|---|
| 92 | 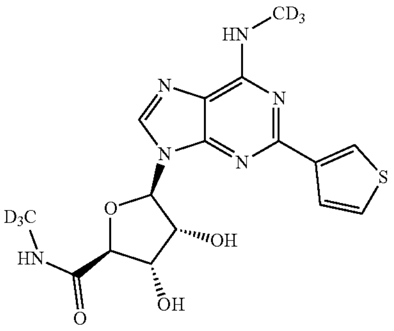 (2S,3S,4R,5R)-3,4-dihydroxyl-N-(methyl-d3)-5-(6-(methyl-d3-amino)-2-(thiophen-3-yl)-9H-purin-9-yl)tetrahydrofuran-2-carboxamide | $^1$H NMR (500 MHz, DMSO-$d_6$): δ: 8.42 (s, 1H), 8.21 (s, 1H), 7.91 (s, 1H), 7.78 (d, 2H), 7.58 (q, 1H), 6.03 (s, 1H), 5.67 (d, 1H), 5.57 (d, 1H), 4.48 (d, 1H), 4.32 (s, 1H) . |
| 93 | 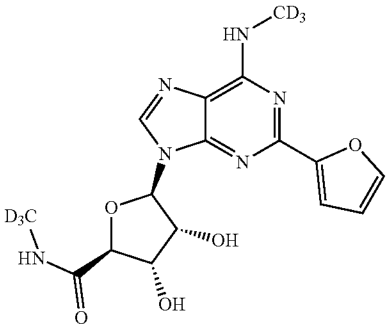 [SMILES: [2H]C([2H])([2H])NC(=O)[C@H]1O[C@@H](n2cnc3c(NC([2H])([2H])[2H])nc(-c4ccco4)nc32)[C@H](O)[C@@H]1O] (2S,3S,4R,5R)-5-(2-(furan-2-yl)-6-((methyl-d3)amino)-9H-purin-9-yl)-3,4-dihydroxyl-N-(methyl-d3)tetrahydrofuran-2-carboxamide | $^1$H NMR (500 MHz, DMSO-$d_6$): δ: 8.43 (s, 1H), 8.05 (s, 1H), 7.84 (s, 1H), 7.16 (s, 1H), 6.64 (q, 1H), 6.02 (d, 1H), 5.71 (d, 1H), 5.58 (d, 1H), 4.80 (q, 1H), 4.35 (s, 1H), 4.23 (m, 1H). |
| 94 | 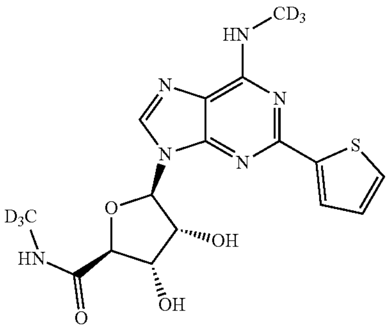 [SMILES: [2H]C([2H])([2H])NC(=O)[C@H]1O[C@@H](n2cnc3c(NC([2H])([2H])[2H])nc(-c4cccs4)nc32)[C@H](O)[C@@H]1O] (2S,3S,4R,5R)-3,4-dihydroxyl-N-(methyl-d3)-5-(6-((methyl-d3)amino)-2-(thiophen-2-yl)-9H-purin-9-yl)tetrahydrofuran-2-carboxamide | $^1$H NMR (500 MHz, DMSO-$d_6$): δ: 8.44 (s, 1H), 7.89 (s, 1H), 7.82 (s, 2H), 7.62 (dd, 1H), 7.14 (t, 1H), 6.02 (d, 1H), 5.68 (d, 1H), 5.58 (d, 1H), 4.83 (q, 1H), 4.32 (m, 2H). |

-continued

| No. | Compound structure and name | Characterization data |
|---|---|---|
| 95 | 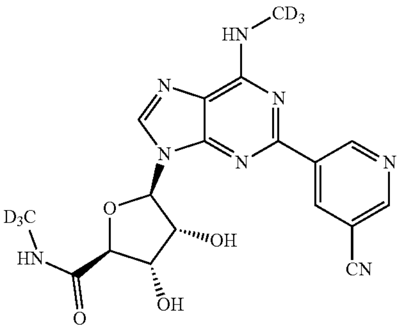 [SMILES: [2H]C([2H])([2H])NC(=O)[C@H]1O[C@@H](n2cnc3c(NC([2H])([2H])[2H])nc(-c4cncc(C#N)c4)nc32)[C@H](O)[C@@H]1O] (2S,3S,4R,5R)-5-(2-(5-cyanopyridin-3-yl)-6-((methyl-d3)amino)-9H-purin-9-yl)-3,4-dihydroxyl-N-((methyl-d3))tetrahydrofuran-2-carboxamide | $^1$H NMR (500 MHz, DMSO-$d_6$): δ: 9.73 (s, 1H), 9.11 (d, 1H), 9.03 (s, 2H), 8.55 (s, 1H), 8.07 (s, 1H), 7.93 (s, 1H), 6.11 (d, 1H), 5.68 (d, 1H), 5.58 (d, 1H), 4.88 (q, 1H), 4.35 (m, 2H). |
| 96 | 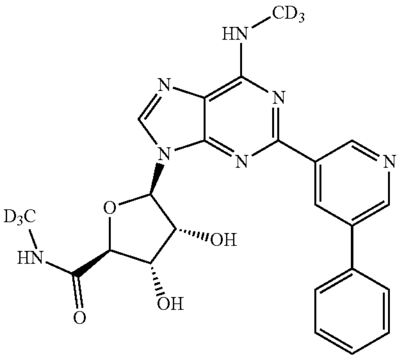 [SMILES: [2H]C([2H])([2H])NC(=O)[C@H]1O[C@@H](n2cnc3c(NC([2H])([2H])[2H])nc(-c4cncc(-c5ccccc5)c4)nc32)[C@H](O)[C@@H]1O] (2S,3S,4R,5R)-3,4-dihydroxyl-N-methyl-d3))-5-(6-((methyl-d3)amino)-2-(5-phenylpyridin-3-yl)-9H-purin-9-yl)tetrahydrofuran-2-carboxamide | $^1$H NMR (500 MHz, DMSO-$d_6$): δ: 9.50 (s, 1H), 8.97 (d, 1H), 8.85 (s, 1H), 8.53 (s, 1H), 7.99 (s, 1H), 7.94 (s, 1H), 7.82 (s, 1H), 7.81 (s, 1H), 7.56 (t, 2H), 7.49 (t, 1H), 6.12 (d, 1H), 5.68 (s, 1H), 5.61 (s, 1H), 4.93 (s, 1H), 4.35 (m, 2H). |
| 97 | 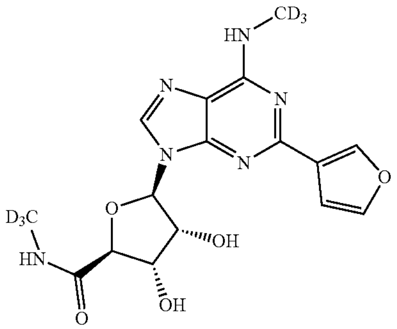 [SMILES: [2H]C([2H])([2H])NC(=O)[C@H]1O[C@@H](n2cnc3c(NC([2H])([2H])[2H])nc(-c4ccoc4)nc32)[C@H](O)[C@@H]1O] (2S,3S,4R,5R)-5-(2-(furan-3-yl)-6-((methyl-d3)amino)-9H-purin-9-yl)-3,4-dihydroxyl-N-(methyl-d)tetrahydrofuran-2-carboxamide | $^1$H NMR (500 MHz, DMSO-$d_6$): δ: 8.40 (s, 1H), 8.26 (s, 1H), 7.90 (s, 1H), 7.73 (t, 2H), 6.97 (s, 1H), 6.02 (d, 1H), 5.5.65 (d, 1H), 5.56 (d, 1H), 4.84 (q, 1H), 4.33 (m, 2H). |

-continued

| No. | Compound structure and name | Characterization data |
|---|---|---|
| 98 | 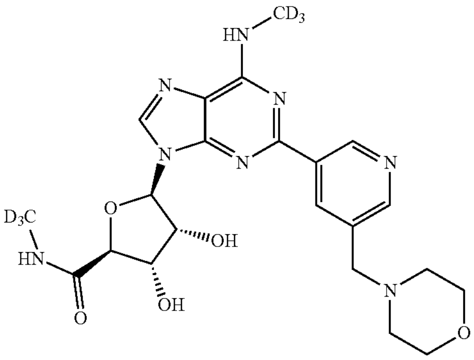 [SMILES: [2H]C([2H])([2H])NC(=O)[C@H]1O[C@@H](n2cnc3c(NC([2H])([2H])[2H])nc(-c4cncc(CN5CCOCC5)c4)nc32)[C@H](O)[C@@H]1O] (2S,3S,4R,5R)-3,4-dihydroxyl-N-(methyl-d3)-5-(6-((methyl-d3)amino)-2-(5-(morpholinomethyl)pyridin-3-yl)-9H-purin-9-yl)tetrahydrofuran-2-carboxamide | $^1$H NMR (500 MHz, DMSO-$d_6$): δ: 9.40 (s, 1H), 8.56 (s, 2H), 8.51 (s, 1H), 7.95 (s, 1H), 7.93 (s, 1H), 6.01 (d, 1H), 5.71 (d, 1H), 5.61 (d, 1H), 4.91 (m, 1H), 4.35 (d, 1H), 4.32 (m, 1H), 3.60 (m, 6H), 2.41 (m, 4H). |
| 99 | 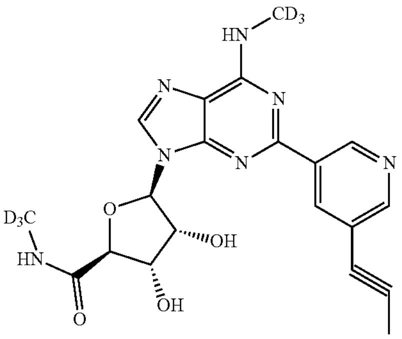 [SMILES: [2H]C([2H])([2H])NC(=O)[C@H]1O[C@@H](n2cnc3c(NC([2H])([2H])[2H])nc(-c4cncc(C#CC)c4)nc32)[C@H](O)[C@@H]1O] (2S,3S,4R,5R)-3,4-dihydroxyl-N-(methyl-d3)-5-(6-((methyl-d3)-amino)-2-(5-(prop-1-yne-1-yl)pyridin-3-yl)-9H-purin-9-yl)tetrahydrofuran-2-carboxamide | $^1$H NMR (500 MHz, DMSO-$d_6$): δ: 9.42 (s, 1H), 8.65 (d, 1H), 8.58 (s, 1H), 8.52 (s, 1H), 7.98 (s, 1H), 7.93 (s, 1H), 6.10 (d, 1H), 5.68 (s, 1H), 5.59 (s, 1H), 4.85 (t, 1H), 4.35 (d, 1H), 4.30 (q, 1H), 2.12 (s, 3H). |
| 100 | 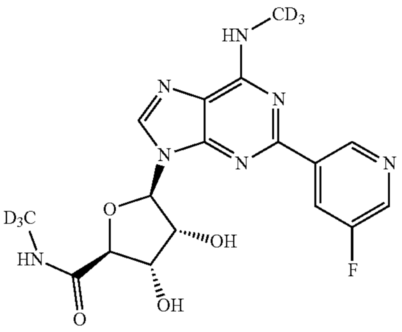 [SMILES: [2H]C([2H])([2H])NC(=O)[C@H]1O[C@@H](n2cnc3c(NC([2H])([2H])[2H])nc(-c4cncc(F)c4)nc32)[C@H](O)[C@@H]1O] (2S,3S,4R,5R)-5-(2-(5-fluoropyridin-3-yl)-6-((methyl-d3)amino)-9H-purin-9-yl)-3,4-dihydroxyl-N-((methyl-d3))tetrahydrofuran-2-carboxamide | $^1$H NMR (500 MHz, DMSO-$d_6$): δ: 9.38 (s, 1H), 8.67 (d, 1H), 8.53 (s, 1H), 8.42 (d, 1H), 8.01 (s, 1H), 7.91 (s, 1H), 6.10 (d, 1H), 5.68 (d, 1H), 5.59 (d, 1H), 4.89 (d, 1H), 4.35 (s, 1H). |

-continued

| No. | Compound structure and name | Characterization data |
|---|---|---|
| 101 | 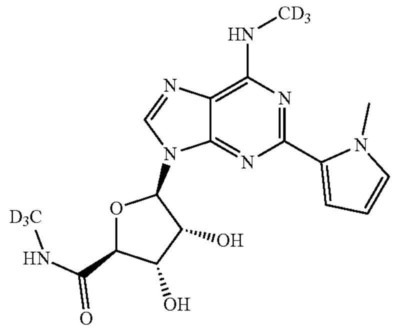 [SMILES: [2H]C([2H])([2H])NC(=O)[C@H]1O[C@@H](n2cnc3c(NC([2H])([2H])[2H])nc(-c4cccn4C)nc32)[C@H](O)[C@@H]1O] (2S,3S,4R,5R)-3,4-dihydroxyl-N-(methyl-d3)-5-(2-(1-methyl-1H-pyrrol)-2-yl)-6-((methyl-d3)amino)-9H-purin-9-yl)tetrahydrofuran-2-carboxamide | $^1$H NMR (500 MHz, DMSO-$d_6$): δ: 8.36 (s, 1H), 8.01 (s, 1H), 7.70 (s, 1H), 6.88 (t, 1H), 6.82 (s, 1H), 6.06 (t, 1H), 5.97 (d, 1H), 5.66 (d, 1H), 5.56 (d, 1H), 4.85 (q, 1H), 4.30 (d, 1H), 4.25 (m, 1H), 4.03 (s, 3H). |
| 102 | 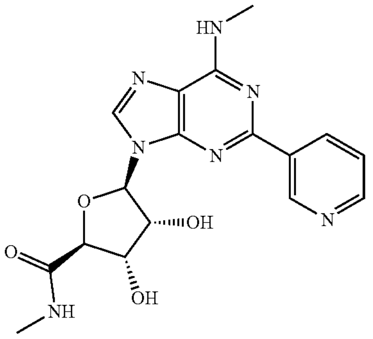 [SMILES: CNC(=O)[C@H]1O[C@@H](n2cnc3c(NC)nc(-c4cccnc4)nc32)[C@H](O)[C@@H]1O] (2S,3S,4R,5R)-3,4-dihydroxyl-N-methyl-5-(6-(methylamino)-2-(pyridin-3-yl)-9H-purin-9-yl)tetrahydrofuran-2-carboxamide | LC-MS m/z [M + 1]$^+$: 386.2; $^1$H NMR (500 MHz, DMSO-$d_6$) δ: 9.51 (s, 1H), 8.65 (d, J = 5.3 Hz, 2H), 8.51 (s, 1H), 7.97 (d, J = 4.7 Hz, 2H), 7.52 (dd, J = 7.7, 5.0 Hz, 1H), 6.09 (d, J =6.9 Hz, 1H), 5.73 (d, J = 4.5 Hz, 1H), 5.62 (d, J = 6.4 Hz, 1H), 4.91 (d, J = 4.7 Hz, 1H), 4.39 - 4.30 (m, 2H), 3.09 (d, J = 3.3 Hz, 3H), 2.52 (d, J = 4.8 Hz, 3H). |
| 103 | 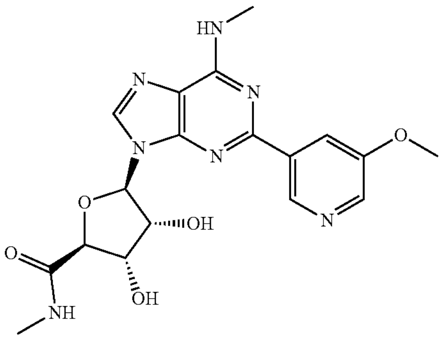 [SMILES: CNC(=O)[C@H]1O[C@@H](n2cnc3c(NC)nc(-c4cncc(OC)c4)nc32)[C@H](O)[C@@H]1O] (2S,3S,4R,5R)-3,4-dihydroxyl-5-(2-(5-methoxypyridin-3-yl)-6-(methylamino)-9H-purin-9-yl)-N-methyltetrahydrofuran-2-carboxamide | LC-MS m/z [M + 1]$^+$: 416.3; $^1$H NMR (500 MHz, DMSO-$d_6$) δ: 9.13 (s, 1H), 8.51 (s, 1H), 8.38 (d, J = 2.8 Hz, 1H), 8.16 (s, 1H), 8.00 (s, 1H), 7.95 (d, J = 4.7 Hz, 1H), 6.08 (d, J =6.8 Hz, 1H), 5.70 (d, J = 4.7 Hz, 1H), 5.61 (d, J = 6.4 Hz, 1H), 4.93 (d, J = 4.6 Hz, 1H), 4.35 (d, J = 6.1 Hz, 2H), 3.94 (s, 3H), 3.09 (s, 3H), 2.52 (s, 3H). |

-continued

| No. | Compound structure and name | Characterization data |
|---|---|---|
| 104 | 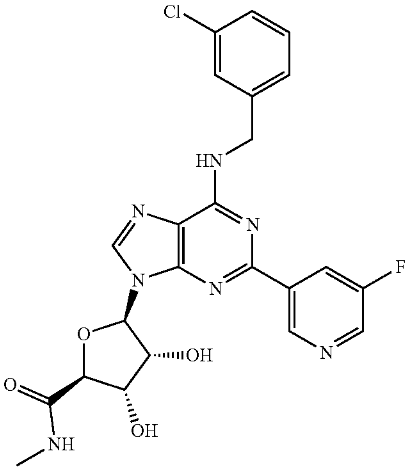 [SMILES: CNC(=O)[C@H]1O[C@@H](n2cnc3c(NCc4cccc(Cl)c4)nc(-c4cncc(F)c4)nc32)[C@H](O)[C@@H]1O] (2S,3S,4R,5R)-5-(6-((3-chlorobenzyl)amino)-2-(5-fluoropyridin-3-yl)-9H-purin-9-yl)-3,4-dihydroxyl-N-methyltetrahydrofuran-2-carboxamide | LC-MS m/z $[M + 1]^+$: 514.2; $^1H$ NMR (500 MHz, DMSO-$d_6$) δ: 9.31 (s, 1H), 8.78 (s, 1H), 8.66 (d, J = 2.7 Hz, 1H), 8.59 (s, 1H), 8.35 (dd, J = 10.0, 1.5 Hz, 1H), 7.94 (d, J = 4.7 Hz, 1H), 7.52 (s, 1H), 7.42 (d, J = 7.5 Hz, 1H), 7.35 (t, J = 7.8 Hz, 1H), 7.28 (d, J = 7.8 Hz, 1H), 6.09 (d, J = 6.8 Hz, 1H), 5.75 - 5.68 (m, 1H), 5.60 (d, J = 6.3 Hz, 1H), 4.90 (dd, J = 11.0, 6.4 Hz, 1H), 4.81 (d, J = 5.0 Hz, 2H), 4.35 (s, 2H), 2.54 (d, J = 4.7 Hz, 3H). |
| 105 | 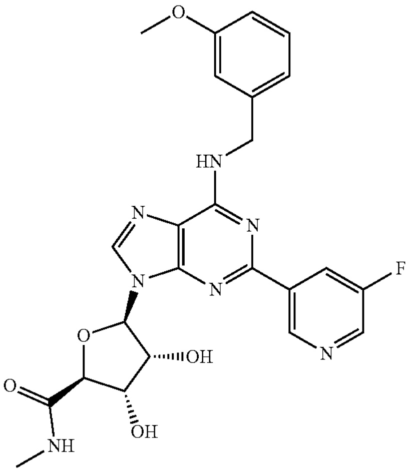 [SMILES: CNC(=O)[C@H]1O[C@@H](n2cnc3c(NCc4cccc(OC)c4)nc(-c4cncc(F)c4)nc32)[C@H](O)[C@@H]1O] (2S,3S,4R,5R)-5-(2-(5-fluoropyridin-3-yl)-6-((3-methoxybenzyl)amino)-9H-purin-9-yl)-3,4-dihydroxyl-N-methyltetrahydrofuran-2-carboxamide | LC-MS m/z $[M + 1]^+$: 510.3; $^1H$ NMR (500 MHz, DMSO-$d_6$) δ: 9.33 (d, J = 1.5 Hz, 1H), 8.73 (s, 1H), 8.66 (d, J = 2.8 Hz, 1H), 8.57 (s, 1H), 8.43 - 8.30 (m, 1H), 7.94 (d, J = 4.7 Hz, 1H), 7.23 (s, 1H), 7.10 - 7.00 (m, 2H), 7.02 (d, J = 7.6 Hz, 1H), 6.79 (d, J = 8.1 Hz, 1H), 6.09 (d, J = 6.8 Hz, 1H), 5.69 (d, J = 4.7 Hz, 1H), 5.60 (d, J = 6.3 Hz, 1H), 4.90 (dd, J = 10.9, 6.3 Hz, 1H), 4.78 (d, J = 5.0 Hz, 2H), 4.35 (s, 2H), 3.71 (s, 3H), 2.54 (d, J = 4.7 Hz, 3H). |

-continued

| No. | Compound structure and name | Characterization data |
|---|---|---|
| 106 | 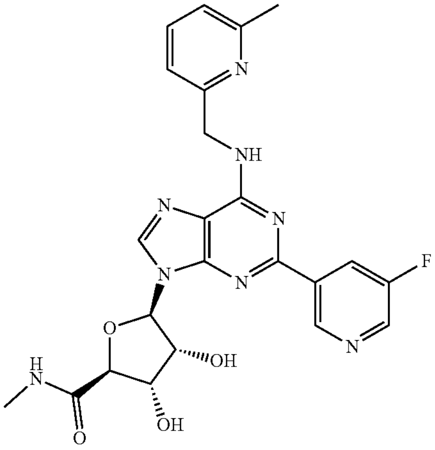 [SMILES: CNC(=O)[C@H]1O[C@@H](n2cnc3c(NCc4cccc(C)n4)nc(-c4cncc(F)c4)nc32)[C@H](O)[C@@H]1O] (2S,3S,4R,5R)-5-(2-(5-fluoropyridin-3-yl)-6-((((6-methylpyridin-2-yl)methyl)amino)-9H-purin-9-yl)-3,4-dihydroxyl-N-methyltetrahydrofuran-2-carboxamide | $^1H$ NMR (500 MHz, DMSO-$d_6$) δ: 9.25 (s, 1H), 8.71 (s, 1H), 8.62 (d, J = 18.1 Hz, 2H), 8.28 (d, J = 9.7 Hz, 1H), 7.94 (d, J = 4.7 Hz, 1H), 7.59 (t, J = 7.7 Hz, 1H), 7.16 (d, J = 7.7 Hz, 1H), 7.10 (d, J = 7.6 Hz, 1H), 6.10 (d, J = 6.8 Hz, 1H), 5.70 (d, J = 4.6 Hz, 1H), 5.60 (d, J = 6.4 Hz, 1H), 4.93 - 4.87 (m, 1H), 4.84 (d, J = 5.1 Hz, 2H), 4.36 (s, 2H), 2.54 (d, J = 4.6 Hz, 3H), 2.50 (s, 3H). LC-MS m/z $[M + H]^+$: 495. |
| 107 | 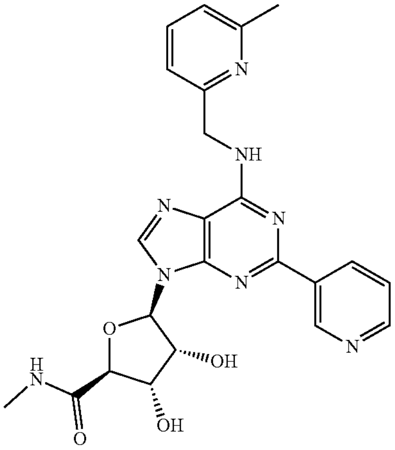 [SMILES: CNC(=O)[C@H]1O[C@@H](n2cnc3c(NCc4cccc(C)n4)nc(-c4cccnc4)nc32)[C@H](O)[C@@H]1O] (2S,3S,4R,5R)-3,4-dihydroxyl-N-methyl-5-(6-((((6-methylpyridin-2-yl)methyl)amino)-2-(pyridin-3-yl)-9H-purin-9-yl)tetrahydrofuran-2-carboxamide | $^1H$ NMR (500 MHz, DMSO-$d_6$) δ: 9.37 (s, 1H), 8.56 (dd, J = 31.7, 15.3 Hz, 4H), 7.95 (d, J = 4.7 Hz, 1H), 7.60 (t, J = 7.7 Hz, 1H), 7.48 (s, 1H), 7.16 (d, J = 7.7 Hz, 1H), 7.10 (d, J = 7.6 Hz, 1H), 6.10 (d, J = 6.9 Hz, 1H), 5.70 (d, J = 4.4 Hz, 1H), 5.60 (d, J = 6.3 Hz, 1H), 4.89 (dd, J = 19.0, 13.1 Hz, 3H), 4.35 (d, J = 4.4 Hz, 2H), 2.53 (d, J = 4.7 Hz, 3H), 2.50 (s, 3H). LC-MS m/z $[M + H]^+$: 477. |
| 108 | 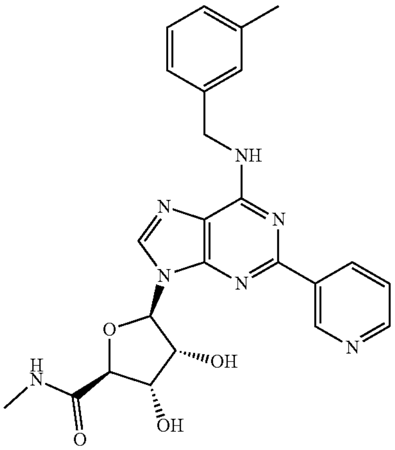 [SMILES: CNC(=O)[C@H]1O[C@@H](n2cnc3c(NCc4cccc(C)c4)nc(-c4cccnc4)nc32)[C@H](O)[C@@H]1O] | $^1H$ NMR (500 MHz, DMSO-$d_6$) δ: 9.45 (d, J = 1.6 Hz, 1H), 8.64 (dd, J = 4.7, 1.6 Hz, 2H), 8.61 - 8.57 (m, 1H), 8.54 (s, 1H), 7.95 (d, J = 4.7 Hz, 1H), 7.51 (dd, J = 7.8, 4.8 Hz, 1H), 7.34 - 7.17 (m, 3H), 7.03 (d, J = 7.2 Hz, 1H), 6.09 (d, J = 6.9 Hz, 1H), 5.71 (d, J = 4.5 Hz, 1H), 5.60 (d, J = 6.3 Hz, 1H), 4.91 (dd, J = 11.1, 6.6 Hz, 1H), 4.78 (s, 2H), 4.34 (dt, J = 6.8, 2.2 Hz, 2H), 2.52 (d, J = 4.8 Hz, 3H), 2.27 (s, 3H). LC-MS m/z $[M + H]^+$: 476. |

-continued

| No. | Compound structure and name | Characterization data |
| --- | --- | --- |
| | (2S,3S,4R,5R)-3,4-dihydroxyl-N-methyl-5-(6-((3-methylbenzyl)amino)-2-(pyridin-3-yl)-9H-purin-9-yl)tetrahydrofuran-2-carboxamide | |
| 109 | 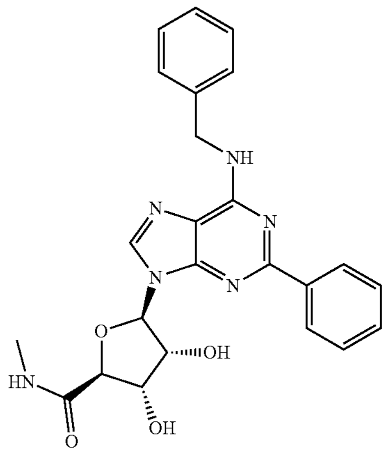 [SMILES: CNC(=O)[C@H]1O[C@@H](n2cnc3c(NCc4ccccc4)nc(-c4ccccc4)nc32)[C@H](O)[C@@H]1O] (2S,3S,4R,5R)-5-(6-(benzylamino)-2-phenyl-9H-purin-9-yl)-3,4-dihydroxyl-N-methyltetrahydrofuran-2-carboxamide | $^1$H NMR (500 MHz, DMSO-$d_6$) δ: 8.51 (d, J = 21.6 Hz, 2H), 8.32 (dd, J = 7.8, 1.8 Hz, 2H), 7.95 (d, J = 4.7 Hz, 1H), 7.48 - 7.41 (m, 5H), 7.32 - 7.26 (m, 2H), 7.21 (t, J = 7.3 Hz, 1H), 6.08 (d, J = 7.0 Hz, 1H), 5.68 (d, J = 4.5 Hz, 1H), 5.58 (d, J = 6.3 Hz, 1H), 4.85 (dd, J = 52.7, 14.7 Hz, 3H), 4.39 - 4.26 (m, 2H), 2.53 - 2.50 (m, 3H). |
| 110 | 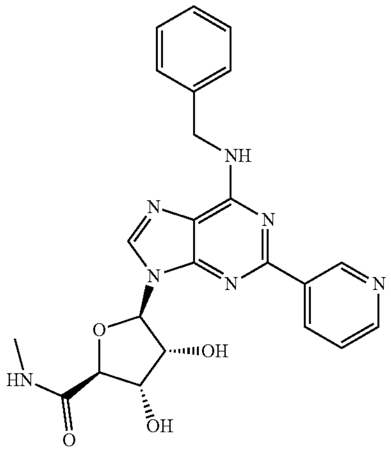 [SMILES: CNC(=O)[C@H]1O[C@@H](n2cnc3c(NCc4ccccc4)nc(-c4cccnc4)nc32)[C@H](O)[C@@H]1O] (2S,3S,4R,5R)-5-(6-(benzylamino)-2-(pyridin-3-yl)-9H-purin-9-yl)-3,4-dihydroxyl-N-methyltetrahydrofuran-2-carboxamide | $^1$H NMR (500 MHz, DMSO-$d_6$) δ: 9.44 (s, 1H), 8.79 - 8.48 (m, 4H), 7.96 (d, J = 4.2 Hz, 1H), 7.55 - 7.39 (m, 3H), 7.27 (dt, J = 49.1, 7.1 Hz, 3H), 6.09 (d, J = 6.8 Hz, 1H), 5.67 (d, J = 49.7 Hz, 2H), 4.87 (d, J = 43.6 Hz, 3H), 4.34 (s, 2H), 2.52 (s, 3H). LC-MS(m/z): 462.2 [M + H]$^+$ |

-continued

| No. | Compound structure and name | Characterization data |
| --- | --- | --- |
| 111 | 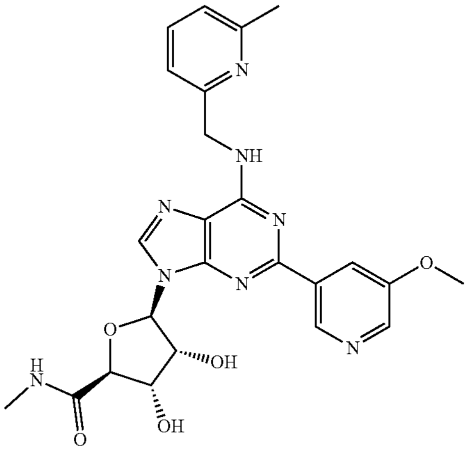 (2S,3S,4R,5R)-3,4-dihydroxyl-5-(2-(5-methoxypyridin-3-yl)-6-((((6-methylpyridin-2-yl))methyl)amino)-9H-purin-9-yl)-N-methyltetrahydrofuran-2-carboxamide | $^1$H NMR (500 MHz, DMSO-$d_6$) δ: 8.99 (s, 1H), 8.64 (s, 1H), 8.57 (s, 1H), 8.34 (s, 1H), 7.99 (s, 1H), 7.97 − 7.89 (m, 1H), 7.59 (t, J = 7.7 Hz, 1H), 7.16 (d, J = 7.7 Hz, 1H), 7.10 (d, J = 7.6 Hz, 1H), 6.10 (d, J = 6.8 Hz, 1H), 5.70 (d, J = 4.7 Hz, 1H), 5.62 (d, J = 6.3 Hz, 1H), 4.94 (dd, J = 10.8, 6.2 Hz, 1H), 4.83 (d, J = 4.5 Hz, 2H), 4.36 (s, 2H), 3.88 (s, 3H), 2.52 (s, 3H), 2.49 (s, 3H). LC-MS (m/z)/2 [M + H]$^+$: 254. |
| 112 | 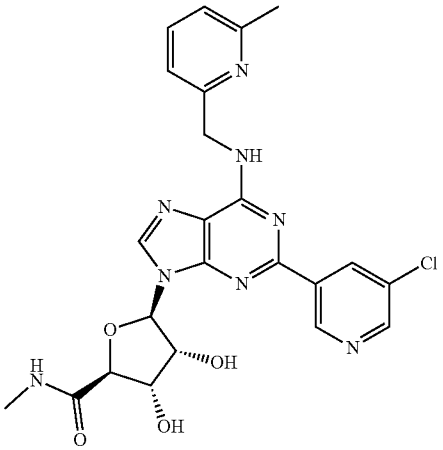 [SMILES: CNC(=O)[C@H]1O[C@@H](n2cnc3c(NCc4cccc(C)n4)nc(-c4cncc(Cl)c4)nc32)[C@H](O)[C@@H]1O] (2S,3S,4R,5R)-5-(2-(5-chloropyridin-3-yl)-6-((((6-methylpyridin-2-yl)methyl)amino)-9H-purin-9-yl)-3,4-dihydroxyl-N-methyltetrahydrofuran-2-carboxamide | $^1$H NMR (500 MHz, DMSO-$d_6$) δ: 9.30 (s, 1H), 8.73 (s, 1H), 8.68 (s, 1H), 8.60 (s, 1H), 8.47 (s, 1H), 7.98 − 7.90 (m, 1H), 7.59 (t, J = 7.7 Hz, 1H), 7.16 (d, J = 7.7 Hz, 1H), 7.10 (d, J = 7.6 Hz, 1H), 6.10 (d, J = 6.9 Hz, 1H), 5.70 (d, J = 4.7 Hz, 1H), 5.60 (d, J = 6.4 Hz, 1H), 4.89 (dd, J = 11.2, 6.4 Hz, 1H), 4.82 (d, J = 5.2 Hz, 2H), 4.38 − 4.27 (m, 2H), 2.55 (d, J = 4.7 Hz, 3H), 2.50 (s, 3H). LC-MS m/z [M + H]$^+$: 511. |
| 113 | 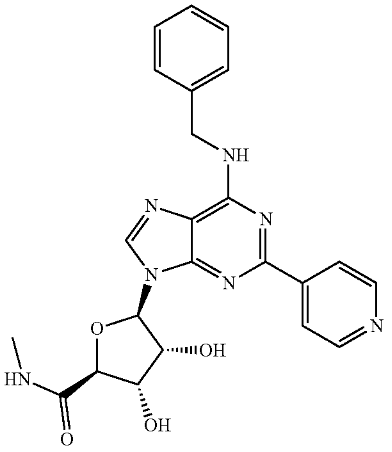 [SMILES: CNC(=O)[C@H]1O[C@@H](n2cnc3c(NCc4ccccc4)nc(-c4ccncc4)nc32)[C@H](O)[C@@H]1O] | $^1$H NMR (500 MHz, DMSO-$d_6$) δ: 8.70 (s, 3H), 8.59 (s, 1H), 8.20 (d, J = 5.6 Hz, 2H), 7.94 (d, J = 4.6 Hz, 1H), 7.45 (d, J = 7.3 Hz, 2H), 7.31 (t, J = 7.6 Hz, 2H), 7.21 (t, J = 7.3 Hz, 1H), 6.10 (d, J = 6.8 Hz, 1H), 5.70 (d, J = 4.2 Hz, 1H), 5.61 (d, J = 6.2 Hz, 1H), 4.87 (dd, J = 19.2, 12.9 Hz, 3H), 4.34 (d, J = 6.1 Hz, 2H), 2.54 (d, J = 4.6 Hz, 3H). LC-MS (m/z): 462.2 [M + H]$^+$. |

-continued

| No. | Compound structure and name | Characterization data |
|---|---|---|
| | (2S,3S,4R,5R)-5-(6-(benzylamino)-2-(pyridin-4-yl)-9H-purin-9-yl)-3,4-dihydroxyl-N-methyltetrahydrofuran-2-carboxamide | |
| 114 | 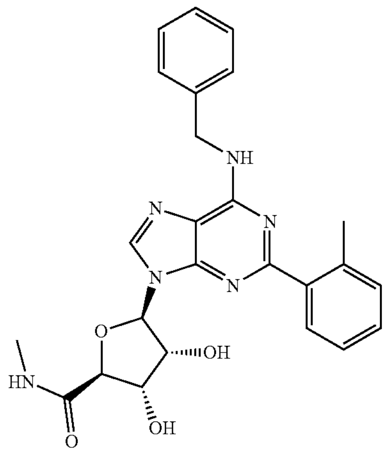 [SMILES: CNC(=O)[C@H]1O[C@@H](n2cnc3c(NCc4ccccc4)nc(-c4ccccc4C)nc32)[C@H](O)[C@@H]1O] (2S,3S,4R,5R)-5-(6-(benzylamino)-2-0-methylphenyl-9H-purin-9-yl)-3,4-dihydroxyl-N-methyltetrahydrofuran-2-carboxamide | $^1$H NMR (500 MHz, DMSO-$d_6$) δ: 8.60 (s, 1H), 8.46 (s, 1H), 8.40 (s, 1H), 7.61 - 7.54 (m, 1H), 7.46 - 7.08 (m, 8H), 5.99 (d, J = 7.6 Hz, 1H), 5.74 (d, J = 4.2 Hz, 1H), 5.59 (d, J = 6.5 Hz, 1H), 4.86 - 4.63 (m, 3H), 4.29 (s, 1H), 4.16 (s, 1H), 2.31 (s, 3H), 2.12 (d, J = 4.5 Hz, 3H).LC-MS (m/z): 475.3 $[M + H]^+$. |
| 115 | 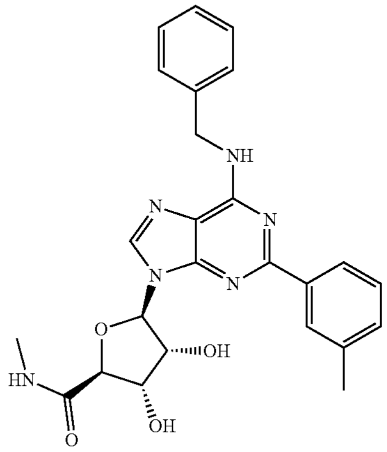 [SMILES: CNC(=O)[C@H]1O[C@@H](n2cnc3c(NCc4ccccc4)nc(-c4cccc(C)c4)nc32)[C@H](O)[C@@H]1O] (2S,3S,4R,5R)-5-(6-(benzylamino)-2-m-methylphenyl-9H-purin-9-yl)-3,4-dihydroxyl-N-methyltetrahydrofuran-2-carboxamide | $^1$H NMR (500 MHz, DMSO-$d_6$) δ: 8.52 (d, J = 25.6 Hz, 2H), 8.10 (d, J = 7.0 Hz, 2H), 7.96 (d, J = 4.8 Hz, 1H), 7.47 - 7.19 (m, 7H), 6.08 (d, J = 7.1 Hz, 1H), 5.70 (d, J = 4.6 Hz, 1H), 5.59 (d, J = 6.4 Hz, 1H), 4.86 (dt, J = 55.1, 12.5 Hz, 3H), 4.38 - 4.25 (m, 2H), 2.51 (d, J = 5.0 Hz, 3H), 2.38 (s, 3H). LC-MS(m/z): 475.3 $[M + H]^+$. |

-continued

| No. | Compound structure and name | Characterization data |
|---|---|---|
| 116 | 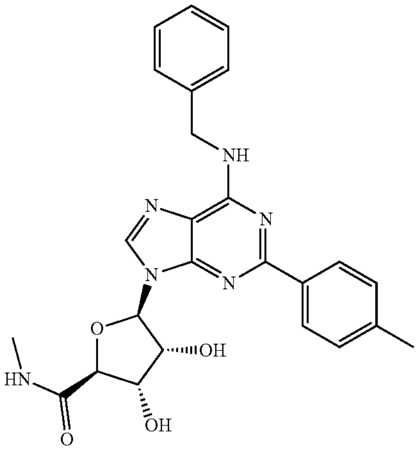 (2S,3S,4R,5R)-5-(6-(benzylamino)-2-p-methylphenyl-9H-purin-9-yl)-3,4-dihydroxyl-N-methyltetrahydrofuran-2-carboxamide | $^1$H NMR (500 MHz, DMSO-$d_6$) δ: 8.46 (s, 2H), 8.21 (d, J = 8.0 Hz, 2H), 7.93 (d, J = 4.4 Hz, 1H), 7.48 - 7.15 (m, 7H), 6.07 (d, J = 6.9 Hz, 1H), 5.66 (d, J = 4.5 Hz, 1H), 5.56 (d, J = 6.3 Hz, 1H), 4.94 - 4.70 (m, 3H), 4.37 - 4.25 (m, 2H), 2.52 (d, J = 4.8 Hz, 3H), 2.35 (s, 3H).LC-MS (m/z): 475.3 $[M + H]^+$. |
| 117 | 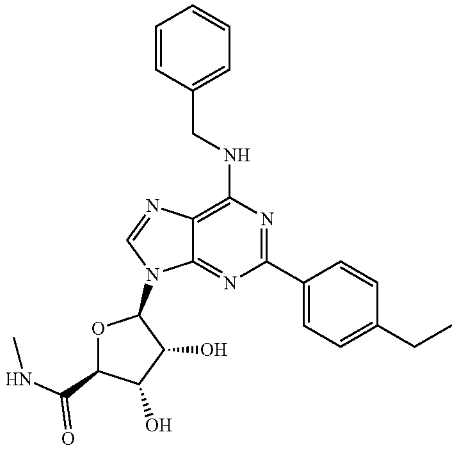 [SMILES: CCc1ccc(-c2nc(NCc3ccccc3)c3ncn([C@@H]4O[C@H](C(=O)NC)[C@@H](O)[C@H]4O)c3n2)cc1] (2S,3S,4R,5R)-5-(6-(benzylamino)-2-(4-ethylphenyl)-9H-purin-9-yl)-3,4-dihydroxyl-N-methyltetrahydrofuran-2-carboxamide | $^1$H NMR (500 MHz, DMSO-$d_6$) δ: 8.50 (d, J = 22.2 Hz, 2H), 8.23 (d, J = 8.2 Hz, 2H), 8.00 - 7.92 (m, 1H), 7.43 (t, J = 8.0 Hz, 2H), 7.26 (ddd, J = 37.5, 15.1, 7.6 Hz, 5H), 6.08 (d, J = 7.0 Hz, 1H), 5.70 (d, J = 4.5 Hz, 1H), 5.60 (d, J = 6.3 Hz, 1H), 4.93 - 4.76 (m, 3H), 4.37 - 4.25 (m, 2H), 2.65 (d, J = 7.6 Hz, 2H), 2.52 (d, J = 4.7 Hz, 3H), 1.23 - 1.19 (m, 3H).LC-MS (m/z): 489.3 $[M + H]^+$. |

-continued

| No. | Compound structure and name | Characterization data |
|---|---|---|
| 118 | 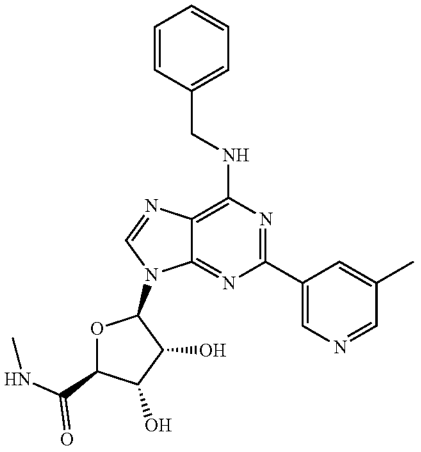 (2S,3S,4R,5R)-5-(6-(benzylamino)-2-(5-methylpyridin-3-yl)-9H-purin-9-yl)-3,4-dihydroxyl-N-methyltetrahydrofuran-2-carboxamide | $^1$H NMR (500 MHz, DMSO-$d_6$) δ: 9.24 (s, 1H), 8.67 (s, 1H), 8.54 (s, 1H), 8.47 (s, 1H), 8.38 (s, 1H), 7.96 (d, J = 4.7 Hz, 1H), 7.44 (d, J = 7.5 Hz, 2H), 7.31 (t, J = 7.6 Hz, 2H), 7.21 (t, J = 7.3 Hz, 1H), 6.09 (d, J = 6.9 Hz, 1H), 5.70 (s, 1H), 5.60 (d, J = 5.5 Hz, 1H), 4.88 (s, 1H), 4.80 (s, 2H), 4.34 (t, J = 5.8 Hz, 2H), 2.52 (d, J = 4.7 Hz, 3H), 2.39 (s, 3H). LC-MS (m/z): 476.3 $[M + H]^+$. |
| 119 | 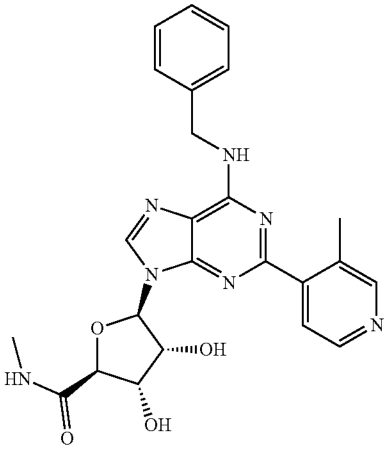 [SMILES: CNC(=O)[C@H]1O[C@@H](n2cnc3c(NCc4ccccc4)nc(-c4ccncc4C)nc32)[C@H](O)[C@@H]1O] (2S,3S,4R,5R)-5-(6-(benzylamino)-2-(3-methylpyridin-4-yl)-9H-purin-9-yl)-3,4-dihydroxyl-N-methyltetrahydrofuran-2-carboxamide | $^1$H NMR (500 MHz, DMSO-$d_6$) δ: 8.74 (s, 1H), 8.53 (d, J = 33.4 Hz, 3H), 8.15 (d, J = 4.1 Hz, 1H), 7.66 (d, J = 4.9 Hz, 1H), 7.28 (ddd, J = 44.7, 17.8, 7.2 Hz, 5H), 6.03 (d, J = 7.2 Hz, 1H), 5.73 (s, 1H), 5.61 (d, J = 6.2 Hz, 1H), 4.76 (d, J = 15.2 Hz, 3H), 4.31 (s, 1H), 4.21 (s, 1H), 2.36 (s, 3H), 2.29 (d, J = 4.2 Hz, 3H). LC-MS (m/z): 476.3 $[M + H]^+$. |

-continued

| No. | Compound structure and name | Characterization data |
|---|---|---|
| 120 | 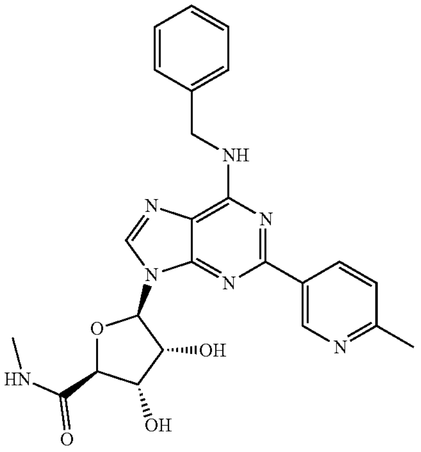 (2S,3S,4R,5R)-5-(6-(benzylamino)-2-(6-methylpyridin-3-yl)-9H-purin-9-yl)-3,4-dihydroxyl-N-methyltetrahydrofuran-2-carboxamide | $^1$H NMR (500 MHz, DMSO-$d_6$) δ: 9.30 (s, 1H), 8.65 (s, 1H), 8.52 (s, 1H), 8.46 (d, J = 8.1 Hz, 1H), 7.94 (d, J = 4.4 Hz, 1H), 7.47 - 7.17 (m, 6H), 6.07 (d, J = 6.8 Hz, 1H), 5.70 (d, J = 4.4 Hz, 1H), 5.60 (d, J = 6.3 Hz, 1H), 4.92 - 4.86 (m, 1H), 4.79 (s, 2H), 4.33 (d, J = 5.8 Hz, 2H), 3.34 (s, 3H), 2.52 (d, J = 3.9 Hz, 3H). LC-MS(m/z): 476.3 $[M + H]^+$. |
| 121 | 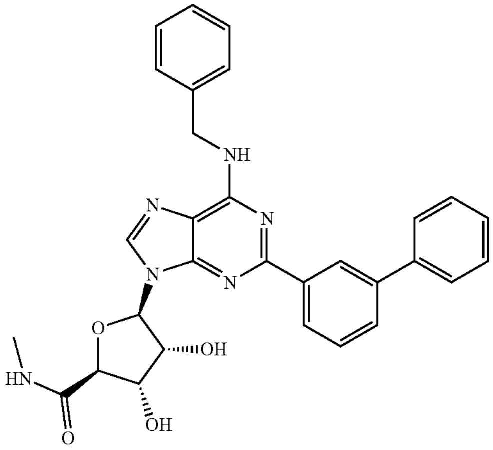 [SMILES: CNC(=O)[C@H]1O[C@@H](n2cnc3c(NCc4ccccc4)nc(-c4cccc(-c5ccccc5)c4)nc32)[C@H](O)[C@@H]1O] (2S,3S,4R,5R)-5-(2-([1,1'-biphenyl]-3-yl)-6-(benzylamino)-9H-purin-9-yl)-3,4-dihydroxyl-N-methyltetrahydrofuran-2-carboxamide | $^1$H NMR (500 MHz, DMSO-$d_6$) δ: 8.64 (s, 1H), 8.53 (d, J = 5.5 Hz, 2H), 8.30 (d, J = 7.7 Hz, 1H), 7.97 (d, J = 4.7 Hz, 1H), 7.71 (dd, J = 25.6, 7.6 Hz, 3H), 7.49 (ddt, J = 29.1, 14.7, 7.5 Hz, 6H), 7.31 (t, J = 7.6 Hz, 2H), 7.21 (t, J = 7.3 Hz, 1H), 6.10 (d, J = 7.0 Hz, 1H), 5.70 (d, J = 4.6 Hz, 1H), 5.62 (d, J = 6.4 Hz, 1H), 4.93 (dd, J = 11.4, 6.6 Hz, 1H), 4.80 (s, 2H), 4.37 - 4.28 (m, 2H), 2.49 (s, 3H). LC-MS (m/z): 537.5 $[M + H]^+$. |

-continued

| No. | Compound structure and name | Characterization data |
|---|---|---|
| 122 | 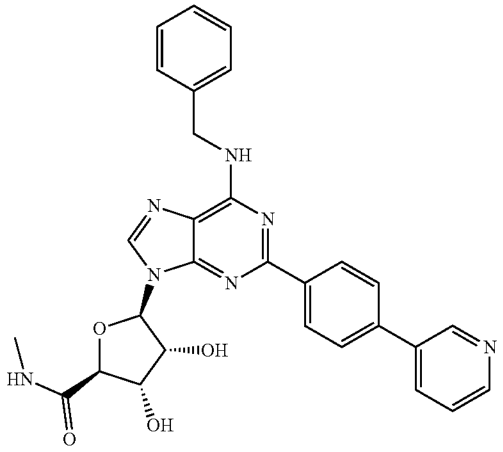 [SMILES: CNC(=O)[C@H]1O[C@@H](n2cnc3c(NCc4ccccc4)nc(-c4ccc(-c5cccnc5)cc4)nc32)[C@H](O)[C@@H]1O]<br>(2S,3S,4R,5R)-5-(6-(benzylamino)-2-(4-(pyridin-3-yl)phenyl)-9H-purin-9-yl)-3,4-dihydroxyl-N-methyltetrahydrofuran-2-carboxamide | $^1$H NMR (500 MHz, DMSO-$d_6$) δ: 8.99 (s, 1H), 8.61 (d, J = 4.7 Hz, 2H), 8.53 (s, 1H), 8.45 (d, J = 8.4 Hz, 2H), 8.18 (d, J = 8.0 Hz, 1H), 7.97 (d, J = 4.7 Hz, 1H), 7.86 (d, J = 8.3 Hz, 2H), 7.54 (dd, J = 7.9, 4.8 Hz, 1H), 7.46 (d, J = 7.4 Hz, 2H), 7.32 (t, J = 7.6 Hz, 2H), 7.22 (t, J = 7.3 Hz, 1H), 6.11 (d, J = 7.0 Hz, 1H), 5.66 (d, J = 38.1 Hz, 2H), 4.96 - 4.80 (m, 3H), 4.34 (dd, J = 15.8, 2.2 Hz, 2H), 2.56 (d, J = 4.6 Hz, 3H). LC-MS (m/z): 538.3 $[M + H]^+$. |
| 123 | 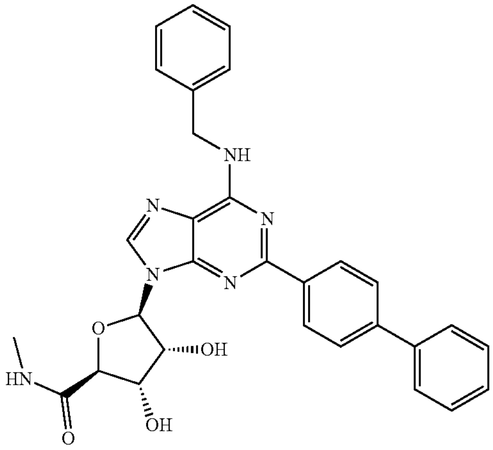 [SMILES: CNC(=O)[C@H]1O[C@@H](n2cnc3c(NCc4ccccc4)nc(-c4ccc(-c5ccccc5)cc4)nc32)[C@H](O)[C@@H]1O]<br>(2S,3S,4R,5R)-5-(2-([1,1'-biphenyl]-4-yl)-6-(benzylamino)-9H-purin-9-yl)-3,4-dihydroxyl-N-methyltetrahydrofuran-2-carboxamide | $^1$H NMR (500 MHz, DMSO-$d_6$) δ: 8.54 (d, J = 24.4 Hz, 2H), 8.41 (d, J = 8.4 Hz, 2H), 7.97 (d, J = 4.7 Hz, 1H), 7.76 (dd, J = 17.9, 7.8 Hz, 4H), 7.53 - 7.43 (m, 4H), 7.39 (t, J = 7.4 Hz, 1H), 7.32 (t, J = 7.6 Hz, 2H), 7.22 (t, J = 7.3 Hz, 1H), 6.11 (d, J = 7.0 Hz, 1H), 5.69 (d, J = 4.6 Hz, 1H), 5.61 (d, J = 6.3 Hz, 1H), 4.95 - 4.76 (m, 3H), 4.37 - 4.28 (m, 2H), 2.55 (d, J = 4.7 Hz, 3H). LC-MS(m/z): 537.5 $[M + H]^+$. |

-continued

| No. | Compound structure and name | Characterization data |
| --- | --- | --- |
| 124 | 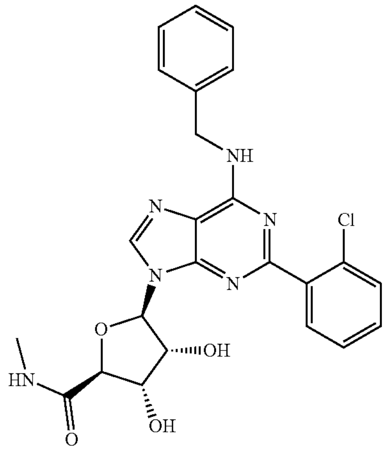 [SMILES: CNC(=O)[C@H]1O[C@@H](n2cnc3c(NCc4ccccc4)nc(-c4ccccc4Cl)nc32)[C@H](O)[C@@H]1O] (2S,3S,4R,5R)-5-(6-(benzylamino)-2-(2-chlorophenyl)-9H-purin-9-yl)-3,4-dihydroxyl-N-methyltetrahydrofuran-2-carboxamide | $^1$H NMR (500 MHz, DMSO-$d_6$) δ: 8.69 (s, 1H), 8.47 (t, J = 10.9 Hz, 2H), 7.66 – 7.15 (m, 9H), 5.98 (d, J = 7.7 Hz, 1H), 5.75 (d, J = 4.2 Hz, 1H), 5.57 (d, J = 6.5 Hz, 1H), 4.73 (s, 2H), 4.29 (s, 1H), 4.13 (s, 2H), 2.13 (d, J = 4.0 Hz, 3H). LC-MS(m/z): 495.3 $[M + H]^+$. |
| 125 | 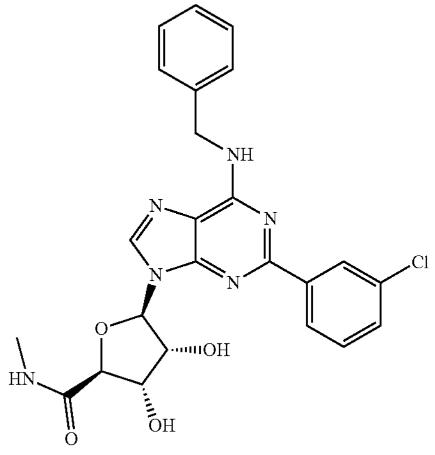 [SMILES: CNC(=O)[C@H]1O[C@@H](n2cnc3c(NCc4ccccc4)nc(-c4cccc(Cl)c4)nc32)[C@H](O)[C@@H]1O] (2S,3S,4R,5R)-5-(6-(benzylamino)-2-(3-chlorophenyl)-9H-purin-9-yl)-3,4-dihydroxyl-N-methyltetrahydrofuran-2-carboxamide | $^1$H NMR (500 MHz, DMSO-$d_6$) δ: 8.65 (s, 1H), 8.54 (s, 1H), 8.31 – 8.22 (m, 2H), 7.94 (d, J = 4.7 Hz, 1H), 7.50 (d, J = 5.0 Hz, 2H), 7.44 (d, J = 7.5 Hz, 2H), 7.31 (t, J = 7.6 Hz, 2H), 7.21 (t, J = 7.3 Hz, 1H), 6.09 (d, J = 7.0 Hz, 1H), 5.69 (d, J = 4.6 Hz, 1H), 5.60 (d, J = 6.4 Hz, 1H), 4.91 – 4.75 (m, 3H), 4.35 (d, J = 2.0 Hz, 1H), 4.30 (td, J = 4.6, 2.2 Hz, 1H), 2.55 (d, J = 4.7 Hz, 3H). LC-MS(m/z): 495.3 $[M + H]^+$. |
| 126 | 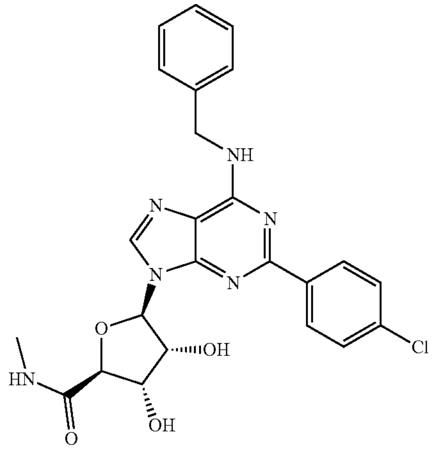 [SMILES: CNC(=O)[C@H]1O[C@@H](n2cnc3c(NCc4ccccc4)nc(-c4ccc(Cl)cc4)nc32)[C@H](O)[C@@H]1O] | $^1$H NMR (500 MHz, DMSO-$d_6$) δ: 8.60 (s, 1H), 8.52 (s, 1H), 8.34 (t, J = 9.1 Hz, 2H), 7.94 (d, J = 4.6 Hz, 1H), 7.53 (d, J = 8.5 Hz, 2H), 7.43 (d, J = 7.5 Hz, 2H), 7.31 (t, J = 7.6 Hz, 2H), 7.21 (t, J = 7.3 Hz, 1H), 6.08 (d, J =7.0 Hz, 1H), 5.68 (d, J = 4.6 Hz, 1H), 5.59 (d, J = 6.3 Hz, 1H), 4.90 – 4.74 (m, 3H), 4.36 – 4.26 (m, 2H), 2.54 (d, J = 4.7 Hz, 3H). LC-MS (m/z): 495.2 $[M + H]^+$. |

-continued

| No. | Compound structure and name | Characterization data |
|---|---|---|
| | (2S,3S,4R,5R)-5-(6-(benzylamino)-2-(4-chlorophenyl)-9H-purin-9-yl)-3,4-dihydroxyl-N-methyltetrahydrofuran-2-carboxamide | |
| 127 | 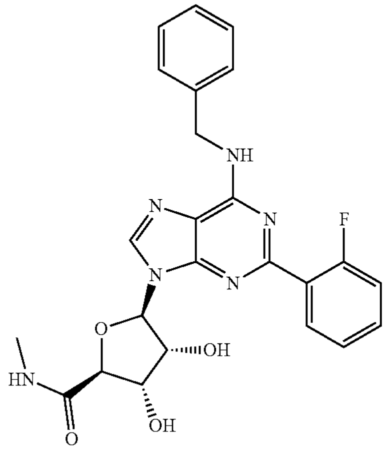 [SMILES: CNC(=O)[C@H]1O[C@@H](n2cnc3c(NCc4ccccc4)nc(-c4ccccc4F)nc32)[C@H](O)[C@@H]1O] (2S,3S,4R,5R)-5-(6-(benzylamino)-2-(2-fluorophenyl)-9H-purin-9-yl)-3,4-dihydroxyl-N-methyltetrahydrofuran-2-carboxamide | $^1$H NMR (500 MHz, DMSO-$d_6$) δ: 8.62 (s, 1H), 8.48 (s, 1H), 8.21 (s, 1H), 7.87 (s, 1H), 7.54 - 7.12 (m, 8H), 6.01 (d, J = 7.4 Hz, 1H), 5.72 (t, J = 11.8 Hz, 1H), 5.56 (d, J = 6.4 Hz, 1H), 4.78 (d, J = 19.2 Hz, 3H), 4.30 (s, 1H), 4.20 (s, 1H), 2.33 (s, 3H). LC-MS (m/z): 479.3 [M + H]$^+$. |
| 128 | 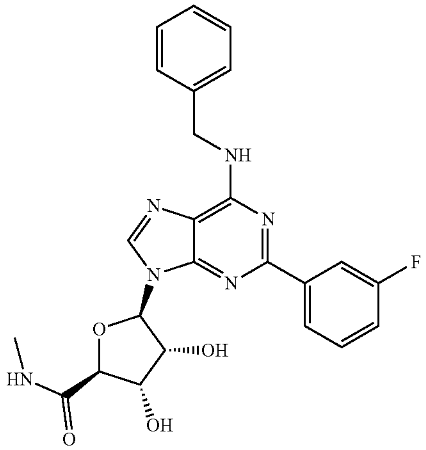 [SMILES: CNC(=O)[C@H]1O[C@@H](n2cnc3c(NCc4ccccc4)nc(-c4cccc(F)c4)nc32)[C@H](O)[C@@H]1O] (2S,3S,4R,5R)-5-(6-(benzylamino)-2-(3-fluorophenyl)-9H-purin-9-yl)-3,4-dihydroxyl-N-methyltetrahydrofuran-2-carboxamide | $^1$H NMR (500 MHz, DMSO-$d_6$) δ: 8.62 (s, 1H), 8.53 (s, 1H), 8.16 (d, J = 7.8 Hz, 1H), 7.97 (dd, J = 37.1, 7.8 Hz, 2H), 7.57 - 7.15 (m, 8H), 6.09 (d, J = 6.9 Hz, 1H), 5.68 (d, J = 4.6 Hz, 1H), 5.58 (d, J = 6.3 Hz, 1H), 4.93 - 4.75 (m, 3H), 4.33 (dd, J = 10.2, 3.2 Hz, 2H), 2.54 (d, J = 4.6 Hz, 3H). LC-MS (m/z): 479.3 [M + H]$^+$. |

-continued

| No. | Compound structure and name | Characterization data |
|---|---|---|
| 129 | 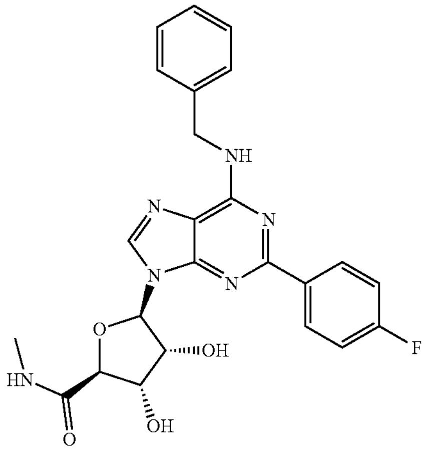 [SMILES: CNC(=O)[C@H]1O[C@@H](n2cnc3c(NCc4ccccc4)nc(-c4ccc(F)cc4)nc32)[C@H](O)[C@@H]1O] (2S,3S,4R,5R)-5-(6-(benzylamino)-2-(4-fluorophenyl)-9H-purin-9-yl)-3,4-dihydroxyl-N-methyltetrahydrofuran-2-carboxamide | $^1H$ NMR (500 MHz, DMSO-$d_6$) δ: 8.59 (s, 1H), 8.50 (s, 1H), 8.36 (dd, J = 8.6, 5.9 Hz, 2H), 7.95 (d, J = 4.6 Hz, 1H), 7.43 (d, J = 7.5 Hz, 2H), 7.30 (dd, J = 17.3, 8.4 Hz, 4H), 7.21 (t, J = 7.3 Hz, 1H), 6.08 (d, J = 7.0 Hz, 1H), 5.70 (d, J = 4.5 Hz, 1H), 5.60 (d, J = 6.3 Hz, 1H), 4.91 – 4.73 (m, 3H), 4.37 – 4.24 (m, 2H), 2.53 (d, J = 4.6 Hz, 3H). LC-MS (m/z): 479.3 $[M + H]^+$. |
| 130 | 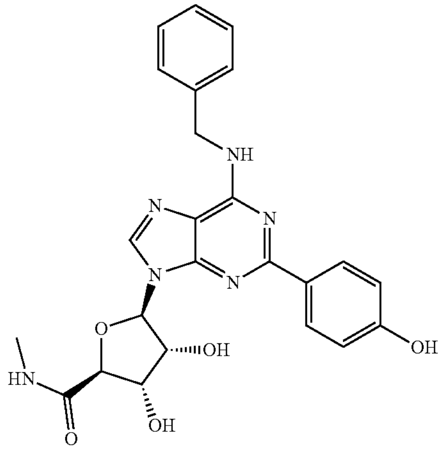 [SMILES: CNC(=O)[C@H]1O[C@@H](n2cnc3c(NCc4ccccc4)nc(-c4ccc(O)cc4)nc32)[C@H](O)[C@@H]1O] (2S,3S,4R,5R)-5-(6-(benzylamino)-2-(4-hydroxylphenyl)-9H-purin-9-yl)-3,4-dihydroxyl-N-methyltetrahydrofuran-2-carboxamide | $^1H$ NMR (500 MHz, DMSO-$d_6$) δ: 9.77 (s, 1H), 8.43 (s, 2H), 8.16 (d, J = 8.6 Hz, 2H), 7.96 (d, J = 4.6 Hz, 1H), 7.43 (d, J = 7.4 Hz, 2H), 7.30 (t, J = 7.6 Hz, 2H), 7.21 (t, J = 7.3 Hz, 1H), 6.82 (d, J = 8.6 Hz, 2H), 6.05 (d, J = 7.1 Hz, 1H), 5.70 (d, J = 4.4 Hz, 1H), 5.59 (d, J = 6.3 Hz, 1H), 4.93 – 4.74 (m, 3H), 4.31 (d, J = 11.7 Hz, 2H), 2.53 (d, J = 4.6 Hz, 3H). LC-MS (m/z): 477.3 $[M + H]^+$. |
| 131 | 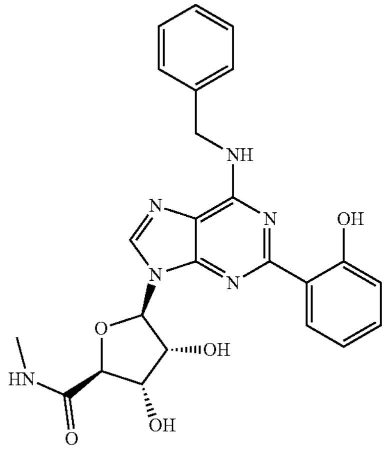 [SMILES: CNC(=O)[C@H]1O[C@@H](n2cnc3c(NCc4ccccc4)nc(-c4ccccc4O)nc32)[C@H](O)[C@@H]1O] | $^1H$ NMR (500 MHz, DMSO-$d_6$) δ: 13.61 (s, 1H), 9.03 (s, 1H), 8.62 (s, 1H), 8.33 (d, J = 7.7 Hz, 1H), 7.97 (s, 1H), 7.32 (ddd, J = 40.3, 35.7, 7.1 Hz, 6H), 6.96 – 6.81 (m, 2H), 6.08 (d, J = 6.4 Hz, 1H), 5.68 (dd, J = 33.4, 5.4 Hz, 2H), 4.88 – 4.61 (m, 3H), 4.39 – 4.25 (m, 2H), 2.58 (d, J = 4.5 Hz, 3H). LC-MS (m/z): 477.3 $[M + H]^+$. |

-continued

| No. | Compound structure and name | Characterization data |
|---|---|---|
| | (2S,3S,4R,5R)-5-(6-(benzylamino)-2-(2-hydroxylphenyl)-9H-purin-9-yl)-3,4-dihydroxyl-N-methyltetrahydrofuran-2-carboxamide | |
| 132 | 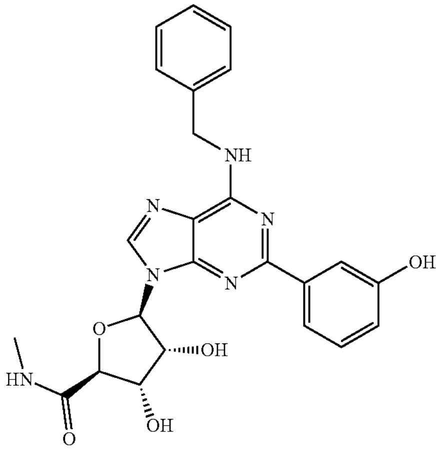 [SMILES: CNC(=O)[C@H]1O[C@@H](n2cnc3c(NCc4ccccc4)nc(-c4cccc(O)c4)nc32)[C@H](O)[C@@H]1O] (2S,3S,4R,5R)-5-(6-(benzylamino)-2-(3-hydroxylphenyl)-9H-purin-9-yl)-3,4-dihydroxyl-N-methyltetrahydrofuran-2-carboxamide | $^{1}H$ NMR (500 MHz, DMSO-$d_6$) δ: 9.50 (s, 1H), 8.50 (d, J = 17.9 Hz, 2H), 7.97 (d, J = 4.6 Hz, 1H), 7.81 − 7.72 (m, 2H), 7.44 (d, J = 7.2 Hz, 2H), 7.26 (ddd, J = 30.3, 14.9, 7.3 Hz, 4H), 6.82 (d, J = 6.3 Hz, 1H), 6.08 (d, J = 7.2 Hz, 1H), 5.72 (d, J = 4.4 Hz, 1H), 5.61 (d, J = 6.3 Hz, 1H), 4.86 (dd, J = 20.8, 14.0 Hz, 3H), 4.30 (d, J = 25.6 Hz, 2H), 2.53 (d, J = 4.6 Hz, 3H). LC-MS (m/z): 477.3 [M + H]+ |
| 133 | 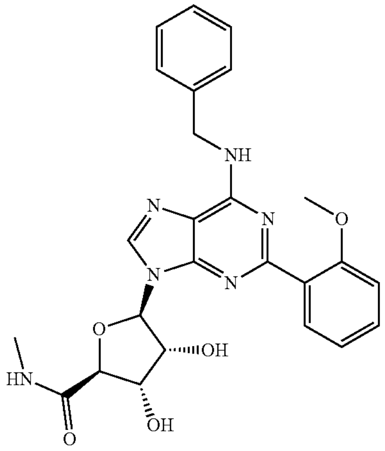 [SMILES: CNC(=O)[C@H]1O[C@@H](n2cnc3c(NCc4ccccc4)nc(-c4ccccc4OC)nc32)[C@H](O)[C@@H]1O] (2S,3S,4R,5R)-5-(6-(benzylamino)-2-(2-methoxyphenyl)-9H-purin-9-yl)-3,4-dihydroxyl-N-methyltetrahydrofuran-2-carboxamide | $^{1}H$ NMR (500 MHz, DMSO-$d_6$) δ: 8.67 (s, 1H), 8.54 (s, 1H), 8.39 (s, 1H), 7.48 − 7.15 (m, 7H), 7.11 (d, J = 8.3 Hz, 1H), 7.01 (t, J = 7.4 Hz, 1H), 5.95 (d, J = 7.9 Hz, 1H), 5.75 (d, J = 4.1 Hz, 1H), 5.58 (d, J = 6.5 Hz, 1H), 4.71 (d, J = 26.3 Hz, 3H), 4.28 (s, 1H), 4.09 (d, J = 17.7 Hz, 1H), 3.70 (s, 3H), 2.06 (d, J = 4.3 Hz, 3H). LC-MS (m/z): 491.3 $[M + H]^+$. |

-continued

| No. | Compound structure and name | Characterization data |
| --- | --- | --- |
| 134 | 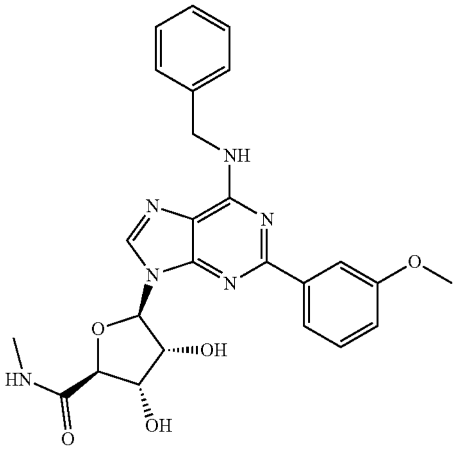 (2S,3S,4R,5R)-5-(6-(benzylamino)-2-(3-methoxyphenyl)-9H-purin-9-yl)-3,4-dihydroxyl-N-methyltetrahydrofuran-2-carboxamide | $^1H$ NMR (500 MHz, DMSO-$d_6$) δ: 8.55 (d, J = 42.3 Hz, 2H), 7.99 – 7.80 (m, 3H), 7.47 – 7.17 (m, 6H), 7.02 (d, J = 7.9 Hz, 1H), 6.08 (d, J = 7.0 Hz, 1H), 5.69 (d, J = 4.5 Hz, 1H), 5.60 (d, J = 6.3 Hz, 1H), 4.96 – 4.88 (m, 1H), 4.80 (s, 2H), 4.33 (d, J = 6.5 Hz, 2H), 3.82 (s, 3H), 2.52 (s, 3H). |
| 135 | 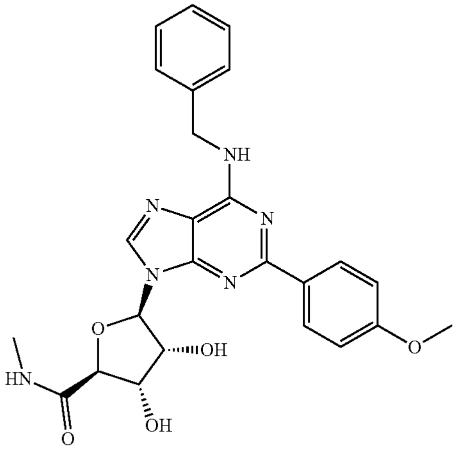 (2S,3S,4R,5R)-5-(6-(benzylamino)-2-(4-methoxyphenyl)-9H-purin-9-yl)-3,4-dihydroxyl-N-methyltetrahydrofuran-2-carboxamide | $^1H$ NMR (500 MHz, DMSO-$d_6$) δ: 8.45 (s, 2H), 8.27 (d, J = 8.7 Hz, 2H), 7.95 (d, J = 4.5 Hz, 1H), 7.44 (d, J = 7.3 Hz, 2H), 7.31 (t, J = 7.5 Hz, 2H), 7.21 (t, J = 7.1 Hz, 1H), 7.01 (d, J = 8.7 Hz, 2H), 6.07 (d, J = 7.0 Hz, 1H), 5.68 (d, J = 4.3 Hz, 1H), 5.58 (d, J = 6.3 Hz, 1H), 4.91 (d, J = 4.7 Hz, 1H), 4.81 (s, 2H), 4.32 (d, J = 13.5 Hz, 2H), 3.82 (s, 3H), 2.54 (d, J = 4.6 Hz, 3H). LC-MS (m/z): 491.3 [M + H]$^+$. |
| 136 | 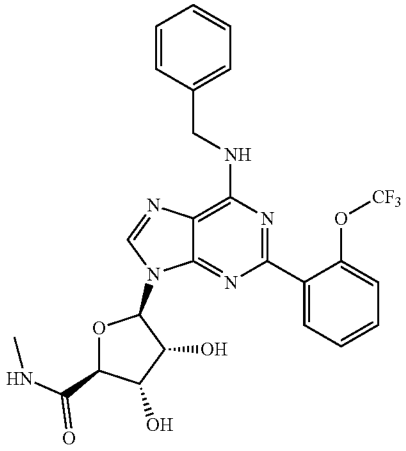 [SMILES: CNC(=O)[C@H]1O[C@@H](n2cnc3c(NCc4ccccc4)nc(-c4ccccc4OC(F)(F)F)nc32)[C@H](O)[C@@H]1O] | $^1H$ NMR (500 MHz, DMSO-$d_6$) δ: 8.66 (s, 1H), 8.50 (s, 1H), 8.31 (d, J = 4.5 Hz, 1H), 7.82 (dd, J = 7.6, 1.6 Hz, 1H), 7.58 (dd, J = 10.9, 4.6 Hz, 1H), 7.53 – 7.45 (m, 2H), 7.36 (d, J = 7.0 Hz, 2H), 7.29 (t, J = 7.4 Hz, 2H), 7.21 (t, J = 7.2 Hz, 1H), 6.01 (d, J = 7.4 Hz, 1H), 5.76 (d, J = 4.3 Hz, 1H), 5.56 (d, J = 6.5 Hz, 1H), 4.73 (d, J = 11.5 Hz, 3H), 4.30 (s, 1H), 4.17 (s, 1H), 2.21 (d, J = 4.0 Hz, 3H). LC-MS (m/z): 545.4 [M + H]$^+$. |

-continued

| No. | Compound structure and name | Characterization data |
|---|---|---|
| | (2S,3S,4R,5R)-5-(6-(benzylamino)-2-(2-(trifluoromethoxy)phenyl)-9H-purin-9-yl)-3,4-dihydroxyl-N-methyltetrahydrofuran-2-carboxamide | |
| 137 | 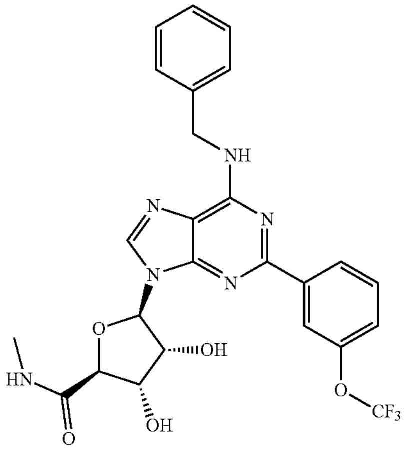 [SMILES: CNC(=O)[C@H]1O[C@@H](n2cnc3c(NCc4ccccc4)nc(-c4cccc(OC(F)(F)F)c4)nc32)[C@H](O)[C@@H]1O]<br>(2S,3S,4R,5R)-5-(6-(benzylamino)-2-(3-(trifluoromethoxy)phenyl)-9H-purin-9-yl)-3,4-dihydroxyl-N-methyltetrahydrofuran-2-carboxamide | $^1$H NMR (500 MHz, DMSO-$d_6$) δ: 8.69 (s, 1H), 8.56 (s, 1H), 8.34 (d, J = 7.8 Hz, 1H), 8.19 (s, 1H), 7.94 (d, J = 4.7 Hz, 1H), 7.61 (t, J = 8.0 Hz, 1H), 7.45 (d, J = 7.7 Hz, 3H), 7.30 (t, J = 7.5 Hz, 2H), 7.21 (t, J = 7.3 Hz, 1H), 6.10 (d, J = 6.9 Hz, 1H), 5.69 (d, J = 4.6 Hz, 1H), 5.61 (d, J = 6.3 Hz, 1H), 4.88 (dd, J = 11.4, 6.5 Hz, 1H), 4.79 (s, 2H), 4.38 – 4.27 (m, 2H), 2.54 (d, J = 4.7 Hz, 3H). LC-MS (m/z): 545.3 [M + H]$^+$. |
| 138 | 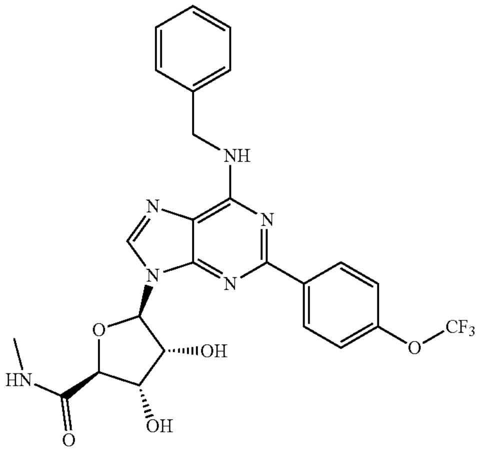 [SMILES: CNC(=O)[C@H]1O[C@@H](n2cnc3c(NCc4ccccc4)nc(-c4ccc(OC(F)(F)F)cc4)nc32)[C@H](O)[C@@H]1O]<br>(2S,3S,4R,5R)-5-(6-(benzylamino)-2-(4-(trifluoromethoxy)phenyl)-9H-purin-9-yl)-3,4-dihydroxyl-N-methyltetrahydrofuran-2-carboxamide | $^1$H NMR (500 MHz, DMSO-$d_6$) δ: 8.63 (s, 1H), 8.53 (s, 1H), 8.46 – 8.40 (m, 2H), 7.99 – 7.93 (m, 1H), 7.45 (t, J = 8.2 Hz, 4H), 7.32 (t, J = 7.6 Hz, 2H), 7.22 (t, J = 7.3 Hz, 1H), 6.09 (d, J = 7.0 Hz, 1H), 5.70 (d, J = 4.6 Hz, 1H), 5.60 (d, J = 6.3 Hz, 1H), 4.91 – 4.75 (m, 3H), 4.36 – 4.29 (m, 2H), 2.54 (d, J = 4.7 Hz, 3H). LC-MS (m/z): 545.4 [M + H]$^+$. |

-continued

| No. | Compound structure and name | Characterization data |
| --- | --- | --- |
| 139 | 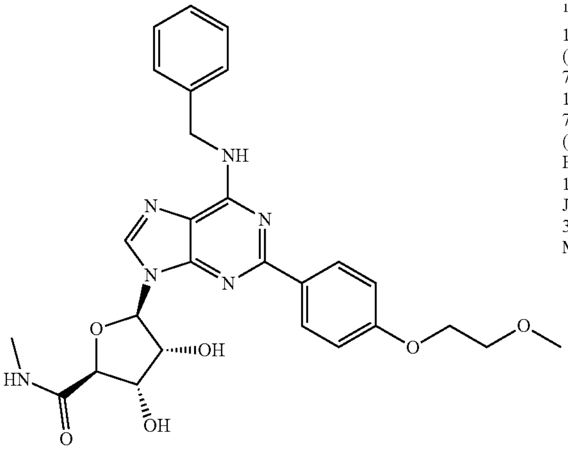<br>(2S,3S,4R,5R)-5-(6-(benzylamino)-2-(4-(2-methoxyethoxy)phenyl)-9H-purin-9-yl)-3,4-dihydroxyl-N-methyltetrahydrofuran-2-carboxamide | $^1$H NMR (500 MHz, DMSO-$d_6$) δ: 8.49 (s, 1H), 8.45 (s, 1H), 8.27 - 8.22 (m, 2H), 7.95 (q, J = 4.5 Hz, 1H), 7.43 (d, J = 7.5 Hz, 2H), 7.30 (t, J = 7.6 Hz, 2H), 7.21 (t, J = 7.3 Hz, 1H), 7.01 (d, J = 8.9 Hz, 2H), 6.06 (d, J = 7.1 Hz, 1H), 5.70 (d, J = 4.5 Hz, 1H), 5.59 (d, J = 6.4 Hz, 1H), 4.90 (dd, J = 11.5, 6.6 Hz, 1H), 4.80 (s, 2H), 4.33 (d, J = 2.0 Hz, 1H), 4.29 (td, J = 4.6, 2.2 Hz, 1H), 4.14 (dd, J = 5.3, 3.7 Hz, 2H), 3.70 - 3.65 (m, 2H), 3.31 (s, 3H), 2.53 (d, J = 4.7 Hz, 3H). LC-MS(m/z): 535.4 $[M + H]^+$. |
| 140 | 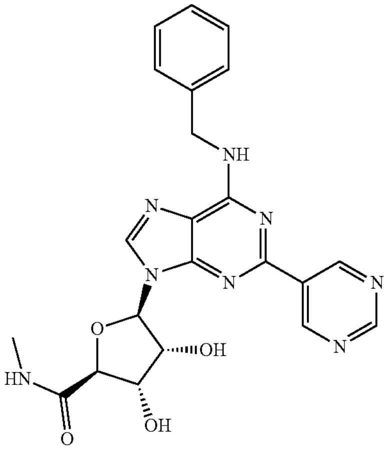 [SMILES: CNC(=O)[C@H]1O[C@@H](n2cnc3c(NCc4ccccc4)nc(-c4cncnc4)nc32)[C@H](O)[C@@H]1O]<br>(2S,3S,4R,5R)-5-(6-(benzylamino)-2-(pyrimidin-5-yl)-9H-purin-9-yl)-3,4-dihydroxyl-N-methyltetrahydrofuran-2-carboxamide | $^1$H NMR (500 MHz, DMSO-$d_6$) δ: 9.53 (s, 2H), 9.26 (s, 1H), 8.81 (t, J = 6.0 Hz, 1H), 8.58 (s, 1H), 7.95 (d, J = 4.6 Hz, 1H), 7.45 (d, J = 7.5 Hz, 2H), 7.32 (t, J = 7.6 Hz, 2H), 7.22 (t, J = 7.3 Hz, 1H), 6.09 (d, J = 6.7 Hz, 1H), 5.71 (d, J = 4.6 Hz, 1H), 5.61 (d, J = 6.3 Hz, 1H), 4.90 (dd, J = 10.8, 6.4 Hz, 1H), 4.82 (d, J = 5.7 Hz, 2H), 4.38 - 4.32 (m, 2H), 2.53 (d, J = 4.7 Hz, 3H).LC-MS (m/z): 463.3 $[M + H]^+$. |
| 141 | 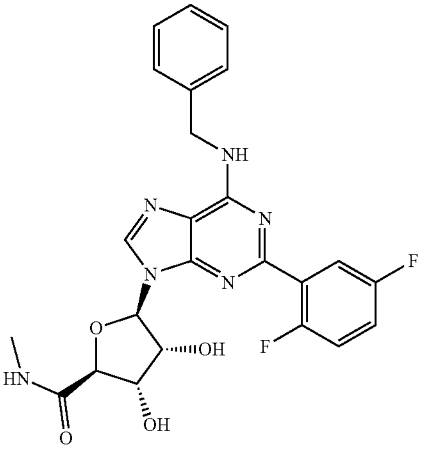 [SMILES: CNC(=O)[C@H]1O[C@@H](n2cnc3c(NCc4ccccc4)nc(-c4cc(F)ccc4F)nc32)[C@H](O)[C@@H]1O] | $^1$H NMR (500 MHz, DMSO-$d_6$) δ: 8.72 (s, 1H), 8.54 (s, 1H), 8.13 (d, J = 4.1 Hz, 1H), 7.65 (s, 1H), 7.43 - 7.27 (m, 6H), 7.22 (t, J = 7.3 Hz, 1H), 6.02 (d, J = 7.3 Hz, 1H), 5.74 (d, J = 4.5 Hz, 1H), 5.59 (d, J = 6.4 Hz, 1H), 4.86 - 4.70 (m, 3H), 4.32 (d, J = 1.6 Hz, 1H), 4.22 (s, 1H), 2.41 (d, J = 4.5 Hz, 3H).LC-MS(m/z): 497.3 $[M + H]^+$. |

-continued

| No. | Compound structure and name | Characterization data |
| --- | --- | --- |
| | (2S,3S,4R,5R)-5-(6-(benzylamino)-2-(2,5-difluorophenyl)-9H-purin-9-yl)-3,4-dihydroxyl-N-methyltetrahydrofuran-2-carboxamide | |
| 142 | 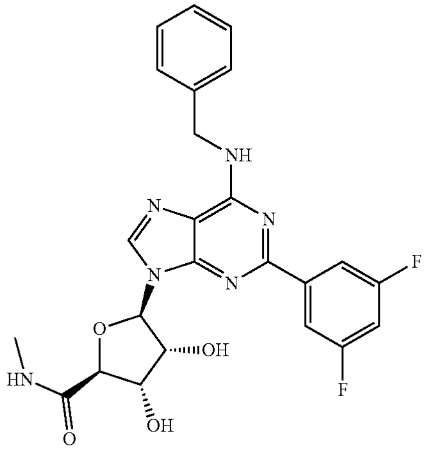 [SMILES: CNC(=O)[C@H]1O[C@@H](n2cnc3c(NCc4ccccc4)nc(-c4cc(F)cc(F)c4)nc32)[C@H](O)[C@@H]1O] (2S,3S,4R,5R)-5-(6-(benzylamino)-2-(3,5-difluorophenyl)-9H-purin-9-yl)-3,4-dihydroxyl-N-methyltetrahydrofuran-2-carboxamide | $^1$H NMR (500 MHz, DMSO-$d_6$) δ: 8.72 (s, 1H), 8.57 (s, 1H), 7.92 (dd, J = 24.6, 5.9 Hz, 3H), 7.43 (d, J = 7.5 Hz, 2H), 7.35 - 7.28 (m, 3H), 7.22 (t, J = 7.3 Hz, 1H), 6.09 (d, J = 6.9 Hz, 1H), 5.70 (d, J = 4.7 Hz, 1H), 5.61 (d, J = 6.4 Hz, 1H), 4.92 - 4.76 (m, 3H), 4.37 - 4.30 (m, 2H), 2.55 (d, J = 4.7 Hz, 3H). LC-MS (m/z): 497.3 $[M + H]^+$. |
| 143 | 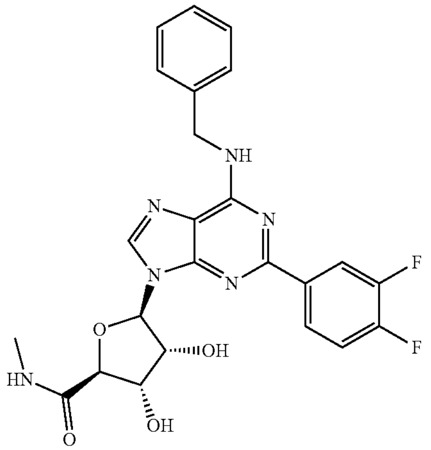 [SMILES: CNC(=O)[C@H]1O[C@@H](n2cnc3c(NCc4ccccc4)nc(-c4ccc(F)c(F)c4)nc32)[C@H](O)[C@@H]1O] (2S,3S,4R,5R)-5-(6-(benzylamino)-2-(3,4-difluorophenyl)-9H-purin-9-yl)-3,4-dihydroxyl-N-methyltetrahydrofuran-2-carboxamide | $^1$H NMR (500 MHz, DMSO-$d_6$) δ: 8.67 (s, 1H), 8.54 (s, 1H), 8.19 (dd, J = 16.2, 11.3 Hz, 2H), 7.95 (d, J = 4.7 Hz, 1H), 7.58 - 7.50 (m, 1H), 7.44 (d, J = 7.5 Hz, 2H), 7.31 (t, J = 7.6 Hz, 2H), 7.22 (t, J = 7.3 Hz, 1H), 6.08 (d, J = 6.9 Hz, 1H), 5.70 (d, J = 4.6 Hz, 1H), 5.61 (dd, J = 6.3, 2.5 Hz, 1H), 4.88 (dd, J = 11.3, 6.5 Hz, 1H), 4.81 (d, J = 4.7 Hz, 2H), 4.33 (ddd, J = 7.5, 6.8, 2.2 Hz, 2H), 2.55 (d, J = 4.7 Hz, 3H).LC-MS (m/z): 497.3 $[M + H]^+$. |

-continued

| No. | Compound structure and name | Characterization data |
|---|---|---|
| 144 | 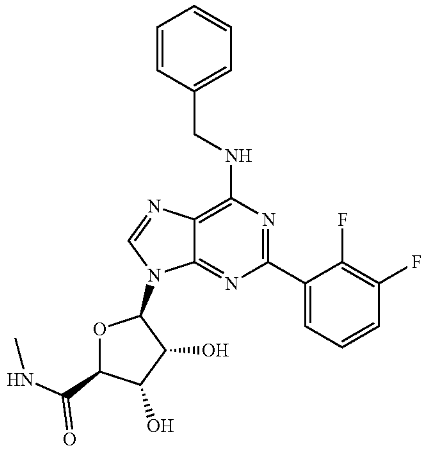 [SMILES: CNC(=O)[C@H]1O[C@@H](n2cnc3c(NCc4ccccc4)nc(-c4cccc(F)c4F)nc32)[C@H](O)[C@@H]1O] (2S,3S,4R,5R)-5-(6-(benzylamino)-2-(2,3-difluorophenyl)-9H-purin-9-yl)-3,4-dihydroxyl-N-methyltetrahydrofuran-2-carboxamide | $^{1}$H NMR (500 MHz, DMSO-$d_6$) δ: 8.71 (s, 1H), 8.54 (s, 1H), 8.13 (d, J = 4.1 Hz, 1H), 7.73 (d, J = 6.6 Hz, 1H), 7.52 (dd, J = 16.8, 7.9 Hz, 1H), 7.40 (d, J = 7.4 Hz, 2H), 7.34 – 7.27 (m, 3H), 7.22 (t, J = 7.3 Hz, 1H), 6.03 (d, J = 7.3 Hz, 1H), 5.75 (d, J = 4.4 Hz, 1H), 5.61 (d, J = 6.4 Hz, 1H), 4.79 (dd, J = 15.3, 8.6 Hz, 3H), 4.32 (d, J = 1.4 Hz, 1H), 4.22 (s, 1H), 2.39 (d, J = 4.4 Hz, 3H).LC-MS (m/z): 497.3 $[M + H]^+$. |
| 145 | 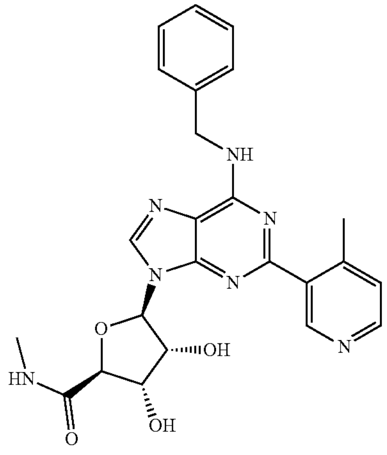 [SMILES: CNC(=O)[C@H]1O[C@@H](n2cnc3c(NCc4ccccc4)nc(-c4cnccc4C)nc32)[C@H](O)[C@@H]1O] (2S,3S,4R,5R)-5-(6-(benzylamino)-2-(4-methylpyridin-3-yl)-9H-purin-9-yl)-3,4-dihydroxyl-N-methyltetrahydrofuran-2-carboxamide | $^{1}$H NMR (500 MHz, DMSO-$d_6$) δ: 8.79 (s, 1H), 8.71 (s, 1H), 8.53 (s, 1H), 8.44 (d, J = 5.0 Hz, 1H), 8.22 (d, J = 4.6 Hz, 1H), 7.40 – 7.16 (m, 6H), 6.03 (d, J = 7.4 Hz, 1H), 5.74 (d, J = 3.8 Hz, 1H), 5.60 (d, J = 6.4 Hz, 1H), 4.88 – 4.62 (m, 3H), 4.31 (d, J = 1.5 Hz, 1H), 4.21 (s, 1H), 2.38 (s, 3H), 2.24 (d, J = 4.6 Hz, 3H). LC-MS (m/z): 476.3 $[M + H]^+$. |
| 146 | 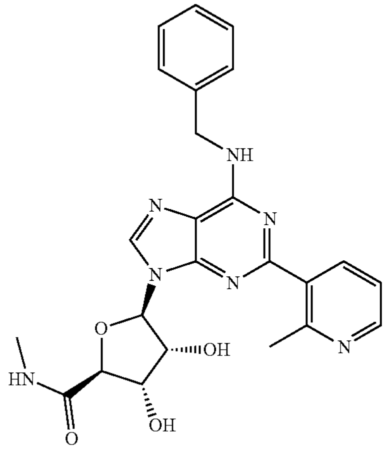 [SMILES: CNC(=O)[C@H]1O[C@@H](n2cnc3c(NCc4ccccc4)nc(-c4cccnc4C)nc32)[C@H](O)[C@@H]1O] | $^{1}$H NMR (500 MHz, DMSO-$d_6$) δ: 8.70 (s, 1H), 8.54 – 8.45 (m, 2H), 8.24 (d, J = 4.0 Hz, 1H), 7.99 (dd, J = 7.7, 1.6 Hz, 1H), 7.29 (tt, J = 44.5, 7.2 Hz, 6H), 6.02 (d, J = 7.4 Hz, 1H), 5.74 (d, J = 4.4 Hz, 1H), 5.60 (d, J = 6.4 Hz, 1H), 4.77 (dd, J = 12.0, 5.4 Hz, 3H), 4.31 (d, J = 1.3 Hz, 1H), 4.20 (s, 1H), 2.52 (d, J = 8.7 Hz, 3H), 2.23 (d, J = 4.4 Hz, 3H). LC-MS (m/z): 476.3 $[M + H]^+$. |

-continued

| No. | Compound structure and name | Characterization data |
|---|---|---|
| | (2S,3S,4R,5R)-5-(6-(benzylamino)-2-(2-methylpyridin-3-yl)-9H-purin-9-yl)-3,4-dihydroxyl-N-methyltetrahydrofuran-2-carboxamide | |
| 147 | 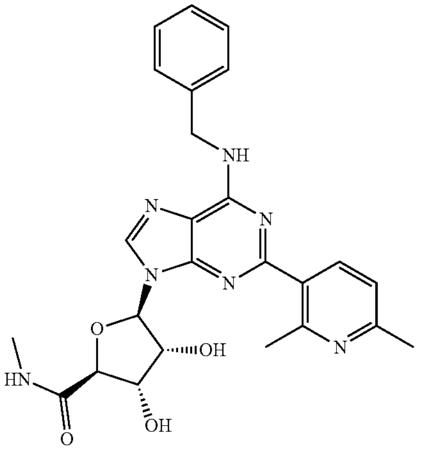 (2S,3S,4R,5R)-5-(6-(benzylamino)-2-(2,6-dimethylpyridin-3-yl)-9H-purin-9-yl)-3,4-dihydroxyl-N-methyltetrahydrofuran-2-carboxamide | $^1$H NMR (500 MHz, DMSO-$d_6$) δ: 8.64 (s, 1H), 8.50 (s, 1H), 8.23 (s, 1H), 7.92 (d, J = 7.9 Hz, 1H), 7.50 - 7.08 (m, 6H), 6.02 (d, J = 7.3 Hz, 1H), 5.72 (d, J = 4.3 Hz, 1H), 5.59 (d, J = 6.4 Hz, 1H), 4.77 (dd, J = 14.9, 8.3 Hz, 3H), 4.31 (s, 1H), 4.21 (s, 1H), 2.46 (s, 3H), 2.27 (d, J = 4.0 Hz, 3H).LC-MS (m/z): 490.3 [M + H]$^+$. |
| 148 | 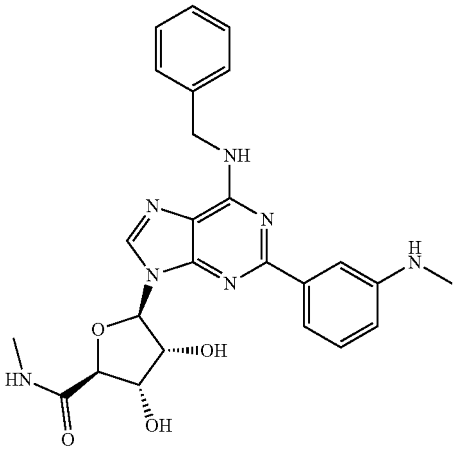 (2S,3S,4R,5R)-5-(6-(benzylamino)-2-(3-(methylamino)phenyl)-9H-purin-9-yl)-3,4-dihydroxyl-N-methyltetrahydrofuran-2-carboxamide | $^1$H NMR (500 MHz, DMSO-$d_6$) δ: 8.48 (d, J = 17.2 Hz, 2H), 7.98 (d, J = 4.3 Hz, 1H), 7.59 - 7.41 (m, 4H), 7.31 (t, J = 7.5 Hz, 2H), 7.19 (dt, J = 15.6, 7.5 Hz, 2H), 6.61 (d, J = 6.6 Hz, 1H), 6.07 (d, J = 7.1 Hz, 1H), 5.73 (d, J = 25.4 Hz, 2H), 5.60 (d, J = 5.8 Hz, 1H), 4.97 - 4.72 (m, 3H), 4.31 (d, J = 13.0 Hz, 2H), 3.34 (s, 3H), 2.73 (s, 3H).LC-MS (m/z): 490.3 [M + H]$^+$. |

-continued

| No. | Compound structure and name | Characterization data |
|---|---|---|
| 149 | 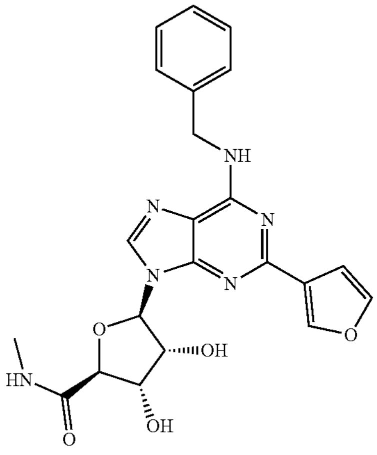 [SMILES: CNC(=O)[C@H]1O[C@@H](n2cnc3c(NCc4ccccc4)nc(-c4ccoc4)nc32)[C@H](O)[C@@H]1O] (2S,3S,4R,5R)-5-(6-(benzylamino)-2-(furan-3-yl)-9H-purin-9-yl)-3,4-dihydroxyl-N-methyltetrahydrofuran-2-carboxamide | $^1$H NMR (500 MHz, DMSO-$d_6$) δ: 8.46 (d, J = 20.8 Hz, 2H), 8.23 (s, 1H), 7.92 (d, J = 4.7 Hz, 1H), 7.72 (t, J = 1.6 Hz, 1H), 7.43 (d, J = 7.4 Hz, 2H), 7.30 (t, J = 7.6 Hz, 2H), 7.20 (t, J = 7.3 Hz, 1H), 6.94 (d, J = 1.2 Hz, 1H), 6.01 (d, J = 6.8 Hz, 1H), 5.65 (d, J = 4.4 Hz, 1H), 5.55 (d, J = 6.3 Hz, 1H), 4.83 (td, J = 6.5, 4.7 Hz, 1H), 4.73 (s, 2H), 4.32 (dt, J = 6.9, 2.2 Hz, 2H), 2.56 (d, J = 4.7 Hz, 3H). LC-MS (m/z): 451.3 [M + H]$^+$. |
| 150 | 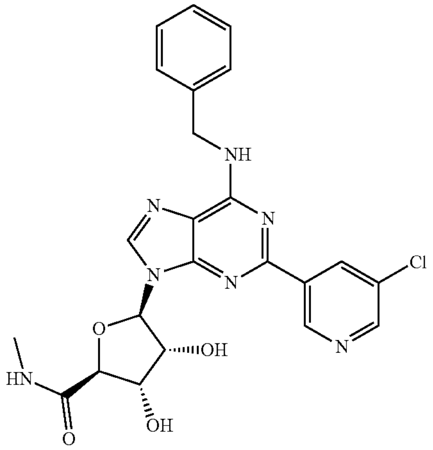 [SMILES: CNC(=O)[C@H]1O[C@@H](n2cnc3c(NCc4ccccc4)nc(-c4cncc(Cl)c4)nc32)[C@H](O)[C@@H]1O] (2S,3S,4R,5R)-5-(6-(benzylamino)-2-(5-chloropyridin-3-yl)-9H-purin-9-yl)-3,4-dihydroxyl-N-methyltetrahydrofuran-2-carboxamide | $^1$H NMR (500 MHz, DMSO-$d_6$) δ: 9.36 (s, 1H), 8.82 – 8.64 (m, 2H), 8.57 (d, J = 14.0 Hz, 2H), 7.94 (d, J = 4.6 Hz, 1H), 7.44 (d, J = 7.5 Hz, 2H), 7.32 (t, J = 7.6 Hz, 2H), 7.22 (t, J = 7.3 Hz, 1H), 6.09 (d, J = 6.9 Hz, 1H), 5.69 (d, J = 4.7 Hz, 1H), 5.60 (d, J = 6.4 Hz, 1H), 4.89 (dd, J = 11.3, 6.6 Hz, 1H), 4.81 (d, J = 4.6 Hz, 2H), 4.34 (ddd, J = 6.9, 6.5, 2.3 Hz, 2H), 2.55 (d, J = 4.7 Hz, 3H). LC-MS (m/z): 496.3 [M + H]$^+$. |
| 151 | 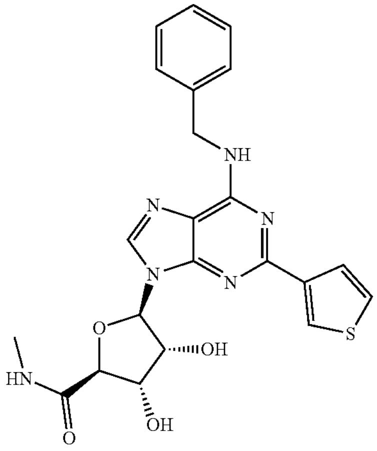 [SMILES: CNC(=O)[C@H]1O[C@@H](n2cnc3c(NCc4ccccc4)nc(-c4ccsc4)nc32)[C@H](O)[C@@H]1O] | $^1$H NMR (400 MHz, DMSO-$d_6$) δ: 8.53 (s, 1H), 8.47 (s, 1H), 8.19 (d, J = 2.4 Hz, 1H), 7.95 (d, J = 4.7 Hz, 1H), 7.74 (d, J = 5.0 Hz, 1H), 7.58 (dd, J = 4.9, 3.1 Hz, 1H), 7.45 (d, J = 7.4 Hz, 2H), 7.31 (t, J = 7.5 Hz, 2H), 7.21 (t, J = 7.4 Hz, 1H), 6.04 (d, J = 6.9 Hz, 1H), 5.70 (d, J = 4.5 Hz, 1H), 5.60 (d, J = 6.3 Hz, 1H), 4.88 (dd, J = 11.0, 6.4 Hz, 1H), 4.76 (d, J = 19.9 Hz, 2H), 4.33 (d, J = 4.6 Hz, 2H), 2.55 (d, J = 4.7 Hz, 3H). LC-MS (m/z): 467.3 [M + H]$^+$. |

-continued

| No. | Compound structure and name | Characterization data |
|---|---|---|
| | (2S,3S,4R,5R)-5-(6-(benzylamino)-2-(thiophen-3-yl)-9H-purin-9-yl)-3,4-dihydroxyl-N-methyltetrahydrofuran-2-carboxamide | |
| 152 | 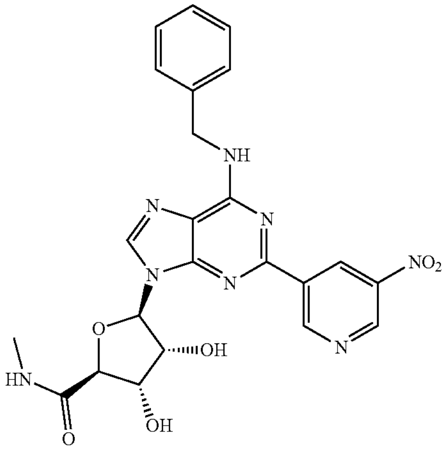 [SMILES: CNC(=O)[C@H]1O[C@@H](n2cnc3c(NCc4ccccc4)nc(-c4cncc([N+](=O)[O-])c4)nc32)[C@H](O)[C@@H]1O] (2S,3S,4R,5R)-5-(6-(benzylamino)-2-(5-nitropyridin-3-yl)-9H-purin-9-yl)-3,4-dihydroxyl-N-methyltetrahydrofuran-2-carboxamide | $^1$H NMR (500 MHz, DMSO-$d_6$) δ: 9.76 (s, 1H), 9.43 (s, 1H), 9.20 (s, 1H), 8.87 (s, 1H), 8.63 (s, 1H), 7.98 (d, J = 4.4 Hz, 1H), 7.48 (d, J = 6.8 Hz, 2H), 7.33 (t, J = 7.4 Hz, 2H), 7.22 (t, J = 6.9 Hz, 1H), 6.13 (d, J = 6.6 Hz, 1H), 5.72 (d, J = 4.6 Hz, 1H), 5.63 (d, J = 6.3 Hz, 1H), 4.95 – 4.69 (m, 3H), 4.35 (d, J = 21.3 Hz, 2H), 2.56 (d, J = 4.4 Hz, 3H). LC-MS (m/z): 507.2 $[M + H]^+$. |
| 153 | 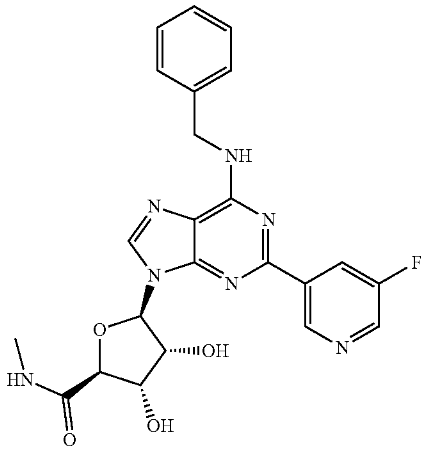 [SMILES: CNC(=O)[C@H]1O[C@@H](n2cnc3c(NCc4ccccc4)nc(-c4cncc(F)c4)nc32)[C@H](O)[C@@H]1O] (2S,3S,4R,5R)-5-(6-(benzylamino)-2-(5-fluoropyridin-3-yl)-9H-purin-9-yl)-3,4-dihydroxyl-N-methyltetrahydrofuran-2-carboxamide | $^1$H NMR (500 MHz, DMSO-$d_6$) δ: 9.31 (s, 1H), 8.75 (s, 1H), 8.66 (d, J = 2.7 Hz, 1H), 8.57 (s, 1H), 8.34 (d, J = 9.8 Hz, 1H), 7.94 (d, J = 4.6 Hz, 1H), 7.45 (d, J = 7.5 Hz, 2H), 7.32 (t, J = 7.6 Hz, 2H), 7.22 (t, J = 7.3 Hz, 1H), 6.09 (d, J = 6.8 Hz, 1H), 5.69 (d, J = 4.7 Hz, 1H), 5.60 (d, J = 6.4 Hz, 1H), 4.94 – 4.73 (m, 3H), 4.38 – 4.31 (m, 2H), 2.54 (d, J = 4.7 Hz, 3H). LC-MS (m/z): 480.2 $[M + H]^+$. |

-continued

| No. | Compound structure and name | Characterization data |
|---|---|---|
| 154 | 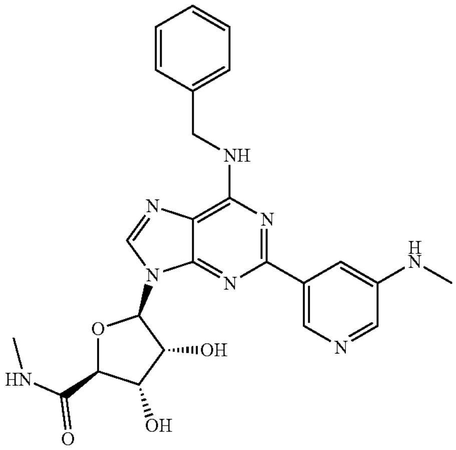<br>(2S,3S,4R,5R)-5-(6-(benzylamino)-2-(5-(methylamino)pyridin-3-yl)-9H-purin-9-yl)-3,4-dihydroxyl-N-methyltetrahydrofuran-2-carboxamide | $^1$H NMR (500 MHz, DMSO-$d_6$) δ: 8.65 (t, J = 10.8 Hz, 2H), 8.50 (s, 1H), 7.96 (dd, J = 15.9, 3.7 Hz, 2H), 7.73 – 7.68 (m, 1H), 7.45 (d, J = 7.4 Hz, 2H), 7.30 (t, J = 7.6 Hz, 2H), 7.21 (t, J = 7.3 Hz, 1H), 6.05 (dd, J = 11.6, 6.0 Hz, 2H), 5.69 (d, J = 4.5 Hz, 1H), 5.60 (d, J = 6.3 Hz, 1H), 4.91 (dd, J = 11.4, 6.5 Hz, 1H), 4.79 (s, 2H), 4.35 – 4.29 (m, 2H), 2.76 (d, J = 5.0 Hz, 3H), 2.51 (s, 3H). LC-MS (m/z): 491.3 [M + H]$^+$. |
| 155 | 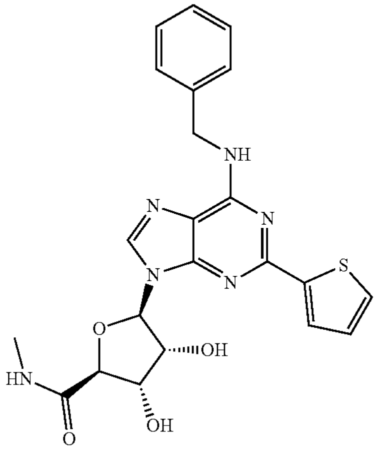 [SMILES: CNC(=O)[C@H]1O[C@@H](n2cnc3c(NCc4ccccc4)nc(-c4cccs4)nc32)[C@H](O)[C@@H]1O]<br>(2S,3S,4R,5R)-5-(6-(benzylamino)-2-(thiophen-2-yl)-9H-purin-9-yl)-3,4-dihydroxyl-N-methyltetrahydrofuran-2-carboxamide | $^1$H NMR (500 MHz, DMSO-$d_6$) δ: 8.58 (s, 1H), 8.47 (d, J = 5.8 Hz, 1H), 7.91 (q, J = 4.5 Hz, 1H), 7.79 (dd, J = 3.6, 1.2 Hz, 1H), 7.62 (dd, J = 5.0, 1.2 Hz, 1H), 7.46 (d, J = 7.1 Hz, 2H), 7.30 (t, J = 7.6 Hz, 2H), 7.21 (t, J = 7.3 Hz, 1H), 7.14 (dd, J = 5.0, 3.7 Hz, 1H), 6.02 (d, J = 6.9 Hz, 1H), 5.67 (d, J = 4.5 Hz, 1H), 5.58 (d, J = 6.3 Hz, 1H), 4.82 (dt, J = 11.1, 5.6 Hz, 1H), 4.73 (s, 2H), 4.31 (dt, J = 6.9, 2.3 Hz, 2H), 2.58 (d, J = 4.6 Hz, 3H). LC-MS (m/z): 467.2 [M + H]$^+$. |
| 156 | 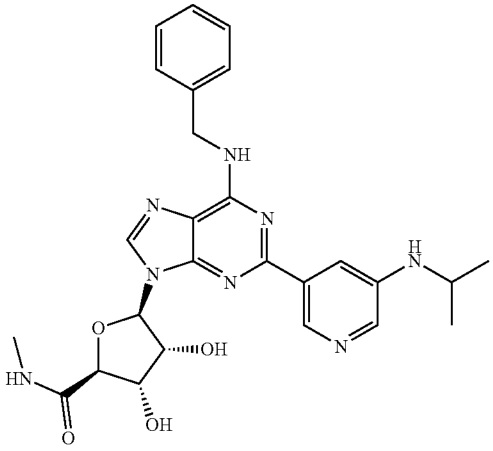 [SMILES: CNC(=O)[C@H]1O[C@@H](n2cnc3c(NCc4ccccc4)nc(-c4cncc(NC(C)C)c4)nc32)[C@H](O)[C@@H]1O] | $^1$H NMR (500 MHz, DMSO-$d_6$) δ: 8.61 (d, J = 1.4 Hz, 2H), 8.50 (s, 1H), 7.97 (dd, J = 13.8, 3.7 Hz, 2H), 7.72 (s, 1H), 7.43 (d, J = 7.4 Hz, 2H), 7.30 (t, J = 7.6 Hz, 2H), 7.21 (t, J = 7.3 Hz, 1H), 6.06 (d, J = 7.0 Hz, 1H), 5.84 (d, J = 7.8 Hz, 1H), 5.69 (d, J = 4.5 Hz, 1H), 5.60 (d, J = 6.3 Hz, 1H), 4.91 (dd, J = 11.4, 6.5 Hz, 1H), 4.79 (s, 2H), 4.36 – 4.27 (m, 2H), 3.60 (d, J = 6.3 Hz, 1H), 2.52 (s, 3H), 1.17 (t, J = 6.4 Hz, 6H). LC-MS (m/z): 519.4 [M + H]$^+$. |

-continued

| No. | Compound structure and name | Characterization data |
|---|---|---|
| | (2S,3S,4R,5R)-5-(6-(benzylamino)-2-(5-(isopropylamino)pyridin-3-yl)-9H-purin-9-yl)-3,4-dihydroxyl-N-methyltetrahydrofuran-2-carboxamide | |
| 157 | 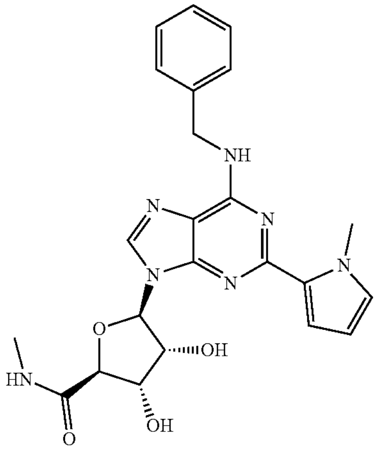 [SMILES: CNC(=O)[C@H]1O[C@@H](n2cnc3c(NCc4ccccc4)nc(-c4cccn4C)nc32)[C@H](O)[C@@H]1O] (2S,3S,4R,5R)-5-(6-(benzylamino)-2-(1-methyl-1H-pyrrol-2-yl)-9//-purin-9-yl)-3,4-dihydroxyl-N-methyltetrahydrofuran-2-carboxamide | $^1$H NMR (500 MHz, DMSO-$d_6$) δ: 8.41 (s, 2H), 8.03 (d, J = 4.7 Hz, 1H), 7.37 (d, J = 7.5 Hz, 2H), 7.30 (t, J = 7.6 Hz, 2H), 7.20 (t, J = 7.3 Hz, 1H), 6.83 (s, 1H), 6.79 (dd, J = 3.7, 1.9 Hz, 1H), 6.04 - 5.98 (m, 2H), 5.67 (d, J = 4.5 Hz, 1H), 5.57 (d, J = 6.4 Hz, 1H), 4.85 (dd, J = 11.5, 6.5 Hz, 1H), 4.73 (s, 2H), 4.31 (d, J = 2.1 Hz, 1H), 4.28 - 4.24 (m, 1H), 3.84 (s, 3H), 2.50 - 2.48 (m, 3H). |
| 158 | 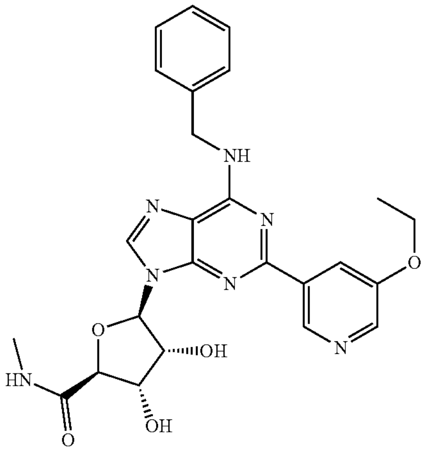 [SMILES: CCOc1cncc(-c2nc(NCc3ccccc3)c3ncn([C@@H]4O[C@H](C(=O)NC)[C@@H](O)[C@H]4O)c3n2)c1] (2S,3S,4R,5R)-5-(6-(benzylamino)-2-(5-ethoxypyridin-3-yl)-9H-purin-9-yl)-3,4-dihydroxyl-N-methyltetrahydrofuran-2-carboxamide | $^1$H NMR (500 MHz, DMSO-$d_6$) δ: 9.03 (s, 1H), 8.68 (s, 1H), 8.54 (s, 1H), 8.33 (d, J = 2.8 Hz, 1H), 8.03 (s, 1H), 7.92 (d, J = 4.7 Hz, 1H), 7.44 (d, J = 7.4 Hz, 2H), 7.31 (t, J = 7.6 Hz, 2H), 7.21 (t, J = 7.3 Hz, 1H), 6.08 (d, J = 6.8 Hz, 1H), 5.66 (s, 1H), 5.58 (d, J = 6.1 Hz, 1H), 4.91 (d, J = 4.6 Hz, 1H), 4.79 (s, 2H), 4.34 (s, 2H), 4.17 (d, J = 6.9 Hz, 2H), 2.52 (s, 3H), 1.39 (t, J = 7.0 Hz, 3H).LC-MS (m/z): 506.4 [M + H]$^+$. |

-continued

| No. | Compound structure and name | Characterization data |
|---|---|---|
| 159 | 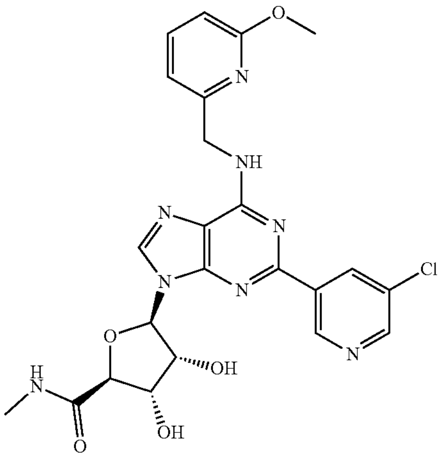 [SMILES: CNC(=O)[C@H]1O[C@@H](n2cnc3c(NCc4cccc(OC)n4)nc(-c4cncc(Cl)c4)nc32)[C@H](O)[C@@H]1O] (2S,3S,4R,5R)-5-(2-(5-chloropyridin-3-yl)-6-((((6-methoxypyridin-2-yl)methyl)amino)-9H-purin-9-yl)-3,4-dihydroxyl-N-methyltetrahydrofuran-2-carboxamide | $^{1}$H NMR (500 MHz, DMSO-d$_6$) δ: 9.31 (s, 1H), 8.73 (s, 1H), 8.68 (s, 1H), 8.60 (s, 1H), 8.48 (s, 1H), 7.94 (d, J = 4.7 Hz, 1H), 7.61 (t, J = 7.8 Hz, 1H), 6.94 (d, J = 7.3 Hz, 1H), 6.66 (d, J = 8.2 Hz, 1H), 6.10 (d, J = 6.9 Hz, 1H), 5.69 (d, J = 4.7 Hz, 1H), 5.60 (d, J = 6.4 Hz, 1H), 4.94 - 4.84 (m, 1H), 4.80 (d, J = 5.3 Hz, 2H), 4.35 (dd, J = 10.4, 3.3 Hz, 2H), 3.89 (s, 3H), 2.55 (d, J = 4.7 Hz, 3H). LC-MS m/z [M + H]$^+$: 527. |
| 160 | 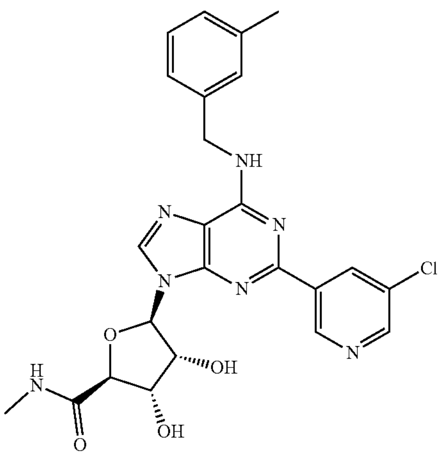 [SMILES: CNC(=O)[C@H]1O[C@@H](n2cnc3c(NCc4cccc(C)c4)nc(-c4cncc(Cl)c4)nc32)[C@H](O)[C@@H]1O] (2S,3S,4R,5R)-5-(2-(5-chloropyridin-3-yl)-6-((3-methylbenzyl)amino)-9H-purin-9-yl)-3,4-dihydroxyl-N-methyltetrahydrofuran-2-carboxamide | $^{1}$H NMR (500 MHz, DMSO-d$_6$) δ: 9.37 (s, 1H), 8.78 - 8.63 (m, 2H), 8.56 (d, J = 7.4 Hz, 2H), 7.93 (d, J = 4.7 Hz, 1H), 7.30 - 7.15 (m, 3H), 7.03 (d, J = 7.0 Hz, 1H), 6.09 (d, J = 6.8 Hz, 1H), 5.68 (d, J = 4.7 Hz, 1H), 5.59 (d, J = 6.3 Hz, 1H), 4.89 (dd, J = 11.3, 6.5 Hz, 1H), 4.75 (d, J = 4.7 Hz, 2H), 4.40 - 4.29 (m, 2H), 2.54 (d, J = 4.7 Hz, 3H), 2.28 (s, 3H). LC-MS m/z [M + H]$^+$: 510. |
| 161 | 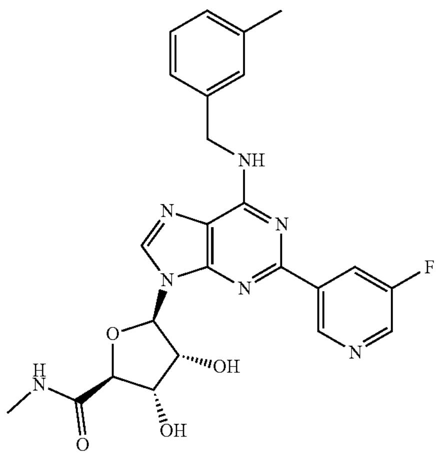 | $^{1}$H NMR (500 MHz, DMSO-d$_6$) δ: 9.31 (s, 1H), 8.89 - 8.60 (m, 2H), 8.55 (d, J = 17.0 Hz, 1H), 8.34 (d, J = 9.8 Hz, 1H), 7.90 (s, 1H), 7.31 - 7.14 (m, 3H), 7.03 (d, J = 7.1 Hz, 1H), 6.09 (d, J = 6.8 Hz, 1H), 5.67 (d, J = 4.7 Hz, 1H), 5.58 (d, J = 6.3 Hz, 1H), 4.89 (dd, J = 11.0, 6.3 Hz, 1H), 4.76 (s, 2H), 4.41 - 4.30 (m, 2H), 2.27 (s, 3H). LC-MS m/z [M + H]$^+$: 497. |

-continued

| No. | Compound structure and name | Characterization data |
|---|---|---|
| | (2S,3S,4R,5R)-5-(2-(5-fluoropyridin-3-yl)-6-((3-methylbenzyl)amino)-9H-purin-9-yl)-3,4-dihydroxyl-N-methyltetrahydrofuran-2-carboxamide | |
| 162 | 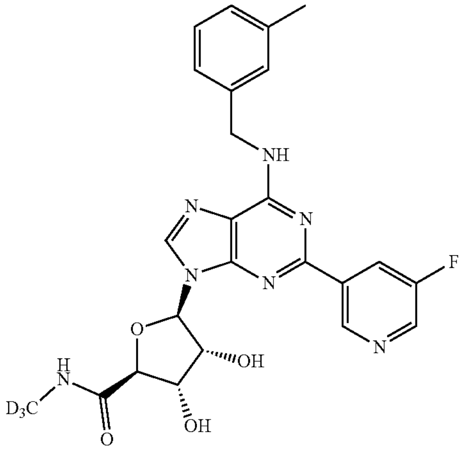 [SMILES: [2H]C([2H])([2H])NC(=O)[C@H]1O[C@@H](n2cnc3c(NCc4cccc(C)c4)nc(-c4cncc(F)c4)nc32)[C@H](O)[C@@H]1O] (2S,3S,4R,5R)-5-(2-(5-fluoropyridin-3-yl)-6-((3-methylbenzyl)amino)-9H-purin-9-yl)-3,4-dihydroxyl-N-(methyl-d3)-tetrahydrofuran-2-carboxamide | $^1$H NMR (500 MHz, DMSO-$d_6$) δ: 9.31 (s, 1H), 8.89 - 8.60 (m, 2H), 8.55 (d, J = 17.0 Hz, 1H), 8.34 (d, J = 9.8 Hz, 1H), 7.90 (s, 1H), 7.31 - 7.14 (m, 3H), 7.03 (d, J = 7.1 Hz, 1H), 6.09 (d, J = 6.8 Hz, 1H), 5.67 (d, J = 4.7 Hz, 1H), 5.58 (d, J = 6.3 Hz, 1H), 4.89 (dd, J = 11.0, 6.3 Hz, 1H), 4.76 (s, 2H), 4.41 - 4.30 (m, 2H), 2.27 (s, 3H). LC-MS m/z $[M + H]^+$: 497. |

Example 10: Synthesis of (2S,3S,4R,5R)-5-(6-(p-methylphenylmethylamino)-2-(5-chloropyridin-3-yl)-9H-purin-9-yl)-3,4-dihydroxyl-N-(methyl-d3)-tetrahydrofuran-2-formamide (compound 163)

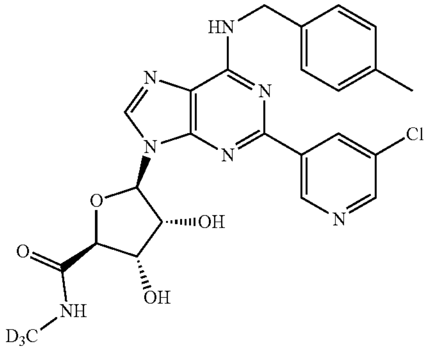

S1: Synthesis of ((3aR,4R,6R,6aR)-6-(6-(amino-2-chloro-9H-purin-9-yl)-2,2-dimethyl-tetrahydrofuran [3,4-d][1,3]-dioxo-4-yl)methanol

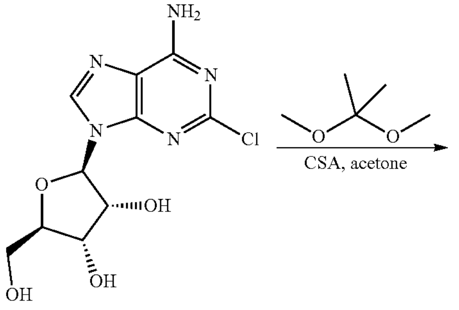

-continued

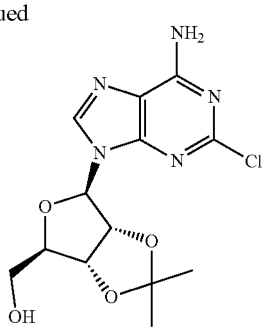

The reaction was performed according to S1 in example 1 to obtain the title compound as a white solid (22 g, yield of 100%).

S2: Synthesis of (3aS,4S,6R,6aR)-6-(6-(amino-2-chloro-9H-purin-9-yl)-2,2-dimethyl-tetrahydrofuran [3,4-d][1,3]-dioxo-4-carboxylic acid

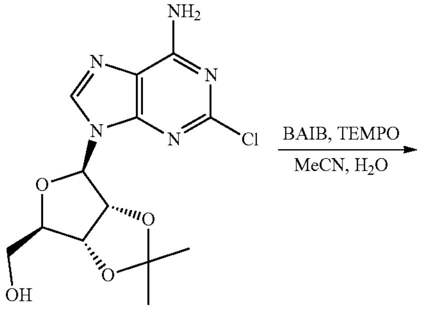

-continued

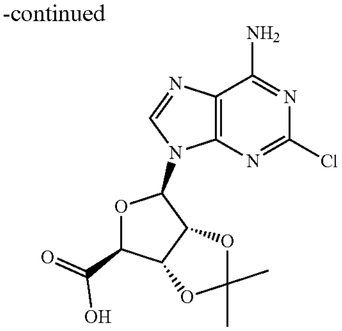

The reaction was performed according to S3 in example 1 to obtain the title compound as a yellow solid (23 g, yield of 100%).

S3: Synthesis of (3aS,4S,6R,6aR)-6-(6-(amino-2-chloro-9H-purin-9-yl)-N-methyl-tetrahydrofuran[3,4-d][1,3]-dioxin-4-formamide

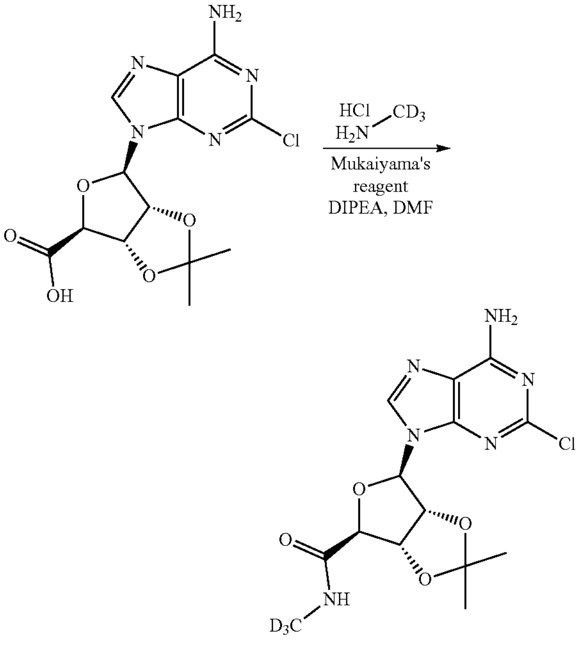

(3aS,4S,6R,6aR)-6-(6-(amino-2-chloro-9H-purin-9-yl)-2,2-dimethyl-tetrahydrofuran[3,4-d][1,3]-dioxo-4-carboxylic acid (7 g, 19.6 mmol) was dissolved in anhydrous DMF (45 mL) solvent, and N,N'-diisopropylethylamine (10.2 g, 78.7 mmol), deuteromethylamine hydrochloride (2.8 g, 39.2 mmol), and Mukaiyama's reagent (7.5 g, 29.4 mmol) were added sequentially. The materials were reacted at a room temperature overnight, and the completion of the reaction was detected by TLC. Water was added to quench the reaction, an extraction was performed with ethyl acetate, organic layers were mixed, the organic layer was washed with water and saturated saline solution, collected, dried with anhydrous sodium sulfate, and filtered, and the residue was concentrated under reduced pressure to obtain the crude product. The crude product was purified by column chromatography (ethyl acetate:n-hexane=1:1) to obtain the target compound as a yellow solid (4.9 g, yield of 67%).

S4: Synthesis of (3aS,4S,6R,6aR)-6-(6-(amino-2-(5-chloropyridin-3-yl)-9H-purin-9-yl)-N-methyl-D3,2,2-dimethyl-tetrahydrofuran[3,4-d][1,3]-dioxo-4-formamide

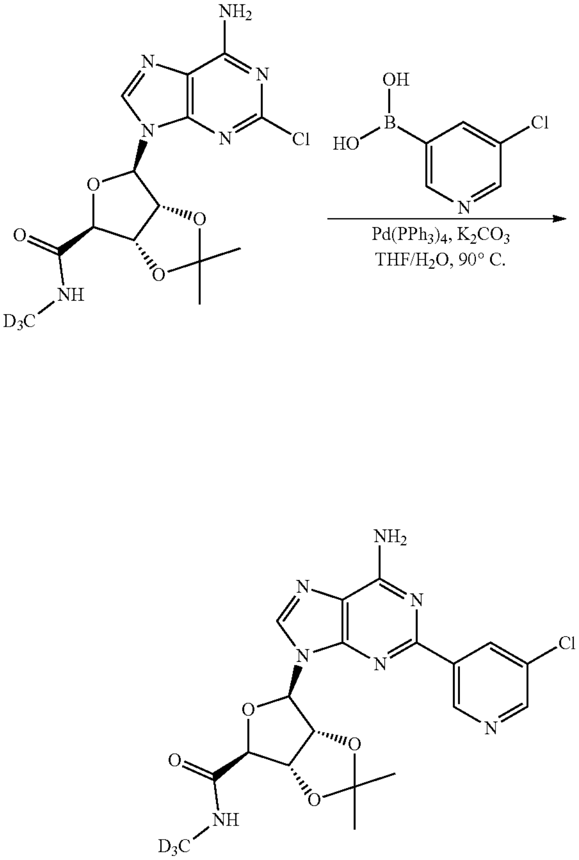

The reaction was performed according to S7 in example 8 to obtain the title compound as a yellow solid (1.8 g, yield of 31%).

S5: Synthesis of (3aS,4S,6R,6aR)-6-(2-(5-chloropyridin-3-yl)-6-iodo-9H-purin-9-yl)-N-methyl-D3,2,2-dimethyl-tetrahydrofuran[3,4-d][1,3]-dioxo-4-formamide

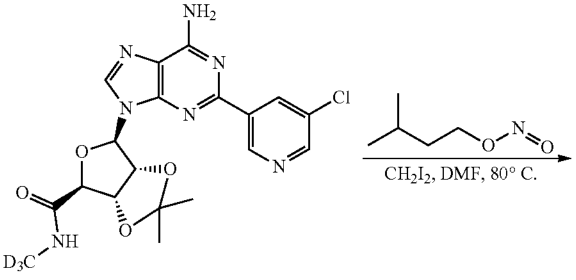

-continued

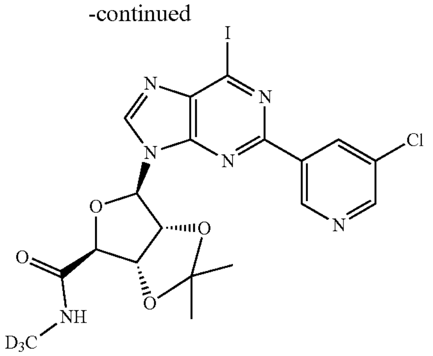

(3aS,4S,6R,6aR)-6-(6-(amino-2-(5-chloropyridin-3-yl)-9H-purin-9-yl)-N,2,2-trimethyl-tetrahydrofuran[3,4-d][1,3]-dioxo-4-deuteroformamide (1.8 g, 4 mmol) were dissolved in anhydrous DMF (40 mL) solvent, and $CH_2I_2$ (3 mL) and isoamyl nitrite (6 mL) were added sequentially. The materials were heated to 80° C. and reacted for 2 hours, and the completion of the reaction was detected by TLC. Water was added to quench the reaction, an extraction was performed with ethyl acetate, organic layers were mixed, the organic layer was washed with water and saturated saline solution, collected, dried with anhydrous sodium sulfate, and filtered, and the residue was concentrated under reduced pressure to obtain the crude product. The crude product was purified by column chromatography (ethyl acetate:n-hexane=3:1) to obtain the target compound as a yellow solid (900 mg, yield of 40%).

S6: Synthesis of (3aS,4S,6R,6aR)-6-(6-(p-methylphenylmethane amino-2-(5-chloropyridin-3-yl)-9H-purin-9-yl)-N-methyl-D3,2,2-dimethyl-tetrahydrofuran[3,4-d][1,3]-dioxo-4-formamide

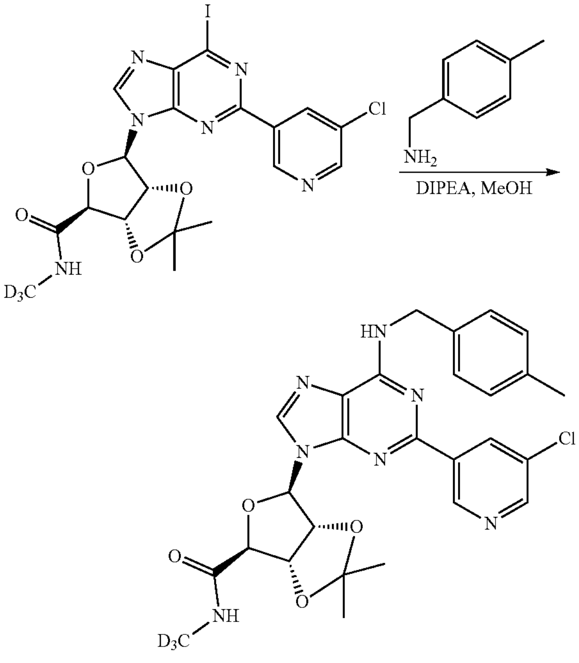

(3aS,4S,6R,6aR)-6-(2-(5-chloropyridin-3-yl)-6-iodo-9H-purin-9-yl)-N-methyl-D3,2,2-dimethyl-tetrahydrofuran[3,4-d][1,3]-dioxo-4-formamide (200 mg, 0.36 mmol) was dissolved in a methanol (15 mL) solvent, and N,N'-diisopropylethylamine (100 mg, 0.71 mmol) and p-toluenformamide (86 mg, 0.71 mmol) were added sequentially. The materials were heated to 70° C. and reacted overnight, and the completion of the reaction was detected by TLC. The crude product was obtained by concentration under reduced pressure. The crude product was purified by column chromatography (ethyl acetate:n-hexane=4:1) to obtain the target compound as a yellow solid (90 mg, yield of 46%). $^1$H NMR (500 MHz, DMSO-$d_6$) δ 9.33 (d, J=1.3 Hz, 1H), 8.69 (d, J=2.4 Hz, 2H), 8.56 (s, 1H), 8.36 (s, 1H), 7.69-7.53 (m, 4H), 7.37 (s, 1H), 7.29 (d, J=7.9 Hz, 2H), 7.10 (d, J=7.9 Hz, 2H), 6.48 (s, 1H), 5.57 (d, J=1.9 Hz, 1H), 5.48 (s, 1H), 4.80-4.67 (m, 2H), 4.62 (d, J=2.0 Hz, 1H), 2.24 (s, 3H), 1.55 (s, 3H), 1.35 (s, 3H).

S7: Synthesis of (2S,3S,4R,5R)-5-(6-(p-methylphenylmethane amino-2-(5-chloropyridin-3-yl)-9H-purin-9-yl)-3,4-dihydroxyl-N-methyl-D3-tetrahydrofuran-2-formamide (compound 163)

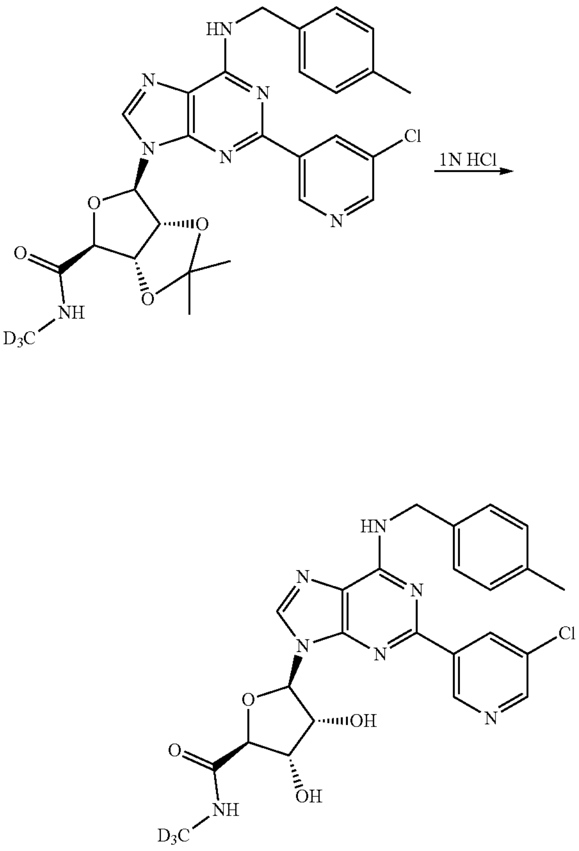

The reaction was performed according to the corresponding steps in example 8 to obtain the title compound as a yellow solid (22 mg, yield of 27%). LC-MS m/z [M+1]+: 513.3; $^1$H NMR (500 MDz, DMSO-$d_6$) δ 9.37 (s, 1H), 8.81-8.66 (1, 2H), 8.62-8.51 (m, 2H), 7.93 (s, 1H), 7.32 (d, J=7.7 Hz, 2H), 7.12 (d, J=7.8 Hz, 2H), 6.09 (d, J=7.0 Hz, 1H), 5.72 (d, J=4.6 Hz, 1H), 5.61 (d, J=6.4 Hz, 1H), 4.89 (d, J=5.1 Hz, 1H), 4.82-4.67 (2, 2H), 4.34 (dd, J=8.2, 3.1 Hz, 2H), 2.24 (s, 3H).

Example 11: Following the Reactions Shown in Example 10, the Compounds in the Table Below were Obtained

| No. | Compound structure and name | Characterization data |
|---|---|---|
| 164 | 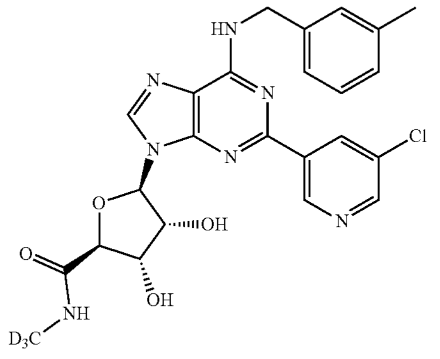 [SMILES: [2H]C([2H])([2H])NC(=O)[C@H]1O[C@@H](n2cnc3c(NCc4cccc(C)c4)nc(-c4cncc(Cl)c4)nc32)[C@H](O)[C@@H]1O] (2S,3S,4R,5R)-5-(6-(m-methylphenylmethylamino)-2-(5-chloropyridin-3-yl)-9H-purin-9-yl)-3,4-dihydroxyl-N-(methyl-d3)-tetrahydrofuran-2-formamide | LC-MS m/z $[M + 1]^+$: 513.3; $^1H$ NMR (500 MHz, DMSO-$d_6$) δ 9.37 (s, 1H), 8.71 (d, J = 9.8 Hz, 2H), 8.65-8.43 (m, 2H), 7.90 (s, 1H), 7.22 (dd, J = 23.6, 19.4 Hz, 3H), 7.03 (s, 2H), 6.09 (d, J = 6.3 Hz, 1H), 5.63 (dd, J = 48.2, 4.9 Hz, 2H), 4.88 (d, J = 4.5 Hz, 1H), 4.75 (s, 2H), 4.34 (d, J = 11.0 Hz, 2H), 2.28 (s, 3H). |
| 165 | 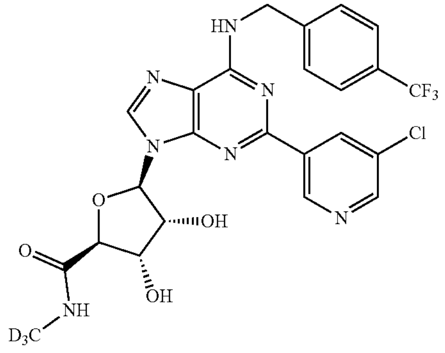 [SMILES: [2H]C([2H])([2H])NC(=O)[C@H]1O[C@@H](n2cnc3c(NCc4ccc(C(F)(F)F)cc4)nc(-c4cncc(Cl)c4)nc32)[C@H](O)[C@@H]1O] (2S,3S,4R,5R)-5-(6-(4-(trifluoromethyl)benzylamino)-2-(5-chloropyridin-3-yl)-9H-purin-9-yl)-3,4-dihydroxyl-N-(methyl-d3)-tetrahydrofuran-2-formamide | LC-MS m/z $[M + 1]^+$: 567.3; $^1H$ NMR (500 MHz, DMSO-$d_6$) δ 9.33 (s, 1H), 8.86 (s, 1H), 8.69 (s, 1H), 8.61 (s, 1H), 8.49 (s, 1H), 7.92 (s, 1H), 7.69 (d, J = 7.7 Hz, 2H), 7.66-7.62 (m, 1H), 6.10 (d, J = 6.7 Hz, 1H), 5.90-5.47 (m, 3H), 4.89 (s, 3H), 4.33 (dd, J = 7.8, 7.3 Hz, 2H). |
| 166 | 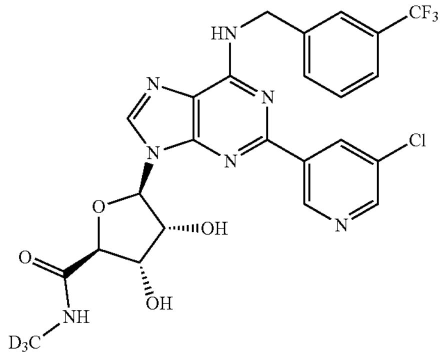 [SMILES: [2H]C([2H])([2H])NC(=O)[C@H]1O[C@@H](n2cnc3c(NCc4cccc(C(F)(F)F)c4)nc(-c4cncc(Cl)c4)nc32)[C@H](O)[C@@H]1O] (2S,3S,4R,5R)-5-(6-(3-(trifluoromethyl)benzylamino)-2-(5-chloropyridin-3-yl)-9H-purin-9-yl)-3,4-dihydroxyl-N-(methyl-d3)-tetrahydrofuran-2-formamide | LC-MS m/z $[M + 1]^+$: 567.3; $^1H$ NMR (500 MHz, DMSO-$d_6$) δ 9.37 (s, 1H), 8.88 (d, J = 5.4 Hz, 1H), 8.71 (s, 1H), 8.61 (s, 1H), 8.55 (s, 1H), 7.93 (s, 1H), 7.86 (s, 1H), 7.79-7.72 (m, 1H), 7.57 (d, J = 8.2 Hz, 2H), 6.09 (d, J = 6.7 Hz, 1H), 5.72 (d, J = 4.5 Hz, 1H), 5.62 (d, J = 6.1 Hz, 1H), 4.88 (s, 3H), 4.34 (dd, J = 5.2, 4.6 Hz, 2H). |

-continued

| No. | Compound structure and name | Characterization data |
|---|---|---|
| 167 | 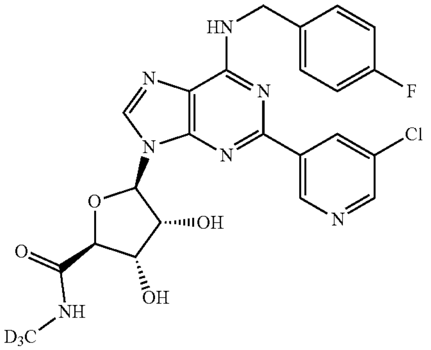 (2S,3S,4R,5R)-5-(6-(4-fluorobenzylamino)-2-(5-chloropyridin-3-yl)-9H-purin-9-yl)-3,4-dihydroxyl-N-(methyl-d3)-tetrahydrofuran-2-formamide | LC-MS m/z $[M + 1]^+$: 517.3; $^1H$ NMR (500 MHz, DMSO-$d_6$) δ 9.37 (s, 1H), 8.76 (s, 2H), 8.57 (d, J = 15.9 Hz, 2H), 7.94 (s, 1H), 7.47 (dd, J = 7.7, 6.0 Hz, 2H), 7.15 (d, J = 8.8 Hz, 2H), 6.09 (d, J = 6.8 Hz, 1H), 5.71 (d, J = 4.6 Hz, 1H), 5.63 (d, J = 6.3 Hz, 1H), 4.88 (d, J = 5.0 Hz, 1H), 4.79 (d, J = 3.7 Hz, 1H), 4.34 (dd, J = 17.4, 1.9 Hz, 2H). |
| 168 | 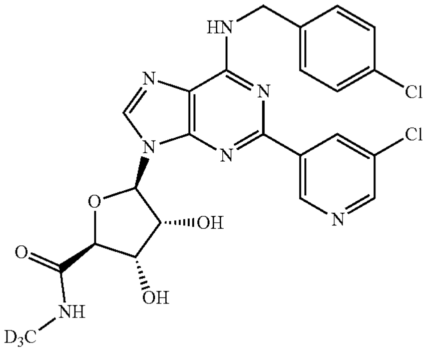 [SMILES: [2H]C([2H])([2H])NC(=O)[C@H]1O[C@@H](n2cnc3c(NCc4ccc(Br)cn4)nc(-c4cncc(Cl)c4)nc32)[C@H](O)[C@@H]1O] (2S,3S,4R,5R)-5-(6-(4-chlorobenzylamino)-2-(5-chloropyridin-3-yl)-9H-purin-9-yl)-3,4-dihydroxyl-N-(methyl-d3)-tetrahydrofuran-2-formamide | LC-MS m/z $[M + 1]^+$: 533.3; $^1H$ NMR (500 MHz, DMSO-$d_6$) δ 9.36 (s, 1H), 8.77 (s, 1H), 8.70 (s, 1H), 8.59 (s, 1H), 8.54 (s, 1H), 7.92 (s, 1H), 7.46 (d, J = 7.3 Hz, 2H), 7.38 (d, J = 7.9 Hz, 2H), 6.10 (d, J = 6.2 Hz, 1H), 5.75-5.61 (m, 2H), 4.88 (s, 1H), 4.80 (s, 2H), 4.36 (s, 1H), 4.33 (s, 1H). |
| 169 | 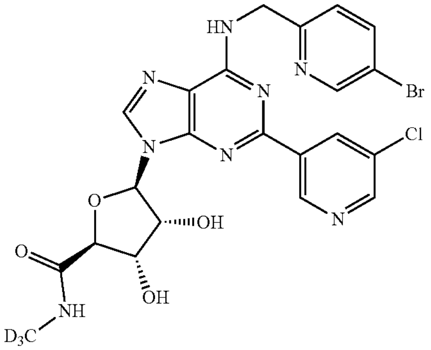 (2S,3S,4R,5R)-5-(6-((5-bromopyridin-2-yl)methylamino)-2-(5-chloropyridin-3-yl)-9H-purin-9-yl)-3,4-dihydroxyl-N-(methyl-d3)-tetrahydrofuran-2-formamide | LC-MS m/z $[M/2 + 1]^+$: 289.6; $^1H$ NMR (500 MHz, DMSO-$d_6$) δ 9.27 (s, 1H), 8.80 (d, J = 1.1 Hz, 1H), 8.75-8.56 (m, 3H), 8.44 (s, 1H), 8.05-7.90 (m, 2H), 7.38 (d, J = 8.4 Hz, 1H), 6.11 (d, J = 6.5 Hz, 1H), 5.70 (dd, J = 38.5, 1.3 Hz, 2H), 4.87 (m, 3H), 4.35 (d, J = 11.8 Hz, 2H). |

-continued

| No. | Compound structure and name | Characterization data |
|---|---|---|
| 170 | 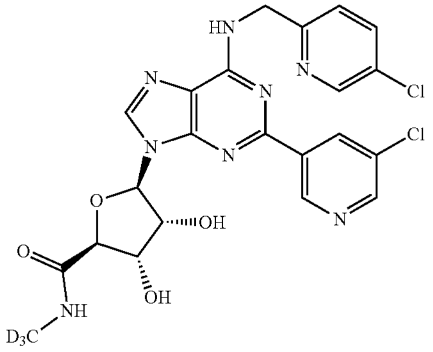 (2S,3S,4R,5R)-5-(6-((5-chloropyridin-2-yl)methylamino)-2-(5-chloropyridin-3-yl)-9H-purin-9-yl)-3,4-dihydroxyl-N-(methyl-d3)-tetrahydrofuran-2-formamide | LC-MS m/z $[M+1]^+$: 534.3; $^1H$ NMR (500 MHz, DMSO-$d_6$) δ 9.26 (s, 1H), 8.75 (s, 1H), 8.70-8.48 (m, 3H), 8.44 (d, J = 0.6 Hz, 1H), 7.96-7.78 (m, 2H), 7.43 (d, J = 8.4 Hz, 1H), 6.10 (d, J = 6.8 Hz, 1H), 5.68 (d, J = 3.9 Hz, 1H), 5.64-5.53 (m, 1H), 5.00-4.78 (m, 3H), 4.41-4.28 (m, 2H). |
| 171 | 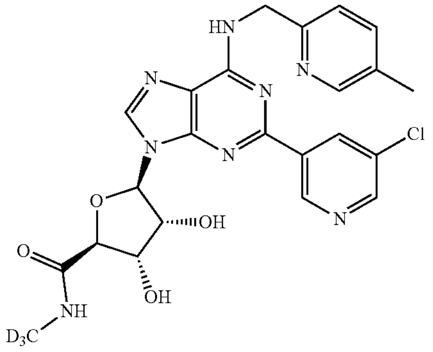 (2S,3S,4R,5R)-5-(2-(5-chloropyridin-3-yl)-6-((5-methylpyridin-2-yl)methylamino)-9H-purin-9-yl)-3,4-dihydroxyl-N-(methyl-d3)-tetrahydrofuran-2-formamide | LC-MS m/z $[M/2+1]^+$: 257.8; $^1H$ NMR (500 MHz, DMSO-$d_6$): δ 9.30 (dd, J = 3.1, 2.2 Hz, 1H), 8.79-8.58 (m, 3H), 8.53-8.44 (m, 1H), 8.37 (d, J = 1.4 Hz, 1H), 7.97 (dd, J = 1.5, 0.9 Hz, 1H), 7.61-7.47 (m, 1H), 7.35-7.21 (m, 1H), 6.11 (dd, J = 3.0, 2.3 Hz, 1H), 5.87-5.64 (m, 2H), 4.99-4.75 (m, 3H), 4.43-4.26 (m, 2H), 2.25 (s, 3H). |
| 172 | 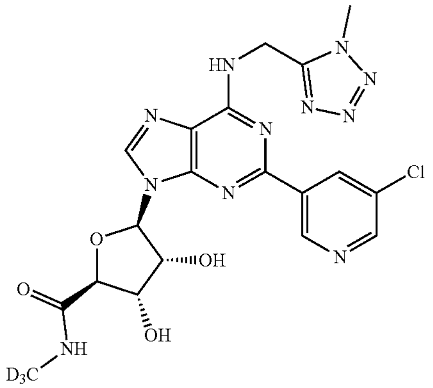 [SMILES: [2H]C([2H])([2H])NC(=O)[C@H]1O[C@@H](n2cnc3c(NCc4nnnn4C)nc(-c4cncc(Cl)c4)nc32)[C@H](O)[C@@H]1O] (2S,3S,4R,5R)-5-(2-(5-chloropyridin-3-yl)-6-((1-methyl-1H-tetrazol-5-yl)methylamino)-9H-purin-9-yl)-3,4-dihydroxyl-N-(methyl-d3)-tetrahydrofuran-2-formamide | LC-MS m/z $[M+1]^+$: 505.3; $^1H$ NMR (500 MHz, DMSO-$d_6$) δ 9.39 (s, 1H), 8.88 (m, 1H), 8.73 (d, J = 1.3 Hz, 1H), 8.64 (dd, J = 9.0, 0.7 Hz, 2H), 7.96 (s, 1H), 6.11 (dd, J = 3.8, 1.6 Hz, 1H), 5.79-5.60 (m, 2H), 5.24-5.03 (m, 2H), 4.95-4.82 (m, 1H), 4.33 (m, 2H), 4.12 (s, 3H). |

-continued

| No. | Compound structure and name | Characterization data |
|---|---|---|
| 173 | 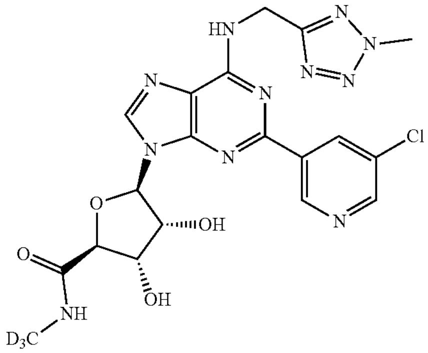 [SMILES: [2H]C([2H])([2H])NC(=O)[C@H]1O[C@@H](n2cnc3c(NCc4nnn(C)n4)nc(-c4cncc(Cl)c4)nc32)[C@H](O)[C@@H]1O]<br>(2S,3S,4R,5R)-5-(2-(5-chloropyridin-3-yl)-6-((2-methyl-2H-tetrazol-5-yl)methylamino)-9H-purin-9-yl)-3,4-dihydroxyl-N-(methyl-d3)-tetrahydrofuran-2-formamide | LC-MS m/z $[M+1]^+$: 505.3; $^1H$ NMR (500 MHz, DMSO-$d_6$) δ 9.35 (s, 1H), 8.86 (s, 1H), 8.71 (d, J = 2.1 Hz, 1H), 8.60 (d, J = 8.0 Hz, 2H), 7.93 (s, 1H), 6.10 (d, J = 6.8 Hz, 1H), 5.72 (d, J = 4.6 Hz, 1H), 5.63 (d, J = 6.4 Hz, 1H), 4.99 (s, 2H), 4.89 (d, J = 4.8 Hz, 1H), 4.38-4.32 (m, 2H), 4.31 (s, 3H). |
| 174 | 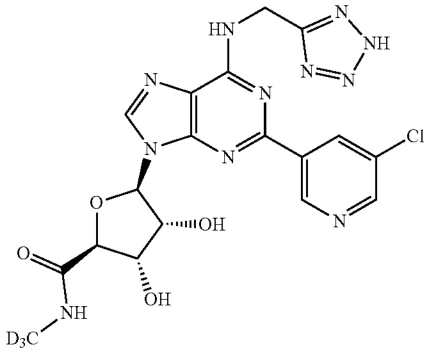 [SMILES: [2H]C([2H])([2H])NC(=O)[C@H]1O[C@@H](n2cnc3c(NCc4nn[nH]n4)nc(-c4cncc(Cl)c4)nc32)[C@H](O)[C@@H]1O]<br>(2S,3S,4R,5R)-5-(6-((1H-tetrazol-5-yl)methylamino)-2-(5-chloropyridin-3-yl)-9H-purin-9-yl)-3,4-dihydroxyl-N-(methyl-d3)-tetrahydrofuran-2-formamide | LC-MS m/z $[M+1]^+$: 491.2; $^1H$ NMR (500 MHz, DMSO-$d_6$) δ 14.82 (s, 1H), 9.41 (s, 1H), 9.03-8.29 (m, 4H), 7.93 (s, 1H), 7.72 (dd, J = 6.0, 5.0 Hz, 1H), 6.22-5.98 (m, 1H), 5.93-5.43 (m, 2H), 4.89 (d, J = 0.7 Hz, 3H), 4.52-4.20 (m, 2H). |
| 175 | 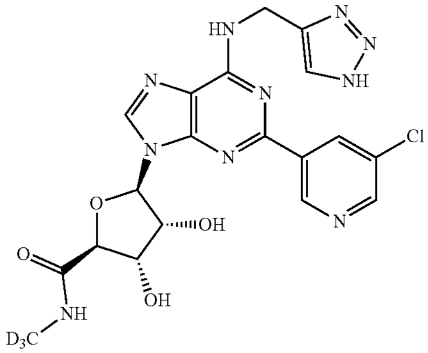 [SMILES: [2H]C([2H])([2H])NC(=O)[C@H]1O[C@@H](n2cnc3c(NCc4c[nH]nn4)nc(-c4cncc(Cl)c4)nc32)[C@H](O)[C@@H]1O]<br>(2S,3S,4R,5R)-5-(6-((1H-1,2,3-thiazol-4-yl)methylamino)-2-(5-chloropyridin-3-yl)-9H-purin-9-yl)-3,4-dihydroxyl-N-(methyl-d3)-tetrahydrofuran-2-formamide | LC-MS m/z $[M+1]^+$: 490.2; $^1H$ NMR (500 MHz, DMSO-$d_6$) δ 14.82 (s, 1H), 9.41 (s, 1H), 9.03-8.29 (m, 4H), 7.93 (s, 1H), 7.72 (dd, J = 6.0, 5.0 Hz, 1H), 6.22-5.98 (m, 1H), 5.93-5.43 (m, 2H), 4.89 (d, J = 0.7 Hz, 3H), 4.52-4.20 (m, 2H). |

-continued

| No. | Compound structure and name | Characterization data |
|---|---|---|
| 176 | 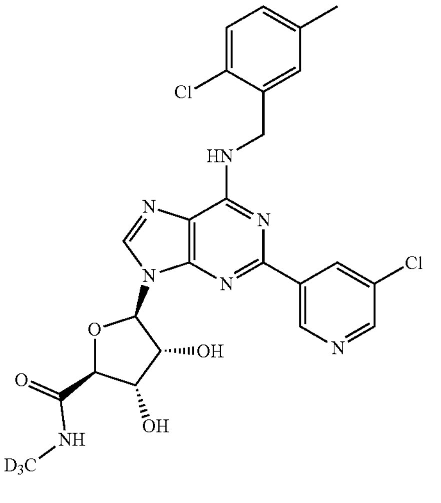 [SMILES: [2H]C([2H])([2H])NC(=O)[C@H]1O[C@@H](n2cnc3c(NCc4cc(C)ccc4Cl)nc(-c4cncc(Cl)c4)nc32)[C@H](O)[C@@H]1O] (2S,3S,4R,5R)-5-(6-(2-chloro-5-methylbenzylamino)-2-(5-chloropyridin-3-yl)-9H-purin-9-yl)-3,4-dihydroxyl-N-(methyl-d3)-tetrahydrofuran-2-formamide | LC-MS m/z $[M + 1]^+$: 547.3; $^1H$ NMR (500 MHz, DMSO-$d_6$) δ 9.32 (s, 1H), 8.65 (dd, J = 68.2, 30.9 Hz, 5H), 7.92 (s, 1H), 7.34 (d, J = 7.8 Hz, 1H), 7.29 (s, 1H), 7.07 (d, J = 7.6 Hz, 1H), 6.10 (d, J = 6.3 Hz, 1H), 4.87 (dd, J = 10.4, 7.1 Hz, 3H), 4.34 (d, J = 13.9 Hz, 3H), 2.21 (s, 3H). |
| 177 | 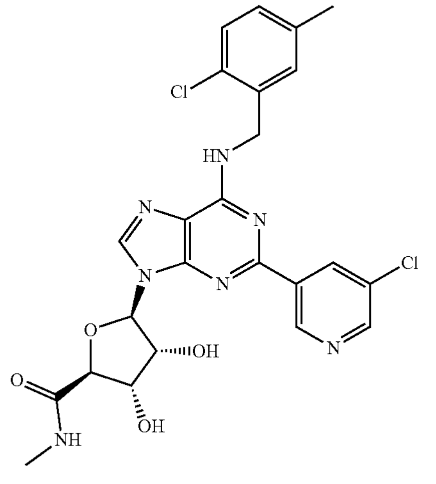 [SMILES: CNC(=O)[C@H]1O[C@@H](n2cnc3c(NCc4cc(C)ccc4Cl)nc(-c4cncc(Cl)c4)nc32)[C@H](O)[C@@H]1O] (2S,3S,4R,5R)-5-(6-(2-chloro-5-methylbenzylamino)-2-(5-chloropyridin-3-yl)-9H-purin-9-yl)-3,4-dihydroxyl-N-methyl-tetrahydrofuran-2-formamide | LC-MS m/z $[M + 1]^+$: 544.3; $^1H$ NMR (500 MHz, DMSO-$d_6$) δ 9.32 (s, 1H), 8.75 (s, 1H), 8.69 (s, 1H), 8.60 (s, 1H), 8.55 (s, 1H), 7.94 (d, J = 4.6 Hz, 1H), 7.34 (d, J = 8.1 Hz, 1H), 7.29 (s, 1H), 7.08 (d, J = 7.8 Hz, 1H), 6.10 (d, J = 6.8 Hz, 1H), 4.87 (d, J = 19.1 Hz, 4H), 4.41-4.25 (m, 3H), 2.55 (d, J = 4.6 Hz, 3H), 2.21 (s, 3H). |
| 178 | 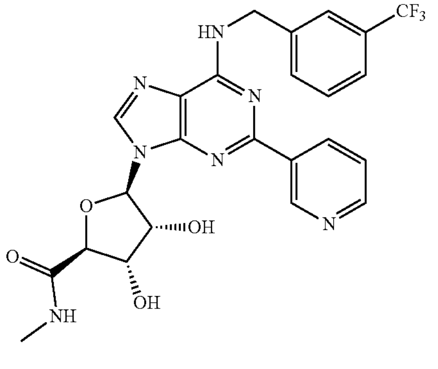 [SMILES: CNC(=O)[C@H]1O[C@@H](n2cnc3c(NCc4cccc(C(F)(F)F)c4)nc(-c4cccnc4)nc32)[C@H](O)[C@@H]1O] (2S,3S,4R,5R)-5-(6-(3-(trifluoromethyl)benzylamino)-2-(pyridin-3-yl)-9H-purin-9-yl)-3,4-dihydroxyl-N-methyl-tetrahydrofuran-2-formamide | LC-MS m/z $[M + 1]^+$: 530.3; $^1H$ NMR (500 MHz, DMSO-$d_6$) δ 9.43 (s, 1H), 8.79 (s, 1H), 8.64 (s, 1H), 8.56 (s, 2H), 7.94 (d, J = 4.6 Hz, 1H), 7.86 (s, 1H), 7.76 (d, J = 7.0 Hz, 1H), 7.57 (dd, J = 12.4, 7.7 Hz, 2H), 7.49 (s, 1H), 6.09 (d, J = 6.8 Hz, 1H), 5.70 (d, J = 4.4 Hz, 1H), 5.60 (d, J = 6.3 Hz, 1H), 4.99-4.82 (m, 3H), 4.34 (d, J = 4.8 Hz, 2H), 2.52 (s, 3H). |

-continued

| No. | Compound structure and name | Characterization data |
|---|---|---|
| 179 | 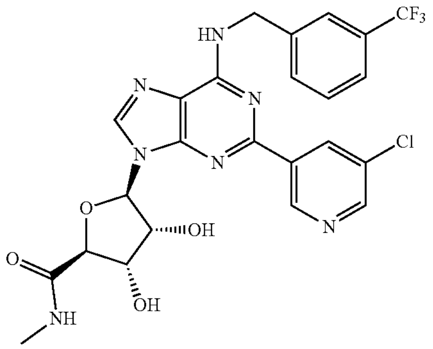 (2S,3S,4R,5R)-5-(6-(3-(trifluoromethyl)benzylamino)-2-(5-chloropyridin-3-yl)-9H-purin-9-yl)-3,4-dihydroxyl-N-methyl-tetrahydrofuran-2-formamide | LC-MS m/z $[M+1]^+$: 564.3; $^1H$ NMR (500 MHz, DMSO-$d_6$) δ 9.37 (s, 1H), 8.86 (s, 1H), 8.70 (d, J = 2.0 Hz, 1H), 8.60 (s, 1H), 8.55 (s, 1H), 7.94 (d, J = 4.7 Hz, 1H), 7.86 (s, 1H), 7.75 (d, J = 7.2 Hz, 1H), 7.58 (dd, J = 12.3, 7.6 Hz, 2H), 6.10 (d, J = 6.8 Hz, 1H), 5.70 (d, J = 4.7 Hz, 1H), 5.60 (d, J = 6.4 Hz, 1H), 4.98-4.81 (m, 3H), 4.40-4.27 (m, 2H), 2.54 (d, J = 4.6 Hz, 3H). |
| 180 | 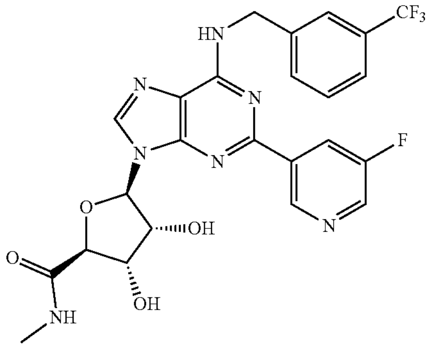 [SMILES: CNC(=O)[C@H]1O[C@@H](n2cnc3c(NCc4cccc(C(F)(F)F)c4)nc(-c4cncc(F)c4)nc32)[C@H](O)[C@@H]1O] (2S,3S,4R,5R)-5-(6-(3-(trifluoromethyl)benzylamino)-2-(5-fluoropyridin-3-yl)-9H-purin-9-yl)-3,4-dihydroxyl-N-methyl-tetrahydrofuran-2-formamide | LC-MS m/z $[M+1]^+$: 548.3; $^1H$ NMR (500 MHz, DMSO-$d_6$) δ 9.31 (s, 1H), 8.85 (d, J = 5.4 Hz, 1H), 8.66 (d, J = 2.4 Hz, 1H), 8.59 (d, J = 5.4 Hz, 1H), 8.34 (d, J = 9.5 Hz, 1H), 7.97-7.91 (m, 1H), 7.88 (s, 1H), 7.75 (d, J = 7.3 Hz, 1H), 7.57 (d, J = 4.5 Hz, 1H), 7.55 (d, J = 7.6 Hz, 1H), 6.09 (d, J = 6.7 Hz, 1H), 5.69 (d, J = 4.7 Hz, 1H), 5.59 (d, J = 6.3 Hz, 1H), 4.94-4.83 (m, 3H), 4.37-4.31 (m, 2H), 2.53 (d, J = 4.7 Hz, 3H). |
| 181 | 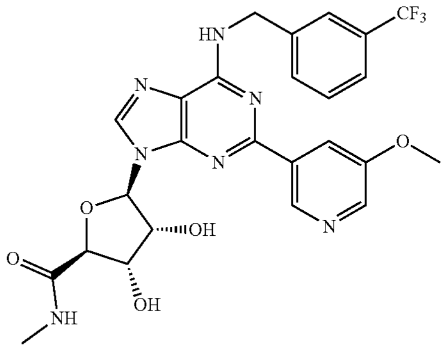 [SMILES: CNC(=O)[C@H]1O[C@@H](n2cnc3c(NCc4cccc(C(F)(F)F)c4)nc(-c4cncc(OC)c4)nc32)[C@H](O)[C@@H]1O] (2S,3S,4R,5R)-5-(6-(3-(trifluoromethyl)benzylamino)-2-(5-methoxypyridin-3-yl)-9/-purin-9-yl)-3,4-dihydroxyl-N-methyl-tetrahydrofuran-2-formamide | LC-MS m/z $[M+1]^+$: 560.3; $^1H$ NMR (500 MHz, DMSO-$d_6$) δ 9.05 (s, 1H), 8.80 (s, 1H), 8.57 (s, 1H), 8.36 (s, 1H), 8.06 (s, 1H), 7.97-7.89 (m, 1H), 7.85 (s, 1H), 7.76 (d, J = 7.1 Hz, 1H), 7.57 (dt, J = 15.2, 7.6 Hz, 2H), 6.09 (d, J = 6.8 Hz, 1H), 5.69 (d, J = 4.6 Hz, 1H), 5.60 (d, J = 6.3 Hz, 1H), 4.97-4.81 (m, 3H), 4.35 (d, J = 6.4 Hz, 2H), 3.90 (s, 3H), 2.51 (s, 3H). |

-continued

| No. | Compound structure and name | Characterization data |
|---|---|---|
| 182 | 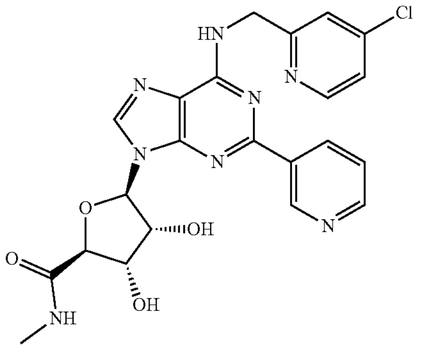 [SMILES: CNC(=O)[C@H]1O[C@@H](n2cnc3c(NCc4cc(Cl)ccn4)nc(-c4cccnc4)nc32)[C@H](O)[C@@H]1O] (2S,3S,4R,5R)-5-(6-((4-chloropyridin-2-yl)methylamino)-2-(pyridin-3-yl)-9H-purin-9-yl)-3,4-dihydroxyl-N-methyl-tetrahydrofuran-2-formamide | LC-MS m/z $[M + 1]^+$: 497.2; $^1H$ NMR (500 MHz, DMSO-$d_6$) δ 9.35 (s, 1H), 8.71-8.47 (m, 5H), 7.97 (dd, J = 6.3, 2.8 Hz, 1H), 7.55-7.45 (m, 2H), 7.41 (dd, J = 5.3, 1.8 Hz, 1H), 6.11 (d, J = 6.9 Hz, 1H), 5.72 (d, J = 4.5 Hz, 1H), 5.63 (d, J = 6.3 Hz, 1H), 4.91 (d, J = 3.7 Hz, 3H), 4.35 (d, J = 4.8 Hz, 2H), 2.56-2.51 (m, 3H). |
| 183 | 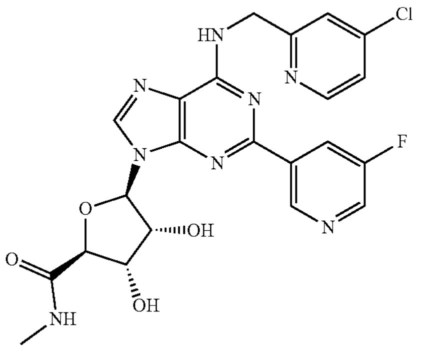 (2S,3S,4R,5R)-5-(6-((4-chloropyridin-2-yl)methylamino)-2-(5-fluoropyridin-3-yl)-9H-purin-9-yl)-3,4-dihydroxyl-N-methyl-tetrahydrofuran-2-formamide | LC-MS m/z $[M + 1]^+$: 515.2; $^1H$ NMR (500 MHz, DMSO-$d_6$) δ 9.23 (s, 1H), 8.74 (s, 1H), 8.63 (d, J = 5.4 Hz, 2H), 8.52 (d, J = 5.3 Hz, 1H), 8.28 (d, J = 9.0 Hz, 1H), 7.98 (d, J = 4.6 Hz, 1H), 7.52 (s, 1H), 7.44-7.38 (m, 1H), 6.11 (d, J = 6.7 Hz, 1H), 5.73 (d, J = 0.9 Hz, 2H), 4.90 (s, 3H), 4.42-4.29 (m, 2H), 2.54 (d, J = 4.5 Hz, 3H). |
| 184 | 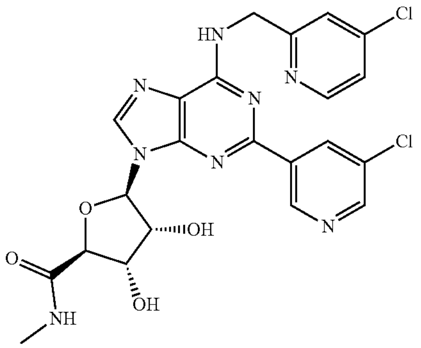 (2S,3S,4R,5R)-5-(6-((4-chloropyridin-2-yl)methylamino)-2-(5-chloropyridin-3-yl)-9H-purin-9-yl)-3,4-dihydroxyl-N-methyl-tetrahydrofuran-2-formamide | LC-MS m/z $[M + 1]^+$: 531.2; $^1H$ NMR (500 MHz, DMSO-$d_6$) δ 9.28 (s, 1H), 8.75 (s, 1H), 8.68 (s, 1H), 8.62 (s, 1H), 8.51 (d, J = 5.4 Hz, 1H), 8.47 (s, 1H), 7.95 (d, J = 4.6 Hz, 1H), 7.51 (d, J = 1.5 Hz, 1H), 7.41 (dd, J = 5.3, 1.9 Hz, 1H), 6.10 (d, J = 6.8 Hz, 1H), 5.69 (s, 2H), 4.88 (s, 3H), 4.36 (d, J = 2.0 Hz, 1H), 4.35-4.32 (m, 1H), 2.55 (d, J = 4.5 Hz, 3H). |

-continued

| No. | Compound structure and name | Characterization data |
|---|---|---|
| 185 | 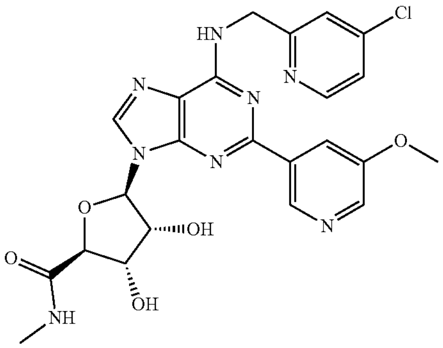 [SMILES: CNC(=O)[C@H]1O[C@@H](n2cnc3c(NCc4cc(Cl)ccn4)nc(-c4cncc(OC)c4)nc32)[C@H](O)[C@@H]1O] (2S,3S,4R,5R)-5-(6-((4-chloropyridin-2-yl)methylamino)-2-(5-methoxypyridin-3-yl)-9H-purin-9-yl)-3,4-dihydroxyl-N-methyl-tetrahydrofuran-2-formamide | LC-MS m/z $[M + 1]^+$: 527.2; $^1H$ NMR (500 MHz, DMSO-$d_6$) δ 8.97 (s, 1H), 8.69 (s, 1H), 8.59 (s, 1H), 8.51 (d, J = 5.4 Hz, 1H), 8.34 (s, 1H), 8.00 (s, 1H), 7.94 (d, J = 4.7 Hz, 1H), 7.51 (d, J = 1.5 Hz, 1H), 7.41 (dd, J = 5.2, 1.7 Hz, 1H), 6.10 (d, J = 6.8 Hz, 1H), 5.70 (d, J = 4.5 Hz, 1H), 5.62 (d, J = 6.3 Hz, 1H), 4.99-4.85 (m, 3H), 4.36 (d, J = 3.6 Hz, 2H), 3.89 (s, 3H), 2.51 (s, 3H). |
| 186 | 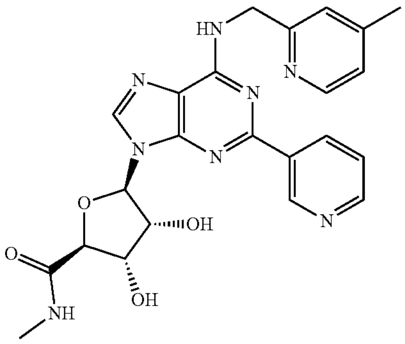 [SMILES: CNC(=O)[C@H]1O[C@@H](n2cnc3c(NCc4cc(C)ccn4)nc(-c4cccnc4)nc32)[C@H](O)[C@@H]1O] (2S,3S,4R,5R)-3,4-dihydroxyl-N-methyl-5-(6-((4-methylpyridin-2-yl)methylamino)-2-(pyridin-3-yl)-9H-purin-9-yl)-tetrahydrofuran-2-formamide | LC-MS m/z $[M/2 + 1]^+$: 239.3; $^1H$ NMR (500 MHz, DMSO-$d_6$) δ 9.37 (s, 1H), 8.61 (d, J = 3.6 Hz, 1H), 8.57 (s, 2H), 8.52 (d, J = 6.9 Hz, 1H), 8.38 (d, J = 5.0 Hz, 1H), 7.96 (d, J = 4.7 Hz, 1H), 7.52-7.44 (m, 1H), 7.24 (s, 1H), 7.08 (d, J = 4.8 Hz, 1H), 6.10 (d, J = 6.9 Hz, 1H), 5.71 (d, J = 4.5 Hz, 1H), 5.62 (d, J = 6.4 Hz, 1H), 4.87 (d, J = 4.3 Hz, 3H), 4.35 (d, J = 5.2 Hz, 2H), 2.53 (d, J = 4.6 Hz, 3H), 2.26 (s, 3H). |
| 187 | 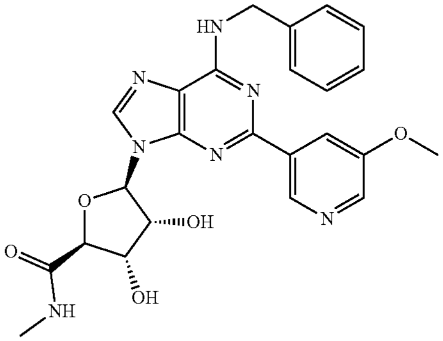 [SMILES: CNC(=O)[C@H]1O[C@@H](n2cnc3c(NCc4ccccc4)nc(-c4cncc(OC)c4)nc32)[C@H](O)[C@@H]1O] (2S,3S,4R,5R)-5-(6-(benzylamino)-2-(5-methoxypyridin-3-yl)-9H-purin-9-yl)-3,4-dihydroxyl-N-methyl-tetrahydrofuran-2-formamide | LC-MS m/z $[M + 1]^+$: 492.3; $^1H$ NMR (500 MHz, DMSO-$d_6$) δ 9.03 (s, 1H), 8.69 (s, 1H), 8.53 (s, 1H), 8.34 (d, J = 2.4 Hz, 1H), 8.05 (s, 1H), 7.91 (d, J = 4.6 Hz, 1H), 7.44 (d, J = 7.4 Hz, 2H), 7.30 (t, J = 7.6 Hz, 2H), 7.20 (d, J = 7.2 Hz, 1H), 6.07 (d, J = 6.8 Hz, 1H), 5.67 (d, J = 4.5 Hz, 1H), 5.58 (d, J = 6.3 Hz, 1H), 4.91 (d, J = 4.6 Hz, 1H), 4.78 (d, J = 2.3 Hz, 2H), 4.33 (s, 2H), 3.89 (s, 3H), 2.49 (s, 3H). |

-continued

| No. | Compound structure and name | Characterization data |
| --- | --- | --- |
| 188 | 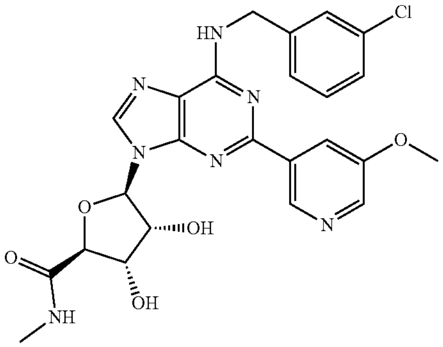 [SMILES: CNC(=O)[C@H]1O[C@@H](n2cnc3c(NCc4cccc(Cl)c4)nc(-c4cncc(OC)c4)nc32)[C@H](O)[C@@H]1O] (2S,3S,4R,5R)-5-(6-(3-chlorobenzylamino)-2-(5-methoxypyridin-3-yl)-9H-purin-9-yl)-3,4-dihydroxyl-N-methyl-tetrahydrofuran-2-formamide | LC-MS m/z $[M + 1]^+$: 526.2; $^1H$ NMR (500 MHz, DMSO-$d_6$) δ 9.04 (s, 1H), 8.74 (d, J = 1.0 Hz, 1H), 8.56 (s, 1H), 8.35 (s, 1H), 8.06 (s, 1H), 7.92 (d, J = 1.6 Hz, 1H), 7.51 (s, 1H), 7.42 (s, 2H), 7.35-7.31 (m, 1H), 7.28 (d, J = 7.6 Hz, 2H), 6.08 (d, J = 5.6 Hz, 1H), 5.68 (s, 1H), 5.60 (d, J = 2.0 Hz, 1H), 4.92 (d, J = 2.0 Hz, 1H), 4.86-4.68 (m, 2H), 4.35 (s, 2H), 3.91 (s, 3H), 3.73 (s, 1H). |
| 189 | 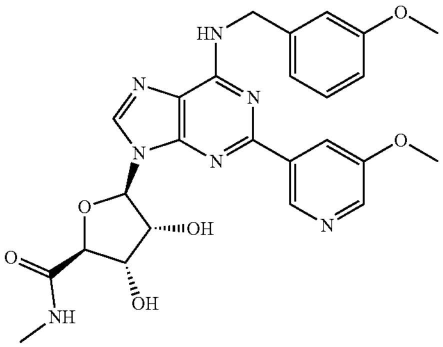 [SMILES: CNC(=O)[C@H]1O[C@@H](n2cnc3c(NCc4cccc(OC)c4)nc(-c4cncc(OC)c4)nc32)[C@H](O)[C@@H]1O] (2S,3S,4R,5R)-5-(6-(3-methoxybenzylamino)-2-(5-methoxypyridin-3-yl)-9H-purin-9-yl)-3,4-dihydroxyl-N-methyl-tetrahydrofuran-2-formamide | LC-MS m/z $[M + 1]^+$: 522.3; $^1H$ NMR (500 MHz, DMSO-$d_6$) δ 9.06 (d, J = 1.5 Hz, 1H), 8.68 (s, 1H), 8.54 (s, 1H), 8.36 (d, J = 2.8 Hz, 1H), 8.07 (s, 1H), 7.92 (d, J = 4.7 Hz, 1H), 7.22 (t, J = 7.9 Hz, 1H), 7.04 (d, J = 10.4 Hz, 2H), 6.78 (d, J = 8.1 Hz, 1H), 6.08 (d, J = 6.8 Hz, 1H), 5.67 (d, J = 4.5 Hz, 1H), 5.59 (d, J = 6.3 Hz, 1H), 4.97-4.89 (m, 1H), 4.75 (dd, J = 2.9, 1.1 Hz, 2H), 4.38-4.30 (m, 2H), 3.91 (s, 3H), 3.70 (s, 3H), 2.51 (d, J = 2.2 Hz, 3H). |
| 190 | 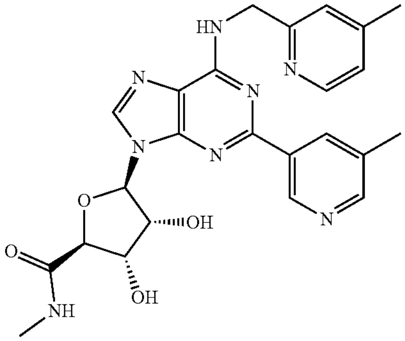 [SMILES: CNC(=O)[C@H]1O[C@@H](n2cnc3c(NCc4cc(C)ccn4)nc(-c4cncc(C)c4)nc32)[C@H](O)[C@@H]1O] (2S,3S,4R,5R)-3,4-dihydroxyl-N-methyl-5-(6-((4-methylpyridin-2-yl)methylamino)-2-(5-methylpyridin-3-yl)-9H-purin-9-yl)-tetrahydrofuran-2-formamide | LC-MS m/z $[M + 1]^+$: 491.5; $^1H$ NMR (500 MHz, DMSO-$d_6$) δ 9.13 (s, 1H), 8.52 (s, 2H), 8.43 (s, 1H), 8.36 (d, J = 5.0 Hz, 1H), 8.29 (s, 1H), 7.96 (d, J = 4.7 Hz, 1H), 7.24 (s, 1H), 7.08 (d, J = 4.9 Hz, 1H), 6.08 (d, J = 6.9 Hz, 1H), 5.76 (d, J = 4.4 Hz, 1H), 5.68 (d, J = 6.2 Hz, 1H), 4.92-4.80 (m, 3H), 4.33 (d, J = 5.3 Hz, 2H), 2.50 (s, 3H), 2.35 (s, 3H), 2.24 (s, 3H). |

-continued

| No. | Compound structure and name | Characterization data |
| --- | --- | --- |
| 191 | 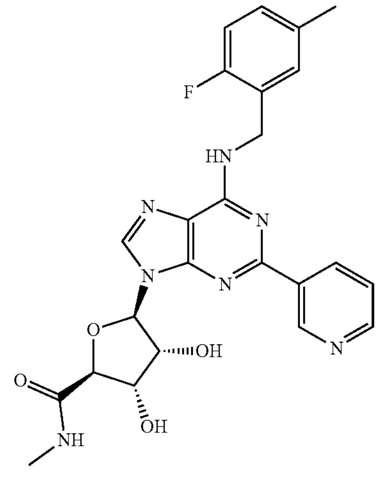 [SMILES: CNC(=O)[C@H]1O[C@@H](n2cnc3c(NCc4cc(C)ccc4F)nc(-c4cccnc4)nc32)[C@H](O)[C@@H]1O] (2S,3S,4R,5R)-5-(6-(2-fluoro-5-methylbenzylamino)-2-(pyridin-3-yl)-9H-purin-9-yl)-3,4-dihydroxyl-N-methyl-tetrahydrofuran-2-formamide | LC-MS m/z $[M + 1]^+$: 494.4; $^1H$ NMR (500 MHz, DMSO-$d_6$) δ 9.44 (s, 1H), 8.69-8.51 (m, 4H), 7.94 (d, J = 4.6 Hz, 1H), 7.50 (dd, J = 7.5, 4.8 Hz, 1H), 7.29 (d, J = 6.4 Hz, 1H), 7.12-7.02 (m, 2H), 6.09 (d, J = 6.9 Hz, 1H), 5.70 (d, J = 4.4 Hz, 1H), 5.60 (d, J = 6.3 Hz, 1H), 4.90 (dd, J = 10.9, 6.2 Hz, 1H), 4.82 (s, 2H), 4.40-4.30 (m, 2H), 2.52 (d, J = 4.6 Hz, 3H), 2.21 (s, 3H). |
| 192 | 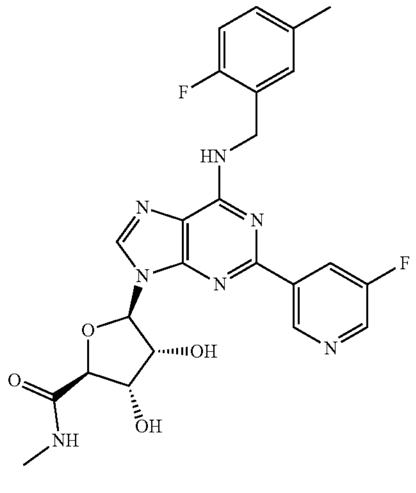 [SMILES: CNC(=O)[C@H]1O[C@@H](n2cnc3c(NCc4cc(C)ccc4F)nc(-c4cncc(F)c4)nc32)[C@H](O)[C@@H]1O] (2S,3S,4R,5R)-5-(6-(2-fluoro-5-methylbenzylamino)-2-(5-fluoropyridin-3-yl)-9H-purin-9-yl)-3,4-dihydroxyl-N-methyl-tetrahydrofuran-2-formamide | LC-MS m/z $[M + 1]^+$: 512.5; $^1H$ NMR (500 MHz, DMSO-$d_6$) δ 9.31 (s, 1H), 8.71 (s, 1H), 8.66 (d, J = 2.5 Hz, 1H), 8.58 (s, 1H), 8.35 (d, J = 9.8 Hz, 1H), 7.93 (d, J = 4.6 Hz, 1H), 7.29 (d, J = 6.7 Hz, 1H), 7.06 (d, J = 8.0 Hz, 2H), 6.09 (d, J = 6.7 Hz, 1H), 5.69 (d, J = 4.6 Hz, 1H), 5.59 (d, J = 6.3 Hz, 1H), 4.89 (d, J = 4.7 Hz, 1H), 4.80 (s, 2H), 4.34 (d, J = 6.7 Hz, 2H), 2.54 (d, J = 4.5 Hz, 3H), 2.21 (s, 3H). |
| 193 | 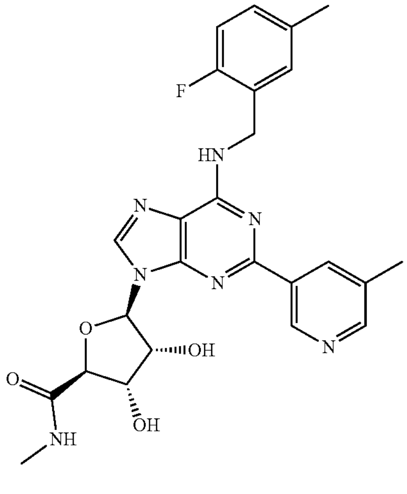 [SMILES: CNC(=O)[C@H]1O[C@@H](n2cnc3c(NCc4cc(C)ccc4F)nc(-c4cncc(C)c4)nc32)[C@H](O)[C@@H]1O] | LC-MS m/z $[M + 1]^+$: 508.5; $^1H$ NMR (500 MHz, DMSO-$d_6$) δ 9.23 (s, 1H), 8.63 (s, 1H), 8.55 (s, 1H), 8.47 (s, 1H), 8.39 (s, 1H), 7.95 (d, J = 4.7 Hz, 1H), 7.29 (d, J = 6.4 Hz, 1H), 7.07 (d, J = 8.7 Hz, 2H), 6.09 (d, J = 6.9 Hz, 1H), 5.70 (d, J = 4.6 Hz, 1H), 5.60 (d, J = 6.3 Hz, 1H), 4.89 (d, J = 4.9 Hz, 1H), 4.80 (s, 2H), 4.37-4.30 (m, 2H), 2.53 (d, J = 4.6 Hz, 3H), 2.39 (s, 3H), 2.21 (s, 3H). |

-continued

| No. | Compound structure and name | Characterization data |
| --- | --- | --- |
| | (2S,3S,4R,5R)-5-(6-(2-fluoro-5-methylbenzylamino)-2-(5-methylpyridin-3-yl)-9H-purin-9-yl)-3,4-dihydroxyl-N-methyl-tetrahydrofuran-2-formamide | |
| 194 | 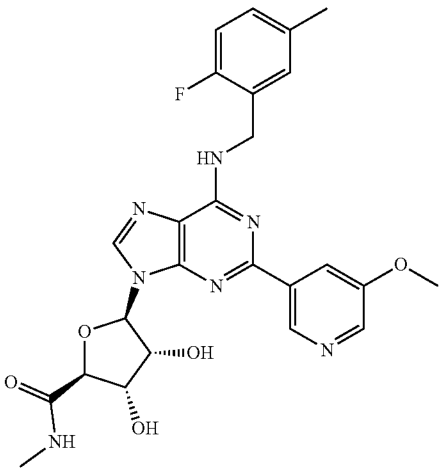 [SMILES: CNC(=O)[C@H]1O[C@@H](n2cnc3c(NCc4cc(C)ccc4F)nc(-c4cncc(OC)c4)nc32)[C@H](O)[C@@H]1O] (2S,3S,4R,5R)-5-(6-(2-fluoro-5-methylbenzylamino)-2-(5-methoxypyridin-3-yl)-9H-purin-9-yl)-3,4-dihydroxyl-N-methyl-tetrahydrofuran-2-formamide | LC-MS m/z $[M + 1]^+$: 524.5; $^1H$ NMR (500 MHz, DMSO-$d_6$) δ 9.05 (s, 1H), 8.68 (s, 1H), 8.56 (s, 1H), 8.36 (s, 1H), 8.09 (s, 1H), 7.93 (d, J = 4.4 Hz, 1H), 7.29 (d, J = 6.3 Hz, 1H), 7.06 (d, J = 8.1 Hz, 2H), 6.08 (d, J = 6.7 Hz, 1H), 5.69 (d, J = 4.5 Hz, 1H), 5.60 (d, J = 6.3 Hz, 1H), 4.93 (d, J = 4.6 Hz, 1H), 4.80 (s, 2H), 4.35 (s, 2H), 3.91 (s, 3H), 2.51 (s, 3H), 2.20 (s, 3H). |
| 195 | 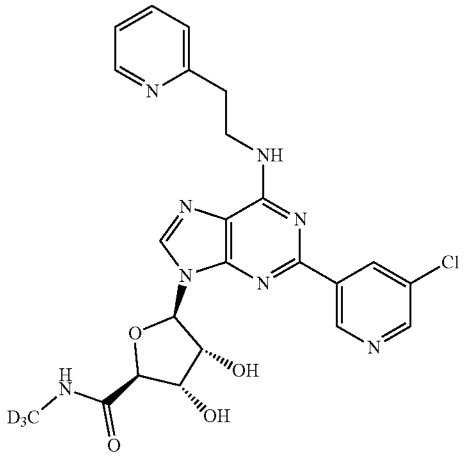 [SMILES: [2H]C([2H])([2H])NC(=O)[C@H]1O[C@@H](n2cnc3c(NCCc4ccccn4)nc(-c4cncc(Cl)c4)nc32)[C@H](O)[C@@H]1O] (2S,3S,4R,5R)-5-(2-(5-chloropyridin-3-yl)-6-((2-(pyridin-2-yl)ethyl)amino)-9H-purin-9-yl)-3,4-dihydroxyl-N-(methyl-d3)-tetrahydrofuran-2-carboxamide | $^1H$ NMR (500 MHz, DMSO-$d_6$) δ: 9.43 (s, 1H), 8.71 (d, J = 2.4 Hz, 1H), 8.67 (s, 1H), 8.59-8.48 (m, 2H), 8.23 (s, 1H), 7.93 (s, 1H), 7.68 (t, J = 7.1 Hz, 1H), 7.32 (d, J = 7.7 Hz, 1H), 7.20 (d, J = 5.5 Hz, 1H), 6.09 (d, J = 6.7 Hz, 1H), 5.70 (s, 2H), 4.87 (dd, J = 6.8, 4.7 Hz, 1H), 4.37-4.29 (m, 2H), 3.97 (d, J = 5.8 Hz, 2H), 3.15 (t, J = 7.3 Hz, 2H). LC-MS m/z $[M + H]^+$: 514. |

-continued

| No. | Compound structure and name | Characterization data |
|---|---|---|
| 196 | 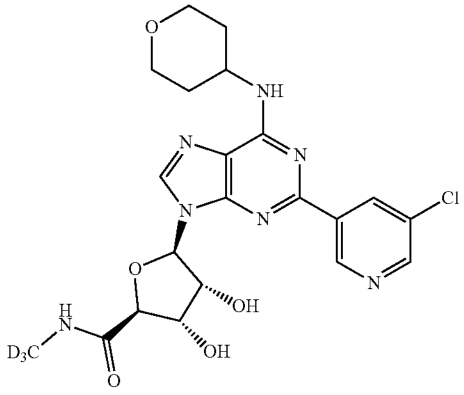 [SMILES: [2H]C([2H])([2H])NC(=O)[C@H]1O[C@@H](n2cnc3c(NC4CCOCC4)nc(-c4cncc(Cl)c4)nc32)[C@H](O)[C@@H]1O] (2S,3S,4R,5R)-5-(2-(5-chloropyridin-3-yl)-6-((tetrahydro-2H-pyridin-4-yl)amino)-9H-purin-9-yl)-3,4-dihydroxyl-N-(methyl-d3)-tetrahydrofuran-2-carboxamide | $^1$H NMR (500 MHz, DMSO-$d_6$) δ: 9.43 (s, 1H), 8.73 (s, 1H), 8.60 (d, J = 13.2 Hz, 2H), 8.26-7.77 (m, 2H), 6.10 (d, J = 6.5 Hz, 1H), 5.71 (s, 2H), 4.89 (s, 1H), 4.49 (s, 1H), 4.34 (d, J = 12.0 Hz, 2H), 3.93 (d, J = 9.1 Hz, 2H), 3.51 (t, J = 11.0 Hz, 2H), 1.82 (d, J = 52.5 Hz, 4H). LC-MS m/z [M + H]$^+$: 493. |
| 197 | 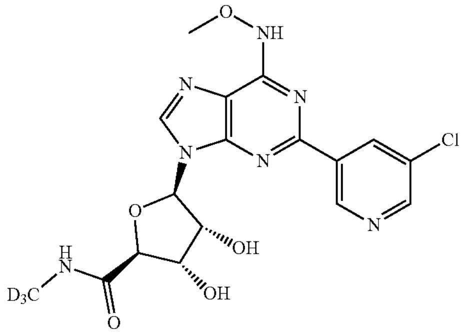 (2S,3S,4R,5R)-5-(2-(5-chloropyridin-3-yl)-6-(methoxyamino)-9H-purin-9-yl)-3,4-dihydroxyl-N-(methyl-d3)-tetrahydrofuran-2-carboxamide | $^1$H NMR (500 MHz, DMSO-$d_6$) δ: 11.28 (s, 1H), 9.35 (s, 1H), 8.70 (d, J = 2.0 Hz, 1H), 8.57 (s, 1H), 8.41 (s, 1H), 8.02 (s, 1H), 6.04 (d, J = 6.5 Hz, 1H), 5.66 (s, 2H), 4.92 (dd, J = 6.7, 4.8 Hz, 1H), 4.36-4.29 (m, 2H), 3.80 (s, 3H). LC-MS m/z [M + H]$^+$: 429. |
| 198 | 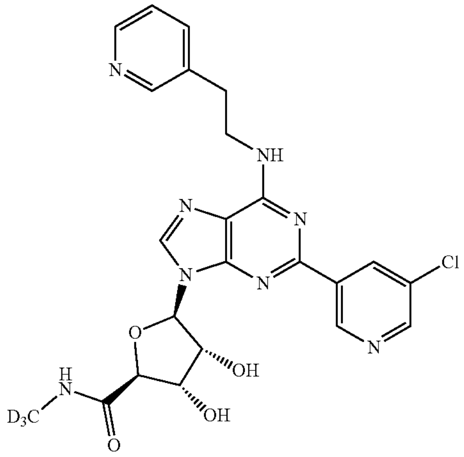 [SMILES: [2H]C([2H])([2H])NC(=O)[C@H]1O[C@@H](n2cnc3c(NCCc4cccnc4)nc(-c4cncc(Cl)c4)nc32)[C@H](O)[C@@H]1O] (2S,3S,4R,5R)-5-(2-(5-chloropyridin-3-yl)-6-((2-(pyridin-3-yl)ethyl)amino)-9H-purin-9-yl)-3,4-dihydroxyl-N-(methyl-d3)-tetrahydrofuran-2-carboxamide | $^1$H NMR (500 MHz, DMSO-$d_6$) δ: 9.42 (s, 1H), 8.73 (d, J = 2.0 Hz, 1H), 8.70-8.46 (m, 3H), 8.38 (s, 1H), 8.28 (s, 1H), 7.94 (s, 1H), 7.73 (d, J = 6.8 Hz, 1H), 7.30 (d, J = 5.2 Hz, 1H), 6.09 (d, J = 6.6 Hz, 1H), 5.72 (d, J = 4.3 Hz, 1H), 5.62 (d, J = 6.2 Hz, 1H), 4.88 (d, J = 5.0 Hz, 1H), 4.34 (d, J = 12.5 Hz, 2H), 3.88 (d, J = 5.4 Hz, 2H), 3.04 (d, J = 6.4 Hz, 2H). LC-MS m/z [M + H]$^+$: 514. |

-continued

| No. | Compound structure and name | Characterization data |
|---|---|---|
| 199 | 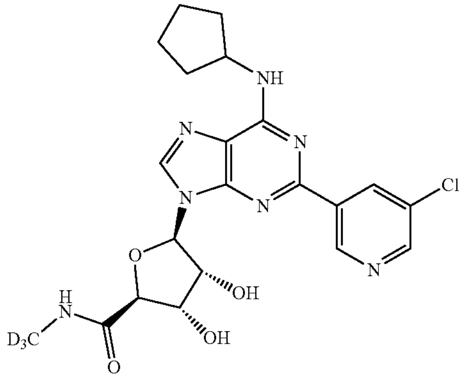 [SMILES: [2H]C([2H])([2H])NC(=O)[C@H]1O[C@@H](n2cnc3c(NC4CCCC4)nc(-c4cncc(Cl)c4)nc32)[C@H](O)[C@@H]1O] (2S,3S,4R,5R)-5-(2-(5-chloropyridin-3-yl)-6-(cyclopentylamino)-9H-purin-9-yl)-3,4-dihydroxyl-N-(methyl-d3)-tetrahydrofuran-2-carboxamide | $^1$H NMR (500 MHz, DMSO-$d_6$) δ: 9.43 (s, 1H), 8.73 (s, 1H), 8.60 (d, J = 18.5 Hz, 2H), 8.10 (s, 1H), 7.95 (s, 1H), 6.09 (d, J = 6.8 Hz, 1H), 4.93-4.85 (m, 1H), 4.67 (s, 1H), 4.34 (dd, J = 12.7, 3.2 Hz, 2H), 2.03 (s, 2H), 1.81-1.53 (m, 6H). LC-MS m/z [M + H]$^+$: 477. |
| 200 | 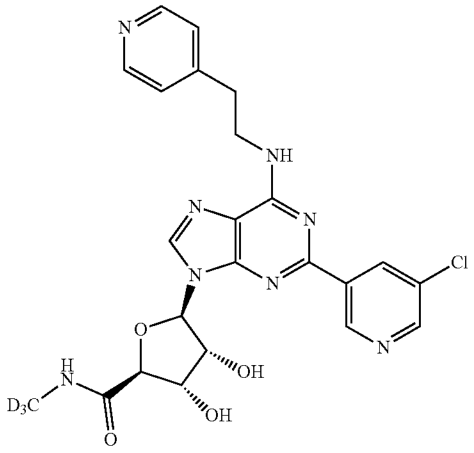 [SMILES: [2H]C([2H])([2H])NC(=O)[C@H]1O[C@@H](n2cnc3c(NCCc4ccncc4)nc(-c4cncc(Cl)c4)nc32)[C@H](O)[C@@H]1O] (2S,3S,4R,5R)-5-(2-(5-chloropyridin-3-yl)-6-((2-(pyridin-4-yl)ethyl)amino)-9H-purin-9-yl)-3,4-dihydroxyl-N-(methyl-d3)-tetrahydrofuran-2-carboxamide | $^1$H NMR (500 MHz, DMSO-$d_6$) δ: 9.49 (s, 1H), 8.79 (d, J = 2.4 Hz, 1H), 8.68 (s, 1H), 8.62 (s, 1H), 8.51 (d, J = 4.3 Hz, 2H), 8.31 (s, 1H), 7.99 (s, 1H), 7.39 (d, J = 4.6 Hz, 2H), 6.16 (d, J = 6.8 Hz, 1H), 5.75 (d, J = 4.7 Hz, 1H), 5.66 (d, J = 6.4 Hz, 1H), 4.94 (dt, J = 11.3, 5.7 Hz, 1H), 4.41 (dd, J = 16.6, 2.3 Hz, 2H), 3.97 (d, J = 5.6 Hz, 2H), 3.11 (t, J = 6.8 Hz, 2H).LC-MS m/z [M + H]$^+$: 514. |
| 201 | 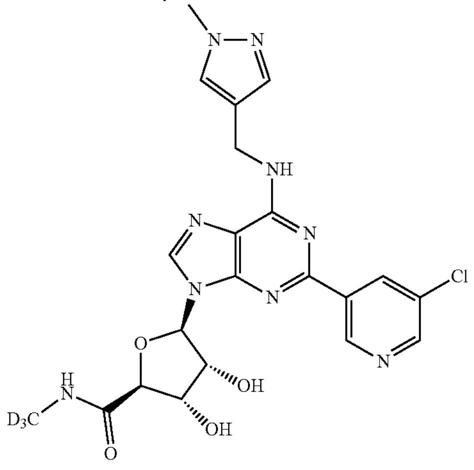 (2S,3S,4R,5R)-5-(2-(5-chloropyridin-3-yl)-6-((((1-methyl-1H-pyrazol-4-yl)methyl)amino)-9H-purin-9-yl)-3,4-dihydroxyl-N-(methyl-d3)-tetrahydrofuran-2-carboxamide | $^1$H NMR (500 MHz, DMSO-$d_6$) δ: 9.46 (s, 1H), 8.72 (t, J = 4.6 Hz, 1H), 8.65 (s, 1H), 8.56 (s, 1H), 8.47 (s, 1H), 7.93 (s, 1H), 7.61 (s, 1H), 7.41 (s, 1H), 6.09 (d, J = 6.6 Hz, 1H), 5.70 (s, 2H), 4.89 (dd, J = 6.6, 4.8 Hz, 1H), 4.64 (s, 2H), 4.33 (dd, J = 9.2, 7.2 Hz, 2H), 3.75 (s, 3H).LC-MS m/z [M + H]$^+$: 503. |

-continued

| No. | Compound structure and name | Characterization data |
| --- | --- | --- |
| 202 | 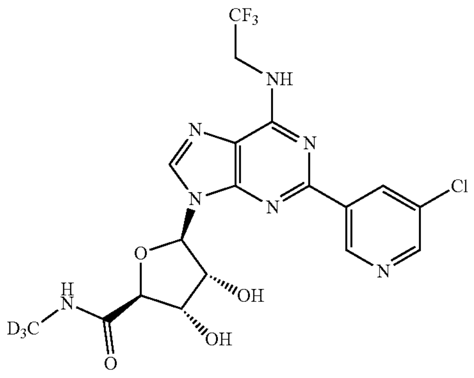 [SMILES: [2H]C([2H])([2H])NC(=O)[C@H]1O[C@@H](n2cnc3c(NCC(F)(F)F)nc(-c4cncc(Cl)c4)nc32)[C@H](O)[C@@H]1O] (2S,3S,4R,5R)-5-(2-(5-chloropyridin-3-yl)-6-(((2,2,2-trifluoroethyl)amino)-9H-purin-9-yl)-3,4-dihydroxyl-N-(methyl-d3)-tetrahydrofuran-2-carboxamide | $^1$H NMR (500 MHz, DMSO-$d_6$) δ: 9.47 (s, 1H), 8.71 (d, J = 25.8 Hz, 4H), 7.96 (s, 1H), 6.13 (d, J = 5.8 Hz, 1H), 5.76 (s, 2H), 4.90 (s, 1H), 4.48 (s, 2H), 4.36 (d, J = 11.5 Hz, 2H). LC-MS m/z [M + H]$^+$: 491. |
| 203 | 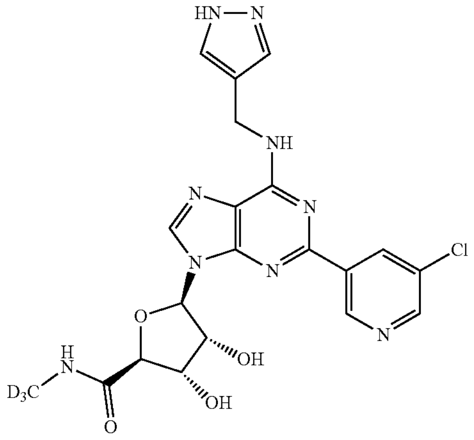 [SMILES: [2H]C([2H])([2H])NC(=O)[C@H]1O[C@@H](n2cnc3c(NCc4cn[nH]c4)nc(-c4cncc(Cl)c4)nc32)[C@H](O)[C@@H]1O] (2S,3S,4R,5R)-5-(6-((((1H-pyrazol-4-yl)methyl)amino)amino)-2-(5-chloropyridin-3-yl)-9H-purin-9-yl)-3,4-dihydroxyl-N-(methyl-d3)-tetrahydrofuran-2-carboxamide | $^1$H NMR (500 MHz, DMSO-$d_6$) δ: 9.47 (s, 2H), 8.86-8.45 (m, 4H), 7.95 (s, 1H), 7.59 (s, 2H), 6.11 (s, 2H), 4.90 (s, 1H), 4.69 (s, 2H), 4.36 (s, 3H). LC-MS m/z [M + H]$^+$: 489. |
| 204 | 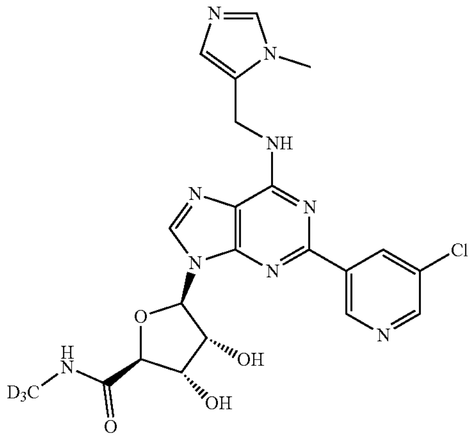 [SMILES: [2H]C([2H])([2H])NC(=O)[C@H]1O[C@@H](n2cnc3c(NCc4cncn4C)nc(-c4cncc(Cl)c4)nc32)[C@H](O)[C@@H]1O] (2S,3S,4R,5R)-5-(2-(5-chloropyridin-3-yl)-6-((((1-methyl-1H-imidazol-5-yl)methyl)amino)-9H-purin-9-yl)-3,4-dihydroxyl-N-(methyl-d3)-tetrahydrofuran-2-carboxamide | $^1$H NMR (500 MHz, DMSO-$d_6$) δ: 9.47 (s, 1H), 8.71 (d, J = 19.6 Hz, 2H), 8.59 (s, 2H), 7.95 (s, 1H), 7.52 (s, 1H), 6.89 (s, 1H), 6.10 (d, J = 6.7 Hz, 1H), 5.72 (s, 2H), 4.87 (dd, J = 18.1, 13.0 Hz, 3H), 4.34 (d, J = 14.7 Hz, 2H), 3.67 (s, 3H). LC-MS m/z [M + H]$^+$: 503. |

-continued

| No. | Compound structure and name | Characterization data |
|---|---|---|
| 205 | 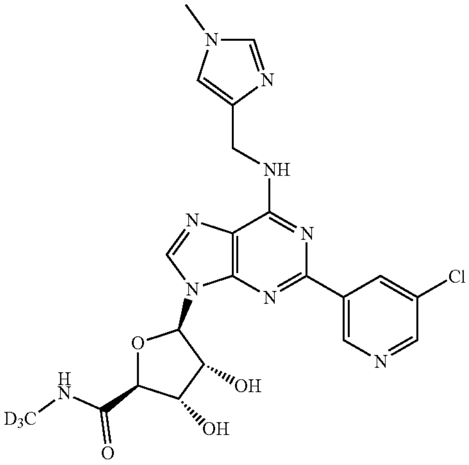 [SMILES: [2H]C([2H])([2H])NC(=O)[C@H]1O[C@@H](n2cnc3c(NCc4cn(C)cn4)nc(-c4cncc(Cl)c4)nc32)[C@H](O)[C@@H]1O] (2S,3S,4R,5R)-5-(2-(5-chloropyridin-3-yl)-6-((((1-methyl-1H-imidazol-4-yl)methyl)amino)-9H-purin-9-yl)-3,4-dihydroxyl-N-(methyl-d3)-tetrahydrofuran-2-carboxamide | $^1$H NMR (500 MHz, DMSO-$d_6$) δ: 9.42 (s, 1H), 8.72 (s, 1H), 8.63 (s, 1H), 8.57 (s, 1H), 8.31 (s, 1H), 7.98 (s, 1H), 7.49 (s, 1H), 6.95 (s, 1H), 6.10 (d, J = 6.6 Hz, 1H), 5.73 (s, 2H), 4.88 (s, 1H), 4.68 (s, 2H), 4.34 (d, J = 18.0 Hz, 2H), 3.57 (s, 3H). LC-MS m/z [M + H]$^+$: 503. |
| 206 | 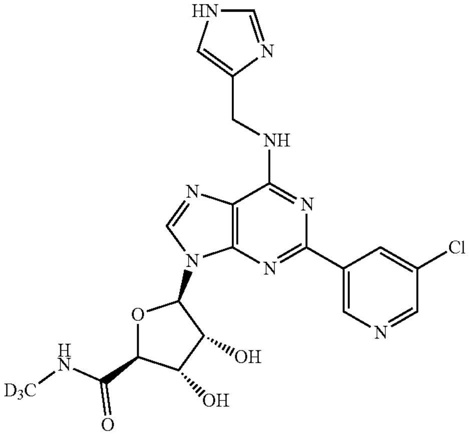 [SMILES: [2H]C([2H])([2H])NC(=O)[C@H]1O[C@@H](n2cnc3c(NCc4c[nH]cn4)nc(-c4cncc(Cl)c4)nc32)[C@H](O)[C@@H]1O] (2S,3S,4R,5R)-5-(6-(((1H-imidazol-4-yl)methyl)amino-2-(5-chloropyridin-3-yl)-9H-purin-9-yl)-3,4-dihydroxyl-N-(methyl-d3)-tetrahydrofuran-2-carboxamide | $^1$H NMR (500 MHz, DMSO-$d_6$) δ: 11.87 (s, 1H), 9.44 (s, 1H), 8.89-8.50 (m, 3H), 8.26 (s, 1H), 7.93 (s, 1H), 7.56 (s, 1H), 6.97 (s, 1H), 6.10 (s, 1H), 5.69 (s, 2H), 4.90-4.74 (m, 3H), 4.35 (s, 2H). LC-MS m/z [M + H]$^+$: 489. |
| 207 | 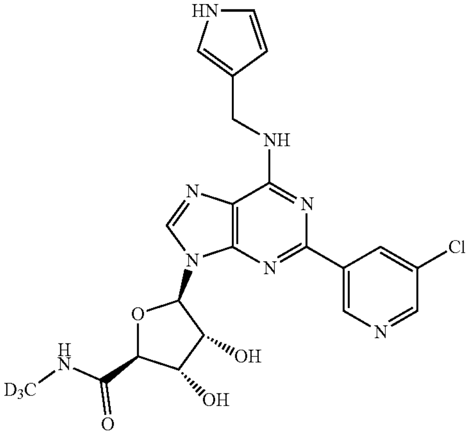 [SMILES: [2H]C([2H])([2H])NC(=O)[C@H]1O[C@@H](n2cnc3c(NCc4cc[nH]c4)nc(-c4cncc(Cl)c4)nc32)[C@H](O)[C@@H]1O] | $^1$H NMR (500 MHz, DMSO-$d_6$) δ: 10.56 (s, 1H), 9.47 (s, 1H), 8.73 (s, 1H), 8.66 (s, 1H), 8.54 (s, 1H), 8.31 (s, 1H), 7.93 (s, 1H), 6.75 (s, 1H), 6.64 (s, 1H), 6.09 (s, 2H), 5.71 (d, J = 4.6 Hz, 1H), 5.61 (d, J = 6.2 Hz, 1H), 4.93-4.88 (m, 1H), 4.64 (s, 2H), 4.34 (d, J = 7.9 Hz, 2H). LC-MS m/z [M + H]$^+$: 488. |

-continued

| No. | Compound structure and name | Characterization data |
|---|---|---|
| | (2S,3S,4R,5R)-5-(6-(((1H-pyrrol-3-yl)methyl)amino-2-(5-chloropyridin-3-yl)-9H-purin-9-yl)-3,4-dihydroxyl-N-(methyl-d3)-tetrahydrofuran-2-carboxamide | |
| 208 | 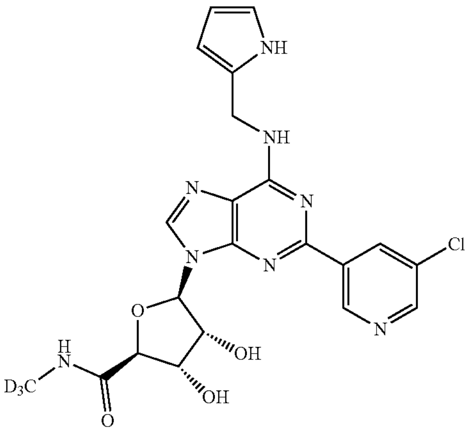 [SMILES: [2H]C([2H])([2H])NC(=O)[C@H]1O[C@@H](n2cnc3c(NCc4ccc[nH]4)nc(-c4cncc(Cl)c4)nc32)[C@H](O)[C@@H]1O] (2S,3S,4R,5R)-5-(6-(((1H-pyrrol-2-yl)methyl)amino-2-(5-chloropyridin-3-yl)-9H-purin-9-yl)-3,4-dihydroxyl-N-D3-methyltetrahydrofuran-2-carboxamide | $^1$H NMR (500 MHz, DMSO-$d_6$) δ: 10.58 (s, 1H), 9.46 (s, 1H), 8.73 (s, 1H), 8.65 (s, 1H), 8.57 (s, 1H), 8.30 (s, 1H), 7.91 (s, 1H), 6.64 (s, 1H), 6.10 (d, J = 6.4 Hz, 1H), 5.99 (s, 1H), 5.91 (s, 1H), 5.69 (d, J = 4.5 Hz, 1H), 5.59 (d, J = 6.3 Hz, 1H), 4.91-4.70 (m, 3H), 4.35 (d, J = 12.3 Hz, 2H). LC-MS m/z [M + H]$^+$: 488. |
| 209 | 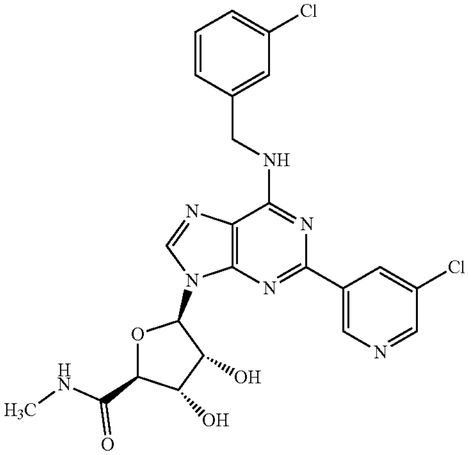 [SMILES: CNC(=O)[C@H]1O[C@@H](n2cnc3c(NCc4cccc(Cl)c4)nc(-c4cncc(Cl)c4)nc32)[C@H](O)[C@@H]1O] (2S,3S,4R,5R)-5-(6-((3-chlorobenzyl))amino-2-(5-chloropyridin-3-yl)-9H-purin-9-yl)-3,4-dihydroxyl-N-methyltetrahydrofuran-2-carboxamide | $^1$H NMR (500 MHz, DMSO-$d_6$) δ: 9.37 (s, 1H), 8.82 (s, 1H), 8.71 (s, 1H), 8.58 (d, J = 21.3 Hz, 2H), 7.96 (s, 1H), 7.51 (s, 1H), 7.44-7.23 (m, 3H), 6.10 (d, J = 4.8 Hz, 1H), 5.71 (s, 2H), 4.84 (d, J = 37.5 Hz, 3H), 4.34 (d, J = 10.5 Hz, 2H), 2.54 (s, 3H). LC-MS m/z [M + H]$^+$: 530. |

-continued

| No. | Compound structure and name | Characterization data |
|---|---|---|
| 210 | 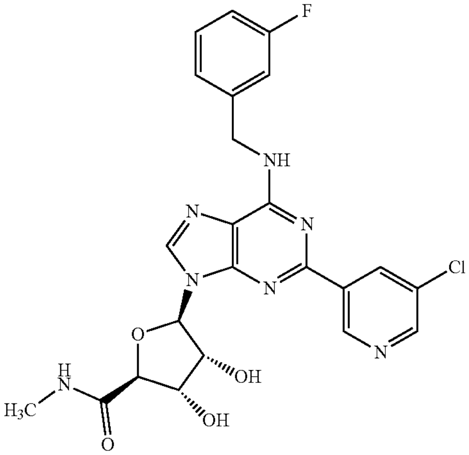 [SMILES: CNC(=O)[C@H]1O[C@@H](n2cnc3c(NCc4cccc(F)c4)nc(-c4cncc(Cl)c4)nc32)[C@H](O)[C@@H]1O] (2S,3S,4R,5R)-5-(2-(5-chloropyridin-3-yl)-6-((3-fluorobenzyl))amino-9H-purin-9-yl)-3,4-dihydroxyl-N-methyltetrahydrofuran-2-carboxamide | $^{1}H$ NMR (500 MHz, DMSO-$d_6$) δ: 9.36 (s, 1H), 8.82 (s, 1H), 8.70 (s, 1H), 8.57 (d, J = 25.1 Hz, 2H), 7.96 (d, J = 4.7 Hz, 1H), 7.37 (dd, J = 14.0, 7.8 Hz, 1H), 7.30-7.21 (m, 2H), 7.05 (t, J = 8.4 Hz, 1H), 6.10 (d, J = 6.9 Hz, 1H), 5.72 (d, J = 4.6 Hz, 1H), 5.62 (d, J = 6.4 Hz, 1H), 4.94-4.73 (m, 3H), 4.39-4.29 (m, 2H), 2.54 (d, J = 4.6 Hz, 3H). LC-MS m/z $[M + H]^+$: 514. |
| 211 | 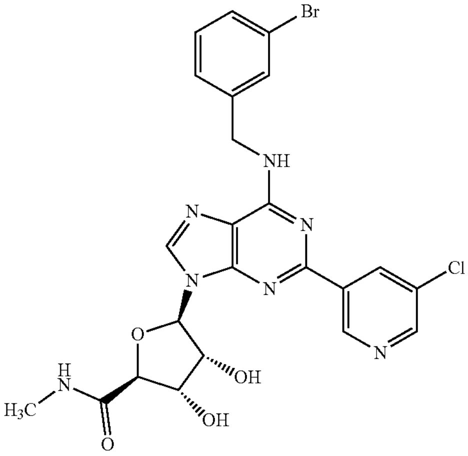 (2S,3S,4R,5R)-5-(6-((3-bromobenzyl))amino-2-(5-chloropyridin-3-yl)-9H-purin-9-yl)-3,4-dihydroxyl-N-methyltetrahydrofuran-2-carboxamide | $^{1}H$ NMR (500 MHz, DMSO-$d_6$) δ: 9.37 (s, 1H), 8.82 (s, 1H), 8.71 (d, J = 2.0 Hz, 1H), 8.58 (d, J = 19.0 Hz, 2H), 7.96 (d, J = 4.8 Hz, 1H), 7.67 (s, 1H), 7.49-7.38 (m, 2H), 7.29 (t, J = 7.8 Hz, 1H), 6.09 (d, J = 6.9 Hz, 1H), 5.72 (d, J = 4.6 Hz, 1H), 5.62 (d, J = 6.3 Hz, 1H), 4.94-4.87 (m, 1H), 4.79 (d, J = 5.3 Hz, 2H), 4.39-4.28 (m, 2H), 2.54 (d, J = 4.5 Hz, 3H). LC-MS m/z $[M + H]^+$: 576. |
| 212 | 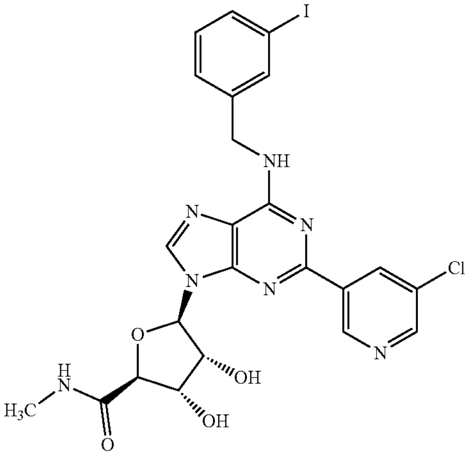 [SMILES: CNC(=O)[C@H]1O[C@@H](n2cnc3c(NCc4cccc(I)c4)nc(-c4cncc(Cl)c4)nc32)[C@H](O)[C@@H]1O] | $^{1}H$ NMR (500 MHz, DMSO-$d_6$) δ: 9.38 (s, 1H), 8.81 (s, 1H), 8.71 (d, J = 2.2 Hz, 1H), 8.58 (d, J = 14.1 Hz, 2H), 7.96 (d, J = 4.7 Hz, 1H), 7.86 (s, 1H), 7.58 (d, J = 7.8 Hz, 1H), 7.46 (d, J = 7.5 Hz, 1H), 7.13 (t, J = 7.8 Hz, 1H), 6.09 (d, J = 6.9 Hz, 1H), 5.72 (d, J = 4.5 Hz, 1H), 5.62 (d, J = 6.3 Hz, 1H), 4.94-4.87 (m, 1H), 4.75 (s, 2H), 4.34 (d, J = 8.1 Hz, 2H), 2.54 (d, J = 4.5 Hz, 3H). LC-MS m/z $[M + H]^+$: 622. |

-continued

| No. | Compound structure and name | Characterization data |
|---|---|---|
| | (2S,3S,4R,5R)-5-(2-(5-chloropyridin-3-yl)-6-((3-iodobenzyl)amino)-9H-purin-9-yl)-3,4-dihydroxyl-N-methyltetrahydrofuran-2-carboxamide | |
| 213 | 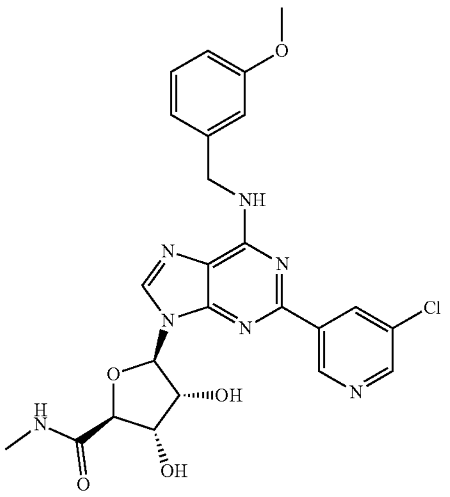 [SMILES: CNC(=O)[C@H]1O[C@@H](n2cnc3c(NCc4cccc(OC)c4)nc(-c4cncc(Cl)c4)nc32)[C@H](O)[C@@H]1O] (2S,3S,4R,5S)-5-(2-(5-chloropyridin-3-yl)-6-((3-methoxybenzyl)amino)-9/-purin-9-yl)-3,4-dihydroxyl-N-methyltetrahydrofuran-2-carboxamide | $^1$H NMR (500 MHz, DMSO-$d_6$) δ 9.38 (d, J = 1.7 Hz, 1H), 8.72 (dd, J = 16.8, 3.8 Hz, 2H), 8.57 (s, 2H), 7.93 (d, J = 4.7 Hz, 1H), 7.22 (t, J = 7.9 Hz, 1H), 7.09-6.96 (m, 2H), 6.84-6.71 (m, 1H), 6.09 (d, J = 6.8 Hz, 1H), 5.68 (d, J = 4.7 Hz, 1H), 5.59 (d, J = 6.4 Hz, 1H), 4.89 (dd, J = 11.2, 6.5 Hz, 1H), 4.77 (s, 2H), 4.41-4.29 (m, 2H), 3.71 (s, 3H), 2.54 (d, J = 4.7 Hz, 3H). LC-MS (m/z): 526.2 [M + H]$^+$. |
| 214 | 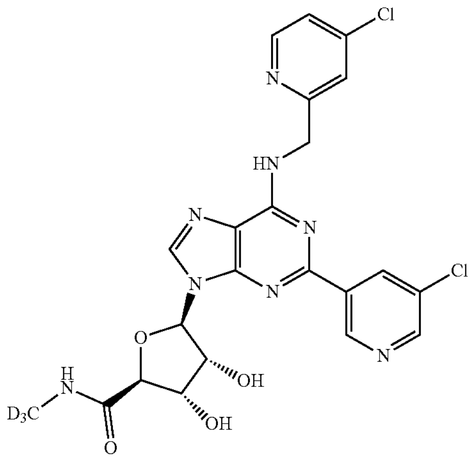 [SMILES: [2H]C([2H])([2H])NC(=O)[C@H]1O[C@@H](n2cnc3c(NCc4cc(Cl)ccn4)nc(-c4cncc(Cl)c4)nc32)[C@H](O)[C@@H]1O] (2S,3S,4R,5R)-5-(6-(((4-chloropyridin-2-yl)methyl)amino-2-(5-chloropyridin-3-yl)-9H-purin-9-yl)-3,4-dihydroxyl-N-(methyl-d3)-tetrahydrofuran-2-carboxamide | $^1$H NMR (500 MHz, DMSO-$d_6$) δ: 9.28 (s, 1H), 8.71 (d, J = 28.2 Hz, 2H), 8.62 (s, 1H), 8.55-8.43 (m, 2H), 7.92 (s, 1H), 7.52 (d, J = 1.5 Hz, 1H), 7.41 (dd, J = 5.3, 1.8 Hz, 1H), 6.10 (d, J = 6.8 Hz, 1H), 5.68 (s, 2H), 4.89 (d, J = 4.7 Hz, 3H), 4.34 (dd, J = 8.2, 6.1 Hz, 2H). |

-continued

| No. | Compound structure and name | Characterization data |
|---|---|---|
| 215 | 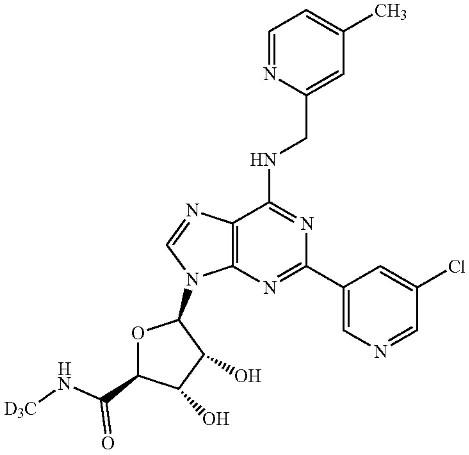 [SMILES: [2H]C([2H])([2H])NC(=O)[C@H]1O[C@@H](n2cnc3c(NCc4cc(C(F)(F)F)ccn4)nc(-c4cncc(Cl)c4)nc32)[C@H](O)[C@@H]1O] (2S,3S,4R,5R)-5-(2-(5-chloropyridin-3-yl)-6-((((4-methylpyridin-2-yl)methyl)amino)-9H-purin-9-yl)-3,4-dihydroxyl-N-(methyl-d3)-tetrahydrofuran-2-carboxamide | 1H NMR (500 MHz, DMSO-d6) δ: 9.30 (s, 1H), 8.65 (d, J = 29.8 Hz, 3H), 8.50 (s, 1H), 8.39 (d, J = 4.6 Hz, 1H), 7.95 (s, 1H), 7.25 (s, 1H), 7.08 (s, 1H), 6.11 (d, J = 6.8 Hz, 1H), 5.71 (s, 2H), 4.87 (d, J = 21.9 Hz, 3H), 4.35 (d, J = 12.9 Hz, 2H), 2.27 (s, 3H). LC-MS m/z [M + H] *: 514. |
| 216 | 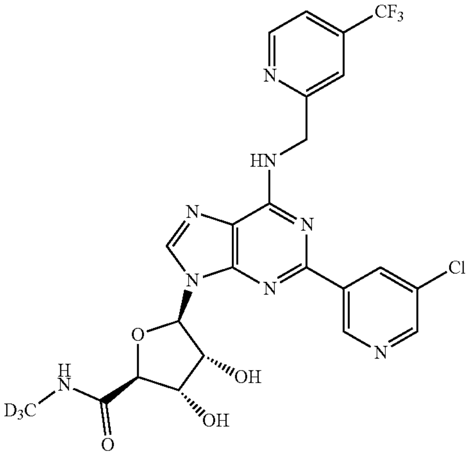 (2S,3S,4R,5R)-5-(2-(5-chloropyridin-3-yl)-6-((((4-(trifluoromethyl)pyridin-2-yl)methyl)amino)-9H-purin-9-yl)-3,4-dihydroxyl-N-(methyl-d3)-tetrahydrofuran-2-carboxamide | $^1$H NMR (500 MHz, DMSO-$d_6$) δ: 9.28 (s, 1H), 8.82 (s, 2H), 8.65 (d, J = 30.7 Hz, 2H), 8.47 (s, 1H), 7.92 (s, 1H), 7.82 (s, 1H), 7.64 (s, 1H), 6.10 (d, J = 5.9 Hz, 1H), 5.67 (s, 2H), 4.99 (s, 2H), 4.88 (s, 1H), 4.35 (d, J = 14.0 Hz, 2H). LC-MS m/z $[M + H]^+$: 568. |
| 217 | 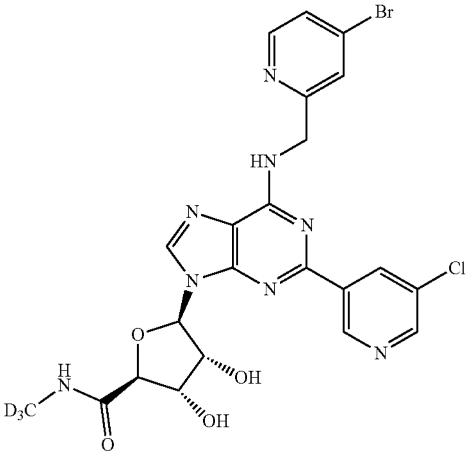 | $^1$H NMR (500 MHz, DMSO-$d_6$) δ: 9.29 (s, 1H), 8.71 (d, J = 24.7 Hz, 2H), 8.61 (s, 1H), 8.49 (s, 1H), 8.43 (d, J = 5.3 Hz, 1H), 7.91 (s, 1H), 7.67 (s, 1H), 7.54 (dd, J = 5.3, 1.7 Hz, 1H), 6.10 (d, J = 6.8 Hz, 1H), 5.75-5.71 (m, 2H), 4.89 (s, 3H), 4.35 (dd, J = 11.7, 3.2 Hz, 2H). LC-MS m/z $[M + H]^+$: 580. |

-continued

| No. | Compound structure and name | Characterization data |
|---|---|---|
| | (2S,3S,4R,5R)-5-(6-(((4-bromopyridin-2-yl)methyl)amino)-2-(5-chloropyridin-3-yl)-9H-purin-9-yl)-3,4-dihydroxyl-N-(methyl-d3)-tetrahydrofuran-2-carboxamide | |
| 218 | 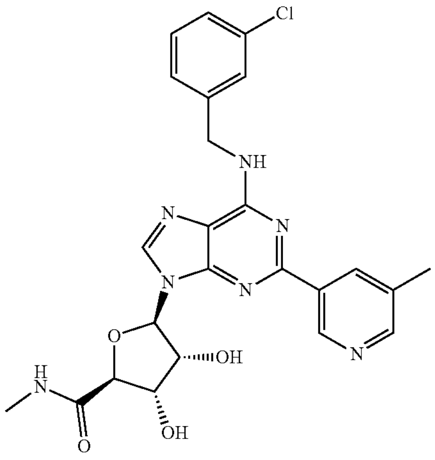 (2S,3S,4R,5S)-5-(6-((3-chlorobenzyl)amino)-2-(5-methylpyridin-3-yl)-9H-purin-9-yl)-3,4-dihydroxyl-N-methyltetrahydrofuran-2-carboxamide | $^1$H NMR (500 MHz, DMSO-$d_6$) δ 9.23 (s, 1H), 8.71 (s, 1H), 8.56 (s, 1H), 8.48 (s, 1H), 8.36 (s, 1H), 7.96 (d, J = 4.7 Hz, 1H), 7.53 (s, 1H), 7.46-7.22 (m, 3H), 6.10 (d, J = 6.9 Hz, 1H), 5.70 (d, J = 4.5 Hz, 1H), 5.60 (d, J = 6.3 Hz, 1H), 4.89 (dd, J = 11.2, 6.4 Hz, 1H), 4.79 (s, 2H), 4.34 (d, J = 6.8 Hz, 2H), 2.53 (d, J = 4.7 Hz, 3H), 2.40 (s, 3H). LC-MS (m/z): 510.3 $[M + H]^+$. |
| 219 | 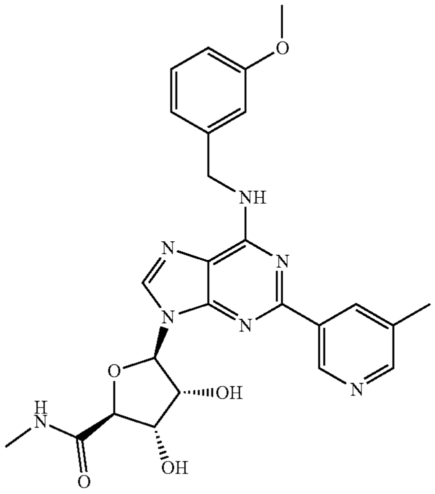 (2S,3S,4R,5S)-3,4-dihydroxyl-5-(6-((3-methoxybenzyl)amino)-2-(5-methylpyridin-3-yl)-9H-purin-9-yl)-N-methyltetrahydrofuran-2-carboxamide | $^1$H NMR (500 MHz, DMSO-$d_6$) δ 9.26 (d, J = 1.7 Hz, 1H), 8.65 (s, 1H), 8.54 (s, 1H), 8.47 (s, 1H), 8.39 (s, 1H), 7.96 (d, J = 4.7 Hz, 1H), 7.23 (t, J = 7.9 Hz, 1H), 7.11-6.95 (m, 2H), 6.79 (dd, J = 8.1, 2.1 Hz, 1H), 6.09 (d, J = 6.9 Hz, 1H), 5.71 (d, J = 4.5 Hz, 1H), 5.60 (d, J = 6.3 Hz, 1H), 4.89 (dd, J = 11.2, 6.5 Hz, 1H), 4.77 (d, J = 4.9 Hz, 2H), 4.38-4.27 (m, 2H), 3.71 (s, 3H), 2.55-2.51 (m, 3H), 2.39 (s, 3H). LC-MS (m/z): 506.3 $[M + H]^+$. |

-continued

| No. | Compound structure and name | Characterization data |
|---|---|---|
| 220 | 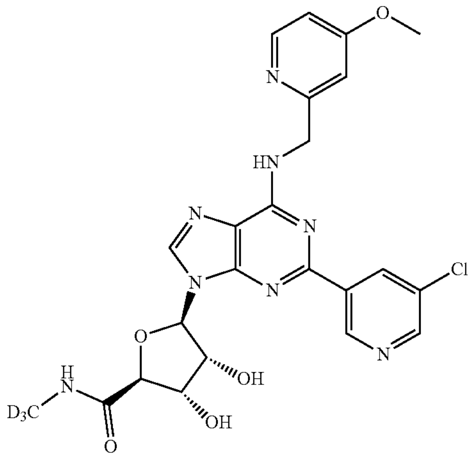 [SMILES: [2H]C([2H])([2H])NC(=O)[C@H]1O[C@@H](n2cnc3c(NCc4cc(OC)ccn4)nc(-c4cncc(Cl)c4)nc32)[C@H](O)[C@@H]1O] (2S,3S,4R,5R)-5-(2-(5-chloropyridin-3-yl)-6-((3-methoxybenzyl)amino)-9H-purin-9-yl)-3,4-dihydroxyl-N-(methyl-d3)-tetrahydrofuran-2-carboxamide | $^1$H NMR (500 MHz, DMSO-$d_6$) δ: 9.33 (s, 1H), 8.87-8.46 (m, 4H), 8.35 (s, 1H), 7.92 (s, 1H), 6.92 (d, J = 71.3 Hz, 2H), 6.10 (s, 1H), 5.74 (s, 2H), 4.86 (d, J = 23.7 Hz, 3H), 4.35 (d, J = 7.6 Hz, 2H), 3.77 (s, 3H). LC-MS m/z [M + H]$^+$: 530. |
| 221 | 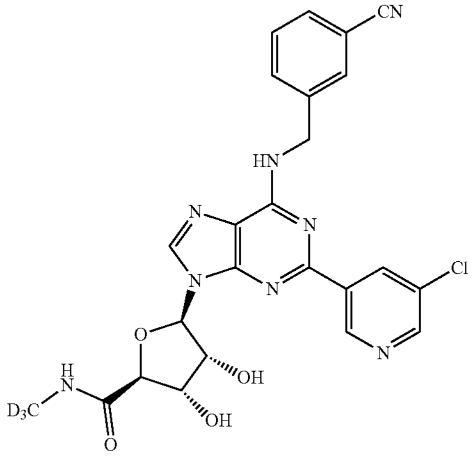 [SMILES: [2H]C([2H])([2H])NC(=O)[C@H]1O[C@@H](n2cnc3c(NCc4cccc(C#N)c4)nc(-c4cncc(Cl)c4)nc32)[C@H](O)[C@@H]1O] (2S,3S,4R,5R)-5-(2-(5-chloropyridin-3-yl)-6-((3-cyanobenzyl)amino)-9H-purin-9-yl)-3,4-dihydroxyl-N-(methyl-d3)-tetrahydrofuran-2-carboxamide | $^1$H NMR (500 MHz, DMSO-$d_6$) δ: 9.35 (s, 1H), 8.81 (s, 1H), 8.70 (s, 1H), 8.61 (s, 1H), 8.52 (s, 1H), 7.91 (d, J = 6.7 Hz, 2H), 7.78 (d, J = 7.7 Hz, 1H), 7.71 (d, J = 7.2 Hz, 1H), 7.54 (t, J = 7.6 Hz, 1H), 6.10 (d, J = 6.7 Hz, 1H), 5.69 (d, J = 4.4 Hz, 1H), 5.59 (d, J = 6.1 Hz, 1H), 4.98-4.74 (m, 3H), 4.35 (d, J = 11.8 Hz, 2H). LC-MS m/z [M + H]$^+$: 524. |
| 222 | 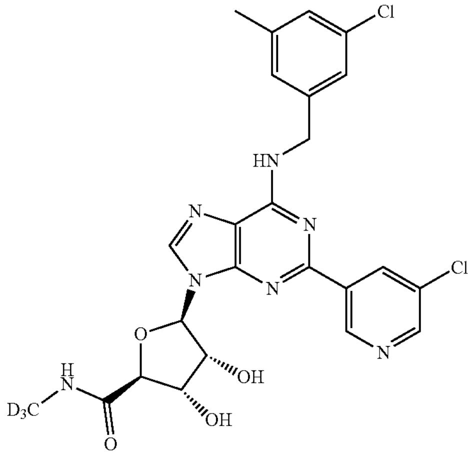 [SMILES: [2H]C([2H])([2H])NC(=O)[C@H]1O[C@@H](n2cnc3c(NCc4cc(C)cc(Cl)c4)nc(-c4cncc(Cl)c4)nc32)[C@H](O)[C@@H]1O] | $^1$H NMR (500 MHz, DMSO-$d_6$) δ: 9.38 (s, 1H), 8.86-8.68 (m, 2H), 8.58 (d, J = 19.9 Hz, 2H), 7.91 (s, 1H), 7.27 (d, J = 20.7 Hz, 2H), 7.12 (s, 1H), 6.10 (d, J = 6.8 Hz, 1H), 5.74 (d, J = 16.6 Hz, 2H), 4.89 (dd, J = 6.7, 4.8 Hz, 1H), 4.75 (s, 2H), 4.46-4.30 (m, 2H), 2.29 (s, 3H). LC-MS m/z [M + H]$^+$: 547. |

-continued

| No. | Compound structure and name | Characterization data |
| --- | --- | --- |
| | (2S,3S,4R,5R)-5-(6-((3-chloro-5-methylbenzyl)amino)-2-(5-chloropyridin-3-yl)-9H-purin-9-yl)-3,4-dihydroxyl-N-(methyl-d3)-tetrahydrofuran-2-carboxamide | |
| 223 | 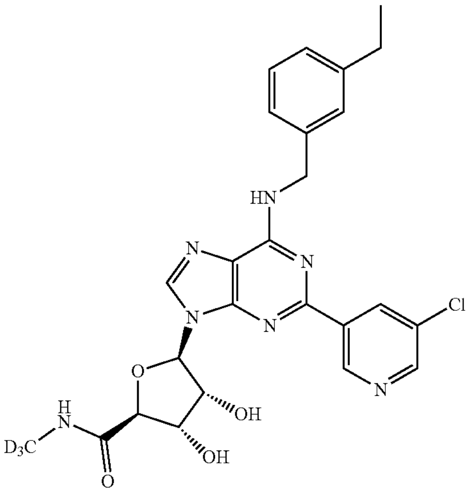 [SMILES: [2H]C([2H])([2H])NC(=O)[C@H]1O[C@@H](n2cnc3c(NCc4cccc(CC)c4)nc(-c4cncc(Cl)c4)nc32)[C@H](O)[C@@H]1O] (2S,3S,4R,5R)-5-(2-(5-chloropyridin-3-yl)-6-((3-ethylbenzyl)amino)-9H-purin-9-yl)-3,4-dihydroxyl-N-(methyl-d3)-tetrahydrofuran-2-carboxamide | $^1$H NMR (500 MHz, DMSO-$d_6$) δ: 9.38 (d, J = 1.5 Hz, 1H), 8.85-8.68 (m, 2H), 8.57 (s, 2H), 7.91 (s, 1H), 7.34 (s, 1H), 7.23 (dt, J = 14.8, 7.5 Hz, 2H), 7.06 (d, J = 7.0 Hz, 1H), 6.09 (d, J = 6.8 Hz, 1H), 5.68 (d, J = 4.7 Hz, 1H), 5.58 (d, J = 6.4 Hz, 1H), 4.89 (dd, J = 11.3, 6.5 Hz, 1H), 4.77 (s, 2H), 4.42-4.29 (m, 2H), 2.58 (dd, J = 15.2, 7.6 Hz, 2H), 1.15 (t, J = 7.6 Hz, 3H). LC-MS m/z [M + H]$^+$: 527. |
| 224 | 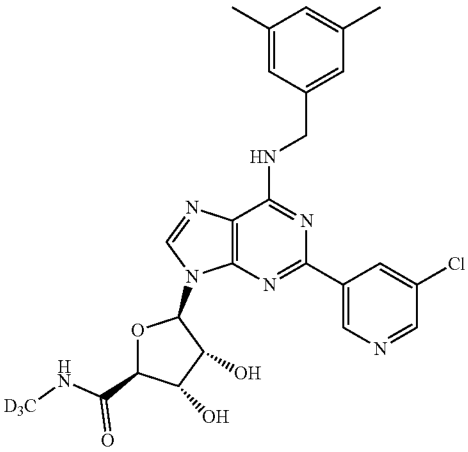 [SMILES: [2H]C([2H])([2H])NC(=O)[C@H]1O[C@@H](n2cnc3c(NCc4cc(C)cc(C)c4)nc(-c4cncc(Cl)c4)nc32)[C@H](O)[C@@H]1O] (2S,3S,4R,5R)-5-(2-(5-chloropyridin-3-yl)-6-((3,5-dimethylbenzyl)amino)-9H-purin-9-yl)-3,4-dihydroxyl-N-(methyl-d3)-tetrahydrofuran-2-carboxamide | $^1$H NMR (500 MHz, DMSO-$d_6$) δ: 9.38 (s, 1H), 8.70 (s, 2H), 8.57 (s, 2H), 7.90 (s, 1H), 7.06 (s, 2H), 6.85 (s, 1H), 6.09 (d, J = 6.7 Hz, 1H), 5.59 (s, 2H), 4.89 (d, J = 4.5 Hz, 1H), 4.70 (s, 2H), 4.45-4.29 (m, 2H), 2.23 (s, 6H). LC-MS m/z [M + H]$^+$: 527. |

-continued

| No. | Compound structure and name | Characterization data |
|---|---|---|
| 225 | 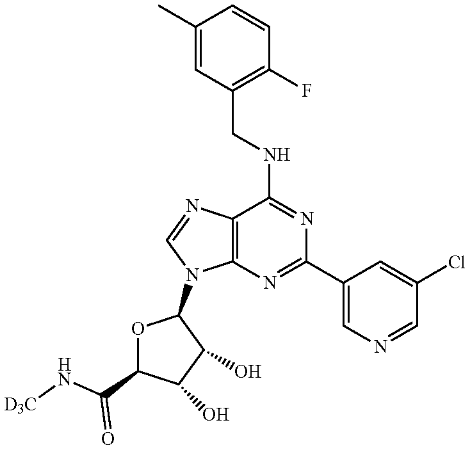<br>(2S,3S,4R,5R)-5-(2-(5-chloropyridin-3-yl)-6-((2-fluoro-5-methylbenzyl)amino)-9H-purin-9-yl)-3,4-dihydroxyl-N-(methyl-d3)-tetrahydrofuran-2-carboxamide | $^1$H NMR (500 MHz, DMSO-$d_6$) δ: 9.30 (s, 1H), 8.58 (d, J = 57.3 Hz, 4H), 7.85 (s, 1H), 7.23 (s, 1H), 7.00 (d, J = 7.6 Hz, 2H), 6.03 (s, 1H), 5.61 (s, 2H), 4.77 (d, J = 42.0 Hz, 3H), 4.28 (d, J = 12.2 Hz, 2H), 2.14 (s, 3H). LC-MS m/z [M + H]$^+$: 531. |
| 226 | 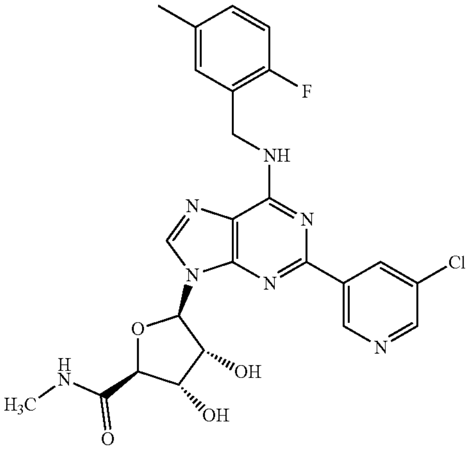<br>(2S,3S,4R,5R)-5-(2-(5-chloropyridin-3-yl)-6-((2-fluoro-5-methylbenzyl)amino)-9H-purin-9-yl)-3,4-dihydroxyl-N-methyltetrahydrofuran-2-carboxamide | $^1$H NMR (500 MHz, DMSO-$d_6$) δ: 9.30 (s, 1H), 8.64 (d, J = 11.6 Hz, 2H), 8.51 (s, 2H), 7.86 (d, J = 4.6 Hz, 1H), 7.22 (d, J = 6.4 Hz, 1H), 6.99 (d, J = 7.8 Hz, 2H), 6.02 (d, J = 6.8 Hz, 1H), 5.53 (s, 2H), 4.91-4.63 (m, 3H), 4.27 (dd, J = 11.7, 3.2 Hz, 2H), 2.48 (d, J = 4.6 Hz, 3H), 2.14 (s, 3H). LC-MS m/z [M + H]$^+$: 528. |
| 227 | 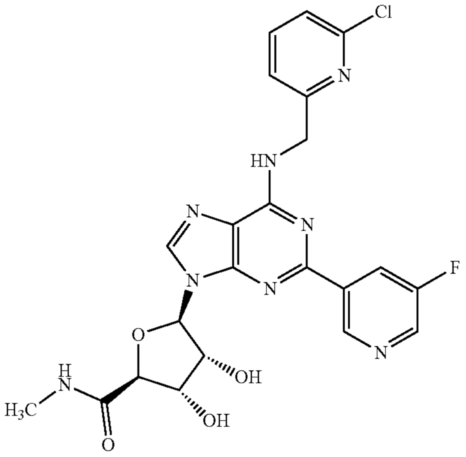 [SMILES: CNC(=O)[C@H]1O[C@@H](n2cnc3c(NCc4cccc(Cl)n4)nc(-c4cncc(F)c4)nc32)[C@H](O)[C@@H]1O] | $^1$H NMR (500 MHz, DMSO-$d_6$) δ: 9.34 (s, 1H), 8.72 (s, 1H), 8.60 (d, J = 14.8 Hz, 2H), 8.51 (d, J = 6.8 Hz, 1H), 7.95 (d, J = 4.4 Hz, 1H), 7.79 (t, J = 7.8 Hz, 1H), 7.47 (s, 1H), 7.38 (dd, J = 13.1, 7.8 Hz, 2H), 6.10 (d, J = 6.9 Hz, 1H), 5.71 (d, J = 4.3 Hz, 1H), 5.62 (d, J = 6.2 Hz, 1H), 4.88 (d, J = 22.4 Hz, 3H), 4.35 (s, 2H), 2.53 (d, J = 4.6 Hz, 3H). LC-MS m/z [M + H]$^+$: 497. |

-continued

| No. | Compound structure and name | Characterization data |
|---|---|---|
| | (2S,3S,4R,5R)-5-(6-(((6-chloropyridin-2-yl)methyl)amino)-2-(5-fluoropyridin-3-yl)-9H-purin-9-yl)-3,4-dihydroxyl-N-methyltetrahydrofuran-2-carboxamide | |
| 228 | 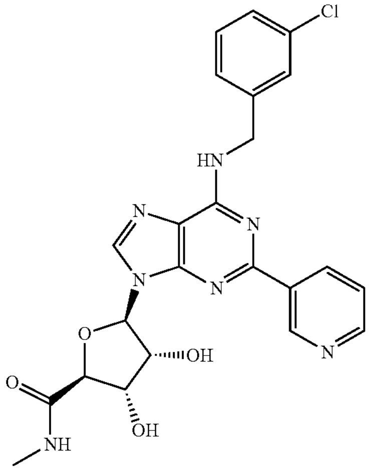 [SMILES: CNC(=O)[C@H]1O[C@@H](n2cnc3c(NCc4cccc(Cl)c4)nc(-c4cccnc4)nc32)[C@H](O)[C@@H]1O] (2S,3S,4R,5R)-5-(6-((3-chlorobenzyl)amino)-2-(pyridin-3-yl)-9H-purin-9-yl)-3,4-dihydroxyl-N-methyltetrahydrofuran-2-carboxamide | $^1$H NMR (500 MHz, DMSO-$d_6$) δ: 9.44 (s, 1H), 8.72 (s, 1H), 8.64 (d, J = 3.5 Hz, 1H), 8.63-8.49 (m, 2H), 7.94 (d, J = 4.5 Hz, 1H), 7.51 (d, J = 12.1 Hz, 2H), 7.42 (d, J = 7.3 Hz, 1H), 7.35 (t, J = 7.7 Hz, 1H), 7.29 (d, J = 7.5 Hz, 1H), 6.10 (d, J = 6.8 Hz, 1H), 5.70 (d, J = 4.2 Hz, 1H), 5.60 (d, J = 6.2 Hz, 1H), 4.91 (d, J = 4.6 Hz, 1H), 4.82 (s, 2H), 4.35 (s, 2H), 2.53 (d, J = 4.8 Hz, 3H). LC-MS m/z [M + H]$^+$: 496. |
| 229 | 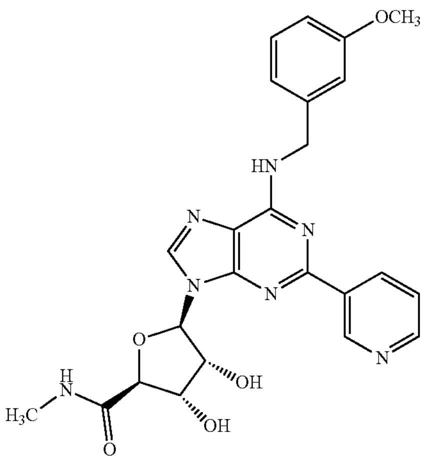 [SMILES: CNC(=O)[C@H]1O[C@@H](n2cnc3c(NCc4cccc(OC)c4)nc(-c4cccnc4)nc32)[C@H](O)[C@@H]1O] (2S,3S,4R,5R)-3,4-dihydroxyl-5-(6-((3-methoxybenzyl)amino)-2-(pyridin-3-yl)-9H-purin-9-yl)-N-methyltetrahydrofuran-2-carboxamide | $^1$H NMR (500 MHz, DMSO-$d_6$) δ: 9.45 (d, J = 1.6 Hz, 1H), 8.70-8.62 (m, 2H), 8.60 (dd, J = 7.9, 1.8 Hz, 1H), 8.54 (s, 1H), 7.94 (d, J = 4.6 Hz, 1H), 7.50 (dd, J = 7.8, 4.8 Hz, 1H), 7.22 (t, J = 7.9 Hz, 1H), 7.08-6.98 (m, 2H), 6.82-6.74 (m, 1H), 6.09 (d, J = 6.9 Hz, 1H), 5.69 (d, J = 4.5 Hz, 1H), 5.59 (d, J = 6.3 Hz, 1H), 4.90 (dd, J = 11.0, 6.5 Hz, 1H), 4.78 (s, 2H), 4.38-4.29 (m, 2H), 3.70 (s, 3H), 2.52 (d, J = 4.7 Hz, 3H). LC-MS m/z [M + H]$^+$: 492. |

-continued

| No. | Compound structure and name | Characterization data |
|---|---|---|
| 230 | 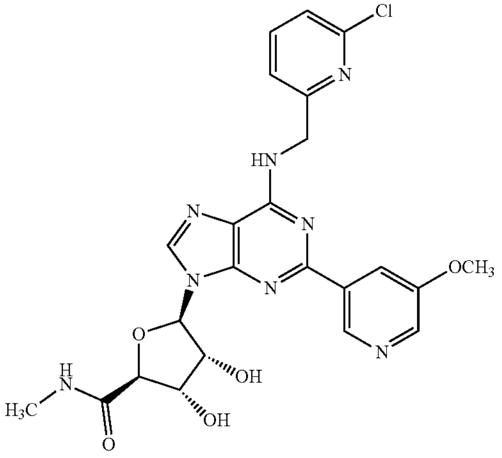 [SMILES: CNC(=O)[C@H]1O[C@@H](n2cnc3c(NCc4cccc(Cl)n4)nc(-c4cncc(OC)c4)nc32)[C@H](O)[C@@H]1O]<br>(2S,3S,4R,5R)-5-(6-(((6-chloropyridin-2-yl)methyl)amino)-2-(5-methoxypyridin-3-ly)-9H-purin-9-yl)-3,4-dihydroxyl-N-methyltetrahydrofuran-2-carboxamide | $^1$H NMR (500 MHz, DMSO-$d_6$) δ: 8.89 (s, 1H), 8.69 (d, J = 11.8 Hz, 1H), 8.51 (s, 1H), 8.26 (s, 1H), 7.88 (dd, J = 10.6, 6.0 Hz, 2H), 7.72 (t, J = 7.8 Hz, 1H), 7.31 (dd, J = 13.6, 7.7 Hz, 2H), 6.02 (d, J = 6.8 Hz, 1H), 5.63 (d, J = 4.7 Hz, 1H), 5.55 (d, J = 6.3 Hz, 1H), 4.86 (d, J = 4.9 Hz, 1H), 4.77 (d, J = 4.8 Hz, 2H), 4.28 (s, 2H), 3.81 (s, 3H), 2.45 (s, 3H). LC-MS m/z [M + H]$^+$: 527. |
| 231 | 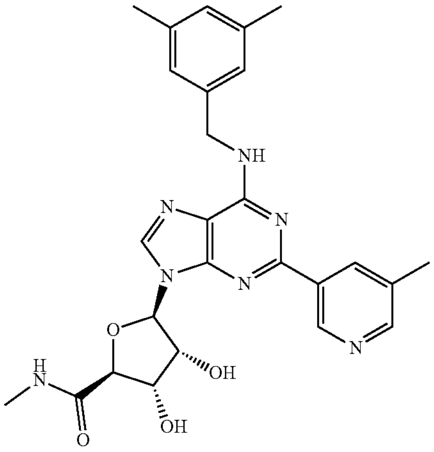<br>(2S,3S,4R,5R)-5-(6-((3,5-dimethylbenzyl)amino)-2-(5-methylpyridin-3-yl)-9H-purin-9-yl)-3,4-dihydroxyl-N-methyltetrahydrofuran-2-carboxamide | $^1$H NMR (500 MHz, DMSO-$d_6$) δ: 9.25 (s, 1H), 8.59 (s, 1H), 8.53 (s, 1H), 8.47 (s, 1H), 8.38 (s, 1H), 7.95 (d, J = 4.7 Hz, 1H), 7.06 (s, 2H), 6.84 (s, 1H), 6.09 (d, J = 6.9 Hz, 1H), 5.70 (d, J = 4.5 Hz, 1H), 5.59 (d, J = 6.3 Hz, 1H), 4.89 (dd, J = 11.3, 6.5 Hz, 1H), 4.71 (s, 2H), 4.41-4.30 (m, 2H), 2.52 (d, J = 4.7 Hz, 3H), 2.40 (s, 3H), 2.23 (s, 6H). LC-MS m/z [M + H]$^+$: 504. |
| 232 | 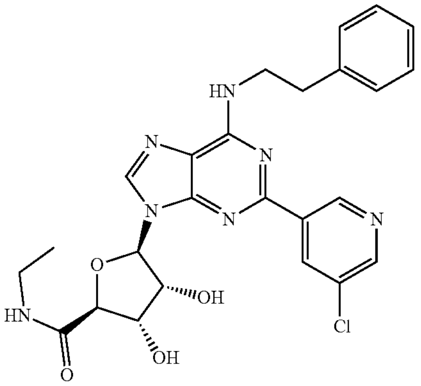 [SMILES: CCNC(=O)[C@H]1O[C@@H](n2cnc3c(NCCc4ccccc4)nc(-c4cncc(Cl)c4)nc32)[C@H](O)[C@@H]1O]<br>(2S,3S,4R,5R)-5-(2-(5-chloropyridin-3-yl)-6-(phenethylamino)-9H-purin-9-yl)-N-ethyl-3,4-dihydroxyltetrahydrofuran-2-carboxamide | $^1$H NMR (500 MHz, DMSO-$d_6$): δ. 9.44 (s, 1H), 8.73 (s, 1H), 8.64 (s, 1H), 8.56 (s, 1H), 8.22 (d, 1H), 8.00 (s, 1H), 7.32 (m, 4H), 7.19 (d, 1H), 6.12 (d, 1H), 5.66 (d, 1H), 5.60 (d, 1H), 4.86 (d, 1H), 4.35 (s, 1H), 4.32 (t, 1H), 3.84 (t, 2H), 3.15 (m, 1H), 3.00 (t, 3H), 0.91 (t, 3H). |

-continued

| No. | Compound structure and name | Characterization data |
|---|---|---|
| 233 | 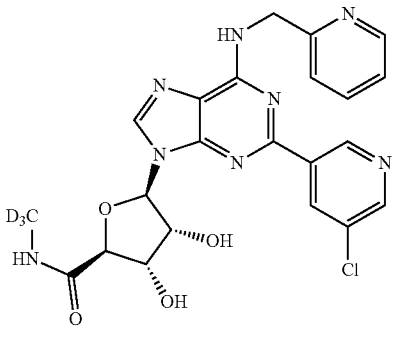 [SMILES: [2H]C([2H])([2H])NC(=O)[C@H]1O[C@@H](n2cnc3c(NCc4ccccn4)nc(-c4cncc(Cl)c4)nc32)[C@H](O)[C@@H]1O]<br>(2S,3S,4R,5R)-5-(2-(5-chloropyridin-3-yl)-6-(pyridin-2-methylamino)-9H-purin-9-yl)-3,4-dihydroxyl-N-(methyl-d3)-tetrahydrofuran-2-carboxamide | $^1$H NMR (500 MHz, DMSO-$d_6$): δ. 9.28 (s, 1H), 8.69 (s, 1H), 8.67 (s, 1H), 8.60 (s, 1H), 8.54 (d, 1H), 8.47 (s, 1H), 7.91 (s, 1H), 7.72 (d, 1H), 7.40 (d, 2H), 7.25 (t, 1H), 6.11 (d, 1H), 5.69 (d, 1H), 5.60 (d, 1H), 4.90 (d, 2H), 4.35 (s, 1H), 4.33 (s, 1H). |
| 234 | 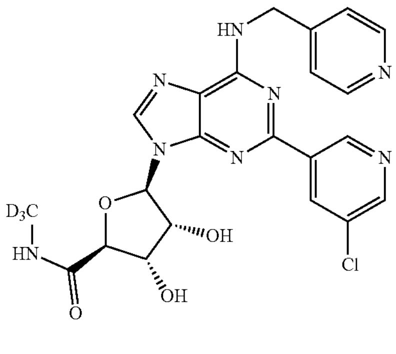 [SMILES: [2H]C([2H])([2H])NC(=O)[C@H]1O[C@@H](n2cnc3c(NCc4ccncc4)nc(-c4cncc(Cl)c4)nc32)[C@H](O)[C@@H]1O]<br>(2S,3S,4R,5R)-5-(2-(5-chloropyridin-3-yl)-6-(pyridin-4-ylmethylamino)-9H-purin-9-yl)-3,4-dihydroxyl-N-(methyl-d3)-tetrahydrofuran-2-carboxamide | $^1$H NMR (500 MHz, DMSO-$d_6$): δ. 9.29 (s, 1H), 8.82 (s, 1H), 8.68 (s, 1H), 8.61 (s, 1H), 8.50 (dd, 3H), 7.91 (s, 1H), 7.41 (d, 2H), 6.11 (d, 1H), 5.69 (d, 1H), 5.60 (d, 1H), 4.89 (q, 1H), 4.83 (d, 2H), 4.36 (d, 1H), 4.33 (m, 1H). |
| 235 | 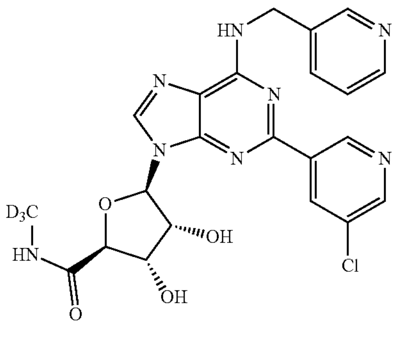 [SMILES: [2H]C([2H])([2H])NC(=O)[C@H]1O[C@@H](n2cnc3c(NCc4cccnc4)nc(-c4cncc(Cl)c4)nc32)[C@H](O)[C@@H]1O]<br>(2S,3S,4R,5R)-5-(2-(5-chloropyridin-3-yl)-6-(pyridin-3-ylmethylamino)-9H-purin-9-yl)-3,4-dihydroxyl-N-(methyl-d3)-tetrahydrofuran-2-carboxamide | $^1$H NMR (500 MHz, DMSO-$d_6$): δ. 9.38 (d, 1H), 8.79 (s, 1H), 8.71 (d, 1H), 8.68 (s, 1H), 8.59 (s, 1H), 8.57 (s, 1H), 8.43 (d, 1H), 7.90 (s, 1H), 7.84 (d, 1H), 7.34 (q, 1H), 6.10 (d, 1H), 5.69 (d, 1H), 5.60 (d, 1H), 4.89 (q, 1H), 4.83 (s, 2H), 4.36 (d, 1H), 4.33 (m, 1H). |

-continued

| No. | Compound structure and name | Characterization data |
|---|---|---|
| 236 | 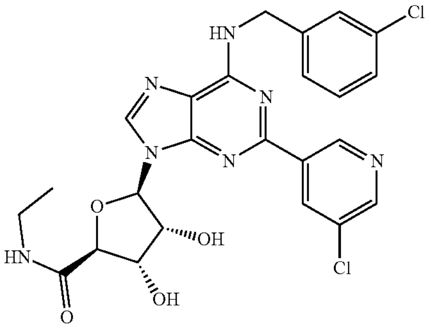 (2S,3S,4R,5R)-5-(6-(3-chlorobenzylamino)-2-(5-chloropyridin-3-yl)-9H-purin-9-yl)-N-ethyl-3,4-dihydroxyltetrahydrofuran-2-carboxamide | $^1$H NMR (500 MHz, DMSO-$d_6$): δ. 9.37 (s, 1H), 8.83 (t, 1H), 8.70 (d, 1H), 8.61 (s, 1H), 8.56 (s, 1H), 8.02 (t, 1H), 7.51 (s, 1H), 7.35 (m, 3H), 6.10 (d, 1H), 5.70 (d, 1H), 5.62 (d, 1H), 4.86 (q, 1H), 4.79 (d, 1H), 4.34 (m, 2H), 3.13 (m, 1H), 2.99 (m, 1H), 0.90 (t, 3H). |
| 237 | 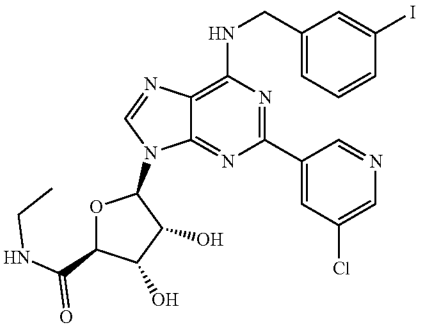 [SMILES: CCNC(=O)[C@H]1O[C@@H](n2cnc3c(NCc4cccc(I)c4)nc(-c4cncc(Cl)c4)nc32)[C@H](O)[C@@H]1O] (2S,3S,4R,5R)-5-(2-(5-chloropyridin-3-yl)-6-(3-iodobenzylamino)-9H-purin-9-yl)-N-ethyl-3,4-dihydroxyltetrahydrofuran-2-carboxamide | $^1$H NMR (500 MHz, DMSO-$d_6$): δ. 9.38 (d, 1H), 8.81 (t, 1H), 8.71 (d, 1H), 8.61 (s, 1H), 8.57 (s, 1H), 8.02 (t, 1H), 7.86 (s, 1H), 7.57 (d, 1H), 7.45 (d, 1H), 7.13 (t, 1H), 6.10 (d, 1H), 5.70 (d, 1H), 5.62 (d, 1H), 4.86 (q, 1H), 4.74 (d, 1H), 4.34 (m, 2H), 3.13 (m, 1H), 2.99 (m, 1H), 0.90 (t, 3H). |
| 238 | 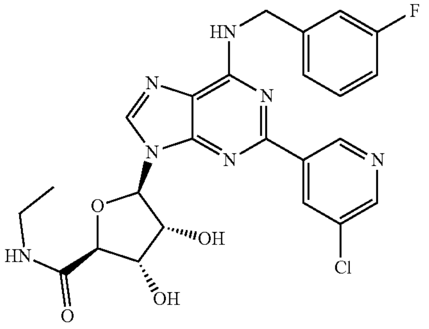 [SMILES: CCNC(=O)[C@H]1O[C@@H](n2cnc3c(NCc4cccc(F)c4)nc(-c4cncc(Cl)c4)nc32)[C@H](O)[C@@H]1O] (2S,3S,4R,5R)-5-(2-(5-chloropyridin-3-yl)-6-(3-fluorobenzylamino)-9H-purin-9-yl)-N-ethyl-3,4-dihydroxyltetrahydrofuran-2-carboxamide | 1H NMR (500 MHz, DMSO-d6): δ. 9.36 (d, 1H), 8.82 (t, 1H), 8.71 (d, 1H), 8.61 (s, 1H), 8.55 (s, 1H), 8.02 (t, 1H), 7.37 (m, 1H), 7.25 (m, 2H), 7.05 (t, 1H), 6.10 (d, 1H), 5.70 (d, 1H), 5.62 (d, 1H), 4.86 (m, 3H), 4.34 (m, 2H), 3.13 (m, 1H), 2.99 (m, 1H), 0.90 (t, 3H). |

-continued

| No. | Compound structure and name | Characterization data |
|---|---|---|
| 239 | 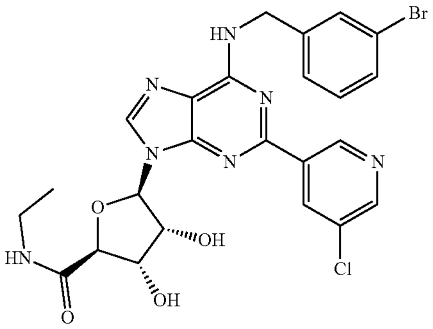 [SMILES: CCNC(=O)[C@H]1O[C@@H](n2cnc3c(NCc4cccc(Br)c4)nc(-c4cncc(Cl)c4)nc32)[C@H](O)[C@@H]1O] (2S,3S,4R,5R)-5-(6-(3-bromobenzylamino)-2-(5-chloropyridin-3-yl)-9H-purin-9-yl)-N-ethyl-3,4-dihydroxyltetrahydrofuran-2-carboxamide | $^1$H NMR (500 MHz, DMSO-$d_6$): δ. 9.38 (d, 1H), 8.82 (t, 1H), 8.71 (d, 1H), 8.62 (s, 1H), 8.57 (s, 1H), 8.02 (t, 1H), 7.66 (s, 1H), 7.44 (t, 1H), 7.29 (t, 1H), 6.10 (d, 1H), 5.70 (d, 1H), 5.62 (d, 1H), 4.86 (q, 1H), 4.80 (d, 2H), 4.34 (m, 2H), 3.14 (m, 1H), 2.99 (m, 1H), 0.90 (t, 3H). |
| 240 | 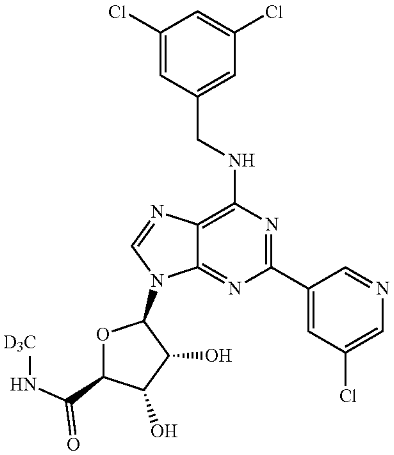 (2S,3S,4R,5R)-5-(2-(5-chloropyridin-3-yl)-6-(3,5-dichlorobenzylamino)-9H-purin-9-yl)-3,4-dihydroxyl-N-(methyl-d3)-tetrahydrofuran-2-carboxamide | $^1$H NMR (500 MHz, DMSO-$d_6$): δ. 9.37 (d, 1H), 8.84 (t, 1H), 8.71 (d, 1H), 8.62 (s, 1H), 8.56 (s, 1H), 7.93 (s, 1H), 7.52 (s, 2H), 7.47 (s, 1H), 6.09 (d, 1H), 5.72 (d, 1H), 5.61 (d, 1H), 4.90 (q, 1H), 4.79 (d, 1H), 4.34 (m, 2H). |
| 241 | 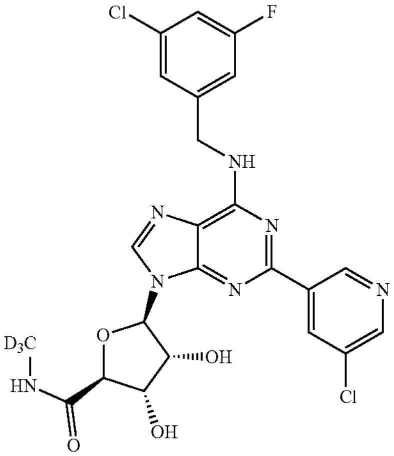 [SMILES: [2H]C([2H])([2H])NC(=O)[C@H]1O[C@@H](n2cnc3c(NCc4cc(F)cc(Cl)c4)nc(-c4cncc(Cl)c4)nc32)[C@H](O)[C@@H]1O] (2S,3S,4R,5R)-5-(6-(3-chloro-5-fluorobenzylamino)-2-(5-chloropyridin-3-yl)-9H-purin-9-yl)-3,4-dihydroxyl-N-(methyl-d3)-tetrahydrofuran-2-carboxamide | $^1$H NMR (500 MHz, DMSO-$d_6$): δ. 9.37 (d, 1H), 8.84 (t, 1H), 8.71 (d, 1H), 8.62 (s, 1H), 8.55 (s, 1H), 7.93 (s, 1H), 7.39 (s, 1H), 7.28 (d, 2H), 6.09 (d, 1H), 5.72 (d, 1H), 5.61 (d, 1H), 4.90 (q, 1H), 4.80 (d, 1H), 4.34 (m, 2H). |

-continued

| No. | Compound structure and name | Characterization data |
|---|---|---|
| 242 | 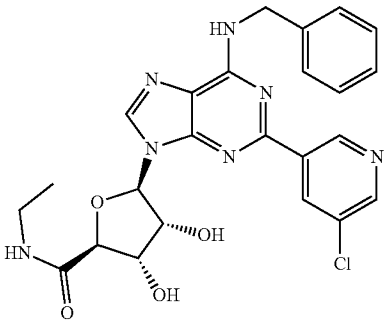 [SMILES: CCNC(=O)[C@H]1O[C@@H](n2cnc3c(NCc4ccccc4)nc(-c4cncc(Cl)c4)nc32)[C@H](O)[C@@H]1O] (2S,3S,4R,5R)-5-(6-(benzylamino)-2-(5-chloropyridin-3-yl)-9H-purin-9-yl)-N-ethyl-3,4-dihydroxyltetrahydrofuran-2-carboxamide | $^1H$ NMR (500 MHz, DMSO-$d_6$): δ. 9.37 (s, 1H), 8.80 (t, 1H), 8.71 (d, 1H), 8.60 (s, 1H), 8.56 (s, 1H), 8.03 (t, 1H), 7.45 (d, 2H), 7.31 (t, 2H), 7.23 (t, 1H), 6.10 (d, 1H), 5.70 (d, 1H), 5.62 (d, 1H), 4.86 (q, 1H), 4.80 (d, 2H), 4.34 (m, 2H), 3.14 (m, 1H), 2.99 (m, 1H), 0.90 (t, 3H). |
| 243 | 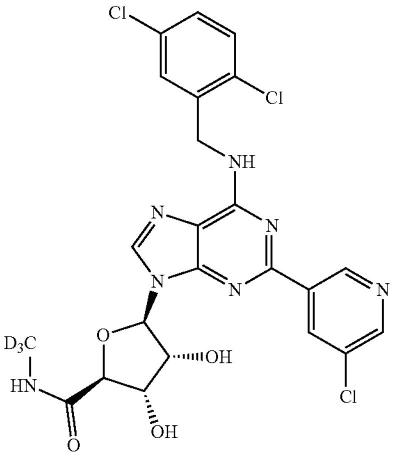 [SMILES: [2H]C([2H])([2H])NC(=O)[C@H]1O[C@@H](n2cnc3c(NCc4cc(Cl)ccc4Cl)nc(-c4cncc(Cl)c4)nc32)[C@H](O)[C@@H]1O] (2S,3S,4R,5R)-5-(2-(5-chloropyridin-3-yl)-6-(2,5-dichlorobenzylamino)-9H-purin-9-yl)-3,4-dihydroxyl-N-((methyl-d3))-tetrahydrofuran-2-carboxamide | $^1H$ NMR (500 MHz, DMSO-$d_6$): δ. 9.32 (d, 1H), 8.88 (t, 1H), 8.70 (d, 1H), 8.64 (s, 1H), 8.54 (s, 1H), 7.94 (s, 1H), 7.55 (d, 1H), 7.49 (d, 1H), 7.37 (dd, 1H), 6.10 (d, 1H), 5.72 (d, 1H), 5.62 (d, 1H), 4.90 (m, 3H), 4.34 (m, 2H). |
| 244 | 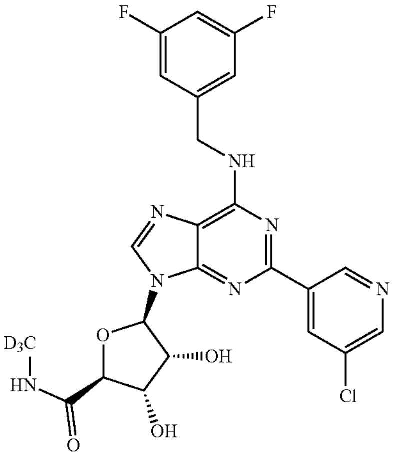 [SMILES: [2H]C([2H])([2H])NC(=O)[C@H]1O[C@@H](n2cnc3c(NCc4cc(F)cc(F)c4)nc(-c4cncc(Cl)c4)nc32)[C@H](O)[C@@H]1O] (2S,3S,4R,5R)-5-(2-(5-chloropyridin-3-yl)-6-(3,5-difluorobenzylamino)-9H-purin-9-yl)-3,4-dihydroxyl-N-((methyl-d3))-tetrahydrofuran-2-carboxamide | $^1H$ NMR (500 MHz, DMSO-$d_6$): δ. 9.36 (s, 1H), 8.84 (t, 1H), 8.70 (d, 1H), 8.62 (s, 1H), 8.54 (s, 1H), 7.94 (s, 1H), 7.16 (d, 2H), 7.09 (t, 1H), 6.10 (d, 1H), 5.72 (d, 1H), 5.62 (d, 1H), 4.90 (m, 1H), 4.80 (d, 2H), 4.34 (m, 2H). |

-continued

| No. | Compound structure and name | Characterization data |
| --- | --- | --- |
| 245 | 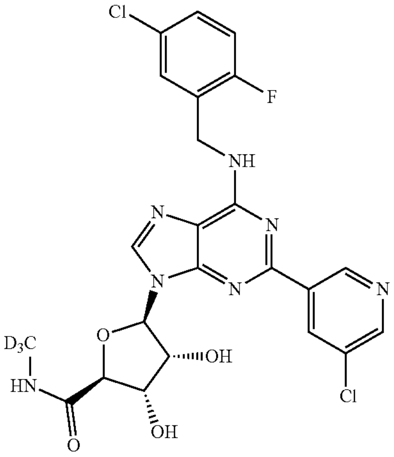 [SMILES: [2H]C([2H])([2H])NC(=O)[C@H]1O[C@@H](n2cnc3c(NCc4cc(Cl)ccc4F)nc(-c4cncc(Cl)c4)nc32)[C@H](O)[C@@H]1O] (2S,3S,4R,5R)-5-(6-(5-chloro-2-fluorobenzylamino)-2-(5-chloropyridin-3-yl)-9H-purin-9-yl)-3,4-dihydroxyl-N-((methyl-d3))-tetrahydrofuran-2-carboxamide | $^1$H NMR (500 MHz, DMSO-$d_6$): δ. 9.36 (s, 1H), 8.84 (t, 1H), 8.71 (d, 1H), 8.62 (s, 1H), 8.57 (s, 1H), 7.93 (s, 1H), 7.53 (d, 1H), 7.36 (m, 1H), 7.28 (t, 1H), 6.10 (d, 1H), 5.72 (d, 1H), 5.62 (d, 1H), 4.90 (q, 1H), 4.82 (s, 2H), 4.34 (m, 2H). |
| 246 | 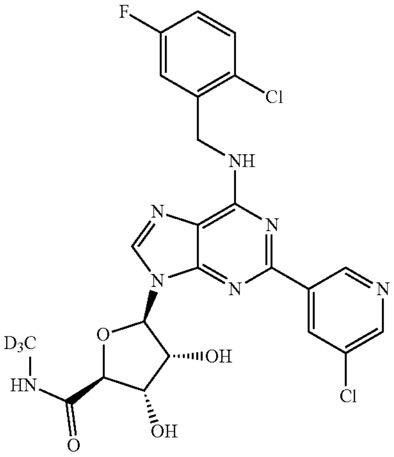 [SMILES: [2H]C([2H])([2H])NC(=O)[C@H]1O[C@@H](n2cnc3c(NCc4cc(F)ccc4Cl)nc(-c4cncc(Cl)c4)nc32)[C@H](O)[C@@H]1O] (2S,3S,4R,5R)-5-(6-(2-chloro-5-fluorobenzylamino)-2-(5-chloropyridin-3-yl)-9H-purin-9-yl)-3,4-dihydroxyl-N-(methyl-d3)-tetrahydrofuran-2-carboxamide | $^1$H NMR (500 MHz, DMSO-$d_6$): δ. 9.30 (s, 1H), 8.87 (t, 1H), 8.69 (d, 1H), 8.64 (s, 1H), 8.52 (s, 1H), 7.94 (s, 1H), 7.55 (q, 1H), 7.22 (dd, 1H), 7.14 (td, 1H), 6.10 (d, 1H), 5.73 (d, 1H), 5.63 (d, 1H), 4.90 (m, 3H), 4.34 (m, 2H). |
| 247 | 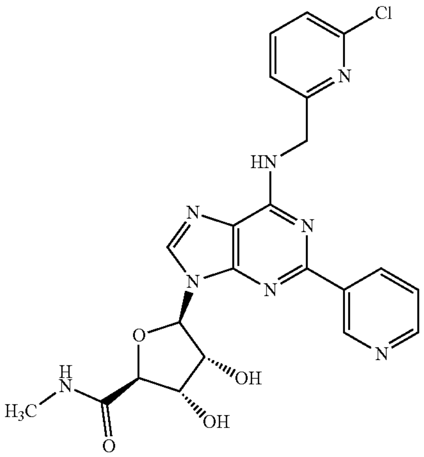 | $^1$H NMR (500 MHz, DMSO-$d_6$) δ: 9.34 (s, 1H), 8.72 (s, 1H), 8.60 (d, J = 14.8 Hz, 2H), 8.51 (d, J = 6.8 Hz, 1H), 7.95 (d, J = 4.4 Hz, 1H), 7.79 (t, J = 7.8 Hz, 1H), 7.47 (s, 1H), 7.38 (dd, J = 13.1, 7.8 Hz, 2H), 6.10 (d, J = 6.9 Hz, 1H), 5.71 (d, J = 4.3 Hz, 1H), 5.62 (d, J = 6.2 Hz, 1H), 4.88 (d, J = 22.4 Hz, 3H), 4.35 (s, 2H), 2.53 (d, J = 4.6 Hz, 3H). LC-MS m/z [M + H]$^+$: 497. |

-continued

| No. | Compound structure and name | Characterization data |
|---|---|---|
| | (2S,3S,4R,5R)-5-(6-((((6-chloropyridin-2-yl)methyl)amino)-2-(pyridin-3-yl)-9H-purin-9-yl)-3,4-dihydroxyl-N-methyltetrahydrofuran-2-carboxamide | |
| 248 | 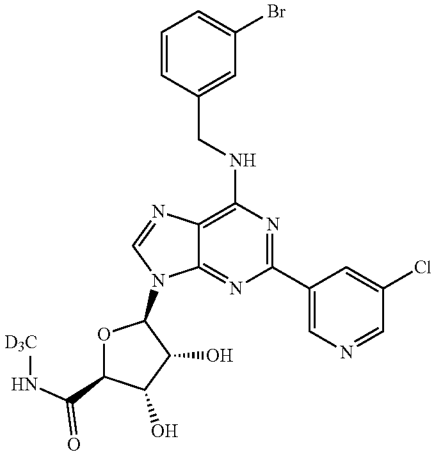 [SMILES: [2H]C([2H])([2H])NC(=O)[C@H]1O[C@@H](n2cnc3c(NCc4cccc(Br)c4)nc(-c4cncc(Cl)c4)nc32)[C@H](O)[C@@H]1O] (2S,3S,4R,5R)-5-(6-((3-bromobenzyl)amino)-2-(5-chloropyridin-3-yl)-9H-purin-9-yl)-3,4-dihydroxyl-N-(methyl-d3)tetrahydrofuran-2-carboxamide | $^1$H NMR (400 MHz, DMSO-$d_6$) δ 9.37 (s, 1H), 8.82 (s, 1H), 8.71 (s, 1H), 8.60 (s, 1H), 8.55 (s, 1H), 7.93 (s, 1H), 7.67 (s, 1H), 7.48-7.40 (m, 2H), 7.29 (t, J = 7.8 Hz, 1H), 6.09 (d, J = 6.9 Hz, 1H), 5.72 (d, J = 4.6 Hz, 1H), 5.62 (d, J = 6.3 Hz, 1H), 4.92-4.86 (m, 1H), 4.79 (s, 2H), 4.38-4.27 (m, 2H). LC-MS (m/z): 577.2 $[M + H]^+$ |
| 249 | 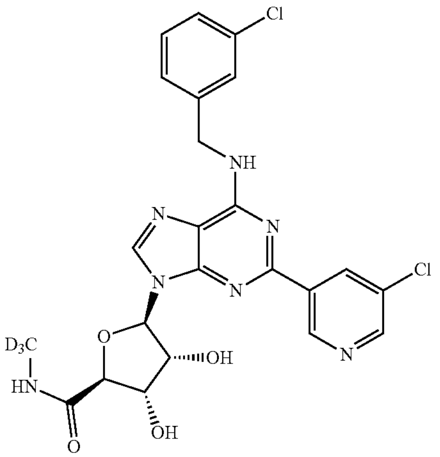 (2S,3S,4R,5R)-5-(6-((3-chlorobenzyl)amino)-2-(5-chloropyridin-3-yl)-9H-purin-9-yl)-3,4-dihydroxyl-N-(methyl-d3)tetrahydrofuran-2-carboxamide | $^1$H NMR (400 MHz, DMSO-$d_6$) δ 9.37 (s, 1H), 8.83 (s, 1H), 8.71 (d, J = 1.8 Hz, 1H), 8.60 (s, 1H), 8.55 (s, 1H), 7.93 (s, 1H), 7.51 (s, 1H), 7.41 (d, J = 7.7 Hz, 1H), 7.35 (t, J = 7.7 Hz, 1H), 7.28 (d, J = 7.7 Hz, 1H), 6.09 (d, J = 6.8 Hz, 1H), 5.72 (d, J = 4.6 Hz, 1H), 5.62 (d, J = 6.3 Hz, 1H), 4.92-4.87 (m, 1H), 4.79 (s, 2H), 4.37-4.29 (m, 2H). LC-MS (m/z): 533.3 $[M + H]^+$. |

-continued

| No. | Compound structure and name | Characterization data |
|---|---|---|
| 250 | 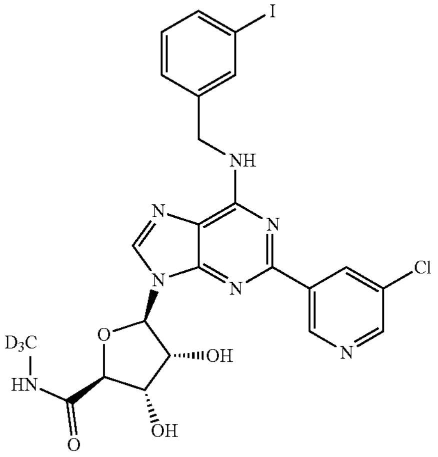 [SMILES: [2H]C([2H])([2H])NC(=O)[C@H]1O[C@@H](n2cnc3c(NCc4cccc(I)c4)nc(-c4cncc(Cl)c4)nc32)[C@H](O)[C@@H]1O] (2S,3S,4R,5R)-5-(2-(5-chloropyridin-3-yl)-6-((3-iodobenzyl)amino)-9H-purin-9-yl)-3,4-dihydroxyl-N-(methyl-d3)tetrahydrofuran-2-carboxamide | $^1$H NMR (400 MHz, DMSO-$d_6$) δ 9.38 (s, 1H), 8.80 (s, 1H), 8.71 (d, J = 2.3 Hz, 1H), 8.58 (d, J = 13.6 Hz, 2H), 7.92 (s, 1H), 7.86 (s, 1H), 7.58 (d, J = 7.6 Hz, 1H), 7.46 (d, J = 7.6 Hz, 1H), 7.13 (t, J = 7.7 Hz, 1H), 6.09 (d, J =6.8 Hz, 1H), 5.71 (d, J = 4.6 Hz, 1H), 5.61 (d, J = 6.3 Hz, 1H), 4.89 (dd, J = 11.2, 6.4 Hz, 1H), 4.75 (d, J = 4.7 Hz, 2H), 4.34 (dd, J = 6.5, 3.3 Hz, 2H). LC-MS (m/z): 625.2 [M + H]$^+$. |
| 251 | 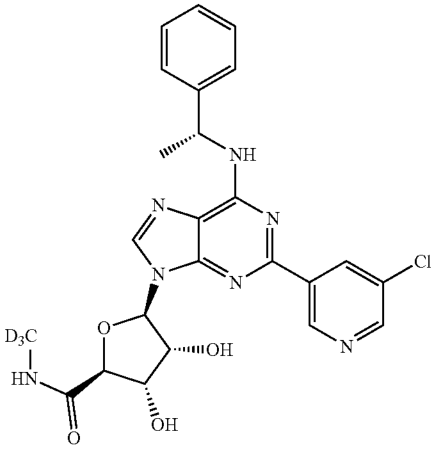 [SMILES: [2H]C([2H])([2H])NC(=O)[C@H]1O[C@@H](n2cnc3c(N[C@H](C)c4ccccc4)nc(-c4cncc(Cl)c4)nc32)[C@H](O)[C@@H]1O] (2S,3S,4R,5R)-5-(2-(5-chloropyridin-3-yl)-6-((((R)-1-phenethyl)amino)-9//-purin-9-yl)-3,4-dihydroxyl-N-(methyl-d3)tetrahydrofuran-2-carboxamide | $^1$H NMR (400 MHz, DMSO-$d_6$) δ 9.32 (s, 1H), 8.68 (d, J = 9.4 Hz, 2H), 8.59 (s, 1H), 8.50 (s, 1H), 7.91 (s, 1H), 7.53 (d, J = 7.5 Hz, 2H), 7.32 (t, J = 7.6 Hz, 2H), 7.19 (t, J = 7.3 Hz, 1H), 6.07 (d, J = 6.8 Hz, 1H), 5.70 (d, J = 4.7 Hz, 1H), 5.57 (dd, J = 17.2, 6.9 Hz, 2H), 4.91-4.82 (m, 1H), 4.36-4.27 (m, 2H), 1.60 (d, J = 7.0 Hz, 3H). LC-MS (m/z): 513.3 [M + H]$^+$. |
| 252 | 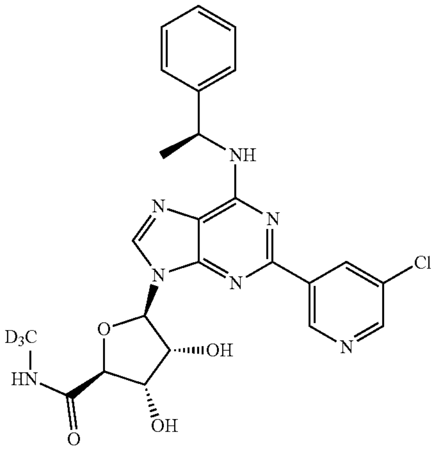 [SMILES: [2H]C([2H])([2H])NC(=O)[C@H]1O[C@@H](n2cnc3c(N[C@@H](C)c4ccccc4)nc(-c4cncc(Cl)c4)nc32)[C@H](O)[C@@H]1O] | $^1$H NMR (400 MHz, DMSO-$d_6$) δ 9.33 (s, 1H), 8.67 (d, J = 16.0 Hz, 2H), 8.58 (s, 1H), 8.52 (s, 1H), 7.91 (s, 1H), 7.52 (d, J = 7.4 Hz, 2H), 7.31 (t, J = 7.4 Hz, 2H), 7.18 (s, 1H), 6.07 (d, J = 6.8 Hz, 1H), 5.69 (d, J = 4.6 Hz, 1H), 5.59 (d, J = 6.2 Hz, 2H), 4.88 (s, 1H), 4.33 (d, J = 7.1 Hz, 2H), 1.60 (d, J = 6.6 Hz, 3H). LC-MS (m/z): 513.3 [M + H]$^+$. |

-continued

| No. | Compound structure and name | Characterization data |
|---|---|---|
| | (2S,3S,4R,5R)-5-(2-(5-chloropyridin-3-yl)-6-((((S)-1-phenethyl)amino)-9H-purin-9-yl)-3,4-dihydroxyl-N-(methyl-d3)tetrahydrofuran-2-carboxamide | |
| 253 | 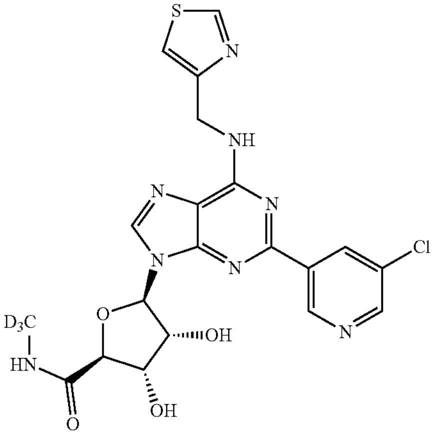 [SMILES: [2H]C([2H])([2H])NC(=O)[C@H]1O[C@@H](n2cnc3c(NCc4cscn4)nc(-c4cncc(Cl)c4)nc32)[C@H](O)[C@@H]1O] (2S,3S,4R,5R)-5-(2-(5-chloropyridin-3-yl)-6-((thiazol-4-ylmethyl)amino)-9H-purin-9-yl)-3,4-dihydroxyl-N-(methyl-d3)tetrahydrofuran-2-carboxamide | $^1$H NMR (500 MHz, DMSO-$d_6$) δ 9.35 (s, 1H), 9.06 (d, J = 1.8 Hz, 1H), 8.69 (d, J = 8.6 Hz, 2H), 8.57 (d, J = 16.6 Hz, 2H), 7.93 (s, 1H), 7.47 (s, 1H), 6.10 (d, J = 6.9 Hz, 1H), 5.71 (d, J = 4.7 Hz, 1H), 5.61 (d, J = 6.4 Hz, 1H), 4.91 (dd, J = 21.7, 15.4 Hz, 3H), 4.34 (dd, J = 11.9, 3.2 Hz, 2H). LC-MS (m/z): 506.2 $[M + H]^+$. |
| 254 | 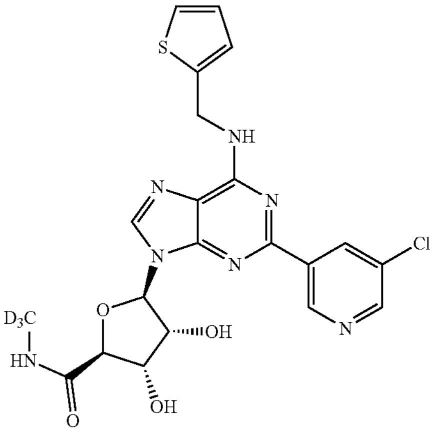 [SMILES: [2H]C([2H])([2H])NC(=O)[C@H]1O[C@@H](n2cnc3c(NCc4cccs4)nc(-c4cncc(Cl)c4)nc32)[C@H](O)[C@@H]1O] (2S,3S,4R,5R)-5-(2-(5-chloropyridin-3-yl)-6-((thiophen-2-ylmethyl)amino)-9H-purin-9-yl)-3,4-dihydroxyl-N-(methyl-d3)tetrahydrofuran-2-carboxamide | $^1$H NMR (500 MHz, DMSO-$d_6$) δ 9.49 (s, 1H), 8.80 (s, 1H), 8.73 (d, J = 2.3 Hz, 1H), 8.69 (s, 1H), 8.58 (s, 1H), 7.93 (s, 1H), 7.34 (d, J = 4.8 Hz, 1H), 7.11 (d, J = 2.9 Hz, 1H), 6.96 (dd, J = 4.9, 3.6 Hz, 1H), 6.10 (d, J = 6.8 Hz, 1H), 5.70 (d, J = 4.6 Hz, 1H), 5.61 (d, J = 6.3 Hz, 1H), 5.01-4.85 (m, 3H), 4.38-4.30 (m, 2H). LC-MS (m/z): 505.2 $[M + H]^+$. |
| 255 | 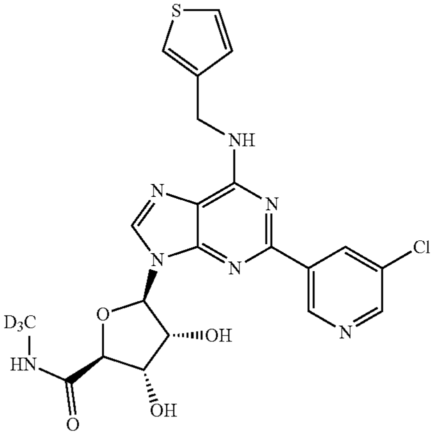 [SMILES: [2H]C([2H])([2H])NC(=O)[C@H]1O[C@@H](n2cnc3c(NCc4ccsc4)nc(-c4cncc(Cl)c4)nc32)[C@H](O)[C@@H]1O] | $^1$H NMR (500 MHz, DMSO-$d_6$) δ 9.41 (s, 1H), 8.72 (d, J = 2.4 Hz, 1H), 8.65 (s, 1H), 8.62-8.59 (m, 1H), 8.57 (s, 1H), 7.92 (s, 1H), 7.46 (dd, J = 4.8, 3.0 Hz, 1H), 7.39 (d, J = 1.9 Hz, 1H), 7.17 (d, J = 4.9 Hz, 1H), 6.09 (d, J = 6.8 Hz, 1H), 5.70 (d, J = 4.7 Hz, 1H), 5.60 (d, J = 6.4 Hz, 1H), 4.93-4.74 (m, 3H), 4.37-4.29 (m, 2H). LC-MS (m/z): 505.2 $[M + H]^+$. |

-continued

| No. | Compound structure and name | Characterization data |
|---|---|---|
| | (2S,3S,4R,5R)-5-(2-(5-chloropyridin-3-yl)-6-((thiophen-3-ylmethyl)amino)-9H-purin-9-yl)-3,4-dihydroxyl-N-(methyl-d3)tetrahydrofuran-2-carboxamide | |
| 256 | 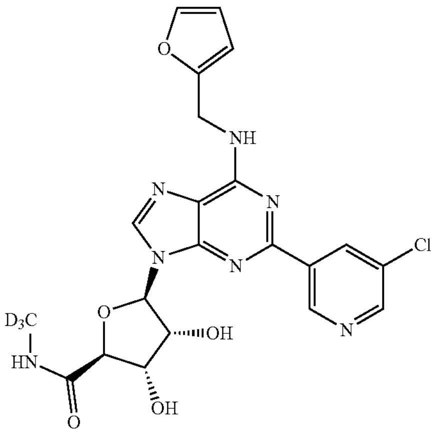 [SMILES: [2H]C([2H])([2H])NC(=O)[C@H]1O[C@@H](n2cnc3c(NCc4ccco4)nc(-c4cncc(Cl)c4)nc32)[C@H](O)[C@@H]1O] (2S,3S,4R,5R)-5-(2-(5-chloropyridin-3-yl)-6-((furan-2-ylmethyl)amino)-9H-purin-9-yl)-3,4-dihydroxyl-N-(methyl-d3)tetrahydrofuran-2-carboxamide; | $^1H$ NMR (400 MHz, DMSO-$d_6$) δ 9.43 (s, 1H), 8.73 (d, J = 2.4 Hz, 1H), 8.64 (s, 2H), 8.59 (s, 1H), 7.93 (s, 1H), 7.56 (s, 1H), 6.38 (dd, J = 3.1, 1.8 Hz, 1H), 6.32 (d, J = 3.1 Hz, 1H), 6.10 (d, J = 6.9 Hz, 1H), 5.71 (d, J = 4.7 Hz, 1H), 5.62 (d, J = 6.4 Hz, 1H), 4.90 (dd, J = 11.2, 6.6 Hz, 1H), 4.80 (s, 2H), 4.37-4.30 (m, 2H). |
| 257 | 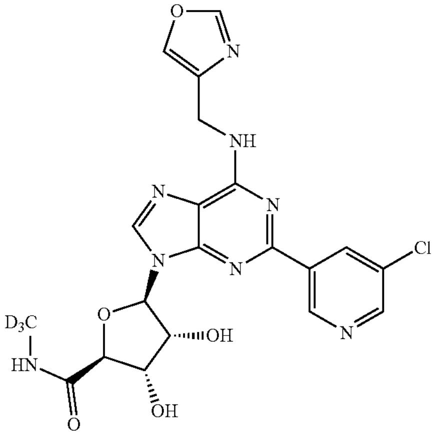 [SMILES: [2H]C([2H])([2H])NC(=O)[C@H]1O[C@@H](n2cnc3c(NCc4cocn4)nc(-c4cncc(Cl)c4)nc32)[C@H](O)[C@@H]1O] (2S,3S,4R,5R)-5-(2-(5-chloropyridin-3-yl)-6-((oxazol-4-ylmethyl)amino)-9H-purin-9-yl)-3,4-dihydroxyl-N-(methyl-d3)tetrahydrofuran-2-carboxamide | $^1H$ NMR (500 MHz, DMSO-$d_6$) δ 9.40 (d, J = 1.5 Hz, 1H), 8.71 (d, J = 2.4 Hz, 1H), 8.64-8.60 (m, 1H), 8.58 (s, 1H), 8.52 (s, 1H), 8.31 (s, 1H), 7.96 (s, 1H), 7.92 (s, 1H), 6.10 (d, J = 6.8 Hz, 1H), 5.70 (d, J = 4.7 Hz, 1H), 5.60 (d, J = 6.4 Hz, 1H), 4.93-4.86 (m, 1H), 4.73 (s, 2H), 4.40-4.28 (m, 2H).LC-MS (m/z): 490.2 [M + H]$^+$. |

-continued

| No. | Compound structure and name | Characterization data |
|---|---|---|
| 258 | 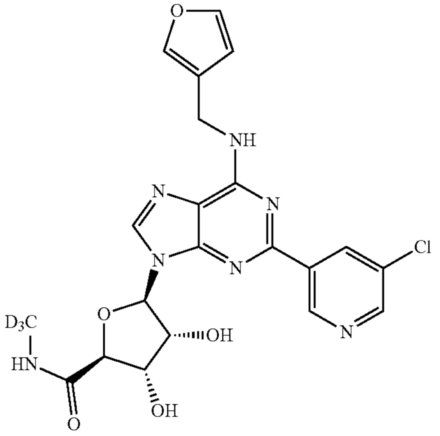 (2S,3S,4R,5R)-5-(2-(5-chloropyridin-3-yl)-6-((furan-3-ylmethyl)amino)-9H-purin-9-yl)-3,4-dihydroxyl-N-(methyl-d3)tetrahydrofuran-2-carboxamide | $^1$H NMR (500 MHz, DMSO-$d_6$) δ 9.44 (s, 1H), 8.72 (d, J = 2.4 Hz, 1H), 8.63 (s, 1H), 8.57 (s, 1H), 8.52 (s, 1H), 7.92 (s, 1H), 7.60 (d, J = 32.2 Hz, 2H), 6.53 (s, 1H), 6.10 (d, J = 6.8 Hz, 1H), 5.70 (d, J = 4.7 Hz, 1H), 5.60 (d, J = 6.4 Hz, 1H), 4.89 (dd, J = 11.3, 6.6 Hz, 1H), 4.66 (s, 2H), 4.45-4.28 (m, 2H). LC-MS (m/z): 489.2 [M + H]$^+$. |
| 259 | 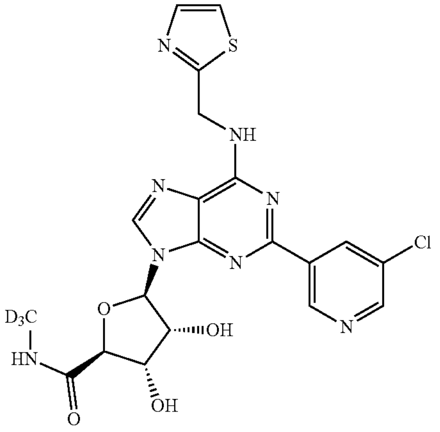 [SMILES: [2H]C([2H])([2H])NC(=O)[C@H]1O[C@@H](n2cnc3c(NCc4nccs4)nc(-c4cncc(Cl)c4)nc32)[C@H](O)[C@@H]1O] (2S,3S,4R,5R)-5-(2-(5-chloropyridin-3-yl)-6-((thiazol-2-ylmethyl)amino)-9//-purin-9-yl)-3,4-dihydroxyl-N-(methyl-d3)tetrahydrofuran-2-carboxamide | $^1$H NMR (400 MHz, DMSO-$d_6$) δ 9.38 (s, 1H), 9.02 (s, 1H), 8.71 (s, 1H), 8.63 (s, 1H), 8.59 (s, 1H), 7.95 (s, 1H), 7.74 (d, J = 3.2 Hz, 1H), 7.58 (d, J = 3.2 Hz, 1H), 6.11 (d, J = 6.9 Hz, 1H), 5.72 (d, J = 4.7 Hz, 1H), 5.64 (d, J = 6.3 Hz, 1H), 5.07 (d, J = 4.8 Hz, 2H), 4.96-4.85 (m, 1H), 4.41-4.26 (m, 2H).LC-MS (m/z): 506.2 [M + H]+. |
| 260 | 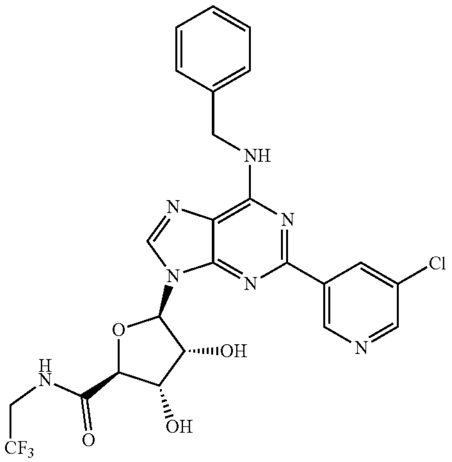 [SMILES: O=C(NCC(F)(F)F)[C@H]1O[C@@H](n2cnc3c(NCc4ccccc4)nc(-c4cncc(Cl)c4)nc32)[C@H](O)[C@@H]1O] (2S,3S,4R,5R)-5-(6-(benzylamino)-2-(5-chloropyridin-3-yl)-9H-purin-9-yl)-3,4- | $^1$H NMR (400 MHz, DMSO-$d_6$) δ 9.37 (s, 1H), 8.77 (t, J = 6.1 Hz, 2H), 8.70 (d, J = 2.0 Hz, 1H), 8.57 (s, 1H), 8.53 (s, 1H), 7.43 (d, J = 7.4 Hz, 2H), 7.31 (t, J = 7.5 Hz, 2H), 7.21 (t, J = 7.2 Hz, 1H), 6.15 (d, J = 6.5 Hz, 1H), 5.78 (d, J = 5.1 Hz, 1H), 5.70 (d, J = 6.2 Hz, 1H), 4.85-4.71 (m, 3H), 4.48 (d, J = 2.5 Hz, 1H), 4.34 (d, J = 2.5 Hz, 1H), 3.96 (dd, J = 20.5, 11.0 Hz, 1H), 3.86-3.76 (m, 1H). LC-MS (m/z): 564.3 [M + H]$^+$. |

-continued

| No. | Compound structure and name | Characterization data |
|---|---|---|
| | dihydroxyl-N-(2,2,2-trifluoroethyl)tetrahydrofuran-2-carboxamide | |
| 261 | 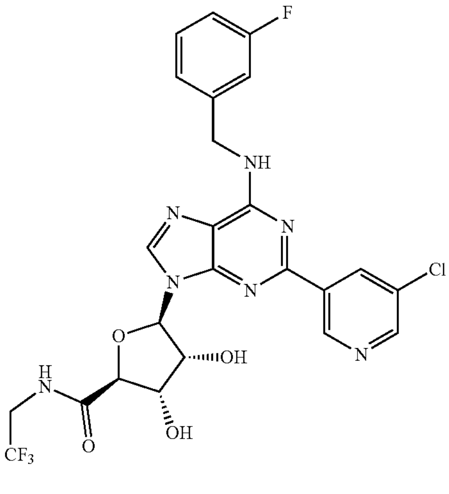 [SMILES: O=C(NCC(F)(F)F)[C@H]1O[C@@H](n2cnc3c(NCc4cccc(F)c4)nc(-c4cncc(Cl)c4)nc32)[C@H](O)[C@@H]1O] (2S,3S,4R,5R)-5-(2-(5-chloropyridin-3-yl)-6-(3-fluorobenzylamino)-9H-purin-9-yl)-3,4-dihydroxyl-N-(2,2,2-trifluoroethyl)tetrahydrofuran-2-carboxamide | $^1$H NMR (400 MHz, DMSO-d$_6$) δ 9.37 (s, 1H), 8.80 (dd, J = 14.6, 8.3 Hz, 2H), 8.71 (d, J = 2.2 Hz, 1H), 8.56 (d, J = 4.8 Hz, 2H), 7.40-7.33 (m, 1H), 7.30-7.20 (m, 2H), 7.05 (t, J = 8.5 Hz, 1H), 6.16 (d, J = 6.4 Hz, 1H), 5.79 (d, J = 5.1 Hz, 1H), 5.72 (d, J = 6.2 Hz, 1H), 4.80 (dd, J = 11.5, 5.3 Hz, 3H), 4.49 (d, J = 2.6 Hz, 1H), 4.36 (d, J = 2.7 Hz, 1H), 4.01-3.91 (m, 1H), 3.87-3.76 (m, 1H). LC-MS (m/z): 582.3 [M + H]$^+$. |
| 262 | 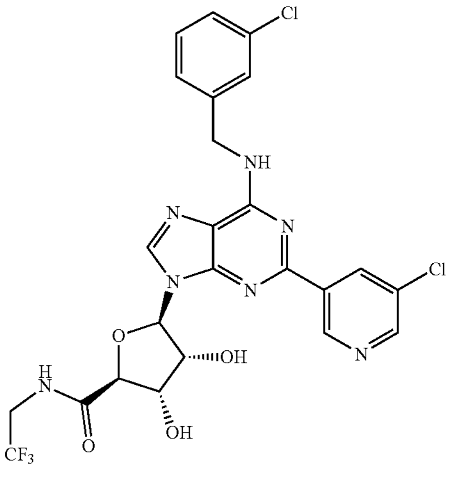 [SMILES: O=C(NCC(F)(F)F)[C@H]1O[C@@H](n2cnc3c(NCc4cccc(Cl)c4)nc(-c4cncc(Cl)c4)nc32)[C@H](O)[C@@H]1O] (2S,3S,4R,5R)-5-(6-(3-chlorobenzylamino)-2-(5-chloropyridin-3-yl)-9H-purin-9-yl)-3,4-dihydroxyl-N-(2,2,2-trifluoroethyl)tetrahydrofuran-2-carboxamide | $^1$H NMR (400 MHz, DMSO-d$_6$) δ 9.38 (s, 1H), 8.80 (dd, J = 16.3, 10.0 Hz, 2H), 8.71 (d, J = 2.2 Hz, 1H), 8.57 (d, J = 8.0 Hz, 2H), 7.51 (s, 1H), 7.44-7.27 (m, 3H), 6.16 (d, J = 6.4 Hz, 1H), 5.79 (d, J = 5.1 Hz, 1H), 5.72 (d, J = 6.2 Hz, 1H), 4.79 (dd, J = 11.2, 6.2 Hz, 3H), 4.49 (d, J = 2.6 Hz, 1H), 4.36 (dd, J = 7.4, 4.8 Hz, 1H), 3.97 (ddd, J = 16.2, 9.8, 6.6 Hz, 1H), 3.85-3.75 (m, 1H). LC-MS (m/z): 598.3 [M + H]$^+$. |

-continued

| No. | Compound structure and name | Characterization data |
|---|---|---|
| 263 | 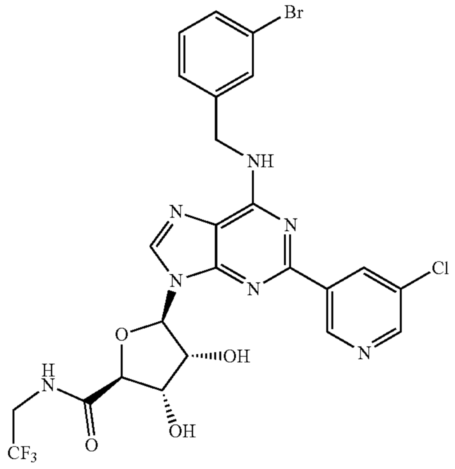 (2S,3S,4R,5R)-5-(6-(3-bromobenzylamino)-2-(5-chloropyridin-3-yl)-9H-purin-9-yl)-3,4-dihydroxyl-N-(2,2,2-trifluoroethyl)tetrahydrofuran-2-carboxamide | $^1$H NMR (400 MHz, DMSO-$d_6$) δ 9.39 (s, 1H), 8.80 (dd, J = 16.3, 9.8 Hz, 2H), 8.71 (d, J = 2.2 Hz, 1H), 8.57 (d, J = 10.5 Hz, 2H), 7.66 (s, 1H), 7.49-7.38 (m, 2H), 7.29 (t, J = 7.8 Hz, 1H), 6.16 (d, J = 6.4 Hz, 1H), 5.79 (d, J = 5.1 Hz, 1H), 5.72 (d, J = 6.2 Hz, 1H), 4.78 (dd, J = 10.7, 6.2 Hz, 3H), 4.49 (d, J = 2.6 Hz, 1H), 4.39-4.32 (m, 1H), 3.95 (dd, J = 9.5, 6.5 Hz, 1H), 3.82 (dd, J = 17.3, 7.8 Hz, 1H). LC-MS (m/z): 642.2 $[M + H]^+$. |
| 264 | 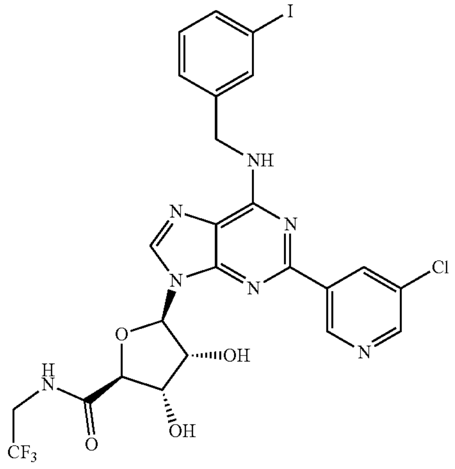 [SMILES: O=C(NCC(F)(F)F)[C@H]1O[C@@H](n2cnc3c(NCc4cccc(I)c4)nc(-c4cncc(Cl)c4)nc32)[C@H](O)[C@@H]1O] (2S,3S,4R,5R)-5-(2-(5-chloropyridin-3-yl)-6-(3-iodobenzylamino)-9H-purin-9-yl)-3,4-dihydroxyl-N-(2,2,2-trifluoroethyl)tetrahydrofuran-2-carboxamide | $^1$H NMR (400 MHz, DMSO-$d_6$) δ 9.39 (d, J = 1.5 Hz, 1H), 8.86-8.74 (m, 2H), 8.72 (d, J = 2.3 Hz, 1H), 8.57 (d, J = 14.8 Hz, 2H), 7.86 (s, 1H), 7.59 (d, J = 7.7 Hz, 1H), 7.46 (d, J = 7.6 Hz, 1H), 7.13 (t, J = 7.8 Hz, 1H), 6.16 (d, J = 6.4 Hz, 1H), 5.78 (t, J = 5.9 Hz, 1H), 5.72 (d, J = 6.2 Hz, 1H), 4.86-4.65 (m, 3H), 4.49 (d, J = 2.5 Hz, 1H), 4.36 (dd, J = 7.3, 4.8 Hz, 1H), 3.96 (dd, J = 20.3, 10.9 Hz, 1H), 3.82 (dd, J = 17.2, 7.5 Hz, 1H). LC-MS (m/z): 690.1 $[M + H]^+$. |

-continued

| No. | Compound structure and name | Characterization data |
|---|---|---|
| 265 | 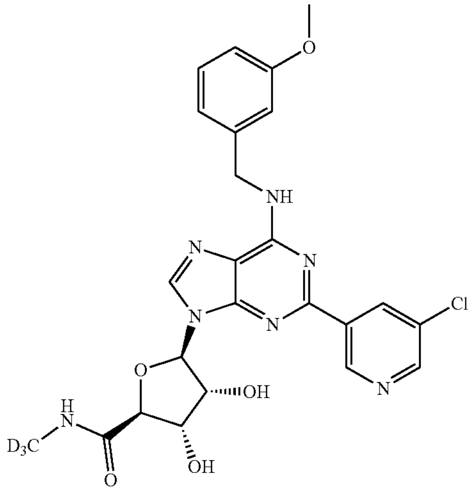 [SMILES: [2H]C([2H])([2H])NC(=O)[C@H]1O[C@@H](n2cnc3c(NCc4cccc(OC)c4)nc(-c4cncc(Cl)c4)nc32)[C@H](O)[C@@H]1O]<br>(2S,3S,4R,5R)-5-(2-(5-chloropyridin-3-yl)-6-(3-methoxybenzylamino)-9H-purin-9-yl)-3,4-dihydroxyl-N-(methyl-d3)-tetrahydrofuran-2-carboxamide | $^1$H NMR (400 MHz, DMSO-$d_6$) δ 9.39 (d, J = 1.7 Hz, 1H), 8.83-8.66 (m, 2H), 8.58 (d, J = 6.0 Hz, 2H), 7.93 (s, 1H), 7.23 (t, J = 7.9 Hz, 1H), 7.09-6.96 (m, 2H), 6.84-6.71 (m, 1H), 6.09 (d, J = 6.9 Hz, 1H), 5.72 (d, J = 4.6 Hz, 1H), 5.62 (d, J = 6.4 Hz, 1H), 4.90 (dd, J = 11.3, 6.6 Hz, 1H), 4.77 (d, J = 5.7 Hz, 2H), 4.40-4.27 (m, 2H), 3.72 (s, 3H). LC-MS (m/z): 529.3 [M + H]$^+$. |
| 266 | 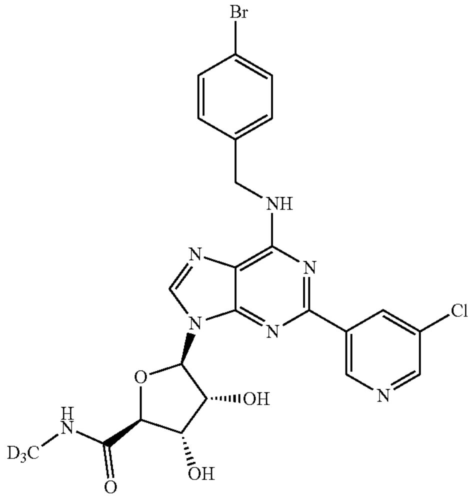 [SMILES: [2H]C([2H])([2H])NC(=O)[C@H]1O[C@@H](n2cnc3c(NCc4ccc(Br)cc4)nc(-c4cncc(Cl)c4)nc32)[C@H](O)[C@@H]1O]<br>(2S,3S,4R,5R)-5-(6-(4-bromobenzylamino)-2-(5-chloropyridin-3-yl)-9H-purin-9-yl)-3,4-dihydroxyl-N-(methyl-d3)-tetrahydrofuran-2-carboxamide | $^1$H NMR (500 MHz, DMSO-$d_6$) δ 9.35 (s, 1H), 8.78 (s, 1H), 8.70 (d, J = 1.9 Hz, 1H), 8.59 (s, 1H), 8.53 (s, 1H), 7.92 (s, 1H), 7.51 (d, J = 8.4 Hz, 2H), 7.39 (d, J = 8.2 Hz, 2H), 6.10 (d, J = 6.8 Hz, 1H), 5.70 (d, J = 4.7 Hz, 1H), 5.60 (d, J = 6.4 Hz, 1H), 4.89 (dd, J = 11.2, 6.3 Hz, 1H), 4.78 (d, J = 4.4 Hz, 2H), 4.38-4.30 (m, 2H). LC-MS (m/z): 577.2 [M + H]$^+$. |

-continued

| No. | Compound structure and name | Characterization data |
|---|---|---|
| 267 | 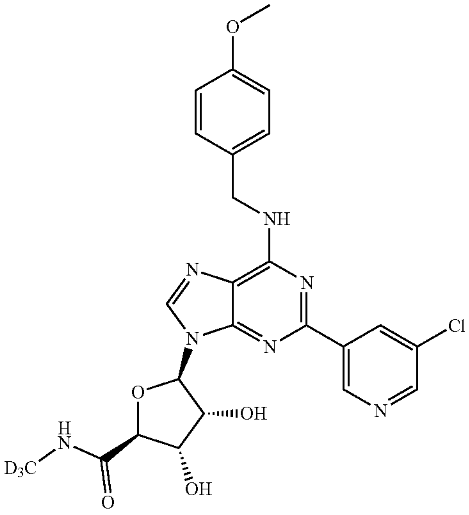 [SMILES: [2H]C([2H])([2H])NC(=O)[C@H]1O[C@@H](n2cnc3c(NCc4ccc(OC)cc4)nc(-c4cncc(Cl)c4)nc32)[C@H](O)[C@@H]1O] (2S,3S,4R,5R)-5-(2-(5-chloropyridin-3-yl)-6-(4-methoxybenzylamino)-9H-purin-9-yl)-3,4-dihydroxyl-N-(methyl-d3)-tetrahydrofuran-2-carboxamide | $^1$H NMR (400 MHz, DMSO-$d_6$) δ 9.40 (s, 1H), 8.72 (s, 2H), 8.58 (s, 2H), 7.93 (s, 1H), 7.37 (d, J = 8.0 Hz, 2H), 6.88 (d, J = 8.5 Hz, 2H), 6.09 (d, J = 6.9 Hz, 1H), 5.72 (d, J = 4.5 Hz, 1H), 5.62 (d, J = 6.3 Hz, 1H), 4.89 (d, J = 4.5 Hz, 1H), 4.73 (s, 2H), 4.34 (d, J = 9.5 Hz, 2H), 3.70 (s, 3H). LC-MS (m/z): 529.3 $[M + H]^+$. |
| 268 | 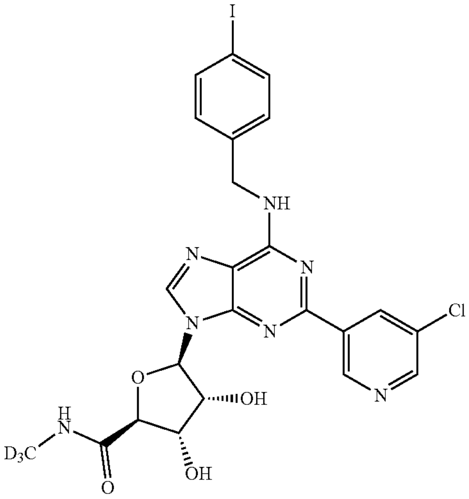 [SMILES: [2H]C([2H])([2H])NC(=O)[C@H]1O[C@@H](n2cnc3c(NCc4ccc(I)cc4)nc(-c4cncc(Cl)c4)nc32)[C@H](O)[C@@H]1O] (2S,3S,4R,5R)-5-(2-(5-chloropyridin-3-yl)-6-(4-iodobenzylamino)-9H-purin-9-yl)-3,4-dihydroxyl-N-(methyl-d3)-tetrahydrofuran-2-carboxamide | $^1$H NMR (400 MHz, DMSO-$d_6$) δ 9.35 (s, 1H), 8.79 (s, 1H), 8.70 (d, J = 2.1 Hz, 1H), 8.59 (s, 1H), 8.52 (s, 1H), 7.93 (s, 1H), 7.67 (d, J = 8.2 Hz, 2H), 7.24 (d, J = 8.2 Hz, 2H), 6.09 (d, J = 6.9 Hz, 1H), 5.72 (d, J = 4.6 Hz, 1H), 5.62 (d, J = 6.5 Hz, 1H), 4.88 (s, 1H), 4.75 (s, 2H), 4.34 (t, J = 6.3 Hz, 2H). LC-MS (m/z): 625.2 $[M + H]^+$. |

-continued

| No. | Compound structure and name | Characterization data |
|---|---|---|
| 269 | 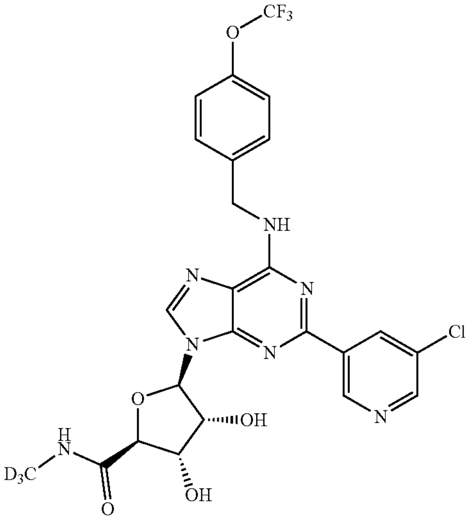 [SMILES: [2H]C([2H])([2H])NC(=O)[C@H]1O[C@@H](n2cnc3c(NCc4ccc(OC(F)(F)F)cc4)nc(-c4cncc(Cl)c4)nc32)[C@H](O)[C@@H]1O] (2S,3S,4R,5R)-5-(2-(5-chloropyridin-3-yl)-6-(4-(trifluoromethoxy)benzylamino)-9H-purin-9-yl)-3,4-dihydroxyl-N-(methyl-d3)-tetrahydrofuran-2-carboxamide | $^1H$ NMR (400 MHz, DMSO-$d_6$) δ 9.36 (s, 1H), 8.82 (s, 1H), 8.71 (d, J = 2.2 Hz, 1H), 8.60 (s, 1H), 8.54 (s, 1H), 7.94 (s, 1H), 7.56 (d, J = 8.6 Hz, 2H), 7.33 (d, J = 8.1 Hz, 2H), 6.10 (d, J = 6.9 Hz, 1H), 5.73 (d, J = 4.7 Hz, 1H), 5.62 (d, J = 6.4 Hz, 1H), 4.94-4.78 (m, 3H), 4.38-4.29 (m, 2H). LC-MS (m/z): 583.3 $[M + H]^+$. |
| 270 | 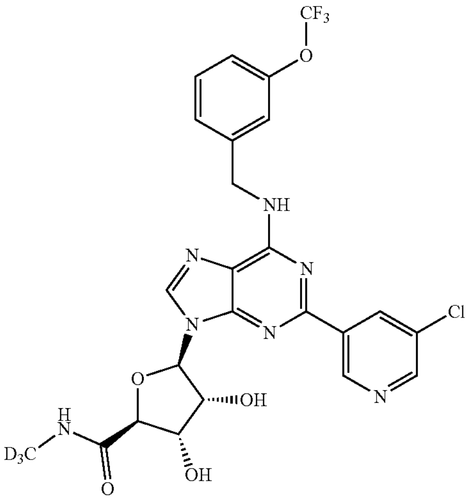 [SMILES: [2H]C([2H])([2H])NC(=O)[C@H]1O[C@@H](n2cnc3c(NCc4cccc(OC(F)(F)F)c4)nc(-c4cncc(Cl)c4)nc32)[C@H](O)[C@@H]1O] (2S,3S,4R,5R)-5-(2-(5-chloropyridin-3-yl)-6-(3-(trifluoromethoxy)benzylamino)-9H-purin-9-yl)-3,4-dihydroxyl-N-(methyl-d3)-tetrahydrofuran-2-carboxamide | $^1H$ NMR (400 MHz, DMSO-$d_6$) δ 9.36 (s, 1H), 8.84 (s, 1H), 8.70 (s, 1H), 8.57 (d, J = 20.4 Hz, 2H), 7.93 (s, 1H), 7.46 (s, 3H), 7.22 (s, 1H), 6.09 (d, J = 6.1 Hz, 1H), 5.71 (s, 1H), 5.61 (d, J = 6.1 Hz, 1H), 4.85 (d, J = 20.0 Hz, 3H), 4.35 (s, 2H). LC-MS (m/z): 583.3 $[M + H]^+$. |

-continued

| No. | Compound structure and name | Characterization data |
|---|---|---|
| 271 | 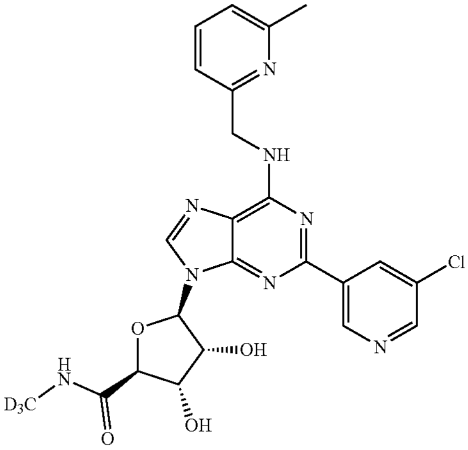 [SMILES: [2H]C([2H])([2H])NC(=O)[C@H]1O[C@@H](n2cnc3c(NCc4cccc(C)n4)nc(-c4cncc(Cl)c4)nc32)[C@H](O)[C@@H]1O] (2S,3S,4R,5R)-5-(2-(5-chloropyridin-3-yl)-6-((6-methylpyridin-2-yl)methylamino)-9H-purin-9-yl)-3,4-dihydroxyl-N-(methyl-d3)-tetrahydrofuran-2-carboxamide | $^1H$ NMR (400 MHz, DMSO-$d_6$) δ 9.30 (s, 1H), 8.75 (s, 1H), 8.69 (s, 1H), 8.61 (s, 1H), 8.47 (s, 1H), 7.93 (s, 1H), 7.60 (t, J = 7.7 Hz, 1H), 7.13 (dd, J = 21.8, 7.6 Hz, 2H), 6.10 (d, J = 6.9 Hz, 1H), 5.73 (d, J = 4.6 Hz, 1H), 5.63 (d, J = 6.4 Hz, 1H), 4.95-4.75 (m, 3H), 4.35 (dd, J = 7.5, 3.3 Hz, 2H), 2.50-2.50 (m, 3H). LC-MS (m/z): 514.2 $[M + H]^+$. |
| 272 | 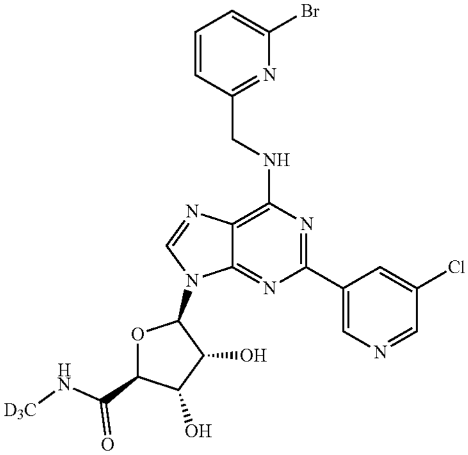 [SMILES: [2H]C([2H])([2H])NC(=O)[C@H]1O[C@@H](n2cnc3c(NCc4cccc(Br)n4)nc(-c4cncc(Cl)c4)nc32)[C@H](O)[C@@H]1O] (2S,3S,4R,5R)-5-(6-((6-bromopyridin-2-yl)methylamino)-2-(5-chloropyridin-3-yl)-9H-purin-9-yl)-3,4-dihydroxyl-N-(methyl-d3)-tetrahydrofuran-2-carboxamide | $^1H$ NMR (400 MHz, DMSO-$d_6$) δ 9.29 (s, 1H), 8.83 (s, 1H), 8.69 (s, 1H), 8.63 (s, 1H), 8.46 (s, 1H), 7.93 (s, 1H), 7.68 (d, J = 7.9 Hz, 1H), 7.51 (d, J = 7.6 Hz, 1H), 7.42 (d, J = 7.6 Hz, 1H), 6.10 (d, J = 6.5 Hz, 1H), 5.72 (s, 1H), 5.62 (d, J = 5.8 Hz, 1H), 4.87 (d, J = 17.2 Hz, 3H), 4.34 (d, J = 10.6 Hz, 2H). LC-MS (m/z): 578.2 $[M + H]^+$. |
| 273 | 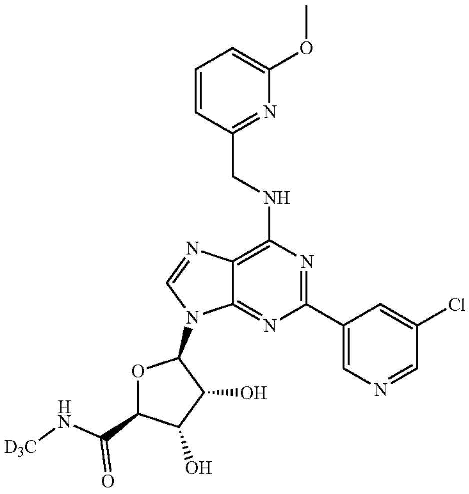 [SMILES: [2H]C([2H])([2H])NC(=O)[C@H]1O[C@@H](n2cnc3c(NCc4cccc(OC)n4)nc(-c4cncc(Cl)c4)nc32)[C@H](O)[C@@H]1O] | $^1H$ NMR (400 MHz, DMSO-$d_6$) δ 9.31 (s, 1H), 8.71 (d, J = 24.1 Hz, 2H), 8.61 (s, 1H), 8.48 (s, 1H), 7.92 (s, 1H), 7.61 (t, J = 7.8 Hz, 1H), 6.94 (d, J = 7.3 Hz, 1H), 6.66 (d, J = 8.1 Hz, 1H), 6.10 (d, J = 6.8 Hz, 1H), 5.70 (d, J = 4.5 Hz, 1H), 5.61 (d, J = 6.3 Hz, 1H), 4.94-4.74 (m, 3H), 4.35 (dd, J = 8.0, 3.3 Hz, 2H), 3.90 (s, 3H). LC-MS (m/z): 530.3 $[M + H]^+$. |

-continued

| No. | Compound structure and name | Characterization data |
|---|---|---|
| | (2S,3S,4R,5R)-5-(2-(5-chloropyridin-3-yl)-6-((6-methoxypyridin-2-yl)methylamino)-9H-purin-9-yl)-3,4-dihydroxyl-N-(methyl-d3)-tetrahydrofuran-2-carboxamide | |
| 274 | 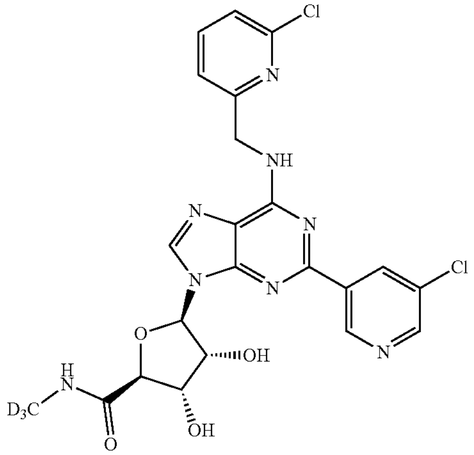 (2S,3S,4R,5R)-5-(6-((6-chloropyridin-2-yl)methylamino)-2-(5-chloropyridin-3-yl)-9H-purin-9-yl)-3,4-dihydroxyl-N-(methyl-d3)-tetrahydrofuran-2-carboxamide | $^{1}$H NMR (400 MHz, DMSO-$d_6$) δ 9.28 (s, 1H), 8.83 (s, 1H), 8.69 (s, 1H), 8.63 (s, 1H), 8.46 (s, 1H), 7.93 (s, 1H), 7.79 (t, J = 7.8 Hz, 1H), 7.38 (t, J = 7.5 Hz, 2H), 6.10 (d, J = 6.9 Hz, 1H), 5.72 (d, J = 4.7 Hz, 1H), 5.62 (d, J = 6.4 Hz, 1H), 4.93-4.76 (m, 3H), 4.35 (dd, J = 8.5, 3.2 Hz, 2H). LC-MS (m/z): 534.3 [M + H]$^+$. |

Example 12: Synthesis of (2S,3S,4R,5R)-5-(6-(benzylamino)-2-ethyl-9H-purin-9-yl)-3,4-dihydroxyl-N-methyl-tetrahydrofuran-2-formamide_(compound 275)

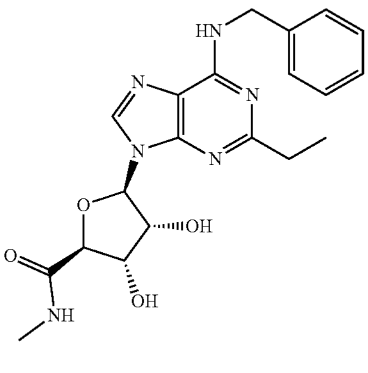 [SMILES: CCc1nc(NCc2ccccc2)c2ncn([C@@H]3O[C@H](C(=O)NC)[C@@H](O)[C@H]3O)c2n1]

S1: Synthesis of 5-propionamido-1H-imidazol-4-carboxamide

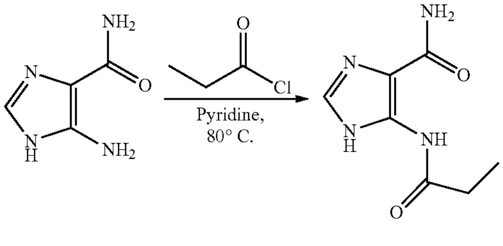

5-amino-1H-imidazol-4-formamide (10 g, 79.3 mmol) was dissolved in pyridine (65 mL) solvent, DMAP (290 mg, 2.4 mmol) and propionyl chloride (8.0 g, 87.2 mmol) were added sequentially slowly at 0° C., the materials were heated to 80° C. and stirred overnight, and the completion of the reaction was detected by TLC. The crude product was obtained by concentration under reduced pressure. The crude product was pulped with water and filtered, and a filter cake was dried to obtain the target compound as a green solid (5.8 g, yield of 40%). $^{1}$H NMR (500 MHz, DMSO-$d_6$) δ 12.55 (s, 1H), 10.12 (s, 1H), 7.31 (d, J=6.7 Hz, 2H), 7.19 (s, 1H), 2.46 (t, J=7.5 Hz, 2H), 1.10 (t, J=7.5 Hz, 3H).

S2: Synthesis of 2-ethyl-9H-purin-6-ol

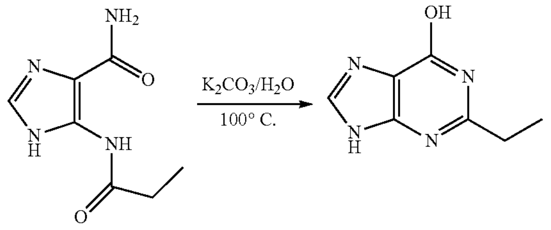

5-propionamido-1H-imidazol-4-carboxamide (5.8 g, 31.72 mmol) was dissolved in water (45 mL) solvent, potassium carbonate (2.5 g, 18.1 mmol) was added, the materials were heated to 100° C. and stirred overnight, and the completion of the reaction was detected by TLC. The reaction solution was adjusted to a pH<7 by using a dilute hydrochloric acid solution at 0° C. and filtered. A filter cake was dried to obtain the target compound as a yellow solid (2.5 g, yield of 48%). $^1H$ NMR (500 MHz, DMSO-$d_6$) δ 12.58 (d, J=26.6 Hz, 1H), 10.12 (s, 1H), 7.30 (s, 1H), 2.44 (dd, J=22.3, 14.9 Hz, 2H), 1.09 (q, J=7.6 Hz, 3H).

S3: Synthesis of 5-chloro-2-ethyl-9H-purin hydrochloride

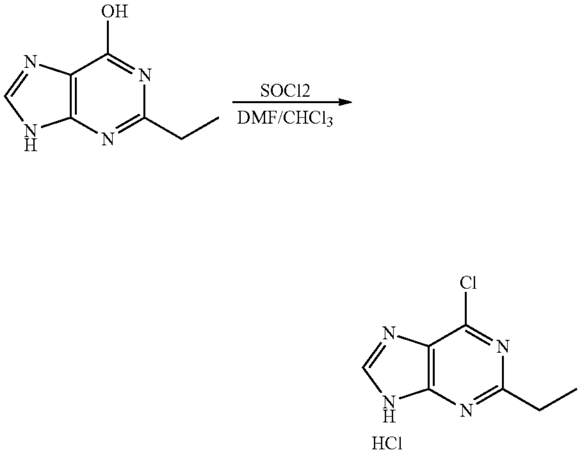

2-ethyl-9H-purin-6-ol (2.5 g, 15.8 mmol) was dissolved in a mixed solvent of anhydrous DMF (15 mL) and $CHCl_3$ (15 mL), and dichlorosulfoxide (19 g, 158 mmol) was slowly added at 0° C., the materials were heated to 80° C. and stirred for 3 hours, and the completion of the reaction was detected by TLC. The reaction solution was concentrated under reduced pressure, water was added to quench the reaction, the reaction solution was adjusted to a pH>7 by using sodium bicarbonate solution at 0° C., an extraction was performed with ethyl acetate, organic layers were mixed, the organic layer was washed with water and saturated saline solution, collected, dried with anhydrous sodium sulfate, and filtered, and the residue was concentrated under reduced pressure to obtain the crude product. The crude product was purified by column chromatography (ethyl acetate:n-hexane=2:1) to obtain the target compound as a brown solid (1.6 g, yield of 59%).

S4: Synthesis of N-benzyl-2-ethyl-9H-purin-6-amine

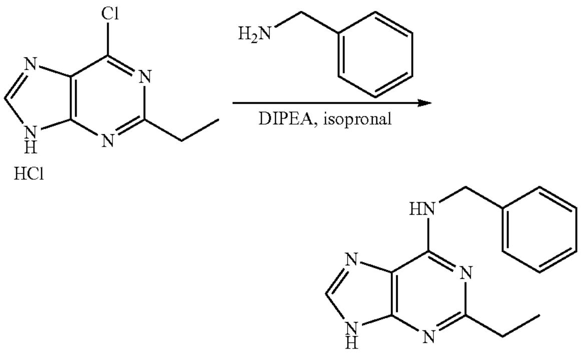

The reaction was performed according S2 in example 1 to obtain the title compound as a white solid (1.1 g, yield of 60%). $^1H$ NMR (500 MHz, DMSO-$d_6$) δ 12.72 (s, 1H), 8.15-7.89 (m, 2H), 7.43-7.16 (m, 5H), 5.22-4.27 (m, 2H), 2.67 (m, 2H), 1.73-1.72 (m, 1H), 1.23 (dt, J=15.0, 7.6 Hz, 3H).

S5: Synthesis of 2',3',5'-tri-O-acetyl-6-(benzylamino)-2-ethylpurine nucleoside

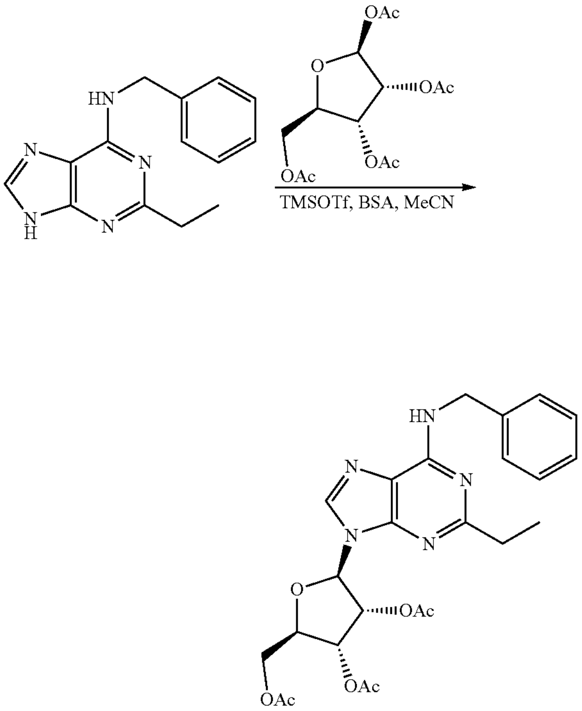

The reaction was performed according to S1 in example 6 to obtain the title compound as a yellow oily substance (1.7 g, yield of 76%). $^1H$ NMR (500 MHz, DMSO-$d_6$) δ 8.38 (s, 1H), 7.39 (s, 5H), 7.25 (s, 1H), 6.24 (s, 1H), 5.99 (s, 1H), 5.77 (s, 1H), 4.74 (d, J=1.0 Hz, 1H), 4.45-4.34 (m, 3H), 4.24 (dd, J=11.4, 5.4 Hz, 1H), 2.79 (s, 2H), 2.11 (s, 3H), 2.07 (s, 3H), 1.97 (s, 3H), 1.24 (d, J=7.5 Hz, 3H).

S6: Synthesis of (2R,3R,4S,5R)-2-(6-(benzylamino)-2-ethyl-9H-purin-9-yl)-5-(hydroxylmethyl)-tetrahydrofuran-3,4-dione

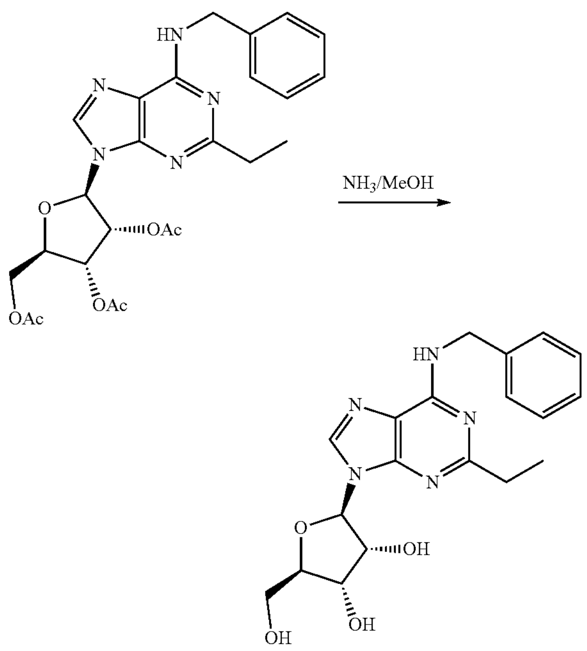

The reaction was performed according to S3 in example 6 to obtain the title compound as a white solid (1.0 g, yield of 78%).

S7: Synthesis of ((3aR,4R,6R,6aR)-6-(6-(benzylamino)-2-ethyl-9H-purin-9-yl)-2,2 dimethyl-tetrahydrofuran[3,4-d][1,3]-dioxo-4-yl)methanol

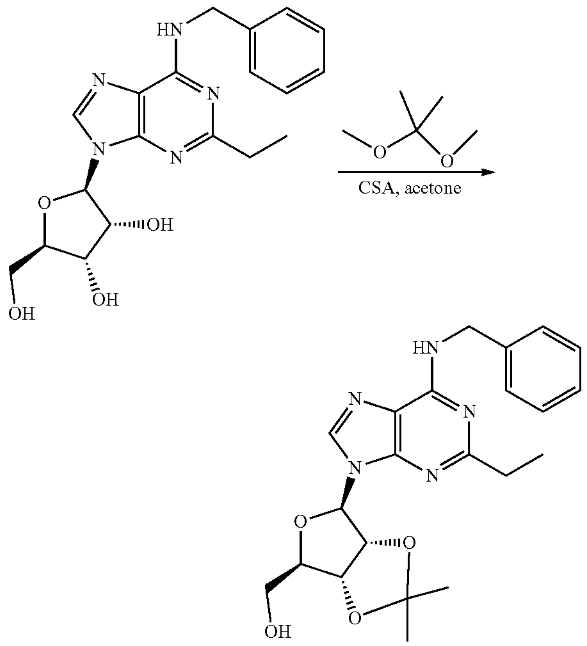

The reaction was performed according to S4 in example 6 to obtain the title compound as a yellow oily substance (1.1 g, yield of 100%). $^{1}$H NMR (500 MHz, DMSO-$d_6$) δ 8.35 (s, 1H), 8.27 (s, 1H), 7.36 (d, J=7.4 Hz, 2H), 7.29 (t, J=7.6 Hz, 2H), 7.20 (t, J=7.3 Hz, 1H), 6.12 (d, J=3.1 Hz, 1H), 5.38-5.30 (m, 2H), 5.00 (dd, J=6.0, 2.5 Hz, 1H), 4.69 (d, J=0.7 Hz, 2H), 4.21 (dd, J=7.2, 4.6 Hz, 1H), 3.62-3.49 (m, 2H), 2.68 (q, J=7.5 Hz, 2H), 1.55 (s, 3H), 1.33 (s, 3H), 1.22 (t, J=7.5 Hz, 3H).

S8: Synthesis of (3aS,4S,6R,6aR)-6-(6-(benzylamino)-2-ethyl-9H-purin-9-yl)-2,2-dimethyl-tetrahydrofuran[3,4-d][1,3]-dioxo-4-carboxylic acid

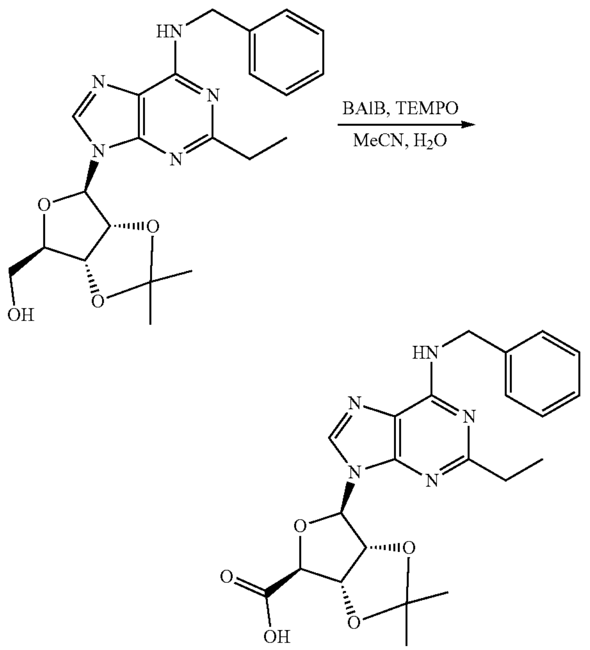

The reaction was performed according to S5 in example 6 to obtain the title compound as a white solid (500 mg, yield of 45%). $^{1}$H NMR (500 MHz, DMSO-$d_6$) δ 12.73 (s, 1H), 8.33 (s, 1H), 8.21 (s, 1H), 7.37 (d, J=7.3 Hz, 2H), 7.30 (t, J=7.4 Hz, 2H), 7.22 (t, J=6.8 Hz, 1H), 6.35 (s, 1H), 5.63 (s, 1H), 5.45 (d, J=5.9 Hz, 1H), 4.69 (s, 2H), 2.70 (d, J=5.9 Hz, 2H), 1.51 (s, 3H), 1.35 (s, 3H), 1.23 (s, 3H).

S9: Synthesis of (3aS,4S,6R,6aR)-6-(6-(benzylamino)-2-ethyl-9H-purin-9-yl)-N,2,2-trimethyl-tetrahydrofuran[3,4-d][1,3]-dioxin-4-formamide

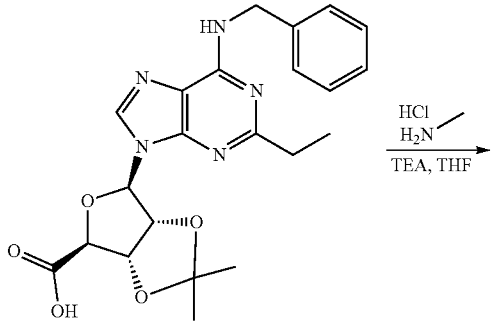

-continued

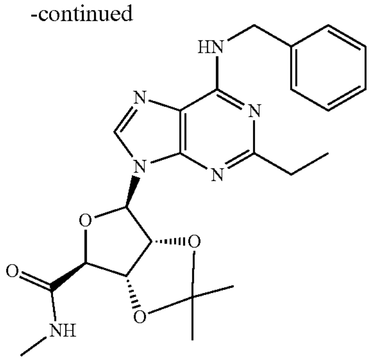

The reaction was performed according to S6 in example 6 to obtain the title compound as a yellow solid (50 mg, yield of 19%). $^1H$ NMR (500 MHz, DMSO-$d_6$) δ 8.19 (s, 2H), 7.39-7.16 (m, 6H), 6.34 (d, J=1.0 Hz, 1H), 5.48 (dd, J=6.1, 2.1 Hz, 1H), 5.35 (d, J=0.8 Hz, 1H), 4.68 (s, 2H), 4.52 (d, J=1.9 Hz, 1H), 4.26 (s, 1H), 2.65 (dd, J=7.6, 2.6 Hz, 2H), 2.19 (d, J=4.7 Hz, 3H), 1.53 (s, 3H), 1.33 (s, 3H), 1.21-1.16 (m, 3H).

S10: Synthesis of (2S,3S,4R,5R)-5-(6-(benzylamino)-2-ethyl-9H-purin-9-yl)-3,4-dihydroxyl-N-methyl-tetrahydrofuran-2-formamide (compound 275)

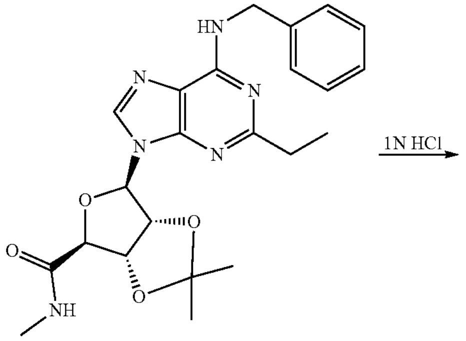

-continued

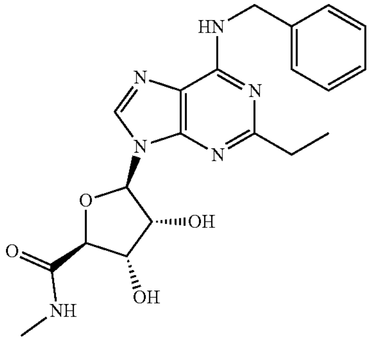

The reaction was performed according to S7 in example 6 to obtain the title compound as a yellow solid (24 mg, yield of 45607). LC-MS m/z $[M+1]^+$: 413.4; $^1H$ NNMR (500 MHz, DMSO-$d_6$) δ 8.48 (s, 1H), 8.39 (s, 1H), 8.33 (s, 1H), 7.37 (d, J=7.3 Hz, 2H), 7.29 (t, J=7.6 Hz, 2H), 7.21 (s, 1H), 5.94 (d, J=7.6 Hz, 1H), 5.72 (d, J=4.3 Hz, 1H), 5.52 (d, J=6.5 Hz, 1H), 4.78-4.57 (m, 3H), 4.31 (s, 1H), 4.16 (s, 1H), 2.70 (dd, J=16.5, 6.1 Hz, 5H), 1.25-1.22 (m, 3H).

Example 13: Following the Reactions Shown in Example 12, the Compounds in the Table Below were Obtained

| No. | Compound structure and name | Characterization data |
|---|---|---|
| 276 | 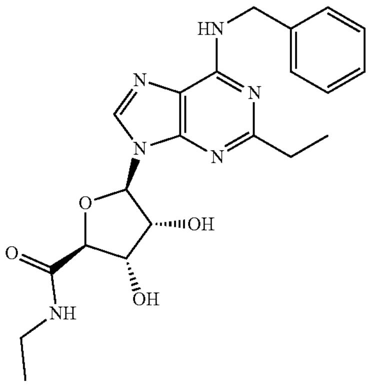 [SMILES: CCNC(=O)[C@H]1O[C@@H](n2cnc3c(NCc4ccccc4)nc(CC)nc32)[C@H](O)[C@@H]1O] (2S,3S,4R,5R)-5-(6-(benzylamino)-2-ethyl-9H-purin-9-yl)-N-ethyl-3,4-dihydroxyltetrahydrofuran-2-formamide | LC-MS m/z $[M + 1]^+$: 427.3; $^1H$ NMR (500 MHz, DMSO-$d_6$) δ 8.51-8.26 (m, 3H), 7.37 (d, J = 7.5 Hz, 2H), 7.29 (t, J = 7.5 Hz, 2H), 7.21 (d, J = 7.2 Hz, 1H), 5.96 (d, J = 7.3 Hz, 1H), 5.65 (s, 2H), 4.77-4.59 (m, 3H), 4.30 (s, 1H), 4.17 (d, J = 3.2 Hz, 1H), 3.23 (d, J = 6.7 Hz, 1H), 3.15 (d, J = 6.5 Hz, 1H), 2.70 (d, J = 7.5 Hz, 2H), 1.23 (t, J = 7.4 Hz, 3H), 1.03 (t, J = 7.1 Hz, 3H). |

-continued

| No. | Compound structure and name | Characterization data |
|---|---|---|
| 277 | 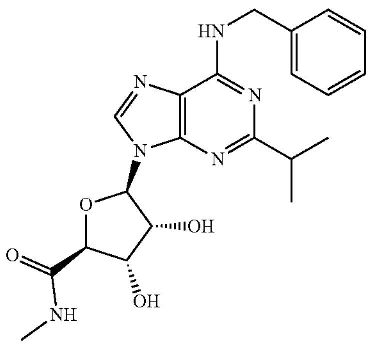 [SMILES: CNC(=O)[C@H]1O[C@@H](n2cnc3c(NCc4ccccc4)nc(C(C)C)nc32)[C@H](O)[C@@H]1O] (2S,3S,4R,5R)-5-(6-(benzylamino)-2-isopropyl-9H-purin-9-yl)-3,4-dihydroxyl-N-methyl-tetrahydrofuran-2-formamide | LC-MS m/z [M + 1]$^+$: 427.3; $^1$H NMR (500 MHz, DMSO-$d_6$) δ 8.35 (s, 3H), 7.39 (d, J = 7.4 Hz, 2H), 7.29 (t, J = 7.5 Hz, 2H), 7.20 (s, 1H), 5.95 (d, J = 7.4 Hz, 1H), 5.70 (d, J = 4.4 Hz, 1H), 5.52 (d, J = 6.4 Hz, 1H), 4.68 (d, J = 6.6 Hz, 3H), 4.30 (s, 1H), 4.19 (s, 1H), 2.91 (m, 1H), 2.70 (d, J = 4.6 Hz, 3H), 1.22 (dd, J = 6.7, 1.8 Hz, 6H). |
| 278 | 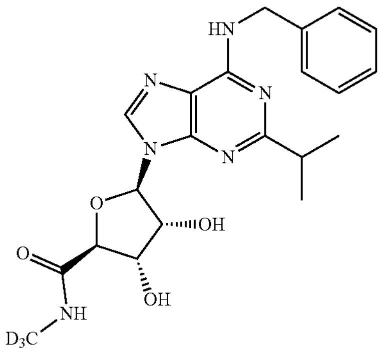 [SMILES: [2H]C([2H])([2H])NC(=O)[C@H]1O[C@@H](n2cnc3c(NCc4ccccc4)nc(C(C)C)nc32)[C@H](O)[C@@H]1O] (2S,3S,4R,5R)-5-(6-(benzylamino)-2-isopropyl-9H-purin-9-yl)-3,4-dihydroxyl-N-(methyl-d3)-tetrahydrofuran-2-formamide | LC-MS m/z [M + 1]$^+$: 430; $^1$H NMR (500 MHz, DMSO-$d_6$) δ 8.35 (m, 3H), 7.39 (d, J = 7.3 Hz, 2H), 7.29 (t, J = 7.6 Hz, 2H), 7.20 (s, 1H), 5.95 (d, J = 7.4 Hz, 1H), 5.71 (s, 1H), 5.53 (d, J = 0.7 Hz, 1H), 4.68 (d, J = 4.9 Hz, 3H), 4.30 (s, 1H), 4.19 (d, J = 2.6 Hz, 1H), 2.92 (s, 1H), 1.22 (dd, J = 6.7, 1.6 Hz, 6H). |
| 279 | 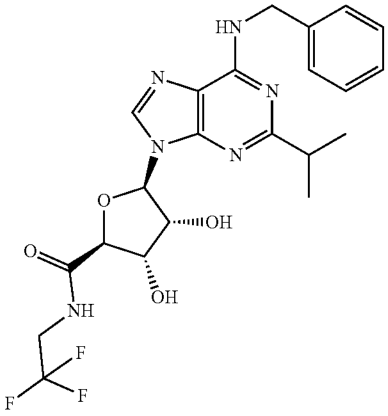 [SMILES: CC(C)c1nc(NCc2ccccc2)c2ncn([C@@H]3O[C@H](C(=O)NCC(F)(F)F)[C@@H](O)[C@H]3O)c2n1] (2S,3S,4R,5R)-5-(6-(benzylamino)-2-isopropyl-9H-purin-9-yl)-3,4-dihydroxyl-N-(2,2,2-trifluoroethyl)-tetrahydrofuran-2-formamide | LC-MS m/z [M + 1]$^+$: 495.3; $^1$H NMR (500 MHz, DMSO-$d_6$) δ 8.88 (s, 1H), 8.47-8.26 (m, 2H), 7.39 (d, J = 7.5 Hz, 2H), 7.29 (t, J = 7.5 Hz, 2H), 7.21 (d, J = 7.3 Hz, 1H), 6.02 (d, J = 6.9 Hz, 1H), 5.82 (s, 1H), 5.67 (s, 1H), 4.65 (d, J = 40.4 Hz, 3H), 4.44 (d, J = 1.6 Hz, 1H), 4.25 (s, 1H), 4.10-3.99 (m, 1H), 3.97-3.87 (m, 1H), 2.90 (s, 1H), 1.21 (dd, J = 6.6, 3.8 Hz, 6H). |

-continued

| No. | Compound structure and name | Characterization data |
|---|---|---|
| 280 | 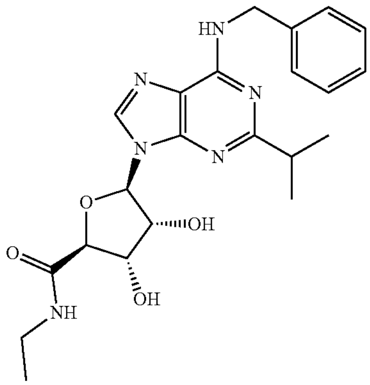 [SMILES: CCNC(=O)[C@H]1O[C@@H](n2cnc3c(NCc4ccccc4)nc(C(C)C)nc32)[C@H](O)[C@@H]1O] (2S,3S,4R,5R)-5-(6-(benzylamino)-2-isopropyl-9H-purin-9-yl)-N-ethyl-3,4-dihydroxyltetrahydrofuran-2-formamide | LC-MS m/z $[M+1]^+$: 441.4; $^1H$ NMR (500 MHz, DMSO-$d_6$) δ 8.38 (m, 3H), 7.39 (s, 1H), 7.29 (t, J = 7.6 Hz, 1H), 7.19 (dd, J = 22.3, 15.0 Hz, 1H), 5.98 (d, J = 7.2 Hz, 1H), 5.70 (d, J = 1.5 Hz, 1H), 5.55 (d, J = 4.6 Hz, 1H), 4.67 (dd, J = 11.5, 5.6 Hz, 3H), 4.30 (d, J = 1.7 Hz, 1H), 4.20 (s, 1H), 3.13 (s, 2H), 2.90 (dd, J = 13.6, 6.8 Hz, 1H), 1.22 (dd, J = 6.5, 4.6 Hz, 6H), 1.03 (t, J = 7.2 Hz, 3H). |

Example 14: Synthesis of (2S,3S,4R,5R)-5-(6-(3-methylbenzylamino)-2-(5-methylpyridin-3-yl)-9H-purin-9-yl)-3,4-dihydroxyl-N-(methyl-d3)-tetrahydrofuran-2-formamide (compound 281)

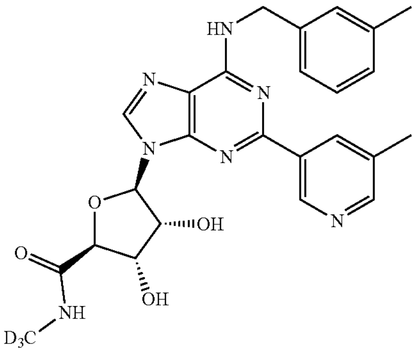

S1: Synthesis of N-(3-methylbenzyl)-2-chloro-9H-purin-6-amine

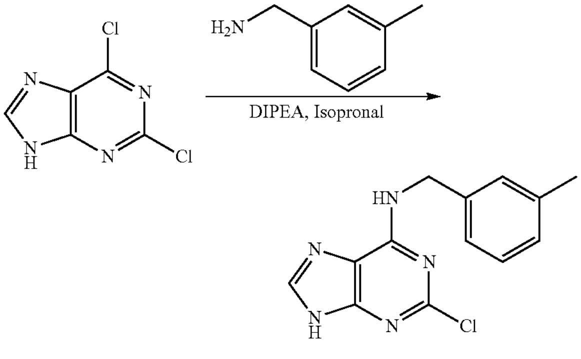

The reaction was performed according S2 in example 1 to obtain the title compound as a white solid (11 g, yield of 96%). $^1H$ NMR (500 MHz, DMSO-$d_6$) δ 12.92 (s, 1H), 8.52 (d, J=66.0 Hz, 1H), 8.14 (s, 1H), 7.20 (t, J=7.5 Hz, 1H), 7.18-7.12 (m, 2H), 7.05 (d, J=7.3 Hz, 1H), 4.61 (s, 2H), 2.28 (s, 3H).

S2: Synthesis of 2',3',5'-tri-O-acetyl-6-(3-methylbenzylamino)-2-chloropurine nucleoside

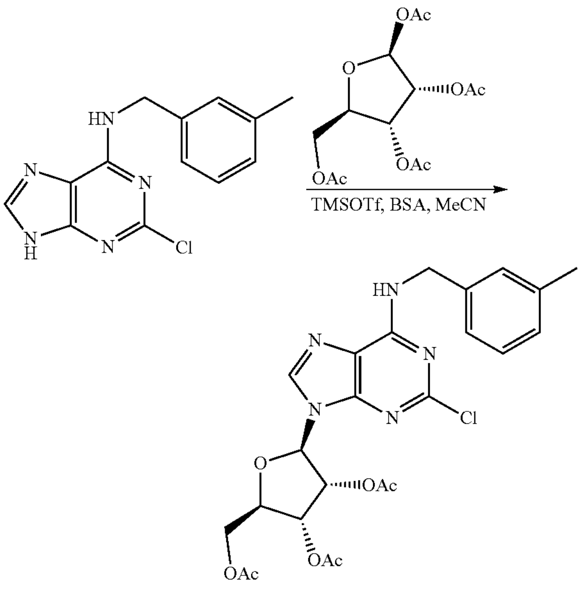

The reaction was performed according to S1 in example 6 to obtain the title compound as a yellow solid (21 g, yield of 100%). $^1H$ NMR (500 MHz, DMSO-$d_6$) δ 8.94 (s, 1H), 8.39 (s, 1H), 7.18 (t, J=7.5 Hz, 1H), 7.14 (s, 1H), 7.11 (d, J=7.6 Hz, 1H), 7.03 (d, J=7.4 Hz, 1H), 6.15 (d, J=5.4 Hz, 1H), 5.87 (d, J=5.6 Hz, 1H), 5.59-5.55 (m, 1H), 4.60 (d, J=6.1 Hz, 2H), 4.38-4.33 (m, 2H), 4.25 (d, J=6.5 Hz, 1H), 2.26 (s, 3H), 2.10 (s, 3H), 2.03 (s, 3H), 2.00 (s, 3H).

S3: Synthesis of (2R,3R,4S,5R)-2-(6-(3-methylbenzylamino)-2-chloro-9H-purin-9-yl)-5-(hydroxylmethyl)-tetrahydrofuran-3,4-diol

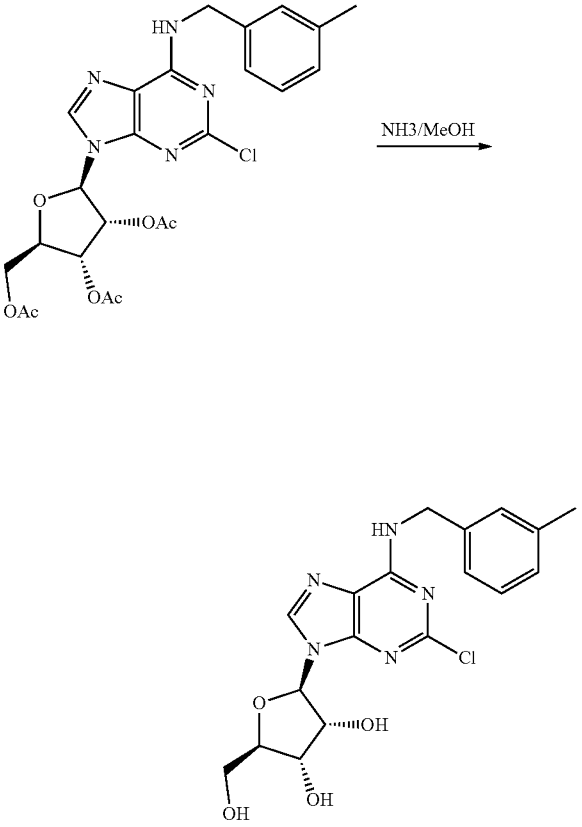

The reaction was according to S3 in example 6 to obtain the title compound as a yellow solid (15 g, yield of 94%). $^1$H NMR (500 MHz, DMSO-$d_6$) δ 9.38 (s, 1H), 8.77 (d, J=5.0 Hz, 1H), 8.71 (d, J=2.2 Hz, 1H), 8.60 (s, 1H), 8.56 (s, 1H), 7.92 (s, 1H), 7.27 (d, J=20.9 Hz, 2H), 7.12 (s, 1H), 6.10 (d, J=6.8 Hz, 1H), 5.74 (d, J=16.6 Hz, 2H), 4.89 (dd, J=6.6, 4.8 Hz, 1H), 4.82-4.63 (m, 2H), 4.43-4.24 (m, 2H), 2.29 (s, 3H).

S4: Synthesis of ((3aR,4R,6R,6aR)-6-(6-(3-methylbenzylamino)-2-chloro-9H-purin-9-yl)-2,2-dimethyltetrahydrofuran[3,4-d][1,3]dioxo-4-yl)methanol

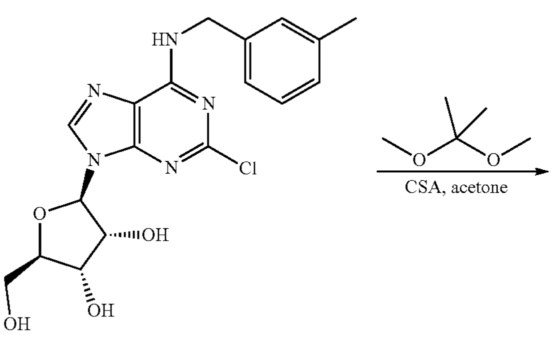

-continued

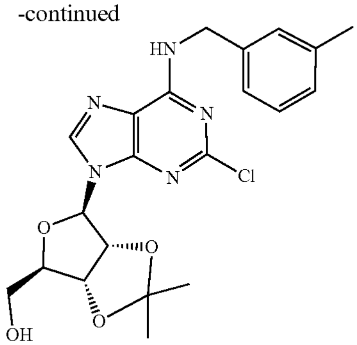

The reaction was performed according to S4 in example 6 to obtain the title compound as a yellow oily substance (8.5 g, yield of 85%). $^1$H NMR (500 MHz, DMSO-$d_6$) δ 8.89 (t, J=6.0 Hz, 1H), 8.37 (d, J=19.4 Hz, 1H), 7.17 (dt, J=21.1, 7.5 Hz, 3H), 7.05 (d, J=7.4 Hz, 1H), 6.08 (d, J=2.6 Hz, 1H), 5.34-5.26 (m, 1H), 5.08 (t, J=5.4 Hz, 1H), 4.94 (dd, J=6.0, 2.5 Hz, 1H), 4.62 (d, J=6.0 Hz, 2H), 4.22 (dd, J=4.8, 2.1 Hz, 1H), 3.61-3.48 (m, 2H), 2.28 (s, 3H), 1.55 (s, 3H), 1.33 (s, 3H).

S5: Synthesis of ((3aR,4S,6R,6aR)-6-(6-(3-methylbenzylamino)-2-chloro-9H-purin-9-yl)-2,2-dimethyltetrahydrofuran[3,4-d][1,3]dioxo-4-carboxylic acid

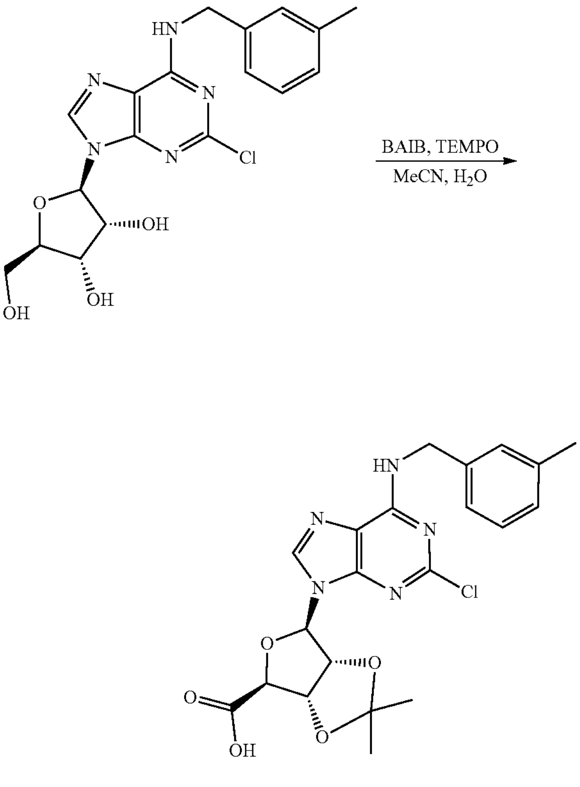

The reaction was performed according to S5 in example 6 to obtain the title compound as a white solid (2.8 g, yield of 33%).

S6: Synthesis of (3aS,4S,6R,6aR)-6-(6-(3-methylbenzylamino)-2-chloro-9H-purin-9-yl)-N-methyl-d3,2,2-dimethyl-tetrahydrofuran[3,4-d][1,3]dioxin-4-formamide

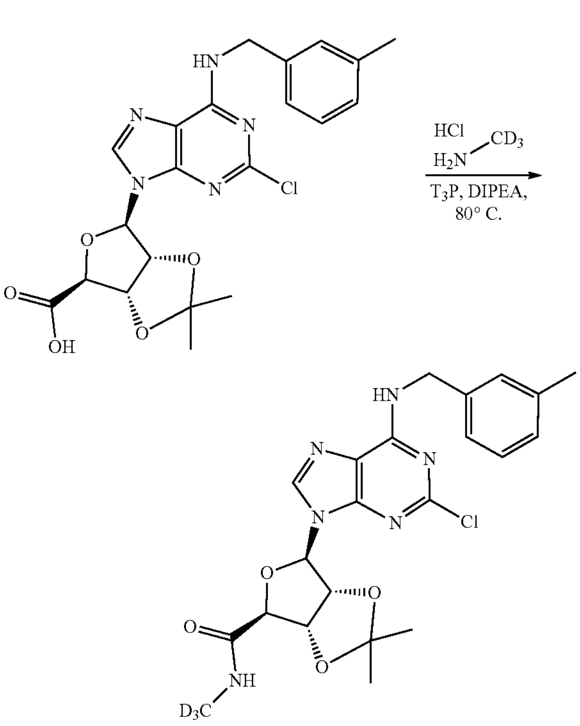

The reaction was performed according S6 in example 6 to obtain the title compound as a yellow solid (690 mg, yield of 36%). $^1$H NMR (500 MHz, DMSO-$d_6$) δ 8.87 (t, J=5.9 Hz, 1H), 8.29 (s, 1H), 7.53 (s, 1H), 7.23-7.10 (m, 3H), 7.05 (d, J=7.4 Hz, 1H), 6.27 (s, 1H), 5.32 (s, 2H), 4.71-4.47 (m, 3H), 2.27 (s, 3H), 1.54 (s, 3H), 1.34 (s, 3H).

S7: Synthesis of (3aS,4S,6R,6aR)-6-(6-(3-methylbenzylamino)-2-(5-methylpyridin-3-yl)-9H-purin-9-yl)-N-methyl-d3,2,2-dimethyl-tetrahydrofuran[3,4-d][1,3]dioxo-4-formamide

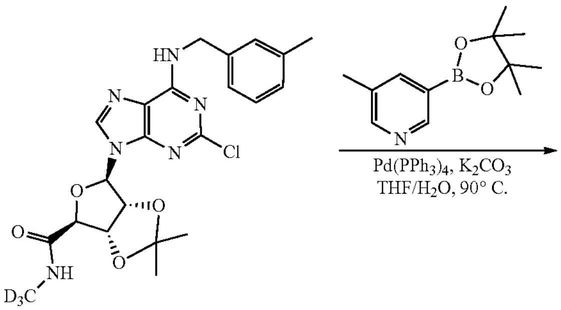

-continued

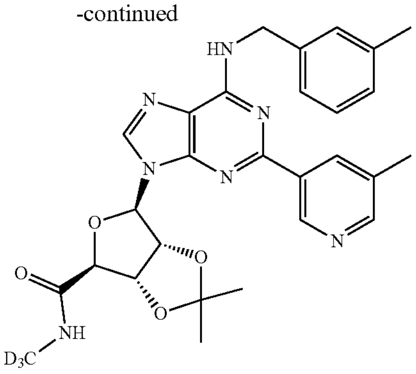

The reaction was performed according to S7 in example 8 to obtain the title compound as a yellow solid (250 mg, yield of 64%).

S8: Synthesis of (2S,3S,4R,5R)-5-(6-(3-methylbenzylamino)-2-(5-methylpyridin-3-yl)-9H-purin-9-yl)-3,4-dihydroxyl-N-(methyl-d3)-tetrahydrofuran-2-formamide (compound 281)

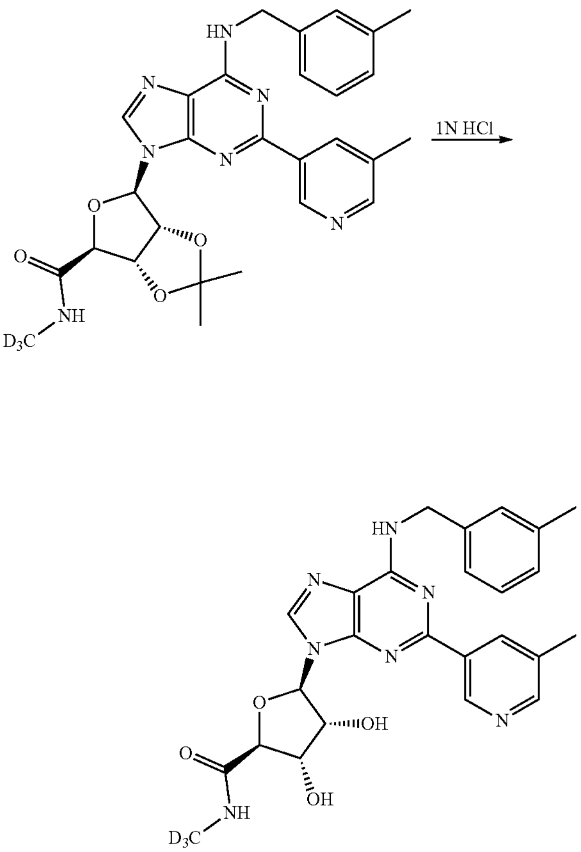

The reaction was performed according S8 in example 8 to obtain the title compound as a white solid (108 mg, yield of 32%). LC-MS m/z $[M+1]^+$: 493.3; $^1$H NMR (500 MHz, DMSO-$d_6$) δ 9.24 (s, 1H), 8.61 (s, 1H), 8.52 (s, 1H), 8.47 (s, 1H), 8.37 (s, 1H), 7.91 (s, 1H), 7.28 (s, 1H), 7.26-7.15 (m, 2H), 7.03 (s, 1H), 6.09 (s, 1H), 5.68 (d, J=3.5 Hz, 1H), 5.58 (s, 1H), 4.89 (s, 1H), 4.76 (d, J=0.8 Hz, 2H), 4.34 (s, 2H), 2.39 (s, 3H), 2.27 (s, 3H).

Example 15: Following the Reactions Shown in Example 14, the Compounds in the Table Below were Obtained

| No. | Compound structure and name | Characterization data |
|---|---|---|
| 282 | 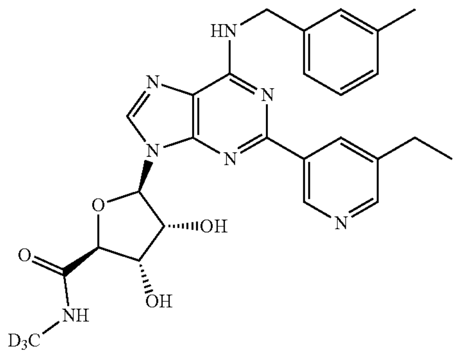 [SMILES: [2H]C([2H])([2H])NC(=O)[C@H]1O[C@@H](n2cnc3c(NCc4cccc(C)c4)nc(-c4cncc(CC)c4)nc32)[C@H](O)[C@@H]1O] (2S,3S,4R,5R)-5-(2-(5-ethylpyridin-3-yl)-6-((3-methylbenzyl)amino)-9H-purin-9-yl)-3,4-dihydroxyl-N-(methyl-d3)tetrahydrofuran-2-formamide | LC-MS m/z $[M + 1]^+$: 507.4; $^1H$ NMR (500 MHz, DMSO-$d_6$) δ 9.26 (s, 1H), 8.64 (s, 1H), 8.53 (d, J = 5.9 Hz, 2H), 8.43 (s, 1H), 7.91 (s, 1H), 7.30-7.16 (m, 3H), 7.02 (d, J = 6.6 Hz, 1H), 6.09 (d, J = 6.7 Hz, 1H), 5.63 (d, J = 41.2 Hz, 2H), 4.90 (s, 1H), 4.76 (s, 2H), 4.34 (s, 2H), 2.73 (d, J = 7.4 Hz, 2H), 2.26 (s, 3H), 1.26 (t, J = 7.5 Hz, 3H). |
| 283 | 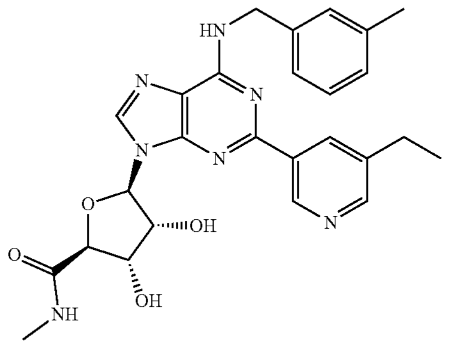 [SMILES: CCc1cncc(-c2nc(NCc3cccc(C)c3)c3ncn([C@@H]4O[C@H](C(=O)NC)[C@@H](O)[C@H]4O)c3n2)c1] (2S,3S,4R,5R)-5-(6-((3-methylbenzylamino)-2-(5-ethylpyridin-3-yl)-9H-purin-9-yl)-3,4-dihydroxyl-N-methyl-tetrahydrofuran-2-formamide | LC-MS m/z $[M + 1]^+$: 504.3; $^1H$ NMR (500 MHz, DMSO-$d_6$) δ 9.25 (s, 1H), 8.65-8.60 (m, 1H), 8.51 (d, J = 12.6 Hz, 2H), 8.38 (s, 1H), 7.93 (d, J = 4.1 Hz, 1H), 7.22 (m, 4H), 7.02 (d, J = 0.7 Hz, 1H), 6.08 (d, J = 6.8 Hz, 1H), 5.67 (d, J = 4.4 Hz, 1H), 5.57 (d, J = 6.3 Hz, 1H), 4.90 (d, J = 1.8 Hz, 1H), 4.75 (s, 2H), 4.33 (d, J = 3.7 Hz, 3H), 2.79-2.66 (m, 3H), 2.26 (s, 3H), 1.25 (t, J = 7.6 Hz, 3H). |

Example 16: Synthesis of (2S,3S,4R,5R)-5-(6-(3-methylbenzylamino)-2-(5-methylpyridin-3-yl)-9H-purin-9-yl)-3,4-dihydroxyl-N-methyl-tetrahydrofuran-2-formamide (compound 284)

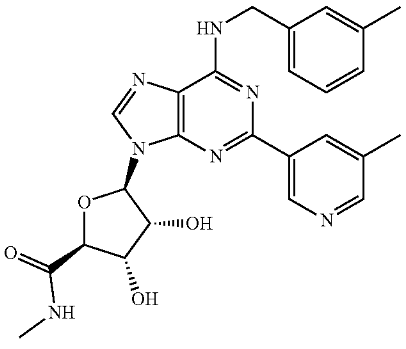

S1: Synthesis of (2S,3S,4R,5S)-3,4,5-triacetoxytetrahydrofuran-2-carboxylate methyl ester

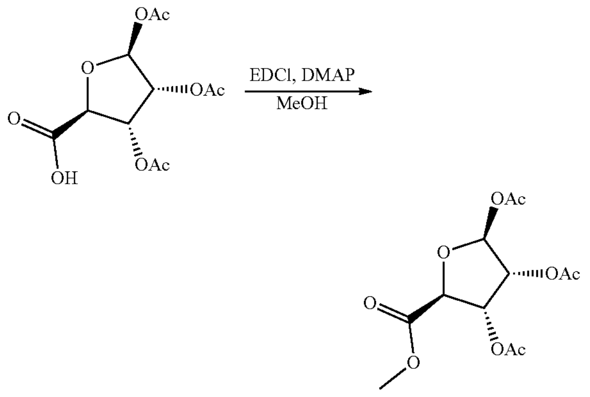

(2S,3S,4R,5S)-3,4,5-triacetoxytetrahydrofuran-2-carboxylate (1.5 g, 5.3 mmol) was dissolved in methanol (15 mL), and then DMAP (64 mg, 0.53 mmol) and EDCI (2.5 g, 13.2 mmol) were added sequentially at 0° C. The materials were reacted at room temperature for 3 hours, and the completion of the reaction was detected by TLC. Water was added to quench the reaction, an extraction was performed with ethyl acetate, organic layers were mixed, the organic layer was washed with water and saturated saline solution, collected, dried with anhydrous sodium sulfate, and filtered, and the residue was concentrated under reduced pressure to obtain the crude product. The crude product was purified by column chromatography (ethyl acetate:n-hexane=1:2) to obtain the target compound as a colorless oily substance (1.1 g, yield of 76%). $^1$H NMR (500 MHz, $CDCl_3$) δ 6.14 (s, 1H), 5.57 (dd, J=6.5, 4.9 Hz, 1H), 5.29 (d, J=4.9 Hz, 1H), 4.54 (d, J=6.5 Hz, 1H), 3.72 (s, 3H), 2.07 (s, 3H), 2.04 (d, J=2.1 Hz, 3H).

S2: Synthesis of N-benzyl-2-chloro-9-(tetrahydro-2H-pyran-2-yl)-9H-purin-6-amine

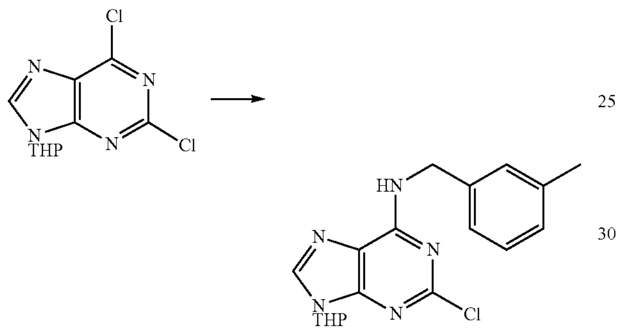

The reaction was performed according S2 in example 14 to obtain the title compound as a white solid (4.1 g, yield of 100%). $^1$H NMR (500 MHz, DMSO-$d_6$) δ 9.30 (s, 1H), 8.54 (s, 1H), 8.47 (s, 1H), 8.42 (d, J=9.0 Hz, 2H), 7.27 (s, 1H), 7.20 (dt, J=14.9, 7.3 Hz, 2H), 7.03 (d, J=7.1 Hz, 1H), 5.81-5.72 (m, 1H), 4.76 (s, 2H), 4.08-4.01 (m, 1H), 3.75 (d, J=3.2 Hz, 1H), 2.40 (s, 3H), 2.34-2.30 (m, 1H), 2.27 (s, 3H), 2.06-1.96 (m, 2H), 1.86-1.74 (m, 1H), 1.61 (d, J=3.3 Hz, 2H).

S3: Synthesis of N-3-methylbenzyl-2-(5-methylpyridin-3-yl)-9-(tetrahydro-2H-pyran)-2-yl)-9H-purin-6-amine

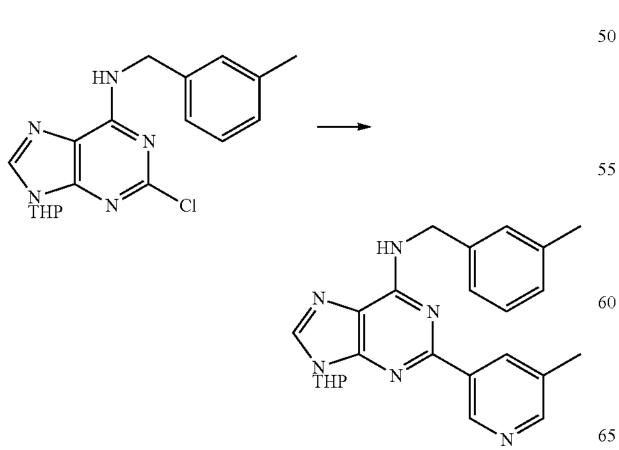

The reaction was performed according S7 in example 8 to obtain the title compound as a white solid (4.1 g, yield of 100%). $^1$H NMR (500 MHz, DMSO-$d_6$) δ 9.30 (s, 1H), 8.54 (s, 1H), 8.47 (s, 1H), 8.42 (d, J=9.0 Hz, 2H), 7.27 (s, 1H), 7.20 (dt, J=14.9, 7.3 Hz, 2H), 7.03 (d, J=7.1 Hz, 1H), 5.81-5.72 (m, 1H), 4.76 (s, 2H), 4.08-4.01 (m, 1H), 3.75 (d, J=3.2 Hz, 1H), 2.40 (s, 3H), 2.34-2.30 (m, 1H), 2.27 (s, 3H), 2.06-1.96 (m, 2H), 1.86-1.74 (m, 1H), 1.61 (d, J=3.3 Hz, 2H).

S4: Synthesis of N-3-methylbenzyl-2-(5-methylpyridin-3-yl)-9H-purin-6-amine

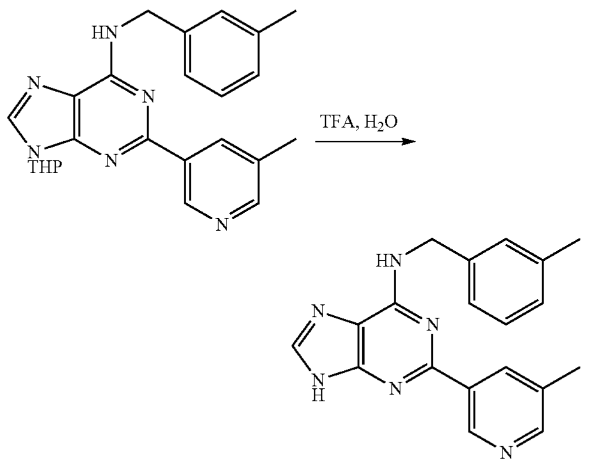

N-3-methylbenzyl-2-(5-methylpyridin-3-yl)-9-(tetrahydro-2H-pyran)-2-yl)-9H-purin-6-amine (4.1 g, 9.9 mmol) was dissolved in a mixed solvent of TFA (5 mL) and water (3 mL), the materials were reacted at room temperature for 3 hours, and the completion of the reaction was detected by TLC. The reaction solution was firstly adjusted to a pH>7 with sodium bicarbonate aqueous solution and filtered, a filter cake was pulped with ethyl acetate, and the filter cake was dried obtain the target compound as a white solid (2.5 g, yield of 90%). $^1$H NMR (500 MHz, DMSO-$d_6$) δ 9.33 (s, 1H), 8.77 (s, 1H), 8.66 (s, 1H), 8.56-8.45 (m, 1H), 8.26 (s, 1H), 7.29 (s, 1H), 7.25 (d, J=7.5 Hz, 1H), 7.20 (t, J=7.4 Hz, 1H), 7.04 (d, J=7.2 Hz, 1H), 4.79 (s, 2H), 2.49 (s, 3H), 2.28 (s, 3H).

S5: Synthesis of (2S,3S,4R,5R)-methyl-3,4-diacetoxy-5-(6-(3-methylbenzylamino)-2-(5-methylpyridin-3-yl)-9H-purin-9-yl)-tetrahydrofuran-2-carboxylate

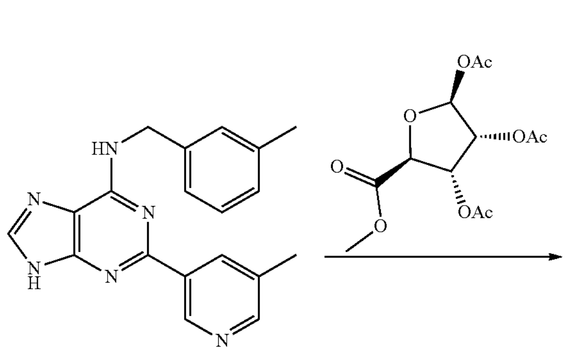

-continued

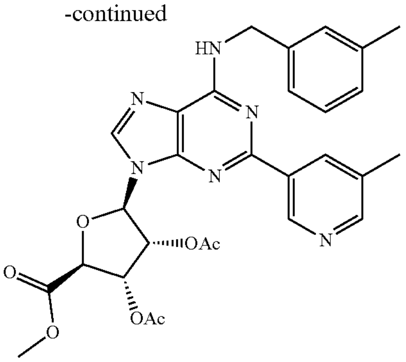

-continued

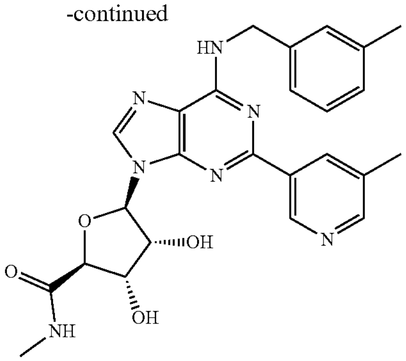

The reaction was performed according S2 in example 14 to obtain the title compound as a yellow oily substance (130 mg, yield of 72%). $^1$H NMR (500 MHz, DMSO-$d_6$) δ 9.32 (s, 1H), 8.83 (s, 2H), 8.71 (s, 1H), 8.46 (s, 1H), 7.23 (dd, J=25.2, 15.3 Hz, 3H), 7.04 (s, 1H), 6.45 (d, J=4.2 Hz, 1H), 6.27 (dd, J=10.6, 4.4 Hz, 2H), 4.92 (d, J=4.2 Hz, 1H), 4.79 (d, J=5.3 Hz, 2H), 3.52 (s, 3H), 2.50-2.49 (m, 3H), 2.27 (s, 3H), 2.18 (s, 3H), 2.07 (s, 3H).

S6 Synthesis of (2S,3S,4R,5R)-5-(6-(3-methylbenzylamino)-2-(5-methylpyridin-3-yl)-9H-purin-9-yl)-3,4-dihydroxyl-N-methyl-tetrahydrofuran-2-formamide (compound 284)

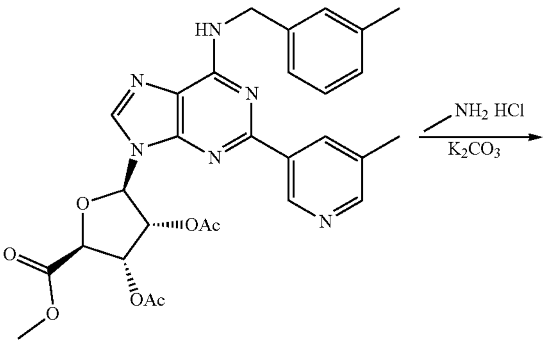

(2S,3S,4R,5R)-methyl-3,4-diacetoxy-5-(6-(3-methylbenzylamino)-2-(5-methylpyridin-3-yl)-9H-purin-9-yl)-tetrahydrofuran-2-carboxylate (130 mg, 0.2 mmol) was dissolved in THE (3 mL), and potassium carbonate (300 mg, 2.2 mmol) and methylamine hydrochloride (300 mg, 4.4 mmol) were added sequentially. The materials were reacted at a room temperature overnight, and the completion of the reaction was detected by TLC. The reaction solution was neutralized to a pH=7, water was added to quench the reaction, an extraction was performed with ethyl acetate, organic layers were mixed, the organic layer was washed with water and saturated saline solution, collected, dried with anhydrous sodium sulfate, and filtered, and the residue was concentrated under reduced pressure to obtain the crude product. The crude product was purified by column chromatography (ethyl acetate:methanol=20:1) to obtain the target compound as a yellow solid (70 mg, yield of 65%). $^1$H NMR (500 MHz, DMSO-$d_6$) δ 9.25 (s, 1H), 8.63 (s, 1H), 8.54 (s, 1H), 8.48 (d, J=1.3 Hz, 1H), 8.38 (s, 1H), 7.96 (d, J=4.7 Hz, 1H), 7.29 (s, 1H), 7.21 (dt, J=14.9, 7.5 Hz, 2H), 7.03 (d, J=7.2 Hz, 1H), 6.09 (d, J=6.9 Hz, 1H), 5.71 (d, J=4.6 Hz, 1H), 5.60 (d, J=6.3 Hz, 1H), 4.89 (d, J=4.8 Hz, 1H), 4.76 (d, J=4.1 Hz, 2H), 4.37-4.30 (m, 2H), 2.53 (d, J=4.6 Hz, 3H), 2.40 (s, 3H), 2.28 (s, 3H). LC-MS m/z $[M+1]^+$: 490.2.

Example 17: Following the Reactions Shown in Example 16, the Compounds in the Table Below were Obtained

| No. | Compound structure and name | Characterization data |
| --- | --- | --- |
| 285 | 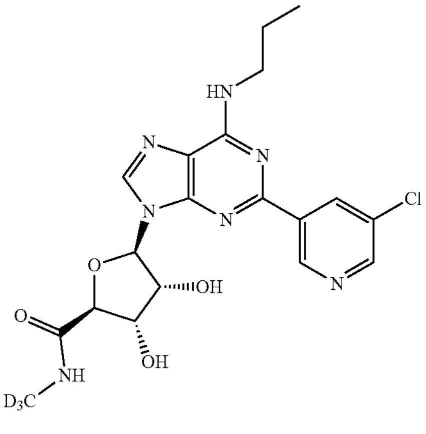 [SMILES: [2H]C([2H])([2H])NC(=O)[C@H]1O[C@@H](n2cnc3c(NCCC)nc(-c4cncc(Cl)c4)nc32)[C@H](O)[C@@H]1O] (2S,3S,4R,5R)-5-(2-(5-chloropyridin-3-yl)-6-(propylamino)-9H-purin-9-yl)-3,4- | $^1$H NMR (500 MHz, DMSO-$d_6$) δ: 9.42 (s, 1H), 8.72 (d, J = 1.7 Hz, 1H), 8.61 (s, 1H), 8.55 (s, 1H), 8.14 (s, 1H), 7.94 (s, 1H), 6.10 (d, J = 6.5 Hz, 1H), 5.68 (s, 2H), 4.88 (s, 1H), 4.34 (d, J = 17.1 Hz, 2H), 3.57 (s, 2H), 1.70 (d, J = 6.7 Hz, 2H), 0.95 (t, J = 7.3 Hz, 3H). LC-MS m/z $[M + H]^+$: 451. |

-continued

| No. | Compound structure and name | Characterization data |
|---|---|---|
| | dihydroxyl-N-(methyl-d3)-tetrahydrofuran-2-carboxamide | |
| 286 | 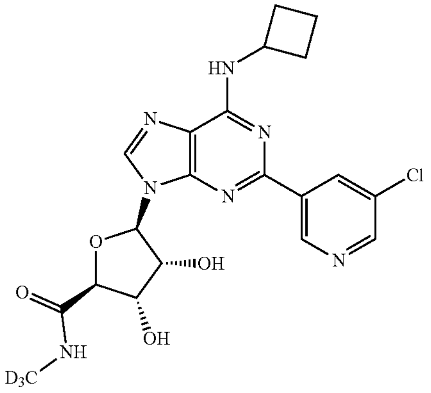 [SMILES: [2H]C([2H])([2H])NC(=O)[C@H]1O[C@@H](n2cnc3c(NC4CCC4)nc(-c4cncc(Cl)c4)nc32)[C@H](O)[C@@H]1O] (2S,3S,4R,5R)-5-(2-(5-chloropyridin-3-yl)-6-(cyclobutylamino)-9H-purin-9-yl)-3,4-dihydroxyl-N-(methyl-d3)-tetrahydrofuran-2-carboxamide | $^1$H NMR (500 MHz, DMSO-$d_6$) δ: 9.43 (s, 1H), 8.72 (d, J = 2.2 Hz, 1H), 8.62 (s, 1H), 8.57 (s, 1H), 8.37 (s, 1H), 7.95 (s, 1H), 6.10 (d, J = 6.5 Hz, 1H), 5.68 (s, 2H), 4.96-4.75 (m, 2H), 4.35 (d, J = 19.1 Hz, 2H), 2.38-2.29 (m, 2H), 2.21 (s, 2H), 1.75 (d, J = 9.1 Hz, 2H). LC-MS m/z [M + H]$^+$: 463. |
| 287 | 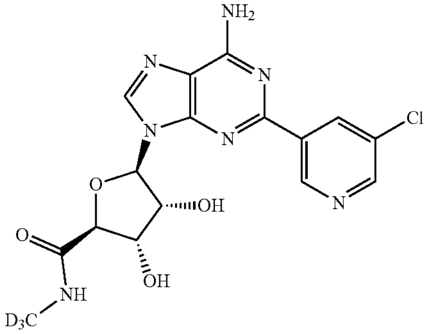 [SMILES: [2H]C([2H])([2H])NC(=O)[C@H]1O[C@@H](n2cnc3c(N)nc(-c4cncc(Cl)c4)nc32)[C@H](O)[C@@H]1O] (2S,3S,4R,5R)-5-(6-amino-2-(5-chloropyridin-3-yl)-9H-purin-9-yl)-3,4-dihydroxyl-N-(methyl-d3)-tetrahydrofuran-2-carboxamide | $^1$H NMR (500 MHz, DMSO-$d_6$) δ: 9.38 (d, J = 1.6 Hz, 1H), 8.71 (d, J = 2.4 Hz, 1H), 8.68-8.59 (m, 1H), 8.55 (s, 1H), 7.92 (s, 1H), 7.59 (s, 2H), 6.09 (d, J = 6.9 Hz, 1H), 5.68 (d, J = 4.7 Hz, 1H), 5.59 (d, J = 6.4 Hz, 1H), 4.88 (dd, J = 11.3, 6.5 Hz, 1H), 4.41-4.29 (m, 2H). LC-MS m/z [M + H]$^+$: 409. |
| 288 | 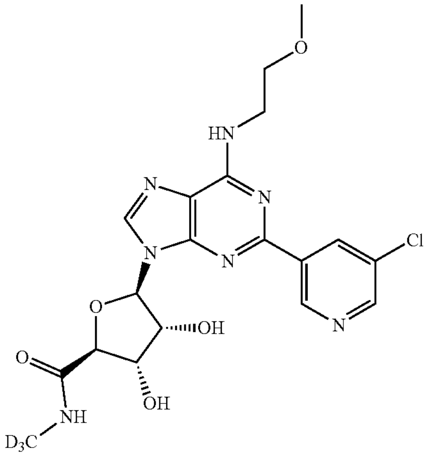 [SMILES: [2H]C([2H])([2H])NC(=O)[C@H]1O[C@@H](n2cnc3c(NCCOC)nc(-c4cncc(Cl)c4)nc32)[C@H](O)[C@@H]1O] (2S,3S,4R,5R)-5-(2-(5-chloropyridin-3-yl)-6-((2-methoxyethyl)amino)-9H-purin-9-yl)-3,4-dihydroxyl-N-(methyl-d3)-tetrahydrofuran-2-carboxamide | $^1$H NMR (500 MHz, DMSO-$d_6$) δ: 9.42 (s, 1H), 8.72 (d, J = 2.4 Hz, 1H), 8.62 (d, J = 1.8 Hz, 1H), 8.56 (s, 1H), 7.97 (d, J = 56.6 Hz, 2H), 6.10 (d, J = 6.8 Hz, 1H), 5.68 (s, 2H), 4.89 (dd, J = 6.5, 4.8 Hz, 1H), 4.39-4.27 (m, 2H), 3.79 (s, 2H), 3.62 (t, J = 5.6 Hz, 2H), 3.32 (s, 3H). LC-MS m/z [M + H]$^+$: 467. |

-continued

| No. | Compound structure and name | Characterization data |
| --- | --- | --- |
| 289 | 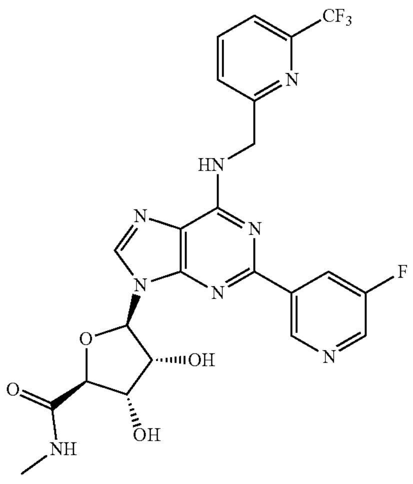 [SMILES: CNC(=O)[C@H]1O[C@@H](n2cnc3c(NCc4cccc(C(F)(F)F)n4)nc(-c4cncc(F)c4)nc32)[C@H](O)[C@@H]1O] (2S,3S,4R,5R)-5-(2-(5-fluoropyridin-3-yl)-6-(((6-(trifluoromethyl)pyridin-2-yl)methyl)amino)-9H-purin-9-yl)-3,4-dihydroxyl-N-methyltetrahydrofuran-2-carboxamide | $^1$H NMR (500 MHz, DMSO-d$_6$) δ: 9.19 (s, 1H), 8.90 (s, 1H), 8.62 (s, 2H), 8.21 (d, J = 9.8 Hz, 1H), 8.02 (d, J = 7.8 Hz, 1H), 7.94 (d, J = 4.7 Hz, 1H), 7.77 (d, J = 7.7 Hz, 1H), 7.69 (d, J = 8.0 Hz, 1H), 6.10 (d, J = 6.8 Hz, 1H), 5.70 (d, J = 4.6 Hz, 1H), 5.60 (d, J = 6.4 Hz, 1H), 4.92 (dd, J = 24.8, 4.9 Hz, 3H), 4.39-4.32 (m, 2H), 2.54 (d, J = 4.5 Hz, 3H). LC-MS m/z [M + H]$^+$: 549. |
| 290 | 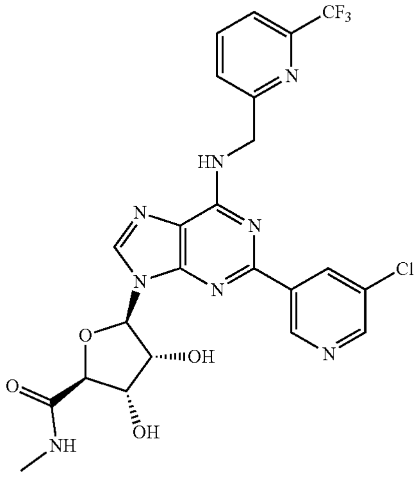 (2S,3S,4R,5R)-5-(2-(5-chloropyridin-3-yl)-6-(((6-(trifluoromethyl)pyridin-2-yl)methyl)amino)-9H-purin-9-yl)-3,4-dihydroxyl-N-methyltetrahydrofuran-2-carboxamide | $^1$H NMR (500 MHz, DMSO-d$_6$) δ: 9.25 (s, 1H), 8.89 (s, 1H), 8.65 (d, J = 18.8 Hz, 2H), 8.41 (s, 1H), 8.05-7.94 (m, 2H), 7.77 (d, J = 7.7 Hz, 1H), 7.69 (d, J = 7.9 Hz, 1H), 6.11 (d, J = 6.8 Hz, 1H), 5.72 (d, J = 4.7 Hz, 1H), 5.62 (d, J = 6.3 Hz, 1H), 4.92 (dd, J = 27.3, 4.9 Hz, 3H), 4.35 (d, J = 13.2 Hz, 2H), 2.51 (s, 3H). LC-MS m/z [M + H]$^+$: 565. |

-continued

| No. | Compound structure and name | Characterization data |
|---|---|---|
| 291 | 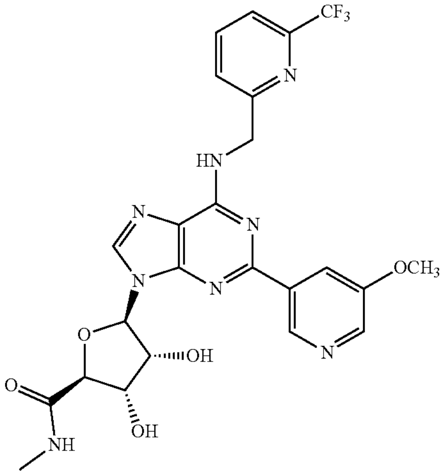 [SMILES: CNC(=O)[C@H]1O[C@@H](n2cnc3c(NCc4cccc(C(F)(F)F)n4)nc(-c4cncc(OC)c4)nc32)[C@H](O)[C@@H]1O] (2S,3S,4R,5R)-3,4-dihydroxyl-5-(2-(5-methoxypyridin-3-yl)-6-(((6-(trifluoromethyl)pyridin-2-yl)methyl)amino)-9H-purin-9-yl)-N-methyltetrahydrofuran-2-carboxamide | $^1$H NMR (500 MHz, DMSO-$d_6$) δ: 8.93 (s, 1H), 8.80 (s, 1H), 8.59 (s, 1H), 8.33 (s, 1H), 8.02 (t, J = 7.8 Hz, 1H), 7.94 (d, J = 4.2 Hz, 2H), 7.77 (d, J = 7.7 Hz, 1H), 7.69 (d, J = 8.0 Hz, 1H), 6.10 (d, J = 6.7 Hz, 1H), 5.70 (d, J = 4.5 Hz, 1H), 5.62 (d, J = 6.2 Hz, 1H), 4.95 (s, 3H), 4.36 (s, 2H), 3.85 (s, 3H), 2.52 (s, 3H). LC-MS m/z [M + H]$^+$: 561. |
| 292 | 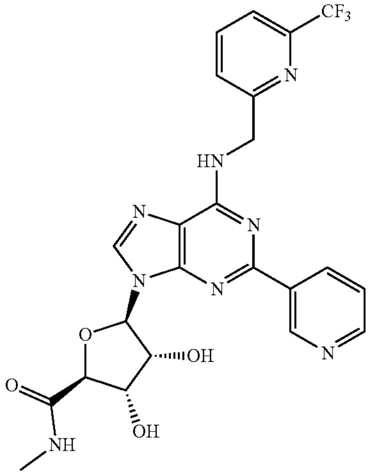 (2S,3S,4R,5R)-3,4-dihydroxyl-N-methyl-5-(2-pyridin-3-yl)-6-(((6-(trifluoromethyl)pyridin-2-yl)methyl)amino)-9H-purin-9-yl)tetrahydrofuran-2-carboxamide | $^1$H NMR (500 MHz, DMSO-$d_6$) δ: 9.31 (s, 1H), 8.81 (s, 1H), 8.59 (s, 2H), 8.45 (d, J = 7.1 Hz, 1H), 8.01 (t, J = 7.8 Hz, 1H), 7.97 (d, J = 20.6 Hz, 1H), 7.76 (d, J = 7.6 Hz, 1H), 7.68 (d, J = 7.9 Hz, 1H), 7.42 (s, 1H), 6.10 (d, J = 6.9 Hz, 1H), 5.71 (s, 2H), 4.91 (dd, J = 18.0, 13.0 Hz, 3H), 4.38-4.30 (m, 2H), 2.52 (s, 3H). LC-MS m/z [M + H]$^+$: 531. |

-continued

| No. | Compound structure and name | Characterization data |
|---|---|---|
| 293 | 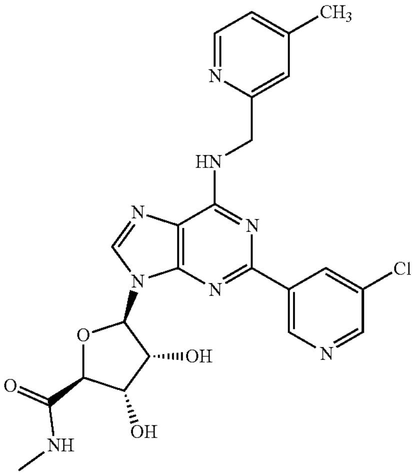 [SMILES: CNC(=O)[C@H]1O[C@@H](n2cnc3c(NCc4cc(C)ccn4)nc(-c4cncc(Cl)c4)nc32)[C@H](O)[C@@H]1O] (2S,3S,4R,5R)-5-(2-(5-chloropyridin-3-yl)-6-(((4-methylpyridin-2-yl)methyl)amino)-9H-purin-9-yl)-3,4-dihydroxyl-N-methyltetrahydrofuran-2-carboxamide | $^1$H NMR (500 MHz, DMSO-$d_6$) δ: 9.29 (s, 1H), 8.68 (s, 2H), 8.60 (s, 1H), 8.49 (s, 1H), 8.38 (d, J = 4.8 Hz, 1H), 7.94 (s, 1H), 7.24 (s, 1H), 7.07 (s, 1H), 6.10 (d, J = 6.8 Hz, 1H), 5.66 (d, J = 40.2 Hz, 2H), 4.86 (d, J = 21.8 Hz, 3H), 4.35 (d, J = 9.4 Hz, 2H), 2.55 (d, J = 4.4 Hz, 3H), 2.25 (d, J = 8.8 Hz, 3H). LC-MS m/z $[M + H]^+$: 511. |
| 294 | 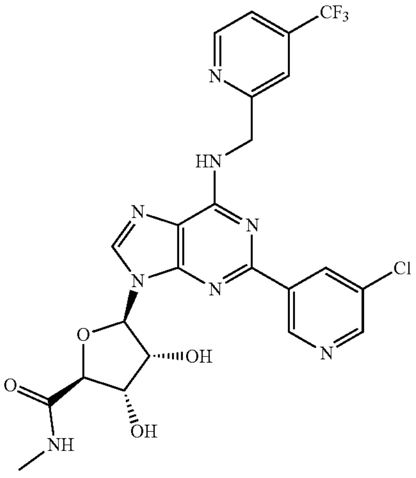 (2S,3S,4R,5R)-5-(2-(5-chloropyridin-3-yl)-6-(((4-(trifluoromethyl)pyridin-2-yl)methyl)amino)-9H-purin-9-yl)-3,4-dihydroxyl-N-methyltetrahydrofuran-2-carboxamide | $^1$H NMR (500 MHz, DMSO-$d_6$) δ: 9.28 (s, 1H), 8.82 (d, J = 5.0 Hz, 2H), 8.68 (s, 1H), 8.62 (s, 1H), 8.48 (s, 1H), 7.94 (d, J = 4.7 Hz, 1H), 7.82 (s, 1H), 7.65 (d, J = 4.5 Hz, 1H), 6.10 (d, J = 6.8 Hz, 1H), 5.69 (d, J = 4.7 Hz, 1H), 5.60 (d, J = 6.3 Hz, 1H), 5.00 (s, 2H), 4.89 (dd, J = 11.2, 6.3 Hz, 1H), 4.35 (dd, J = 9.1, 3.3 Hz, 2H), 2.55 (d, J = 4.6 Hz, 3H). LC-MS m/z $[M + H]^+$: 565. |

-continued

| No. | Compound structure and name | Characterization data |
|---|---|---|
| 295 | 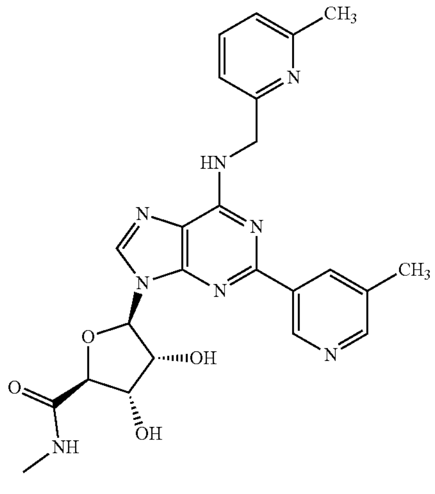 [SMILES: CNC(=O)[C@H]1O[C@@H](n2cnc3c(NCc4cccc(C)n4)nc(-c4cncc(C)c4)nc32)[C@H](O)[C@@H]1O] (2S,3S,4R,5R)-3,4-dihydroxyl-N-methyl-5-(6-(((6-methylpyridin-2-yl)methyl)amino)-2-(5-methylpyridin-3-yl)-9H-purin-9-yl)tetrahydrofuran-2-carboxamide | $^1$H NMR (500 MHz, DMSO-d$_6$) δ: 9.17 (s, 1H), 8.60 (s, 1H), 8.56 (s, 1H), 8.45 (s, 1H), 8.28 (s, 1H), 7.96 (q, J = 4.5 Hz, 1H), 7.59 (dd, J = 9.5, 5.8 Hz, 1H), 7.16 (d, J = 7.7 Hz, 1H), 7.10 (d, J = 7.6 Hz, 1H), 6.10 (d, J = 7.0 Hz, 1H), 5.71 (d, J = 4.6 Hz, 1H), 5.61 (d, J = 6.4 Hz, 1H), 4.94-4.78 (m, 3H), 4.39-4.31 (m, 2H), 2.53 (d, J = 4.7 Hz, 3H), 2.49 (d, J = 1.3 Hz, 3H), 2.36 (s, 3H). LC-MS m/z [M + H]$^+$: 491. |

Example 18: Synthesis of (2S,3S,4R,5R)-5-(2-(5-chloropyridin-3-yl)-6-(((4-methoxypyridin-2-yl)methyl)amino)-9H-purin-9-yl)-3,4-dihydroxyl-N-methyltetrahydrofuran-2-carboxamide (compound 296)

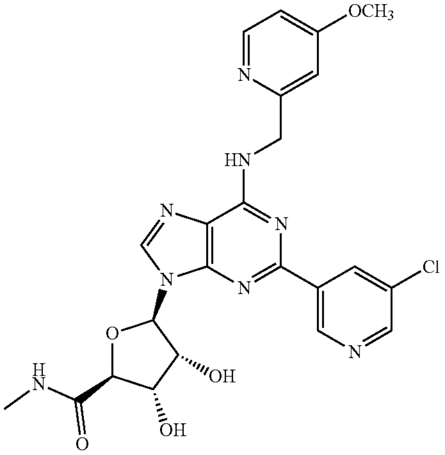 [SMILES: CNC(=O)[C@H]1O[C@@H](n2cnc3c(NCc4cc(OC)ccn4)nc(-c4cncc(Cl)c4)nc32)[C@H](O)[C@@H]1O]

S1: Synthesis of (3aS,4S,6R,6aR)-6-(2-chloro-6-((((4-methoxypyridin-2-yl)methyl)amino)-9H-purin-9-yl)-N,2,2-trimethyltetrahydrofuran[3,4-d][1,3]dioxazol-4-carboxamide

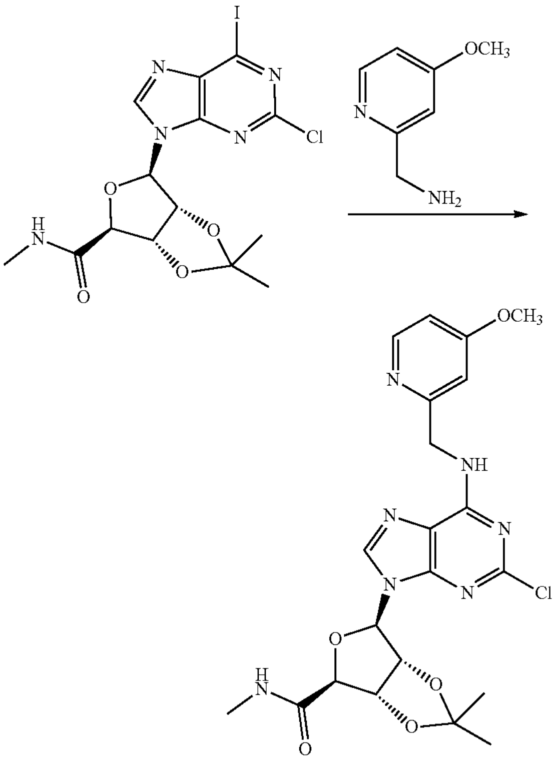

The reaction was performed according to the corresponding steps in example 8 to obtain the title compound as a white solid (0.489 g, yield of 99.1%). $^1$H NMR (500 MHz, DMSO-$d_6$) δ: 8.76 (s, 1H), 8.38-8.31 (m, 2H), 7.56 (d, J=4.6 Hz, 1H), 6.87 (s, 2H), 6.28 (s, 1H), 5.33 (s, 2H), 4.69 (d, J=5.4 Hz, 2H), 4.57 (s, 1H), 3.78 (s, 3H), 2.35 (d, J=4.5 Hz, 3H), 1.54 (s, 3H), 1.34 (s, 3H).

S2: Synthesis of (3aS,4S,6R,6aR)-6-(2-(5-chloropyridin-3-yl)-6-(((4-methoxypyridin-2-yl)methyl)amino)-9H-purin-9-yl)-N,2,2-trimethyltetrahydrofuran[3,4-d][1,3]dioxazol-4-carboxamide

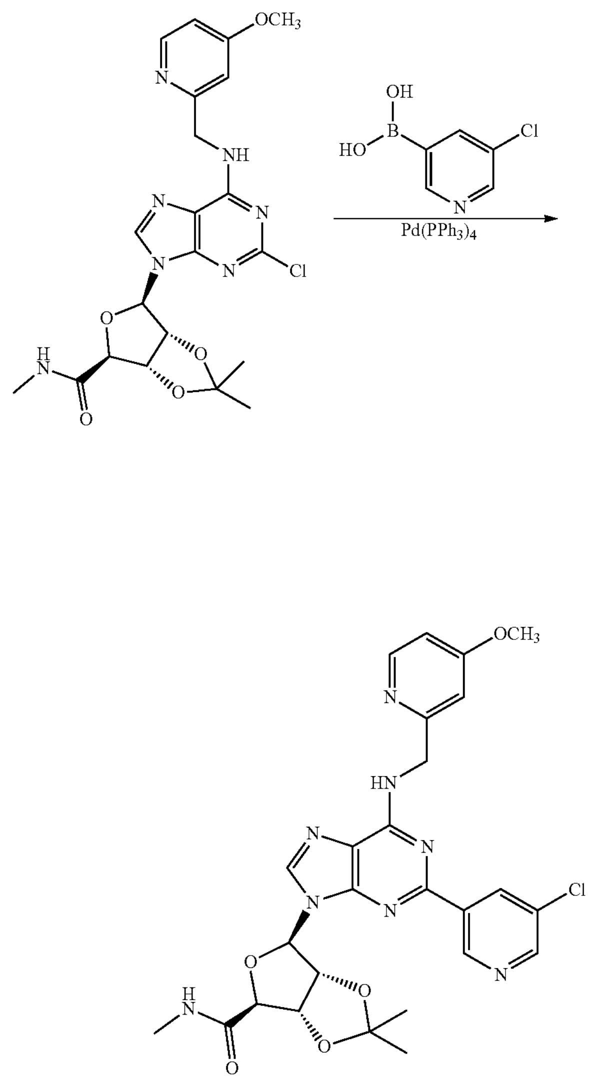

The reaction was performed according to step S7 in example 8 to obtain the title compound as a white solid (0.268 g, yield of 49.4%). $^1$H NMR (500 MHz, DMSO-$d_6$) δ: 9.28 (s, 1H), 8.75-8.44 (m, 3H), 8.35 (dd, J=17.4, 12.4 Hz, 2H), 7.38 (s, 1H), 6.89 (d, J=48.5 Hz, 2H), 6.49 (s, 1H), 5.54 (d, J=40.7 Hz, 2H), 4.81 (s, 2H), 4.63 (s, 1H), 3.75 (d, J=5.9 Hz, 3H), 2.03 (s, 3H), 1.55 (d, J=5.8 Hz, 3H), 1.36 (d, J=5.7 Hz, 3H).

S3: Synthesis of (2S,3S,4R,5R)-5-(2-(5-chloropyridin-3-yl)-6-(((4-methoxypyridin-2-yl)methyl)amino)-9H-purin-9-yl)-3,4-dihydroxyl-N-methyltetrahydrofuran-2-carboxamide (compound 296)

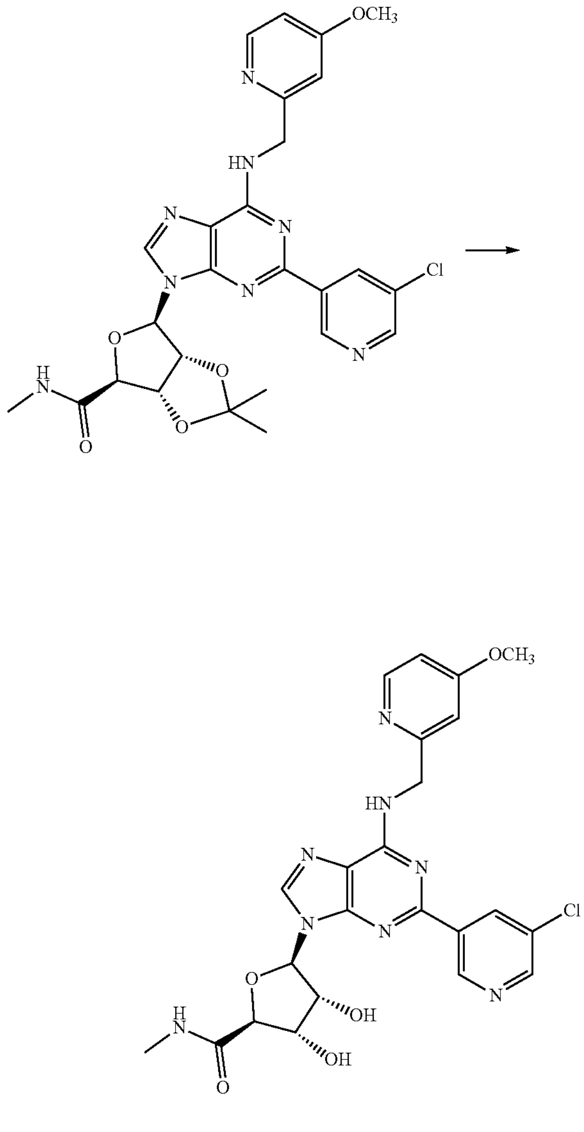

The reaction was performed according to step 8 in example 8 to obtain the title compound as a white solid (0.2044 g, yield of 82.0%). $^1$H NMR (500 MHz, DMSO-$d_6$) δ: 9.32 (s, 1H), 8.69 (s, 1H), 8.64 (s, 1H), 8.60 (s, 1H), 8.52 (s, 1H), 8.35 (d, J=5.7 Hz, 1H), 7.95 (d, J=4.2 Hz, 1H), 6.99 (s, 1H), 6.85 (dd, J=5.6, 2.2 Hz, 1H), 6.10 (d, J=6.8 Hz, 1H), 5.73 (s, 2H), 4.88 (dd, J=19.9, 14.1 Hz, 3H), 4.34 (d, J=13.1 Hz, 2H), 3.77 (s, 3H), 2.55 (d, J=3.7 Hz, 3H). LC-MS m/z $[M+H]^+$: 527.

Example 19: Following the Reactions Shown in Example 18, the Compounds in the Table Below were Obtained

| No. | Compound structure and name | Characterization data |
| --- | --- | --- |
| 297 | 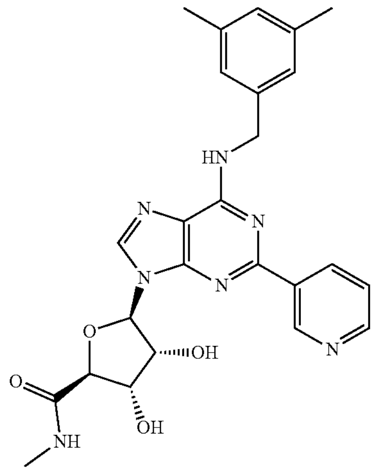 [SMILES: CNC(=O)[C@H]1O[C@@H](n2cnc3c(NCc4cc(C)cc(C)c4)nc(-c4cccnc4)nc32)[C@H](O)[C@@H]1O] (2S,3S,4R,5S)-5-(6-((3,5-dimethylbenzyl)amino)-2-(pyridin-3-yl)-9H-purin-9-yl)-3,4-dihydroxyl-N-methyltetrahydrofuran-2-carboxamide | $^1$H NMR (500 MHz, DMSO-$d_6$) δ: 9.45 (s, 1H), 8.67-8.56 (m, 3H), 8.53 (s, 1H), 7.95 (d, J = 4.7 Hz, 1H), 7.51 (dd, J = 7.7, 4.8 Hz, 1H), 7.06 (s, 2H), 6.84 (s, 1H), 6.09 (d, J = 6.9 Hz, 1H), 5.70 (d, J = 4.5 Hz, 1H), 5.60 (d, J = 6.3 Hz, 1H), 4.90 (dd, J = 11.1, 6.5 Hz, 1H), 4.73 (d, J = 4.9 Hz, 2H), 4.33 (dd, J = 5.7, 3.5 Hz, 2H), 2.52 (d, J = 4.8 Hz, 3H), 2.22 (s, 6H). LC-MS m/z [M + H]$^+$: 490. |
| 298 | 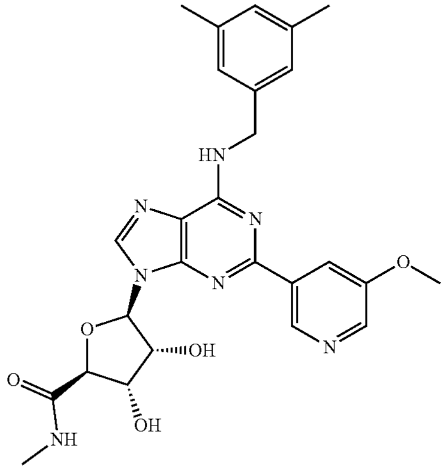 [SMILES: CNC(=O)[C@H]1O[C@@H](n2cnc3c(NCc4cc(C)cc(C)c4)nc(-c4cncc(OC)c4)nc32)[C@H](O)[C@@H]1O] (2S,3S,4R,5S)-5-(6-((3,5-dimethylbenzyl)amino)-2-(5-methoxypyridin-3-yl)-9H-purin-9-yl)-3,4-dihydroxyl-N-methyltetrahydrofuran-2-carboxamide | $^1$H NMR (500 MHz, DMSO-$d_6$) δ: 9.06 (s, 1H), 8.63 (s, 1H), 8.53 (s, 1H), 8.36 (d, J = 2.8 Hz, 1H), 8.08 (s, 1H), 7.92 (d, J = 4.7 Hz, 1H), 7.06 (s, 2H), 6.84 (s, 1H), 6.08 (d, J = 6.8 Hz, 1H), 5.68 (d, J = 4.6 Hz, 1H), 5.59 (d, J = 6.3 Hz, 1H), 4.92 (dd, J = 11.0, 6.5 Hz, 1H), 4.71 (d, J = 4.7 Hz, 2H), 4.39-4.30 (m, 2H), 3.91 (s, 3H), 2.51 (d, J = 1.9 Hz, 3H), 2.22 (s, 6H). LC-MS m/z [M + H]$^+$: 520. |
| 299 | 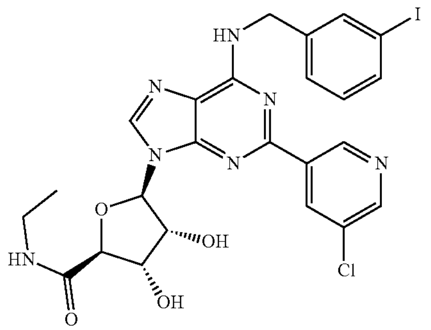 | $^1$H NMR (500 MHz, DMSO-$d_6$) δ: 9.32 (s, 1H), 8.68 (d, J = 15.1 Hz, 2H), 8.57 (s, 1H), 8.34 (d, J = 9.3 Hz, 1H), 7.94 (d, J = 4.2 Hz, 1H), 7.06 (s, 2H), 6.84 (s, 1H), 6.09 (d, J = 6.6 Hz, 1H), 5.69 (d, J = 4.1 Hz, 1H), 5.59 (d, J = 6.2 Hz, 1H), 4.89 (d, J = 4.6 Hz, 1H), 4.71 (d, J = 4.4 Hz, 2H), 4.35 (s, 2H), 2.53 (d, J = 4.4 Hz, 3H), 2.22 (s, 6H). LC-MS m/z [M + H]$^+$: 508. |

-continued

| No. | Compound structure and name | Characterization data |
|---|---|---|
| | (2S,3S,4R,5S)-5-(6-((3,5-dimethylbenzyl)amino)-2-(5-fluoropyridin-3-yl)-9H-purin-9-yl)-3,4-dihydroxyl-N-methyltetrahydrofuran-2-carboxamide | |
| 300 | 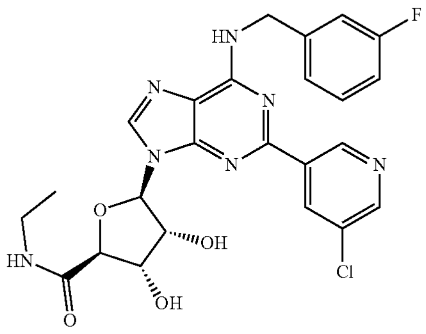 (2S,3S,4R,5S)-3,4-dihydroxyl-5-(2-(5-methoxypyridin-3-yl)-6-((3-methylbenzylamino)-9H-purin-9-yl)-N-methyltetrahydrofuran-2-carboxamide | $^1$H NMR (500 MHz, DMSO-d$_6$) δ 9.05 (s, 1H), 8.65 (s, 1H), 8.53 (s, 1H), 8.36 (d, J = 2.8 Hz, 1H), 8.07 (s, 1H), 7.91 (d, J = 4.7 Hz, 1H), 7.30-7.15 (m, 3H), 7.02 (d, J = 7.3 Hz, 1H), 6.08 (d, J = 6.8 Hz, 1H), 5.66 (d, J = 4.5 Hz, 1H), 5.58 (d, J = 6.3 Hz, 1H), 4.92 (dd, J = 11.0, 6.5 Hz, 1H), 4.75 (s, 2H), 4.39-4.28 (m, 2H), 3.91 (s, 3H), 2.51 (s, 3H), 2.26 (s, 3H). LC-MS (m/z): 506.3 [M + H]$^+$. |
| 301 | 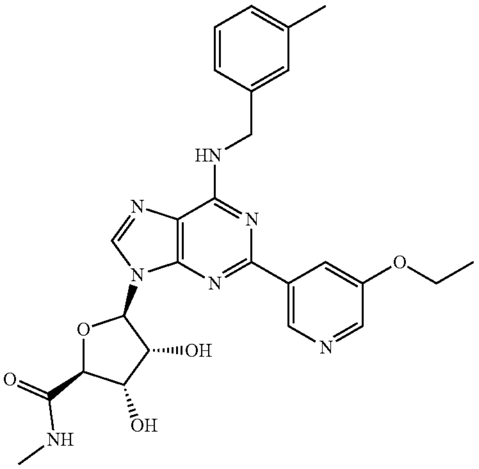 [SMILES: CCOc1cncc(-c2nc(NCc3cccc(C)c3)c3ncn([C@@H]4O[C@H](C(=O)NC)[C@@H](O)[C@H]4O)c3n2)c1] (2S,3S,4R,5S)-5-(2-(5-ethoxypyridin-3-yl)-6-((3-methylbenzyl)amino)-9H-purin-9-yl)-3,4-dihydroxyl-N-methyltetrahydrofuran-2-carboxamide | $^1$H NMR (500 MHz, DMSO-d$_6$) δ 9.03 (s, 1H), 8.65 (s, 1H), 8.53 (s, 1H), 8.33 (d, J = 2.7 Hz, 1H), 8.04 (s, 1H), 7.92 (d, J = 4.7 Hz, 1H), 7.29-7.14 (m, 3H), 7.02 (d, J = 7.2 Hz, 1H), 6.08 (d, J = 6.8 Hz, 1H), 5.66 (d, J = 4.5 Hz, 1H), 5.58 (d, J = 6.3 Hz, 1H), 4.91 (dd, J = 10.8, 6.3 Hz, 1H), 4.75 (s, 2H), 4.34 (d, J = 4.3 Hz, 2H), 4.17 (q, J = 6.4 Hz, 2H), 2.52 (s, 3H), 2.27 (s, 3H), 1.39 (t, J = 6.9 Hz, 3H). LC-MS (m/z): 520.3 [M + H]$^+$. |
| 302 | 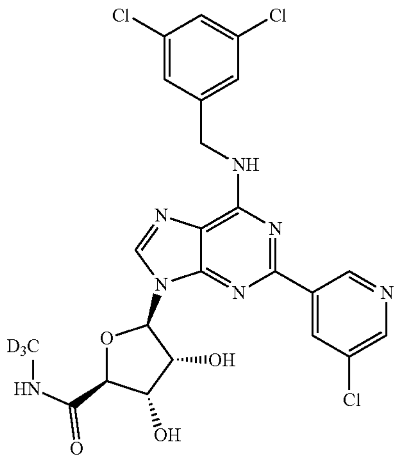 | $^1$H NMR (500 MHz, DMSO-d$_6$) δ 9.05 (s, 1H), 8.65 (s, 1H), 8.53 (s, 1H), 8.36 (d, J = 2.8 Hz, 1H), 8.07 (s, 1H), 7.89 (s, 1H), 7.32-7.13 (m, 3H), 7.02 (d, J = 7.3 Hz, 1H), 6.08 (d, J = 6.8 Hz, 1H), 5.66 (d, J = 4.5 Hz, 1H), 5.58 (d, J = 6.3 Hz, 1H), 4.92 (dd, J = 10.9, 6.4 Hz, 1H), 4.75 (s, 2H), 4.40-4.31 (m, 2H), 3.91 (s, 3H), 2.26 (s, 3H). LC-MS (m/z): 509.3 [M + H]$^+$. |

-continued

| No. | Compound structure and name | Characterization data |
|---|---|---|
| | (2S,3S,4R,5S)-3,4-dihydroxyl-5-(2-(5-methoxypyridin-3-yl)-6-((3-methylbenzylamino)-9H-purin-9-yl)-N-methyl-D3-tetrahydrofuran-2-carboxamide | |
| 303 | 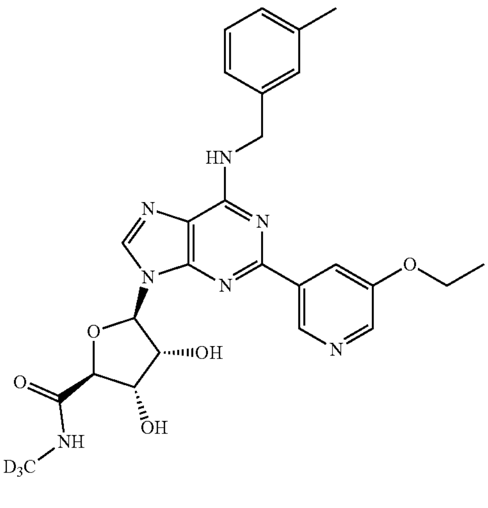 [SMILES: [2H]C([2H])([2H])NC(=O)[C@H]1O[C@@H](n2cnc3c(NCc4cccc(C)c4)nc(-c4cncc(OCC)c4)nc32)[C@H](O)[C@@H]1O] (2S,3S,4R,5S)-5-(2-(5-ethoxypyridin-3-yl)-6-((3-methylbenzyl)amino)-9H-purin-9-yl)-3,4-dihydroxyl-N-(methyl-d3)-tetrahydrofuran-2-carboxamide | $^1$H NMR (500 MHz, DMSO-$d_6$) δ 9.03 (s, 1H), 8.65 (s, 1H), 8.53 (s, 1H), 8.33 (d, J = 2.8 Hz, 1H), 8.04 (s, 1H), 7.90 (s, 1H), 7.31-7.13 (m, 3H), 7.02 (d, J = 7.2 Hz, 1H), 6.08 (d, J = 6.8 Hz, 1H), 5.67 (d, J = 4.6 Hz, 1H), 5.58 (d, J = 6.3 Hz, 1H), 4.91 (dd, J = 10.8, 6.4 Hz, 1H), 4.75 (s, 2H), 4.39-4.28 (m, 2H), 4.17 (dd, J = 13.1, 6.2 Hz, 2H), 2.27 (s, 3H), 1.39 (t, J = 6.9 Hz, 3H). LC-MS (m/z): 523.3 [M + H]$^+$. |
| 304 | 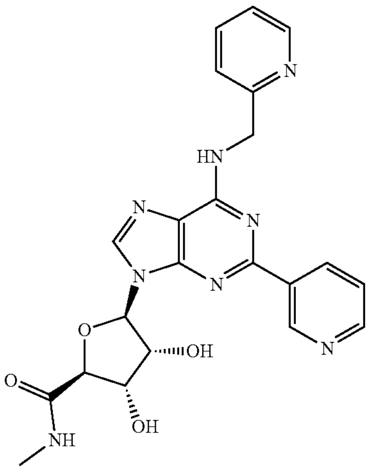 [SMILES: CNC(=O)[C@H]1O[C@@H](n2cnc3c(NCc4ccccn4)nc(-c4cccnc4)nc32)[C@H](O)[C@@H]1O] (2S,3S,4R,5S)-3,4-dihydroxyl-N-methyl-5-(6-((pyridin-2-ylmethyl)amino)-2-(pyridin-3-yl)-9H-purin-9-yl)tetrahydrofuran-2-carboxamide | $^1$H NMR (500 MHz, DMSO-$d_6$) δ 9.35 (s, 1H), 8.77-8.42 (m, 5H), 7.95 (dd, J = 9.1, 4.4 Hz, 1H), 7.72 (td, J = 7.7, 1.7 Hz, 1H), 7.48 (d, J = 4.6 Hz, 1H), 7.38 (d, J = 7.9 Hz, 1H), 7.24 (dd, J = 7.0, 5.2 Hz, 1H), 6.10 (d, J = 6.9 Hz, 1H), 5.70 (d, J = 4.5 Hz, 1H), 5.61 (d, J = 6.4 Hz, 1H), 4.91 (d, J = 4.7 Hz, 3H), 4.34 (d, J = 5.1 Hz, 2H), 2.52 (d, J = 4.7 Hz, 3H). LC-MS (m/z): 463.2 [M + H]$^+$. |

-continued

| No. | Compound structure and name | Characterization data |
|---|---|---|
| 305 | 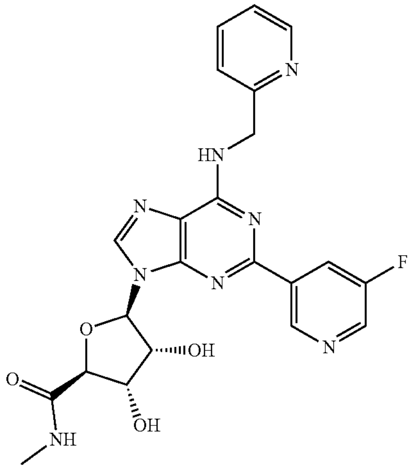 [SMILES: CNC(=O)[C@H]1O[C@@H](n2cnc3c(NCc4ccccn4)nc(-c4cncc(F)c4)nc32)[C@H](O)[C@@H]1O] (2S,3S,4R,5S)-5-(2-(5-fluoropyridin-3-yl)-6-((pyridin-2-ylmethyl)amino)-9H-purin-9-yl)-3,4-dihydroxyl-N-methyltetrahydrofuran-2-carboxamide | $^1$H NMR (500 MHz, DMSO-d$_6$) δ 9.22 (s, 1H), 8.81-8.49 (m, 4H), 8.26 (d, J = 9.1 Hz, 1H), 8.00-7.90 (m, 1H), 7.72 (td, J = 7.7, 1.5 Hz, 1H), 7.39 (d, J = 7.9 Hz, 1H), 7.25 (dd, J = 7.0, 5.2 Hz, 1H), 6.10 (d, J = 6.8 Hz, 1H), 5.69 (d, J = 4.6 Hz, 1H), 5.60 (d, J = 6.4 Hz, 1H), 4.90 (d, J = 4.8 Hz, 3H), 4.36 (s, 2H), 2.54 (d, J = 4.7 Hz, 3H). LC-MS (m/z): 481.2 [M + H]$^+$. |
| 306 | 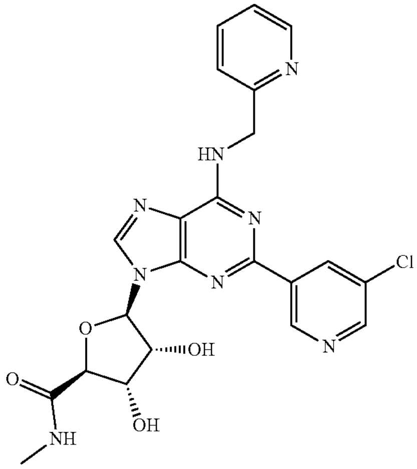 [SMILES: CNC(=O)[C@H]1O[C@@H](n2cnc3c(NCc4ccccn4)nc(-c4cncc(Cl)c4)nc32)[C@H](O)[C@@H]1O] (2S,3S,4R,5S)-5-(2-(5-chloropyridin-3-yl)-6-((pyridin-2-lymethyl)amino)-9H-purin-9-yl)-3,4-dihydroxyl-N-methyltetrahydrofuran-2-carboxamide | $^1$H NMR (500 MHz, DMSO-d$_6$) δ 9.28 (s, 1H), 8.77-8.35 (m, 5H), 7.94 (d, J = 4.7 Hz, 1H), 7.73 (dd, J = 10.7, 4.5 Hz, 1H), 7.39 (d, J = 7.9 Hz, 1H), 7.27-7.16 (m, 1H), 6.10 (d, J = 6.8 Hz, 1H), 5.68 (d, J = 4.7 Hz, 1H), 5.59 (d, J = 6.4 Hz, 1H), 4.89 (d, J = 3.9 Hz, 3H), 4.43-4.23 (m, 2H), 2.55 (d, J = 4.6 Hz, 3H). LC-MS (m/z): 497.2 [M + H]$^+$. |
| 307 | 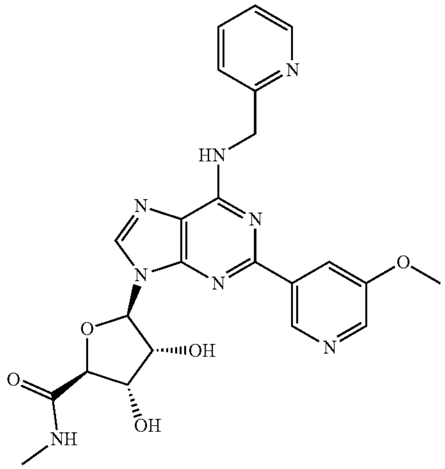 [SMILES: CNC(=O)[C@H]1O[C@@H](n2cnc3c(NCc4ccccn4)nc(-c4cncc(OC)c4)nc32)[C@H](O)[C@@H]1O] | $^1$H NMR (500 MHz, DMSO-d$_6$) δ 8.97 (s, 1H), 8.56 (dd, J = 39.7, 21.4 Hz, 3H), 8.33 (s, 1H), 8.06-7.85 (m, 2H), 7.72 (t, J = 7.6 Hz, 1H), 7.39 (d, J = 7.7 Hz, 1H), 7.29-7.18 (m, 1H), 6.09 (d, J = 6.8 Hz, 1H), 5.67 (d, J = 3.7 Hz, 1H), 5.59 (d, J = 6.3 Hz, 1H), 4.91 (dd, J = 14.3, 8.5 Hz, 3H), 4.35 (s, 2H), 3.88 (s, 3H), 2.52 (s, 3H). LC-MS (m/z): 493.2 [M + H]$^+$. |

-continued

| No. | Compound structure and name | Characterization data |
|---|---|---|
| | (2S,3S,4R,5S)-3,4-dihydroxyl-5-(2-(5-methoxypyridin-3-yl)-6-((pyridin-2-ylmethyl)amino)-9H-purin-9-yl)-N-methyltetrahydrofuran-2-carboxamide | |
| 308 | 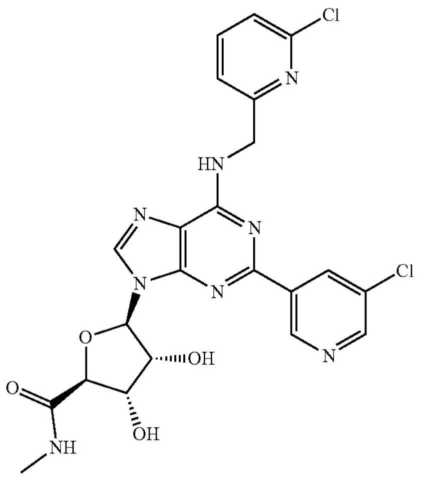 [SMILES: CNC(=O)[C@H]1O[C@@H](n2cnc3c(NCc4cccc(Cl)n4)nc(-c4cncc(Cl)c4)nc32)[C@H](O)[C@@H]1O] (2S,3S,4R,5S)-5-(6-((((6-chloropyridin-2-yl)methyl)amino)-2-(5-chloropyridin-3-ly)-9H-purin-9-yl)-3,4-dihydroxyl-N-methyltetrahydrofuran-2-carboxamide | $^1$H NMR (500 MHz, DMSO-$d_6$) δ 9.29 (s, 1H), 8.82 (s, 1H), 8.69 (s, 1H), 8.62 (s, 1H), 8.46 (s, 1H), 7.95 (d, J = 4.7 Hz, 1H), 7.80 (t, J = 7.8 Hz, 1H), 7.39 (dd, J = 11.1, 7.8 Hz, 2H), 6.11 (d, J = 6.9 Hz, 1H), 5.70 (d, J = 4.7 Hz, 1H), 5.61 (d, J = 6.4 Hz, 1H), 4.94-4.69 (m, 3H), 4.35 (dd, J = 10.2, 3.4 Hz, 2H), 2.55 (d, J = 4.7 Hz, 3H). LC-MS (m/z): 531.2 $[M + H]^+$. |
| 309 | 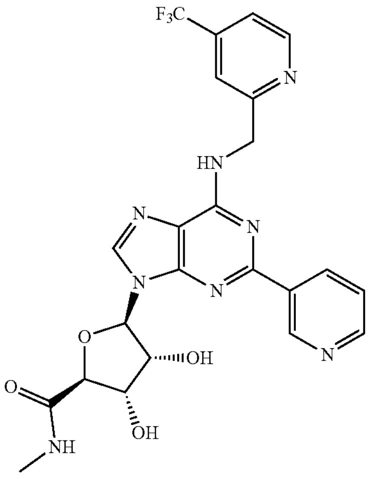 [SMILES: CNC(=O)[C@H]1O[C@@H](n2cnc3c(NCc4cc(C(F)(F)F)ccn4)nc(-c4cccnc4)nc32)[C@H](O)[C@@H]1O] (2S,3S,4R,5S)-3,4-dihydroxyl-N-methyl-5-(2-(pyridin-3-yl)-6-((((4-(trifluoromethyl)pyridin-2-yl] methyl)amino)-9H-purin-9-yl)tetrahydrofuran-2-carboxamide | $^1$H NMR (500 MHz, DMSO-$d_6$) δ 9.34 (s, 1H), 8.82 (d, J = 5.1 Hz, 1H), 8.74 (s, 1H), 8.66-8.54 (m, 2H), 8.49 (d, J = 7.3 Hz, 1H), 7.95 (d, J = 4.7 Hz, 1H), 7.81 (s, 1H), 7.65 (d, J = 4.9 Hz, 1H), 7.46 (s, 1H), 6.10 (d, J = 6.9 Hz, 1H), 5.70 (d, J = 4.5 Hz, 1H), 5.61 (d, J = 6.3 Hz, 1H), 5.00 (s, 2H), 4.91 (dd, J = 11.0, 6.5 Hz, 1H), 4.35 (d, J = 4.3 Hz, 2H), 2.55-2.51 (m, 3H). LC-MS (m/z): 531.4 $[M + H]^+$. |

-continued

| No. | Compound structure and name | Characterization data |
|---|---|---|
| 310 | 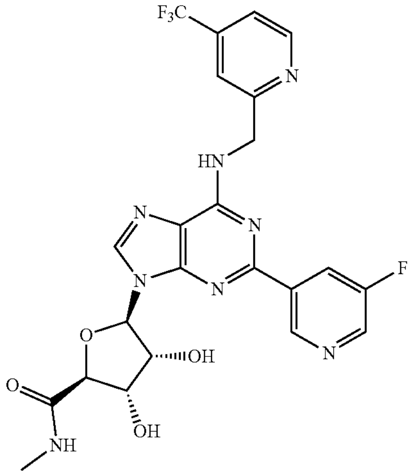 [SMILES: CNC(=O)[C@H]1O[C@@H](n2cnc3c(NCc4cc(C(F)(F)F)ccn4)nc(-c4cncc(F)c4)nc32)[C@H](O)[C@@H]1O] (2S,3S,4R,5S)-5-(2-(5-fluoropyridin-3-yl)-6-((((4-(trifluoromethyl)pyridin-2-yl)methyl)amino)-9H-purin-9-yl)-3,4-dihydroxyl-N-methyltetrahydrofuran-2-carboxamide | $^1$H NMR (500 MHz, DMSO-$d_6$) δ 9.22 (s, 1H), 8.82 (d, J = 5.1 Hz, 2H), 8.71-8.56 (m, 2H), 8.27 (d, J = 9.3 Hz, 1H), 7.94 (d, J = 4.7 Hz, 1H), 7.84 (s, 1H), 7.64 (d, J = 4.7 Hz, 1H), 6.10 (d, J = 6.7 Hz, 1H), 5.69 (d, J = 4.7 Hz, 1H), 5.60 (d, J = 6.3 Hz, 1H), 5.00 (d, J = 4.4 Hz, 2H), 4.93-4.85 (m, 1H), 4.35 (d, J = 6.8 Hz, 2H), 2.54 (d, J = 4.7 Hz, 3H). LC-MS (m/z): 549.3 $[M + H]^+$. |
| 311 | 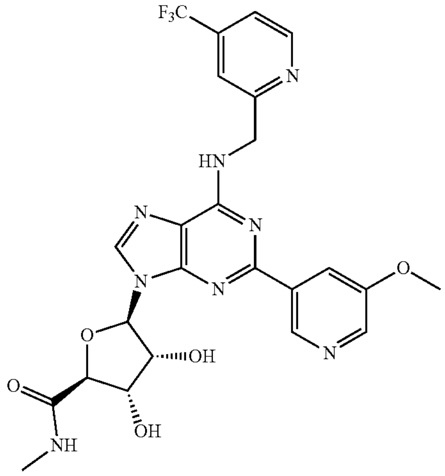 [SMILES: CNC(=O)[C@H]1O[C@@H](n2cnc3c(NCc4cc(C(F)(F)F)ccn4)nc(-c4cncc(OC)c4)nc32)[C@H](O)[C@@H]1O] (2S,3S,4R,5S)-3,4-dihydroxyl-5-(2-(5-methoxypyridin-3-yl)-6-((((4-(trifluoromethyl)pyridin-2-yl)methyl)amino)-9H-purin-9-yl)-N-methyltetrahydrofuran-2-carboxamide | $^1$H NMR (500 MHz, DMSO-$d_6$) δ 8.96 (s, 1H), 8.82 (d, J = 5.1 Hz, 1H), 8.75 (s, 1H), 8.59 (s, 1H), 8.34 (s, 1H), 7.99 (s, 1H), 7.94 (d, J = 4.7 Hz, 1H), 7.79 (s, 1H), 7.65 (d, J = 4.8 Hz, 1H), 6.10 (d, J = 6.7 Hz, 1H), 5.69 (d, J = 4.6 Hz, 1H), 5.61 (d, J = 6.3 Hz, 1H), 5.07-4.86 (m, 3H), 4.36 (d, J = 3.5 Hz, 2H), 3.88 (s, 3H), 2.52 (d, J = 4.6 Hz, 3H). LC-MS (m/z): 561.3 $[M + H]^+$. |

-continued

| No. | Compound structure and name | Characterization data |
| --- | --- | --- |
| 312 | 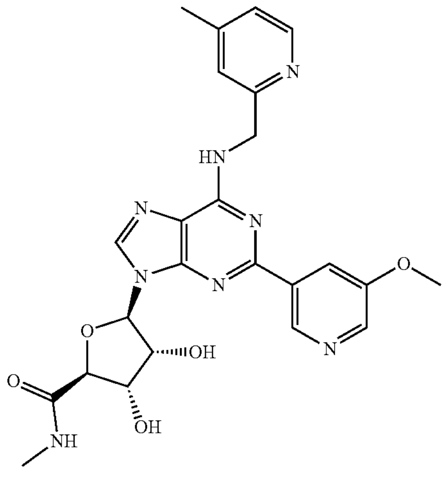 [SMILES: CNC(=O)[C@H]1O[C@@H](n2cnc3c(NCc4cc(C)ccn4)nc(-c4cncc(OC)c4)nc32)[C@H](O)[C@@H]1O] (2S,3S,4R,5S)-3,4-dihydroxyl-5-(2-(5-methoxypyridin-3-yl)-6-((((4-(methylpyridin-2-yl)methyl)amino)-9H-purin-9-yl)-N-methyltetrahydrofuran-2-carboxamide | $^1$H NMR (500 MHz, DMSO-$d_6$) δ 8.99 (s, 1H), 8.59 (d, J = 16.0 Hz, 2H), 8.41-8.30 (m, 2H), 8.02 (s, 1H), 7.94 (dd, J = 9.1, 4.4 Hz, 1H), 7.24 (s, 1H), 7.08 (d, J = 4.8 Hz, 1H), 6.10 (d, J = 6.8 Hz, 1H), 5.69 (d, J = 4.7 Hz, 1H), 5.61 (d, J = 6.3 Hz, 1H), 4.98-4.91 (m, 1H), 4.86 (s, 2H), 4.36 (s, 2H), 3.89 (s, 3H), 2.52 (s, 3H), 2.26 (s, 3H). LC-MS (m/z) : 507.3 [M + H]$^+$. |

Example 20: Synthesis of (2S,3S,4R,5R)-5-(2-benzyl-6-(methylamino)-9H-purin-9-yl)-N-ethyl-3,4-dihydroxyltetrahydrofuran-2-carboxamide (compound 313)

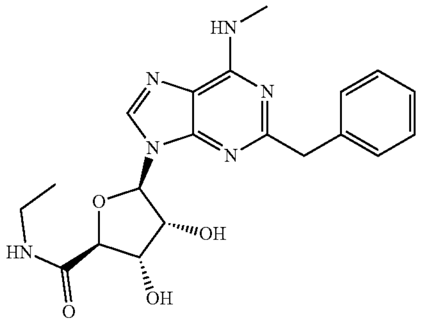 [SMILES: CCNC(=O)[C@H]1O[C@@H](n2cnc3c(NC)nc(Cc4ccccc4)nc32)[C@H](O)[C@@H]1O]

S1: Referring to example 8, (3aS,4S,6R,6aR)-6-(2-chloro-6-(methylamino)-9H-purin)-N-ethyl-2,2-dimethyltetrahydrofuran[3,4-d][1,3]dioxazol-4-carboxamide was obtained S2: Synthesis of (3aS,4S,6R,6aR)-6-(2-benzyl-6-(methylamino)-9H-purin)-N-ethyl-2,2-dimethyltetrahydrofuran[3,4-d][1,3]dioxazol-4-carboxamide

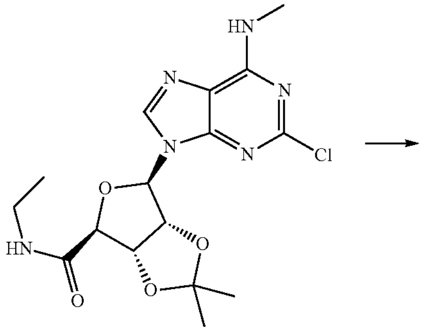

-continued

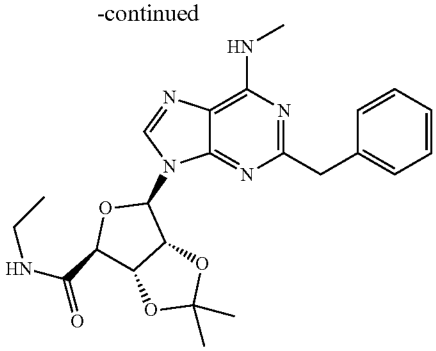

(3aS,4S,6R,6aR)-6-(2-chloro-6-(methylamino)-9H-purin)-N-ethyl-2,2-dimethyltetrahydrofuran[3,4-d][1,3]dioxazol-4-carboxamide (0.20 g, 0.5 mmol) was dissolved in tetrahydrofuran (6 mL) and water (2 mL), and benzyl potassium trifluoroborate (396 mg, 1 mmol), cesium carbonate (651 mg, 2 mmol), and dictriphenyl phosphorus palladium dichloride (82 mg, 0.1 mmol) were added sequentially. Nitrogen was replaced three times, and the materials were sealed in a high-pressure reactor and heated at 100° C. for 15 hours. After cooled, the reaction solution was concentrated and dried. It was dissolved in ethyl acetate (30 mL), and the organic phase (10 mL×2 times) was washed with water. The organic phase was dried and concentrated, and purified by silica gel column chromatography (methanol:dichloromethane=1:80) to obtain 75 mg of a white solid with a yield of 33.2%. $^1$H NMR (500 MHz, DMSO-$d_6$): δ. 8.08 (s, 1H), 7.60 (s, 1H), 7.29 (d, 2H), 7.19 (t, 3H), 7.10 (d, 1H), 6.25 (s, 1H), 5.36 (dd, 1H), 5.17 (d, 1H), 4.44 (d, 1H), 3.88 (s, 2H), 2.85 (s, 3H), 2.65 (m, 2H), 1.43 (s, 3H), 1.20 (s, 3H), 0.43 (t, 3H).

S3: Synthesis of (2S,3S,4R,5R)-5-(2-benzyl-6-(methylamino)-9H-purin-9-yl)-N-ethyl-3,4-dihydroxyltetrahydrofuran-2-carboxamide (compound 313)

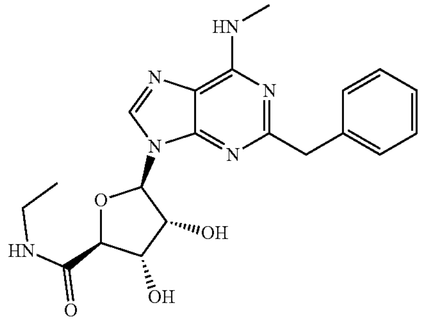 [SMILES: CCNC(=O)[C@H]1O[C@@H](n2cnc3c(NC)nc(Cc4ccccc4)nc32)[C@H](O)[C@@H]1O]

The reaction was performed according S8 in example 8 to obtain the title compound as 40 mg of a white solid with a yield of 58.5%. $^1$H NMR (500 MHz, DMSO-$d_6$): δ. 8.38 (s, 2H), 7.79 (d, 1H), 7.33 (d, 2H), 7.27 (t, 2H), 7.18 (t, 2H), 5.98 (d, 1H), 5.71 (d, 1H), 5.56 (d, 1H), 4.63 (q, 1H), 4.30 (s, 2H), 4.18 (t, 1H), 4.02 (s, 2H), 3.15 (m, 2H), 2.93 (s, 3H), 0.99 (t, 3H).

Example 21: Synthesis of (2S,3S,4R,5R)-5-(2-(5-ethoxypyridin-3-yl)-6-(methylamino)-9H-purin-9-yl)-3,4-dihydroxyl-N-methoxytetrahydrofuran-2-carboxamide (compound 314)

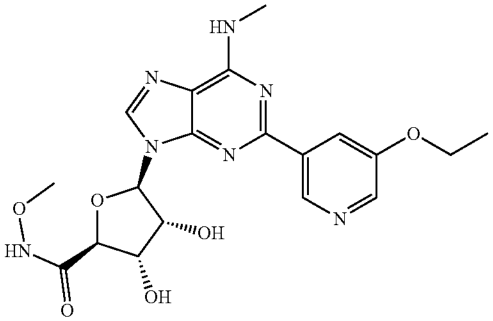 [SMILES: CCOc1cncc(-c2nc(NC)c3ncn([C@@H]4O[C@H](C(=O)NOC)[C@@H](O)[C@H]4O)c3n2)c1]

S1: Synthesis of (3aS,4S,6R,6aR)-6-(2-chloro-6-(methylamino)-9H-purin)-N-methoxy-2,2-dimethyltetrahydrofuran[3,4-d][1,3]dioxazol-4-carboxamide

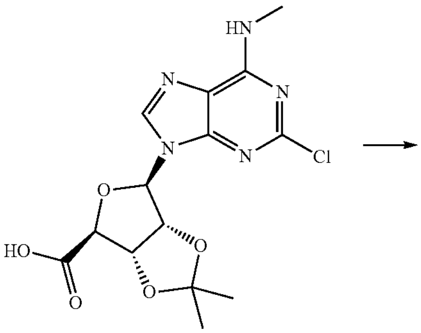

-continued

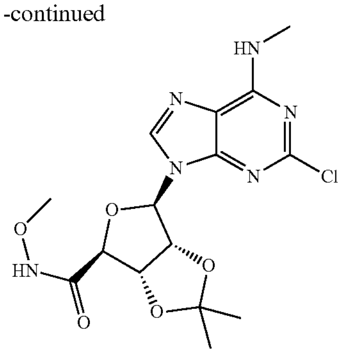

((3aS,4S,6R,6aR)-6-(2-chloro-6-(methylamino)-9H-purin)-2,2-dimethyltetrahydrofuran[3,4-d][1,3]dioxazol-4-carboxamide (1.00 g, 2.7 mmol) was dissolved in DMF (10 mL), and 1-propyl phosphoric anhydride (3.44 g, 5.4 mmol, 50%), methoxamine hydrochloride (339 mg, 4 mmol), and N,N-diisopropylethylamine (1.04 g, 8.1 mmol) were added respectively. The materials were heated at 80° C. for 3 hours. After cooled, the reaction solution was diluted with water (50 mL) and extracted with ethyl acetate (20 mL×3 times). The organic phase was dried and concentrated, and purified by silica gel column chromatography to obtain 0.60 g of a white solid with a yield of 55.7%. $^1$H NMR (500 MHz, DMSO-$d_6$): δ. 11.02 (s, 1H), 8.29 (d, 1H), 8.26 (s, 1H), 6.29 (s, 1H), 5.43 (dd, 1H), 5.37 (d, 1H), 4.57 (d, 1H), 3.25 (s, 3H), 2.90 (d, 3H), 1.52 (s, 3H), 1.35 (s, 3H).

S2: Synthesis of (3aS,4S,6R,6aR)-6-(2-(5-ethoxypyridin)-6-(methylamino)-9H-purin)-N-methoxy-2,2-dimethyltetrahydrofuran[3,4-d][1,3]dioxazol-4-carboxamide

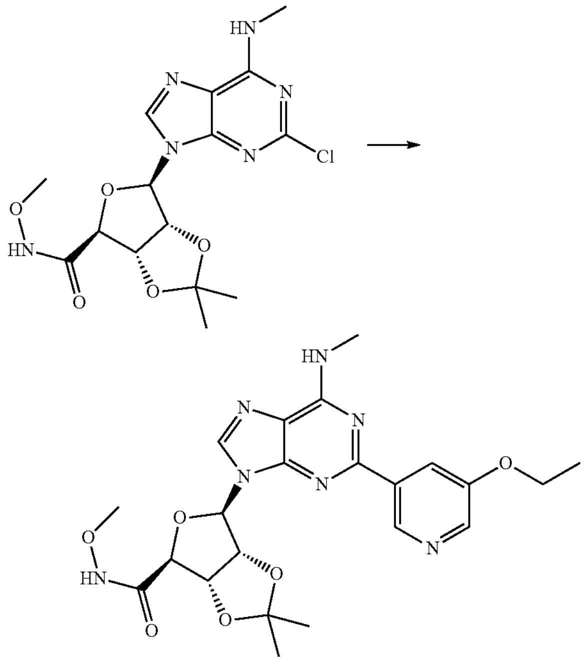

(3aS,4S,6R,6aR)-6-(2-chloro-6-(methylamino)-9H-purin)-N-methoxy-2,2-dimethyltetrahydrofuran[3,4-d][1,3]dioxazol-4-carboxamide (0.15 g, 0.38 mmol) was dissolved in tetrahydrofuran (6 mL) and water (2 mL), and 3-ethoxy-5-pyridin borate pinanol ester (112 mg, 0.45 mmol), potassium carbonate (155 mg, 1.13 mmol), and tetra(triphenylphosphine)palladium (43 mg, 0.038 mmol) were added respectively. Nitrogen was replaced three times, and the materials were heated at 80° C. for 15 hours. The reaction solution was concentrated and dried. It was dissolved in ethyl acetate (30 mL), and the organic phase (10 mL×2 times) was washed with water. The organic phase was dried and concentrated, and purified by silica gel column chromatography (methanol:dichloromethane=1:70) to obtain 63 mg of a white solid with a yield of 34.2%. $^{1}H$ NMR (500 MHz, DMSO-$d_6$): δ. 10.82 (s, 1H), 9.00 (s, 1H), 8.27 (d, 1H), 8.12 (s, 1H), 7.86 (s, 1H), 6.42 (s, 1H), 5.68 (dd, 1H), 5.48 (d, 1H), 4.61 (d, 1H), 4.22 (q, 2H), 2.98 (s, 3H), 2.81 (s, 3H), 1.47 (s, 3H), 1.35 (t, 3H), 1.29 (s, 3H).

S2: Synthesis of (2S,3S,4R,5R)-5-(2-(5-ethoxypyridin-3-yl)-6-(methylamino)-9H-purin-9-yl)-3,4-dihydroxyl-N-methoxytetrahydrofuran-2-carboxamide (compound 314)

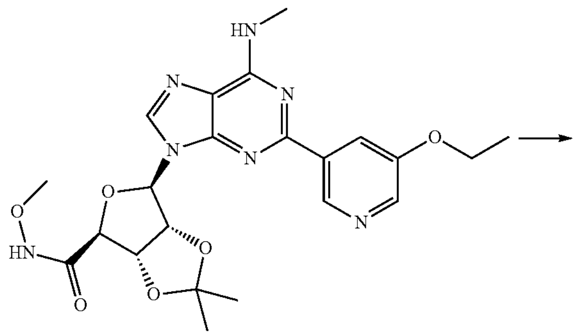

-continued

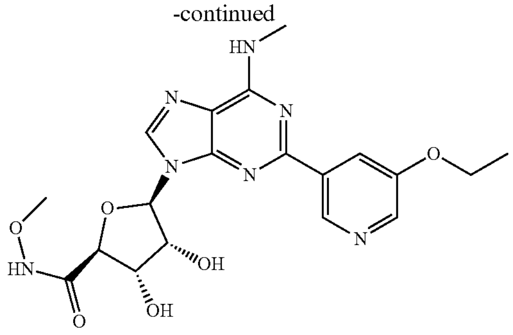

The reaction was performed according S8 in example 8 to obtain the title compound as 28 mg of a white solid with a yield of 50.1%. $^{1}H$ NMR (500 MHz, DMSO-$d_6$): δ. 9.15 (s, 1H), 8.43 (s, 1H), 8.36 (d, 1H), 8.19 (s, 1H), 7.97 (s, 1H), 6.16 (d, 1H), 5.89 (s, 1H), 5.74 (s, 1H), 4.80 (t, 1H), 4.54 (d, 1H), 4.49 (d, 1H), 4.23 (q, 2H), 3.68 (s, 3H), 3.09 (s, 3H), 1.40 (t, 3H).

Example 22: Following the Reactions Shown in Example 21, the Compounds in the Table Below were Obtained

| No. | Compound structure and name | Characterization data |
|---|---|---|
| 315 | 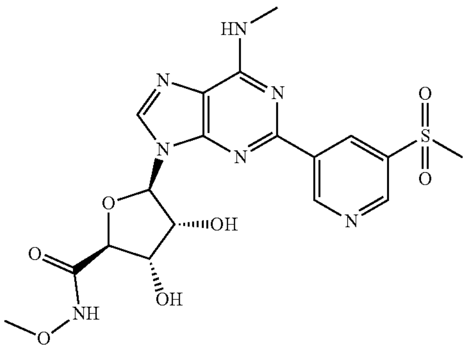 (2S,3S,4R,5R)-3,4-dihydroxyl-N-methoxy-5-(6-(methylamino)-2-(5-(methylsulfonyl)pyridin-3-yl)-9H-purin-9-yl)tetrahydrofuran-2-carboxamide | $^{1}H$ NMR (500 MHz, DMSO-$d_6$): δ. 9.82 (s, 1H), 9.18 (d, 1H), 9.07 (s, 1H), 8.50 (s, 1H), 8.12 (s, 1H), 6.21 (d, 1H), 5.94 (d, 1H), 5.76 (d, 1H), 4.78 (d, 1H), 4.46 (d, 1H), 4.44 (q, 1H), 3.70 (s, 3H), 3.43 (s, 3H), 3.12 (d, 3H). |

-continued

| No. | Compound structure and name | Characterization data |
|---|---|---|
| 316 | 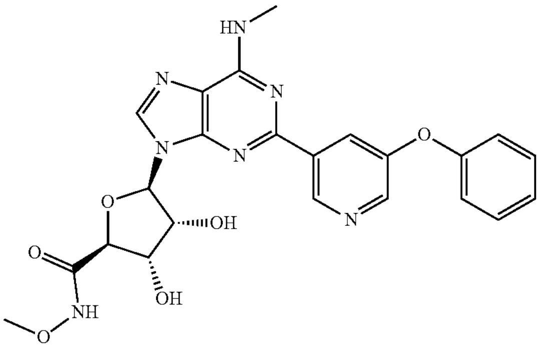 [SMILES: CNc1nc(-c2cncc(Oc3ccccc3)c2)nc2c1ncn2[C@@H]1O[C@H](C(=O)NOC)[C@@H](O)[C@H]1O] (2S,3S,4R,5R)-3,4-dihydroxyl-N-methoxy-5-(6-(methylamino)-2-(5-phenoxypyridin-3-yl)-9H-purin-9-yl)tetrahydrofuran-2-carboxamide | $^1$H NMR (500 MHz, DMSO-$d_6$): δ. 9.34 (s, 1H), 8.44 (d, 2H), 8.26 (s, 1H), 7.99 (s, 1H), 7.46 (t, 2H), 7.22 (t, 1H), 7.14 (d, 2H), 6.13 (d, 1H), 5.87 (s, 1H), 5.71 (s, 1H), 4.76 (s, 1H), 4.52 (d, 1H), 4.44 (s, 1H), 3.67 (s, 3H), 3.02 (s, 3H). |
| 317 | 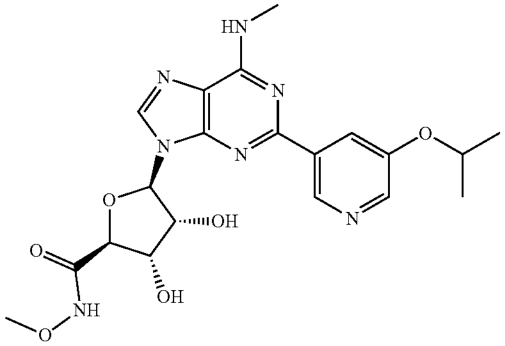 [SMILES: CNc1nc(-c2cncc(OC(C)C)c2)nc2c1ncn2[C@@H]1O[C@H](C(=O)NOC)[C@@H](O)[C@H]1O] (2S,3S,4R,5R)-3,4-dihydroxyl-5-(2-(5-isopropoxypyridin-3-yl)-6-(methylamino)-9H-purin-9-yl)-N-methoxytetrahydrofuran-2-carboxamide | $^1$H NMR (500 MHz, DMSO-$d_6$): δ. 9.12 (s, 1H), 8.44 (s, 1H), 8.35 (d, 1H), 8.18 (s, 1H), 7.97 (s, 1H), 6.15 (d, 1H), 5.87 (s, 1H), 5.74 (s, 1H), 4.82 (m, 2H), 4.54 (d, 1H), 4.50 (t, 1H), 3.68 (s, 3H), 3.09 (s, 3H), 1.35 (d, 6H). |
| 318 | 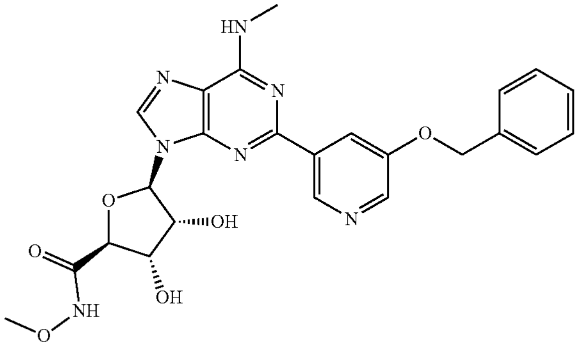 [SMILES: CNc1nc(-c2cncc(OCc3ccccc3)c2)nc2c1ncn2[C@@H]1O[C@H](C(=O)NOC)[C@@H](O)[C@H]1O] (2S,3S,4R,5R)-5-(2-(5-(benzyloxy)pyridin-3-yl)-6-(methylamino)-9H-purin-9-yl)-3,4-dihydroxyl-N-methoxytetrahydrofuran-2-carboxamide | $^1$H NMR (500 MHz, DMSO-$d_6$): δ. 10.92 (s, 1H), 9.09 (s, 1H), 8.42 (d, 1H), 8.30 (s, 1H), 8.28 (s, 1H), 7.93 (s, 1H), 7.54 (d, 2H), 7.43 (t, 3H), 7.36 (t, 1H), 6.49 (s, 1H), 5.75 (dd, 1H), 5.51 (d, 1H), 5.36 (q, 1H), 4.07 (d, 1H), 3.05 (s, 3H), 2.92 (s, 3H), 1.55 (s, 3H), 1.36 (s, 3H). |

Example 23: Synthesis of (2S,3S,4R,5R)-5-(2-(5-chloropyridin-3-yl)-6-(isopropylamino)-9H-purin-9-yl)-3,4-dihydroxyl-N-(methyl-d3)tetrahydrofuran-2-carboxamide (compound 319)

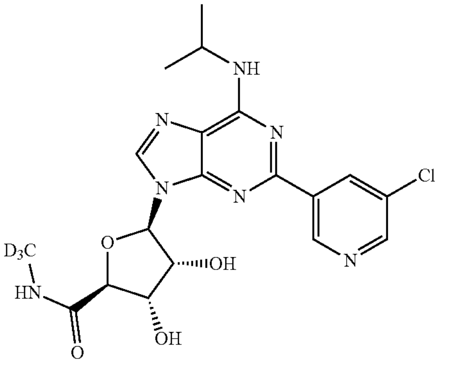 [SMILES: [2H]C([2H])([2H])NC(=O)[C@H]1O[C@@H](n2cnc3c(NC(C)C)nc(-c4cncc(Cl)c4)nc32)[C@H](O)[C@@H]1O]

S1: Synthesis of 6-(2,6-dichlorpurin-9-yl)-2,2-dimethyl-tetrahydrofuran[3,4-d][1,3]dioxazol-4-carboxylate formamide-d3

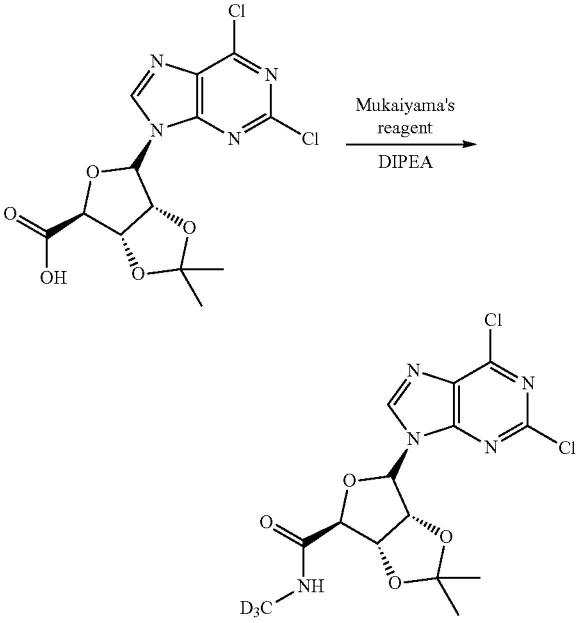

6-(2,6-dichlorpurin-9-yl)-2,2-dimethyl-tetrahydrofuran[3,4-d][1,3]dioxazol-4-carboxylic acid (1.67 g, 4.45 mmol), Mukaiyama's reagent (2.28 g, 8.9 mmol), DIPEA (2.30 g, 17.8 mmol), and deuteromethylamine hydrochloride (471 mg, 6.68 mmol) were added into DMF (20 mL), and the materials were stirred at a room temperature for 1 h. The end point of the reaction was monitored by TLC. Water (100 mL) was added, EtOAc (30 mL×4) was used for an extraction, organic phases were mixed, the organic phase was respectively washed once with water and saturated saline solution, dried with anhydrous $Na_2SO_4$, subjected to suction filtration, and concentrated under reduced pressure, and the sample was stirred and passed through a column to be purified to obtain a white solid (580 mg, yield of 33.3%).

S2: Synthesis of 6-(2-chloro-6-isopropylaminopurin-9-yl)-2,2-dimethyl-tetrahydrofuran[3,4-d][1,3]dioxazol-4-carboxylate formamide-d3

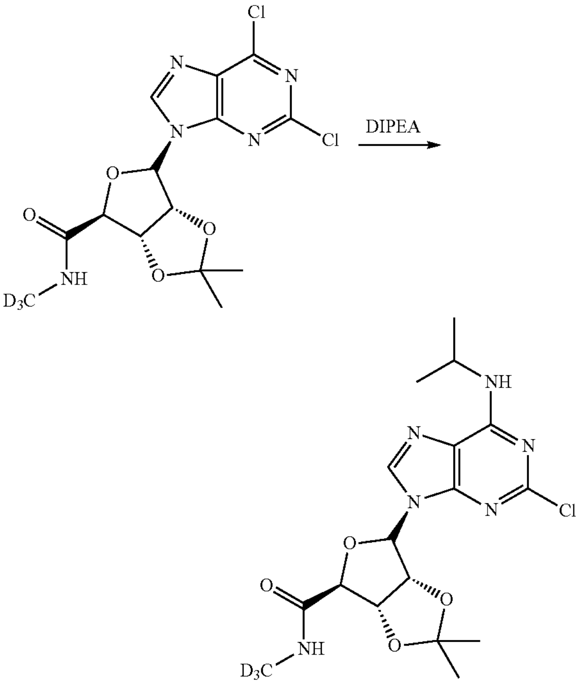

6-(2,6-dichlorpurin-9-yl)-2,2-dimethyl-tetrahydrofuran[3,4-d][1,3]dioxazol-4-carboxylate formamide-d3 (200 mg, 0.51 mmol), isopropylamine (60 mg, 1.02 mmol), and DIPEA (132 mg, 49.7 mmol) were added into methanol (5 mL), and the materials were stirred at 50° C. and reacted for 1 h. The end point of the reaction was monitored by TLC. The reaction solution was concentrated and dried, water (30 mL) was added, EA (20 mL×3) was used for an extraction, organic phases were mixed, the organic phase was respectively washed once with water and saturated saline solution, dried with anhydrous $Na_2SO_4$, subjected to suction filtration, and concentrated under reduced pressure, and the sample was stirred and passed through a column to be purified to obtain a white solid (140 mg, yield of 66.7%).

S3: 6-[2-(5-chloropyridin-3-yl)-6-isopropylaminopurin-9-yl]-2,2-dimethyl-tetrahydrofuran[3,4-d][1,3]dioxazol-4-carboxylate formamide-d3

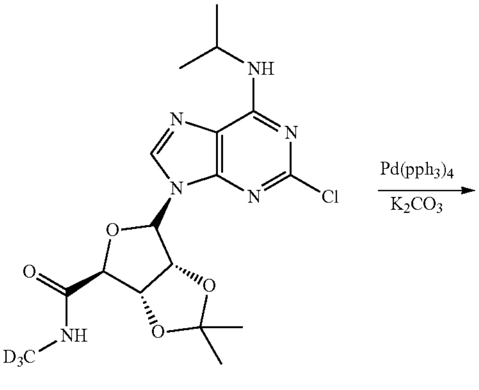

-continued

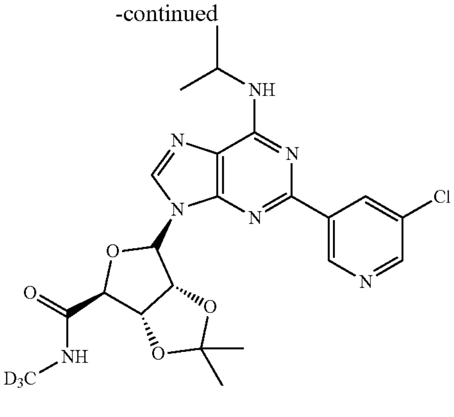

6-(2-chloro-6-isopropylaminopurin-9-yl)-2,2-dimethyl-tetrahydrofuran[3,4-d][1,3]dioxazol-4-carboxylate formamide-d3 (140 mg, 0.34 mmol), 5-chloro-3-pyridin boric acid (80 mg, 0.51 mmol), $Pd(PPh_3)_4$ (40 mg, 0.034 mmol), $K_2CO_3$ (141 mg, 1.02 mmol), THE (6 mL), and water (2 mL) were added into a sealed vial, and the materials were blew with $N_2$ for 3 min and stirred at 90° C. overnight. The end point of the reaction was monitored by TLC. Water (20 mL) was added, EtOAc (15 mL×3) was used for an extraction, organic phases were mixed, the organic phase was respectively washed once with water and saturated saline solution, dried with anhydrous $Na_2SO_4$, subjected to suction filtration, and concentrated under reduced pressure, and the sample was stirred and passed through a column to be purified to obtain a white solid (100 mg, yield of 58.8%).

S4: Synthesis of (2S,3S,4R,5R)-5-(2-(5-chloropyridin-3-yl)-6-(isopropylamino)-9H-purin-9-yl)-3,4-dihydroxyl-N-(methyl-d3)tetrahydrofuran-2-carboxamide (compound 319)

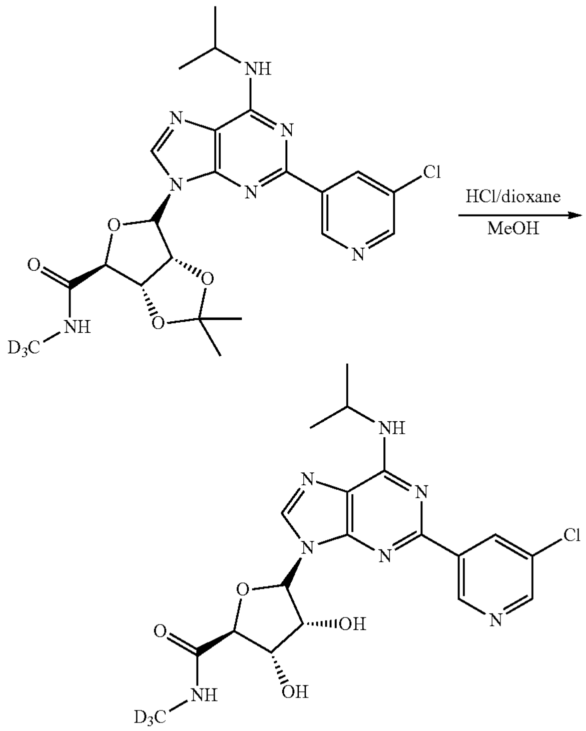

The reaction was performed according S8 in example 8 to obtain a white solid (20.5 mg, yield of 22.7%). $^1H$ NMR (500 MHz, DMSO-$d_6$) δ 9.34 (s, 1H), 8.65 (d, J=2.4 Hz, 1H), 8.54 (dd, J=2.4, 1.8 Hz, 1H), 8.47 (s, 1H), 7.84 (s, 2H), 6.02 (d, J=6.8 Hz, 1H), 5.61 (d, J=4.7 Hz, 1H), 5.51 (d, J=6.4 Hz, 1H), 4.82 (dt, J=11.3, 5.7 Hz, 1H), 4.56 (s, 1H), 4.30-4.22 (m, 2H), 1.21 (t, J=10.5 Hz, 6H). LC-MS (m/z): 451.2 $[M+H]^+$.

Example 24: Following the Reactions Shown in Example 23, the Compounds in the Table Below were Obtained

| No. | Compound structure and name | Characterization data |
|---|---|---|
| 320 | 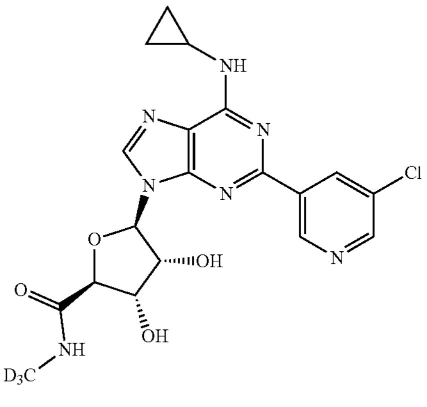 [SMILES: [2H]C([2H])([2H])NC(=O)[C@H]1O[C@@H](n2cnc3c(NC4CC4)nc(-c4cncc(Cl)c4)nc32)[C@H](O)[C@@H]1O] (2S,3S,4R,5R)-5-(2-(5-chloropyridin-3-yl)-6-(cyclopropylamino)-9H-purin-9-yl)-3,4-dihydroxyl-N-(methyl-d3)tetrahydrofuran-2-carboxamide | $^1H$ NMR (500 MHz, DMSO-$d_6$) δ 9.47 (s, 1H), 8.73 (d, J = 2.3 Hz, 1H), 8.66 (s, 1H), 8.56 (s, 1H), 8.26 (s, 1H), 7.92 (s, 1H), 6.10 (d, J = 6.8 Hz, 1H), 5.69 (d, J = 4.7 Hz, 1H), 5.60 (d, J = 6.4 Hz, 1H), 4.89 (dd, J = 11.3, 6.4 Hz, 1H), 4.40-4.29 (m, 2H), 1.25 (d, J = 8.1 Hz, 1H), 0.87-0.78 (m, 2H), 0.69 (s, 2H).LC-MS (m/z): 449.2 $[M + H]^+$. |

-continued

| No. | Compound structure and name | Characterization data |
|---|---|---|
| 321 | 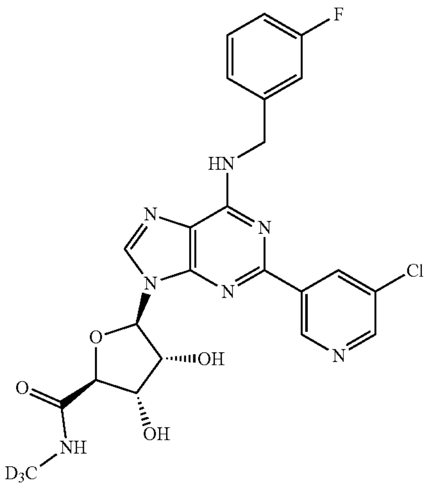 [SMILES: [2H]C([2H])([2H])NC(=O)[C@H]1O[C@@H](n2cnc3c(NCc4cccc(F)c4)nc(-c4cncc(Cl)c4)nc32)[C@H](O)[C@@H]1O] (2S,3S,4R,5R)-5-(2-(5-chloropyridin-3-yl)-6-((3-fluorobenzylamino)-9H-purin-9-yl)-3,4-dihydroxyl-N-(methyl-d3)-tetrahydrofuran-2-carboxamide | $^1$H NMR (500 MHz, DMSO-$d_6$) δ 9.35 (s, 1H), 8.77 (s, 1H), 8.69 (d, J = 2.1 Hz, 1H), 8.59 (s, 1H), 8.53 (s, 1H), 7.90 (s, 1H), 7.39-7.32 (m, 1H), 7.26 (dd, J = 18.1, 8.8 Hz, 2H), 7.04 (dd, J = 11.8, 5.3 Hz, 1H), 6.09 (d, J = 6.8 Hz, 1H), 5.67 (d, J = 81.7 Hz, 2H), 4.91-4.74 (m, 3H), 4.39-4.28 (m, 2H). LC-MS (m/z): 517.2 $[M + H]^+$. |
| 322 | 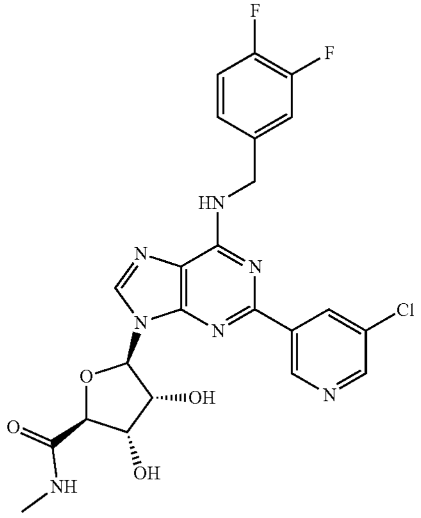 (2S,3S,4R,5R)-5-(2-(5-chloropyridin-3-yl)-6-((3,4-difluorobenzyl)amino)-9H-purin-9-yl)-3,4-dihydroxyl-N-methyltetrahydrofuran-2-carboxamide | $^1$H NMR (500 MHz, DMSO-$d_6$) δ 9.37 (d, J = 1.5 Hz, 1H), 8.76 (s, 1H), 8.71 (d, J = 2.3 Hz, 1H), 8.60 (s, 1H), 8.55 (s, 1H), 7.91 (s, 1H), 7.53-7.45 (m, 1H), 7.38 (dt, J = 10.7, 8.4 Hz, 1H), 7.29 (s, 1H), 6.10 (d, J = 6.8 Hz, 1H), 5.69 (d, J = 4.7 Hz, 1H), 5.59 (d, J = 6.4 Hz, 1H), 4.89 (dd, J = 11.3, 6.5 Hz, 1H), 4.79 (s, 2H), 4.38-4.30 (m, 2H). LC-MS (m/z) $[M + H]^+$: 535.3. |

-continued

| No. | Compound structure and name | Characterization data |
| --- | --- | --- |
| 323 | 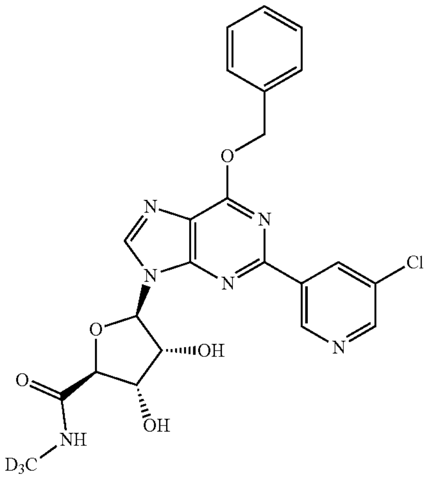 [SMILES: [2H]C([2H])([2H])NC(=O)[C@H]1O[C@@H](n2cnc3c(OCc4ccccc4)nc(-c4cncc(Cl)c4)nc32)[C@H](O)[C@@H]1O] (2S,3S,4R,5R)-5-(6-(benzyloxy)-2-(5-chloropyridin-3-yl)-9H-purin-9-yl)-3,4-dihydroxyl-N-(methyl-d3)-tetrahydrofuran-2-formamide | $^1$H NMR (500 MHz, DMSO-$d_6$) δ 9.51 (d, J = 1.7 Hz, 1H), 8.82 (s, 1H), 8.79 (d, J = 2.4 Hz, 1H), 8.72 (t, J = 2.1 Hz, 1H), 7.95 (s, 1H), 7.59 (d, J = 7.1 Hz, 2H), 7.39 (ddd, J = 10.9, 9.7, 5.8 Hz 3H), 6.18 (d, J = 6.7 Hz, 1H), 5.8 (s, 2H), 5.74 (d, J = 4.7 Hz, 1H), 5.67 (d, J = 6.3 Hz, 1H), 4.92 (dt, J = 11.0, 5.5 Hz, 1H), 4.37 (dt, J = 6.9, 2.4 Hz, 2H), LC-MS m/z $[M + H]^+$: 500.2. |
| 324 | 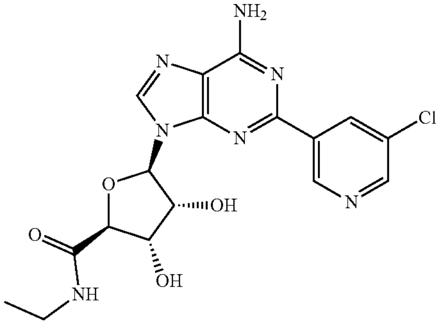 [SMILES: CCNC(=O)[C@H]1O[C@@H](n2cnc3c(N)nc(-c4cncc(Cl)c4)nc32)[C@H](O)[C@@H]1O] (2S,3S,4R,5R)-5-(6-amino-2-(5-chloropyridin-3-yl)-9H-purin-9-yl)-N-ethyl-3,4-dihydroxyltetrahydrofuran-2-formamide | $^1$H NMR (500 MHz, DMSO-d6) δ: 9.39 (d, J = 1.6 Hz, 1H), 8.71 (d, J = 2.4 Hz, 1H), 8.61 (t, J = 4.0 Hz, 1H), 8.56 (s, 1H), 7.99 (s, 1H), 7.58 (br, 2H), 6.10 (d, J = 6.9 Hz, 1H), 5.64 (br, 2H), 4.86 (dd, J = 11.3, 6.5 Hz, 1H), 4.35-4.32 (m, 2H), 3.14-3.0 (m, 2H), 0.91 (t, 7 Hz, 3 H). LC-MS m/z $[M + H]^+$: 420. |

Example 25: Synthesis of (2S,3S,4R,5S)-5-(6-(benzylamino)-2-(pyridin-2-yl)-9H-purin-9-yl)-3,4-dihydroxyl-N-methyltetrahydrofuran-2-carboxamide (compound 325)

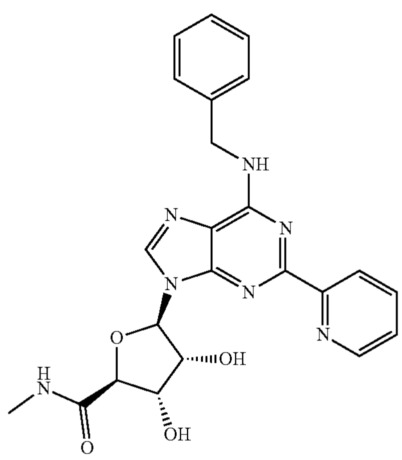 [SMILES: CNC(=O)[C@H]1O[C@@H](n2cnc3c(NCc4ccccc4)nc(-c4ccccn4)nc32)[C@H](O)[C@@H]1O]

S1: Synthesis of 9-(((3aR,4S,6R,6aR)-6-(hydroxylmethyl)-2,2-dimethyltetrahydrofuran[3,4-d][1,3] dioxypentyl-4-yl)-2-(pyridin-2-yl)-9H-purin-6-ol

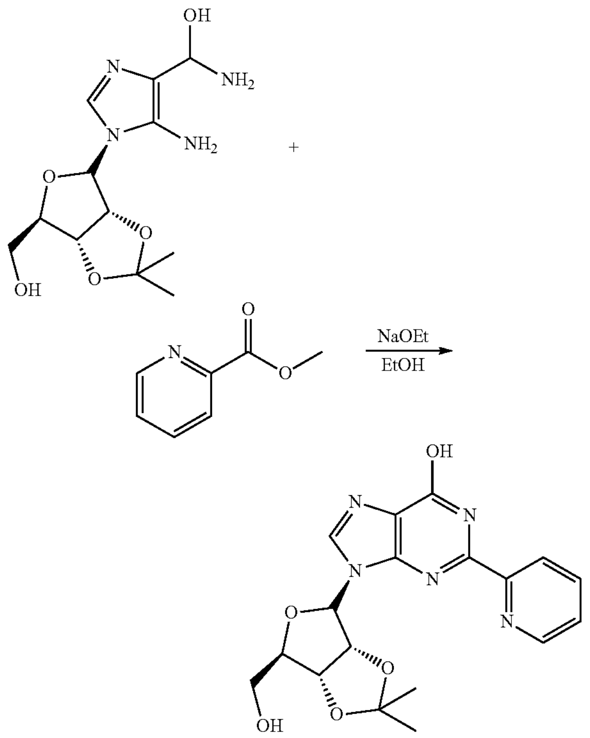

NaOEt (4.1 g, 60.3 mmol) was added to anhydrous MeCN (150 mL) and the materials were stirred for 30 min. 5-amino-1-(((3aR,4S,6R,6aR)-6-(hydroxylmethyl)-2,2-dimethyltetrahydrofuran[3,4-d][1,3]dioxypentyl-4-yl)-1H-imidazol-4-carboxamide (6.0 g, 20.1 mmol) and methyl pyridinate were added, and the materials were reacted at 85° C. for 24 h. The end point of the reaction was monitored by TLC. The reaction solution was concentrated and dried, DCM (100 mL) was added, and the sample was stirred and passed through a column to be purified to obtain a white solid (1.3 g, yield of 16.9%). $^1$H NMR (500 MHz, DMSO-$d_6$) δ 11.79 (s, 1H), 8.76 (d, J=4.6 Hz, 1H), 8.39 (t, J=3.9 Hz, 2H), 8.11 (td, J=7.8, 1.6 Hz, 1H), 7.70-7.58 (m, 1H), 6.25 (d, J=2.7 Hz, 1H), 5.41 (dd, J=6.2, 2.7 Hz, 1H), 5.06 (dd, J=8.8, 3.9 Hz, 2H), 4.23 (td, J=5.0, 3.0 Hz, 1H), 3.63-3.48 (m, 2H), 1.58 (s, 3H), 1.36 (s, 3H). LC-MS (m/z): 386.2 $[M+H]^+$.

S2: Synthesis of (3aS,4S,6S,6aR)-6-(6-hydroxyl-2-(pyridin-2-yl)-9H-purin-9-yl)-2,2-dimethyltetrahydrofuran[3,4-d][1,3]dioxazol-4-carboxylic acid

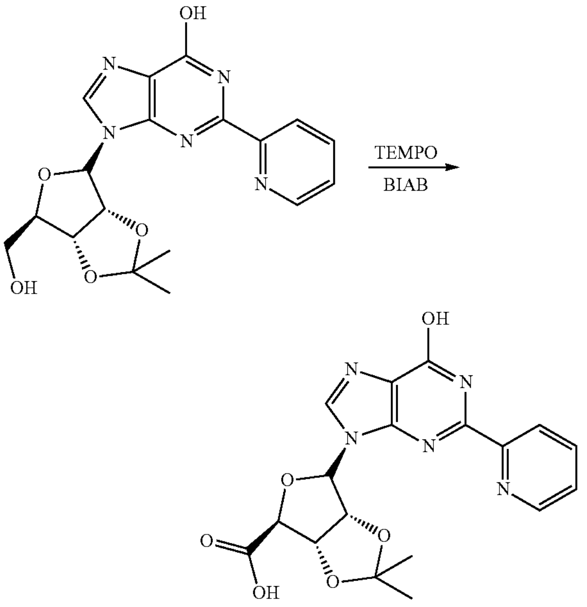

The reaction was performed referring to corresponding operations in example 8 to obtain a white solid (1.1 g, yield of 79.4%). LC-MS (m z): 400.2 $[M+H]^+$ S3: Synthesis of (3aS,4S,6S,6aR)-6-(6-hydroxyl-2-(pyridin-2-yl)-9H-purin-9-yl)-N,2,2-trimethyltetrahydrofuran[3,4-d][1,3]dioxazol-4-carboxamide

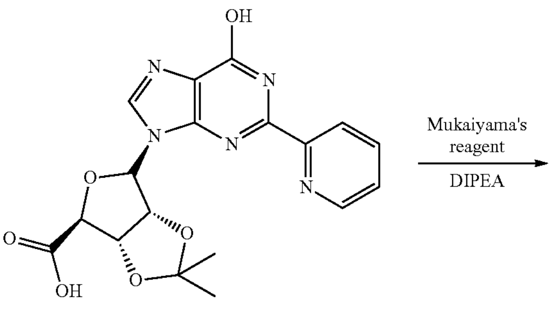

-continued

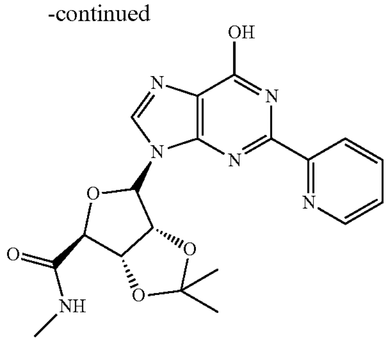

The reaction was performed referring to corresponding operations in example 8 to obtain a white solid (630 mg, yield of 56.3%). LC-MS (m z): 413.3 [M+H]$^+$.

S4: Synthesis of (3aS,4S,6S,6aR)-6-(6-chloro-2-(pyridin-2-yl)-9H-purin-9-yl)-N,2,2-trimethyltetrahydrofuran[3,4-d][1,3]dioxazol-4-carboxamide

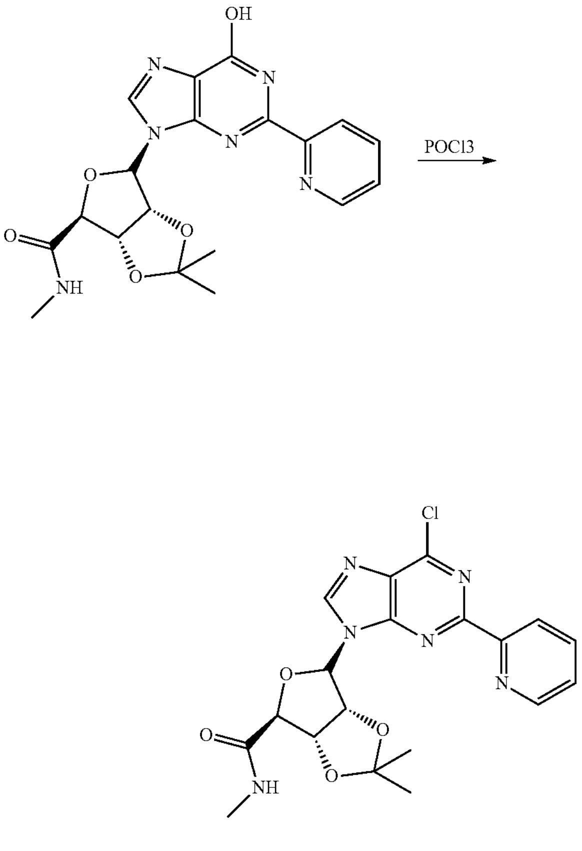

(3aS,4S,6S,6aR)-6-(6-hydroxyl-2-(pyridin-2-yl)-9H-purin-9-yl)-N,2,2-trimethyltetrahydrofuran[3,4-d][1,3]dioxazol-4-carboxamide (100 mg, 0.24 mmol), $Et_4NCl$ (81 mg, 0.48 mmol), and $PhNMe_2$ (30 mg, 0.24 mmol) were added into anhydrous MeCN (5 mL), and the materials were stirred for 10 min. $POCl_3$ (0.135 mL, 1.44 mmol) was added, and the materials were reacted at 100° C. for 15 min. The end point of the reaction was monitored by TLC. The materials were concentrated and dried, water (300 mL) was added, EtOAc (200 mL×3) was used for an extraction, organic phases were mixed, the organic phase was respectively washed once with water and saturated saline solution, dried with anhydrous $Na_2SO_4$, subjected to suction filtration, and concentrated under reduced pressure, and the sample was stirred and passed through a column to be purified to obtain a white solid (50 mg, yield of 48.4%). $^1H$ NMR (500 MHz, DMSO-$d_6$) δ 8.85 (s, 1H), 8.77 (d, J=4.1 Hz, 1H), 8.41 (d, J=7.9 Hz, 1H), 8.02 (t, J=7.7 Hz, 1H), 7.59-7.47 (m, 2H), 6.60 (s, 1H), 5.63 (d, J=6.0 Hz, 1H), 5.58 (d, J=6.1 Hz, 1H), 4.68 (s, 1H), 2.04 (d, J=4.5 Hz, 3H), 1.56 (s, 3H), 1.37 (s, 3H). LC-MS (m z): 431.2 [M+H]$^+$.

S5: Synthesis of (3aS,4S,6S,6aR)-6-(6-(benzylamino)-2-(pyridin-2-yl)-9H-purin-9-yl)-N,2,2-trimethyltetrahydrofuran[3,4-d][1,3]dioxazol-4-carboxamide

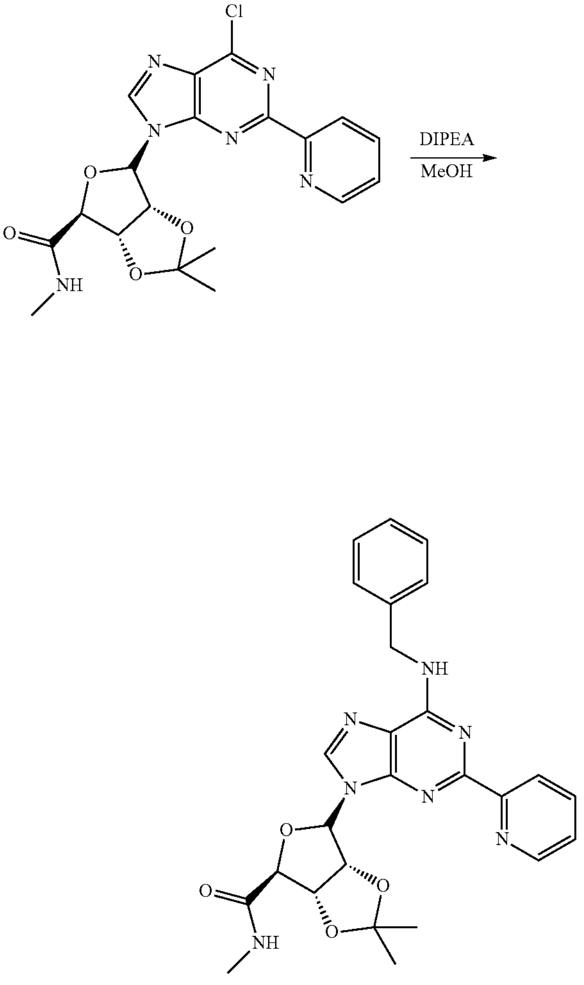

The reaction was performed referring to corresponding operations in example 8 to obtain a white solid (60 mg, yield of 60.9%). $^1H$ NMR (500 MHz, DMSO-$d_6$) δ 8.69 (d, J=3.7 Hz, 1H), 8.53 (s, 1H), 8.45-8.26 (m, 2H), 7.91 (t, J=7.7 Hz, 1H), 7.58 (s, 1H), 7.54-7.38 (m, 3H), 7.29 (t, J=7.6 Hz, 2H), 7.20 (t, J=7.3 Hz, 1H), 6.42 (d, J=1.6 Hz, 1H), 5.61-5.41 (m, 2H), 4.83 (s, 2H), 4.57 (d, J=2.3 Hz, 1H), 2.21 (s, 3H), 1.56 (s, 3H), 1.35 (s, 3H). LC-MS (m/z): 502.2 [M+H]$^+$.

S6: Synthesis of (2S,3S,4R,5S)-5-(6-(benzylamino)-2-(pyridin-2-yl)-9H-purin-9-yl)-3,4-dihydroxyl-N-methyltetrahydrofuran-2-carboxamide (compound 325)

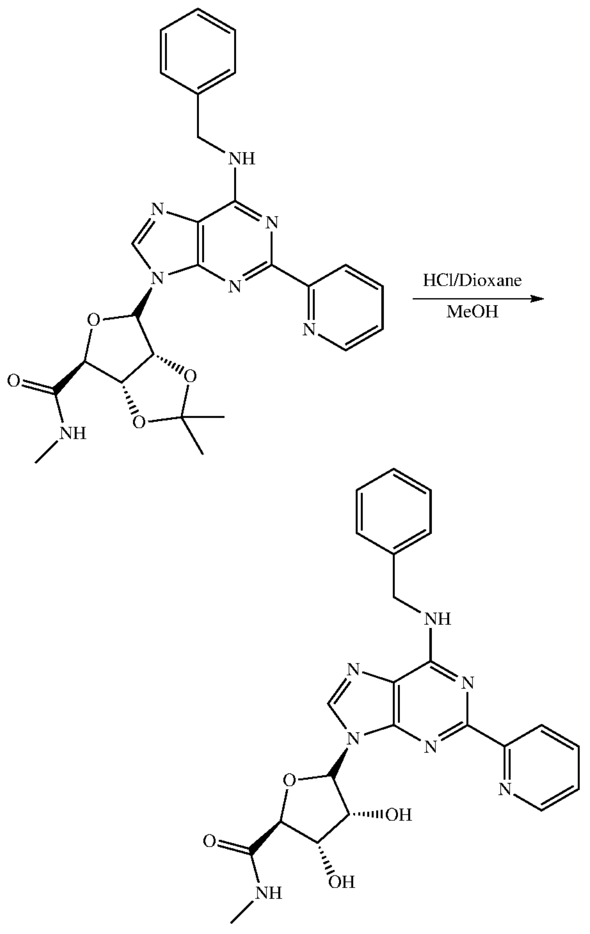

The reaction was performed referring to corresponding operations in example 8 to obtain a white solid (34.6 mg, yield of 62.5%). $^1$H NMR (500 MHz, DMSO-$d_6$) δ 8.64 (d, J=4.6 Hz, 1H), 8.57 (s, 1H), 8.45 (s, 1H), 8.28-8.11 (m, 2H), 7.85 (t, J=7.6 Hz, 1H), 7.38 (dd, J=11.8, 7.8 Hz, 3H), 7.24 (t, J=7.6 Hz, 2H), 7.14 (t, J=7.3 Hz, 1H), 6.01 (d, J=7.4 Hz, 1H), 5.67 (d, J=4.4 Hz, 1H), 5.54 (d, J=6.3 Hz, 1H), 4.74 (dd, J=12.4, 6.0 Hz, 3H), 4.26 (d, J=1.5 Hz, 1H), 4.16 (s, 1H), 2.47 (d, J=3.9 Hz, 3H). LC-MS (m/z): 462.2 $[M+H]^+$.

Example 26: Test the Effect of Compound on Intracellular cAMP Level by Adenosine A3 Receptor Agonism 1. Test Steps
   1) 1×HBSS with Ca2+ and Mg2+ (14 mL), 1 M HEPES (75 μL), a 7.5% (w/v) BSA stabilizer (pH 7.4, 200 μL), and 20 mM rolipram (7.5 μL) were respectively prepared as cAMP assay buffer.
   2) Preparation of compound source plate
   a. A 1 mM stock solution was subjected to a 3-fold serial dilution by 100% (v/v) DMSO to prepare 10 doses of NECA.

b. A 10 mM stock solution was subjected to a 3-fold serial dilution by 100% (v/v) DMSO to prepare 10 doses of the test substance.
   c. 1 mM of Forskolin was prepared by 100% (v/v) DMSO.
   3) Preparation of test plate
   a. Prior to the assay, CHO cells stably expressing ADORA3 receptor were harvested and the cells were counted by using a Countess cell counter. Only the cells with a survival rate >85% were used for the following assay.
   B. The cells were diluted to $2\times10^5$ cells/ml with the cAMP analytical buffer.
   C. The cells were seeded at a density of 2,000 cells/well in a 384-well plate.
   4) 10 nL/well of the serially diluted compound and 10 nL/well of 1 mM of forskolin were transferred to each well with ADORA3 receptor expressing cells by using Echo550.
   5) A cell plate was centrifuged at 1,000 rpm for 1 minute and then stirred at 600 rpm for 2 minutes. The plate was incubated at 37° C.
   6) An Eu-cAMP tracer working solution and an Ulight-anti-cAMP working solution were prepared according to the following table.

| Eu-CAMP tracer working solution | | Ulight-anti-cAMP working solution | |
|---|---|---|---|
| Reagent | Vol. | Reagent | Vol. |
| Eu-CAMP tracer Stock | 20 μl | Ulight-anti-cAMP Stock | 10 μl |
| cAMP detection Buffer | 2 ml | cAMP detection Buffer | 2 ml |

7) 5 μl/well of the Eu-cAMP tracer working solution and 5 μl/well of the Ulight-anti-cAMP working solution were added to each well of the plate. The plate was centrifuged at 1,000 rpm for 1 minute and then stirred at 600 rpm for 2 minutes.
   8) The plate was read by using an EnVison microplate reader (λex=320 nm, and λem=615 nm and 665 nm), and a relationship between a ratio of 665 nm to 615 nm emissivity and a compound concentration was plotted to establish a curve, and EC50 was calculated.
2. Data Analysis
   1) An activation percentage was calculated by using the following formula:

$$\%\ \text{Activation} = 100\% \times \frac{\text{Ratio}_{cpd} - \text{Ratio}_{Low\ Control}}{\text{Ratio}_{High\ Control} - \text{Ratio}_{Low\ Control}}$$

% Activation: activation percentage
$\text{Ratio}_{cpd}$: ratio of emissivity of test compound
$\text{Ratio}_{Low\ control}$: ratio of low emissivity
$\text{Ratio}_{High\ control}$: ratio of high emissivity
   2) EC50 was calculated by an XLfit using the Hill equation to fit the activity percentage and a log of a compound concentration.
3. Test Result

| Compound No. | EC50 (nM) | Compound No. | EC50 (nM) |
|---|---|---|---|
| 24 | 5.77 | 226 | 1.20 |
| 70 | 1.23 | 230 | 8.68 |
| 71 | <0.51 | 245 | 0.28 |
| 92 | <0.51 | 246 | 1.18 |

-continued

| Compound No. | EC50 (nM) | Compound No. | EC50 (nM) |
|---|---|---|---|
| 102 | 1.41 | 247 | 4.16 |
| 106 | 3.02 | 254 | 9.51 |
| 107 | 5.22 | 255 | 8.58 |
| 108 | 1.58 | 256 | 11.62 |
| 111 | 7.32 | 282 | 4.00 |
| 112 | 3.53 | 284 | 2.85 |
| 159 | 4.42 | 289 | 6.81 |
| 160 | 3.53 | 290 | 12.43 |
| 161 | 0.74 | 293 | <0.51 |
| 177 | 2.08 | 294 | 2.62 |
| 179 | 9.44 | 296 | 1.28 |
| 182 | <0.51 | 300 | 2.13 |
| 183 | <0.51 | 301 | 3.78 |
| 184 | <0.51 | 302 | 2.26 |
| 185 | <0.51 | 305 | 2.73 |
| 186 | <0.51 | 306 | 5.81 |
| 187 | 14.50 | 307 | 9.40 |
| 222 | 0.89 | 308 | 3.27 |
| 223 | 15.24 | 312 | <0.51 |
| 224 | 1.34 | 325 | 9.62 |
| NECA | 3.10 | / | / |

NECA (CAS: 35920-39-9) was a non-selective adenosine A3 receptor agonist and used as a positive control in the test. According to the data above, it can be seen that, when tested for the intracellular cAMP level, all the compounds in the table exhibit very high adenosine A3 receptor agonistic activity.

Example 27: Agonistic Effect of Compound on Adenosine A3 Receptor by FLIPR Assay (Calcium Flux Assay)

1. Test Steps

First Day: Cell Inoculation

1) With regard to ADORA3 receptor, cultured cells were used for inoculation: the culture medium was aspirated and the cells were washed twice with 10 mL of DPBS. 2 mL of 0.05% EDTA-trypsin was added and the cells were incubated at 37° C. for 1 minute. Then 10 mL of the culture medium was added to stop the digestion and the cell suspension was transferred to a 50-mL tapered tube.

2) The 50-mL tapered tube containing the various cells was centrifuged at 300 g for 5 minutes.

3) A supernatant was aspirated and no cells should be aspirated.

4) The cell precipitate was resuspended in 6-8 mL of the culture medium, and then 0.5 mL of the cells were taken out for cell counting by using a Vi-cell XR cell viability analyzer.

5) The cell suspension was diluted to $1\times10^6$ cells/mL (20 μL of 20,000 cells per well) in the culture medium and the cells were inoculated into a cell plate (384-well Poly-D-lysine protein-coated plate, Greiner-781946).

6) The plate was placed in a 37° C./5% $CO_2$ incubator for 16-20 hours.

Second Day:

1) Preparation of 2×Fluo-4 Direct™ uptaking dye a. Preparation of probenecid solution 1 mL of FLIPR assay buffer was added to 77 mg of probenecid (provided by Fluo-4 Direct™ calcium assay kit) to be prepared into 250 mM of a probenecid solution. The fresh probenecid solution was used daily.

b. 2×(8 μM) Fluo-4 Direct™ loading dye (per 10 mL)

A vial of the Fluo-4 Direct™ crystal was thawed and then 10 mL of the FLTPR analytical buffer was added to the vial. Then 0.2 mL of 250 mM of a probe solution was added to every 10 mL Fluo-4 Direct™ crystal to a final assay concentration of 2.5 mM. The solution was vortexed and stood for >5 min at a dark place. 2×Fluo-4 Direct™ uptaking dye was freshly prepared daily.

2) Compound preparation a. Preparation of compound plate: all reference and test compounds were serially diluted 4-fold in 10 points by using an Echo liquid processor and then 900 nL of the diluted compounds were transferred to a compound plate.

b. 30 μL FLIPR analytical buffer was added to the compound plate and the plate was centrifuged at 300 g for 1 minute.

3) FLIPR analysis a. With regard to ADORA3 receptor: firstly, the cell plate was taken out from a culture box. The culture medium was then aspirated and 20 μL of the FLIPR analytical buffer was added. The cell plate was placed in an incubator for 45 minutes and at a room temperature for 15 minutes.

b. To run an experimental solution on FLIPRTETRA, 10 μL of the FLIPR analytical buffer was transferred from the compound plate to a cell plate, and then the fluorescent signal was read. Then 10 μL of a compound solution was transferred from the compound plate to the cell plate and the fluorescence signal was read. "Max−min" was calculated from Reader 91 to an allowed maximum value.

c. With regard to agonist: activation %=(RLU−LC)/(HC−LC)*100, wherein RLU=relative light unit, allowed maximum signal was 91; HC=average signal of high concentration agonist; and LC=mean signal of DMSO well.

d. Data were fitted to a model "log (agonist) versus response-variable slope" by using GraphPad Prism 5 to determine an EC50 value.

e. Maximum activation of NECA was used to establish 100% efficacy, and then the efficacy of each compound was calculated by using the following equation: efficacy (%)=maximal activation of test compound/maximal activation of NECA*100.

2. Test Result

| Compound No. | EC50 (nM) |
|---|---|
| 42 | 12.73 |
| 43 | 11.41 |
| 71 | 1.929 |
| 72 | 20.58 |
| 73 | 29.57 |
| 90 | 25.25 |
| 106 | 17.59 |
| 112 | 44.36 |
| 159 | 59.27 |
| 177 | 70.30 |
| 183 | 9.07 |
| 184 | 13.00 |
| 186 | 11.80 |
| 190 | 9.06 |
| 191 | 5.29 |
| 192 | 9.24 |
| 193 | 10.87 |
| 194 | 10.65 |
| 226 | 33.55 |
| 227 | 3.528 |
| 231 | 11.19 |
| 256 | 98.48 |
| 293 | 3.27 |
| 296 | 53.57 |

-continued

| Compound No. | EC50 (nM) |
|---|---|
| 297 | 12.92 |
| 298 | 37.03 |
| 299 | 19.43 |
| 305 | 10.92 |
| 306 | 39.18 |
| 308 | 71.40 |
| 312 | 4.05 |
| NECA | 9.7-35.49 |

NECA (CAS: 35920-39-9) was a non-selective adenosine A3 receptor agonist and used as a positive control in the test. According to the data above, it can be seen that, when tested for the intracellular calcium flux level (FLTPR assay), all the compounds in the table exhibit very high adenosine A3 receptor agonistic activity.

Example 28: Pharmacokinetic Test of Compound in SD Rat

1. Test Information

The animal species used in this experiment were SD rats. There were 3 animals per group. The rats were dosed in cassette format, i.e., multiple (1-6) different compounds were dosed simultaneously to the same group of the SD rats. The vehicle used for the drug was 5% DMSO+5% Solutl+90% (0.500 methylcellulose M450), and the administration route was intragastric administration (IG).

Pharmacokinetic Test Result

| Compound No. | AUC_D (hr*kg*ng/ml/mg) |
|---|---|
| 1 | 343.50 |
| 3 | 152.40 |
| 10 | 146.00 |
| 11 | 174.00 |
| 12 | 79.00 |
| 15 | 807.78 |
| 16 | 1291.00 |
| 17 | 168.00 |
| 19 | 74.00 |
| 24 | 86.00 |
| 32 | 1384.00 |
| 33 | 1578.00 |
| 34 | 578.00 |
| 43 | 87.99 |
| 58 | 110.00 |
| 69 | 360.90 |
| 71 | 757.44 |
| 72 | 75.08 |
| 74 | 213.00 |
| 77 | 81.00 |
| 92 | 83.00 |
| 97 | 115.00 |
| 106 | 521.57 |
| 108 | 801.47 |
| 110 | 276.50 |
| 111 | 230.72 |
| 112 | 1790.18 |
| 118 | 347.00 |
| 120 | 86.00 |
| 143 | 80.00 |
| 149 | 337.00 |
| 150 | 1821.60 |
| 151 | 89.00 |
| 152 | 1352.37 |
| 153 | 829.00 |
| 158 | 602.00 |
| 160 | 1900.75 |
| 160 | 1515.94 |
| 161 | 994.72 |

-continued

| Compound No. | AUC_D (hr*kg*ng/ml/mg) |
|---|---|
| 162 | 1156.15 |
| 164 | 845.57 |
| 165 | 564.70 |
| 168 | 1551.15 |
| 177 | 5247.70 |
| 179 | 273.37 |
| 180 | 81.74 |
| 181 | 72.67 |
| 182 | 235.62 |
| 183 | 947.63 |
| 185 | 589.63 |
| 186 | 786.27 |
| 187 | 1269.78 |
| 190 | 2205.59 |
| 191 | 1183.39 |
| 192 | 3329.08 |
| 193 | 2969.40 |
| 194 | 2043.13 |
| 202 | 138.00 |
| 209 | 1347.60 |
| 210 | 580.90 |
| 213 | 360.90 |
| 214 | 765.47 |
| 215 | 785.90 |
| 220 | 295.19 |
| 221 | 278.77 |
| 225 | 11356.86 |
| 226 | 20055.61 |
| 227 | 233.07 |
| 230 | 212.91 |
| 231 | 17240.04 |
| 235 | 1456.00 |
| 240 | 1024.58 |
| 241 | 440.67 |
| 242 | 811.33 |
| 245 | 1182.41 |
| 248 | 3298.00 |
| 250 | 2137.00 |
| 251 | 610.00 |
| 252 | 532.00 |
| 253 | 299.00 |
| 254 | 703.00 |
| 255 | 406.00 |
| 256 | 706.00 |
| 257 | 96.00 |
| 265 | 764.50 |
| 267 | 82.98 |
| 271 | 1131.18 |
| 284 | 8902.66 |
| 285 | 175.00 |
| 288 | 118.00 |
| 289 | 106.30 |
| 290 | 216.77 |
| 293 | 2016.46 |
| 294 | 639.00 |
| 295 | 610.66 |
| 297 | 2349.41 |
| 298 | 4423.94 |
| 299 | 14283.90 |
| 300 | 729.20 |
| 301 | 744.06 |
| 305 | 161.47 |
| 306 | 659.04 |
| 307 | 173.85 |
| 308 | 986.00 |
| 312 | 1820.66 |
| 319 | 74.00 |
| 321 | 1167.46 |
| 322 | 97.03 |
| 323 | 1309.00 |
| 324 | 78.00 |

It can be seen from the SD rat pharmacokinetic parameters above that the compounds in the table have very high exposure in rats. This excellent pharmacokinetic property suggests that the compound of formula I may have excellent pharmacological effect.

What is claimed is:

1. The compound of formula IV:

Formula IV

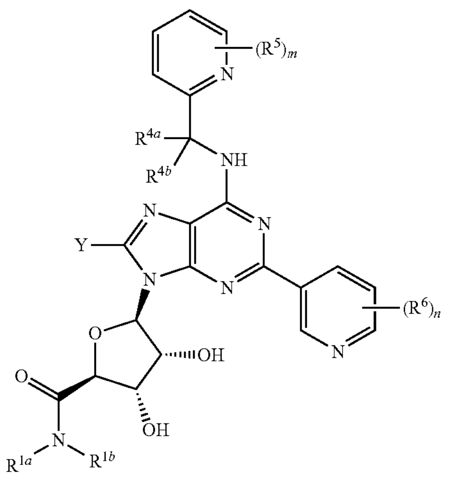

wherein $R^{1a}$ is selected from hydrogen and the following groups: $C_1$-$C_2$ alkyl, $C_1$-$C_2$ alkoxy, and cyclopropyl;

$R^5$ and $R^6$ are each independently selected from halogen, cyano, $C_1$-$C_2$ alkyl, $C_1$-$C_2$ alkoxy, $C_2$-$C_3$ alkenyl, and $C_2$-$C_3$ alkynyl, and m and n are each independently any integer from 0 to 2; and $R^{1b}$, $R^{4a}$, $R^{4b}$, and Y are all hydrogen.

2. The compound of formula IV according to claim 1, being a compound of formula VI:

Formula VI

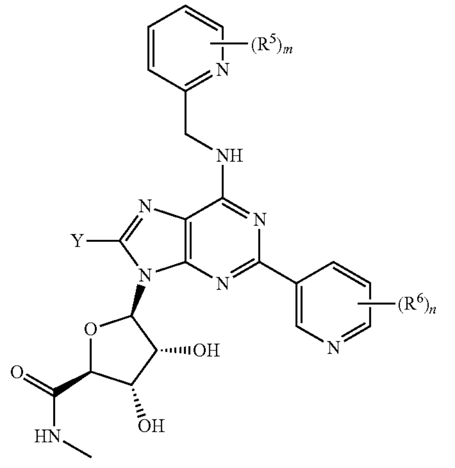

wherein $R^5$ and $R^6$ are each independently selected from halogen, methyl, ethyl, methoxy, and ethoxy, and m and n are each independently any integer from 0 to 2; and Y is hydrogen.

3. The compound of formula V:

Formula V

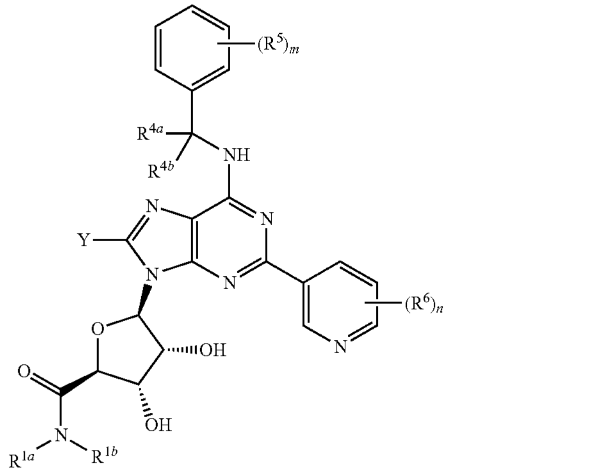

wherein $R^{1a}$ is selected from hydrogen and the following groups: $C_1$-$C_2$ alkyl, $C_1$-$C_2$ alkoxy, and cyclopropyl;

$R^5$ and $R^6$ are each independently selected from halogen, cyano, $C_1$-$C_2$ alkyl, $C_1$-$C_2$ alkoxy, $C_2$-$C_3$ alkenyl, and $C_2$-$C_3$ alkynyl, and m is any integer from 0 to 2 and n is any integer from 0 to; and $R^{1b}$, $R^{4a}$, $R^{4b}$ and Y are all hydrogen.

4. The compound of formula V according to claim 3, being a compound of formula VII:

Formula VII

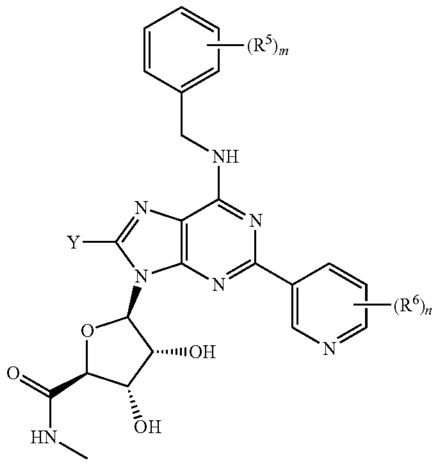

wherein $R^5$ and $R^6$ are each independently selected from halogen, methyl, ethyl, methoxy, and ethoxy, and m is any integer from n to 2 and the n is any integer from 0 to 1; and Y is hydrogen.

5. A compound selected from:

(2S,3S,4R,5R)-5-(6-(benzylamino)-2-(pyridin-3-yl)-9H-purin-9-yl)-3,4-dihydroxyl-N-(methyl-d3)-tetrahydrofuran-2-formamide;

(2S,3S,4R,5R)-5-(6-(benzylamino)-2-(5-chloropyridin-3-yl)-9H-purin-9-yl)-3,4-dihydroxyl-N-(methyl-d3)-tetrahydrofuran-2-formamide;

(2S,3S,4R,5R)-5-(6-(benzylamino)-2-(5-methylpyridin-3-yl)-9H-purin-9-yl)-3,4-dihydroxyl-N-(methyl-d3)-tetrahydrofuran-2-formamide;

(2S,3S,4R,5R)-5-(6-(benzylamino)-2-(5-cyanopyridin-3-yl)-9H-purin-9-yl)-3,4-dihydroxyl-N-(methyl-d3)-tetrahydrofuran-2-formamide;

(2S,3S,4R,5R)-5-(6-(benzylamino)-2-(5-fluoropyridin-3-yl)-9H-purin-9-yl)-3,4-dihydroxyl-N-(methyl-d3)-tetrahydrofuran-2-formamide;

(2S,3S,4R,5R)-5-(6-(benzylamino)-2-(5-methoxypyridin-3-yl)-9H-purin-9-yl)-3,4-dihydroxyl-N-(methyl-d3)-tetrahydrofuran-2-formamide;

(2S,3S,4R,5R)-3,4-dihydroxyl-N-methyl-5-(2-(5-methylpyridin-3-yl)-6-((pyridin-2-ylmethyl)amino)-9H-purin-9-yl)-tetrahydrofuran-2-carboxamide;

(2S,3S,4R,5R)-5-(2-(5-fluoropyridin-3-yl)-6-(((4-methylpyridin-2-yl)methyl)amino)-9H-purin-9-yl)-3,4-dihydroxyl-N-methyltetrahydrofuran-2-carboxamide;

(2S,3S,4R,5R)-5-(6-((3-chlorobenzyl)amino)-2-(5-fluoropyridin-3-yl)-9H-purin-9-yl)-3,4-dihydroxyl-N-methyltetrahydrofuran-2-carboxamide;

(2S,3S,4R,5R)-5-(2-(5-fluoropyridin-3-yl)-6-((3-methoxybenzyl)amino)-9H-purin-9-yl)-3,4-dihydroxyl-N-methyltetrahydrofuran-2-carboxamide;

(2S,3S,4R,5R)-5-(2-(5-fluoropyridin-3-yl)-6-(((6-methylpyridin-2-yl)methyl)amino)-9H-purin-9-yl)-3,4-dihydroxyl-N-methyltetrahydrofuran-2-carboxamide;

(2S,3S,4R,5R)-3,4-dihydroxyl-N-methyl-5-(6-(((6-methylpyridin-2-yl)methyl)amino)-2-(pyridin-3-yl)-9H-purin-9-yl)tetrahydrofuran-2-carboxamide;

(2S,3S,4R,5R)-3,4-dihydroxyl-N-methyl-5-(6-((3-methylbenzyl)amino)-2-(pyridin-3-yl)-9H-purin-9-yl)tetrahydrofuran-2-carboxamide;

(2S,3S,4R,5R)-5-(6-(benzylamino)-2-(pyridin-3-yl)-9H-purin-9-yl)-3,4-dihydroxyl-N-methyltetrahydrofuran-2-carboxamide;

(2S,3S,4R,5R)-3,4-dihydroxyl-5-(2-(5-methoxypyridin-3-yl)-6-(((6-methylpyridin-2-yl))methyl)amino)-9H-purin-9-yl)-N-methyltetrahydrofuran-2-carboxamide;

((2S,3S,4R,5R)-5-(2-(5-chloropyridin-3-yl)-6-(((6-methylpyridin-2-yl))methyl)amino)-9H-purin-9-yl)-3,4-dihydroxyl-N-methyltetrahydrofuran-2-carboxamide;

(2S,3S,4R,5R)-5-(6-(benzylamino)-2-(5-chloropyridin-3-yl)-9H-purin-9-yl)-3,4-dihydroxyl-N-methyltetrahydrofuran-2-carboxamide;

(2S,3S,4R,5R)-5-(6-(benzylamino)-2-(5-fluoropyridin-3-yl)-9H-purin-9-yl)-3,4-dihydroxyl-N-methyltetrahydrofuran-2-carboxamide;

(2S,3S,4R,5R)-5-(2-(5-chloropyridin-3-yl)-6-((((6-methoxypyridin-2-yl)methyl)amino)-9H-purin-9-yl)-3,4-dihydroxyl-N-methyltetrahydrofuran-2-carboxamide;

(2S,3S,4R,5R)-5-(2-(5-chloropyridin-3-yl)-6-((3-methylbenzyl)amino)-9H-purin-9-yl)-3,4-dihydroxyl-N-methyltetrahydrofuran-2-carboxamide;

(2S,3S,4R,5R)-5-(2-(5-fluoropyridin-3-yl)-6-((3-methylbenzyl)amino)-9H-purin-9-yl)-3,4-dihydroxyl-N-methyltetrahydrofuran-2-carboxamide;

(2S,3S,4R,5R)-5-(2-(5-fluoropyridin-3-yl)-6-((3-methylbenzyl)amino)-9H-purin-9-yl)-3,4-dihydroxyl-N-(methyl-d3)-tetrahydrofuran-2-carboxamide;

(2S,3S,4R,5R)-5-(6-(p-methylphenylmethylamino)-2-(5-chloropyridin-3-yl)-9H-purin-9-yl)-3,4-dihydroxyl-N-(methyl-d3)-tetrahydrofuran-2-formamide;

(2S,3S,4R,5R)-5-(6-(m-methylphenylmethylamino)-2-(5-chloropyridin-3-yl)-9H-purin-9-yl)-3,4-dihydroxyl-N-(methyl-d3)-tetrahydrofuran-2-formamide;

(2S,3S,4R,5R)-5-(6-(2-chloro-5-methylbenzylamino)-2-(5-chloropyridin-3-yl)-9H-purin-9-yl)-3,4-dihydroxyl-N-(methyl-d3)-tetrahydrofuran-2-formamide;

(2S,3S,4R,5R)-5-(6-(2-chloro-5-methylbenzylamino)-2-(5-chloropyridin-3-yl)-9H-purin-9-yl)-3,4-dihydroxyl-N-methyl-tetrahydrofuran-2-formamide;

(2S,3S,4R,5R)-5-(6-((4-chloropyridin-2-yl)methylamino)-2-(pyridin-3-yl)-9H-purin-9-yl)-3,4-dihydroxyl-N-methyl-tetrahydrofuran-2-formamide;

(2S,3S,4R,5R)-5-(6-((4-chloropyridin-2-yl)methylamino)-2-(5-fluoropyridin-3-yl)-9H-purin-9-yl)-3,4-dihydroxyl-N-methyl-tetrahydrofuran-2-formamide;

(2S,3S,4R,5R)-5-(6-((4-chloropyridin-2-yl)methylamino)-2-(5-chloropyridin-3-yl)-9H-purin-9-yl)-3,4-dihydroxyl-N-methyl-tetrahydrofuran-2-formamide;

(2S,3S,4R,5R)-5-(6-((4-chloropyridin-2-yl)methylamino)-2-(5-methoxypyridin-3-yl)-9H-purin-9-yl)-3,4-dihydroxyl-N-methyl-tetrahydrofuran-2-formamide;

(2S,3S,4R,5R)-3,4-dihydroxyl-N-methyl-5-(6-((4-methylpyridin-2-yl)methylamino)-2-(pyridin-3-yl)-9H-purin-9-yl)-tetrahydrofuran-2-formamide;

(2S,3S,4R,5R)-5-(6-(benzylamino)-2-(5-methoxypyridin-3-yl)-9H-purin-9-yl)-3,4-dihydroxyl-N-methyl-tetrahydrofuran-2-formamide;

(2S,3S,4R,5R)-3,4-dihydroxyl-N-methyl-5-(6-((4-methylpyridin-2-yl)methylamino)-2-(5-methylpyridin-3-yl)-9H-purin-9-yl)-tetrahydrofuran-2-formamide;

(2S,3S,4R,5R)-5-(6-(2-fluoro-5-methylbenzylamino)-2-(pyridin-3-yl)-9H-purin-9-yl)-3,4-dihydroxyl-N-methyl-tetrahydrofuran-2-formamide;

(2S,3S,4R,5R)-5-(6-(2-fluoro-5-methylbenzylamino)-2-(5-fluoropyridin-3-yl)-9H-purin-9-yl)-3,4-dihydroxyl-N-methyl-tetrahydrofuran-2-formamide;

(2S,3S,4R,5R)-5-(6-(2-fluoro-5-methylbenzylamino)-2-(5-methylpyridin-3-yl)-9H-purin-9-yl)-3,4-dihydroxyl-N-methyl-tetrahydrofuran-2-formamide;

(2S,3S,4R,5R)-5-(6-(2-fluoro-5-methylbenzylamino)-2-(5-methoxypyridin-3-yl)-9H-purin-9-yl)-3,4-dihydroxyl-N-methyl-tetrahydrofuran-2-formamide;

(2S,3S,4R,5R)-5-(6-((((4-chloropyridin-2-yl)methyl)amino-2-(5-chloropyridin-3-yl)-9H-purin-9-yl)-3,4-dihydroxyl-N-(methyl-d3)-tetrahydrofuran-2-carboxamide;

(2S,3S,4R,5R)-5-(2-(5-chloropyridin-3-yl)-6-((((4-methylpyridin-2-yl)methyl)amino)-9H-purin-9-yl)-3,4-dihydroxyl-N-(methyl-d3)-tetrahydrofuran-2-carboxamide;

(2S,3S,4R,5R)-5-(2-(5-chloropyridin-3-yl)-6-((3-methoxybenzyl)amino)-9H-purin-9-yl)-3,4-dihydroxyl-N-(methyl-d3)-tetrahydrofuran-2-carboxamide;

(2S,3S,4R,5R)-5-(2-(5-chloropyridin-3-yl)-6-((3,5-dimethylbenzyl)amino)-9H-purin-9-yl)-3,4-dihydroxyl-N-(methyl-d3)-tetrahydrofuran-2-carboxamide;

(2S,3S,4R,5R)-5-(2-(5-chloropyridin-3-yl)-6-((2-fluoro-5-methylbenzyl)amino)-9H-purin-9-yl)-3,4-dihydroxyl-N-(methyl-d3)-tetrahydrofuran-2-carboxamide;

(2S,3S,4R,5R)-5-(2-(5-chloropyridin-3-yl)-6-((2-fluoro-5-methylbenzyl)amino)-9H-purin-9-yl)-3,4-dihydroxyl-N-methyltetrahydrofuran-2-carboxamide;

(2S,3S,4R,5R)-5-(6-((3,5-dimethylbenzyl)amino)-2-(5-methylpyridin-3-yl)-9H-purin-9-yl)-3,4-dihydroxyl-N-methyltetrahydrofuran-2-carboxamide;

(2S,3S,4R,5R)-5-(2-(5-chloropyridin-3-yl)-6-(pyridin-2-methylamino)-9H-purin-9-yl)-3,4-dihydroxyl-N-(methyl-d3)-tetrahydrofuran-2-carboxamide;

(2S,3S,4R,5R)-5-(2-(5-chloropyridin-3-yl)-6-(pyridin-4-ylmethylamino)-9H-purin-9-yl)-3,4-dihydroxyl-N-(methyl-d3)-tetrahydrofuran-2-carboxamide;

(2S,3S,4R,5R)-5-(2-(5-chloropyridin-3-yl)-6-(pyridin-3-ylmethylamino)-9H-purin-9-yl)-3,4-dihydroxyl-N-(methyl-d3)-tetrahydrofuran-2-carboxamide;

(2S,3S,4R,5R)-5-(6-(benzylamino)-2-(5-chloropyridin-3-yl)-9H-purin-9-yl)-N-ethyl-3,4-dihydroxyltetrahydrofuran-2-carboxamide;

(2S,3S,4R,5R)-5-(2-(5-chloropyridin-3-yl)-6-((6-methylpyridin-2-yl)methylamino)-9H-purin-9-yl)-3,4-dihydroxyl-N-(methyl-d3)-tetrahydrofuran-2-carboxamide;

(2S,3S,4R,5R)-5-(2-(5-chloropyridin-3-yl)-6-(((4-methylpyridin-2-yl)methyl)amino)-9H-purin-9-yl)-3,4-dihydroxyl-N-methyltetrahydrofuran-2-carboxamide;

(2S,3S,4R,5R)-5-(2-(5-chloropyridin-3-yl)-6-(((4-(trifluoromethyl)pyridin-2-yl)methyl)amino)-9H-purin-9-yl)-3,4-dihydroxyl-N-methyltetrahydrofuran-2-carboxamide;

(2S,3S,4R,5R)-3,4-dihydroxyl-N-methyl-5-(6-(((6-methylpyridin-2-yl)methyl)amino)-2-(5-methylpyridin-3-yl)-9H-purin-9-yl)tetrahydrofuran-2-carboxamide;

(2S,3S,4R,5R)-5-(2-(5-chloropyridin-3-yl)-6-(((4-methoxypyridin-2-yl)methyl)amino)-9H-purin-9-yl)-3,4-dihydroxyl-N-methyltetrahydrofuran-2-carboxamide;

(2S,3S,4R,5S)-5-(6-((3,5-dimethylbenzyl)amino)-2-(pyridin-3-yl)-9H-purin-9-yl)-3,4-dihydroxyl-N-methyltetrahydrofuran-2-carboxamide;

(2S,3S,4R,5S)-5-(6-((3,5-dimethylbenzyl)amino)-2-(5-methoxypyridin-3-yl)-9H-purin-9-yl)-3,4-dihydroxyl-N-methyltetrahydrofuran-2-carboxamide;

(2S,3S,4R,5S)-5-(6-((3,5-dimethylbenzyl)amino)-2-(5-fluoropyridin-3-yl)-9H-purin-9-yl)-3,4-dihydroxyl-N-methyltetrahydrofuran-2-carboxamide;

(2S,3S,4R,5S)-3,4-dihydroxyl-5-(2-(5-methoxypyridin-3-yl)-6-((3-methylbenzylamino)-9H-purin-9-yl)-N-methyltetrahydrofuran-2-carboxamide;

(2S,3S,4R,5S)-3,4-dihydroxyl-N-methyl-5-(6-((pyridin-2-ylmethyl)amino)-2-(pyridin-3-yl)-9H-purin-9-yl)tetrahydrofuran-2-carboxamide;

(2S,3S,4R,5S)-5-(2-(5-fluoropyridin-3-yl)-6-((pyridin-2-ylmethyl)amino)-9H-purin-9-yl)-3,4-dihydroxyl-N-methyltetrahydrofuran-2-carboxamide; (2S,3S,4R,5S)-5-(2-(5-chloropyridin-3-yl)-6-((pyridin-2-lymethyl)amino)-9H-purin-9-yl)-3,4-dihydroxyl-N-methyltetrahydrofuran-2-carboxamide;

(2S,3S,4R,5S)-3,4-dihydroxyl-5-(2-(5-methoxypyridin-3-yl)-6-((pyridin-2-ylmethyl)amino)-9H-purin-9-yl)-N-methyltetrahydrofuran-2-carboxamide;

(2S,3S,4R,5S)-3,4-dihydroxyl-N-methyl-5-(2-(pyridin-3-yl)-6-((((4-(trifluoromethyl)pyridin-2-yl)methyl)amino)-9H-purin-9-yl)tetrahydrofuran-2-carboxamide;

(2S,3S,4R,5S)-5-(2-(5-fluoropyridin-3-yl)-6-((((4-(trifluoromethyl)pyridin-2-yl)methyl)amino)-9H-purin-9-yl)-3,4-dihydroxyl-N-methyltetrahydrofuran-2-carboxamide;

(2S,3S,4R,5S)-3,4-dihydroxyl-5-(2-(5-methoxypyridin-3-yl)-6-((((4-(trifluoromethyl)pyridin-2-yl)methyl)amino)-9H-purin-9-yl)-N-methyltetrahydrofuran-2-carboxamide;

(2S,3S,4R,5S)-3,4-dihydroxyl-5-(2-(5-methoxypyridin-3-yl)-6-((((4-(methylpyridin-2-yl)methyl)amino)-9H-purin-9-yl)-N-methyltetrahydrofuran-2-carboxamide;

(2S,3S,4R,5S)-5-(6-(benzylamino)-2-(pyridin-2-yl)-9H-purin-9-yl)-3,4-dihydroxyl-N-methyltetrahydrofuran-2-carboxamide.

* * * * *